United States Patent
Kobayashi et al.

(10) Patent No.: US 7,001,897 B2
(45) Date of Patent: Feb. 21, 2006

(54) 1-METHYLCARBAPENEM DERIVATIVES

(75) Inventors: Yoshiyuki Kobayashi, Sagamihara (JP); Tsuyoshi Shinozuka, Yokohama (JP); Osamu Kanno, Kawasaki (JP)

(73) Assignee: Sankyo Company, Limited, Tokyo (JP)

( * ) Notice: Subject to any disclaimer, the term of this patent is extended or adjusted under 35 U.S.C. 154(b) by 145 days.

(21) Appl. No.: 10/439,198

(22) Filed: May 15, 2003

(65) Prior Publication Data

US 2004/0014962 A1 Jan. 22, 2004

Related U.S. Application Data

(63) Continuation-in-part of application No. PCT/JP01/09960, filed on Nov. 14, 2001.

(30) Foreign Application Priority Data

Nov. 16, 2000 (JP) ........................... 2000-350063

(51) Int. Cl.
  C07D 477/20  (2006.01)
  A61K 31/454  (2006.01)
  A61K 31/421  (2006.01)
  A61K 31/426  (2006.01)
  A61P 31/04   (2006.01)

(52) U.S. Cl. .................. 514/210.12; 540/350
(58) Field of Classification Search ........... 540/350; 514/210.1
  See application file for complete search history.

(56) References Cited

U.S. PATENT DOCUMENTS 4,921,852 A    5/1990  Masayoshi et al.
5,534,510 A  * 7/1996  Abe et al. ................... 540/350
5,869,517 A    2/1999  Müller et al.
6,180,622 B1 * 1/2001  Aihara et al. .......... 514/210.12

FOREIGN PATENT DOCUMENTS

| HU | 218298 | 5/1998 |
| JP | 8-53453 A | 2/1996 |
| JP | 2004043438 A * | 2/2004 |
| WO | WO 93/23402 | 11/1993 |
| WO | WO 2003095454 A1 * | 11/2003 |

* cited by examiner

*Primary Examiner*—Mark L. Berch
(74) *Attorney, Agent, or Firm*—Frishauf, Holtz, Goodman & Chick, P.C.

(57) ABSTRACT

A 1-methylcarbapenem compound represented by the formula (I):

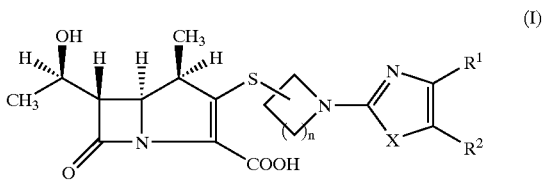

having antibacterial activity, pharmacologically acceptable esters or salts thereof and pharmaceutical compositions (particularly antibacterial agents) containing them as an active ingredient are described. In addition, the invention includes the use of these compounds, ester derivatives or salts for the manufacture of pharmaceutical compositions, or a method for the prevention or treatment of diseases (particularly bacterial infections) by administering a pharmacologically effective amount of the compounds, ester derivatives or salts to warm-blooded animals (particularly human beings).

41 Claims, No Drawings

1-METHYLCARBAPENEM DERIVATIVES

This is a Continuation-in-Part application of International Application No. PCT/JP01/09960 filed Nov. 14, 2001, which is incorporated herein by reference in its entirety.

BACKGROUND OF THE INVENTION

The present invention relates to 1-methylcarbapenem compounds having excellent antibacterial activity, pharmacologically acceptable esters or salts thereof, pharmaceutical compositions (particularly antibacterial agents) containing them as an active ingredient, use of said compounds, ester derivatives or salts for the manufacture of said pharmaceutical compositions, or a method for the prevention or treatment of diseases (particularly bacterial infections) which comprises administering a pharmacologically effective amount of said compounds, ester derivatives or salts to warm-blooded animals (particularly human beings).

There is a need for development of carbapenem derivatives having strong and balanced antibacterial activity against a wide range of pathogenic bacteria. 1-methylcarbapenem compounds having a structure analogous to that of the present invention are disclosed in Japanese Patent Application (Kokai) No. Hei 8-53453.

BRIEF SUMMARY OF THE INVENTION

It has been found that when compared with conventional 1-methylcarbapenem derivatives, the compounds of formula (I) of the present invention have stronger antibacterial power. The compounds and their use as an antibacterial agents for the treatment or prevention (particularly the treatment) of bacterial infections, particularly infections to the respiratory system, comprise the present invention.

DETAILED DESCRIPTION OF THE INVENTION

The present invention relates to 1-methylcarbapenem compounds represented by the formula (I):

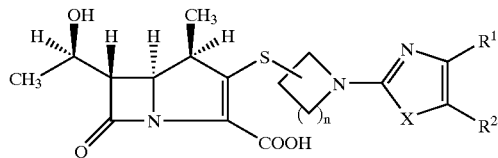

or pharmacologically acceptable salts or esters thereof.

In the formula, $R^1$ represents
(1) a group represented by the formula $COOR^3$
[wherein $R^3$ represents a hydrogen atom, a $C_1$–$C_6$ alkyl group or a $C_3$–$C_6$ cycloalkyl group],
(2) a group represented by the formula $CONR^4R^5$
[wherein $R^4$ and $R^5$ may be the same or different and each represents a hydrogen atom, a $C_1$–$C_6$ alkyl group (which may be substituted by one or two groups which may be the same or different and are selected from substituent group A below), a $C_3$–$C_6$ cycloalkyl group or a 3- to 6-membered heterocyclic group or a $C_6$–$C_{10}$ aryl group (which may be substituted by one or two groups, which may be the same or different and are selected from substituent group B below), or, together with the nitrogen atom to which they are bonded, represent a 3- to 6-membered nitrogen-containing heterocycle (which may be substituted by one or two groups, which may be the same or different and are selected from substituent group B below)],
(3) a cyano group,
(4) a group represented by the formula $CH_2OR^6$
[wherein $R^6$ represents a hydrogen atom, a $C_1$–$C_6$ alkyl group or a $C_3$–$C_6$ cycloalkyl group] or
(5) a group represented by the formula $CH_2NR^7R^8$
[wherein $R^7$ represents a hydrogen atom, a $C_1$–$C_6$ alkyl group or a $C_3$–$C_6$ cycloalkyl group, and $R^8$ represents a hydrogen atom, a $C_1$–$C_6$ alkyl group, a $C_3$–$C_6$ cycloalkyl group, a $C_1$–$C_6$ alkanoyl group, a ($C_6$–$C_{10}$ aryl)carbonyl group (which may be substituted by one or two groups which may be the same or different and are selected from substituent group B below), a ($C_1$–$C_6$ alkoxy)carbonyl group, a 5- or 6-membered aromatic heterocyclylcarbonyl group, a $C_1$–$C_6$ alkylsulfonyl group or a $C_6$–$C_{10}$ arylsulfonyl group, or $R^7$ and $R^8$, together with the nitrogen atom to which they are bonded, represent a succinimide group (which may be condensed with a phenyl group)];

$R^2$ represents a hydrogen atom or a $C_1$–$C_6$ alkyl group;

n represents 1, 2 or 3;

X represents a sulfur atom or an oxygen atom;

substituent group A comprises a hydroxyl group, an amino group (which may be substituted by one or two $C_1$–$C_6$ alkyl groups), a carbamoyl group (the amino moiety of which may be substituted by one or two $C_1$–$C_6$ alkyl groups), a carboxyl group, a cyano group and a $C_1$–$C_6$ alkoxy group; and substituent group B comprises a hydroxy-$C_1$–$C_4$-alkyl group, an amino-$C_1$–$C_4$-alkyl group (the amino moiety of which may be substituted by one or two $C_1$–$C_6$ alkyl groups), a carbamoyl group (the amino moiety of which may be substituted by one or two $C_1$–$C_6$ alkyl groups), a carboxyl group, a hydroxyl group, an amino group (which may be substituted by one or two $C_1$–$C_6$ alkyl groups), a $C_1$–$C_6$ alkoxy group and a $C_1$–$C_6$ alkyl group].

In the above description, the "$C_1$–$C_6$ alkyl group" in the definitions of $R^2$, $R^3$, $R^4$, $R^5$, $R^6$, $R^7$, $R^8$, substituent group A and substituent group B is a straight or branched saturated hydrocarbon group having from 1 to 6 carbon atoms. Examples of such a group include the methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl and 1-methyl-2-methylpropyl groups. In the definitions of $R^2$, $R^3$, $R^6$, $R^7$, $R^8$, substituent group A and substituent group B, a $C_1$–$C_3$ alkyl group is preferred and a methyl group is particularly preferred. In the definition of $R^4$, a $C_1$–$C_3$ alkyl group is preferred and a methyl or isopropyl group is particularly preferred. In the definition of $R^5$, a $C_2$–$C_6$ alkyl group is preferred and a 1-methyl-2-methylpropyl group is most preferred.

The "$C_3$–$C_6$ cycloalkyl group" in the definitions of $R^3$, $R^4$, $R^5$, $R^6$, $R^7$ and $R^8$, is a cyclic hydrocarbon group having from 3 to 6 carbon atoms. Examples of such a group include the cyclopropyl, cyclobutyl, cyclopentyl and cyclohexyl groups, of which a cyclopropyl group is preferred.

The "3- to 6-membered heterocyclic group" in the definitions of $R^4$ and $R^5$ is a saturated heterocyclic group including one or two oxygen, nitrogen and sulfur atoms. Examples of such a group include the aziridinyl, azetidinyl, pyrrolidinyl, piperidinyl, oxiranyl, oxetanyl, tetrahydrofuranyl, tetrahydropyranyl, tetrahydrothienyl, morpholinyl, piperazinyl and thiomorpholinyl groups, of which a 4- to 6-membered nitrogen-containing heterocyclic group is preferred and an azetidinyl, pyrrolidinyl or piperidinyl group is more preferred.

Examples of the "$C_6$–$C_{10}$ aryl group" in the definitions of $R^4$ and $R^5$ and the "$C_6$–$C_{10}$ aryl" moiety of the "($C_6$–$C_{10}$ aryl)carbonyl group" and the "$C_6$–$C_{10}$ arylsulfonyl group" in the definition of $R^8$ include the phenyl, indenyl and naphthyl groups, of which the phenyl group is preferred.

The "nitrogen-containing heterocycle" of the "3- to 6-membered nitrogen-containing heterocycle" in the definitions of the group formed by $R^4$ and $R^5$, together with the nitrogen atom to which they are bonded, is a saturated heterocyclic group containing one or two nitrogen atoms and which may contain an oxygen or sulfur atom. Examples of such a group include the aziridino, azetidino, pyrrolidino, piperidino, morpholino, piperazino and thiomorpholino groups, of which a 4- to 6-membered nitrogen-containing heterocycle is preferred and the azetidino, piperazino, morpholino or thiomorpholino groups are more preferred.

The "$C_1$–$C_6$ alkanoyl group" in the definition of $R^8$ is a straight or branched alkanoyl group having from 1 to 6 carbon atoms. Examples of such a group include the formyl, acetyl, propionyl, butyryl, isobutyryl, valeryl, isovaleryl, pivaloyl and hexanoyl groups, of which a $C_1$–$C_3$ alkanoyl group is preferred and an acetyl group is most preferred.

The "$C_1$–$C_6$ alkoxy" moiety of the "($C_1$–$C_6$ alkoxy)carbonyl group" in the definition of $R^8$ and the "$C_1$–$C_6$ alkoxy group" in the definitions of the substituent groups is a straight or branched alkoxy group having from 1 to 6 carbon atoms. Examples of such a group include the methoxy, ethoxy, propoxy, isopropoxy, butoxy, pentyloxy and hexyloxy groups, of which a $C_1$–$C_3$ alkoxy group is preferred and a methoxy group is most preferred.

The "5- or 6-membered aromatic heterocyclic" moiety of the "5- or 6-membered aromatic heterocyclylcarbonyl group" in the definition of $R^8$ is an aromatic heterocycle containing from one to three oxygen, nitrogen and sulfur atoms. Examples of such a heterocycle include pyrrole, imidazole, thiazole, oxazole, isoxazole, furan, thiophene, triazole, thiadiazole, pyridine, pyrimidine, pyridazine and triazine, of which furan, thiophene or pyridine is preferred.

Examples of the "hydroxy-$C_1$–$C_4$-alkyl group" in substituent group B include the hydroxymethyl, hydroxyethyl, hydroxypropyl and hydroxybutyl groups, of which a hydroxy-$C_1$–$C_2$-alkyl group is preferred and a hydroxymethyl group is most preferred.

Examples of the "amino-$C_1$–$C_4$-alkyl group" in substituent group B include the aminomethyl, aminoethyl, aminopropyl and aminobutyl groups, of which an amino-$C_1$–$C_2$-alkyl group is preferred and an aminomethyl group is most preferred.

Preferably substituent group A comprises a hydroxyl group, an amino group (which may be substituted by one or two $C_1$–$C_3$ alkyl groups) and a carbamoyl group, of which an amino group (which may be substituted by one or two methyl or ethyl groups) is most preferred.

Preferably substituent group B comprises a hydroxy-$C_1$–$C_4$-alkyl group, an amino-$C_1$–$C_4$-alkyl group (the amino moiety of which may be substituted by one or two $C_1$–$C_3$ alkyl groups), a carbamoyl group (the amino moiety of which may be substituted by one or two $C_1$–$C_3$ alkyl groups), a hydroxyl group and an amino group (which may be substituted by one or two $C_1$–$C_3$ alkyl groups), of which a group comprising a hydroxymethyl group, an aminomethyl group (the amino moiety of which may be substituted by one or two methyl or ethyl groups), a carbamoyl group (the amino moiety of which may be substituted by one or two methyl or ethyl groups), a hydroxyl group and an amino group (which may be substituted by one or two methyl or ethyl groups) is more preferred, an aminomethyl group and an amino group being further preferred.

The "pharmacologically acceptable ester" of compound (I) is an ester in which some of carboxyl groups or hydroxyl groups of compound (I) are protected by a group which may be cleaved in the body of a human being or an animal by a chemical or biological method such as hydrolysis to afford the original compound (I) or a salt thereof. Whether a derivative is or is not such an ester can be determined by orally or intravenously administering the derivative to an experimental animal such as a rat or mouse, studying the body fluid of the animal and detecting the original compound (I) or the salt thereof.

Examples of the protective group which forms an ester of a carboxyl group include a $C_1$–$C_{10}$ alkyl group, a $C_3$–$C_6$ cycloalkyl group, a $C_3$–$C_6$ cycloalkyl-$C_1$–$C_4$-alkyl group, a $C_2$–$C_{10}$ alkanoyloxy-$C_1$–$C_4$-alkyl group, a ($C_1$–$C_{10}$ alkoxy)carbonyloxy-$C_1$–$C_4$-alkyl group, a phenyl group (said phenyl group may be substituted by one or two groups selected from a halogen atom, a $C_1$–$C_4$ alkyl group, a $C_1$–$C_4$ alkoxy group, a methylenedioxy group and a $C_1$–$C_6$ alkanoyloxy group), a $C_1$–$C_{10}$ alkanoyloxybenzyl group, a phthalidyl group and a 5-methyl-2-oxo-1,3-dioxolen-4-ylmethyl group.

Examples of the protective group which forms an ester of a hydroxyl group include a $C_1$–$C_{10}$ alkanoyl group, a ($C_6$–$C_{10}$ aryl)carbonyl group, a ($C_1$–$C_{10}$ alkoxy)carbonyl group and an aminoacyl group.

Examples of the above "$C_1$–$C_{10}$ alkyl group" include the methyl, ethyl, propyl, isopropyl, butyl, isobutyl, s-butyl, t-butyl, pentyl, 2-pentyl, 3-pentyl, isopentyl, hexyl, 2-hexyl, 3-hexyl, isohexyl, heptyl, octyl, nonyl and decyl groups, of which a $C_1$–$C_6$ alkyl group is preferred, a $C_2$–$C_4$ alkyl group is more preferred and an ethyl group is most preferred.

Examples of the "$C_3$–$C_6$ cycloalkyl group" include the cyclopropyl, cyclobutyl, cyclopentyl and cyclohexyl groups, of which the cyclopentyl or cyclohexyl group is preferred.

Examples of the "$C_3$–$C_6$ cycloalkyl-$C_1$–$C_4$-alkyl group" include the cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl and cyclohexylethyl groups, of which the cyclopropylmethyl group is preferred.

Examples of the "$C_2$–$C_{10}$ alkanoyloxy-$C_1$–$C_4$-alkyl group" include the acetoxymethyl, 1-(acetoxy)ethyl, 1-(acetoxy)propyl, 1-(acetoxy)butyl, propionyloxymethyl, 1-(propionyloxy)ethyl, isopropionyloxymethyl, 1-(isopropionyloxy)ethyl, butyryloxymethyl, 1-(butyryloxy)ethyl, isobutyryloxymethyl, 1-(isobutyryloxy)ethyl, pivaloyloxymethyl, 1-(pivaloyloxy)ethyl, valeryloxymethyl, 1-(valeryloxy)ethyl, isovaleryloxymethyl, 1-(isovaleryloxy)ethyl, hexanoyloxymethyl, 1-(hexanoyloxy)ethyl, octanoyloxymethyl, 1-(octanoyloxy)ethyl, decanoyloxymethyl, cyclopentylcarbonyloxymethyl, 1-methylcyclopentylcarbonyloxymethyl, cyclohexylcarbonyloxymethyl and 1-methylcyclohexylcarbonyloxymethyl groups, of which a $C_2$–$C_6$ alkanoyloxymethyl or 1-($C_2$–$C_6$ alkanoyloxy)ethyl group is preferred.

Examples of the "($C_1$–$C_{10}$ alkoxy)carbonyloxy-$C_1$–$C_4$-alkyl group" include the methoxycarbonyloxymethyl, 1-(methoxycarbonyloxy)ethyl, ethoxycarbonyloxymethyl, 1-(ethoxycarbonyloxy)ethyl, 1-(ethoxycarbonyloxy)propyl, 1-(ethoxycarbonyloxy)butyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethyl, 1-(isobutoxycarbonyloxy)ethyl, s-butoxycarbonyloxymethyl, 1-(s-butoxycarbonyloxy)ethyl, t-butoxycarbonyloxymethyl, 1-(t-butoxycarbonyloxy)ethyl, pentyloxycarbonyloxymethyl, 1-(pentyloxycarbonyloxy)ethyl, (1-methylbutyloxycarbonyloxy)methyl, 1-(1-methylbutyloxycarbonyloxy)ethyl, (2-methylbutyloxycarbonyloxy)methyl, 1-(2-methylbutyloxycarbonyloxy)ethyl, (3-methylbutyloxycarbonyloxy)methyl, 1-(3-methylbutyloxycarbonyloxy)ethyl, (1-ethylpropyloxycarbonyloxy)methyl, 1-(1-ethylpropyloxycarbonyloxy)ethyl, hexyloxycarbonyloxymethyl, 1-(hexyloxycarbonyloxy)ethyl, (1-methylpentyloxycarbonyloxy)methyl, 1-(1-methylpentyloxycarbonyloxy)ethyl, octyloxycarbonyloxymethyl, 1-(octyloxycarbonyloxy)ethyl, decyloxycarbonyloxymethyl, 1-(decyloxycarbonyloxy)ethyl, cyclopentylcarbonyloxymethyl, 1-(cyclopentyloxycarbonyloxy)ethyl, cyclohexylcarbonyloxymethyl and 1-(cyclohexyloxycarbonyloxy)ethyl groups, of which a ($C_1$–$C_6$ alkoxy)carbonyloxymethyl or 1-(($C_1$–$C_6$ alkoxy)carbonyloxy)ethyl group is preferred.

Examples of the "phenyl group which may be substituted" include the phenyl, 3-fluorophenyl, 4-fluorophenyl, 3,4-difluorophenyl, 3-methylphenyl, 4-methylphenyl, 3-methoxyphenyl, 4-methoxyphenyl, 3,4-dimethoxyphenyl, 3,4-methylenedioxyphenyl, 3-acetoxyphenyl and 4-acetoxyphenyl groups, of which an unsubstituted phenyl group is preferred.

Examples of the "$C_2$–$C_{10}$ alkanoyloxybenzyl group" include the 2-acetoxybenzyl, 3-acetoxybenzyl, 4-acetoxybenzyl, 3-propionyloxybenzyl, 4-propionyloxybenzyl, 4-butyryloxybenzyl, 4-valeryloxybenzyl, 4-hexanoyloxybenzyl, 4-octanoyloxybenzyl and 4-decanoyloxybenzyl groups, of which the 3- or 4-($C_2$–$C_4$ alkanoyloxy)benzyl group is preferred.

Examples of the "$C_1$–$C_{10}$ alkanoyl group" include the formyl, acetyl, propionyl, butyryl, pentanoyl, hexanoyl, octanoyl and decanoyl groups, of which a $C_2$–$C_6$ alkanoyl group is preferred.

Examples of the "($C_6$–$C_{10}$ aryl)carbonyl group" include the benzoyl, 1-naphthoyl and 2-naphthoyl groups, of which the benzoyl group is preferred.

Examples of the "($C_1$–$C_{10}$ alkoxy)carbonyl group" include the methoxycarbonyl, ethoxycarbonyl, propoxycarbonyl, butoxycarbonyl, pentyloxycarbonyl, hexyloxycarbonyl, octyloxycarbonyl and decyloxycarbonyl groups, of which a $C_2$–$C_6$ alkoxycarbonyl group is preferred.

Examples of the "aminoacyl group" include an amino acid group such as glycyl, alanyl, β-alanyl, leucyl, isoleucyl, phenylalanyl, histidyl, asparagyl, prolyl and lysyl, of which a glycyl group is preferred.

The compounds (I) and pharmacologically acceptable esters thereof of the present invention can form pharmacologically acceptable salts if necessary.

The "pharmacologically acceptable salt thereof" is a salt to which the compound (I) of the present invention can be converted. Preferred examples of such a salt include alkali metal salts such as a sodium salt, a potassium salt and a lithium salt; alkaline earth metal salts such as a calcium salt and a magnesium salt; metal salts such as an aluminium salt, an iron salt, a zinc salt, a copper salt, a nickel salt and a cobalt salt; amine salts such as inorganic salts such as an ammonium salt and organic salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt and a tris(hydroxymethyl)aminomethane salt; inorganic acid salts such as hydrohalic acid salts such as a hydrofluoride, a hydrochloride, a hydrobromide or a hydroiodide, a nitrate, a perchlorate, a sulfate or a phosphate; lower alkanesulfonates such as a methanesulfonate, trifluoromethanesulfonate or an ethanesulfonate; arylsulfonates such as a benzenesulfonate or a p-toluenesulfonate; and organic acid salts such as an acetate, a malate, a fumarate, a succinate, a citrate, a tartrate, an oxalate or a maleate; and amino acid salts such as a glycine salt, a lysine salt, an arginine salt, an ornithine salt, a glutamate or an aspartate.

The compounds (I), pharmacologically acceptable salts and ester derivatives thereof of the present invention include hydrates or solvates thereof.

In the compounds of the formula (I), the following compounds are preferred.

(1) Regarding $R^1$:
(1-1) compounds wherein $R^1$ represents a group represented by the formula $CONR^4R^5$, a cyano group or a group represented by the formula $CH_2NR^7R^8$;
(1-2) compounds wherein $R^1$ represents a group represented by the formula $CONR^4R^5$ or a group represented by the formula $CH_2NR^7R^8$;
(1-3) compounds wherein $R^1$ represents a group represented by the formula $CONR^4R^5$.

(2) Regarding $R^2$:
(2-1) compounds wherein $R^2$ represents a hydrogen atom or a $C_1$–$C_3$ alkyl group;
(2-2) compounds wherein $R^2$ represents a hydrogen atom.

(3) Regarding $R^3$:
(3-1) compounds wherein $R^3$ represents a hydrogen atom or a $C_1$–$C_3$ alkyl group;
(3-2) compounds wherein $R^3$ represents a hydrogen atom, a methyl group or an ethyl group.

(4) Regarding $R^4$:
(4-1) compounds wherein $R^4$ represents a hydrogen atom or a $C_1$–$C_3$ alkyl group;
(4-2) compounds wherein $R^4$ represents a hydrogen atom, a methyl group or an isopropyl group.

(5) Regarding $R^5$:
(5-1) compounds in which $R^5$ represents a hydrogen atom, a $C_1$–$C_6$ alkyl group (which may be substituted by one or two groups which may be the same or different and are selected from substituent group A) or a 4- to 6-membered nitrogen-containing heterocyclic group;
(5-2) compounds wherein $R^5$ represents a hydrogen atom, a $C_1$–$C_6$ alkyl group (which may be substituted by one or two groups which may be the same or different and are selected from substituent group A), or an azetidinyl, pyrrolidinyl or piperidinyl group.

(6) Regarding $R^4$ and $R^5$:
(6-1) compounds wherein $R^4$ and $R^5$, together with the nitrogen atom to which they are bonded, represent a 4- to 6-membered nitrogen-containing heterocycle (which may be substituted by one or two groups which may be the same or different and are selected from substituent group B);
(6-2) compounds wherein $R^4$ and $R^5$, together with the nitrogen atom to which they are bonded, represent an azetidino, piperazino, morpholino or thiomorpholino group (which may be substituted by one or two groups which may be the same or different and are selected from substituent group B).

(7) Regarding $R^6$:

(7-1) compounds wherein $R^6$ represents a hydrogen atom or a $C_1$–$C_3$ alkyl group;

(7-2) compounds wherein $R^6$ represents a hydrogen atom.

(8) Regarding $R^7$:

(8-1) compounds wherein $R^7$ represents a hydrogen atom or a $C_1$–$C_3$ alkyl group;

(8-2) compounds wherein $R^7$ represents a hydrogen atom or a methyl group;

(8-3) compounds wherein $R^7$ represents a hydrogen atom.

(9) Regarding $R^8$:

(9-1) compounds wherein $R^8$ represents a hydrogen atom, a $C_1$–$C_3$ alkyl group, a $C_1$–$C_3$ alkanoyl group, a benzoyl group (which may be substituted by one or two groups which may be the same or different and are selected from the substituent group B), a ($C_1$–$C_3$ alkoxy)carbonyl group, a thienylcarbonyl group, a furylcarbonyl group or a pyridylcarbonyl group;

(9-2) compounds wherein $R^8$ represents a hydrogen atom, a benzoyl group (which may be substituted by one or two groups which may be the same or different and are selected from substituent group B), a (2-thienyl)carbonyl group, a (2-furyl)carbonyl group or a (3-pyridyl)carbonyl group.

(10) Regarding n:

(10-1) compounds wherein n represents 1.

(11) Regarding X:

(11-1) compounds wherein X represents an oxygen atom.

Compounds obtained by arbitrarily combining 2 or more of the above listed preferred substituents are more preferred. More preferred examples of the compounds include the following compounds:

(12) compounds wherein $R^1$ represents a group represented by the formula $CONR^4R^5$ (wherein $R^4$ represents a hydrogen atom or a $C_1$–$C_3$ alkyl group; and $R^5$ represents a hydrogen atom, a $C_1$–$C_6$ alkyl group (which may be substituted by one or two groups which may be the same or different and are selected from substituent group A) or a 4- to 6-membered nitrogen-containing heterocyclic group); $R^2$ represents a hydrogen atom; n represents 1; and X represents an oxygen atom or a sulfur atom.

(13) compounds wherein $R^1$ represents a group represented by the formula $CONR^4R^5$ (wherein $R^4$ represents a hydrogen atom, a methyl group or an isopropyl group; and $R^5$ represents a hydrogen atom, a $C_1$–$C_6$ alkyl group (which may be substituted by one or two groups which may be the same or different and are selected from substituent group A), or an azetidinyl, pyrrolidinyl or piperidinyl group); n represents 1; and X represents an oxygen atom or a sulfur atom.

(14) compounds wherein $R^1$ represents a group represented by the formula $CONR^4R^5$ (wherein $R^4$ and $R^5$, together with the nitrogen atom to which they are bonded, represent a 4- to 6-membered nitrogen-containing heterocycle (which may be substituted by one or two groups which may be the same or different and are selected from substituent group B); $R^2$ represents a hydrogen atom; n represents 1; and X represents an oxygen atom or a sulfur atom.

(15) compounds wherein $R^1$ represents a group represented by the formula $CONR^4R^5$ (wherein $R^4$ and $R^5$, together with the nitrogen atom to which they are bonded, represent an azetidino, piperazino, morpholino or thiomorpholino group (which may be substituted by one or two groups which may be the same or different and are selected from substituent group B)); $R^2$ represents a hydrogen atom; n represents 1; and X represents an oxygen atom or a sulfur atom.

(16) compounds wherein $R^1$ represents a cyano group; $R^2$ represents a hydrogen atom; n represents 1; and X represents an oxygen atom or a sulfur atom.

(17) compounds wherein $R^1$ represents a group represented by the formula $CH_2NR^7R^8$ (wherein $R^7$ represents a hydrogen atom or a $C_1$–$C_3$ alkyl group; and $R^8$ represents a hydrogen atom, a $C_1$–$C_3$ alkyl group, a $C_1$–$C_3$ alkanoyl group, a benzoyl group (which may be substituted by one or two groups which may be the same or different and are selected from substituent group B), a ($C_1$–$C_3$ alkoxy)carbonyl group, a thienylcarbonyl group, furylcarbonyl group or a pyridylcarbonyl group); $R^2$ represents a hydrogen atom; n represents 1; and X represents an oxygen atom or a sulfur atom.

(18) compounds wherein $R^1$ represents a group represented by the formula $CH_2NR^7R^8$ (wherein $R^7$ represents a hydrogen atom or a methyl group; and $R^8$ represents a hydrogen atom, a benzoyl group (which may be substituted by one or two groups which may be the same or different and are selected from substituent group B), a (2-thienyl)-carbonyl group, a (2-furyl)-carbonyl group or a (3-pyridyl)-carbonyl group); $R^2$ represents a hydrogen atom; n represents 1, and X represents an oxygen atom or a sulfur atom.

Certain compounds (I) of the present invention are specifically exemplified in Tables 1 to 5. It should be noted that the compounds (I) of the present invention are not limited to these exemplification compounds.

In Tables 1 to 5, Me represents a methyl group, Et an ethyl group, Pr a propyl group, iPr an isopropyl group, Bu a butyl group, Pen a pentyl group, Hex a hexyl group, cPr a cyclopropyl group, cBu a cyclobutyl group, cPen a cyclopentyl group, cHex a cyclohexyl group, Azt an azetidinyl group, Pyr a pyrrolidinyl group, Pip a piperidinyl group, and Ph a phenyl group. The term "position" means the bonding position of the sulfur atom.

TABLE 1

(I-1)

| Cpd No. | X | n | position | $R^2$ | $R^3$ |
|---|---|---|---|---|---|
| 1 | S | 1 | 3 | H | H |
| 2 | S | 1 | 3 | H | Me |
| 3 | S | 1 | 3 | H | Et |
| 4 | S | 1 | 3 | H | Pr |
| 5 | S | 1 | 3 | H | iPr |
| 6 | S | 1 | 3 | H | Bu |
| 7 | S | 1 | 3 | H | Pen |
| 8 | S | 1 | 3 | H | Hex |
| 9 | S | 1 | 3 | H | cPr |
| 10 | S | 1 | 3 | H | cBu |
| 11 | S | 1 | 3 | H | cPen |
| 12 | S | 1 | 3 | H | cHex |
| 13 | S | 1 | 3 | Me | H |
| 14 | S | 1 | 3 | Me | Me |
| 15 | S | 1 | 3 | Me | Et |
| 16 | S | 1 | 3 | Me | Pr |
| 17 | S | 1 | 3 | Me | iPr |
| 18 | S | 1 | 3 | Me | Bu |
| 19 | S | 1 | 3 | Me | Pen |
| 20 | S | 1 | 3 | Me | Hex |
| 21 | S | 1 | 3 | Me | cPr |
| 22 | S | 1 | 3 | Me | cBu |
| 23 | S | 1 | 3 | Me | cPen |
| 24 | S | 1 | 3 | Me | cHex |

TABLE 1-continued (I-1)

| Cpd No. | X | n | position | R² | R³ |
|---|---|---|---|---|---|
| 26 | S | 2 | 3 | H | H |
| 27 | S | 2 | 3 | H | Me |
| 28 | S | 2 | 3 | H | Et |
| 29 | S | 2 | 3 | H | Pr |
| 30 | S | 2 | 3 | H | iPr |
| 31 | S | 2 | 3 | H | Bu |
| 32 | S | 2 | 3 | H | Pen |
| 33 | S | 2 | 3 | H | Hex |
| 34 | S | 2 | 3 | H | cPr |
| 35 | S | 2 | 3 | H | cBu |
| 36 | S | 2 | 3 | H | cPen |
| 37 | S | 2 | 3 | H | cHex |
| 38 | S | 2 | 3 | Me | H |
| 39 | S | 2 | 3 | Me | Me |
| 40 | S | 2 | 3 | Me | Et |
| 41 | S | 2 | 3 | Me | Pr |
| 42 | S | 2 | 3 | Me | iPr |
| 43 | S | 2 | 3 | Me | Bu |
| 44 | S | 2 | 3 | Me | Pen |
| 45 | S | 2 | 3 | Me | Hex |
| 46 | S | 2 | 3 | Me | cPr |
| 47 | S | 2 | 3 | Me | cBu |
| 48 | S | 2 | 3 | Me | cPen |
| 49 | S | 2 | 3 | Me | cHex |
| 51 | S | 2 | 3 | H | H |
| 52 | S | 2 | 3 | H | Me |
| 53 | S | 2 | 3 | H | Et |
| 54 | S | 3 | 4 | H | Pr |
| 55 | S | 3 | 4 | H | iPr |
| 56 | S | 3 | 4 | H | Bu |
| 57 | S | 3 | 4 | H | Pen |
| 58 | S | 3 | 4 | Me | Hex |
| 59 | S | 3 | 4 | H | Hex |
| 60 | S | 3 | 4 | H | cPr |
| 61 | S | 3 | 4 | H | cPr |
| 62 | S | 3 | 4 | H | cHex |
| 63 | S | 3 | 4 | Me | H |
| 64 | S | 3 | 4 | Me | Me |
| 65 | S | 3 | 4 | Me | Et |
| 66 | S | 3 | 4 | Me | Pr |
| 67 | S | 3 | 4 | Me | iPr |
| 68 | S | 3 | 4 | Me | Bu |
| 69 | S | 3 | 4 | Me | Pen |
| 70 | S | 3 | 4 | Me | Hex |
| 71 | S | 3 | 4 | Me | cPr |
| 72 | S | 3 | 4 | Me | cBu |
| 73 | S | 3 | 4 | Me | cPen |
| 74 | S | 3 | 4 | Me | cHex |
| 76 | O | 1 | 3 | H | H |
| 77 | O | 1 | 3 | H | Me |
| 78 | O | 1 | 3 | H | Et |
| 79 | O | 1 | 3 | H | Pr |
| 80 | O | 1 | 3 | H | iPr |
| 81 | O | 1 | 3 | H | Bu |
| 82 | O | 1 | 3 | H | Pen |
| 83 | O | 1 | 3 | H | Hex |
| 84 | O | 1 | 3 | H | cPr |
| 85 | O | 1 | 3 | H | cBu |
| 86 | O | 1 | 3 | H | cPen |
| 87 | O | 1 | 3 | H | cHex |
| 88 | O | 1 | 3 | Me | H |
| 89 | O | 1 | 3 | Me | Me |
| 90 | O | 1 | 3 | Me | Et |
| 91 | O | 1 | 3 | Me | Pr |
| 92 | O | 1 | 3 | Me | iPr |
| 93 | O | 1 | 3 | Me | Bu |
| 94 | O | 1 | 3 | Me | Pen |

TABLE 1-continued (I-1)

| Cpd No. | X | n | position | R² | R³ |
|---|---|---|---|---|---|
| 95 | O | 1 | 3 | Me | Hex |
| 96 | O | 1 | 3 | Me | cPr |
| 97 | O | 1 | 3 | Me | cBu |
| 98 | O | 1 | 3 | Me | cPen |
| 99 | O | 1 | 3 | Me | cHex |
| 101 | O | 2 | 3 | H | H |
| 102 | O | 2 | 3 | H | Me |
| 103 | O | 2 | 3 | H | Et |
| 104 | O | 2 | 3 | H | Pr |
| 105 | O | 2 | 3 | H | iPr |
| 106 | O | 2 | 3 | H | Bu |
| 107 | O | 2 | 3 | H | Pen |
| 108 | O | 2 | 3 | H | Hex |
| 109 | O | 2 | 3 | H | cPr |
| 110 | O | 2 | 3 | H | cBu |
| 111 | O | 2 | 3 | H | cPen |
| 112 | O | 2 | 3 | H | cHex |
| 113 | O | 2 | 3 | Me | H |
| 114 | O | 2 | 3 | Me | Me |
| 115 | O | 2 | 3 | Me | Et |
| 116 | O | 2 | 3 | Me | Pr |
| 117 | O | 2 | 3 | Me | iPr |
| 118 | O | 2 | 3 | Me | Bu |
| 119 | O | 2 | 3. | Me | Pen |
| 120 | O | 2 | 3 | Me | Hex |
| 121 | O | 2 | 3 | Me | cPr |
| 122 | O | 2 | 3 | Me | cBu |
| 123 | O | 2 | 3 | Me | cPen |
| 124 | O | 2 | 3 | Me | cHex |
| 126 | O | 3 | 4 | H | H |
| 127 | O | 3 | 4 | H | Me |
| 128 | O | 3 | 4 | H | Et |
| 129 | O | 3 | 4 | H | Pr |
| 130 | O | 3 | 4 | H | iPr |
| 131 | O | 3 | 4 | H | Bu |
| 132 | O | 3 | 4 | H | Pen |
| 133 | O | 3 | 4 | H | Hex |
| 134 | O | 3 | 4 | H | cPr |
| 135 | O | 3 | 4 | H | cBu |
| 136 | O | 3 | 4 | H | cPen |
| 137 | O | 3 | 4 | H | cHex |
| 138 | O | 3 | 4 | Me | H |
| 139 | O | 3 | 4 | Me | Me |
| 140 | O | 3 | 4 | Me | Et |
| 141 | O | 3 | 4 | Me | Pr |
| 142 | O | 3 | 4 | Me | iPr |
| 143 | O | 3 | 4 | Me | Bu |
| 144 | O | 3 | 4 | Me | Pen |
| 145 | O | 3 | 4 | Me | Hex |
| 146 | O | 3 | 4 | Me | cPr |
| 147 | O | 3 | 4 | Me | cBu |
| 148 | O | 3 | 4 | Me | cPen |
| 149 | O | 3 | 4 | Me | cHex |

TABLE 2

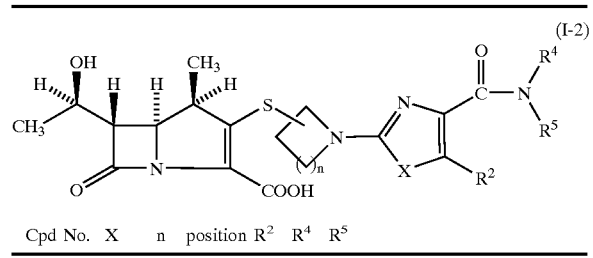

(I-2)

| Cpd No. | X | n | position | R² | R⁴ | R⁵ |
|---|---|---|---|---|---|---|
| 1 | S | 1 | 3 | H | H | H |
| 2 | S | 1 | 3 | H | H | Me |
| 3 | S | 1 | 3 | H | H | Et |
| 4 | S | 1 | 3 | H | H | Pr |
| 5 | S | 1 | 3 | H | H | iPr |
| 6 | S | 1 | 3 | H | H | Bu |
| 7 | S | 1 | 3 | H | Me | Me |
| 8 | S | 1 | 3 | H | Me | Et |
| 9 | S | 1 | 3 | H | Me | Pr |
| 10 | S | 1 | 3 | H | Me | iPr |
| 11 | S | 1 | 3 | H | Me | Bu |
| 12 | S | 1 | 3 | H | Et | Et |
| 13 | S | 1 | 3 | H | Et | Pr |
| 14 | S | 1 | 3 | H | Et | iPr |
| 15 | S | 1 | 3 | H | Et | Bu |
| 16 | S | 1 | 3 | H | Pr | Pr |
| 17 | S | 1 | 3 | H | Pr | iPr |
| 18 | S | 1 | 3 | H | Pr | Bu |
| 19 | S | 1 | 3 | H | iPr | iPr |
| 20 | S | 1 | 3 | H | iPr | Bu |
| 21 | S | 1 | 3 | H | Bu | Bu |
| 22 | S | 1 | 3 | H | H | $CH_2CH_2OH$ |
| 23 | S | 1 | 3 | H | Me | $CH_2CH_2OH$ |
| 24 | S | 1 | 3 | H | Et | $CH_2CH_2OH$ |
| 25 | S | 1 | 3 | H | Pr | $CH_2CH_2OH$ |
| 26 | S | 1 | 3 | H | iPr | $CH_2CH_2OH$ |
| 27 | S | 1 | 3 | H | H | $CH(CH_3)CH_2OH$ |
| 28 | S | 1 | 3 | H | H | $CH(CH_2OH)CH_2OH$ |
| 29 | S | 1 | 3 | H | H | $CH(CH_2CH_3)CH_2OH$ |
| 30 | S | 1 | 3 | H | H | $CH(CH(CH_3)_2)CH_2OH$ |
| 31 | S | 1 | 3 | H | H | $CH_2CH_2NH_2$ |
| 32 | S | 1 | 3 | H | H | $CH(CH_3)CH_2NH_2$ |
| 33 | S | 1 | 3 | H | H | $CH(CH_2CH_3)CH_2NH_2$ |
| 34 | S | 1 | 3 | H | H | $CH(CH(CH_3)_2)CH_2NH_2$ |
| 35 | S | 1 | 3 | H | H | $CH_2COOH$ |
| 36 | S | 1 | 3 | H | H | $CH(CH_3)COOH$ |
| 37 | S | 1 | 3 | H | H | $CH(CH_2OH)COOH$ |
| 38 | S | 1 | 3 | H | H | $CH(CH_2CH_3)COOH$ |
| 39 | S | 1 | 3 | H | H | $CH(CH(CH_3)_2)COOH$ |
| 40 | S | 1 | 3 | H | H | $CH_2CONH_2$ |
| 41 | 5 | 1 | 3 | H | H | $CH(CH_3)CONH_2$ |
| 42 | S | 1 | 3 | H | H | $CH(CH_2OH)CONH_2$ |
| 43 | S | 1 | 3 | H | H | $CH(CH_2CH_3)CONH_2$ |
| 44 | S | 1 | 3 | H | H | $CH(CH(CH_3)_2)CONH_2$ |
| 45 | S | 1 | 3 | H | H | cPr |
| 46 | S | 1 | 3 | H | H | cBu |
| 47 | S | 1 | 3 | H | H | cPen |
| 48 | S | 1 | 3 | H | H | cHex |
| 49 | S | 1 | 3 | H | H | 3-Azt |
| 50 | S | 1 | 3 | H | H | 3-Pyr |
| 51 | S | 1 | 3 | H | H | 3-Pip |
| 52 | S | 1 | 3 | H | H | 4-Pip |
| 53 | S | 1 | 3 | H | H | 2-COOH—Ph |
| 54 | S | 1 | 3 | H | H | 2-$CONH_2$—Ph |
| 55 | S | 1 | 3 | H | H | 3-COOH—Ph |
| 56 | S | 1 | 3 | H | H | 3-$CONH_2$—Ph |
| 57 | S | 1 | 3 | H | H | 4-COOH—Ph |
| 58 | S | 1 | 3 | H | H | 4-$CONH_2$—Ph |
| 59 | S | 1 | 3 | H | —$CH_2CH_2CH_2$— | |
| 60 | S | 1 | 3 | H | —$CH_2CH_2CH_2CH_2$— | |
| 61 | S | 1 | 3 | H | —$CH_2CH_2CH_2CH_2CH_2$— | |
| 62 | S | 1 | 3 | H | —$CH_2CH_2OCH_2CH_2$— | |
| 63 | S | 1 | 3 | H | —$CH_2CH_2SCH_2CH_2$— | |
| 64 | S | 1 | 3 | H | —$CH_2CH_2NHCH_2CH_2$— | |
| 65 | S | 1 | 3 | H | —$CH_2CH(OH)OH_2$— | |
| 66 | S | 1 | 3 | H | —$CH_2CH(OH)CH_2$— | |
| 67 | S | 1 | 3 | H | —$CH_2CH(OH)CH_2CH_2$ | |
| 68 | S | 1 | 3 | H | —$CH_2CH_2CH(OH)CH_2CH_2$ | |
| 69 | S | 1 | 3 | H | —$CH(COOH)CH_2CH_2$— | |
| 70 | S | 1 | 3 | H | —$CH(CONH_2)CH_2CH_2$— | |
| 71 | S | 1 | 3 | H | —$CH(CH_2OH)CH_2CH_2$— | |
| 72 | S | 1 | 3 | H | —$CH(CH_2NH_2)CH_2CH_2$— | |
| 73 | S | 1 | 3 | H | —$CH(COOH)CH_2CH_2CH_2$— | |
| 74 | S | 1 | 3 | H | —$CH(CONH_2)CH_2CH_2CH_2$— | |
| 75 | S | 1 | 3 | H | —$CH(CH_2OH)CH_2CH_2CH_2$— | |
| 76 | S | 1 | 3 | H | —$CH(CH_2NH_2)CH_2CH_2CH_2$— | |
| 77 | S | 1 | 3 | H | —$CH(COOH)CH_2CH_2CH_2CH_2$— | |
| 78 | S | 1 | 3 | H | —$CH(CONH_2)CH_2CH_2CH_2CH_2$ | |
| 79 | S | 1 | 3 | H | —$CH(CH_2OH)CH_2CH_2CH_2CH_2$— | |
| 80 | S | 1 | 3 | H | —$CH(CH_2NH_2)CH_2CH_2CH_2CH_2$— | |
| 81 | S | 1 | 3 | H | —$CH_2CH(COOH)CH_2CH_2CH_2$— | |
| 82 | S | 1 | 3 | H | —$CH_2CH(CONH_2)CH_2CH_2CH_2$— | |
| 83 | S | 1 | 3 | H | —$CH_2CH(CH_2OH)CH_2CH_2CH_2$— | |
| 84 | S | 1 | 3 | H | —$CH_2CH(CH_2NH_2)CH_2CH_2CH_2$— | |
| 85 | S | 1 | 3 | H | —$CH_2CH_2CH(COOH)CH_2CH_2$— | |
| 86 | S | 1 | 3 | H | —$CH_2CH_2CH(CONH_2)CH_2CH_2$— | |
| 87 | S | 1 | 3 | H | —$CH_2CH_2CH(CH_2OH)CH_2CH_2$— | |
| 88 | S | 1 | 3 | H | —$CH_2CH_2CH(CH_2NH_2)CH_2CH_2$— | |
| 89 | S | 1 | 3 | Me | H | H |
| 90 | S | 1 | 3 | Me | H | Me |
| 91 | S | 1 | 3 | Me | H | Et |
| 92 | S | 1 | 3 | Me | H | Pr |
| 93 | S | 1 | 3 | Me | H | iPr |
| 94 | S | 1 | 3 | Me | H | Bu |
| 95 | S | 1 | 3 | Me | Me | Me |
| 96 | S | 1 | 3 | Me | Me | Et |
| 97 | S | 1 | 3 | Me | Me | Pr |
| 98 | S | 1 | 3 | Me | Me | iPr |
| 99 | S | 1 | 3 | Me | Me | Bu |
| 100 | S | 1 | 3 | Me | Et | Et |
| 101 | S | 1 | 3 | Me | Et | Pr |
| 102 | S | 1 | 3 | Me | Et | iPr |
| 103 | S | 1 | 3 | Me | Et | Bu |
| 104 | S | 1 | 3 | Me | Pr | Pr |
| 105 | S | 1 | 3 | Me | Pr | iPr |
| 106 | S | 1 | 3 | Me | Pr | Bu |
| 107 | S | 1 | 3 | Me | iPr | iPr |
| 108 | S | 1 | 3 | Me | iPr | Bu |
| 109 | S | 1 | 3 | Me | Bu | Bu |
| 110 | S | 1 | 3 | Me | H | $CH_2CH_2OH$ |
| 111 | S | 1 | 3 | Me | Me | $CH_2CH_2OH$ |
| 112 | S | 1 | 3 | Me | Et | $CH_2CH_2OH$ |
| 113 | S | 1 | 3 | Me | Pr | $CH_2CH_2OH$ |
| 114 | S | 1 | 3 | Me | iPr | $CH_2CH_2OH$ |
| 115 | S | 1 | 3 | Me | H | $CH(CH_3)CH_2OH$ |
| 116 | S | 1 | 3 | Me | H | $CH(CH_2OH)CH_2OH$ |
| 117 | S | 1 | 3 | Me | H | $CH(CH_2CH_3)CH_2OH$ |
| 118 | S | 1 | 3 | Me | H | $CH(CH(CH_3)_2)CH_2OH$ |
| 119 | S | 1 | 3 | Me | H | $CH_2CH_2NH_2$ |
| 120 | S | 1 | 3 | Me | H | $CH(CH_3)CH_2NH_2$ |
| 121 | S | 1 | 3 | Me | H | $CH(CH_2CH_3)CH_2NH_2$ |
| 122 | S | 1 | 3 | Me | H | $CH(CH(CH_3)_2)CH_2NH_2$ |
| 123 | S | 1 | 3 | Me | H | $CH_2COOH$ |
| 124 | S | 1 | 3 | Me | H | $CH(CH_3)COOH$ |
| 125 | S | 1 | 3 | Me | H | $CH(CH_2OH)COOH$ |
| 126 | S | 1 | 3 | Me | H | $CH(CH_2CH_3)COOH$ |
| 127 | S | 1 | 3 | Me | H | $CH(CH(CH_3)_2)COOH$ |
| 128 | S | 1 | 3 | Me | H | $CH_2CONH_2$ |
| 129 | S | 1 | 3 | Me | H | $CH(CH3)CONH_2$ |
| 130 | S | 1 | 3 | Me | H | $CH(CH_2OH)CONH_2$ |
| 131 | S | 1 | 3 | Me | H | $CH(CH_2CH_3)CONH_2$ |
| 132 | S | 1 | 3 | Me | H | $CH(CH(CH_3)_2)CONH_2$ |
| 133 | S | 1 | 3 | Me | H | cPr |
| 134 | S | 1 | 3 | Me | H | cBu |

TABLE 2-continued

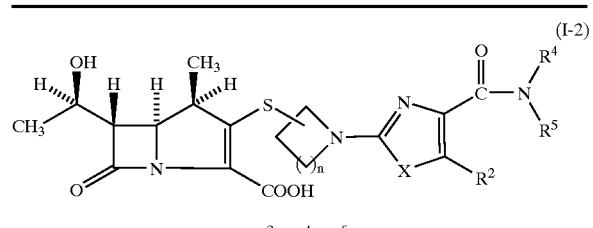

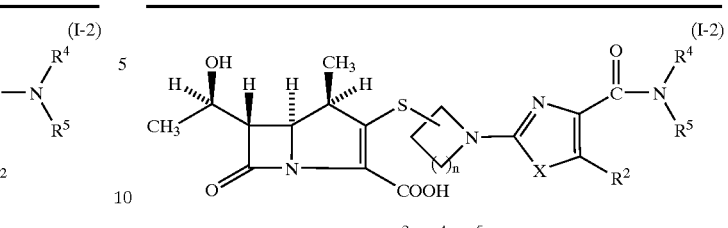

| Cpd No. | X | n | position | R² | R⁴ | R⁵ |
|---|---|---|---|---|---|---|
| 135 | S | 1 | 3 | Me | H | cPen |
| 136 | S | 1 | 3 | Me | H | cHex |
| 137 | S | 1 | 3 | Me | H | 3-Azt |
| 138 | S | 1 | 3 | Me | H | 3-Pyr |
| 139 | S | 1 | 3 | Me | H | 3-Pip |
| 140 | S | 1 | 3 | Me | H | 4-Pip |
| 141 | S | 1 | 3 | Me | H | 2-COOH—Ph |
| 142 | S | 1 | 3 | Me | H | 2-CONH₂—Ph |
| 143 | S | 1 | 3 | Me | H | 3-COOH—Ph |
| 144 | S | 1 | 3 | Me | H | 3-CONH₂—Ph |
| 145 | S | 1 | 3 | Me | H | 4-COOH—Ph |
| 146 | S | 1 | 3 | Me | H | 4-CONH₂—Ph |
| 147 | S | 1 | 3 | Me | —CH₂CH₂CH₂— | |
| 148 | S | 1 | 3 | Me | —CH₂CH₂CH₂CH₂— | |
| 149 | S | 1 | 3 | Me | —CH₂CH₂CH₂CH₂CH₂— | |
| 150 | S | 1 | 3 | Me | —CH₂CH₂OCH2CH₂— | |
| 151 | S | 1 | 3 | Me | —CH₂CH₂SCH₂CH₂— | |
| 152 | S | 1 | 3 | Me | —CH₂CH₂NHCH₂CH₂— | |
| 153 | S | 1 | 3 | Me | —CH₂CH(OH)CH₂— | |
| 154 | S | 1 | 3 | Me | —CH₂CH(OH)CH₂CH₂— | |
| 155 | S | 1 | 3 | Me | —CH₂CH(OH)CH₂CH₂CH₂— | |
| 156 | S | 1 | 3 | Me | —CH₂CH₂CH(OH)CH₂CH₂— | |
| 157 | S | 1 | 3 | Me | —CH(COOH)CH₂CH₂— | |
| 158 | S | 1 | 3 | Me | —CH(CONH₂)CH₂CH₂— | |
| 159 | S | 1 | 3 | Me | —CH(CH₂OH)CH₂CH₂— | |
| 160 | S | 1 | 3 | Me | —CH(CH₂NH₂)CH₂CH₂— | |
| 161 | S | 1 | 3 | Me | —CH(COOH)CH₂CH₂CH₂— | |
| 162 | S | 1 | 3 | Me | —CH(CONH₂)CH₂CH₂CH₂— | |
| 163 | S | 1 | 3 | Me | —CH(CH₂OH)CH₂CH₂CH₂— | |
| 164 | S | 1 | 3 | Me | —CH(CH₂NH₂)CH₂CH₂CH₂— | |
| 165 | S | 1 | 3 | Me | —CH(COOH)CH₂CH₂CH₂CH₂— | |
| 166 | S | 1 | 3 | Me | —CH(CONH₂)CH₂CH₂CH₂CH₂— | |
| 167 | S | 1 | 3 | Me | —CH(CH₂OH)CH₂CH₂CH₂CH₂— | |
| 168 | S | 1 | 3 | Me | —CH(CH₂NH₂)CH₂CH₂CH₂CH₂— | |
| 169 | S | 1 | 3 | Me | —CH₂CH(COOH)CH₂CH₂CH₂— | |
| 170 | S | 1 | 3 | Et | —CH₂CH(CONH₂)CH₂CH₂CH₂— | |
| 171 | S | 1 | 3 | Pr | —CH₂CH(CH₂OH)CH₂CH₂CH₂— | |
| 172 | S | 1 | 3 | iPr | —CH₂CH(CH₂NH₂)CH₂CH₂CH₂— | |
| 173 | S | 1 | 3 | Bu | —CH₂CH₂CH(COOH)CH₂CH₂— | |
| 174 | S | 1 | 3 | Me | —CH₂CH₂CH(CONH₂)CH₂CH₂— | |
| 175 | S | 1 | 3 | Et | —CH₂CH₂CH(CH₂OH)CH₂CH₂— | |
| 176 | S | 1 | 3 | Pr | —CH₂CH₂CH(CH₂NH₂)CH₂CH₂— | |
| 177 | S | 2 | 3 | H | H | H |
| 178 | S | 2 | 3 | H | H | Me |
| 179 | S | 2 | 3 | H | H | Et |
| 180 | S | 2 | 3 | H | H | Pr |
| 181 | S | 2 | 3 | H | H | iPr |
| 182 | S | 2 | 3 | H | H | Bu |
| 183 | S | 2 | 3 | H | Me | Me |
| 184 | S | 2 | 3 | H | Me | Et |
| 185 | S | 2 | 3 | H | Me | Pr |
| 186 | S | 2 | 3 | H | Me | iPr |
| 187 | S | 2 | 3 | H | Me | Bu |
| 188 | S | 2 | 3 | H | Et | Et |
| 189 | S | 2 | 3 | H | Et | Pr |
| 190 | S | 2 | 3 | H | Et | iPr |
| 191 | S | 2 | 3 | H | Et | Bu |
| 192 | S | 2 | 3 | H | Pr | Pr |
| 193 | S | 2 | 3 | H | Pr | iPr |
| 194 | S | 2 | 3 | H | Pr | Bu |
| 195 | S | 2 | 3 | H | iPr | iPr |
| 196 | S | 2 | 3 | H | iPr | Bu |
| 197 | S | 2 | 3 | H | Bu | Bu |
| 198 | S | 2 | 3 | H | H | CH₂CH₂OH |
| 199 | S | 2 | 3 | H | Me | CH₂CH₂OH |
| 200 | S | 2 | 3 | H | Et | CH₂CH₂OH |
| 201 | S | 2 | 3 | H | Pr | CH₂CH₂OH |
| 202 | S | 2 | 3 | H | iPr | CH₂CH₂OH |
| 203 | S | 2 | 3 | H | H | CH(CH₃)CH₂OH |
| 204 | S | 2 | 3 | H | H | CH(CH₂OH)CH₂OH |
| 205 | S | 2 | 3 | H | H | CH(CH₂CH₃)CH₂OH |
| 206 | S | 2 | 3 | H | H | CH(CH(CH₃)₂)CH₂OH |
| 207 | S | 2 | 3 | H | H | CH₂CH₂NH₂ |
| 208 | S | 2 | 3 | H | H | CH(CH₃)CH₂NH₂ |
| 209 | S | 2 | 3 | H | H | CH(CH₂CH₃)CH₂NH₂ |
| 210 | S | 2 | 3 | H | H | CH(CH(0H3)₂)CH₂NH₂ |
| 211 | S | 2 | 3 | H | H | CH₂COOH |
| 212 | S | 2 | 3 | H | H | CH(CH₃)COOH |
| 213 | S | 2 | 3 | H | H | CH(CH₂OH)COOH |
| 214 | S | 2 | 3 | H | H | CH(CH₂CH₃)COOH |
| 215 | S | 2 | 3 | H | H | CH(CH(CH₃)₂)COOH |
| 216 | S | 2 | 3 | H | H | CH₂CONH₂ |
| 217 | S | 2 | 3 | H | H | CH(CH₃)CONH₂ |
| 218 | S | 2 | 3 | H | H | CH(CH₂OH)CONH₂ |
| 219 | S | 2 | 3 | H | H | CH(CH₂CH₃)CONH₂ |
| 220 | S | 2 | 3 | H | H | CH(CH(CH₃)₂)CONH₂ |
| 221 | S | 2 | 3 | H | H | cPr |
| 222 | S | 2 | 3 | H | H | cBu |
| 223 | S | 2 | 3 | H | H | cPen |
| 224 | S | 2 | 3 | H | H | cHex |
| 225 | S | 2 | 3 | H | H | 3-Azt |
| 226 | S | 2 | 3 | H | H | 3-Pyr |
| 227 | S | 2 | 3 | H | H | 3-Pip |
| 228 | S | 2 | 3 | H | H | 4-Pip |
| 229 | S | 2 | 3 | H | H | 2-COOH—Ph |
| 230 | S | 2 | 3 | H | H | 2-CONH₂—Ph |
| 231 | S | 2 | 3 | H | H | 3-COOH—Ph |
| 232 | S | 2 | 3 | H | H | 3-CONH₂—Ph |
| 233 | S | 2 | 3 | H | H | 4-COOH—Ph |
| 234 | S | 2 | 3 | H | H | 4-CONH₂—Ph |
| 235 | S | 2 | 3 | H | —CH₂CH₂CH₂— | |
| 236 | S | 2 | 3 | H | —CH₂CH₂CH₂CH₂— | |
| 237 | S | 2 | 3 | H | —CH₂CH₂CH₂CH₂CH₂— | |
| 238 | S | 2 | 3 | H | —CH₂CH₂OCH₂CH₂— | |
| 239 | S | 2 | 3 | H | —CH₂CH₂SCH₂CH₂— | |
| 240 | S | 2 | 3 | H | —CH₂CH₂NHCH₂CH₂— | |
| 241 | S | 2 | 3 | H | —CH₂CH(OH)CH₂— | |
| 242 | S | 2 | 3 | H | —CH₂CH(OH)CH₂CH₂— | |
| 243 | S | 2 | 3 | H | —CH₂CH(OH)CH₂CH₂CH₂— | |
| 244 | S | 2 | 3 | H | —CH₂CH₂CH(OH)CH₂CH₂— | |
| 245 | S | 2 | 3 | H | —CH(COOH)CH₂CH₂— | |
| 246 | S | 2 | 3 | H | —CH(CONH₂)CH₂CH₂— | |
| 247 | S | 2 | 3 | H | —CH(CH₂OH)CH₂CH₂— | |
| 248 | S | 2 | 3 | H | —CH(CH₂NH₂)CH₂CH₂— | |
| 249 | S | 2 | 3 | H | —CH(COOH)CH₂CH₂CH₂— | |
| 250 | S | 2 | 3 | H | —CH(CONH₂)CH₂CH₂CH₂— | |
| 251 | S | 2 | 3 | H | —CH(CH₂OH)CH₂CH₂CH₂— | |
| 252 | S | 2 | 3 | H | —CH(CH₂NH₂)CH₂CH₂CH₂— | |
| 253 | S | 2 | 3 | H | —CH(COOH)CH₂CH₂CH₂CH₂— | |
| 254 | S | 2 | 3 | H | —CH(CONH₂)CH₂CH₂CH₂CH₂— | |
| 255 | S | 2 | 3 | H | —CH(CH₂OH)CH₂CH₂CH₂CH₂— | |
| 256 | S | 2 | 3 | H | —CH(CH₂NH₂)CH₂CH₂CH₂CH₂— | |
| 257 | S | 2 | 3 | H | —CH₂CH(COOH)CH₂CH₂CH₂— | |
| 258 | S | 2 | 3 | H | —CH₂CH(CONH₂)CH₂CH₂CH₂— | |
| 259 | S | 2 | 3 | H | —CH₂CH(CH₂OH)CH₂CH₂CH₂— | |
| 260 | S | 2 | 3 | H | —CH₂CH(CH₂NH₂)CH₂CH₂CH₂— | |
| 261 | S | 2 | 3 | H | —CH₂CH₂CH(COOH)CH₂CH₂— | |
| 262 | S | 2 | 3 | H | —CH₂CH₂CH(CONH₂)CH₂CH₂— | |
| 263 | S | 2 | 3 | H | —CH₂CH₂CH(CH₂OH)CH₂CH₂— | |
| 264 | S | 2 | 3 | H | —CH₂CH₂CH(CH₂NH₂)CH₂CH₂— | |
| 265 | S | 2 | 3 | Me | H | H |
| 266 | S | 2 | 3 | Me | H | Me |
| 267 | S | 2 | 3 | Me | H | Et |
| 268 | S | 2 | 3 | Me | H | Pr |

TABLE 2-continued

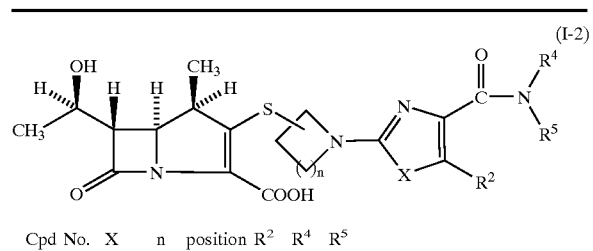

(I-2)

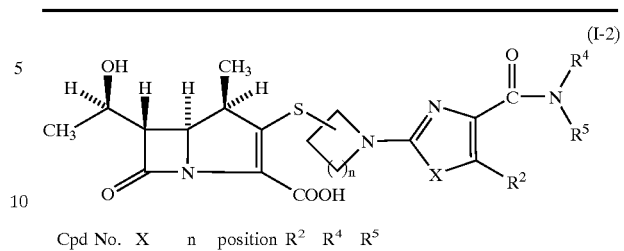

(I-2)

| Cpd No. | X | n | position | R² | R⁴ | R⁵ |
|---|---|---|---|---|---|---|
| 269 | S | 2 | 3 | Me | H | iPr |
| 270 | S | 2 | 3 | Me | H | Bu |
| 271 | S | 2 | 3 | Me | Me | Me |
| 272 | S | 2 | 3 | Me | Me | Et |
| 273 | S | 2 | 3 | Me | Me | Pr |
| 274 | S | 2 | 3 | Me | Me | iPr |
| 275 | S | 2 | 3 | Me | Me | Bu |
| 276 | S | 2 | 3 | Me | Et | Et |
| 277 | S | 2 | 3 | Me | Et | Pr |
| 278 | S | 2 | 3 | Me | Et | iPr |
| 279 | S | 2 | 3 | Me | Et | Bu |
| 280 | S | 2 | 3 | Me | Pr | Pr |
| 281 | S | 2 | 3 | Me | Pr | iPr |
| 282 | S | 2 | 3 | Me | Pr | Bu |
| 283 | S | 2 | 3 | Me | iPr | iPr |
| 284 | S | 2 | 3 | Me | iPr | Bu |
| 285 | S | 2 | 3 | Me | Bu | Bu |
| 286 | S | 2 | 3 | Me | H | CH₂CH₂OH |
| 287 | S | 2 | 3 | Me | Me | CH₂CH₂OH |
| 288 | S | 2 | 3 | Me | Et | CH₂CH₂OH |
| 289 | S | 2 | 3 | Me | Pr | CH₂CH₂OH |
| 290 | S | 2 | 3 | Me | iPr | CH₂CH₂OH |
| 291 | S | 2 | 3 | Me | H | CH(CH₃)CH₂OH |
| 292 | S | 2 | 3 | Me | H | CH(CH₂OH)CH₂OH |
| 293 | S | 2 | 3 | Me | H | CH(CH₂CH₃)CH₂OH |
| 294 | S | 2 | 3 | Me | H | CH(CH(CH₃)₂)CH₂OH |
| 295 | S | 2 | 3 | Me | H | CH₂CH₂NH₂ |
| 296 | S | 2 | 3 | Me | H | CH(CH₃)CH₂NH₂ |
| 297 | S | 2 | 3 | Me | H | CH(CH₂CH₃)CH₂NH₂ |
| 298 | S | 2 | 3 | Me | H | CH(CH(CH₃)₂)CH₂NH₂ |
| 299 | S | 2 | 3 | Me | H | CH₂COOH |
| 300 | S | 2 | 3 | Me | H | CH(CH₃)COOH |
| 301 | S | 2 | 3 | Me | H | CH(CH₂OH)COOH |
| 302 | S | 2 | 3 | Me | H | CH(CH₂CH₃)COOH |
| 303 | S | 2 | 3 | Me | H | CH(CH(CH₃)₂)COOH |
| 304 | S | 2 | 3 | Me | H | CH₂CONH₂ |
| 305 | S | 2 | 3 | Me | H | CH(CH₃)CONH₂ |
| 306 | S | 2 | 3 | Me | H | CH(CH₂OH)CONH₂ |
| 307 | S | 2 | 3 | Me | H | CH(CH₂CH₃)CONH₂ |
| 308 | S | 2 | 3 | Me | H | CH(CH(CH₃)₂)CONH₂ |
| 309 | S | 2 | 3 | Me | H | cPr |
| 310 | S | 2 | 3 | Me | H | cBu |
| 311 | S | 2 | 3 | Me | H | cPen |
| 312 | S | 2 | 3 | Me | H | cHex |
| 313 | S | 2 | 3 | Me | H | 3-Azt |
| 314 | S | 2 | 3 | Me | H | 3-Pyr |
| 315 | S | 2 | 3 | Me | H | 3-Pip |
| 316 | S | 2 | 3 | Me | H | 4-Pip |
| 317 | S | 2 | 3 | Me | H | 2-COOH—Ph |
| 318 | S | 2 | 3 | Me | H | 2-CONH₂—Ph |
| 319 | S | 2 | 3 | Me | H | 3-COOH—Ph |
| 320 | S | 2 | 3 | Me | H | 3-CONH₂—Ph |
| 321 | S | 2 | 3 | Me | H | 4-COOH—Ph |
| 322 | S | 2 | 3 | Me | H | 4-CONH₂—Ph |
| 323 | S | 2 | 3 | Me | —CH₂CH₂CH₂— | |
| 324 | S | 2 | 3 | Me | —CH₂CH₂CH₂CH₂— | |
| 325 | S | 2 | 3 | Me | —CH₂CH₂CH₂CH₂CH₂— | |
| 326 | S | 2 | 3 | Me | —CH₂CH₂OCH₂CH₂— | |
| 327 | S | 2 | 3 | Me | —CH₂CH₂SCH₂CH₂— | |
| 328 | S | 2 | 3 | Me | —CH₂CH₂NHCH₂CH₂— | |
| 329 | S | 2 | 3 | Me | —CH₂CH(OH)CH₂— | |
| 330 | S | 2 | 3 | Me | —CH₂CH(OH)CH₂CH₂— | |
| 331 | S | 2 | 3 | Me | —CH₂CH(OH)CH₂CH₂CH₂— | |
| 332 | S | 2 | 3 | Me | —CH₂CH₂CH(OH)CH₂CH₂— | |
| 333 | S | 2 | 3 | Me | —CH(COOH)CH₂CH₂— | |
| 334 | S | 2 | 3 | Me | —CH(CONH₂)CH₂CH₂— | |
| 335 | S | 2 | 3 | Me | —CH(CH₂OH)CH₂CH₂— | |
| 336 | S | 2 | 3 | Me | —CH(CH₂NH₂)CH₂CH₂— | |
| 337 | S | 2 | 3 | Me | —CH(COOH)CH₂CH₂CH₂— | |
| 338 | S | 2 | 3 | Me | —CH(CONH₂)CH₂CH₂CH₂— | |
| 339 | S | 2 | 3 | Me | —CH(CH₂OH)CH₂CH₂CH₂— | |
| 340 | S | 2 | 3 | Me | —CH(CH₂NH₂)CH₂CH₂CH₂— | |
| 341 | S | 2 | 3 | Me | —CH(COOH)CH₂CH₂CH₂CH₂— | |
| 342 | S | 2 | 3 | Me | —CH(CONH₂)CH₂CH₂CH₂CH₂— | |
| 343 | S | 2 | 3 | Me | —CH(CH₂OH)CH₂CH₂CH₂CH₂— | |
| 344 | S | 2 | 3 | Me | —CH(CH₂NH₂)CH₂CH₂CH₂CH₂— | |
| 345 | S | 2 | 3 | Me | —CH₂CH(COOH)CH₂CH₂CH₂— | |
| 346 | S | 2 | 3 | Me | —CH₂CH(CONH₂)CH₂CH₂CH₂— | |
| 347 | S | 2 | 3 | Me | —CH₂CH(CH₂OH)CH₂CH₂CH₂— | |
| 348 | S | 2 | 3 | Me | —CH₂CH(CH₂NH₂)CH₂CH₂CH₂— | |
| 349 | S | 2 | 3 | Me | —CH₂CH₂CH(COOH)CH₂CH₂— | |
| 350 | S | 2 | 3 | Me | —CH₂CH₂CH(CONH₂)CH₂CH₂— | |
| 351 | S | 2 | 3 | Me | —CH₂CH₂CH(CH₂OH)CH₂CH₂— | |
| 352 | S | 2 | 3 | Me | —CH₂CH₂CH(CH₂NH₂)CH₂CH₂— | |
| 353 | S | 3 | 4 | H | H | H |
| 354 | S | 3 | 4 | H | H | Me |
| 355 | S | 3 | 4 | H | H | Et |
| 356 | S | 3 | 4 | H | H | Pr |
| 357 | S | 3 | 4 | H | H | iPr |
| 358 | S | 3 | 4 | H | H | Bu |
| 359 | S | 3 | 4 | H | Me | Me |
| 360 | S | 3 | 4 | H | Me | Et |
| 361 | S | 3 | 4 | H | Me | Pr |
| 362 | S | 3 | 4 | H | Me | iPr |
| 363 | S | 3 | 4 | H | Me | Bu |
| 364 | S | 3 | 4 | H | Et | Et |
| 365 | S | 3 | 4 | H | Et | Pr |
| 366 | S | 3 | 4 | H | Et | iPr |
| 367 | S | 3 | 4 | H | Et | Bu |
| 368 | S | 3 | 4 | H | Pr | Pr |
| 369 | S | 3 | 4 | H | Pr | iPr |
| 370 | S | 3 | 4 | H | Pr | Bu |
| 371 | S | 3 | 4 | H | iPr | iPr |
| 372 | S | 3 | 4 | H | iPr | Bu |
| 373 | S | 3 | 4 | H | Bu | Bu |
| 374 | S | 3 | 4 | H | H | CH₂CH₂OH |
| 375 | S | 3 | 4 | H | Me | CH₂CH₂OH |
| 376 | S | 3 | 4 | H | Et | CH₂CH₂OH |
| 377 | S | 3 | 4 | H | Pr | CH₂CH₂OH |
| 378 | S | 3 | 4 | H | iPr | CH₂CH₂OH |
| 379 | S | 3 | 4 | H | H | CH(CH₃)CH₂OH |
| 380 | S | 3 | 4 | H | H | CH(CH₂OH)CH₂OH |
| 381 | S | 3 | 4 | H | H | CH(CH₂CH₃)CH₂OH |
| 382 | S | 3 | 4 | H | H | CH(CH(CH₃)₂)CH₂OH |
| 383 | S | 3 | 4 | H | H | CH₂CH₂NH₂ |
| 384 | S | 3 | 4 | H | H | CH(CH₃)CH₂NH₂ |
| 385 | S | 3 | 4 | H | H | CH(CH₂CH₃)CH₂NH₂ |
| 386 | S | 3 | 4 | H | H | CH(CH(CH₃)₂)CH₂NH₂ |
| 387 | S | 3 | 4 | H | H | CH₂COOH |
| 388 | S | 3 | 4 | H | H | CH(CH₃)COOH |
| 389 | S | 3 | 4 | H | H | CH(CH₂OH)COOH |
| 390 | S | 3 | 4 | H | H | CH(CH₂CH₃)COOH |
| 391 | S | 3 | 4 | H | H | CH(CH(CH₃)₂)COOH |
| 392 | S | 3 | 4 | H | H | CH₂CONH₂ |
| 393 | S | 3 | 4 | H | H | CH(CH₃)CONH₂ |
| 394 | S | 3 | 4 | H | H | CH(CH₂OH)CONH₂ |
| 395 | S | 3 | 4 | H | H | CH(CH₂CH₃)CONH₂ |
| 396 | S | 3 | 4 | H | H | CH(CH(CH₃)₂)CONH₂ |
| 397 | S | 3 | 4 | H | H | cPr |
| 398 | S | 3 | 4 | H | H | cBu |
| 399 | S | 3 | 4 | H | H | cPen |
| 400 | S | 3 | 4 | H | H | cHex |
| 401 | S | 3 | 4 | H | H | 3-Azt |
| 402 | S | 3 | 4 | H | H | 3-Pyr |

TABLE 2-continued

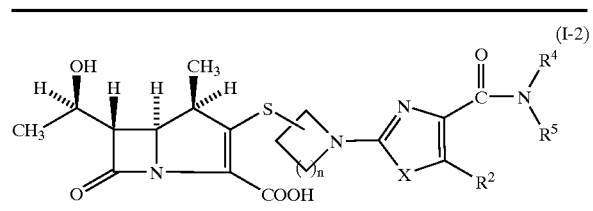
(I-2)

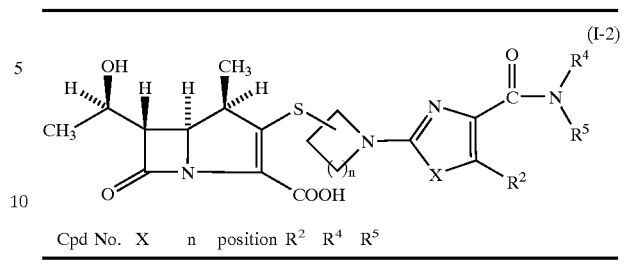
(I-2)

| Cpd No. | X | n | position | R² | R⁴ | R⁵ |
|---|---|---|---|---|---|---|
| 403 | S | 3 | 4 | H | H | 3-Pip |
| 404 | S | 3 | 4 | H | H | 4-Pip |
| 405 | S | 3 | 4 | H | H | 2-COOH—Ph |
| 406 | S | 3 | 4 | H | H | 2-CONH₂—Ph |
| 407 | S | 3 | 4 | H | H | 3-COOH—Ph |
| 408 | S | 3 | 4 | H | H | 3-CONH₂—Ph |
| 409 | S | 3 | 4 | H | H | 4-COOH—Ph |
| 410 | S | 3 | 4 | H | H | 4-CONH₂—Ph |
| 411 | S | 3 | 4 | H | —CH₂CH₂CH₂— | |
| 412 | S | 3 | 4 | H | —CH₂CH₂CH₂CH₂— | |
| 413 | S | 3 | 4 | H | —CH₂CH₂CH₂CH₂CH₂— | |
| 414 | S | 3 | 4 | H | —CH₂CH₂OCH₂CH₂— | |
| 415 | S | 3 | 4 | H | —CH₂CH₂SCH₂CH₂— | |
| 416 | S | 3 | 4 | H | —CH₂CH₂NHCH₂CH₂— | |
| 417 | S | 3 | 4 | H | —CH₂CH(OH)CH₂— | |
| 418 | S | 3 | 4 | H | —CH₂CH(OH)CH₂CH₂— | |
| 419 | S | 3 | 4 | H | —CH₂CH(OH)CH₂CH₂CH₂— | |
| 420 | S | 3 | 4 | H | —CH₂CH₂CH(OH)CH₂CH₂— | |
| 421 | S | 3 | 4 | H | —CH(COOH)CH₂CH₂— | |
| 422 | S | 3 | 4 | H | —CH(CONH₂)CH₂CH₂— | |
| 423 | S | 3 | 4 | H | —CH(CH₂OH)CH₂CH₂— | |
| 424 | S | 3 | 4 | H | —CH(CH₂NH₂)CH₂CH₂— | |
| 425 | S | 3 | 4 | H | —CH(COOH)CH₂CH₂CH₂— | |
| 426 | S | 3 | 4 | H | —CH(CONH₂)CH₂CH₂CH₂— | |
| 427 | S | 3 | 4 | H | —CH(CH₂OH)CH₂CH₂CH₂— | |
| 428 | S | 3 | 4 | H | —CH(CH₂NH₂)CH₂CH₂CH₂— | |
| 429 | S | 3 | 4 | H | —CH(COOH)CH₂CH₂CH₂CH₂— | |
| 430 | S | 3 | 4 | H | —CH(CONH₂)CH₂CH₂CH₂CH₂— | |
| 431 | S | 3 | 4 | H | —CH(CH₂OH)CH₂CH₂CH₂CH₂— | |
| 432 | S | 3 | 4 | H | —CH(CH₂NH₂)CH₂CH₂CH₂CH₂— | |
| 433 | S | 3 | 4 | H | —CH₂CH(COOH)CH₂CH₂CH₂— | |
| 434 | S | 3 | 4 | H | —CH₂CH(CONH₂)CH₂CH₂CH₂— | |
| 435 | S | 3 | 4 | H | —CH₂CH(CH₂OH)CH₂CH₂CH₂— | |
| 436 | S | 3 | 4 | H | —CH₂CH(CH₂NH₂)CH₂CH₂CH₂— | |
| 437 | S | 3 | 4 | H | —CH₂CH₂CH(COOH)CH₂CH₂— | |
| 438 | S | 3 | 4 | H | —CH₂CH₂CH(CONH₂)CH₂CH₂— | |
| 439 | S | 3 | 4 | H | —CH₂CH₂CH(CH₂OH)CH₂CH₂— | |
| 440 | S | 3 | 4 | H | —CH₂CH₂CH(CH₂NH₂)CH₂CH₂— | |
| 441 | S | 3 | 4 | Me | H | H |
| 442 | S | 3 | 4 | Me | H | Me |
| 443 | S | 3 | 4 | Me | H | Et |
| 444 | S | 3 | 4 | Me | H | Pr |
| 445 | S | 3 | 4 | Me | H | iPr |
| 446 | S | 3 | 4 | Me | H | Bu |
| 447 | S | 3 | 4 | Me | Me | Me |
| 448 | S | 3 | 4 | Me | Me | Et |
| 449 | S | 3 | 4 | Me | Me | Pr |
| 450 | S | 3 | 4 | Me | Me | iPr |
| 451 | S | 3 | 4 | Me | Me | Bu |
| 452 | S | 3 | 4 | Me | Et | Et |
| 453 | S | 3 | 4 | Me | Et | Pr |
| 454 | S | 3 | 4 | Me | Et | iPr |
| 455 | S | 3 | 4 | Me | Et | Bu |
| 456 | S | 3 | 4 | Me | Pr | Pr |
| 457 | S | 3 | 4 | Me | Pr | iPr |
| 458 | S | 3 | 4 | Me | Pr | Bu |
| 459 | S | 3 | 4 | Me | iPr | iPr |
| 460 | S | 3 | 4 | Me | iPr | Bu |
| 461 | S | 3 | 4 | Me | Bu | Bu |
| 462 | S | 3 | 4 | Me | H | CH₂CH₂OH |
| 463 | S | 3 | 4 | Me | Me | CH₂CH₂OH |
| 464 | S | 3 | 4 | Me | Et | CH₂CH₂OH |
| 465 | S | 3 | 4 | Me | Pr | CH₂CH₂OH |
| 466 | S | 3 | 4 | Me | iPr | CH₂CH₂OH |
| 467 | S | 3 | 4 | Me | H | CH(₃)CH₂OH |
| 468 | S | 3 | 4 | Me | H | CH(CH₂OH)CH₂OH |
| 469 | S | 3 | 4 | Me | H | CH(CH₂CH₃)CH₂OH |
| 470 | S | 3 | 4 | Me | H | CH(CH(CH₃)₂)CH₂OH |
| 471 | S | 3 | 4 | Me | H | CH₂CH₂NH₂ |
| 472 | S | 3 | 4 | Me | H | CH(CH₃)CH₂NH₂ |
| 473 | S | 3 | 4 | Me | H | CH(CH₂CH₃)CH₂NH₂ |
| 474 | S | 3 | 4 | Me | H | CH(CH(CH₃)₂)CH₂NH₂ |
| 475 | S | 3 | 4 | Me | H | CH₂COOH |
| 476 | S | 3 | 4 | Me | H | CH(CH₃)COOH |
| 477 | S | 3 | 4 | Me | H | CH(CH₂OH)COOH |
| 478 | S | 3 | 4 | Me | H | CH(CH₂CH₃)COOH |
| 479 | S | 3 | 4 | Me | H | CH(CH(CH₃)₂)COOH |
| 480 | S | 3 | 4 | Me | H | CH₂CONH₂ |
| 481 | S | 3 | 4 | Me | H | CH(CH₃)CONH₂ |
| 482 | S | 3 | 4 | Me | H | CH(CH₂OH)CONH₂ |
| 483 | S | 3 | 4 | Me | H | CH(CH₂CH₃)CONH₂ |
| 484 | S | 3 | 4 | Me | H | CH(CH(CH₃)₂)CONH₂ |
| 485 | S | 3 | 4 | Me | H | cPr |
| 486 | S | 3 | 4 | Me | H | cBu |
| 487 | S | 3 | 4 | Me | H | cPen |
| 488 | S | 3 | 4 | Me | H | cHex |
| 489 | S | 3 | 4 | Me | H | 3-Azt |
| 490 | S | 3 | 4 | Me | H | 3-Pyr |
| 491 | S | 3 | 4 | Me | H | 3-Pip |
| 492 | S | 3 | 4 | Me | H | 4-Pip |
| 493 | S | 3 | 4 | Me | H | 2-COOH—Ph |
| 494 | S | 3 | 4 | Me | H | 2-CONH₂—Ph |
| 495 | S | 3 | 4 | Me | H | 3-COOH—Ph |
| 496 | S | 3 | 4 | Me | H | 3-CONH₂—Ph |
| 497 | S | 3 | 4 | Me | H | 4-COOH—Ph |
| 498 | S | 3 | 4 | Me | H | 4-CONH₂—Ph |
| 499 | S | 3 | 4 | Me | —CH₂CH₂CH₂— | |
| 500 | S | 3 | 4 | Me | —CH₂CH₂CH₂CH₂— | |
| 501 | S | 3 | 4 | Me | —CH₂CH₂CH₂CH₂CH₂— | |
| 502 | S | 3 | 4 | Me | —CH₂CH₂OCH₂CH₂— | |
| 503 | S | 3 | 4 | Me | —CH₂CH₂SCH₂CH₂— | |
| 504 | S | 3 | 4 | Me | —CH₂CH₂NHCH₂CH₂— | |
| 505 | S | 3 | 4 | Me | —CH₂CH(OH)CH₂— | |
| 506 | S | 3 | 4 | Me | —CH₂CH(OH)CH₂CH₂— | |
| 507 | S | 3 | 4 | Me | —CH₂CH(OH)CH₂CH₂CH₂— | |
| 508 | S | 3 | 4 | Me | —CH₂CH₂CH(OH)CH₂CH₂— | |
| 509 | S | 3 | 4 | Me | —CH(COOH)CH₂CH₂— | |
| 510 | S | 3 | 4 | Me | —CH(CONH₂)CH₂CH₂— | |
| 511 | S | 3 | 4 | Me | —CH(CH₂OH)CH₂CH₂— | |
| 512 | S | 3 | 4 | Me | —CH(CH₂NH₂)CH₂CH₂— | |
| 513 | S | 3 | 4 | Me | —CH(COOH)CH₂CH₂CH₂— | |
| 514 | S | 3 | 4 | Me | —CH(CONH₂)CH₂CH₂CH₂— | |
| 515 | S | 3 | 4 | Me | —CH(CH₂OH)CH₂CH₂CH₂— | |
| 516 | S | 3 | 4 | Me | —CH(CH₂NH₂)CH₂CH₂CH₂— | |
| 517 | S | 3 | 4 | Me | —CH(COOH)CH₂CH₂CH₂CH₂— | |
| 518 | S | 3 | 4 | Me | —CH(CONH₂)CH₂CH₂CH₂CH₂— | |
| 519 | S | 3 | 4 | Me | —CH(CH₂OH)CH₂CH₂CH₂CH₂— | |
| 520 | S | 3 | 4 | Me | —CH(CH₂NH₂)CH₂CH₂CH₂CH₂— | |
| 521 | S | 3 | 4 | Me | —CH₂CH(COOH)CH₂CH₂CH₂— | |
| 522 | S | 3 | 4 | Me | —CH₂CH(CONH₂)CH₂CH₂CH₂— | |
| 523 | S | 2 | 3 | Me | —CH₂CH(CH₂OH)CH₂CH₂CH₂— | |
| 524 | S | 3 | 4 | Me | —CH₂CH(CH₂NH₂)CH₂CH₂CH₂— | |
| 525 | S | 3 | 4 | Me | —CH₂CH₂CH(COOH)CH₂CH₂— | |
| 526 | S | 3 | 4 | Me | —CH₂CH₂CH(CONH₂)CH₂CH₂— | |
| 527 | S | 3 | 4 | Me | —CH₂CH₂CH(CH₂OH)CH₂CH₂— | |
| 528 | S | 3 | 4 | Me | —CH₂CH₂CH(CH₂NH₂)CH₂CH₂— | |
| 529 | O | 1 | 3 | H | H | H |
| 530 | O | 1 | 3 | H | H | Me |
| 531 | O | 1 | 3 | H | H | Et |
| 532 | O | 1 | 3 | H | H | Pr |
| 533 | O | 1 | 3 | H | H | iPr |
| 534 | O | 1 | 3 | H | H | Bu |
| 535 | O | 1 | 3 | H | Me | Me |
| 536 | O | 1 | 3 | H | Me | Et |

TABLE 2-continued (I-2)

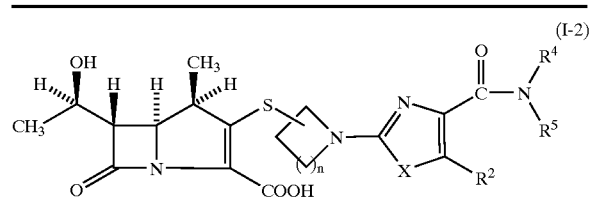

| Cpd No. | X | n | position | R² | R⁴ | R⁵ |
|---|---|---|---|---|---|---|
| 537 | O | 1 | 3 | H | Me | Pr |
| 538 | O | 1 | 3 | H | Me | iPr |
| 539 | O | 1 | 3 | H | Me | Bu |
| 540 | O | 1 | 3 | H | Et | Et |
| 541 | O | 1 | 3 | H | Et | Pr |
| 542 | O | 1 | 3 | H | Et | iPr |
| 543 | O | 1 | 3 | H | Et | Bu |
| 544 | O | 1 | 3 | H | Pr | Pr |
| 545 | O | 1 | 3 | H | Pr | iPr |
| 546 | O | 1 | 3 | H | Pr | Bu |
| 547 | O | 1 | 3 | H | iPr | iPr |
| 548 | O | 1 | 3 | H | iPr | Bu |
| 549 | O | 1 | 3 | H | Bu | Bu |
| 550 | O | 1 | 3 | H | H | CH₂CH₂OH |
| 551 | O | 1 | 3 | H | Me | CH₂CH₂OH |
| 552 | O | 1 | 3 | H | Et | CH₂CH₂OH |
| 553 | O | 1 | 3 | H | Pr | CH₂CH₂OH |
| 554 | O | 1 | 3 | H | iPr | CH₂CH₂OH |
| 555 | O | 1 | 3 | H | H | CH(CH₃)CH₂OH |
| 556 | O | 1 | 3 | H | H | CH(CH₂OH)CH₂OH |
| 557 | O | 1 | 3 | H | H | CH(CH₂CH₃)CH₂OH |
| 558 | O | 1 | 3 | H | H | CH(CH(CH₃)₂)CH₂OH |
| 559 | O | 1 | 3 | H | H | CH₂CH₂NH₂ |
| 560 | O | 1 | 3 | H | H | CH(CH₃)CH₂NH₂ |
| 561 | O | 1 | 3 | H | H | CH(CH₂CH₃)CH₂NH₂ |
| 562 | O | 1 | 3 | H | H | CH(CH(CH₃)₂)CH₂NH₂ |
| 563 | O | 1 | 3 | H | H | CH₂COOH |
| 564 | O | 1 | 3 | H | H | CH(CH₃)COOH |
| 565 | O | 1 | 3 | H | H | CH(CH₂OH)COOH |
| 566 | O | 1 | 3 | H | H | CH(CH₂CH₃)COOH |
| 567 | O | 1 | 3 | H | H | CH(CH(CH₃)₂)COOH |
| 568 | O | 1 | 3 | H | H | CH₂CONH₂ |
| 569 | O | 1 | 3 | H | H | CH(CH₃)CONH₂ |
| 570 | O | 1 | 3 | H | H | CH(CH₂OH)CONH₂ |
| 571 | O | 1 | 3 | H | H | CH(CH₂CH₃)CONH₂ |
| 572 | O | 1 | 3 | H | H | CH(CH(CH₃)₂)CONH₂ |
| 573 | O | 1 | 3 | H | H | cPr |
| 574 | O | 1 | 3 | H | H | cBu |
| 575 | O | 1 | 3 | H | H | cPen |
| 576 | O | 1 | 3 | H | H | cHex |
| 577 | O | 1 | 3 | H | H | 3-Azt |
| 578 | O | 1 | 3 | H | H | 3-Pyr |
| 579 | O | 1 | 3 | H | H | 3-Pip |
| 580 | O | 1 | 3 | H | H | 4-Pip |
| 581 | O | 1 | 3 | H | H | 2-COOH—Ph |
| 582 | O | 1 | 3 | H | H | 2-CONH₂—Ph |
| 583 | O | 1 | 3 | H | H | 3-COOH—Ph |
| 584 | O | 1 | 3 | H | H | 3-CONH₂—Ph |
| 585 | O | 1 | 3 | H | H | 4-COOH—Ph |
| 586 | O | 1 | 3 | H | H | 4-CONH₂—Ph |
| 587 | O | 1 | 3 | H | —CH₂CH₂CH₂— | |
| 588 | O | 1 | 3 | H | —CH₂CH₂CH₂CH₂— | |
| 589 | O | 1 | 3 | H | —CH₂CH₂CH₂CH₂CH₂— | |
| 590 | O | 1 | 3 | H | —CH₂CH₂OCH₂CH₂— | |
| 591 | O | 1 | 3 | H | —CH₂CH₂SCH₂CH₂— | |
| 592 | O | 1 | 3 | H | —CH₂CH₂NHCH₂CH₂— | |
| 593 | O | 1 | 3 | H | —CH₂CH(OH)CH₂— | |
| 594 | O | 1 | 3 | H | —CH₂CH(OH)CH₂CH₂— | |
| 595 | O | 1 | 3 | H | —CH₂CH(OH)CH₂CH₂CH₂— | |
| 596 | O | 1 | 3 | H | —CH₂CH₂CH(OH)CH₂CH₂— | |
| 597 | O | 1 | 3 | H | —CH(COOH)CH₂CH₂— | |
| 598 | O | 1 | 3 | H | —CH(CONH₂)CH₂CH₂— | |
| 599 | O | 1 | 3 | H | —CH(CH₂OH)CH₂CH₂— | |
| 600 | O | 1 | 3 | H | —CH(CH₂NH₂)CH₂CH₂— | |
| 601 | O | 1 | 3 | H | —CH(COOH)CH₂CH₂CH₂— | |
| 602 | O | 1 | 3 | H | —CH(CONH₂)CH₂CH₂CH₂— | |
| 603 | O | 1 | 3 | H | —CH(CH₂OH)CH₂CH₂CH₂— | |

TABLE 2-continued (I-2)

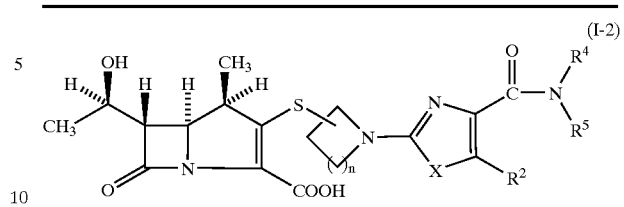

| Cpd No. | X | n | position | R² | R⁴ | R⁵ |
|---|---|---|---|---|---|---|
| 604 | O | 1 | 3 | H | —CH(CH₂NH₂)CH₂CH₂CH₂— | |
| 605 | O | 1 | 3 | H | —CH(COOH)CH₂CH₂CH₂CH₂— | |
| 606 | O | 1 | 3 | H | —CH(CONH₂)CH₂CH₂CH₂CH₂— | |
| 607 | O | 1 | 3 | H | —CH(CH₂OH)CH₂CH₂CH₂CH₂— | |
| 608 | O | 1 | 3 | H | —CH(CH₂NH₂)CH₂CH₂CH₂CH₂— | |
| 609 | O | 1 | 3 | H | —CH₂CH(COOH)CH₂CH₂CH₂— | |
| 610 | O | 1 | 3 | H | —CH₂CH(CONH₂)CH₂CH₂CH₂— | |
| 611 | O | 1 | 3 | H | —CH₂CH(CH₂OH)CH₂CH₂CH₂— | |
| 612 | O | 1 | 3 | H | —CH₂CH(CH₂NH₂)CH₂CH₂CH₂— | |
| 613 | O | 1 | 3 | H | —CH₂CH₂CH(COOH)CH₂CH₂— | |
| 614 | O | 1 | 3 | H | —CH₂CH₂CH(CONH₂)CH₂CH₂— | |
| 615 | O | 1 | 3 | H | —CH₂CH₂CH(CH₂OH)CH₂CH₂— | |
| 616 | O | 1 | 3 | H | —CH₂CH₂CH(CH₂NH₂)CH₂CH₂— | |
| 617 | O | 1 | 3 | Me | H | H |
| 618 | O | 1 | 3 | Me | H | Me |
| 619 | O | 1 | 3 | Me | H | Et |
| 620 | O | 1 | 3 | Me | H | Pr |
| 621 | O | 1 | 3 | Me | H | iPr |
| 622 | O | 1 | 3 | Me | H | Bu |
| 623 | O | 1 | 3 | Me | Me | Me |
| 624 | O | 1 | 3 | Me | Me | Et |
| 625 | O | 1 | 3 | Me | Me | Pr |
| 626 | O | 1 | 3 | Me | Me | iPr |
| 627 | O | 1 | 3 | Me | Me | Bu |
| 628 | O | 1 | 3 | Me | Et | Et |
| 629 | O | 1 | 3 | Me | Et | Pr |
| 630 | O | 1 | 3 | Me | Et | iPr |
| 631 | O | 1 | 3 | Me | Et | Bu |
| 632 | O | 1 | 3 | Me | Pr | Pr |
| 633 | O | 1 | 3 | Me | Pr | iPr |
| 634 | O | 1 | 3 | Me | Pr | Bu |
| 635 | O | 1 | 3 | Me | iPr | iPr |
| 636 | O | 1 | 3 | Me | iPr | Bu |
| 637 | O | 1 | 3 | Me | Bu | Bu |
| 638 | O | 1 | 3 | Me | H | CH₂CH₂OH |
| 639 | O | 1 | 3 | Me | Me | CH₂CH₂OH |
| 640 | O | 1 | 3 | Me | Et | CH₂CH₂OH |
| 641 | O | 1 | 3 | Me | Pr | CH₂CH₂OH |
| 642 | O | 1 | 3 | Me | iPr | CH₂CH₂OH |
| 643 | O | 1 | 3 | Me | H | CH(CH₃)CH₂OH |
| 644 | O | 1 | 3 | Me | H | CH(CH₂OH)CH₂OH |
| 645 | O | 1 | 3 | Me | H | CH(CH₂CH₃)CH₂OH |
| 646 | O | 1 | 3 | Me | H | CH(CH(CH₃)₂)CH₂OH |
| 647 | O | 1 | 3 | Me | H | CH₂CH₂NH₂ |
| 648 | O | 1 | 3 | Me | H | CH(CH₃)CH₂NH₂ |
| 649 | O | 1 | 3 | Me | H | CH(CH₂CH₃)CH₂NH₂ |
| 650 | O | 1 | 3 | Me | H | CH(CH(CH₃)₂)CH₂NH₂ |
| 651 | O | 1 | 3 | Me | H | CH₂COOH |
| 652 | O | 1 | 3 | Me | H | CH(CH₃)COOH |
| 653 | O | 1 | 3 | Me | H | CH(CH₂OH)COOH |
| 654 | O | 1 | 3 | Me | H | CH(CH₂CH₃)COOH |
| 655 | O | 1 | 3 | Me | H | CH(CH(CH₃)₂)COOH |
| 656 | O | 1 | 3 | Me | H | CH₂CONH₂ |
| 657 | O | 1 | 3 | Me | H | CH(CH₃)CONH₂ |
| 658 | O | 1 | 3 | Me | H | CH(CH₂OH)CONH₂ |
| 659 | O | 1 | 3 | Me | H | CH(CH₂CH₃)CONH₂ |
| 660 | O | 1 | 3 | Me | H | CH(CH(CH₃)₂)CONH₂ |
| 661 | O | 1 | 3 | Me | H | cPr |
| 662 | O | 1 | 3 | Me | H | cBu |
| 663 | O | 1 | 3 | Me | H | cPen |
| 664 | O | 1 | 3 | Me | H | cHex |
| 665 | O | 1 | 3 | Me | H | 3-Azt |
| 666 | O | 1 | 3 | Me | H | 3-Pyr |
| 667 | O | 1 | 3 | Me | H | 3-Pip |
| 668 | O | 1 | 3 | Me | H | 4-Pip |
| 669 | O | 1 | 3 | Me | H | 2-COOH—Ph |
| 670 | O | 1 | 3 | Me | H | 2-CONH₂—Ph |

TABLE 2-continued (I-2)

| Cpd No. | X | n | position | R² | R⁴ | R⁵ |
|---|---|---|---|---|---|---|
| 671 | O | 1 | 3 | Me | H | 3-COOH—Ph |
| 672 | O | 1 | 3 | Me | H | 3-CONH₂—Ph |
| 673 | O | 1 | 3 | Me | H | 4-COOH—Ph |
| 674 | O | 1 | 3 | Me | H | 4-CONH₂—Ph |
| 675 | O | 1 | 3 | Me | —CH₂CH₂CH₂— | |
| 676 | O | 1 | 3 | Me | —CH₂CH₂CH₂CH₂— | |
| 677 | O | 1 | 3 | Me | —CH₂CH₂CH₂CH₂CH₂— | |
| 678 | O | 1 | 3 | Me | —CH₂CH₂OCH₂CH₂— | |
| 679 | O | 1 | 3 | Me | —CH₂CH₂SCH₂CH₂— | |
| 680 | O | 1 | 3 | Me | —CH₂CH₂NHCH₂CH₂— | |
| 681 | O | 1 | 3 | Me | —CH₂CH(OH)0H2— | |
| 682 | O | 1 | 3 | Me | —CH₂CH(OH)CH₂CH₂— | |
| 683 | O | 1 | 3 | Me | —CH₂CH(OH)CH₂CH₂CH₂— | |
| 684 | O | 1 | 3 | Me | —CH₂CH₂CH(OH)CH₂CH₂— | |
| 685 | O | 1 | 3 | Me | —CH(COOH)0H20H2— | |
| 686 | O | 1 | 3 | Me | —CH(CONH₂)CH₂CH₂— | |
| 687 | O | 1 | 3 | Me | —CH(CH₂OH)CH₂CH₂— | |
| 688 | O | 1 | 3 | Me | —CH(CH₂NH₂)CH₂CH₂— | |
| 689 | O | 1 | 3 | Me | —CH(COOH)CH₂CH₂CH₂— | |
| 690 | O | 1 | 3 | Me | —CH(CONH₂)CH₂CH₂CH₂— | |
| 691 | O | 1 | 3 | Me | —CH(CH₂OH)CH₂CH₂CH₂— | |
| 692 | O | 1 | 3 | Me | —CH(CH₂NH₂)CH₂CH₂CH₂— | |
| 693 | O | 1 | 3 | Me | —CH(COOH)CH₂CH₂CH₂CH₂— | |
| 694 | O | 1 | 3 | Me | —CH(CONH₂)CH₂CH₂CH₂CH₂— | |
| 695 | O | 1 | 3 | Me | —CH(CH₂OH)CH₂CH₂CH₂CH₂— | |
| 696 | O | 1 | 3 | Me | —CH(CH₂NH₂)CH₂CH₂CH₂CH₂— | |
| 697 | O | 1 | 3 | Me | —CH₂CH(COOH)CH₂CH₂CH₂— | |
| 698 | O | 1 | 3 | Me | —CH₂CH(CONH₂)CH₂CH₂CH₂— | |
| 699 | O | 1 | 3 | Me | —CH₂CH(CH₂OH)CH₂CH₂CH₂— | |
| 700 | O | 1 | 3 | Me | —CH₂CH(CH₂NH₂)CH₂CH₂CH₂— | |
| 701 | O | 1 | 3 | Me | —CH₂CH₂CH(COOH)CH₂CH₂— | |
| 702 | O | 1 | 3 | Me | —CH₂CH₂CH(CONH₂)CH₂CH₂— | |
| 703 | O | 1 | 3 | Me | —CH₂CH₂CH(CH₂OH)CH₂CH₂— | |
| 704 | O | 1 | 3 | Me | —CH₂CH₂CH(CH₂NH₂)CH₂CH₂— | |
| 705 | O | 2 | 3 | H | H | H |
| 706 | O | 2 | 3 | H | H | Me |
| 707 | O | 2 | 3 | H | H | Et |
| 708 | O | 2 | 3 | H | H | Pr |
| 709 | O | 2 | 3 | H | H | iPr |
| 710 | O | 2 | 3 | H | H | Bu |
| 711 | O | 2 | 3 | H | Me | Me |
| 712 | O | 2 | 3 | H | Me | Et |
| 713 | O | 2 | 3 | H | Me | Pr |
| 714 | O | 2 | 3 | H | Me | iPr |
| 715 | O | 2 | 3 | H | Me | Bu |
| 716 | O | 2 | 3 | H | Et | Et |
| 717 | O | 2 | 3 | H | Et | Pr |
| 718 | O | 2 | 3 | H | Et | iPr |
| 719 | O | 2 | 3 | H | Et | Bu |
| 720 | O | 2 | 3 | H | Pr | Pr |
| 721 | O | 2 | 3 | H | Pr | iPr |
| 722 | O | 2 | 3 | H | Pr | Bu |
| 723 | O | 2 | 3 | H | iPr | iPr |
| 724 | O | 2 | 3 | H | iPr | Bu |
| 725 | O | 2 | 3 | H | Bu | Bu |
| 726 | O | 2 | 3 | H | H | CH₂CH₂OH |
| 727 | O | 2 | 3 | H | Me | CH₂CH₂OH |
| 728 | O | 2 | 3 | H | Et | CH₂CH₂OH |
| 729 | O | 2 | 3 | H | Pr | |
| 730 | O | 2 | 3 | H | iPr | |
| 731 | O | 2 | 3 | H | H | CH(CH₃)CH₂OH |
| 732 | O | 2 | 3 | H | H | CH(CH₂OH)CH₂OH |
| 733 | O | 2 | 3 | H | H | CH(CH₂CH₃)CH₂OH |
| 734 | O | 2 | 3 | H | H | CH(CH(CH₃)₂)CH₂OH |
| 735 | O | 2 | 3 | H | H | CH₂CH₂NH₂ |
| 736 | O | 2 | 3 | H | H | CH(CH₃)CH₂NH₂ |
| 737 | O | 2 | 3 | H | H | CH(CH₂CH₃)CH₂NH₂ |
| 738 | O | 2 | 3 | H | H | CH(CH(CH₃)₂)CH₂NH₂ |
| 739 | O | 2 | 3 | H | H | CH₂COOH |
| 740 | O | 2 | 3 | H | H | CH(CH₃)COOH |
| 741 | O | 2 | 3 | H | H | CH(CH₂OH)COOH |
| 742 | O | 2 | 3 | H | H | CH(CH₂CH₃)COOH |
| 743 | O | 2 | 3 | H | H | CH(CH(CH₃)₂)COOH |
| 744 | O | 2 | 3 | H | H | CH₂CONH₂ |
| 745 | O | 2 | 3 | H | H | CH(CH₃)CONH₂ |
| 746 | O | 2 | 3 | H | H | CH(CH₂OH)CONH₂ |
| 747 | O | 2 | 3 | H | H | CH(CH₂CH₃)CONH₂ |
| 748 | O | 2 | 3 | H | H | CH(CH(CH₃)₂)CONH₂ |
| 749 | O | 2 | 3 | H | H | cPr |
| 750 | O | 2 | 3 | H | H | cBu |
| 751 | O | 2 | 3 | H | H | cPen |
| 752 | O | 2 | 3 | H | H | cHex |
| 753 | O | 2 | 3 | H | H | 3-Azt |
| 754 | O | 2 | 3 | H | H | 3-Pyr |
| 755 | O | 2 | 3 | H | H | 3-Pip |
| 756 | O | 2 | 3 | H | H | 4-Pip |
| 757 | O | 2 | 3 | H | H | 2-COOH—Ph |
| 758 | O | 2 | 3 | H | H | 2-CONH₂—Ph |
| 759 | O | 2 | 3 | H | H | 3-COOH—Ph |
| 760 | O | 2 | 3 | H | H | 3-CONH₂—Ph |
| 761 | O | 2 | 3 | H | H | 4-COOH—Ph |
| 762 | O | 2 | 3 | H | H | 4-CONH₂—Ph |
| 763 | O | 2 | 3 | H | —CH₂CH₂CH₂— | |
| 764 | O | 2 | 3 | H | —CH₂CH₂CH₂CH₂— | |
| 765 | O | 2 | 3 | H | —CH₂CH₂CH₂CH₂CH₂— | |
| 766 | O | 2 | 3 | H | —CH₂CH₂00H2CH₂— | |
| 767 | O | 2 | 3 | H | —CH₂CH₂SCH₂CH₂— | |
| 768 | O | 2 | 3 | H | —CH₂CH₂NHCH₂CH₂— | |
| 769 | O | 2 | 3 | H | —CH₂CH(OH)CH₂— | |
| 770 | O | 2 | 3 | H | —CH₂CH(OH)CH₂CH₂— | |
| 771 | O | 2 | 3 | H | —CH₂CH(OH)CH₂CH₂CH₂— | |
| 772 | O | 2 | 3 | H | —CH₂CH₂CH(OH)CH₂CH₂— | |
| 773 | O | 2 | 3 | H | —CH(COOH)CH₂CH₂— | |
| 774 | O | 2 | 3 | H | —CH(CONH₂)CH₂CH₂— | |
| 775 | O | 2 | 3 | H | —CH(CH₂OH)CH₂CH₂— | |
| 776 | O | 2 | 3 | H | —CH(CH₂NH₂)CH₂CH₂— | |
| 777 | O | 2 | 3 | H | —CH(COOH)CH₂CH₂CH₂— | |
| 778 | O | 2 | 3 | H | —CH(CONH₂)CH₂CH₂CH₂— | |
| 779 | O | 2 | 3 | H | —CH(CH₂OH)CH₂CH₂CH₂— | |
| 780 | O | 2 | 3 | H | —CH(CH₂NH₂)CH₂CH₂CH₂— | |
| 781 | O | 2 | 3 | H | —CH(COOH)CH₂CH₂CH₂CH₂— | |
| 782 | O | 2 | 3 | H | —CH(CONH₂)CH₂CH₂CH₂CH₂— | |
| 783 | O | 2 | 3 | H | —CH(CH₂OH)CH₂CH₂CH₂CH₂— | |
| 784 | O | 2 | 3 | H | —CH(CH₂NH₂)CH₂CH₂CH₂CH₂— | |
| 785 | O | 2 | 3 | H | —CH₂CH(COOH)CH₂CH₂CH₂— | |
| 786 | O | 2 | 3 | H | —CH₂CH(CONH₂)CH₂CH₂CH₂— | |
| 787 | O | 2 | 3 | H | —CH₂CH(CH₂OH)CH₂CH₂CH₂— | |
| 788 | O | 2 | 3 | H | —CH₂CH(CH₂NH₂)CH₂CH₂CH₂— | |
| 789 | O | 2 | 3 | H | —CH₂CH₂CH(COOH)CH₂CH₂— | |
| 790 | O | 2 | 3 | H | —CH₂CH₂CH(CONH₂)CH₂CH₂— | |
| 791 | O | 2 | 3 | H | —CH₂CH₂CH(CH₂OH)CH₂CH₂— | |
| 792 | O | 2 | 3 | H | —CH₂CH₂CH(CH₂NH₂)CH₂CH₂— | |
| 793 | O | 2 | 3 | Me | H | H |
| 794 | O | 2 | 3 | Me | H | Me |
| 795 | O | 2 | 3 | Me | H | Et |
| 796 | O | 2 | 3 | Me | H | Pr |
| 797 | O | 2 | 3 | Me | H | iPr |
| 798 | O | 2 | 3 | Me | H | Bu |
| 799 | O | 2 | 3 | Me | Me | Me |
| 800 | O | 2 | 3 | Me | Me | Et |
| 801 | O | 2 | 3 | Me | Me | Pr |
| 802 | O | 2 | 3 | Me | Me | iPr |
| 803 | O | 2 | 3 | Me | Me | Bu |
| 804 | O | 2 | 3 | Me | Et | Et |

TABLE 2-continued

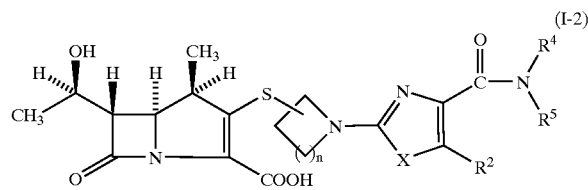

(I-2)

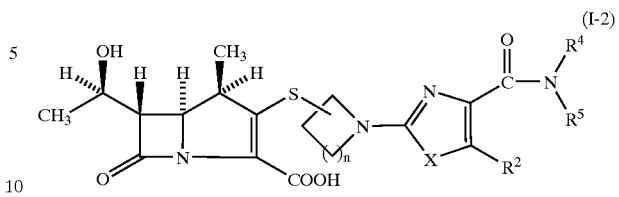

(I-2)

| Cpd No. | X | n | position | R² | R⁴ | R⁵ |
|---|---|---|---|---|---|---|
| 805 | O | 2 | 3 | Me | Et | Pr |
| 806 | O | 2 | 3 | Me | Et | iPr |
| 807 | O | 2 | 3 | Me | Et | Bu |
| 808 | O | 2 | 3 | Me | Pr | Pr |
| 809 | O | 2 | 3 | Me | Pr | iPr |
| 810 | O | 2 | 3 | Me | Pr | Bu |
| 811 | O | 2 | 3 | Me | iPr | iPr |
| 812 | O | 2 | 3 | Me | iPr | Bu |
| 813 | O | 2 | 3 | Me | Bu | Bu |
| 814 | O | 2 | 3 | Me | H | CH₂CH₂OH |
| 815 | O | 2 | 3 | Me | Me | CH₂CH₂OH |
| 816 | O | 2 | 3 | Me | Et | CH₂CH₂OH |
| 817 | O | 2 | 3 | Me | Pr | CH₂CH₂OH |
| 818 | O | 2 | 3 | Me | iPr | CH₂CH₂OH |
| 819 | O | 2 | 3 | Me | H | CH(CH₃)CH₂OH |
| 820 | O | 2 | 3 | Me | H | CH(CH₂OH)CH₂OH |
| 821 | O | 2 | 3 | Me | H | CH(CH₂CH₃)CH₂OH |
| 822 | O | 2 | 3 | Me | H | CH(CH(CH₃)₂)CH₂OH |
| 823 | O | 2 | 3 | Me | H | CH₂CH₂NH₂ |
| 824 | O | 2 | 3 | Me | H | CH(CH₃)CH₂NH₂ |
| 825 | O | 2 | 3 | Me | H | CH(CH₂CH₃)CH₂NH₂ |
| 826 | O | 2 | 3 | Me | H | CH(CH(CH₃)₂)CH₂NH₂ |
| 827 | O | 2 | 3 | Me | H | CH₂COOH |
| 828 | O | 2 | 3 | Me | H | CH(CH₃)COOH |
| 829 | O | 2 | 3 | Me | H | CH(CH₂OH)COOH |
| 830 | O | 2 | 3 | Me | H | CH(CH₂CH₃)COOH |
| 831 | O | 2 | 3 | Me | H | CH(CH(CH₃)₂)COOH |
| 832 | O | 2 | 3 | Me | H | CH₂CONH₂ |
| 833 | O | 2 | 3 | Me | H | CH(CH₃)CONH₂ |
| 834 | O | 2 | 3 | Me | H | CH(CH₂OH)CONH₂ |
| 835 | O | 2 | 3 | Me | H | CH(CH₂CH₃)CONH₂ |
| 836 | O | 2 | 3 | Me | H | CH(CH(CH₃)₂)CONH₂ |
| 837 | O | 2 | 3 | Me | H | cPr |
| 838 | O | 2 | 3 | Me | H | cBu |
| 839 | O | 2 | 3 | Me | H | cPen |
| 840 | O | 2 | 3 | Me | H | cHex |
| 841 | O | 2 | 3 | Me | H | 3-Azt |
| 842 | O | 2 | 3 | Me | H | 3-Pyr |
| 843 | O | 2 | 3 | Me | H | 3-Pip |
| 844 | O | 2 | 3 | Me | H | 4-Pip |
| 845 | O | 2 | 3 | Me | H | 2-COOH—Ph |
| 846 | O | 2 | 3 | Me | H | 2-CONH₂—Ph |
| 847 | O | 2 | 3 | Me | H | 3-COOH—Ph |
| 848 | O | 2 | 3 | Me | H | 3-CONH₂—Ph |
| 849 | O | 2 | 3 | Me | H | 4-COOH—Ph |
| 850 | O | 2 | 3 | Me | H | 4-CONH₂—Ph |
| 851 | O | 2 | 3 | Me | —CH₂CH₂CH₂— | |
| 852 | O | 2 | 3 | Me | —CH₂CH₂CH₂CH₂— | |
| 853 | O | 2 | 3 | Me | —CH₂CH₂CH₂CH₂CH₂— | |
| 854 | O | 2 | 3 | Me | —CH₂OCH₂CH₂— | |
| 855 | O | 2 | 3 | Me | —CH₂CH₂SCH₂CH₂— | |
| 856 | O | 2 | 3 | Me | —CH₂CH₂NHCH₂CH₂— | |
| 857 | O | 2 | 3 | Me | —CH₂CH(OH)CH₂— | |
| 858 | O | 2 | 3 | Me | —CH₂CH(OH)CH₂CH₂— | |
| 859 | O | 2 | 3 | Me | —CH₂CH(OH)CH₂CH₂CH₂— | |
| 860 | O | 2 | 3 | Me | —CH₂CH₂CH(OH)CH₂CH₂— | |
| 861 | O | 2 | 3 | Me | —CH(COOH)CH₂CH₂— | |
| 862 | O | 2 | 3 | Me | —CH(CONH₂)CH₂CH₂— | |
| 863 | O | 2 | 3 | Me | —CH(CH₂OH)CH₂CH₂— | |
| 864 | O | 2 | 3 | Me | —CH(CH₂NH₂)CH₂CH₂— | |
| 865 | O | 2 | 3 | Me | —CH(COOH)CH₂CH₂CH₂— | |
| 866 | O | 2 | 3 | Me | —CH(CONH₂)CH₂CH₂CH₂— | |
| 867 | O | 2 | 3 | Me | —CH(CH₂OH)CH₂CH₂CH₂— | |
| 868 | O | 2 | 3 | Me | —CH(CH₂NH₂)CH₂CH₂CH₂— | |
| 869 | O | 2 | 3 | Me | —CH(COOH)CH₂CH₂CH₂CH₂— | |
| 870 | O | 2 | 3 | Me | —CH(CONH₂)CH₂CH₂CH₂CH₂— | |
| 871 | O | 2 | 3 | Me | —CH(CH₂OH)CH₂CH₂CH₂CH₂— | |
| 872 | O | 2 | 3 | Me | —CH(CH₂NH₂)CH₂CH₂CH₂CH₂— | |
| 873 | O | 2 | 3 | Me | —CH₂CH(COOH)CH₂CH₂CH₂— | |
| 874 | O | 2 | 3 | Me | —CH₂CH(CONH₂)CH₂CH₂CH₂— | |
| 875 | O | 2 | 3 | Me | —CH₂CH(CH₂OH)CH₂CH₂CH₂— | |
| 876 | O | 2 | 3 | Me | —CH₂CH(CH₂NH₂)CH₂CH₂CH₂— | |
| 877 | O | 2 | 3 | Me | —CH₂CH₂CH(COOH)CH₂CH₂— | |
| 878 | O | 2 | 3 | Me | —CH₂CH₂CH(CONH₂)CH₂CH₂— | |
| 879 | O | 2 | 3 | Me | —CH₂CH₂CH(CH₂OH)CH₂CH₂— | |
| 880 | O | 2 | 3 | Me | —CH₂CH₂CH(CH₂NH₂)CH₂CH₂— | |
| 881 | O | 3 | 4 | H | H | H |
| 882 | O | 3 | 4 | H | H | Me |
| 883 | O | 3 | 4 | H | H | Et |
| 884 | O | 3 | 4 | H | H | Pr |
| 885 | O | 3 | 4 | H | H | iPr |
| 886 | O | 3 | 4 | H | H | Bu |
| 887 | O | 3 | 4 | H | Me | Me |
| 888 | O | 3 | 4 | H | Me | Et |
| 889 | O | 3 | 4 | H | Me | Pr |
| 890 | O | 3 | 4 | H | Me | iPr |
| 891 | O | 3 | 4 | H | Me | Bu |
| 892 | O | 3 | 4 | H | Et | Et |
| 893 | O | 3 | 4 | H | Et | Pr |
| 894 | O | 3 | 4 | H | Et | iPr |
| 895 | O | 3 | 4 | H | Et | Bu |
| 896 | O | 3 | 4 | H | Pr | Pr |
| 897 | O | 3 | 4 | H | Pr | iPr |
| 898 | O | 3 | 4 | H | Pr | Bu |
| 899 | O | 3 | 4 | H | iPr | iPr |
| 900 | O | 3 | 4 | H | iPr | Bu |
| 901 | O | 3 | 4 | H | Bu | Bu |
| 902 | O | 3 | 4 | H | H | CH₂CH₂OH |
| 903 | O | 3 | 4 | H | Me | CH₂CH₂OH |
| 904 | O | 3 | 4 | H | Et | CH₂CH₂OH |
| 905 | O | 3 | 4 | H | Pr | CH₂CH₂OH |
| 906 | O | 3 | 4 | H | iPr | CH₂CH₂OH |
| 907 | O | 3 | 4 | H | H | CH(CH₃)CH₂OH |
| 908 | O | 3 | 4 | H | H | CH(CH₂OH)CH₂OH |
| 909 | O | 3 | 4 | H | H | CH(CH₂CH₃)CH₂OH |
| 910 | O | 3 | 4 | H | H | CH(CH(CH₃)₂)CH₂OH |
| 911 | O | 3 | 4 | H | H | CH₂CH₂NH₂ |
| 912 | O | 3 | 4 | H | H | CH(CH₃)CH₂NH₂ |
| 913 | O | 3 | 4 | H | H | CH(CH₂CH₃)CH₂NH₂ |
| 914 | O | 3 | 4 | H | H | CH(CH(CH₃)₂)CH₂NH₂ |
| 915 | O | 3 | 4 | H | H | CH₂COOH |
| 916 | O | 3 | 4 | H | H | CH(CH₃)COOH |
| 917 | O | 3 | 4 | H | H | CH(CH₂OH)COOH |
| 918 | O | 3 | 4 | H | H | CH(CH₂CH₃)COOH |
| 919 | O | 3 | 4 | H | H | CH(CH(CH₃)₂)COOH |
| 920 | O | 3 | 4 | H | H | CH₂CONH₂ |
| 921 | O | 3 | 4 | H | H | CH(CH₃)CONH₂ |
| 922 | O | 3 | 4 | H | H | CH(CH₂OH)CONH₂ |
| 923 | O | 3 | 4 | H | H | CH(CH₂CH₃)CONH₂ |
| 924 | O | 3 | 4 | H | H | CH(CH(CH₃)₂)CONH₂ |
| 925 | O | 3 | 4 | H | H | cPr |
| 926 | O | 3 | 4 | H | H | cBu |
| 927 | O | 3 | 4 | H | H | cPen |
| 928 | O | 3 | 4 | H | H | cHex |
| 929 | O | 3 | 4 | H | H | 3-Azt |
| 930 | O | 3 | 4 | H | H | 3-Pyr |
| 931 | O | 3 | 4 | H | H | 3-Pip |
| 932 | O | 3 | 4 | H | H | 4-Pip |
| 933 | O | 3 | 4 | H | H | 2-COOH—Ph |
| 934 | O | 3 | 4 | H | H | 2-CONH₂—Ph |
| 935 | O | 3 | 4 | H | H | 3-COOH—Ph |
| 936 | O | 3 | 4 | H | H | 3-CONH₂—Ph |
| 937 | O | 3 | 4 | H | H | 4-COOH—Ph |
| 938 | O | 3 | 4 | H | H | 4-CONH₂—Ph |

TABLE 2-continued

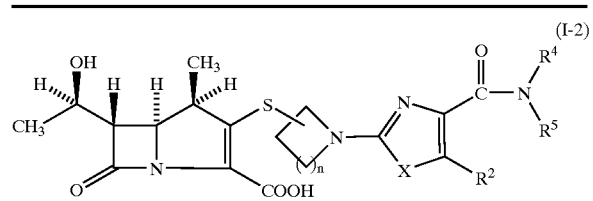

(I-2)

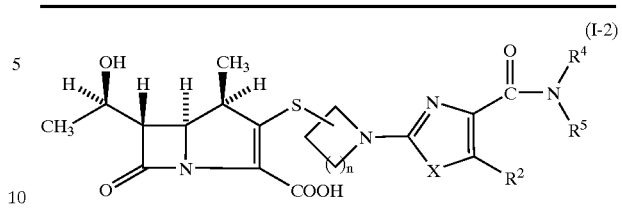

(I-2)

| Cpd No. | X | n | position | R² | R⁴ | R⁵ |
|---|---|---|---|---|---|---|
| 939 | O | 3 | 4 | H | —CH₂CH₂CH₂— | |
| 940 | O | 3 | 4 | H | —CH₂CH₂CH₂CH₂— | |
| 941 | O | 3 | 4 | H | —CH₂CH₂CH₂CH₂CH₂— | |
| 942 | O | 3 | 4 | H | —CH₂CH₂OCH₂CH₂— | |
| 943 | O | 3 | 4 | H | —CH₂CH₂SCH₂CH₂— | |
| 944 | O | 3 | 4 | H | —CH₂CH₂NHCH₂CH₂— | |
| 945 | O | 3 | 4 | H | —CH(OH)CH₂— | |
| 946 | O | 3 | 4 | H | —CH₂CH(OH)CH₂CH₂— | |
| 947 | O | 3 | 4 | H | —CH₂CH(OH)CH₂CH₂CH₂— | |
| 948 | O | 3 | 4 | H | —CH₂CH₂CH(OH)CH₂CH₂— | |
| 949 | O | 3 | 4 | H | —CH(COOH)CH₂CH₂— | |
| 950 | O | 3 | 4 | H | —CH(CONH₂)CH₂CH₂— | |
| 951 | O | 3 | 4 | H | —CH(CH₂OH)CH₂CH₂— | |
| 952 | O | 3 | 4 | H | —CH(CH₂NH₂)CH₂CH₂— | |
| 953 | O | 3 | 4 | H | —CH(COOH)CH₂CH₂CH₂— | |
| 954 | O | 3 | 4 | H | —CH(CONH₂)CH₂CH₂CH₂— | |
| 955 | O | 3 | 4 | H | —CH(CH₂OH)CH₂CH₂CH₂— | |
| 956 | O | 3 | 4 | H | —CH(CH₂NH₂)CH₂CH₂CH₂— | |
| 957 | O | 3 | 4 | H | —CH(COOH)CH₂CH₂CH₂CH₂— | |
| 958 | O | 3 | 4 | H | —CH(CONH₂)CH₂CH₂CH₂CH₂— | |
| 959 | O | 3 | 4 | H | —CH(CH₂OH)CH₂CH₂CH₂CH₂— | |
| 960 | O | 3 | 4 | H | —CH(CH₂NH₂)CH₂CH₂CH₂CH₂— | |
| 961 | O | 3 | 4 | H | —CH₂CH(COOH)CH₂CH₂CH₂— | |
| 962 | O | 3 | 4 | H | —CH₂CH(CONH₂)CH₂CH₂CH₂— | |
| 963 | O | 3 | 4 | H | —CH₂CH(CH₂OH)CH₂CH₂CH₂— | |
| 964 | O | 3 | 4 | H | —CH₂CH(CH₂NH₂)CH₂CH₂CH₂— | |
| 965 | O | 3 | 4 | H | —CH₂CH₂CH(COOH)CH₂CH₂— | |
| 966 | O | 3 | 4 | H | —CH₂CH₂CH(CONH₂)CH₂CH₂— | |
| 967 | O | 3 | 4 | H | —CH₂CH₂CH(CH₂OH)CH₂CH₂— | |
| 968 | O | 3 | 4 | H | —CH₂CH₂CH(CH₂NH₂)CH₂CH₂— | |
| 969 | O | 3 | 4 | Me | H | H |
| 970 | O | 3 | 4 | Me | H | Me |
| 971 | O | 3 | 4 | Me | H | Et |
| 972 | O | 3 | 4 | Me | H | Pr |
| 973 | O | 3 | 4 | Me | H | iPr |
| 974 | O | 3 | 4 | Me | H | Bu |
| 975 | O | 3 | 4 | Me | Me | Me |
| 976 | O | 3 | 4 | Me | Me | Et |
| 977 | O | 3 | 4 | Me | Me | Pr |
| 978 | O | 3 | 4 | Me | Me | Pr |
| 979 | O | 3 | 4 | Me | Me | Bu |
| 980 | O | 3 | 4 | Me | Et | Et |
| 981 | O | 3 | 4 | Me | Et | Pr |
| 982 | O | 3 | 4 | Me | Et | iPr |
| 983 | O | 3 | 4 | Me | Et | Bu |
| 984 | O | 3 | 4 | Me | Pr | Pr |
| 985 | O | 3 | 4 | Me | Pr | iPr |
| 986 | O | 3 | 4 | Me | Pr | Bu |
| 987 | O | 3 | 4 | Me | iPr | iPr |
| 988 | O | 3 | 4 | Me | iPr | Bu |
| 989 | O | 3 | 4 | Me | Bu | Bu |
| 990 | O | 3 | 4 | Me | H | CH₂CH₂OH |
| 991 | O | 3 | 4 | Me | Me | CH₂CH₂OH |
| 992 | O | 3 | 4 | Me | Et | CH₂CH₂OH |
| 993 | O | 3 | 4 | Me | Pr | CH₂CH₂OH |
| 994 | O | 3 | 4 | Me | iPr | CH₂CH₂OH |
| 995 | O | 3 | 4 | Me | H | CH(CH₃)CH₂OH |
| 996 | O | 3 | 4 | Me | H | CH(CH₂OH)CH₂OH |
| 997 | O | 3 | 4 | Me | H | CH(CH₂CH₃)CH₂OH |
| 998 | O | 3 | 4 | Me | H | CH(CH(CH₃)₂)CH₂OH |
| 999 | O | 3 | 4 | Me | H | CH₂CH₂NH₂ |
| 1000 | O | 3 | 4 | Me | H | CH(CH₃)CH₂NH₂ |
| 1001 | O | 3 | 4 | Me | H | CH(CH₂CH₃)CH₂NH₂ |
| 1002 | O | 3 | 4 | Me | H | CH(CH(CH₃)₂)CH₂NH₂ |
| 1003 | O | 3 | 4 | Me | H | CH₂COOH |
| 1004 | O | 3 | 4 | Me | H | CH(CH₃)COOH |
| 1005 | O | 3 | 4 | Me | H | CH(CH₂OH)COOH |
| 1006 | O | 3 | 4 | Me | H | CH(CH₂CH₃)COOH |
| 1007 | O | 3 | 4 | Me | H | CH(CH(CH₃)₂)COOH |
| 1008 | O | 3 | 4 | Me | H | CH₂CONH₂ |
| 1009 | O | 3 | 4 | Me | H | CH(CH₃)CONH₂ |
| 1010 | O | 3 | 4 | Me | H | CH(CH₂OH)CONH₂ |
| 1011 | O | 3 | 4 | Me | H | CH(CH₂CH₃)CONH₂ |
| 1012 | O | 3 | 4 | Me | H | CH(CH(CH₃)₂)CONH₂ |
| 1013 | O | 3 | 4 | Me | H | cPr |
| 1014 | O | 3 | 4 | Me | H | cBu |
| 1015 | O | 3 | 4 | Me | H | cPen |
| 1016 | O | 3 | 4 | Me | H | cHex |
| 1017 | O | 3 | 4 | Me | H | 3-Azt |
| 1018 | O | 3 | 4 | Me | H | 3-Pyr |
| 1019 | O | 3 | 4 | Me | H | 3-Pip |
| 1020 | O | 3 | 4 | Me | H | 4-Pip |
| 1021 | O | 3 | 4 | Me | H | 2-COOH—Ph |
| 1022 | O | 3 | 4 | Me | H | 2-CONH₂—Ph |
| 1023 | O | 3 | 4 | Me | H | 3-COOH—Ph |
| 1024 | O | 3 | 4 | Me | H | 3-CONH₂—Ph |
| 1025 | O | 3 | 4 | Me | H | 4-COOH—Ph |
| 1026 | O | 3 | 4 | Me | H | 4-CONH₂—Ph |
| 1027 | O | 3 | 4 | Me | —CH₂CH₂CH₂— | |
| 1028 | O | 3 | 4 | Me | —CH₂CH₂CH₂CH₂— | |
| 1029 | O | 3 | 4 | Me | —CH₂CH₂CH₂CH₂CH₂— | |
| 1030 | O | 3 | 4 | Me | —CH₂CH₂OCH₂CH₂— | |
| 1031 | O | 3 | 4 | Me | —CH₂CH₂SCH₂CH₂— | |
| 1032 | O | 3 | 4 | Me | —CH₂CH₂NHCH₂CH₂— | |
| 1033 | O | 3 | 4 | Me | —CH(OH)CH₂— | |
| 1034 | O | 3 | 4 | Me | —CH₂CH(OH)CH₂CH₂— | |
| 1035 | O | 3 | 4 | Me | —CH₂CH(OH)CH₂CH₂CH₂— | |
| 1036 | O | 3 | 4 | Me | —CH₂CH₂CH(OH)CH₂CH₂— | |
| 1037 | O | 3 | 4 | Me | —CH(COOH)CH₂CH₂— | |
| 1038 | O | 3 | 4 | Me | —CH(CONH₂)CH₂CH₂— | |
| 1039 | O | 3 | 4 | Me | —CH(CH₂OH)CH₂CH₂— | |
| 1040 | O | 3 | 4 | Me | —CH(CH₂NH₂)CH₂CH₂— | |
| 1041 | O | 3 | 4 | Me | —CH(COOH)CH₂CH₂CH₂— | |
| 1042 | O | 3 | 4 | Me | —CH(CONH₂)CH₂CH₂CH₂— | |
| 1043 | O | 3 | 4 | Me | —CH(CH₂OH)CH₂CH₂CH₂— | |
| 1044 | O | 3 | 4 | Me | —CH(CH₂NH₂)CH₂CH₂CH₂— | |
| 1045 | O | 3 | 4 | Me | —CH(COOH)CH₂CH₂CH₂CH₂— | |
| 1046 | O | 3 | 4 | Me | —CH(CONH₂)CH₂CH₂CH₂CH₂— | |
| 1047 | O | 3 | 4 | Me | —CH(CH₂OH)CH₂CH₂CH₂CH₂— | |
| 1048 | O | 3 | 4 | Me | —CH(CH₂NH₂)CH₂CH₂CH₂CH₂— | |
| 1049 | O | 3 | 4 | Me | —CH₂CH(COOH)CH₂CH₂CH₂— | |
| 1050 | O | 3 | 4 | Me | —CH₂CH(CONH₂)CH₂CH₂CH₂— | |
| 1051 | O | 3 | 4 | Me | —CH₂CH(CH₂OH)CH₂CH₂CH₂— | |
| 1052 | O | 3 | 4 | Me | —CH₂CH(CH₂NH₂)CH₂CH₂CH₂— | |
| 1053 | O | 3 | 4 | Me | —CH₂CH₂CH(COOH)CH₂CH₂— | |
| 1054 | O | 3 | 4 | Me | —CH₂CH₂CH(CONHDCH₂CH₂— | |
| 1055 | O | 3 | 4 | Me | —CH₂CH₂CH(CH₂OH)CH₂CH₂— | |
| 1056 | O | 3 | 4 | Me | —CH₂CH₂CH(CH₂NH₂)CH₂CH₂— | |
| 1057 | S | 1 | 3 | H | H | CH(CH₂(CH₃)₂)CH₂OH |
| 1058 | S | 1 | 3 | H | H | CH(CH₂(CH₃)₂)CH₂NH₂ |
| 1059 | S | 1 | 3 | H | H | CH(CH₂(CH₃)₂)COOH |
| 1060 | S | 1 | 3 | H | H | CH(CH₂(CH₃)₂)CONH₂ |
| 1061 | S | 1 | 3 | H | H | CH(CH₂OH)CH₂NH₂ |
| 1062 | S | 1 | 3 | H | H | CH(CH(CH₃)CH₂CH₃)CH₂OH |
| 1063 | S | 1 | 3 | H | H | CH(CH(CH₃)CH₂CH₃)CH₂NH₂ |
| 1064 | S | 1 | 3 | H | H | CH(CH(CH₃)CH₂CH₃)COOH |
| 1065 | S | 1 | 3 | H | H | CH(CH(CH₃)CH₂CH₃)CONH₂ |
| 1066 | S | 1 | 3 | H | Me | CH₂CH₂NH₂ |
| 1067 | S | 1 | 3 | H | Me | CH₂COOH |
| 1068 | S | 1 | 3 | H | Me | CH₂C0NH₂ |
| 1069 | S | 1 | 3 | H | iPr | CH₂CH₂NH₂ |
| 1070 | S | 1 | 3 | H | iPr | CH₂COOH |
| 1071 | S | 1 | 3 | H | iPr | CH₂CONH₂ |
| 1072 | S | 1 | 3 | H | CH₂CH(NH₂)CH₂ | |

TABLE 2-continued (I-2)

| Cpd No. | X | n | position | R² | R⁴ | R⁵ |
|---|---|---|---|---|---|---|
| 1073 | S | 1 | 3 | H | | CH₂CH(OCH₃)CH₂ |
| 1074 | S | 1 | 3 | H | | CH₂CH(NCH₃)CH₂CH₂ |
| 1075 | S | 2 | 3 | H | H | CH(CH₂(CH₃)₂)CH₂OH |
| 1076 | S | 2 | 3 | H | H | CH(CH₂(CH₃)₂)CH₂NH₂ |
| 1077 | S | 2 | 3 | H | H | CH(CH₂(CH₃)₂)COOH |
| 1078 | S | 2 | 3 | H | H | CH(CH₂(CH₃)₂)CONH₂ |
| 1079 | S | 2 | 3 | H | H | CH(CH₂OH)CH₂NH₂ |
| 1080 | S | 2 | 3 | H | H | CH(CH(CH₃)CH₂CH₃)CH₂OH |
| 1081 | S | 2 | 3 | H | H | CH(CH(CH₃)CH₂CH₃)CH₂NH₂ |
| 1082 | S | 2 | 3 | H | H | CH(CH(CH₃)CH₂CH₃)COOH |
| 1083 | S | 2 | 3 | H | H | CH(CH(CH₃)CH₂CH₃)CONH₂ |
| 1084 | S | 2 | 3 | H | Me | CH₂CH₂NH₂ |
| 1085 | S | 2 | 3 | H | Me | CH₂COOH |
| 1086 | S | 2 | 3 | H | Me | CH₂CONH₂ |
| 1087 | S | 2 | 3 | H | iPr | CH₂CH₂NH₂ |
| 1088 | S | 2 | 3 | H | iPr | CH₂COOH |
| 1089 | S | 2 | 3 | H | iPr | CH₂CONH₂ |
| 1090 | S | 2 | 3 | H | | CH₂CH(NH₂)CH₂ |
| 1091 | S | 2 | 3 | H | | CH₂CH(OCH₃)CH₂ |
| 1092 | S | 2 | 3 | H | | CH₂CH(NCH₃)CH₂CH₂ |
| 1093 | S | 3 | 4 | H | H | CH(CH₂(CH₃)₂)CH₂OH |
| 1094 | S | 3 | 4 | H | H | CH(CH₂(OH3)₂)CH₂NH₂ |
| 1095 | S | 3 | 4 | H | H | CH(CH₂(CH₃)₂)COOH |
| 1096 | S | 3 | 4 | H | H | CH(CH₂(CH₃)₂)CONH₂ |
| 1097 | S | 3 | 4 | H | H | CH(CH₂OH)CH₂NH₂ |
| 1098 | S | 3 | 4 | H | H | CH(CH(CH₃)CH₂CH₃)CH₂OH |
| 1099 | S | 3 | 4 | H | H | CH(CH(CH₃)CH₂CH₃)CH₂NH₂ |
| 1100 | S | 3 | 4 | H | H | CH(CH(CH₃)CH₂CH₃)COOH |
| 1101 | S | 3 | 4 | H | H | CH(CH(CH₃)CH₂CH₃)CONH₂ |
| 1102 | S | 3 | 4 | H | Me | CH₂CH₂NH₂ |
| 1103 | S | 3 | 4 | H | Me | CH₂COOH |
| 1104 | S | 3 | 4 | H | Me | CH₂CONH₂ |
| 1105 | S | 3 | 4 | H | iPr | CH₂CH₂NH₂ |
| 1106 | S | 3 | 4 | H | iPr | CH₂COOH |
| 1107 | S | 3 | 4 | H | iPr | CH₂CONH₂ |
| 1108 | S | 3 | 4 | H | | CH₂CH(NH₂)CH₂ |
| 1109 | S | 3 | 4 | H | | CH₂CH(OCH₃)CH₂ |
| 1110 | S | 3 | 4 | H | | CH₂CH(NCH₃)CH₂CH₂ |
| 1111 | O | 1 | 3 | H | H | CH(CH₂(CH₃)₂)CH₂OH |
| 1112 | O | 1 | 3 | H | H | CH(CH₂(CH₃)₂)CH₂NH₂ |
| 1113 | O | 1 | 3 | H | H | CH(CH₂(CH₃)₂)COOH |
| 1114 | O | 1 | 3 | H | H | CH(CH₂(CH₃)₂)CONH₂ |
| 1115 | O | 1 | 3 | H | H | CH(CH₂OH)CH₂NH₂ |
| 1116 | O | 1 | 3 | H | H | CH(CH(CH₃)CH₂CH₃)CH₂OH |
| 1117 | O | 1 | 3 | H | H | CH(CH(CH₃)CH₂CH₃)CH₂NH₂ |
| 1118 | O | 1 | 3 | H | H | CH(CH(CH₃)CH₂CH₃)COOH |
| 1119 | O | 1 | 3 | H | H | CH(CH(CH₃)CH₂CH₃)CONH₂ |
| 1120 | O | 1 | 3 | H | Me | CH₂CH₂NH₂ |
| 1121 | O | 1 | 3 | H | Me | CH₂COOH |
| 1122 | O | 1 | 3 | H | Me | CH₂CONH₂ |
| 1123 | O | 1 | 3 | H | iPr | CH₂CH₂NH₂ |
| 1124 | O | 1 | 3 | H | iPr | CH₂COOH |
| 1125 | O | 1 | 3 | H | iPr | CH₂CONH₂ |
| 1126 | O | 1 | 3 | H | | CH₂CH(NH₂)CH₂ |
| 1127 | O | 1 | 3 | H | | CH₂CH(OCH₃)CH₂ |
| 1128 | O | 1 | 3 | H | | CH₂CH(NCH₃)CH₂CH₂ |
| 1129 | O | 2 | 3 | H | H | CH(CH₂(CH₃)₂)CH₂OH |
| 1130 | O | 2 | 3 | H | H | CH(CH₂(CH₃)₂)CH₂NH₂ |
| 1131 | O | 2 | 3 | H | H | CH(CH₂(CH₃)₂)COOH |
| 1132 | O | 2 | 3 | H | H | CH(CH₂(CH₃)₂)CONH₂ |
| 1133 | O | 2 | 3 | H | H | CH(CH₂OH)CH₂NH₂ |
| 1134 | O | 2 | 3 | H | H | CH(CH(CH₃)CH₂CH₃)CH₂OH |
| 1135 | O | 2 | 3 | H | H | CH(CH(CH₃)CH₂CH₃)CH₂NH₂ |
| 1136 | O | 2 | 3 | H | H | CH(CH(CH₃)CH₂CH₃)COOH |
| 1137 | O | 2 | 3 | H | H | CH(CH(CH₃)CH₂CH₃)CONH₂ |
| 1138 | O | 2 | 3 | H | Me | CH₂CH₂NH₂ |
| 1139 | O | 2 | 3 | H | Me | CH₂COOH |
| 1140 | O | 2 | 3 | H | Me | CH₂CONH₂ |
| 1141 | O | 2 | 3 | H | iPr | CH₂CH₂NH₂ |
| 1142 | O | 2 | 3 | H | iPr | CH₂COOH |
| 1143 | O | 2 | 3 | H | iPr | CH₂CONH₂ |
| 1144 | O | 2 | 3 | H | | CH₂CH(NH₂)CH₂ |
| 1145 | O | 2 | 3 | H | | CH₂CH(OCH₃)CH₂ |
| 1146 | O | 2 | 3 | H | | CH₂CH(NCH₃)CH₂CH₂ |
| 1147 | O | 3 | 4 | H | H | CH(CH₂(CH₃)₂)CH₂OH |
| 1148 | O | 3 | 4 | H | H | CH(CH₂(CH₃)₂)CH₂NH₂ |
| 1149 | O | 3 | 4 | H | H | CH(CH₂(CH₃)₂)COOH |
| 1150 | O | 3 | 4 | H | H | CH(CH₂(CH₃)₂)CONH₂ |
| 1151 | O | 3 | 4 | H | H | CH(CH₂OH)CH₂NH₂ |
| 1152 | O | 3 | 4 | H | H | CH(CH(CH₃)CH₂CH₃)CH₂OH |
| 1153 | O | 3 | 4 | H | H | CH(CH(CH₃)CH₂CH₃)CH₂NH₂ |
| 1154 | O | 3 | 4 | H | H | CH(CH(CH₃)CH₂CH₃)COOH |
| 1155 | O | 3 | 4 | H | H | CH(CH(CH₃)CH₂CH₃)CONH₂ |
| 1156 | O | 3 | 4 | H | Me | CH₂CH₂NH₂ |
| 1157 | O | 3 | 4 | H | Me | CH₂COOH |
| 1158 | O | 3 | 4 | H | Me | CH₂CONH₂ |
| 1159 | O | 3 | 4 | H | iPr | CH₂CH₂NH₂ |
| 1160 | O | 3 | 4 | H | iPr | CH₂COOH |
| 1161 | O | 3 | 4 | H | iPr | CH₂CONH₂ |
| 1162 | O | 3 | 4 | H | | CH₂CH(NH₂)CH₂ |
| 1163 | O | 3 | 4 | H | | CH₂CH(OCH₃)CH₂ |
| 1164 | O | 3 | 4 | H | | CH₂CH(NCH₃)CH₂CH₂ |

TABLE 3

(I-3)

| Cpd No. | X | n | position | R² |
|---|---|---|---|---|
| 1 | S | 1 | 3 | H |
| 2 | S | 1 | 3 | Me |
| 3 | S | 2 | 3 | H |
| 4 | S | 2 | 3 | Me |
| 5 | S | 3 | 4 | H |
| 6 | S | 3 | 4 | Me |
| 7 | O | 1 | 3 | H |
| 8 | O | 1 | 3 | Me |
| 9 | O | 2 | 3 | H |
| 10 | O | 2 | 3 | Me |
| 11 | O | 3 | 4 | H |
| 12 | O | 3 | 4 | Me |

TABLE 4

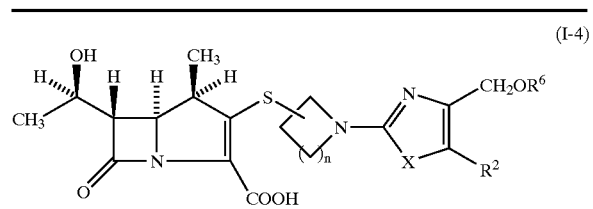

(I-4)

| Cpd No. | X | n | position | R² | R⁶ |
|---|---|---|---|---|---|
| 1 | S | 1 | 3 | H | H |
| 2 | S | 1 | 3 | H | Me |
| 3 | S | 1 | 3 | H | Et |
| 4 | S | 1 | 3 | H | Pr |
| 5 | S | 1 | 3 | H | iPr |
| 6 | S | 1 | 3 | H | Bu |
| 7 | S | 1 | 3 | H | cPr |
| 8 | S | 1 | 3 | H | cBu |
| 9 | S | 1 | 3 | H | cPen |
| 10 | S | 1 | 3 | H | cHex |
| 11 | S | 1 | 3 | Me | H |
| 12 | S | 1 | 3 | Me | Me |
| 13 | S | 1 | 3 | Me | Et |
| 14 | S | 1 | 3 | Me | Pr |
| 15 | S | 1 | 3 | Me | iPr |
| 16 | S | 1 | 3 | Me | Bu |
| 17 | S | 1 | 3 | Me | cPr |
| 18 | S | 1 | 3 | Me | cBu |
| 19 | S | 1 | 3 | Me | cPen |
| 20 | S | 1 | 3 | Me | cHex |
| 21 | S | 2 | 3 | H | H |
| 22 | S | 2 | 3 | H | Me |
| 23 | S | 2 | 3 | H | Et |
| 24 | S | 2 | 3 | H | Pr |
| 25 | S | 2 | 3 | H | iPr |
| 26 | S | 2 | 3 | H | Bu |
| 27 | S | 2 | 3 | H | cPr |
| 28 | S | 2 | 3 | H | cBu |
| 29 | S | 2 | 3 | H | cPen |
| 30 | S | 2 | 3 | H | cHex |
| 31 | S | 2 | 3 | Me | H |
| 32 | S | 2 | 3 | Me | Me |
| 33 | S | 2 | 3 | Me | Et |
| 34 | S | 2 | 3 | Me | Pr |
| 35 | S | 2 | 3 | Me | iPr |
| 36 | S | 2 | 3 | Me | Bu |
| 37 | S | 2 | 3 | Me | cPr |
| 38 | S | 2 | 3 | Me | cBu |
| 39 | S | 2 | 3 | Me | cPen |
| 40 | S | 2 | 3 | Me | cHex |
| 41 | S | 3 | 4 | H | H |
| 42 | S | 3 | 4 | H | Me |
| 43 | S | 3 | 4 | H | Et |
| 44 | S | 3 | 4 | H | Pr |
| 45 | S | 3 | 4 | H | iPr |
| 46 | S | 3 | 4 | H | Bu |
| 47 | S | 3 | 4 | H | cPr |
| 48 | S | 3 | 4 | H | cBu |
| 49 | S | 3 | 4 | H | oPen |
| 50 | S | 3 | 4 | H | cHex |
| 51 | S | 3 | 4 | Me | H |
| 52 | S | 3 | 4 | Me | Me |
| 53 | S | 3 | 4 | Me | Et |
| 54 | S | 3 | 4 | Me | Pr |
| 55 | S | 3 | 4 | Me | iPr |
| 56 | S | 3 | 4 | Me | Bu |
| 57 | S | 3 | 4 | Me | cPr |
| 58 | S | 3 | 4 | Me | cBu |
| 59 | S | 3 | 4 | Me | cPen |
| 60 | S | 3 | 4 | Me | cHex |
| 61 | O | 1 | 3 | H | H |
| 62 | O | 1 | 3 | H | Me |
| 63 | O | 1 | 3 | H | Et |
| 64 | O | 1 | 3 | H | Pr |
| 65 | O | 1 | 3 | H | iPr |
| 66 | O | 1 | 3 | H | Bu |
| 67 | O | 1 | 3 | H | cPr |
| 68 | O | 1 | 3 | H | cBu |
| 69 | O | 1 | 3 | H | cPen |
| 70 | O | 1 | 3 | H | cHex |
| 71 | O | 1 | 3 | Me | H |
| 72 | O | 1 | 3 | Me | Me |
| 73 | O | 1 | 3 | Me | Et |
| 74 | O | 1 | 3 | Me | Pr |
| 75 | O | 1 | 3 | Me | iPr |
| 76 | O | 1 | 3 | Me | Bu |
| 77 | O | 1 | 3 | Me | cPr |
| 78 | O | 1 | 3 | Me | cBu |
| 79 | O | 1 | 3 | Me | cPen |
| 80 | O | 1 | 3 | Me | cHex |
| 81 | O | 2 | 3 | H | H |
| 82 | O | 2 | 3 | H | Me |
| 83 | O | 2 | 3 | H | Et |
| 84 | O | 2 | 3 | H | Pr |
| 85 | O | 2 | 3 | H | iPr |
| 86 | O | 2 | 3 | H | Bu |
| 87 | O | 2 | 3 | H | cPr |
| 88 | O | 2 | 3 | H | cBu |
| 89 | O | 2 | 3 | H | cPen |
| 90 | O | 2 | 3 | H | cHex |
| 91 | O | 2 | 3 | Me | H |
| 92 | O | 2 | 3 | Me | Me |
| 93 | O | 2 | 3 | Me | Et |
| 94 | O | 2 | 3 | Me | Pr |
| 95 | O | 2 | 3 | Me | iPr |
| 96 | O | 2 | 3 | Me | Bu |
| 97 | O | 2 | 3 | Me | cPr |
| 98 | O | 2 | 3 | Me | cBu |
| 99 | O | 2 | 3 | Me | cPen |
| 100 | O | 2 | 3 | Me | cHex |
| 101 | O | 3 | 4 | H | H |
| 102 | O | 3 | 4 | H | Me |
| 103 | O | 3 | 4 | H | Et |
| 104 | O | 3 | 4 | H | Pr |
| 105 | O | 3 | 4 | H | iPr |
| 106 | O | 3 | 4 | H | Bu |
| 107 | O | 3 | 4 | H | cPr |
| 108 | O | 3 | 4 | H | cBu |
| 109 | O | 3 | 4 | H | cPen |
| 110 | O | 3 | 4 | H | cHex |
| 111 | O | 3 | 4 | Me | H |
| 112 | O | 3 | 4 | Me | Me |
| 113 | O | 3 | 4 | Me | Et |
| 114 | O | 3 | 4 | Me | Pr |
| 115 | O | 3 | 4 | Me | iPr |
| 116 | O | 3 | 4 | Me | Bu |
| 117 | O | 3 | 4 | Me | cPr |
| 118 | O | 3 | 4 | Me | cBu |
| 119 | O | 3 | 4 | Me | cPen |
| 120 | O | 3 | 4 | Me | cHex |

TABLE 5

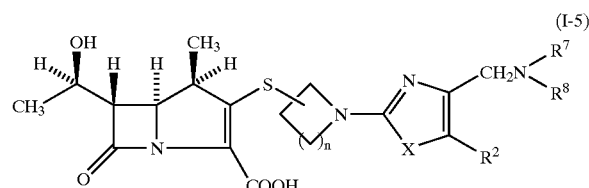
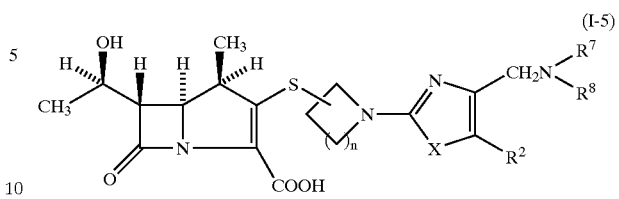

(I-5)

| Cpd No. | X | n | position | R² | R⁷ | R⁸ |
|---|---|---|---|---|---|---|
| 1 | S | 1 | 3 | H | H | H |
| 2 | S | 1 | 3 | H | H | Me |
| 3 | S | 1 | 3 | H | H | Et |
| 4 | S | 1 | 3 | H | H | COCH₃ |
| 5 | S | 1 | 3 | H | H | COCH₂CH₃ |
| 6 | S | 1 | 3 | H | H | COCH₂CH₂CH₃ |
| 7 | S | 1 | 3 | H | H | COPh |
| 8 | S | 1 | 3 | H | H | COOMe |
| 9 | S | 1 | 3 | H | H | COOEt |
| 10 | S | 1 | 3 | H | Me | Me |
| 11 | S | 1 | 3 | H | Et | Et |
| 12 | S | 1 | 3 | H | Me | COCH₃ |
| 13 | S | 1 | 3 | H | Me | COPh |
| 14 | S | 1 | 3 | H | Me | COOMe |
| 15 | S | 1 | 3 | H | Me | COOEt |
| 16 | S | 1 | 3 | Me | H | H |
| 17 | S | 1 | 3 | Me | H | Me |
| 18 | S | 1 | 3 | Me | H | Et |
| 19 | S | 1 | 3 | Me | H | COCH₃ |
| 20 | S | 1 | 3 | Me | H | COCH₂CH₃ |
| 21 | S | 1 | 3 | Me | H | COCH₂CH₂CH₃ |
| 22 | S | 1 | 3 | Me | H | COPh |
| 23 | S | 1 | 3 | Me | H | COOMe |
| 24 | S | 1 | 3 | Me | H | COOEt |
| 25 | S | 1 | 3 | Me | Me | Me |
| 26 | S | 1 | 3 | Me | Et | Et |
| 27 | S | 1 | 3 | Me | Me | COCH₃ |
| 28 | S | 1 | 3 | Me | Me | COPh |
| 29 | S | 1 | 3 | Me | Me | COOMe |
| 30 | S | 1 | 3 | Me | Me | COOEt |
| 31 | S | 2 | 3 | H | H | H |
| 32 | S | 2 | 3 | H | H | Me |
| 33 | S | 2 | 3 | H | H | Et |
| 34 | S | 2 | 3 | H | H | COCH₃ |
| 35 | S | 2 | 3 | H | H | COCH₂CH₃ |
| 36 | S | 2 | 3 | H | H | COCH₂CH₂CH₃ |
| 37 | S | 2 | 3 | H | H | COPh |
| 38 | S | 2 | 3 | H | H | COOMe |
| 39 | S | 2 | 3 | H | H | COOEt |
| 40 | S | 2 | 3 | H | Me | Me |
| 41 | S | 2 | 3 | H | Et | Et |
| 42 | S | 2 | 3 | H | Me | COCH₃ |
| 43 | S | 2 | 3 | H | Me | COPh |
| 44 | S | 2 | 3 | H | Me | COOMe |
| 45 | S | 2 | 3 | H | Me | COOEt |
| 46 | S | 2 | 3 | Me | H | H |
| 47 | S | 2 | 3 | Me | H | Me |
| 48 | S | 2 | 3 | Me | H | Et |
| 49 | S | 2 | 3 | Me | H | COCH₃ |
| 50 | S | 2 | 3 | Me | H | COCH₂CH₃ |
| 51 | S | 2 | 3 | Me | H | COCH₂CH₂CH₃ |
| 52 | S | 2 | 3 | Me | H | COPh |
| 53 | S | 2 | 3 | Me | H | COOMe |
| 54 | S | 2 | 3 | Me | H | COOEt |
| 55 | S | 2 | 3 | Me | Me | Me |
| 56 | S | 2 | 3 | Me | Et | Et |
| 57 | S | 2 | 3 | Me | Me | COCH₃ |
| 58 | S | 2 | 3 | Me | Me | COPh |
| 59 | S | 2 | 3 | Me | Me | COOMe |
| 60 | S | 2 | 3 | Me | Me | COOEt |
| 61 | S | 3 | 4 | H | H | H |
| 62 | S | 3 | 4 | H | H | Me |
| 63 | S | 3 | 4 | H | H | Et |
| 64 | S | 3 | 4 | H | H | COCH₃ |
| 65 | S | 3 | 4 | H | H | COCH₂CH₃ |
| 66 | S | 3 | 4 | H | H | COCH₂CH₂CH₃ |
| 67 | S | 3 | 4 | H | H | COPh |
| 68 | S | 3 | 4 | H | H | COOMe |
| 69 | S | 3 | 4 | H | H | COOEt |
| 70 | S | 3 | 4 | H | Me | Me |
| 71 | S | 3 | 4 | H | Et | Et |
| 72 | S | 3 | 4 | H | Me | COCH₃ |
| 73 | S | 3 | 4 | H | Me | COPh |
| 74 | S | 3 | 4 | H | Me | COOMe |
| 75 | S | 3 | 4 | H | Me | COOEt |
| 76 | S | 3 | 4 | Me | H | H |
| 77 | S | 3 | 4 | Me | H | Me |
| 78 | S | 3 | 4 | Me | H | Et |
| 79 | S | 3 | 4 | Me | H | COCH₃ |
| 80 | S | 3 | 4 | Me | H | COCH₂CH₃ |
| 81 | S | 3 | 4 | Me | H | COCH₂CH₂CH₃ |
| 82 | S | 3 | 4 | Me | H | COPh |
| 83 | S | 3 | 4 | Me | H | COOMe |
| 84 | S | 3 | 4 | Me | H | COOEt |
| 85 | S | 3 | 4 | Me | Me | Me |
| 86 | S | 3 | 4 | Me | Et | Et |
| 87 | S | 3 | 4 | Me | Me | COCH₃ |
| 88 | S | 3 | 4 | Me | Me | COPh |
| 89 | S | 3 | 4 | Me | Me | COOMe |
| 90 | S | 3 | 4 | Me | Me | COOEt |
| 91 | O | 1 | 3 | H | H | H |
| 92 | O | 1 | 3 | H | H | Me |
| 93 | O | 1 | 3 | H | H | Et |
| 94 | O | 1 | 3 | H | H | COCH₃ |
| 95 | O | 1 | 3 | H | H | COCH₂CH₃ |
| 96 | O | 1 | 3 | H | H | COCH₂CH₂CH₃ |
| 97 | O | 1 | 3 | H | H | COPh |
| 98 | O | 1 | 3 | H | H | COOMe |
| 99 | O | 1 | 3 | H | H | COOEt |
| 100 | O | 1 | 3 | H | Me | Me |
| 101 | O | 1 | 3 | H | Et | Et |
| 102 | O | 1 | 3 | H | Me | COCH₃ |
| 103 | O | 1 | 3 | H | Me | COPh |
| 104 | O | 1 | 3 | H | Me | COOMe |
| 105 | O | 1 | 3 | H | Me | COOEt |
| 106 | O | 1 | 3 | Me | H | H |
| 107 | O | 1 | 3 | Me | H | Me |
| 108 | O | 1 | 3 | Me | H | Et |
| 109 | O | 1 | 3 | Me | H | COCH₃ |
| 110 | O | 1 | 3 | Me | H | COCH₂CH₃ |
| 111 | O | 1 | 3 | Me | H | COCH₂CH₂CH₃ |
| 112 | O | 1 | 3 | Me | H | COPh |
| 113 | O | 1 | 3 | Me | H | COOMe |
| 114 | O | 1 | 3 | Me | H | COOEt |
| 115 | O | 1 | 3 | Me | Me | Me |
| 116 | O | 1 | 3 | Me | Et | Et |
| 117 | O | 1 | 3 | Me | Me | COCH₃ |
| 118 | O | 1 | 3 | Me | Me | COPh |
| 119 | O | 1 | 3 | Me | Me | COOMe |
| 120 | O | 1 | 3 | Me | Me | COOEt |
| 121 | O | 2 | 3 | H | H | H |
| 122 | O | 2 | 3 | H | H | Me |
| 123 | O | 2 | 3 | H | H | Et |
| 124 | O | 2 | 3 | H | H | COCH₃ |
| 125 | O | 2 | 3 | H | H | COCH₂CH₃ |
| 126 | O | 2 | 3 | H | H | COCH₂CH₂CH₃ |
| 127 | O | 2 | 3 | H | H | COPh |
| 128 | O | 2 | 3 | H | H | COOMe |
| 129 | O | 2 | 3 | H | H | COOEt |
| 130 | O | 2 | 3 | H | Me | Me |
| 131 | O | 2 | 3 | H | Et | Et |
| 132 | O | 2 | 3 | H | Me | COCH₃ |
| 133 | O | 2 | 3 | H | Me | COPh |
| 134 | O | 2 | 3 | H | Me | COOMe |

TABLE 5-continued

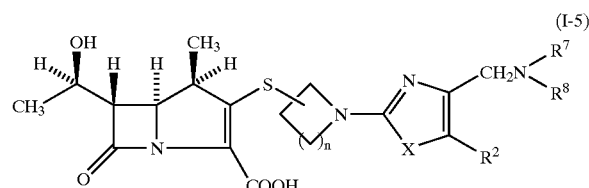

(I-5)

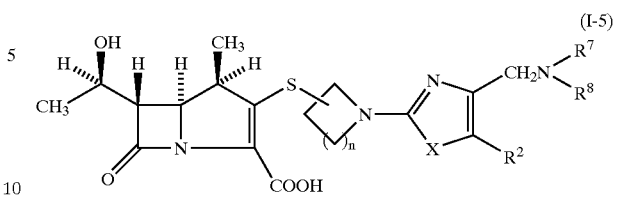

(I-5)

| Cpd No. | X | n | position | R² | R⁷ | R⁸ |
|---|---|---|---|---|---|---|
| 135 | O | 2 | 3 | H | Me | COOEt |
| 136 | O | 2 | 3 | Me | H | H |
| 137 | O | 2 | 3 | Me | H | Me |
| 138 | O | 2 | 3 | Me | H | Et |
| 139 | O | 2 | 3 | Me | H | COCH₃ |
| 140 | O | 2 | 3 | Me | H | COCH₂CH₃ |
| 141 | O | 2 | 3 | Me | H | COCH₂CH₂CH₃ |
| 142 | O | 2 | 3 | Me | H | COPh |
| 143 | O | 2 | 3 | Me | H | COOMe |
| 144 | O | 2 | 3 | Me | H | COOEt |
| 145 | O | 2 | 3 | Me | Me | Me |
| 146 | O | 2 | 3 | Me | Et | Et |
| 147 | O | 2 | 3 | Me | Me | COCH₃ |
| 148 | O | 2 | 3 | Me | Me | COPh |
| 149 | O | 2 | 3 | Me | Me | COOMe |
| 150 | O | 2 | 3 | Me | Me | COOEt |
| 151 | O | 3 | 4 | H | H | H |
| 152 | O | 3 | 4 | H | H | Me |
| 153 | O | 3 | 4 | H | H | Et |
| 154 | O | 3 | 4 | H | H | COCH₃ |
| 155 | O | 3 | 4 | H | H | COCH₂CH₃ |
| 156 | O | 3 | 4 | H | H | COCH₂CH₂CH₃ |
| 157 | O | 3 | 4 | H | H | COPh |
| 158 | O | 3 | 4 | H | H | COOMe |
| 159 | O | 3 | 4 | H | H | COOEt |
| 160 | O | 3 | 4 | H | Me | Me |
| 161 | O | 3 | 4 | H | Et | Et |
| 162 | O | 3 | 4 | H | Me | COCH₃ |
| 163 | O | 3 | 4 | H | Me | COPh |
| 164 | O | 3 | 4 | H | Me | COOMe |
| 165 | O | 3 | 4 | H | Me | COOEt |
| 167 | O | 3 | 4 | Me | H | H |
| 168 | O | 3 | 4 | Me | H | Me |
| 169 | O | 3 | 4 | Me | H | Et |
| 170 | O | 3 | 4 | Me | H | COCH₃ |
| 171 | O | 3 | 4 | Me | H | COCH₂CH₃ |
| 172 | O | 3 | 4 | Me | H | COCH₂CH₂CH₃ |
| 173 | O | 3 | 4 | Me | H | COPh |
| 174 | O | 3 | 4 | Me | H | COOMe |
| 175 | O | 3 | 4 | Me | H | COOEt |
| 176 | O | 3 | 4 | Me | Me | Me |
| 177 | O | 3 | 4 | Me | Et | Et |
| 178 | O | 3 | 4 | Me | Me | COCH₃ |
| 179 | O | 3 | 4 | Me | Me | COPh |
| 180 | O | 3 | 4 | Me | Me | COOMe |
| 181 | O | 3 | 4 | Me | Me | COOEt |
| 182 | S | 1 | 3 | H | H | CO-cPr |
| 183 | S | 1 | 3 | H | H | CO-cBu |
| 184 | S | 1 | 3 | H | H | CO-cPen |
| 185 | S | 1 | 3 | H | H | CO-cHex |
| 186 | S | 1 | 3 | H | H | CO-2-thienyl |
| 187 | S | 1 | 3 | H | H | CO-2-furyl |
| 188 | S | 1 | 3 | H | H | CO-2-pyridyl |
| 189 | S | 1 | 3 | H | H | CO-3-pyridyl |
| 190 | S | 1 | 3 | H | H | CO-4-pyridyl |
| 191 | S | 1 | 3 | H | H | SO₂—Ph |
| 192 | S | 1 | 3 | H | H | CO—Ph-2-COOH |
| 193 | S | 1 | 3 | H | H | CO—Ph-2-CONH₂ |
| 194 | S | 1 | 3 | H | H | CO—Ph-2-CH₂OH |
| 195 | S | 1 | 3 | H | H | CO—Ph-2-CH₂NH₂ |
| 196 | S | 1 | 3 | H | H | CO—Ph-3-COOH |
| 197 | S | 1 | 3 | H | H | CO—Ph-3-CONH₂ |
| 198 | S | 1 | 3 | H | H | CO—Ph-3-CH₂OH |
| 199 | S | 1 | 3 | H | H | CO—Ph-3-CH₂NH₂ |
| 200 | S | 1 | 3 | H | H | CO—Ph-4-COOH |
| 201 | S | 1 | 3 | H | H | CO—Ph-4-CONH₂ |
| 202 | S | 1 | 3 | H | H | CO—Ph-4-CH₂OH |
| 203 | S | 1 | 3 | H | H | CO—Ph-4-CH₂NH₂ |
| 204 | S | 2 | 3 | H | H | CO-cPr |
| 205 | S | 2 | 3 | H | H | CO-cBu |
| 206 | S | 2 | 3 | H | H | CO-cPen |
| 207 | S | 2 | 3 | H | H | CO-cHex |
| 208 | S | 2 | 3 | H | H | CO-2-thienyl |
| 209 | S | 2 | 3 | H | H | CO-2-furyl |
| 210 | S | 2 | 3 | H | H | CO-2-pyridyl |
| 211 | S | 2 | 3 | H | H | CO-3-pyridyl |
| 212 | S | 2 | 3 | H | H | CO-4-pyridyl |
| 213 | S | 2 | 3 | H | H | SO₂—Ph |
| 214 | S | 2 | 3 | H | H | CO—Ph-2-COOH |
| 215 | S | 2 | 3 | H | H | CO—Ph-2-CONH₂ |
| 216 | S | 2 | 3 | H | H | CO—Ph-2-CH₂OH |
| 217 | S | 2 | 3 | H | H | CO—Ph-2-CH₂NH₂ |
| 218 | S | 2 | 3 | H | H | CO—Ph-3-COOH |
| 219 | S | 2 | 3 | H | H | CO—Ph-3-CONH₂ |
| 220 | S | 2 | 3 | H | H | CO—Ph-3-CH₂OH |
| 221 | S | 2 | 3 | H | H | CO—Ph-3-CH₂NH₂ |
| 222 | S | 2 | 3 | H | H | CO—Ph-4-COOH |
| 223 | S | 2 | 3 | H | H | CO—Ph-4-CONH₂ |
| 224 | S | 2 | 3 | H | H | CO—Ph-4-CH₂OH |
| 225 | S | 2 | 3 | H | H | CO—Ph-4-CH₂NH₂ |
| 226 | S | 3 | 4 | H | H | CO-cPr |
| 227 | S | 3 | 4 | H | H | CO-cBu |
| 228 | S | 3 | 4 | H | H | CO-cPen |
| 229 | S | 3 | 4 | H | H | CO-cHex |
| 230 | S | 3 | 4 | H | H | CO-2-thienyl |
| 231 | S | 3 | 4 | H | H | CO-2-furyl |
| 232 | S | 3. | 4 | H | H | CO-2-pyridyl |
| 233 | S | 3 | 4 | H | H | CO-3-pyridyl |
| 234 | S | 3 | 4 | H | H | CO-4-pyridyl |
| 235 | S | 3 | 4 | H | H | SO₂—Ph |
| 236 | S | 3 | 4 | H | H | CO—Ph-2-COOH |
| 237 | S | 3 | 4 | H | H | CO—Ph-2-CONH₂ |
| 238 | S | 3 | 4 | H | H | CO—Ph-2-CH₂OH |
| 239 | S | 3 | 4 | H | H | CO—Ph-2-CH₂NH₂ |
| 240 | S | 3 | 4 | H | H | CO—Ph-3-COOH |
| 241 | S | 3 | 4 | H | H | CO—Ph-3-CONH₂ |
| 242 | S | 3 | 4 | H | H | CO—Ph-3-CH₂OH |
| 243 | S | 3 | 4 | H | H | CO—Ph-3-CH₂NH₂ |
| 244 | S | 3 | 4 | H | H | CO—Ph-4-COOH |
| 245 | S | 3 | 4 | H | H | CO—Ph-4-CONH₂ |
| 246 | S | 3 | 4 | H | H | CO—Ph-4-CH₂OH |
| 247 | S | 3 | 4 | H | H | CO—Ph-4-CH₂NH₂ |
| 248 | O | 1 | 3 | H | H | CO-cPr |
| 249 | O | 1 | 3 | H | H | CO-cBu |
| 250 | O | 1 | 3 | H | H | CO-cPen |
| 251 | O | 1 | 3 | H | H | CO-cHex |
| 252 | O | 1 | 3 | H | H | CO-2-thienyl |
| 253 | O | 1 | 3 | H | H | CO-2-furyl |
| 254 | O | 1 | 3 | H | H | CO-2-pyridyl |
| 255 | O | 1 | 3 | H | H | CO-3-pyridyl |
| 256 | O | 1 | 3 | H | H | CO-4-pyridyl |
| 257 | O | 1 | 3 | H | H | SO₂—Ph |
| 258 | O | 1 | 3 | H | H | CO—Ph-2-CO0H |
| 259 | O | 1 | 3 | H | H | CO—Ph-2-CONH₂ |
| 260 | O | 1 | 3 | H | H | CO—Ph-2-CH₂OH |
| 261 | O | 1 | 3 | H | H | CO—Ph-2-CH₂NH₂ |
| 262 | O | 1 | 3 | H | H | CO—Ph-3-COOH |
| 263 | O | 1 | 3 | H | H | CO—Ph-3-CONH₂ |
| 264 | O | 1 | 3 | H | H | CO—Ph-3-CH₂0H |
| 265 | O | 1 | 3 | H | H | CO—Ph-3-CH₂NH₂ |
| 266 | O | 1 | 3 | H | H | CO—Ph-4-COOH |
| 267 | O | 1 | 3 | H | H | CO—Ph-4-CONH₂ |
| 268 | O | 1 | 3 | H | H | CO—Ph-4-CH₂OH |
| 269 | O | 1 | 3 | H | H | CO—Ph-4-CH₂NH₂ |

TABLE 5-continued (I-5)

[Structure shown with OH, CH₃, H substituents on bicyclic β-lactam core with S linker to azetidine-thiazole with CH₂N(R⁷)(R⁸) group, and COOH]

| Cpd No. | X | n | position | R² | R⁷ | R⁸ |
|---|---|---|---|---|---|---|
| 270 | O | 2 | 3 | H | H | CO-cPr |
| 271 | O | 2 | 3 | H | H | CO-cBu |
| 272 | O | 2 | 3 | H | H | CO-cPen |
| 273 | O | 2 | 3 | H | H | CO-cHex |
| 274 | O | 2 | 3 | H | H | CO-2-thienyl |
| 275 | O | 2 | 3 | H | H | CO-2-furyl |
| 276 | O | 2 | 3 | H | H | CO-2-pyridyl |
| 277 | O | 2 | 3 | H | H | CO-3-pyridyl |
| 278 | O | 2 | 3 | H | H | CO-4-pyridyl |
| 279 | O | 2 | 3 | H | H | SO₂—Ph |
| 280 | O | 2 | 3 | H | H | CO—Ph-2-COOH |
| 281 | O | 2 | 3 | H | H | CO—Ph-2-CONH₂ |
| 282 | O | 2 | 3 | H | H | CO—Ph-2-CH₂OH |
| 283 | O | 2 | 3 | H | H | CO—Ph-2-CH₂NH₂ |
| 284 | O | 2 | 3 | H | H | CO—Ph-3-COOH |
| 285 | O | 2 | 3 | H | H | CO—Ph-3-CONH₂ |
| 286 | O | 2 | 3 | H | H | CO—Ph-3-CH₂OH |
| 287 | O | 2 | 3 | H | H | CO—Ph-3-CH₂NH₂ |
| 288 | O | 2 | 3 | H | H | CO—Ph-4-COOH |
| 289 | O | 2 | 3 | H | H | CO—Ph-4-CONH₂ |
| 290 | O | 2 | 3 | H | H | CO—Ph-4-CH₂OH |
| 291 | O | 2 | 3 | H | H | CO—Ph-4-CH₂NH₂ |
| 292 | O | 3 | 4 | H | H | CO-cPr |
| 293 | O | 3 | 4 | H | H | CO-cBu |
| 294 | O | 3 | 4 | H | H | CO-cPen |
| 295 | O | 3 | 4 | H | H | CO-cHex |
| 296 | O | 3 | 4 | H | H | CO-2-thienyl |
| 297 | O | 3 | 4 | H | H | CO-2-furyl |
| 298 | O | 3 | 4 | H | H | CO-2-pyridyl |
| 299 | O | 3 | 4 | H | H | CO-3-pyridyl |
| 300 | O | 3 | 4 | H | H | CO-4-pyridyl |
| 301 | O | 3 | 4 | H | H | SO₂—Ph |
| 302 | O | 3 | 4 | H | H | CO—Ph-2-COOH |
| 303 | O | 3 | 4 | H | H | CO—Ph-2-CONH₂ |
| 304 | O | 3 | 4 | H | H | CO—Ph-2-CH₂OH |
| 305 | O | 3 | 4 | H | H | CO—Ph-2-CH₂NH₂ |
| 306 | O | 3 | 4 | H | H | CO—Ph-3-COOH |
| 307 | O | 3 | 4 | H | H | CO—Ph-3-CONH₂ |
| 308 | O | 3 | 4 | H | H | CO—Ph-3-CH₂OH |
| 309 | O | 3 | 4 | H | H | CO—Ph-3-CH₂NH₂ |
| 310 | O | 3 | 4 | H | H | CO—Ph-4-COOH |
| 311 | O | 3 | 4 | H | H | CO—Ph-4-CONH₂ |
| 312 | O | 3 | 4 | H | H | CO—Ph-4-CH₂OH |
| 313 | O | 3 | 4 | H | H | CO—Ph-4-CH₂NH₂ |
| 314 | S | 1 | 3 | H | | CO—CH₂CH₂—CO |
| 315 | S | 1 | 3 | H | | CO-1,2-Ph—CO |
| 316 | S | 2 | 3 | H | | CO—CH₂CH₂CO |
| 317 | S | 2 | 3 | H | | CO-1,2-Ph—CO |
| 318 | S | 3 | 4 | H | | CO—CH₂CH₂CO |
| 319 | S | 3 | 4 | H | | CO-1,2-Ph—CO |
| 320 | O | 1 | 3 | H | | CO—CH₂CH₂CO |
| 321 | O | 1 | 3 | H | | CO-1,2-Ph—CO |
| 322 | O | 2 | 3 | H | | CO—CH₂CH₂CO |
| 323 | O | 2 | 3 | H | | CO-1,2-Ph—CO |
| 324 | O | 3 | 4 | H | | CO—CH₂CH₂—CO |
| 325 | O | 3 | 4 | H | | CO-1,2-Ph—CO |

Among the compounds exemplified in the above tables, the compounds of Exemplification compound numbers: 1, 2, 3, 13, 14, 15, 26, 27, 28, 38, 39, 40, 51, 52, 53, 63, 64, 65, 76, 77, 78, 88, 89, 90, 101, 102, 103, 113, 114, 115, 126, 127, 128, 138, 139 and 140 in Table 1 are preferred, the compounds of Exemplification compound numbers: 1, 2, 7, 22, 26, 31, 32, 34, 35, 39, 40, 44, 49, 50, 51, 52, 59, 62, 63, 64, 65, 89, 90, 95, 110, 114, 119, 120, 122, 123, 127, 128, 132, 137, 138, 139, 140, 147, 150, 151, 152, 153, 177, 178, 183, 198, 202, 207, 208, 210, 211, 215, 216, 220, 225, 226, 227, 228, 235, 238, 239, 240, 241, 265, 266, 271, 286, 290, 295, 296, 298, 299, 303, 304, 308, 313, 314, 315, 316, 323, 326, 327, 328, 329, 353, 354, 359, 374, 378, 383, 384, 386, 387, 391, 392, 396, 401, 402, 403, 404, 411, 414, 415, 416, 417, 441, 442, 447, 462, 466, 471, 472, 474, 475, 479, 480, 484, 489, 490, 491, 492, 499, 502, 503, 504, 505, 529, 530, 535, 550, 554, 559, 560, 562, 563, 567, 568, 572, 577, 578, 579, 580, 587, 590, 591, 592, 593, 617, 618, 623, 638, 640, 647, 648, 650, 651, 655, 656, 660, 665, 666, 675, 678, 679, 680, 681, 705, 706, 711, 726, 730, 735, 753, 754, 755, 756, 763, 766, 767, 768, 769, 793, 794, 799, 814, 818, 823, 824, 826, 827, 831, 832, 836, 841, 851, 854, 855, 856, 857, 881, 882, 887, 902, 906, 911, 912, 914, 915, 919, 920, 924, 929, 930, 931, 932, 939, 942, 943, 944, 945, 969, 970, 975, 990, 994, 999, 1000, 1002, 1003, 1007, 1008, 1012, 1017, 1018, 1019, 1020, 1027, 1030, 1031, 1032, 1033, 1057, 1058, 1059, 1060, 1063, 1064, 1065, 1066, 1067, 1068, 1069, 1070, 1071, 1072, 1073, 1074, 1075, 1076, 1077, 1078, 1081, 1082, 1083, 1084, 1085, 1086, 1087, 1088, 1089, 1090, 1091, 1092, 1093, 1094, 1095, 1096, 1099, 1100, 1101, 1102, 1103, 1104, 1105, 1106, 1107, 1108, 1109, 1110, 1111, 1112, 1113, 1114, 1117, 1118, 1119, 1120, 1121, 1122, 1123, 1124, 1125, 1126, 1127, 1128, 1129, 1130, 1131, 1132, 1135, 1136, 1137, 1138, 1139, 1140, 1141, 1142, 1143, 1144, 1145, 1146, 1147, 1148, 1149, 1150, 1153, 1154, 1155, 1156, 1157, 1158, 1159, 1160, 1161, 1162, 1163 and 1164 in Table 2 are preferred, the compounds of Exemplification compound numbers: 1, 3, 5, 7, 9 and 11 in Table 3 are preferred, the compounds of Exemplification compound numbers: 1, 2, 11, 12, 21, 22, 31, 32, 41, 42, 51, 52, 61, 62, 71, 72, 81, 82, 91, 92, 101, 102, 111 and 112 in Table 4 are preferred, and the compounds of Exemplification compound numbers: 1, 2, 4, 7, 8, 10, 12, 13, 14, 16, 17, 19, 22, 23, 25, 27, 28, 29, 31, 32, 34, 37, 38, 40, 42, 43, 44, 46, 47, 49, 52, 53, 55, 57, 58, 59, 61, 62, 64, 67, 68, 70, 72, 73, 74, 76, 77, 79, 82, 83, 85, 87, 88, 89, 91, 92, 94, 97, 98, 100, 102, 103, 104, 106, 107, 109, 112, 113, 115, 117, 118, 119, 121, 122, 124, 127, 128, 130, 132, 133, 134, 136, 137, 139, 142, 143, 145, 147, 148, 149, 151, 152, 154, 157, 158, 160, 162, 163, 164, 167, 168, 170, 173, 174, 176, 178, 179, 180, 182, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325 and 326 in Table 5 are preferred.

Of these, the compounds of Exemplification compound numbers: 3, 28, 53, 78, 103 and 128 in Table 1 are more preferred, the compounds of Exemplification compound numbers: 1, 2, 7, 26, 31, 32, 34, 35, 39, 40, 44, 49, 50, 51, 52, 59, 62, 63, 64, 65, 529, 530, 535, 554, 559, 560, 562, 563, 567, 568, 572, 577, 578, 579, 580, 587, 590, 591, 592, 593, 1057, 1058, 1059, 1060, 1063, 1069, 1070, 1071, 1072, 1073, 1074, 1111, 1112, 1113, 1114, 1117, 1123, 1124, 1125, 1126, 1127 and 1128 in Table 2 are more preferred, the compounds of Exemplification compound numbers: 1, 3, 7 and 11 in Table 3 are more preferred, the compounds of Exemplification compound numbers: 1, 2, 21, 22, 41, 42, 61, 62, 81, 82, 101 and 102 in Table 4 are more preferred, and the compounds of Exemplification compound numbers: 1, 2, 4, 7, 8, 91, 92, 94, 97, 98, 182, 183, 184, 185, 186, 187, 188, 189, 190, 191, 192, 193, 194, 195, 196, 197, 198, 199, 200, 201, 202, 203, 248, 249, 250, 251, 252, 253, 254, 255, 256, 257, 258, 259, 260, 261, 262, 263, 264, 265, 266, 267, 268, 269, 314, 315, 320 and 321 in Table 5 are more preferred.

The most preferred compounds are listed below:

(1R,5S,6S)-2-[1-(4-carbamoyl-1,3-thiazol-2-yl)azetidin-3-yl]thio-6-[(1R)-1-hydroxyethyl]-1-methyl-carbapen-2-em-3-carboxylic acid, (1R,5S,6S)-2-[1-(4-carbamoyl-1,3-oxazol-2-yl)azetidin-3-yl]thio-6-[(1R)-1-hydroxyethyl]-1-methyl-carbapen-2-em-3-carboxylic acid, (1R,5S,6S)-2-[1-(4-hydroxymethyl-1,3-thiazol-2-yl)azetidin-3-yl]thio-6-[(1R)-1-hydroxyethyl]-1-methyl-carbapen-2-em-3-carboxylic acid, (1R,5S,6S)-2-[1-(4-hydroxymethyl-1,3-oxazol-2-yl)azetidin-3-yl]thio-6-[(1R)-1-hydroxyethyl]-1-methyl-carbapen-2-em-3-carboxylic acid, (1R,5S,6S)-2-[1-(4-cyano-1,3-thiazol-2-yl)azetidin-3-yl]thio-6-[(1R)-1-hydroxyethyl]-1-methyl-carbapen-2-em-3-carboxylic acid, (1R,5S,6S)-2-[1-(4-cyano-1,3-oxazol-2-yl)azetidin-3-yl]thio-6-[(1R)-1-hydroxyethyl]-1-methyl-carbapen-2-em-3-carboxylic acid, (1R,5S,6S)-2-[1-(4-morpholinocarbonyl-1,3-thiazol-2-yl)azetidin-3-yl]thio-6-[(1R)-1-hydroxyethyl]-1-methyl-carbapen-2-em-3-carboxylic acid, (1R,5S,6S)-2-[1-(4-morpholinocarbonyl-1,3-oxazol-2-yl)azetidin-3-yl]thio-6-[(1R)-1-hydroxyethyl]-1-methyl-carbapen-2-em-3-carboxylic acid, (1R,5S,6S)-2-[1-(4-azetidinocarbonyl-1,3-thiazol-2-yl)azetidin-3-yl]thio-6-[(1R)-1-hydroxyethyl]-1-methyl-carbapen-2-em-3-carboxylic acid, (1R,5S,6S)-2-[1-(4-azetidinocarbonyl-1,3-oxazol-2-yl)azetidin-3-yl]thio-6-[(1R)-1-hydroxyethyl]-1-methyl-carbapen-2-em-3-carboxylic acid, (1R,5S,6S)-2-{1-[4-(3-aminoazetidino)carbonyl-1,3-thiazol-2-yl]azetidin-3-yl}thio-6-[(1R)-1-hydroxyethyl]-1-methyl-carbapen-2-em-3-carboxylic acid, (1R,5S,6S)-2-{1-[4-(3-aminoazetidino)carbonyl-1,3-oxazol-2-yl]azetidin-3-yl}thio-6-[(1R)-1-hydroxyethyl]-1-methyl-carbapen-2-em-3-carboxylic acid, (1R,5S,6S)-2-{1-[4-(3-hydroxyazetidino)carbonyl-1,3-thiazol-2-yl]azetidin-3-yl}thio-6-[(1R)-1-hydroxyethyl]-1-methyl-carbapen-2-em-3-carboxylic acid, (1R,5S,6S)-2-{1-[4-(3-hydroxyazetidino)carbonyl-1,3-oxazol-2-yl]azetidin-3-yl}thio-6-[(1R)-1-hydroxyethyl]-1-methyl-carbapen-2-em-3-carboxylic acid, (1R,5S,6S)-2-[1-(4-thiomorpholinocarbonyl-1,3-thiazol-2-yl)azetidin-3-yl]thio-6-[(1R)-1-hydroxyethyl]-1-methyl-carbapen-2-em-3-carboxylic acid, (1R,5S,6S)-2-[1-(4-thiomorpholinocarbonyl-1,3-oxazol-2-yl)azetidin-3-yl]thio-6-[(1R)-1-hydroxyethyl]-1-methyl-carbapen-2-em-3-carboxylic acid, (1R,5S,6S)-2-{1-[4-(piperidin-4-ylcarbamoyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-(piperidin-4-ylcarbamoyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-(azetidin-3-ylcarbamoyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-(azetidin-3-ylcarbamoyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-((3S)-pyrrolidin-3-ylcarbamoyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-((3S)-pyrrolidin-3-ylcarbamoyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-((3R)-pyrrolidin-3-ylcarbamoyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-((3R)-pyrrolidin-3-ylcarbamoyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-(piperazine-1-carbonyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-(piperazine-1-carbonyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-(2-amino-ethylcarbamoyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-(2-amino-ethylcarbamoyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-((1S)-1-aminomethyl-2-methyl-propylcarbamoyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-((1S)-1-aminomethyl-2-methyl-propylcarbamoyl)-1,3-oxazol-2-yl]azetidin-3-yl}thio-6-[(R)-1-hydroxyethyl]-1-methyl-carbapen-2-em-3-carboxylic acid, (1R,5S,6S)-2-(1-{4-[N-(2-amino-ethyl)-N-isopropyl-carbamoyl]-1,3-thiazol-2-yl}azetidin-3-yl}thio-6-[(R)-1-hydroxyethyl]-1-methyl-carbapen-2-em-3-carboxylic acid, (1R,5S,6S)-2-(1-{4-[N-(2-amino-ethyl)-N-isopropyl-carbamoyl]-1,3-oxazol-2-yl}azetidin-3-yl}thio-6-[(R)-1-hydroxyethyl]-1-methyl-carbapen-2-em-3-carboxylic acid, (1R,5S,6S)-2-(1-{4-[N-(2-hydroxy-ethyl)-N-isopropyl-carbamoyl]-1,3-thiazol-2-yl}azetidin-3-yl}thio-6-[(R)-1-hydroxyethyl]-1-methyl-carbapen-2-em-3-carboxylic acid, (1R,5S,6S)-2-(1-{4-[N-(2-hydroxy-ethyl)-N-isopropyl-carbamoyl]-1,3-oxazol-2-yl}azetidin-3-yl}thio-6-[(R)-1-hydroxyethyl]-1-methyl-carbapen-2-em-3-carboxylic acid, (1R,5S,6S)-2-[1-(4-aminomethyl-1,3-thiazol-2-yl)azetidin-3-yl]thio-6-[(R)-1-hydroxyethyl]-1-methyl-carbapen-2-em-3-carboxylic acid, (1R,5S,6S)-2-[1-(4-aminomethyl-1,3-oxazol-2-yl)azetidin-3-yl]thio-6-[(R)-1-hydroxyethyl]-1-methyl-carbapen-2-em-3-carboxylic acid, (1R,5S,6S)-2-{1-[4-(benzoylaminomethyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1'-[4-(benzoylaminomethyl)-1,3-oxazol-2-yl]azetidin-3-yl}thio-6-[(R)-1-hydroxyethyl]-1-methyl-carbapen-2-em-3-carboxylic acid, (1R,5S,6S)-2-{1-[4-(benzenesulfonylaminomethyl)-1,3-thiazol-2-yl]azetidin-3-yl}thio-6-[(R)-1-hydroxyethyl]-1-methyl-carbapen-2-em-3-carboxylic acid, (1R,5S,6S)-2-{1-[4-(benzenesulfonylaminomethyl)-1,3-oxazol-2-yl]azetidin-3-yl}thio-6-[(R)-1-hydroxyethyl]-1-methyl-carbapen-2-em-3-carboxylic acid, (1R,5S,6S)-2-(1-{4-[(thiophene-2-carbonylamino)methyl]-1,3-thiazol-2-yl}azetidin-3-yl)thio-6-[(R)-1-hydroxyethyl]-1-methyl-carbapen-2-em-3-carboxylic acid, (1R,5S,6S)-2-(1-{4-[(thiophene-2-carbonylamino)methyl]-1,3-oxazol-2-yl}azetidin-3-yl)thio-6-[(R)-1-hydroxyethyl]-1-methyl-carbapen-2-em-3-carboxylic acid, (1R,5S,6S)-2-(1-{4-[(furan-2-carbonylamino)methyl]-1,3-thiazol-2-yl}azetidin-3-yl)thio-6-[(R)-1-hydroxyethyl]-1-methyl-carbapen-2-em-3-carboxylic acid, and (1R,5S,6S)-2-(1-{4-[(furan-2-carbonylamino)methyl]-1,3-oxazol-2-yl}azetidin-3-yl)thio-6-[(R)-1-hydroxyethyl]-1-methyl-carbapen-2-em-3-carboxylic acid.

The 1-methylcarbapenem derivative represented by formula (I) of the present invention can be prepared by methods described in Process A and Process B below.

[Process A]

Process A is a method for preparing a compound of formula (I) by reacting a carbapenem derivative of formula (II) with a mercapto compound of formula (III) and subsequently carrying out a deprotection reaction.

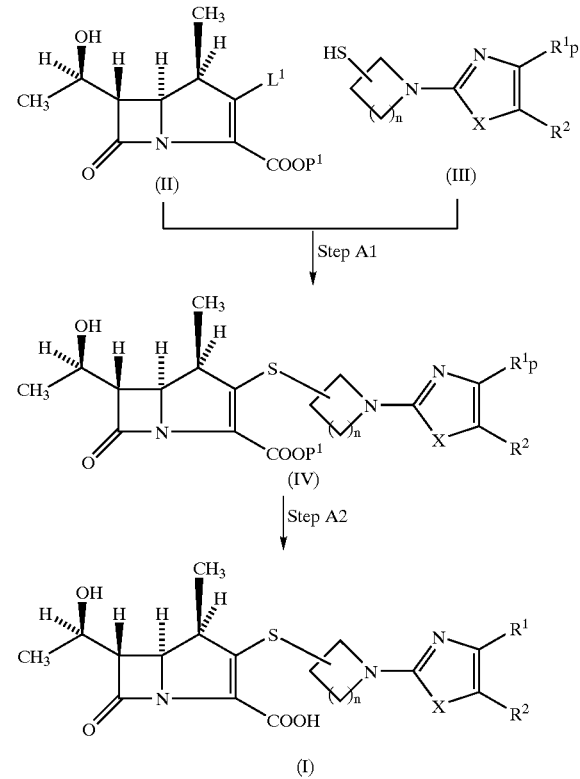

In the above formulae, $R^1$, $R^2$, X and n have the same meanings as defined above; $L^1$ represents a group to be eliminated; $P^1$ represents a protective group of a carboxyl group; and $R^1p$ represents $R^1$ which may have a protective group.

Examples of the "protective group of a carboxyl group" suitable as $P^1$ include a benzyl group which may have a substituent (the substituent is nitro, methyl, chloro or methoxy) such as benzyl, 4-methoxybenzyl, 4-nitrobenzyl or 2-nitrobenzyl; a benzhydryl group; an allyl group which may have a substituent at the 2-position (the substituent is chloro or methyl) such as allyl, 2-chloroallyl or 2-methylallyl; and a group forming the above pharmacologically acceptable ester, of which a benzyl group which may have a substituent (particularly a 4-nitrobenzyl group) is preferred.

Examples of the "group to be eliminated" as $L^1$ include a group of formula —$OR^{11}$ or —$S(O)R^{12}$.

Examples of the group $R^{11}$ include a $C_1$–$C_4$ alkanesulfonyl group such as a methanesulfonyl, trifluoromethanesulfonyl, ethanesulfonyl, propanesulfonyl, isopropanesulfonyl or butanesulfonyl group; a $C_6$–$C_{10}$ arylsulfonyl group such as phenylsulfonyl, tolylsulfonyl or naphthylsulfonyl; a di-$C_1$–$C_6$ alkylphosphoryl group such as dimethylphosphoryl, diethylphosphoryl, dipropylphosphoryl, diisopropylphosphoryl, dibutylphosphoryl, dipentylphosphoryl or dihexylphosphoryl; or a di-$C_6$–$C_{10}$ arylphosphoryl group such as diphenylphosphoryl or ditolylphosphoryl, of which a diphenylphosphoryl group is preferred.

Examples of the group $R^{12}$ include a $C_1$–$C_4$ alkyl group such as methyl, ethyl, propyl or isopropyl; a halogeno $C_1$–$C_4$ alkyl group such as fluoromethyl, chloromethyl, fluoroethyl, chloroethyl, fluoropropyl, difluoromethyl, difluoroethyl, dichloroethyl, trifluoromethyl or trifluoroethyl; a 2-acetylaminoethyl group; a 2-acetylaminovinyl group; or a $C_6$–$C_{10}$ aryl group (the aryl group may have from 1 to 3 substituents, which may be the same or different, and the substituents may comprise a halogen atom such as fluorine, chlorine or bromine; a $C_1$–$C_4$ alkyl group such as methyl, ethyl, propyl or isopropyl; a $C_1$–$C_4$ alkoxy group such as methoxy, ethoxy, propoxy or isopropoxy; a ($C_1$–$C_4$ alkoxy) carbonyl group such as methoxycarbonyl, ethoxycarbonyl or t-butoxycarbonyl; carbamoyl, a mono- or di-($C_1$–$C_4$ alkyl) carbamoyl group; a nitro group; a hydroxyl group; or a cyano group) such as phenyl or naphthyl which may have substituents; or a heteroaryl group which may have one or two nitrogen atoms (the heteroaryl group may have from one to three substituents, which may be the same or different, and the substituents may comprise a halogen atom such as fluorine, chlorine or bromine; a $C_1$–$C_4$ alkyl group such as methyl, ethyl, propyl or isopropyl; a $C_1$–$C_4$ alkoxy group such as methoxy, ethoxy, propoxy or isopropoxy; a ($C_1$–$C_4$ alkoxy)carbonyl group such as methoxycarbonyl, ethoxycarbonyl or t-butoxycarbonyl; carbamoyl or a mono- or di-($C_1$–$C_4$ alkyl)carbamoyl group; a nitro group; a hydroxyl group; or a cyano group) such as pyridyl or pyrimidinyl which may have substituents.

Examples of the "protective group of a hydroxyl group" included in the definition of $R^1p$ include a benzyloxycarbonyl group which may be substituted (the substituent may comprise nitro, methyl, chloro or methoxy) such as benzyloxycarbonyl, 4-nitrobenzyloxycarbonyl, 4-chlorobenzyloxycarbonyl or 4-methoxybenzyloxycarbonyl; an allyloxycarbonyl group which may be substituted at the 2-position (the substituent may comprise chloro or methyl) such as allyloxycarbonyl, 2-chloroallyloxycarbonyl and 2-methylallyloxycarbonyl; a tri-($C_1$–$C_4$ alkyl)silyl group such as trimethylsilyl, triethylsilyl or t-butyldimethylsilyl; and a group forming the above pharmacologically acceptable ester, of which a tri-($C_1$–$C_4$ alkyl)silyl group (particularly a t-butyldimethylsilyl group) is preferred.

Examples of the "protective group of an amino group" included in $R^1p$ include an allyloxycarbonyl group which may be substituted at the 2-position (the substituent may comprise chloro or methyl) such as allyloxycarbonyl, 2-chloroallyloxycarbonyl and 2-methylallyloxycarbonyl; and a benzyloxycarbonyl group which may be substituted (the substituent may comprise methyl, methoxy, chloro or nitro) such as benzyloxycarbonyl, 4-methylbenzyloxycarbonyl, 4-methoxybenzyloxycarbonyl, 4-chlorobenzyloxycarbonyl or 4-nitrobenzyloxycarbonyl, of which an allyloxycarbonyl group or a 4-nitrobenzyloxycarbonyl group is preferred and a 4-nitrobenzyloxycarbonyl group is more preferred.

The protective group used as the above $P^1$ can be employed as the "protective group of a carboxyl group" included in $R^1p$.

The present process is a process in which a compound of formula (IV) is prepared by reacting a compound of formula (II) with a compound of formula (III) in the presence of a base (Step A1) and a compound of formula (I) is subsequently prepared by removing any protective groups (Step A2). In the case where $L^1$ represents a group represented by the formula: —$OR^{11}$, the compound of formula (II) which is used as a starting material is prepared by a method described in D. H. Shih et al., Heterocycles 21, 29 (1984) or a method analogous to it. In the case where $L^1$ represents a group represented by formula: —$S(O)R^{12}$, the starting compound (II) is prepared by a method described in Japanese Patent Application (Kokai) No. Sho 62-30781 or a method analogous to it. Each step will be described below.

(Step A1)

Step A1 is a step to prepare a compound of formula (IV), which is accomplished by reacting a compound of formula (II) with a mercaptan derivative of formula (III) in the presence of a base in an inert solvent.

There is no particular limitation on the nature of the solvent to be employed, provided that it has no adverse effect on the reaction and it dissolves the starting materials to a certain extent. Examples of suitable solvents include halogenated hydrocarbons such as methylene chloride, 1,2-dichloroethane or chloroform; nitriles such as acetonitrile; amides such as N,N-dimethylformamide or N,N-dimethylacetamide; esters such as ethyl acetate or methyl acetate; and ethers such as diethyl ether, tetrahydrofuran or dioxane, of which acetonitrile, N,N-dimethylformamide or tetrahydrofuran is preferred and acetonitrile is particularly preferred.

Preferred examples of the base to be employed include organic amines such as triethylamine, diisopropylethylamine, pyridine or dimethylaminopyridine; or inorganic bases such as potassium carbonate, sodium carbonate or sodium hydrogencarbonate, of which organic amines (particularly diisopropylethylamine) are preferred.

The reaction is usually carried out at a temperature from –20° C. to 40° C. (preferably from –10° C. to 20° C.). The reaction time ranges from 30 minutes to 108 hours (preferably from one hour to 18 hours).

After completion of the reaction, the desired compound of formula (IV), which is the product of the present step, is obtained from the reaction mixture by known means; for example, adding to the reaction mixture or to the residue obtained by distilling off the solvent from the reaction mixture an organic solvent which is not miscible with water, followed by washing with water and distilling off the solvent. If necessary, the desired compound thus obtained can be further purified by known means, for example, by recrystallization, reprecipitation or chromatography. It is also possible to subject the desired compound of formula (IV) to the next subsequent step without isolation, if desired.

(Step A2)

Step A2 is a step to convert a compound of formula (IV) to a compound of formula (I), which is accomplished by removal of any protective groups contained in the compound of formula (IV).

Although the method for removal of a protective group depends on the kind of the protective group, it is accomplished by a method ordinarily employed in the field of organic synthetic chemistry (for example, a method described in Protective Groups in Organic Synthesis, Second Edition, John Wiley & Sons, Inc. 1991 written by T. W. Greene and P. G. M. Wuts).

(1) When the protective group is a benzyl group which may have a substituent, a benzhydryl group or a benzyloxycarbonyl group which may have a substituent, these protective groups can be removed by reaction with hydrogen in the presence of a catalytic reducing agent in a solvent.

Examples of the catalytic reducing agent to be employed include a palladium-carbon catalyst, a platinum catalyst or a rhodium-carbon catalyst, of which a palladium-carbon catalyst is preferred.

There is no particular limitation on the nature of the solvent to be employed, provided that it has no adverse effect on the reaction and it dissolves the starting materials to a certain extent. Preferred examples of suitable solvents include alcohols such as methanol or ethanol; ethers such as tetrahydrofuran or dioxane; and a mixture of these organic solvents and water, of which a mixture of tetrahydrofuran and water is preferred.

The reaction temperature usually ranges from 0° C. to 50° C. (preferably from 10° C. to 40° C.). Although the reaction time depends on the starting compound and the nature of the catalyst, it usually ranges from 5 minutes to 12 hours (preferably from 30 minutes to 4 hours).

After completion of the reaction, the desired compound is obtained from the reaction mixture by known means. For example, the desired compound can be obtained by filtering off insolubles, such as the catalyst, from the reaction mixture and then distilling off the solvent. If necessary, the compound thus obtained can be purified by conventional procedures such as recrystallization, preparative thin layer chromatography or column chromatography.

(2) When the protective group is an allyl group which may be substituted or an allyloxycarbonyl group which may be substituted, these protective groups can be removed by reacting with a tri-($C_1$–$C_6$ alkyl)tin hydride and an organic carboxylic acid alkali metal salt in the presence of a palladium compound in a solvent. Organic bases or organic substances for capturing allyl groups may be added.

The palladium compound may preferably comprise bis(triphenylphosphine)palladium chloride or tetrakis(triphenylphosphine)palladium. The trialkyltin hydride may preferably comprise tributyltin hydride. The organic carboxylic acid alkali metal salt may preferably comprise potassium 2-ethylhexanoate or sodium 2-ethylhexanoate. The organic base for capturing allyl groups may preferably comprise morpholine and the organic substance for capturing allyl groups may preferably comprise dimedone.

Preferable combinations of deprotecting agents may include a combination of bis(triphenylphosphine)palladium chloride and tributyltin hydride or a combination of tetrakis(triphenylphosphine)palladium and potassium 2-ethylhexanoate.

There is no particular limitation on the nature of the solvent to be employed, provided that it has no adverse effect on the reaction and it dissolves the starting materials to a certain extent. Examples of suitable solvents include halogenated hydrocarbons such as methylene chloride, chloroform or 1,2-dichloroethane; esters such as ethyl acetate; ethers such as tetrahydrofuran, dioxane or 1,2-dimethoxyethane; nitriles such as acetonitrile; alcohols such as methanol, ethanol or propanol; water; or a mixture of these solvents, of which methylene chloride, ethyl acetate or a solvent mixture thereof is preferred.

Although there is no particular limitation on the reaction temperature, the reaction is usually carried out at a temperature from −20° C. to 100° C. (preferably from 0° C. to 60° C.). The reaction time usually ranges from 30 minutes to 48 hours (preferably from 30 minutes to 12 hours).

After completion of the reaction, the desired compound is obtained from the reaction mixture by known means. For example, the desired compound can be obtained by filtering off insolubles precipitated from the reaction mixture and then distilling off the solvent. If necessary, the compound thus obtained can be purified by conventional procedures such as recrystallization, preparative thin layer chromatography or column chromatography.

(3) When the protective group is a silyl-based protective group, this protective group can be removed by treatment with fluoride anion source such as tetrabutylammonium fluoride, hydrofluoric acid, hydrofluoric acid-pyridine or potassium fluoride, or treating with an organic acid such as acetic acid, methanesulfonic acid, para-toluenesulfonic acid, trifluoroacetic acid or trifluoromethanesulfonic acid, or an inorganic acid such as hydrochloric acid, in a solvent.

When the protective group is removed by a fluoride anion, the reaction sometimes progresses under mild conditions by the addition of an organic acid such as formic acid, acetic acid or propionic acid.

There is no particular limitation on the nature of the solvent to be employed, provided that it has no adverse effect on the reaction and it dissolves the starting materials to a certain extent. Preferred examples of suitable solvents include ethers such as diethyl ether, diisopropyl ether, tetrahydrofuran, dioxane, dimethoxyethane or diethylene glycol dimethyl ether; nitriles such as acetonitrile or isobutyronitrile; water; organic acids such as acetic acid; and a mixture of these solvents.

The reaction temperature usually ranges from 0° C. to 100° C. (preferably from 10° C. to 30° C.). Although there is no particular limitation on the reaction time, it usually ranges from one hour to 24 hours (preferably from one hour to 4 hours).

After completion of the reaction, the desired compound is obtained from the reaction mixture by known means, for example, adding to the reaction mixture or to the residue obtained by distilling off the solvent from the reaction mixture an organic solvent which is not miscible with water, followed by washing with water and distilling off the solvent. If necessary, the desired compound thus obtained can be further purified by known means, for example, recrystallization, reprecipitation or chromatography.

(4) When the protective group is a group forming a pharmacologically acceptable ester of a carboxyl group or a hydroxyl group, these protective groups are removed by reacting a hydrolase thereon in water or a mixture of water and an organic solvent.

Preferred examples of the organic solvent mixed with water include an ether or alcohol miscible with water such as tetrahydrofuran, dioxane, methanol, ethanol or propanol.

It is preferred that an alkali metal salt such as sodium phosphate, sodium acetate or sodium hydrogencarbonate is added to water or a mixture of water and an organic solvent or the pH is maintained in the range of from 6 to 8 using a pH buffer solution such as a phosphoric acid buffer solution.

There is no limitation on the nature of the hydrolase provided that it can hydrolyze an ester bond. Examples of such a hydrolase include esterase derived from pig liver.

The reaction time usually ranges from 10 minutes to 8 hours (preferably from 30 minutes to 2 hours) and the reaction temperature from 10° C. to 50° C. (preferably from 30° C. to 40° C.).

After completion of the reaction, the desired compound can be isolated and purified by ion exchange chromatography, reverse phase column chromatography, reprecipitation, recrystallization, etc.

When the compound of formula (IV) contains two or more kinds of protective groups, the desired compound of formula (I) can be obtained by successively carrying out the above deprotection reactions in combination. When the pharmacologically acceptable ester of the compound of formula (I) is desired, it is not necessary to remove the group forming the pharmacologically acceptable ester as the protective group.

The compound of formula (I) thus obtained can be converted to a pharmacologically acceptable salt or ester, if necessary, according to a method or a technology known in the field of medicinal chemistry, particularly that of β-lactam based antibiotics.

The pharmacologically acceptable esters of the carboxyl group of the compound of formula (I) can be prepared by reacting a halogenated compound corresponding to the desired ester residue of the compound of formula (I) in the presence of a base in a solvent.

Examples of the halogenated compound to be employed include a chloride, a bromide or an iodide, of which an iodide is preferred. When a chloride or a bromide is used, the reaction can be promoted by adding a catalytic amount of sodium iodide to the reaction solution.

Examples of the base to be employed include organic amines such as triethylamine, diisopropylethylamine, 4-dimethylaminopyridine or pyridine; and alkali metal carbonates such as potassium carbonate, sodium carbonate or sodium hydrogencarbonate, of which organic amines (particularly 4-dimethylaminopyridine) are preferred.

There is no particular limitation on the nature of the solvent to be employed, provided that it has no adverse effect on the reaction and it dissolves the starting materials to a certain extent. Examples of the solvent include nitriles such as acetonitrile; amides such as N,N-dimethylformamide; and halogenated hydrocarbons such as methylene chloride, of which amides (particularly dimethylacetamide) or nitrites (particularly acetonitrile) are preferred.

The reaction temperature usually ranges from −20° C. to 50° C. (preferably from −10° C. to 20° C.) and the reaction time usually ranges from 0.5 hours to 108 hours (preferably from one hour to 24 hours).

The compound previously isolated as a salt by reacting the compound of formula (I) with a base can be also reacted with the halides as mentioned above.

Alternatively, the compound of formula (I) can be prepared by reacting an alcohol corresponding to the desired ester residue on the compound of formula (I) in the presence of a condensation agent and a base.

Examples of the condensation agent include Mitsunobu reagents such as diethyl azodicarboxylate; phosphoric ester-based condensation agents such as diphenylphosphorylazide; carbodiimide-based condensation agents such as dicyclohexylcarbodiimide or 1-ethyl-3-(3-dimethylaminopropyl)carbodiimide; and onium based condensation agents such as 2-chloro-1-methylpyridinium iodide.

Example of the base to be employed include organic amines such as triethylamine, tributylamine, diisopropylethylamine or 4-dimethylaminopyridine.

Examples of other additives include phosphines such as triphenylphosphine and tributylphosphine; and alcohols for forming an active ester such as 1-hydroxybenzotriazole.

Examples of the solvent include halogenated hydrocarbons such as methylene chloride or dichloroethane; amides such as N,N-dimethylformamide; nitriles such as acetonitrile; and ethers such as tetrahydrofuran.

Examples of a preferable combination of these include diethyl azodicarboxylate and triphenylphosphine; 2-chloro-1-methylpyridinium iodide and tributylamine or triethylamine; 1-ethyl-3-(3-dimethylaminopropyl)carbodiimide and 4-dimethylaminopyridine or 1-hydroxybenzotriazole.

After completion of the reaction, the desired compound is obtained from the reaction mixture by known means, for example, adding to the reaction mixture, or to the residue obtained by distilling off the solvent from the reaction mixture, an organic solvent which is not miscible with water, followed by washing with water and distilling off the solvent. If necessary, the desired compound thus obtained can be further purified by known means, for example, recrystallization, reprecipitation or chromatography.

[Process B]

Process B is a method to prepare a compound of formula (III) used as a starting material in Process A.

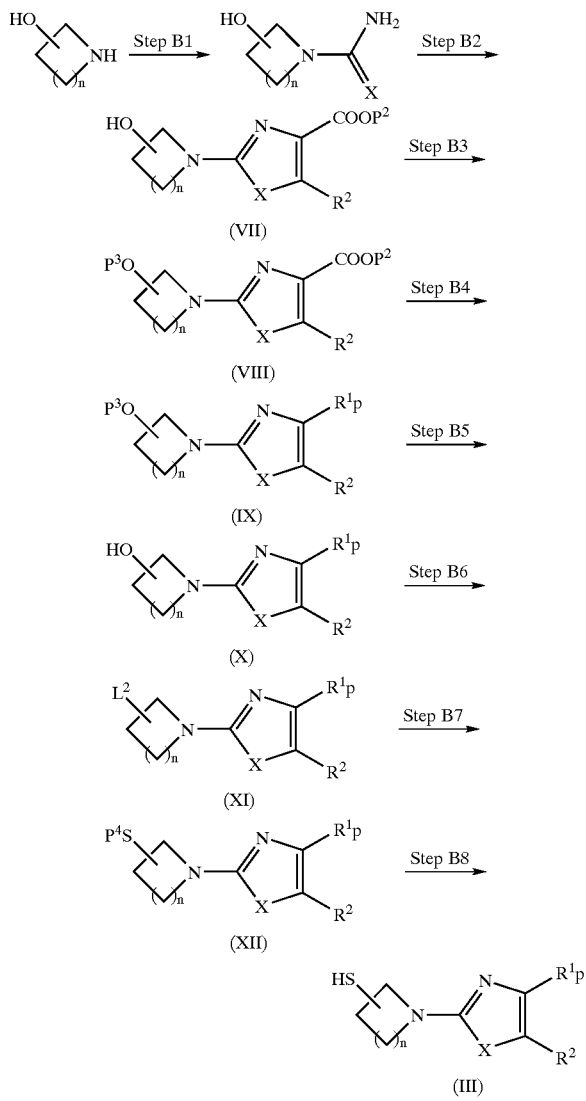

In the above scheme:

$R^1p$, $R^2$, X and n have the same meanings as defined above;

$P^2$ represents a protective group of a carboxyl group; examples of $P^2$ include a $C_1$–$C_4$ alkyl group such as methyl, ethyl, propyl or butyl; and a benzyl group which may be substituted such as benzyl or 4-methoxybenzyl, of which a $C_1$–$C_4$ alkyl group is preferred and an ethyl group is particularly preferred;

$P^3$ represents a protective group of a hydroxyl group; examples of $P^3$ include a silyl-based protective group such as trimethylsilyl, triethylsilyl, t-butyldimethylsilyl or t-butyldiphenylsilyl, of which a t-butyldiphenylsilyl group is preferred;

$L^2$ represents a leaving group; examples of $L^2$ include a halogen atom such as a chlorine atom, a bromine atom or an iodine atom; a $C_1$–$C_4$ alkylsulfonyloxy group which may be substituted by fluorine or a benzenesulfonyloxy group which may be substituted by alkyl such as methanesulfonyloxy, ethanesulfonyloxy, trifluoromethanesulfonyloxy, benzenesulfonyloxy or toluenesulfonyloxy, of which a $C_1$–$C_4$ alkylsulfonyloxy group which may be substituted by fluorine is preferred; and $P^4$ represents a protective group of a mercapto group; examples of $P^4$ include a $C_1$–$C_4$ alkanoyl group such as formyl, acetyl, propionyl or butyryl and a benzoyl group which may be substituted such as benzoyl, toluoyl or anisoyl, of which a $C_1$–$C_4$ alkanoyl group (particularly an acetyl group) is preferred.

(Step B1)

Step B1 is a step for preparing a compound of formula (VI) by introducing an amide group represented by the formula C(=X)NH$_2$ to the nitrogen atom of a compound of formula (V).

(1) This step is accomplished by reacting a cyanate or thiocyanate with the compound of formula (V) in a solvent.

There is no particular limitation on the nature of the solvent to be employed, provided that it has no adverse effect on the reaction and it dissolves the starting materials to a certain extent. Examples of the solvent include ethers such as tetrahydrofuran or diethyl ether; halogenated hydrocarbons such as methylene chloride or dichloroethane; and a mixture of these solvents and water, of which a mixture of an ether and water (particularly a mixture of tetrahydrofuran and water) is preferred.

Examples of the salt of cyanic acid or thiocyanic acid include alkali metal salts such as a sodium salt or a potassium salt; an ammonium salt; or organic ammonium salts such as a triethylammonium salt, of which alkali metal salts (particularly a potassium salt) are preferred.

Acids can be also employed in order to convert a cyanate or a thiocyanate to the corresponding acid in the system. Examples of such an acid include organic acids such as acetic acid and mineral acids such as hydrochloric acid, of which acetic acid or hydrochloric acid is preferred.

The reaction temperature usually ranges from –20° C. to 150° C. (preferably from –10° C. to 100° C.) and the reaction time usually ranges from 0.5 to 108 hours (preferably from 1 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(2) Alternatively, this step may be accomplished by the following process. The present method comprises a reaction for preparing the following compound of formula (XIII) from a compound of formula (V) and a reaction for preparing a compound of formula (VI) from the compound of formula (XIII).

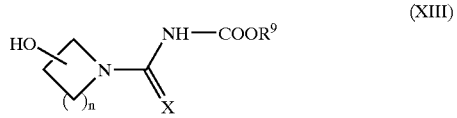
(XIII)

In the above formula, X and n have the same meanings as defined above and $R^9$ represents a $C_1$–$C_4$ alkyl group (preferably an ethyl group).

The step for preparing a compound (XIII) from a compound (V) is accomplished by reacting a compound represented by the formula X=C=N—COOR$^9$ (wherein X and $R^9$ have the same meanings as defined above) on the compound of formula (V) in a solvent.

There is no particular limitation on the nature of the solvent to be employed, provided that it has no adverse effect on the reaction and it dissolves the starting materials to a certain extent. Examples of the solvent include ethers such as tetrahydrofuran or diethyl ether; halogenated hydrocarbons such as methylene chloride or dichloroethane; and a mixture of these solvents and water, of which an ether or a mixture of an ether and water (particularly tetrahydrofuran or a mixture of tetrahydrofuran and water) is preferred.

The reaction temperature usually ranges from −20° C. to 150° C. (preferably from −10° C. to 50° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

The step for preparing a compound of formula (VI) from a compound of formula (XIII) is accomplished by reacting a base with the compound (XIII) in a solvent.

There is no particular limitation on the nature of the solvent to be employed, provided that it has no adverse effect on the reaction and it dissolves the starting materials to a certain extent. Examples of the solvent include alcohols such as methanol or ethanol; ethers such as tetrahydrofuran or diethyl ether; and a mixture of these solvents and water, of which an alcohol or a mixture of an alcohol and water (particularly ethanol or a mixture of ethanol and water) is preferred.

Examples of the base to be employed include inorganic bases such as sodium hydroxide, potassium hydroxide, sodium hydrogencarbonate, sodium carbonate and potassium carbonate; and organic bases such as sodium methoxide and sodium ethoxide, of which sodium hydroxide is preferred.

The reaction temperature usually ranges from −20° C. to 15° C. (preferably from −10° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(Step B2)

Step B2 is a step for preparing a compound of formula (VII) by subjecting an amide group of a compound of formula (VI) to a ring-closure reaction.

This step is accomplished by reacting a compound represented by the formula $R^2CHL^3COCOOP^2$ (wherein $R^2$ and $P^2$ have the same meanings as defined above and $L^3$ represents a leaving group) with the compound of formula (VI) in the presence of a base in a solvent. Preferred examples of the leaving group $L^3$ include a halogen atom, of which a bromine atom is particularly preferred.

There is no particular limitation on the nature of the solvent to be employed, provided that it has no adverse effect on the reaction and it dissolves the starting materials to a certain extent. Examples of the solvent include alcohols such as methanol or ethanol; ethers such as tetrahydrofuran or diethyl ether; halogenated hydrocarbons such as methylene chloride or dichloroethane; and amides such as N,N-dimethylformamide, of which alcohols (particularly ethanol) are preferred.

Examples of the base to be employed include organic bases such as triethylamine and diisopropylamine; and inorganic bases such as sodium carbonate, potassium carbonate and sodium hydrogencarbonate, of which organic bases (particularly triethylamine) are preferred.

The reaction temperature usually ranges from −20° C. to 150° C. (preferably from −10° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(Step B3)

Step B3 is a step for preparing a compound of formula (VIII) by introducing a protective group $P^3$ to a hydroxyl group of a compound of formula (VII).

This step can be accomplished by a method usually used in the field of synthetic organic chemistry (for example, a method described in Protective Groups in Organic Synthesis, Second Edition, John Wiley & Sons, Inc. 1991, authors T. W. Greene and P. G. M. Wuts).

Introduction of a silyl-based protective group is accomplished by reacting a silyl halide or a silyl triflate having a desired substituent with a compound of formula (VII) in the presence of a base in a solvent.

Examples of the silyl halide include trimethylsilyl chloride, triethylsilyl chloride, t-butyldimethylsilyl chloride and t-butyldiphenylsilyl chloride, of which t-butyldiphenylsilyl chloride is preferred.

Examples of the silyl triflate include trimethylsilyl triflate, triethylsilyl triflate, t-butyldimethylsilyl triflate and t-butyldiphenylsilyl triflate, of which t-butyldiphenylsilyl triflate is preferred.

There is no particular limitation on the nature of the solvent to be employed, provided that it has no adverse effect on the reaction and it dissolves the starting materials to a certain extent. Examples of the solvent include amides such as dimethylformamide; halogenated hydrocarbons such as methylene chloride or dichloroethane; and ethers such as tetrahydrofuran or diethyl ether, of which amides (particularly dimethylformamide) or halogenated hydrocarbons (particularly methylene chloride) are preferred.

Examples of the base to be employed include organic bases such as imidazole, triethylamine, lutidine, pyridine or dimethylaminopyridine, of which imidazole or 2,6-lutidine is preferred.

The reaction temperature usually ranges from −20° C. to 50° C. (preferably from −10° C. to 40° C.) and the reaction time usually ranges from 0.5 to 108 hours (preferably from 1 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(Step B4)

Step B4 is a step for preparing a compound of formula (IX) by converting a group represented by the formula $COOP^2$ in a compound (VIII) to a desired group $R^1p$.

This step can be accomplished by applying a functional group conversion reaction usually used in the field of synthetic organic chemistry. Details are described in Process C to Process H, below.

(Step B5)

Step B5 is a step for preparing a compound of formula (X) by removal of the protective group $P^3$ of a hydroxyl group of the compound of formula (IX).

This step can be accomplished by a method usually used in the field of synthetic organic chemistry (for example, a method described in Protective Groups in Organic Synthesis, Second Edition, John Wiley & Sons, Inc. 1991, authors T. W. Greene and P. G. M. Wuts).

When the protective group $P^3$ of a hydroxyl group is a silyl-based protective group, elimination thereof is accomplished in a similar manner to the method described in Step A2 (3).

(Step B6)

Step B6 is a step to prepare a compound (XI) by converting the hydroxyl group of a compound of formula (X) to a leaving group $L^2$.

(1) When the leaving group $L^2$ represents a type of sulfonyloxy group, this step is accomplished by reacting a sulfonylating agent with a compound of formula (X) in the presence of a base in a solvent.

Examples of the sulfonylating agent to be employed include methanesulfonyl chloride, ethanesulfonyl chloride, trifluoromethanesulfonyl chloride, benzenesulfonyl chloride or toluenesulfonyl chloride, of which methanesulfonyl chloride is preferred.

There is no particular limitation on the nature of the solvent to be employed, provided that it has no adverse effect on the reaction and it dissolves the starting materials to a certain extent. Examples of the solvent include halogenated hydrocarbons such as methylene chloride, dichloroethane or chloroform; and ethers such as tetrahydrofuran or diethyl ether, of which halogenated hydrocarbons (particularly methylene chloride) are preferred.

Examples of the base to be employed include organic bases such as triethylamine, diisopropylethylamine, pyridine or dimethylaminopyridine, of which triethylamine is preferred.

The reaction temperature usually ranges from −20° C. to 80° C. (preferably from −10° C. to 40° C.) and the reaction time usually ranges from 0.5 to 108 hours (preferably from 1 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(2) When the leaving group $L^2$ is a halogen atom, this step is accomplished by reacting a halogenating agent with a compound of formula (X) in a solvent.

Examples of the halogenating agent to be employed include phosphorus pentachloride, thionyl chloride, phosphorus oxychloride, iodine, carbon tetrabromide, carbon tetrachloride, N-chlorosuccinimide, N-bromosuccinimide or diethylaminosulfur trifluoride, of which carbon tetrabromide is preferred.

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane; and ethers such as tetrahydrofuran or diethyl ether, of which halogenated hydrocarbons (particularly methylene chloride) are preferred.

Examples of the additives to be employed include phosphines such as triphenylphosphine and tributylphosphine, of which triphenylphosphine is preferred.

The reaction temperature usually ranges from −20° C. to 100° C. (preferably from −10° C. to 50° C.) and the reaction time usually ranges from 10 minutes to 108 hours (preferably from 0.5 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(Step B7)

Step B7 is a step for preparing a compound of formula (XII) by converting the leaving group $L^2$ of the compound of formula (XI) to a protected mercapto group.

This step is accomplished by reacting a mercapto-forming agent with a compound of formula (XI) in a solvent.

Examples of the mercapto forming agent to be employed include alkali metal salts of thiocarboxylic acids such as sodium thioacetate, potassium thioacetate, sodium thiopropionate or sodium thiobenzoate; or alkali metal salts of 4-methoxybenzyl mercaptan, of which potassium thioacetate is preferred.

There is no particular limitation on the nature of the solvent to be employed, provided that it has no adverse effect on the reaction and it dissolves the starting materials to a certain extent. Examples of the solvent include ethers such as tetrahydrofuran or dioxane; acetates such as ethyl acetate or methyl acetate; nitriles such as acetonitrile; and amides such as dimethylformamide or dimethylacetamide, of which an amide (particularly dimethylformamide) is preferred.

The reaction temperature usually ranges from −20° C. to 150° C. (preferably from 0° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

(Step B8)

Step B8 is a step for preparing a compound of formula (III) by removing a protective group $P^4$ of the mercapto group of the compound of formula (XII).

(1) When the protective group $P^4$ is an alkanoyl group or an arylcarbonyl group, this step is accomplished by reacting a salt of a hydrazine compound with a compound (XII) in a solvent.

Examples of the salt of the hydrazine compound include hydrazine/acetic acid or N,N-dimethylhydrazine/acetic acid, of which hydrazine/acetic acid is preferred.

As the solvent to be employed, the solvents used in the above first step can be used.

The reaction temperature is not particularly limited and usually ranges from −10° C. to 40° C. (preferably from 10° C. to 30° C.). Although the reaction time depends on the solvent, the reaction temperature and the nature of the reagent, it usually ranges from 30 minutes to 24 hours (preferably from one hour to 8 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, washing with water and distilling off the solvent. The desired compound thus obtained can be further purified, if necessary, by conventional procedures such as recrystallization, reprecipitation or chromatography.

When a salt of a hydrazine compound is used as the deprotecting agent, the compound of formula (III) can be used as a starting material of the above Step A1 without isolating it from the reaction solution.

The present step is also accomplished by reacting a base with the compound of formula (XII) in a solvent.

Examples of the base to be employed include salts of an alkali metal such as sodium hydroxide, potassium hydroxide, potassium carbonate, sodium carbonate, sodium methoxide or sodium ethoxide, of which sodium methoxide is preferred.

There is no particular limitation on the nature of the solvent to be employed, provided that it has no adverse effect on the reaction and it dissolves the starting materials to a certain extent. Examples of the solvent include alcohols such as methanol or ethanol; ethers such as tetrahydrofuran or diethyl ether; amides such as dimethylformamide; and halogenated hydrocarbons such as methylene chloride or dichloroethane, of which alcohols (particularly methanol) are preferred.

The reaction temperature usually ranges from −20° C. to 100° C. (preferably from −10° C. to 40° C.) and the reaction time usually ranges from 10 minutes to 108 hours (preferably from 0.5 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(2) When $P^4$ is a 4-methoxybenzyl group, this step is accomplished by reacting an acid with the compound of formula (XII) in a solvent.

Examples of the acid to be employed include sulfonic acids such as methanesulfonic acid or trifluoromethanesulfonic acid, of which trifluoromethanesulfonic acid is preferred. The reaction can be accelerated by co-existing anisole or thioanisole.

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane; ethers such as tetrahydrofuran or diethyl ether; and optionally substituted acetic acids such as acetic acid and trifluoroacetic acid, of which optionally substituted acetic acids (particularly trifluoroacetic acid) are preferred.

The reaction temperature usually ranges from −20° C. to 100° C. (preferably from −10° C. to 80° C.) and the reaction time usually ranges from 10 minutes to 108 hours (preferably from 0.5 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

[Process C]

Process C is a method for preparing a compound of formula (IX-1) having a desired ester residue group by converting a protected carboxyl group of a compound of formula (VII).

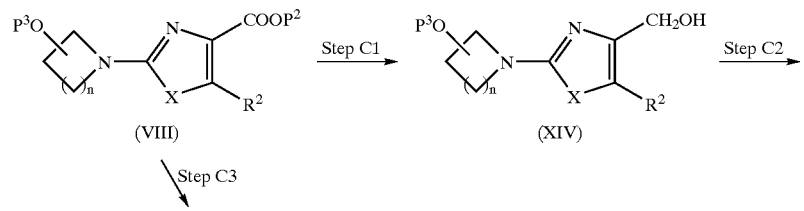

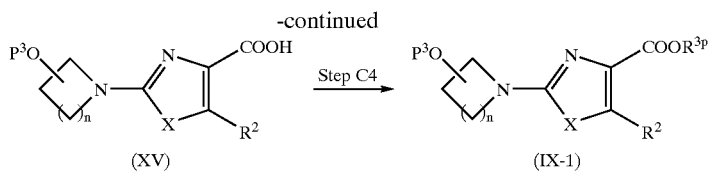

In the above scheme, $R^2$, X, n, $P^2$ and $P^3$ have the same meanings as defined above, and $R^{3p}$ represents $R^3$ which may be protected.

(Step C1)

Step C1 is a step for preparing a compound (XIV) by reducing the carboxylic ester group of a compound of formula (VIII) to a hydroxymethyl group. This step is accomplished by reacting a reducing agent with the compound of formula (VIII) in a solvent.

The reducing agent to be employed is not particularly limited so long as it can convert a carboxylic ester group to a hydroxymethyl group by reduction. Examples of the reducing agent include alkali metal aluminum hydrides such as lithium aluminum hydride; and alkali metal boron hydrides such as lithium borohydride or sodium borohydride, of which lithium aluminum hydride is preferred.

There is no particular limitation on the nature of the solvent to be employed, provided that it has no adverse effect on the reaction and it dissolves the starting materials to a certain extent. Examples of the solvent include ethers such as tetrahydrofuran or diethyl ether, of which tetrahydrofuran is preferred.

The reaction temperature usually ranges from −20° C. to 100° C. (preferably from −10° C. to 40° C.) and the reaction time usually ranges from 10 minutes to 24 hours (preferably from 0.5 to 24 hours).

After completion of the reaction, the desired compound is obtained from the reaction mixture by known means. For example, the desired compound may be obtained by adding an organic solvent immiscible with water to the reaction mixture, neutralizing it, washing with water and distilling off the solvent. The desired compound thus obtained can be further purified, if necessary, by conventional procedures such as recrystallization, reprecipitation or chromatography.

(Step C2)

Step C2 is a step for preparing a compound of formula (XV) by oxidizing a hydroxymethyl group of a compound of formula (XIV).

This step is accomplished by reacting an oxidizing agent with the compound of formula (XIV) in a solvent and comprises a step of oxidizing a hydroxymethyl group to an aldehyde group and a step of oxidizing the aldehyde group to a carboxyl group.

(1) Step of Oxidizing a Hydroxymethyl Group to an Aldehyde Group

The oxidizing agent to be employed is not particularly limited so long as it can oxidize a hydroxymethyl group to convert it to an aldehyde group. Examples include pyridinium chlorochromate, oxalyl chloride-dimethyl sulfoxide, anhydrous trifluoroacetic acid-dimethyl sulfoxide, active manganese dioxide or the Dess-Martin reagent, of which active manganese dioxide is preferred.

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane, of which methylene chloride is preferred.

The reaction temperature usually ranges from −100° C. to 100° C. (preferably from −100° C. to 50° C.) and the reaction time usually ranges from 30 minutes to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(2) Step of Oxidizing the Aldehyde Group to a Carboxyl Group

The oxidizing agent to be employed is not particularly limited so long as it can oxidize an aldehyde group to convert it to a carboxyl group. Examples of the oxidizing agent include potassium permanganate, ruthenium tetroxide, sodium chlorite-sodium (or potassium) dihydrogenphosphate-2-methyl-2-butene, of which sodium chlorite-sodium dihydrogenphosphate-2-methyl-2-butene is preferred.

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane; ethers such as tetrahydrofuran or diethyl ether; alcohols such as t-butanol; and a mixture of these solvents and water, of which a mixture of tetrahydrofuran-methylene chloride-water-t-butanol is preferred.

The reaction temperature usually ranges from −20° C. to 50° C. (preferably from −10° C. to 40° C.) and the reaction time usually ranges from 10 minutes to 108 hours (preferably from 0.5 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(Step C3)

Step C3 is a step for preparing a carboxylic acid compound of formula (XV) in an alternative manner and is accomplished by removing the protective group of a compound (VII). This step can be carried out in a similar manner to Step A2 of Process A.

(Step C4)

Step C4 is a step for preparing a compound of formula (IX-1) by esterifying the carboxyl group of the compound of formula (XV).

(1) This step is accomplished by reacting a desired alcohol compound represented by the formula $R^{3p}OH$ with a compound of formula (XV) in the presence of a condensation agent in a solvent.

As the condensation agent to be employed, those described in the section of the ester formation described in Step A2 of Process A can be used. The condensation may also be accomplished via an acid chloride using oxalyl chloride.

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane; ethers such as tetrahydrofuran or diethyl ether; amides such as dimethylformamide; and nitrites such as acetonitrile, of which halogenated hydrocarbons (particularly methylene chloride) are preferred.

The reaction temperature usually ranges from −50° C. to 100° C. (preferably from −20° C. to 50° C.) and the reaction time usually ranges from 0.5 to 108 hours (preferably from 1 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(2) The present step is also accomplished by reacting a desired compound represented by the formula $R^{3p}L^3$ with a compound of formula (XV) in the presence of a base in a solvent. $L^3$ represents a leaving group, preferably a halogen atom (particularly an iodine atom or a bromine atom).

As the base to be employed, inorganic bases or organic bases can be used. The inorganic base may comprise a carbonate such as sodium carbonate, potassium carbonate or cesium carbonate or a hydrogencarbonate such as sodium hydrogencarbonate or potassium hydrogencarbonate, preferably cesium carbonate. The organic base may comprise a tertiary amine such as triethylamine or diisopropylethylamine; or a bicyclic organic base such as DBU or DBN, preferably diisopropylethylamine.

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane; ethers such as tetrahydrofuran or diethyl ether; amides such as dimethylformamide; and nitriles such as acetonitrile, of which amides (particularly dimethylformamide) are preferred.

The reaction temperature usually ranges from −50° C. to 100° C. (preferably from −20° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water, and distilling off the solvent. The desired compound thus obtained can be further purified, if necessary, by conventional procedures such as recrystallization, reprecipitation or chromatography.

[Process D]

Process D is a method for preparing a compound of formula (IX-2) having a desired amide residue by conversion of the carboxyl group of a compound (XV).

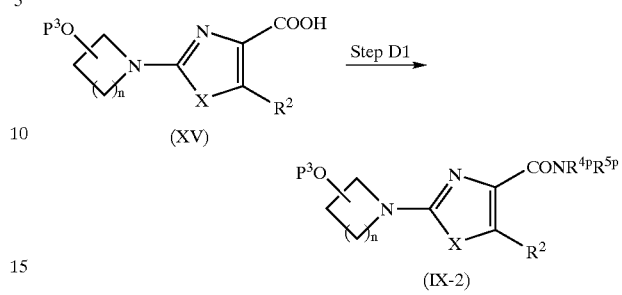

In the above scheme, $R^2$, X, n and $P^3$ have the same meanings as defined above, and $R^{4p}$ and $R^{5p}$ represent $R^4$ and $R^5$ which may be protected.

(Step D1)

This step is accomplished by reacting a desired compound having the formula $HNR^{4p}R^{5p}$ with a compound of formula (XV) in the presence of a condensation agent in a solvent.

The present step can be carried out using an amino compound of formula $HNR^{4p}R^{5p}$ instead of the alcohol compound of formula $R^{3p}OH$ in the above Step C4 of Process C.

Examples of the condensation agent include a phosphoric acid ester-based condensation agent such as diethylphosphoryl cyanide; and a carbonate-based condensation agent such as carbonyldiimidazole, of which diethylphosphoryl cyanide or carbonyldiimidazole are preferred.

[Process E]

Process E is a method for preparing a desired compound of formula (IX-2) having an amide residue group by converting a carboxylic ester group of a compound (VIII).

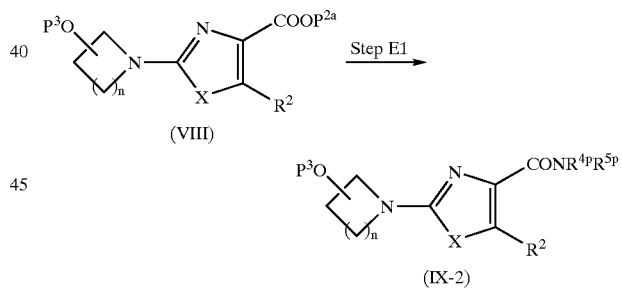

In the above scheme, $R^2$, X, n, $P^3$, $R^{4p}$ and $R^{5p}$ have the same meanings as defined above, and $P^{2a}$ represents a $C_1$–$C_4$ alkyl group as a protective group $P^2$ of the above carboxyl group.

(Step E1)

This step is accomplished by reacting a desired amino compound represented by the formula $HNR^{4p}R^{5p}$ with a compound of formula (VIII) in the presence of a catalyst in a solvent.

Examples of the catalyst to be employed include tri-$C_1$–$C_4$ alkyl aluminiums such as trimethylaluminium, of which trimethylaluminium is preferred.

There is no particular limitation on the nature of the solvent to be employed, provided that it has no adverse effect on the reaction and it dissolves the starting materials to a certain extent. Examples of the solvent include aromatic solvents such as benzene, toluene or mesitylene; and halogenated hydrocarbons such as methylene chloride or dichloroethane, of which aromatic solvents (particularly benzene or toluene) are preferred.

The reaction temperature usually ranges from −20° C. to 150° C. (preferably from −10° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

[Process F]

Process F is a method for preparing a cyano compound of formula (IX-3) by converting a carboxylic ester group of a compound of formula (VIII).

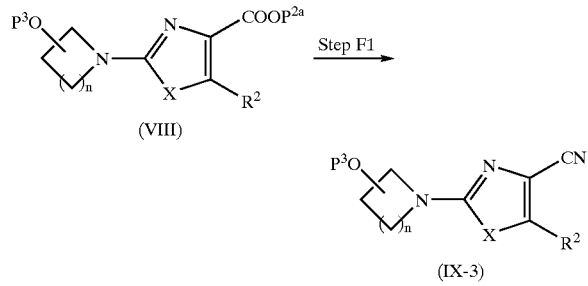

In the above scheme, $R^2$, $X$, $n$, $P^3$ and $P^{2a}$ have the same meanings as defined above.

(Step F1)

This step is accomplished by using an ammonium salt instead of the amino compound in the above Step E1 of Process E and reacting it at a higher reaction temperature.

Ammonium chloride is preferably used as the ammonium salt and the reaction temperature usually ranges from −20° C. to 150° C. (preferably from −10° C. to 100° C.).

[Process G]

Process G is a method for preparing a compound of formula (IX-4) by introducing a desired substituent $R^6$ to a hydroxyl group of a compound of formula (XIV).

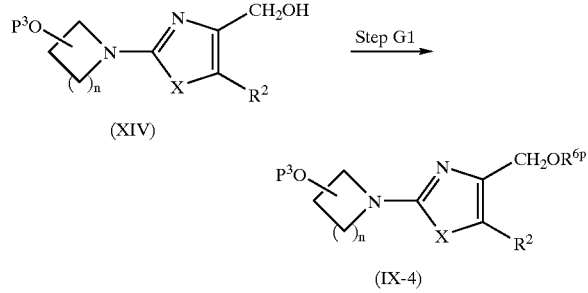

This step is accomplished by reacting an alkylating agent with a compound of formula (XIV) in the presence of a base in a solvent or reacting a reducing agent and a desired carbonyl compound with the compound of formula (XIV) in the presence of an acid catalyst in a solvent.

(1) Alkylating Method Under Basic Conditions

Examples of the solvent to be employed include amides such as N,N-dimethylformamide; and ethers such as tetrahydrofuran or diethyl ether, of which amides (particularly N,N-dimethylformamide) are preferred.

Examples of the base to be employed include alkali metal hydrides such as sodium hydride or potassium hydride; inorganic bases such as sodium hydroxide or potassium hydroxide; and organic bases such as triethylamine or diisopropylamine, of which alkali metal hydrides (particularly sodium hydride) are preferred.

Examples of the alkylating agent to be employed include alkyl halides such as methyl iodide or ethyl iodide; and dialkyl sulfates such as dimethyl sulfate and diethyl sulfate, of which alkyl halides (particularly alkyl iodide) are preferred.

The reaction temperature usually ranges from −50° C. to 100° C. (preferably from −10° C. to 40° C.) and the reaction time usually ranges from 10 minutes to 108 hours (preferably from 0.5 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(2) Alkylating Method Under Acidic Conditions

There is no particular limitation on the nature of the solvent to be employed, provided that it has no adverse effect on the reaction and it dissolves the starting materials to a certain extent. Examples of the solvent include halogenated hydrocarbons such as methylene chloride or dichloroethane; and ethers such as tetrahydrofuran or diethyl ether, of which halogenated hydrocarbons (particularly methylene chloride) are preferred.

Examples of the acid catalyst include trialkylsilyl triflates such as trimethylsilyl triflate, triethylsilyl triflate or t-butyldimethylsilyl triflate, of which trimethylsilyl triflate is preferred.

Examples of the desired carbonyl compound include ketones such as acetone, methyl ethyl ketone and cyclohexyl ketone; and alkyl aldehydes such as acetaldehyde and propionaldehyde, of which ketones are preferred.

Examples of the reducing agent include trialkylsilanes such as triethylsilane and diphenylmethylsilane, of which trialkylsilanes (particularly triethylsilane) are preferred.

The reaction temperature usually ranges from −50° C. to 100° C. (preferably from −10° C. to 40° C.) and the reaction time usually ranges from 10 minutes to 108 hours (preferably from 0.5 to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

[Process H]

Process H is a method for preparing a compound of formula (IX-5) by converting a hydroxyl group of a compound of formula (XIV) to a desired group represented by the formula $NR^{7p}R^{8p}$.

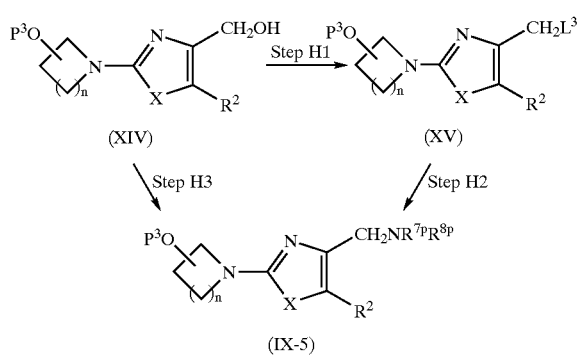

(Step H1)

Step H1 is a step for preparing a compound of formula (XV) by introducing a leaving group $L^3$ to a compound of formula (XIV) and can be accomplished in a similar manner to Step B6 of Process B above.

(Step H2)

Step H2 is a step for preparing an amine compound of formula (IX-5a) from a compound of formula (XV) and for preparing a compound of formula (IX-5b), if necessary, by introducing a substituent.

(A) Preparation of an Amine Compound of Formula (IX-5a)

This step can be accomplished by reacting an aminating agent with the compound of formula (XV) in a solvent. This step can also be accomplished by preparing an azide compound by reacting an azidating agent with a compound of formula (XV) in a solvent, followed by reaction with a reducing agent.

(1) Method in Which an Aminating Agent is Used

There is no particular limitation on the nature of the solvent to be employed, provided that it has no adverse effect on the reaction and it dissolves the starting materials to a certain extent. Examples of the solvent include amides such as dimethylformamide; alcohols such as methanol or ethanol; and ethers such as tetrahydrofuran or diethyl ether, preferably the amides (particularly dimethylformamide).

Examples of the aminating agent to be employed include primary alkylamines which may be substituted such as methylamine or ethylamine; aromatic amines which may be substituted such as aniline or aminothiazole; secondary alkylamines which may be substituted such as methylethylamine or dimethylamine; and salts of these amines (for example, hydrochloride), of which primary or secondary alkylamines which may be substituted and salts thereof (particularly methylamine hydrochloride or dimethylamine hydrochloride) are preferred.

The reaction temperature usually ranges from 0° C. to 150° C. (preferably from 10° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(2) Method in Which an Azidating Agent and a Reducing Agent are Used

There is no particular limitation on the nature of the solvent to be employed, provided that it has no adverse effect on the reaction and it dissolves the starting materials to a certain extent. Examples of the solvent include amides such as dimethylformamide; alcohols such as methanol or ethanol; and ethers such as tetrahydrofuran or diethyl ether, of which amides (particularly dimethylformamide) are preferred.

Examples of the azidating agent include alkali metal azides such as sodium azide or lithium azide, of which alkali metal azides (particularly sodium azide) are preferred.

The reaction temperature usually ranges from 0° C. to 150° C. (preferably from 10° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

The azide thus obtained is converted to an amine of formula (IX-5a) by a reduction reaction.

Examples of the reducing agent to be employed include alkali metal aluminum hydrides such as lithium aluminum hydride; phosphines such as triphenylphosphine; and catalytic hydrogenation using metal catalysts such as palladium-carbon or platinum catalyst, of which catalytic hydrogenation (particularly in the case where palladium-carbon is used as the catalyst) is preferred.

There is no particular limitation on the nature of the solvent to be employed, provided that it has no adverse effect on the reaction and it dissolves the starting materials to a certain extent. Examples of the solvent include ethers such as tetrahydrofuran or diethyl ether; and alcohols such as methanol or ethanol, of which ethers (particularly tetrahydrofuran) are preferred.

Examples of the solvent to be employed in catalytic hydrogenation include alcohols such as methanol or ethanol, of which methanol is preferred.

The reaction temperature usually ranges from −10° C. to 150° C. (preferably from 0° C. to 100° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(B) Preparation of a Compound (IX-5b)

This step is a step carried out if necessary in order to prepare a compound of formula (IX-5b) by introducing a substituent to an amine compound of formula (IX-5a).

The present step is accomplished by reacting a desired acylating agent, a sulfonylating agent, a phosphorylating agent or a chloroformic acid ester with an amine compound of formula (IX-5a) in the presence of a base in a solvent.

Examples of the acylating agent include acid anhydrides such as acetic anhydride or benzoic anhydride; and acid chlorides such as acetyl chloride or benzoyl chloride, of which acid chlorides (particularly acetyl chloride) are preferred.

Examples of the sulfonylating agent include acid chlorides such as methanesulfonyl chloride or p-toluenesulfonyl chloride; and acid anhydrides such as methanesulfonic anhydride or p-toluenesulfonic anhydride, of which acid chlorides (particularly methanesulfonyl chloride) are preferred.

Examples of the phosphorylating agent include acid chlorides such as diethylphosphoryl chloride or dimethylphosphoryl chloride, of which diethylphosphoryl chloride is preferred.

Examples of the chloroformic acid ester include ester compounds such as methyl chloroformate, ethyl chloroformate or benzyl chloroformate, of which chloroformic acid esters (particularly methyl chloroformate) are preferred.

Examples of the base to be employed include organic bases such as triethylamine, diisopropylethylamine or pyridine; and inorganic bases such as sodium carbonate, potassium carbonate or sodium hydrogencarbonate, of which organic bases (particularly triethylamine) are preferred.

There is no particular limitation on the nature of the solvent to be employed, provided that it has no adverse effect on the reaction and it dissolves the starting materials to a certain extent. Examples of the solvent include ethers such as tetrahydrofuran or diethyl ether; and halogenated hydrocarbons such as methylene chloride or dichloroethane, of which ethers (particularly tetrahydrofuran) are preferred.

The reaction temperature usually ranges from 0° C. to 100° C. (preferably from 10° C. to 50° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(Step H3)

Step H3 is a step for preparing an amine compound of formula (IX-5a) from a compound of formula (XIV) via an azide compound and for preparing a compound of formula (IX-5b) by introducing a substituent if necessary.

(A) Preparation of an Azide Compound

The present step is carried out by reacting an azidating compound (particularly diphenylphosphoryl azide), diethylazodicarboxylate and triphenylphosphine with a compound of formula (XIV) in a solvent.

There is no particular limitation on the nature of the solvent to be employed, provided that it has no adverse effect on the reaction and it dissolves the starting materials to a certain extent. Examples of the solvent include amides such as dimethylformamide; and ethers such as tetrahydrofuran or diethyl ether, of which ethers (particularly tetrahydrofuran) are preferred.

The reaction temperature usually ranges from 0° C. to 50° C. (preferably from 10° C. to 30° C.) and the reaction time usually ranges from 0.5 to 108 hours (preferably from one to 24 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(B) Preparation of an Amine Compound

This is a step for preparing an amine of formula (IX-5a) by reducing an azide compound and can be carried out in a similar manner to the reduction described in Step H2 (A)(2).

(C) Preparation of a Compound (IX-5b)

This step, carried out if necessary, is a step for preparing a compound of formula (IX-5b) by introducing a substituent to the amine of formula (IX-5a) and can be carried out in a similar manner to Step H2 (B) above.

The compounds of formula (IX-1) to (IX-5) obtained in Process C to Process H can be converted to a compound of formula (III) which is used as a starting material of a side chain at the 2-position of a compound of formula (I) according to the steps after Step B5 of Process B.

[Process I]

Process I is a method for preparing a compound of formula (IX-6) which is a compound of formula (IX), an intermediate in the synthetic route of Process B, wherein X is an oxygen atom, in a different manner.

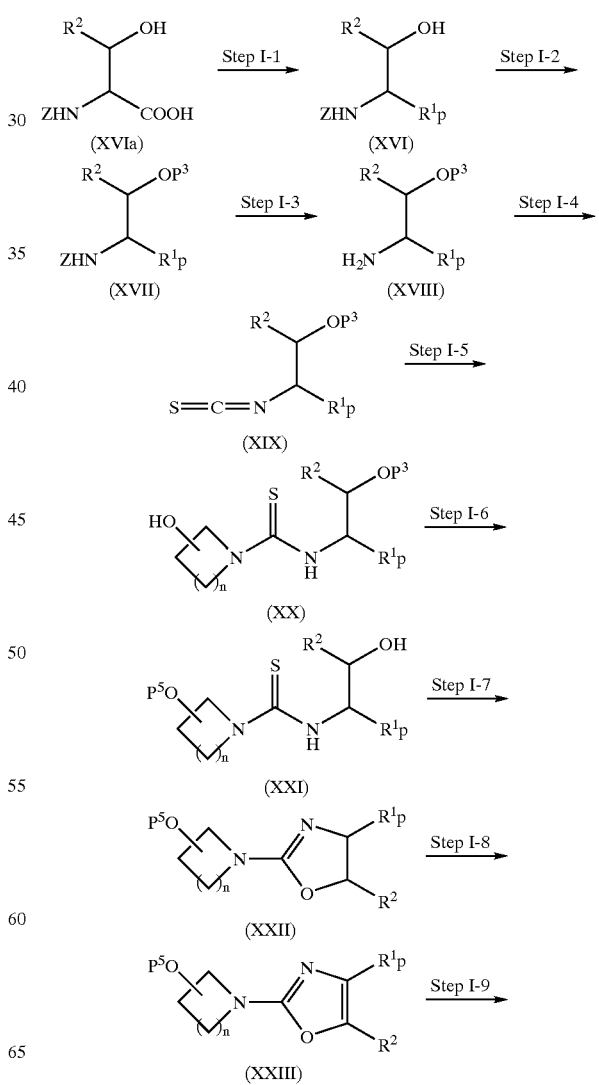

-continued

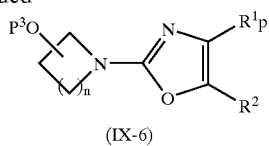

(IX-6)

In the above scheme, $R^1p$, $R^2$, $P^3$ and n have the same meanings as defined above; Z represents a protective group of an amino group, preferably a benzyloxycarbonyl group; and $P^5$ represents a protective group of a hydroxyl group, preferably an acyl-based protective group such as acetyl, benzoyl or pivaloyl, and most preferably a benzoyl group.

(Step I-1)

Step I-1 is a step for preparing a compound of formula (XVI) by converting a carboxyl group of an amino acid compound (XVIa) of which amino group is protected to the desired $R^1p$.

This step can be carried out according to a method selected from the above Processes C to H. It should be noted that in the compound of formula (XVIa) which forms the starting material, a compound wherein $R^2$ is a hydrogen atom can be prepared from serine and a compound wherein $R^2$ is a methyl group can be prepared from threonine. Compounds wherein $R^2$ is a group other than a hydrogen atom or a methyl group can also be prepared by a method known by a person skilled in the art.

(Step I-2)

Step I-2 is a step for preparing a compound of formula (XVII) by introducing a protective group to a hydroxyl group of a compound of formula (XVI).

This step can be carried out in a similar manner to Step B3 of Process B. Preferred examples of the silyl-based protective group suitable as $P^3$ include a t-butyidimethylsilyl group.

(Step I-3)

Step I-3 is a step for preparing a compound of formula (XVIII) by removing the protective group from the amino group of the compound of formula (XVII).

This step can be carried out in a similar manner to a method of Step A2 (1) of Process A. The preferred solvent is methanol.

(Step I-4)

Step I-4 is a step for preparing a compound of formula (XIX) by converting the amino group of the compound of formula (XVIII) to an isothiocyanate group.

This step is accomplished by reacting carbon disulfide and a dehydrosulfidation agent with the compound of formula (XVIII) in the presence of a base in a solvent.

Preferred examples of the solvent include halogenated hydrocarbons (particularly methylene chloride).

Preferred examples of the dehydrosulfidation agent include halogenated formic acid esters (particularly ethyl chloroformate) or quaternary nitrogen-containing reagents (particularly 2-chloro-1-methylpyridinium iodide or 2-chloro-1-ethylbenzoxazolium tetrafluoroborate).

Preferred examples of the base include tertiary amines such as triethylamine, diisopropylethylamine or tributylamine (particularly triethylamine).

The reaction temperature usually ranges from −20° C. to 100° C. (preferably from 0° C. to 60° C.) and the reaction time usually ranges from 0.5 to 48 hours (preferably from one to 12 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(Step I-5)

Step I-5 is a step for preparing a compound of formula (XX) by reacting the desired cyclic amine with the compound of formula (XIX). This step can be carried out according to Step B1 of Process B.

(Step I-6)

Step I-6 is a step for preparing a compound of formula (XXI) by introducing an acyl-based protective group $P^5$ to a hydroxyl group of a compound (XX) and subsequently removing a silyl based protective group $P^3$.

(1) Introduction of an Acyl-based Protective Group $P^5$

This step can be carried out according to Step H2 (B) of Process H.

(2) Removal Step of a Silyl Based Protective Group $P^3$

This step can be carried out according to Step A2 of Process A.

(Step I-7)

Step I-7 is a step for preparing a compound of formula (XXII) by subjecting a compound of formula (XXI) to a ring-closure reaction. This step is accomplished by reacting a cyclization agent (dehydrosulfidation agent) with the compound of formula (XXI) in the presence of a base in a solvent.

Examples of the solvent include amides such as dimethylformamide or dimethylacetamide; halogenated hydrocarbons such as methylene chloride; and nitriles such as acetonitrile; of which acetonitrile is preferred.

Preferred examples of the base include tertiary amines such as triethylamine, diisopropylethylamine or tributylamine (particularly triethylamine).

Preferred examples of the cyclization (dehydrosulfidation) agent include mercury salts such as mercury oxide and mercury chloride; or quaternary nitrogen-containing reagents (particularly 2-chloro-1-methylpyridinium iodide or 2-chloro-1-ethylbenzoxazolium tetrafluoroborate).

The reaction temperature usually ranges from −20° C. to 100° C. (preferably from 0° C. to 60° C.) and the reaction time usually ranges from 0.5 to 48 hours (preferably from one to 12 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, neutralizing it, washing with water and distilling off the solvent. The desired compound thus obtained can be further purified, if necessary, by conventional procedures such as recrystallization, reprecipitation or chromatography.

(Step I-8)

Step I-8 is a step for preparing a compound of formula (XXIII) by dehydrogenation of the compound of formula (XXII).

This step is accomplished by reacting a dehydrogenating agent with the compound of formula (XXII) in a solvent.

Examples of the solvent include aromatic hydrocarbons such as benzene or toluene; and halogenated hydrocarbons such as methylene chloride or dichloroethane.

Examples of the dehydrogenating agent include oxidizing agents such as manganese dioxide.

The reaction temperature usually ranges from 0° C. to 100° C. (preferably from 0° C. to 60° C.) and the reaction time usually ranges from 0.5 to 48 hours (preferably from one to 12 hours).

After completion of the reaction, the desired compound is obtained from the reaction mixture by known means. For example, the desired compound may be obtained by adding an organic solvent immiscible with water to a residue obtained by distilling off the reaction mixture or the solvent in the reaction mixture, removing the insolubles by filtration, washing with water and distilling off the solvent. The desired compound thus obtained can be further purified, if necessary, by conventional procedures such as recrystallization, reprecipitation or chromatography.

(Step I-9)

Step I-9 is a step for preparing a compound of formula (IX-6) by removing the acyl-based protective group $P^5$ of the compound of formula (XXIII) and subsequently introducing a silyl-based protective group $P^3$.

(1) Elimination of the Acyl-based Protective Group $P^5$

This step can be carried out according to a method for preparing the compound of formula (VI) from the compound of formula (XIII) in Step B1 (2) of Process B.

(2) Introduction of the Silyl-based Protective Group $P^3$

This step can be carried out according to Step B3 of Process B.

[Process J]

The compound of formula (I) can be also prepared in a different manner from Process A by the following Process J. Process J can be applied to the preparation of the compound of formula (I-1) or (I-2) wherein $R^1$ is represented by the formula $COOR^3$ or the formula $CONR^4R^5$.

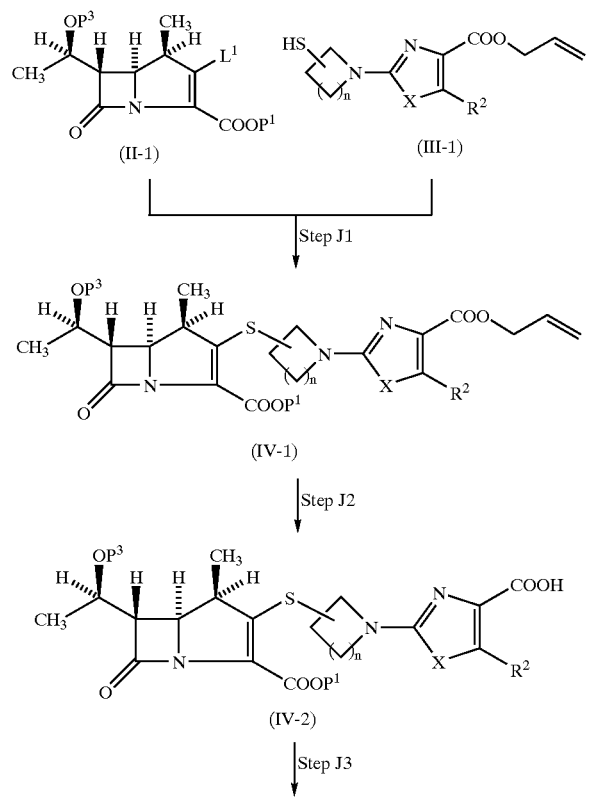

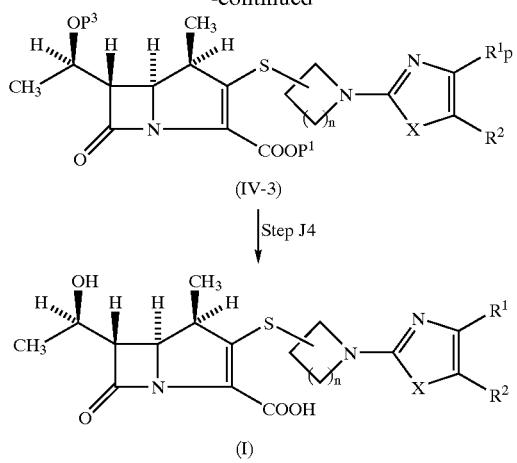

In the above scheme, $R^1$, $R^1p$, $R^2$, $P^1$, $P^3$, X, $L^1$ and n have the same meanings as defined above. A preferred example of $P^3$ is a t-butyldimethylsilyl group.

(Step J1)

Step J1 is a step for preparing a compound of formula (IV-1) by condensing a compound of formula (II-1) which is protected by a silyl-based protective group $P^3$ and a compound of formula (III-1) in which $R^1p$ is a carboxyl group protected by an allyl group.

This step can be carried out in a similar manner to Step A1 of Process A. The compound of formula (II-1) used as a starting material can be prepared by reacting a silylating agent with a compound of formula (II) and this step can be carried out according to Step B3 of Process B. The compound of formula (III-1) can be prepared by Process B.

(Step J2)

Step J2 is a step for preparing the compound of formula (IV-2) by removing the allyl protective group from the compound of formula (IV-1). This step can be carried out according to Step A2 (2) of Process A.

(Step J3)

Step J3 is a step for preparing a compound of formula (IV-3) by modifying a carboxyl group of the compound of formula (IV-2). This step can be carried out according to Step B4 of Process B (particularly Process C and Process D).

(Step J4)

Step J4 is a step for preparing a compound of formula (I) by removing the protective groups $P^3$ and $P^1$ from the compound of formula (IV-3).

(1) Elimination of the Protective Group $P^3$

This step can be carried out according to Step A2 (3) of Process A.

(2) Elimination of the Protective Group $P^1$

This step can be carried out in a similar manner to Step A2 of Process A.

Compounds of formula (I) or pharmacologically acceptable salts thereof of the present invention exhibit strong and broad antibacterial activity against various pathogenic bacteria including Gram-positive bacteria such as *Staphylococcus* and *Bacillus subtilis*, Gram-negative bacteria such as *Escherichia coli, Klebsiella pneumoniae, Shigella, Proteus vulgaris, Serratia, Enterobacter* and *Pseudomonas aerginosa*, and anaerobic bacteria such as *Bacteroides fragilis*, and, in particular, have a strong antibacterial activity against *Streptococcus pneumoniae* (including penicillin-resistant bacteria) and *Haemophilus influenzae* (including β-lactamase producing bacteria), which cause respiratory tract infection. Compounds of formula (I) of the present invention have a high stability against β-lactamases including metallo β-lactamase. Compounds of formula (I) of the present invention show good pharmacokinetics such as a high maximum concentration in serum and a long half-life in serum when administered either orally or non-orally. Therefore, compounds of formula (I) of the present invention are expected to have a potent therapeutic effect even if administered less frequently or with fewer doses in comparison with existing drugs. Compounds of formula (I) of the present invention have low toxicity to the kidney. Accordingly, compounds of formula (I) or pharmacologically acceptable salts or ester thereof of the present invention, are useful, for example, as pharmaceuticals and are particularly useful as antibacterial agents for the treatment or prevention (preferably treatment) of bacterial infections caused by various kinds of pathogenic bacteria, particularly bacteria causing respiratory tract infection.

When compounds of formula (I), pharmacologically acceptable esters or salts thereof are used as pharmaceuticals, particularly antibacterial agents, they can be administered orally in the form of tablets, capsules, granules, powders or syrups by using them as they are or mixing them with appropriate pharmacologically acceptable additive such as excipients or diluents, or administered parenterally in the form of injections.

These formulations can be prepared in a known manner by using additives. Examples of the additives include excipients (e.g. sugar derivatives such as lactose, sucrose, glucose, mannitol and sorbitol; starch derivatives such as corn starch, potato starch, α-starch, dextrin and carboxymethyl starch; cellulose derivatives such as crystalline cellulose, low-substituted hydroxypropyl cellulose, hydroxypropylmethyl cellulose, carboxymethyl cellulose, calcium carboxymethyl cellulose and internally cross-linked sodium carboxymethyl cellulose; gum arabic; dextran; and pullulan; silicate derivatives such as light silicic anhydride, synthetic aluminum silicate and magnesium aluminometasilicate; phosphate derivatives such as calcium phosphate; carbonate derivatives such as calcium carbonate; or sulfate derivatives such as calcium sulfate), binders (e.g. the above-exemplified excipients; gelatin; polyvinyl pyrrolidone; or Macrogol); disintegrators (e.g. the above-exemplified excipients; or chemically modified starch or cellulose derivatives such as sodium croscarmellose or sodium carboxymethyl starch; or cross-linked polyvinylpyrrolidone); lubricants (e.g. talc; stearic acid; metal salts of stearic acid such as calcium stearate or magnesium stearate; colloidal silica; veegum; waxes such as bees wax and spermaceti; boric acid; glycol; carboxylic acids such as fumaric acid or adipic acid; sodium carboxylates such as sodium benzoate; sulfates such as sodium sulfate; leucine; lauryl sulfates such as sodium lauryl sulfate or magnesium lauryl sulfate; silicic acids such as silicic anhydride or silicic hydrate; or starch derivatives exemplified above as the excipient), stabilizers (e.g. p-hydroxy benzoic acid esters such as methyl paraben or propyl paraben; alcohols such as chlorobutanol, benzyl alcohol or phenylethyl alcohol; benzalkonium chloride; phenols such as phenol and cresol; thimerosal; acetic anhydride; or sorbic acid), corrigents (e.g. ordinarily-employed sweetener, souring agents or flavors), suspending agents (e.g. Polysorbate 80 or sodium carboxymethyl cellulose), diluents and solvents for formulation (e.g. water, ethanol or glycerine).

The dose of the compounds of formula (I) will vary depending on the condition and age of the patient. Orally, they are administered (e.g. to an adult human) in an amount of 10 mg (preferably 50 mg) in a single dose as a lower limit and 2000 mg (preferably 1000 mg) in a single dose as an upper limit, while intravenously, they are administrered in an amount of 10 mg (preferably 100 mg) in a single dose as a lower limit and 3000 mg (preferably 2000 mg) in a single dose as an upper limit. It is desirable that the compound is administered to an adult human in a single dose or in divided doses (sixths) per day depending on the condition of the patient.

The present invention will now be illustrated in further detail by the following Examples, Reference Examples, Test Examples and Formulation Examples. The scope of the present invention is not limited by these Examples. In the nuclear magnetic resonance spectra in the Examples and Reference Examples, sodium trimethylsilylpropionate-$d_4$ was used as an internal standard for the measurement in deuterated water, while tetramethylsilane was used as an internal standard in the other solvents. Incidentally, when an internal standard was not used in the measurement in deuterated water, the measurement was made on the basis that the signal of HOD in deuterated water appears at 4.65 ppm.

EXAMPLE 1

(1R,5S,6S)-2-[1-(4-Ethoxycarbonyl-1,3-thiazol-2-yl)azetidin-3-yl]thio-6-[(R)-1-hydroxyethyl]-1-methylcarbapen-2-em-3-carboxylic acid sodium salt

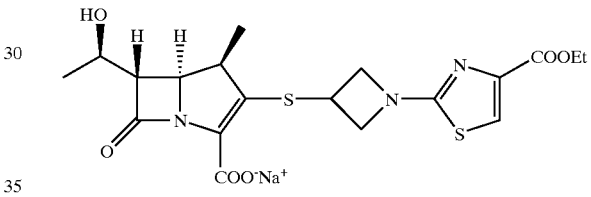

(1) p-Nitrobenzyl (1R,5S,6S)-2-[1-(4-ethoxycarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-ethoxycarbonyl-1,3-thiazol-2-yl)azetidine (468 mg, 1.71 mmol) (obtained as described in Reference Example 1) in dimethylformamide (15 ml) was added hydrazine acetate (171.0 mg, 1.86 mmol) at room temperature under an atmosphere of nitrogen and the mixture was stirred for 1.5 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (1.02 g, 1.72 mmol) in acetonitrile (30 ml) was added dropwise to the resulting mixture in an ice bath under an atmosphere of nitrogen, followed by the addition of diisopropylethylamine (1.5 ml, 8.61 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate) to afford p-nitrobenzyl (1R,5S,6S)-2-[1-(4-ethoxycarbonyl-1,3-thiazol-2-yl)azetidin-3-yl]thio-6-[(R)-1-hydroxyethyl]-1-methylcarbapen-2-em-3-carboxylate as a pale yellow solid (752 mg, yield 75%).

¹H-NMR (400 MHz, CDCl₃): δ (ppm) 8.23 (2H, d, J=8.6 Hz), 7.66 (2H, d, J=8.6 Hz), 7.50 (1H, s), 5.50 (1H, d, J=13.7 Hz), 5.25 (1H, d, J=13.7 Hz), 4.55 (2H, dd, J=14.4, 8.0 Hz), 4.36 (2H, q, J=7.1 Hz), 4.35–4.20 (3H, m), 4.20–4.05 (2H, m), 3.29 (1H, dd, J=6.7, 2.4 Hz), 3.20 (1H, dq, J=10.3, 8.3 Hz), 1.82 (1H, br s), 1.42 (3H, d, J=6.3 Hz), 1.40 (3H, t, J=7.1 Hz), 1.26 (3H, t, J=7.5 Hz).

Mass spectrum (FAB⁺): 589 [M+H]⁺.

(2) (1R,5S,6S)-2-[1-(4-Ethoxycarbonyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-ethoxycarbonyl-1,3-thiazol-2-yl)azetidin-3-yl]thio-6-[(R)-1-hydroxyethyl]-1-methylcarbapen-2-em-3-carboxylate (744 mg, 1.26 mmol) (obtained as described in Example 1(1)) in a mixture of tetrahydrofuran (46 ml) and distilled water (23 ml) was subjected to catalytic hydrogenation in the presence of 20% palladium hydroxide (736 mg) in a water bath (30° C.) for 1.5 hours. After checking the completion of the reaction, the reaction mixture was filtered and to the filtrate were added sodium hydrogencarbonate (106 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water—3% acetonitrile; distilled water—5% acetonitrile; distilled water—7% acetonitrile and distilled water as the eluant. The eluate was lyophilized to afford the desired compound (1R,5S,6S)-2-[1-(4-ethoxycarbonyl-1,3-thiazol-2-yl)azetidin-3-yl]thio-6-[(R)-1-hydroxyethyl]-1-methylcarbapen-2-em-3-carboxylic acid sodium salt (376 mg, yield 63%) as a white solid.

¹H-NMR (400 MHz, D₂O): δ (ppm) 7.68 (1H, s), 4.50 (2H, t, J=12.6 Hz), 4.40–4.10 (5H, m including q at 4.30 ppm, J=8.4 Hz), 4.10–3.95 (2H, m), 3.45–3.35 (1H, m), 3.30–3.25 (1H, m), 1.30 (3H, t, J=8.4 Hz), 1.25 (3H, d, J=6.7 Hz), 1.15 (3H, d, J=9.2 Hz).

IR (KBr): 1749, 1720, 1602, 1544, 1395, 1316 cm⁻¹.

Mass spectrum (FAB⁺): 476 [M+H]⁺.

High-resolution mass spectrum (FAB⁺): calculated for C₁₉H₂₃O₆N₃S₂Na: 476.0912, Found: 476.0938 [M+H]⁺.

EXAMPLE 2

(1R,5S,6S)-2-[1-(4-Carboxyl-1,3-thiazol-2-yl)azetidin-3-yl]thio-6-[(R)-1-hydroxyethyl]-1-methylcarbapen-2-em-3-carboxylic acid disodium salt

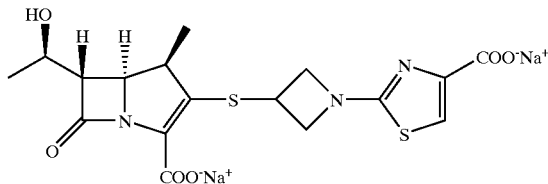

(1) p-Nitrobenzyl (1R,5S,6S)-2-[1-(4-p-nitrobenzyloxycarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-p-nitrobenzyloxycarbonyl-1,3-thiazol-2-yl)azetidine (380 mg, 1.0 mmol) (obtained as described in Reference Example 2) in dimethylformamide (15 ml) was added hydrazine acetate (115 mg, 1.25 mmol) at room temperature under an atmosphere of nitrogen and the mixture was stirred for 3 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (695 mg, 1.17 mmol) in acetonitrile (30 ml) was added dropwise to the resulting mixture in an ice bath under an atmosphere of nitrogen, followed by the addition of diisopropylethylamine (0.84 ml, 4.82 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate) to afford p-nitrobenzyl (1R,5S,6S)-2-[1-(4-p-nitrobenzyloxycarbonyl-1,3-thiazol-2-yl)azetidin-3-yl]thio-6-[(R)-1-hydroxyethyl]-1-methylcarbapen-2-em-3-carboxylate as a brown foaming solid (336 mg, yield 50%).

¹H-NMR (400 MHz, CDCl₃): δ (ppm) 8.23 (2H, d, J=8.6 Hz), 8.22 (2H, d, J=8.6 Hz), 7.66 (2H, d, J=8.6 Hz), 7.59 (2H, d, J=8.6 Hz), 7.57 (1H, s), 5.51 (1H, d, J=13.7 Hz), 5.43 (2H, s), 5.25 (1H, d, J=13.7 Hz), 4.56 (2H, dd, J=15.7, 8.7 Hz), 4.31–4.20 (3H, m), 4.19–4.05 (3H, m), 3.29 (1H, dd, J=7.1, 2.9 Hz), 3.20 (1H, dq, J=9.2, 7.4 Hz), 1.38 (3H, d, J=6.5 Hz), 1.27 (3H, d, J=7.2 Hz).

Mass spectrum (FAB⁺): 696 [M+H]⁺.

(2) (1R,5S,6S)-2-[1-(4-Carboxyl-1,3-thiazol-2-yl)azetidin-3-yl]thio-6-[(R)-1-hydroxyethyl]-1-methylcarbapen-2-em-3-carboxylic acid disodium salt p-Nitrobenzyl (1R,5S,6S)-2-[1-(4-p-nitrobenzyloxycarbonyl-1,3-thiazol-2-yl)azetidin-3-yl]thio-6-[(R)-1-hydroxyethyl]-1-methylcarbapen-2-em-3-carboxylate (330 mg, 0.474 mmol) (obtained as described in Example 2(1)) in a mixture of tetrahydrofuran (16 ml) and distilled water (8 ml) was subjected to catalytic hydrogenation in the presence of 20% palladium hydroxide (325 mg) in a water bath (30° C.) for 1.5 hours. After checking the completion of the reaction, the reaction mixture was filtered and to the filtrate were added sodium hydrogencarbonate (45 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water as the eluant. The eluate was lyophilized to afford the desired compound (1R,5S,6S)-2-[1-(4-carboxyl-1,3-thiazol-2-yl)azetidin-3-yl]thio-6-[(R)-1-hydroxyethyl]-1-methylcarbapen-2-em-3-carboxylic acid disodium salt (86 mg, yield 41%) as a white solid.

¹H-NMR (400 MHz, D₂O): δ (ppm) 7.10 (1H, s), 4.35 (2H, t, J=8.0 Hz), 4.20–4.10 (1H, m), 4.10–4.00 (2H, m), 3.90–3.80 (2H, m), 3.25–3.20 (1H, m), 3.15–3.00 (1H, m), 1.12 (3H, d, J=6.0 Hz), 1.00 (3H, d, J=9.2 Hz).

IR (KBr): 1745, 1594, 1541, 1400, 1316, 1282 cm⁻¹.

Mass spectrum (FAB⁺): 470 [M+H]⁺.

EXAMPLE 3

(1R,5S,6S)-2-[1-(4-Carbamoyl-1,3-thiazol-2-yl)azetidin-3-yl]thio-6-[(R)-1-hydroxyethyl]-1-methylcarbapen-2-em-3-carboxylic acid sodium salt

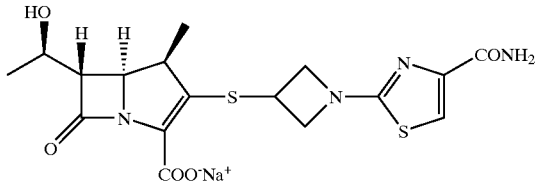

(1) p-Nitrobenzyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-carbamoyl-1,3-thiazol-2-yl)azetidine (1.13 g, 4.39 mmol) (obtained as described in Reference Example 3) in dimethylformamide (57 ml) was added hydrazine acetate (485 mg, 5.27 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (2.61 g, 4.39 mmol) in acetonitrile (130 ml) was added dropwise to the resulting mixture in an ice bath under an atmosphere of nitrogen, followed by the addition of diisopropylethylamine (3.1 ml, 17.6 mmol). The mixture was stirred for 3 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M aqueous sodium chloride solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using methylene chloride-3% methanol, methylene chloride-6% methanol, methylene chloride-9% methanol and methylene chloride as the eluant to afford p-nitrobenzyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate as a pale yellow solid (2.61 g, yield 94%).

$^1$H-NMR (400 MHz, CDCl$_3$): δ (ppm) 8.23 (2H, d, J=8.8 Hz), 7.66 (2H, d, J=8.8 Hz), 7.48 (1H, s), 6.99 (1H, br s), 5.55 (1H, bs), 5.51 (1H, d, J=13.9 Hz), 5.25 (1H, d, J=13.9 Hz), 4.50 (2H, dd, J=16.0, 8.0 Hz), 4.31–4.20 (3H, m), 4.10–4.00 (2H, m), 3.30 (1H, dd, J=6.6, 2.2 Hz), 3.21 (1H, dq, J=10.6, 8.0 Hz), 1.83 (1H, br s), 1.38 (3H, d, J=6.6 Hz), 1.28 (3H, d, J=7.3 Hz).

Mass spectrum (FAB$^+$): 566 [M+H]$^+$.

(2) (1R,5S,6S)-2-[1-(4-Carbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate (2.2 g, 3.93 mmol) (obtained as described in Example 3(1)) in a mixture of tetrahydrofuran (110 ml) and distilled water (110 ml) was subjected to catalytic hydrogenation in the presence of 10% palladium on charcoal (2.2 g) at room temperature for 2 hours. After checking the completion of the reaction, the reaction mixture was filtered and to the filtrate were added sodium hydrogencarbonate (330 mg), ethyl acetate and distilled water. The mixture was shaken in a separatory funnel. The aqueous layer was separated and concentrated under reduced pressure. The residue was purified by chromatography on a Cosmosil column using distilled water—2% acetonitrile; distilled water—4% acetonitrile; distilled water—6% acetonitrile; distilled water—8% acetonitrile and distilled water as the eluant. The eluate was lyophilized to afford the desired compound (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylic acid sodium salt (1.12 g, yield 64%) as a white solid.

$^1$H-NMR (400 MHz, D$_2$O, TSP): δ (ppm) 7.54 (1H, s), 4.56 (2H, t, J=8.6 Hz), 4.40–4.30 (1H, m), 4.52 (1H, quintet, J=6.2 Hz), 4.21 (1H, dd, J=9.1, 2.5 Hz), 4.07 (2H, m), 3.44 (1H, dd, J=6.2, 2.5 Hz), 4.07 (2H, dt, J=8.6, 4.2 Hz), 3.44 (1H, dd, J=6.2, 2.5 Hz), 3.26 (1H, dd, J=9.1, 7.2 Hz), 1.30 (3H, d, J=6.2 Hz), 1.20 (3H, d, J=7.2 Hz).

IR (KBr): 1749, 1671,1598, 1546, 1394, 1287 cm$^{-1}$.

Mass spectrum (FAB$^+$): 447 [M+H]$^+$.

High-resolution mass spectrum (FAB$^+$): calculated for C$_{17}$H$_{20}$O$_5$N$_4$S$_2$Na: 447.0773, Found: 447.0734 [M+H]$^+$.

EXAMPLE 4

(1R,5S,6S)-2-[1-(4-Cyano-1,3-thiazol-2-yl)azetidin-3-yl]thio-6-[(R)-1-hydroxyethyl]-1-methylcarbapen-2-em-3-carboxylic acid sodium salt

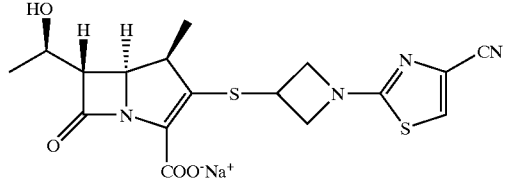

(1) p-Nitrobenzyl (1R,5S,6S)-2-[1-(4-cyano-1,3-thiazol-2-yl)azetidin-3-yl]thio-6-[(R)-1-hydroxyethyl]-1-methylcarbapen-2-em-3-carboxylate To a solution of 3-acetylthio-1-(4-cyano-1,3-thiazol-2-yl)azetidine (760 mg, 3.18 mmol) (obtained as described in Reference Example 4) in dimethylformamide (38 ml) was added hydrazine acetate (351 mg, 3.81 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (1.89 g, 3.18 mmol) in acetonitrile (95 ml) was added dropwise to the resulting mixture in an ice bath under an atmosphere of nitrogen, followed by the addition of diisopropylethylamine (2.21 ml, 12.7 mmol). The mixture was stirred for 4 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M aqueous sodium chloride solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:4) and ethyl acetate as the eluant to afford p-nitrobenzyl (1R,5S,6S)-2-[1-(4-cyano-1,3-thiazol-2-yl)azetidin-3-yl]thio-6-[(R)-1-hydroxyethyl]-1- methylcarbapen-2-em-3-carboxylate as a pale yellow solid (1.65 g, yield 96%).

$^1$H-NMR (400 MHz, CDCl$_3$): δ (ppm) 8.23 (2H, d, J=8.8 Hz), 7.66 (2H, d, J=8.8 Hz), 7.29 (1H, s), 5.51 (1H, d, 13.9 Hz), 5.25 (1H, d, J=13.9 Hz), 4.54 (2H, dd, J=16.0, 8.0 Hz), 4.36–4.24 (3H, m), 4.12–4.04 (2H, m), 3.30 (1H, dd, J=6.6, 2.9 Hz), 3.20 (1H, dq, J=9.4, 7.3 Hz), 1.80 (1H, br s), 1.38 (3H, d, J=5.9 Hz), 1.27 (3H, d, J=7.3 Hz).

Mass spectrum (FAB$^+$): 542 [M+H]$^+$.

(2) (1R,5S,6S)-2-[1-(4-Cyano-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-cyano-1,3-thiazol-2-yl)azetidin-3-yl]thio-6-[(R)-1-hydroxyethyl]-1-methylcarbapen-2-em-3-carboxylate (600 mg, 1.11 mmol) (obtained as described in Example 4(1)) in a mixture of tetrahydrofuran (30 ml) and distilled water (30 ml) was subjected to catalytic hydrogenation in the presence of 10% palladium on charcoal (600 mg) at room temperature for 2 hours. After checking the completion of the reaction, the reaction mixture was filtered and to the filtrate were added sodium hydrogencarbonate (93 mg), ethyl acetate and distilled water. The mixture was shaken in a separatory funnel. The aqueous layer was separated and concentrated under reduced pressure. The residue was purified by chromatography on a Cosmosil column using distilled water—3% acetonitrile; distilled water—6% acetonitrile; distilled water—9% acetonitrile; distilled water—12% acetonitrile; distilled water—15% acetonitrile; distilled water—18% acetonitrile and distilled water as the eluant. The eluate was lyophilized to afford the desired compound (1R,5S,6S)-2-[1-(4-cyano-1,3-thiazol-2-yl)azetidin-3-yl]thio-6-[(R)-1-hydroxyethyl]-1-methylcarbapen-2-em-3-carboxylic acid sodium salt (285 mg, yield 60%) as a white solid.

$^1$H-NMR (400 MHz, D$_2$O, TSP): δ (ppm) 7.68 (1H, s), 4.57 (2H, t, J=8.2 Hz), 4.44–4.32 (1H, m), 4.25 (1H, quintet, J=6.2 Hz), 4.21 (1H, dd, J=9.0, 2.3 Hz), 4.07 (2H, dt, 8.2, 4.7 Hz), 3.44 (1H, dd, J=6.2, 2.3 Hz), 3.25 (1H, dq, J=9.0, 7.2 Hz), 1.31 (3H, d, J=6.2 Hz), 1.20 (3H, d, J=7.2 Hz).

IR (KBr): 2231, 1750, 1599, 1549, 1470, 1397, 1307 cm$^{-1}$.

Mass spectrum (FAB$^+$): 429 [M+H]$^+$.

High-resolution mass spectrum (FAB$^+$): calculated for C$_{17}$H$_{18}$O$_4$N$_4$S$_2$Na 429.0668, Found: 429.0662 [M+H]$^+$.

EXAMPLE 5

(1R,5S,6S)-2-[1-(4-N-Methylcarbamoyl-1,3-thiazol-2-yl)azetidin-3-yl]thio-6-[(R)-1-hydroxyethyl]-1-methylcarbapen-2-em-3-carboxylic acid sodium salt

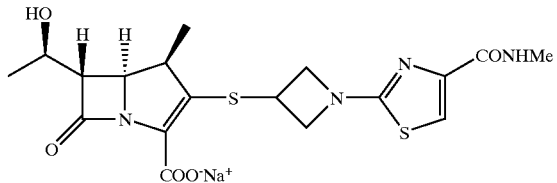

(1) p-Nitrobenzyl (1R,5S,6S)-2-[1-(4-N-methylcarbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-N-methylcarbamoyl-1,3-thiazol-2-yl)azetidine (570 mg, 2.10 mmol) (obtained as described in Reference Example 5) in dimethylformamide (28 ml) was added hydrazine acetate (291 mg, 3.16 mmol) at room temperature under an atmosphere of nitrogen and the mixture was stirred for 2 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (1.25 g, 2.10 mmol) in acetonitrile (25 ml) was added dropwise to the resulting mixture in an ice bath under an atmosphere of nitrogen, followed by the addition of diisopropylethylamine (1.83 ml, 10.5 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using toluene:acetonitrile (2:3) as the eluant to afford p-nitrobenzyl (1R,5S,6S)-2-[1-(4-N-methylcarbamoyl-1,3-thiazol-2-yl)azetidin-3-yl]thio-6-[(R)-1-hydroxyethyl]-1-methylcarbapen-2-em-3-carboxylate as a pale yellow solid (774 mg, yield 64%).

$^1$H-NMR (400 MHz, CDCl$_3$): δ (ppm) 8.21 (2H, d, J=8.8 Hz), 7.66 (2H, d, J=8.8 Hz), 7.34 (1H, s), 7.14 (1H, s), 5.51 (1H, d, J=13.8 Hz), 5.25 (1H, d, J=13.8 Hz), 4.48 (2H, dd, J=17.2, 8.9 Hz), 4.35–4.20 (3H, m), 4.10–4.00 (2H, m), 3.35–3.15 (2H, m), 2.96 (3H, d, J=5.1 Hz), 1.70 (1H, br s), 1.38 (3H, d, J=6.2 Hz), 1.27 (3H, d, J=7.3 Hz).

Mass spectrum (FAB$^+$): 574 [M+H]$^+$.

(2) (1R,5S,6S)-2-[1-(4-N-Methylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-methylcarbamoyl-1,3-thiazol-2-yl)azetidin-3-yl]thio-6-[(R)-1-hydroxyethyl]-1-methylcarbapen-2-em-3-carboxylate (768 mg, 1.34 mmol) (obtained as described in Example 5(1)) in a mixture of tetrahydrofuran (38 ml) and distilled water (19 ml) was subjected to catalytic hydrogenation in the presence of 20% palladium hydroxide (757 mg) in a water bath (30° C.) for 1.5 hours. After checking the completion of the reaction, the reaction mixture was filtered and to the filtrate were added sodium hydrogencarbonate (115 mg), a mixture of ethyl acetate and tetrahydrofuran (1:1) and distilled water. The mixture was shaken in a separatory funnel. The aqueous layer was washed with a mixture of ethyl acetate and tetrahydrofuran (1:1), separated and concentrated under reduced pressure. The residue was purified by chromatography on a Cosmosil column using distilled water—3% acetonitrile; distilled water—5% acetonitrile and distilled water as the eluant. The eluate was lyophilized to afford the desired compound (1R,5S,6S)-2-[1-(4-N-methylcarbamoyl-1,3-thiazol-2-yl)azetidin-3-yl]thio-6-[(R)-1-hydroxyethyl]-1-methylcarbapen-2-em-3-carboxylic acid sodium salt (392 mg, yield 64%) as a white solid.

$^1$H-NMR (400 MHz, D$_2$O): δ (ppm) 7.30 (1H, s), 4.40 (2H, t, J=8.0 Hz), 4.30–4.18 (1H, m), 4.18–4.00 (2H, m), 3.90–3.85 (2H, m), 3.30 (1H, dd, J=6.3, 3.8 Hz), 3.20–3.05 (1H, m), 1.18 (3H, d, J=6.4 Hz), 1.06 (3H, d, J=7.2 Hz).

IR (KBr): 1749, 1650, 1599, 1552, 1397, 1316 cm$^{-1}$.

Mass spectrum (FAB$^+$) 461 [M+H]$^+$.

EXAMPLE 6

(1R,5S,6S)-2-[1-(4-N,N-Dimethylcarbamoyl-1,3-thiazol-2-yl)azetidin-3-yl]thio-6-[(R)-1-hydroxyethyl]-1-methylcarbapen-2-em-3-carboxylic acid sodium salt

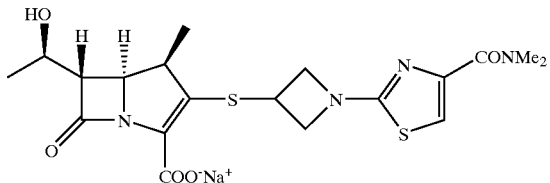

(1) p-Nitrobenzyl (1R,5S,6S)-2-[1-(4-N,N-dimethylcarbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-N,N-dimethylcarbamoyl-1,3-thiazol-2-yl)azetidine (563 mg, 1.49 mmol) (obtained as described in Reference Example 6) in dimethylformamide (28 ml) was added hydrazine acetate (264 mg, 2.87 mmol) at room temperature under an atmosphere of nitrogen and the mixture was stirred for 3 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (1.15 g, 1.94 mmol) in acetonitrile (23 ml) was added dropwise to the resulting mixture in an ice bath under an atmosphere of nitrogen, followed by the addition of diisopropylethylamine (1.7 ml, 9.76 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using toluene:acetonitrile (2:3) as the eluant to afford p-nitrobenzyl (1R,5S,6S)-2-[1-(4-N,N-dimethylcarbamoyl-1,3-thiazol-2-yl)azetidin-3-yl]thio-6-[(R)-1-hydroxyethyl]-1-methylcarbapen-2-em-3-carboxylate as a pale yellow solid (777 mg, yield 68%).

$^1$H-NMR (400 MHz, CDCl$_3$): δ (ppm) 8.22 (2H, d, J=8.2 Hz), 7.66 (2H, d, J=8.2 Hz), 7.09 (1H, s), 5.50 (1H, d, J=13.5 Hz), 5.25 (1H, d, J=13.5 Hz), 4.60–4.40 (2H, m), 4.35–4.20 (3H, m), 4.20–4.00 (2H, m), 3.32–3.25 (1H, m), 3.25–3.12 (4H, m), 3.05 (3H, br s), 1.57 (1H, br s), 1.38 (3H, d, J=6.2 Hz), 1.25 (3H, d, J=7.1 Hz).

Mass spectrum (FAB$^+$): 588 [M+H]$^+$.

(2) (1R,5S,6S)-2-[1-(4-N,N-Dimethylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N,N-dimethylcarbamoyl-1,3-thiazol-2-yl)azetidin-3-yl]thio-6-[(R)-1-hydroxyethyl]-1-methylcarbapen-2-em-3-carboxylate (772 mg, 1.31 mmol) (obtained as described in Example 6(1)) in a mixture of tetrahydrofuran (38 ml) and distilled water (19 ml) was subjected to catalytic hydrogenation in the presence of 20% palladium hydroxide (768 mg) in a water bath (30° C.) for 1.5 hours. After checking the completion of the reaction, the reaction mixture was filtered and to the filtrate were added sodium hydrogencarbonate (112 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column. The eluate was lyophilized to afford the desired compound (1R,5S,6S)-2-[1-(4-N,N-dimethylcarbamoyl-1,3-thiazol-2-yl)azetidin-3-yl]thio-6-[(R)-1-hydroxyethyl]-1-methylcarbapen-2-em-3-carboxylic acid sodium salt (375 mg, yield 60%) as a white solid.

$^1$H-NMR (400 MHz, D$_2$O): δ (ppm) 7.00 (1H, s), 4.56–4.36 (2H, m), 4.31–4.21 (1H, m), 4.21–4.06 (2H, m), 4.01–3.91 (2H, m), 3.41–3.32 (1H, m), 3.21–3.11 (1H, m), 3.00 (3H, s), 2.91 (3H, s), 1.21 (3H, d, J=6.4 Hz), 1.11 (3H, d, J=7.1 Hz).

IR (KBr): 1750, 1610, 1540, 1397, 1305 cm$^{-1}$.

Mass spectrum (FAB$^+$): 475 [M+H]$^+$.

High-resolution mass spectrum (FAB$^+$): calculated for C$_{19}$H$_{24}$O$_5$N$_4$S$_2$Na: 475.1087, Found: 475.1085 [M+H]$^+$.

EXAMPLE 7

(1R,5S,6S)-2-[1-(4-N-Ethylcarbamoyl-1,3-thiazol-2-yl)azetidin-3-yl]thio-6-[(R)-1-hydroxyethyl]-1-methylcarbapen-2-em-3-carboxylic acid sodium salt

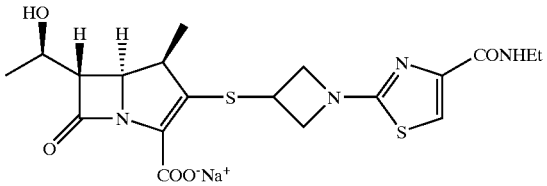

(1) p-Nitrobenzyl (1R,5S,6S)-2-[1-(4-N-ethylcarbamoyl-1,3-thiazol-2-yl)azetidin-3yl]thio-6-[(R)-1-hydroxyethyl]-1-methylcarbapen-2-em-3-carboxylate To a solution of 3-acetylthio-1-(4-N-ethylcarbamoyl-1,3-thiazol-2-yl)azetidine (450 mg, 1.58 mmol) (obtained as described in Reference Example 7) in dimethylformamide (23 ml) was added hydrazine acetate (174 mg, 1.89 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (939 mg, 1.58 mmol) in acetonitrile (47 ml) was added dropwise to the resulting mixture in an ice bath under an atmosphere of nitrogen, followed by the addition of diisopropylethylamine (1.10 ml, 6.31 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate—10% methanol and ethyl acetate as the eluant to afford p-nitrobenzyl (1R,5S,6S)-2-[1-(4-N-ethylcarbamoyl-1,3-thiazol-2-yl)azetidin-3-yl]thio-6-[(R)-1-hydroxyethyl]-1-methylcarbapen-2-em-3-carboxylate as a pale yellow solid (753 mg, yield 81%).

¹H-NMR (400 MHz, CDCl₃): δ (ppm) 8.23 (2H, d, J=8.8 Hz), 7.66 (2H, d, J=8.8 Hz), 7.43 (1H, s), 7.12 (1H, t, J=5.1 Hz), 5.51 (1H, d, J=13.9 Hz), 5.25 (1H, d, J=13.9 Hz), 4.49 (2H, dd, J=16.1, 8.1 Hz), 4.32–4.20 (3H, m), 4.10–4.00 (2H, m), 3.44 (2H, dq, J=7.3, 5.0 Hz), 3.29 (1H, dd, J=7.3, 2.9 Hz), 3.21 (1H, dq, J=8.9, 7.3 Hz), 1.38 (3H, d, J=5.9 Hz), 1.28 (3H, d, J=7.3 Hz), 1.23 (3H, t, J=7.3 Hz).

Mass spectrum (FAB⁺): 588 [M+H]⁺.

(2) (1R,5S,6S)-2-[1-(4-N-Ethylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-ethylcarbamoyl-1,3-thiazol-2-yl)azetidin-3-yl]thio-6-[(R)-1-hydroxyethyl]-1-methylcarbapen-2-em-3-carboxylate (750 mg, 1.23 mmol) (obtained as described in Example 7(1)) in a mixture of tetrahydrofuran (38 ml) and distilled water (38 ml) was subjected to catalytic hydrogenation in the presence of 10% palladium on charcoal (750 mg) at room temperature for 1.7 hours. After checking the completion of the reaction, the reaction mixture was filtered and to the filtrate were added sodium hydrogencarbonate (103 mg), ethyl acetate and distilled water. The mixture was shaken in a separatory funnel. The aqueous layer was separated and concentrated under reduced pressure. The residue was purified by chromatography on a Cosmosil column using distilled water— 3% acetonitrile; distilled water—6% acetonitrile; distilled water—9% acetonitrile; distilled water—12% acetonitrile; distilled water—15% acetonitrile; distilled water—18% acetonitrile; distilled water—21% acetonitrile; and distilled water as the eluant. The eluate was lyophilized to afford the desired compound (1R,5S,6S)-2-[1-(4-N-ethylcarbamoyl-1,3-thiazol-2-yl)azetidin-3-yl]thio-6-[(R)-1-hydroxyethyl]-1-methylcarbapen-2-em-3-carboxylic acid sodium salt (384 mg, yield 66%) as a white solid.

¹H-NMR (400 MHz, D₂O, TSP): δ (ppm) 7.45 (1H, s), 4.60–4.48 (2H, m), 4.40–4.29 (1H, m), 4.25 (1H, quintet, J=6.2 Hz), 4.20 (1H, dd, J=9.1, 2.3 Hz), 4.12–4.00 (2H, m), 3.43 (1H, dd, J=6.2, 2.3 Hz), 3.37 (3H, q, J=7.2 Hz), 3.32–3.18 (1H, m), 1.30 (3H, d, J=6.2 Hz), 1.20 (3H, d, J=7.2 Hz), 1.19 (3H, t, J=7.2 Hz).

IR (KBr): 1750, 1659, 1604, 1548, 1394, 1315 cm⁻¹.

Mass spectrum (FAB⁺): 475 [M+H]⁺.

High-resolution mass spectrum (FAB⁺): calculated for C₁₉H₂₄O₅N₄S₂Na: 475.1086, Found: 475.1070 [M+H]⁺.

EXAMPLE 8

(1R,5S,6S)-2-[1-(4-N-Isopropylcarbamoyl-1,3-thiazol-2-yl)azetidin-3-yl]thio-6-[(R)-1-hydroxyethyl]-1-methylcarbapen-2-em-3-carboxylic acid sodium salt

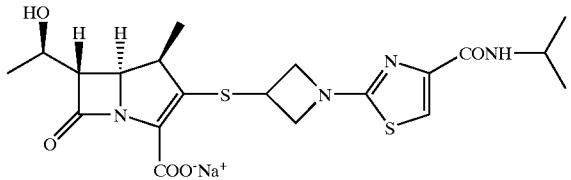

(1) p-Nitrobenzyl (1R,5S,6S)-2-[1-(4-N-isopropylcarbamoyl-1,3-thiazol-2-yl)azetidin-3-yl]thio-6-[(R)-1-yl]thio-6-[(R)-1-hydroxyethyl]-1-methylcarbapen-2-em-3-carboxylate To a solution of 3-acetylthio-1-(4-N-isopropylcarbamoyl-1,3-thiazol-2-yl)azetidine (460 mg, 1.65 mmol) (obtained as described in Reference Example 8) in dimethylformamide (23 ml) was added hydrazine acetate (182 mg, 1.98 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (981 mg, 1.65 mmol) in acetonitrile (49 ml) was added dropwise to the resulting mixture in an ice bath under an atmosphere of nitrogen, followed by the addition of diisopropylethylamine (1.15 ml, 6.60 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using n-hexane: ethyl acetate (1:2); ethyl acetate—5% methanol and ethyl acetate as the eluant to afford p-nitrobenzyl (1R,5S,6S)-2-[1-(4-N-isopropylcarbamoyl-1,3-thiazol-2-yl)azetidin-3-yl]thio-6-[(R)-1-hydroxyethyl]-1-methylcarbapen-2-em-3-carboxylate as a pale yellow solid (790 mg, yield 80%).

¹H-NMR (400 MHz, CDCl₃): δ (ppm) 8.23 (2H, d, J=8.8 Hz), 7.66 (2H, d, J=8.8 Hz), 7.42 (1H, s), 6.95 (1H, d, J=8.1 Hz), 5.51 (1H, d, J=13.6 Hz), 5.25 (1H, d, J=13.6 Hz), 4.49 (2H, dd, J=14.6, 8.1 Hz), 4.32–3.40 (5H, m), 3.30 (1H, dd, J=7.3, 2.9 Hz), 3.21 (1H, dq, J=8.8, 7.3 Hz), 1.60 (1H, br s), 1.38 (1H, d, J=6.6 Hz), 1.30–1.20 (9H, m).

Mass spectrum (FAB⁺): 602 [M+H].

(2) (1R,5S,6S)-2-[1-(4-N-isopropylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-isopropylcarbamoyl-1,3-thiazol-2-yl)azetidin-3-yl]thio-6-[(R)-1-hydroxyethyl]-1-methylcarbapen-2-em-3-carboxylate (790 mg,1.31 mmol) (obtained as described in Example 8(1)) in a mixture of tetrahydrofuran (40 ml) and distilled water (40 ml) was subjected to catalytic hydrogenation in the presence of 10% palladium on charcoal (790 mg) at room temperature for 1.7 hours. After checking the completion of the reaction, the reaction mixture was filtered and to the filtrate were added sodium hydrogencarbonate (110 mg), ethyl acetate and distilled water. The mixture was shaken in a separatory funnel. The aqueous layer was separated and concentrated under reduced pressure. The residue was purified by chromatography on a Cosmosil column using distilled water—4% acetonitrile; distilled water—8% acetonitrile; distilled water—12% acetonitrile; distilled water—16% acetonitrile; distilled water—20% acetonitrile and distilled water as the eluant. The eluate was lyophilized to afford the desired compound (1R,5S,6S)-2-[1-(4-N-isopropylcarbamoyl-1,3-thiazol-2-yl)azetidin-3-yl]thio-6-[(R)-1-hydroxyethyl]-1-methylcarbapen-2-em-3-carboxylic acid sodium salt (389 mg, yield 61%) as a white solid.

¹H-NMR (400 MHz, D₂O, TSP): δ (ppm) 7.45 (1H, s), 4.55 (2H, t, J=8.4 Hz), 4.40–4.30 (1H, m), 4.25 (1H, quintet, J=6.3 Hz), 4.19 (1H, dd, J=9.0, 2.4 Hz), 4.14–4.03 (3H, m), 3.43 (1H, dd, J=6.3, 2.4 Hz), 3.25 (1H, dq, J=9.0, 7.2 Hz), 1.30 (3H, d, J=6.3 Hz), 1.23 (6H, d, J=6.7 Hz), 1.20 (3H, d, J=7.2 Hz).

IR (KBr): 1751, 1657, 1548, 1492, 1469, 1393, 1303, 1263 cm$^{-1}$.

Mass spectrum (FAB$^+$): 489 [M+H]$^+$.

High-resolution mass spectrum (FAB$^+$): calculated for $C_{20}H_{26}O_5N_4S_2Na$: 489.1242, Found: 489.1234 [M+H]$^+$.

EXAMPLE 9

(1R,5S,6S)-2-[1-(4-N-Cyclopentylcarbamoyl-1,3-thiazol-2-yl)azetidin-3-yl]thio-6-[(R)-1-hydroxyethyl]-1-methylcarbapen-2-em-3-carboxylic acid sodium salt

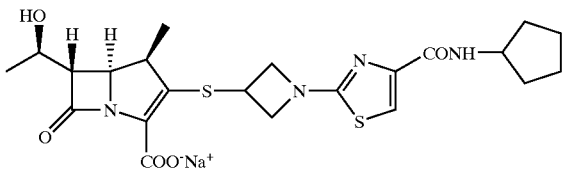

(1) p-Nitrobenzyl (1R,5S,6S)-2-[1-(4-N-cyclopentylcarbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-N-cyclopentylcarbamoyl-1,3-thiazol-2-yl)azetidine (550 mg, 1.67 mmol) (obtained as described in Reference Example 9) in dimethylformamide (28 ml) was added hydrazine acetate (187 mg, 2.03 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (993 mg, 1.67 mmol) in acetonitrile (50 ml) was added dropwise to the resulting mixture in an ice bath under an atmosphere of nitrogen, followed by the addition of diisopropylethylamine (1.16 ml, 6.68 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column to afford p-nitrobenzyl (1R,5S,6S)-2-[1-(4-N-cyclopentylcarbamoyl-1,3-thiazol-2-yl)azetidin-3-yl]thio-6-[(R)-1-hydroxyethyl]-1-methylcarbapen-2-em-3-carboxylate as a pale yellow solid (346 mg, yield 33%).

$^1$H-NMR (400 MHz, CDCl$_3$): δ (ppm) 8.24 (2H, d, J=8.0 Hz), 7.66 (2H, d, J=8.0 Hz), 7.42 (1H, s), 7.05 (1H, bd, J=8.0 Hz), 5.51 (1H, d, J=13.6 Hz), 5.26 (1H, d, J=13.6 Hz), 4.49 (2H, dd, J=15.6, 8.1 Hz), 4.38–4.24 (3H, m), 4.10–4.00 (2H, m), 3.30 (1H, dd, J=6.2, 2.1 Hz), 3.22 (1H, dq, J=9.4, 8.3 Hz), 2.12–2.00 (2H, m), 1.81 (1H, br s), 1.78–1.44 (6H, m), 1.38 (3H, d, J=5.8 Hz), 1.28 (3H, d, J=7.3 Hz).

Mass spectrum (FAB$^+$): 628 [M+H]$^+$.

(2) (1R,5S,6S)-2-[1-(4-N-cyclopentylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-cyclopentylcarbamoyl-1,3-thiazol-2-yl)azetidin-3-yl]thio-6-[(R)-1-hydroxyethyl]-1-methylcarbapen-2-em-3-carboxylate (340 mg, 0.542 mmol) (obtained as described in Example 9(1)) in a mixture of tetrahydrofuran (17 ml) and distilled water (17 ml) was subjected to catalytic hydrogenation in the presence of 10% palladium on charcoal (340 mg) at room temperature for 2 hours. After checking the completion of the reaction, the reaction mixture was filtered and to the filtrate were added sodium hydrogencarbonate (46 mg), ethyl acetate and distilled water. The mixture was shaken in a separatory funnel. The aqueous layer was separated and concentrated under reduced pressure. The residue was purified by chromatography on a Cosmosil column using distilled water—4% acetonitrile; distilled water—8% acetonitrile; distilled water—12% acetonitrile; distilled water—16% acetonitrile; distilled water—20% acetonitrile; distilled water—24% acetonitrile; distilled water—28% acetonitrile and distilled water as the eluant. The eluate was lyophilized to afford the desired compound (1R,5S,6S)-2-[1-(4-N-cyclopentylcarbamoyl-1,3-thiazol-2-yl)azetidin-3-yl]thio-6-[(R)-1-hydroxyethyl]-1-methylcarbapen-2-em-3-carboxylic acid sodium salt (159 mg, yield 57%) as a white solid.

$^1$H-NMR (400 MHz, D$_2$O, TSP): δ (ppm) 7.45 (1H, s), 4.55 (1H, dt, J=8.1, 1.3 Hz), 4.40–4.30 (1H, m), 4.30–4.16 (3H, m including q at 4.25, J=6.3 Hz, and dd at 4.19, J=9.1, 2.6 Hz), 4.12–4.00 (2H, m), 3.43 (1H, dd, J=6.3, 2.6 Hz), 3.24 (1H, dq, J=9.1, 7.3 Hz), 2.06–1.94 (2H, m), 1.80–1.50 (6H, m), 1.30 (3H, d, J=6.3 Hz), 1.19 (3H, d, J=7.3 Hz).

IR (KBr): 1751, 1658, 1605, 1547, 1393, 1315 cm$^{-1}$.

Mass spectrum (FAB$^+$): 515 [M+H]$^+$.

High-resolution mass spectrum (FAB$^+$): calculated for $C_{22}H_{28}O_5N_4S_2Na$: 515.1399, Found: 515.1398 [M+H]$^+$.

EXAMPLE 10

(1R,5S,6S)-2-[1-(4-N-Cyclohexylcarbamoyl-1,3-thiazol-2-yl)azetidin-3-yl]thio-6-[(R)-1-hydroxyethyl]-1-methylcarbapen-2-em-3-carboxylic acid sodium salt

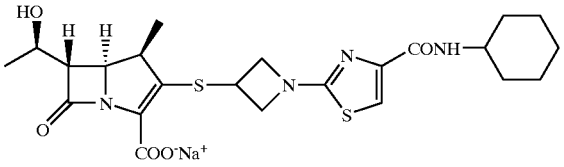

(1) p-Nitrobenzyl (1R,5S,6S)-2-[1-(4-N-cyclohexylcarbamoyl-1,3-thiazol-2-yl)azetidin-yl]thio-6-[(R)-1-hydroxyethyl]-1-methylcarbapen-2-em-3-carboxylate To a solution of 3-acetylthio-1-(4-N-cyclohexylcarbamoyl-1,3-thiazol-2-yl)azetidine (121 mg, 1.09 mmol) (obtained as described in Reference Example 10) in dimethylformamide (19 ml) was added hydrazine acetate (121 mg, 1.31 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (648 mg, 1.09 mmol) in acetonitrile (32 ml) was added dropwise to the resulting mixture in an ice bath under an atmosphere of nitrogen, followed by the addition of diisopropylethylamine (0.759 ml, 4.36 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using n-hexane: ethyl acetate (1:4); ethyl acetate—5% methanol and ethyl acetate as the eluant to afford p-nitrobenzyl (1R,5S,6S)-2-[1-(4-N-cyclohexylcarbamoyl-1,3-thiazol-2-yl)azetidin-3-yl]thio-6-[(R)-1-hydroxyethyl]-1-methylcarbapen-2-em-3-carboxylate as a pale yellow solid (598 mg, yield 86%).

$^1$H-NMR (400 MHz, CDCl$_3$): δ (ppm) 8.23 (2H, d, J=8.8 Hz), 7.66 (2H, d, J=8.8 Hz), 7.42 (1H, s), 7.00 (1H, d, J=8.8 Hz), 5.51 (1H, d, J=13.5 Hz), 5.25 (1H, d, J=13.5 Hz), 4.49 (2H, dd, J=15.4, 8.8 Hz), 4.32–4.20 (3H, m), 4.11–4.00 (2H, m), 3.96–3.80 (1H, m), 3.29 (1H, dd, J=6.6, 2.2 Hz), 3.21 (1H, dq, J=8.8, 7.3 Hz), 2.01–1.18 (16H, m including 3H, d at 1.38, J=5.9 Hz and 3H, d at 1.28, J=7.3 Hz).

Mass spectrum (FAB$^+$): 642 [M+H]$^+$.

(2) (1R,5S,6S)-2-[1-(4-N-Cyclohexylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-cyclohexylcarbamoyl-1,3-thiazol-2-yl)azetidin-3-yl]thio-6-[(R)-1-hydroxyethyl]-1-methylcarbapen-2-em-3-carboxylate (590 mg, 0.919 mmol) (obtained as described in Example 10(1)) in a mixture of tetrahydrofuran (30 ml) and distilled water (30 ml) was subjected to catalytic hydrogenation in the presence of 10% palladium on charcoal (590 mg) at room temperature for 3 hours. After checking the completion of the reaction, the reaction mixture was filtered and to the filtrate were added sodium hydrogencarbonate (77 mg), ethyl acetate and distilled water. The mixture was shaken in a separatory funnel. The aqueous layer was separated and concentrated under reduced pressure. The residue was purified by chromatography on a Cosmosil column using distilled water—4% acetonitrile; distilled water—8% acetonitrile; distilled water—12% acetonitrile; distilled water—16% acetonitrile; distilled water—20% acetonitrile; distilled water—24% acetonitrile; distilled water—28% acetonitrile and distilled water as the eluant. The eluate was lyophilized to afford the desired compound (1R,5S,6S)-2-[1-(4-N-cyclohexylcarbamoyl-1,3-thiazol-2-yl)azetidin-3-yl]thio-6-[(R)-1-hydroxyethyl]-1-methylcarbapen-2-em-3-carboxylic acid sodium salt (318 mg, yield 66%) as a white solid.

$^1$H-NMR (400 MHz, D$_2$O, TSP): δ (ppm) 7.45 (1H, s), 4.55 (2H, dt, J=8.5, 1.9 Hz), 4.40–4.30 (1H, m), 4.25 (1H, quintet, J=6.3 Hz), 4.19 (1H, dd, J=9.0, 2.4 Hz), 4.10–4.00 (2H, m), 3.80–3.70 (1H, m), 3.43 (1H, dd, J=6.3, 2.4 Hz), 3.24 (1H, dq, J=9.0, 7.1 Hz), 1.96–1.84 (2H, m), 1.83–1.70 (2H, m), 1.69–1.58 (1H, m), 1.46–1.10 (11H, m including 3H, d, at 1.30, J=6.3 Hz, and 3H, d, at 1.19, J=7.1 Hz).

IR (KBr): 1751, 1660, 1605, 1545, 1492, 1393, 1310, 1296 cm$^{-1}$.

Mass spectrum (FAB$^+$): 529 [M+H]$^+$.

High-resolution mass spectrum (FAB$^+$): calculated for C$_{23}$H$_{30}$O$_5$N$_4$S$_2$Na: 529.1555, Found: 529.1575 [M+H]$^+$.

EXAMPLE 11

(1R,5S,6S)-2-[1-(4-Morpholinocarbonyl-1,3-thiazol-2-yl)azetidin-3-yl]thio-6-[(R)-1-hydroxyethyl]-1-methylcarbapen-2-em-3-carboxylic acid sodium salt

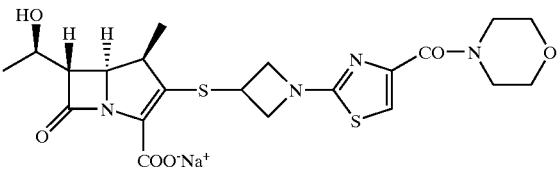

(1) p-Nitrobenzyl (1R,5S,6S)-2-[1-(4-morpholinocarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-morpholinocarbonyl-1,3-thiazol-2-yl)azetidine (410 mg, 1.50 mmol) (obtained as described in Reference Example 11) in dimethylformamide (20 ml) was added hydrazine acetate (138 mg, 1.50 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (743 mg, 1.25 mmol) in acetonitrile (37 ml) was added dropwise to the resulting mixture in an ice bath under an atmosphere of nitrogen, followed by the addition of diisopropylethylamine (0.873 ml, 5.01 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate—10% methanol and ethyl acetate as the eluant to afford p-nitrobenzyl (1R,5S,6S)-2-[1-(4-morpholinocarbonyl-1,3-thiazol-2-yl)azetidin-3-yl]thio-6-[(R)-1-hydroxyethyl]-1-methylcarbapen-2-em-3-carboxylate as a pale yellow solid (485 mg, yield 62%).

$^1$H-NMR (400 MHz, CDCl$_3$): δ (ppm) 8.23 (2H, d, J=8.8 Hz), 7.66 (2H, d, J=8.8 Hz), 7.19 (1H, s), 5.51 (1H, d, J=13.9 Hz), 5.25 (1H, d, J=13.9 Hz), 4.50 (2H, ddd, J=13.9, 8.1, 2.2 Hz), 4.35–4.20 (3H, m), 4.10–4.00 (2H, m), 3.95–3.60 (8H, m), 3.29 (1H, dd, J=6.6, 2.2 Hz), 3.20 (1H, dq, J=8.8, 7.3 Hz), 1.38 (3H, d, J=6.6 Hz), 1.27 (3H, d, J=7.3 Hz).

Mass spectrum (FAB$^+$): 630 [M+H]$^+$.

(2) (1R,5S,6S)-2-[1-(4-Morpholinocarbonyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-morpholinocarbonyl-1,3-thiazol-2-yl)azetidin-3-yl]thio-6-[(R)-1-hydroxyethyl]-1-methylcarbapen-2-em-3-carboxylate (480 mg, 0.762 mmol) (obtained as described in Example 11(1)) in a mixture of tetrahydrofuran (24 ml) and distilled water (24 ml) was subjected to catalytic hydrogenation in the presence of 10% palladium on charcoal (480 mg) at room temperature for 1.3 hours. After checking the completion of the reaction, the reaction mixture was filtered and to the filtrate were added sodium hydrogencarbonate (64 mg), ethyl acetate and distilled water. The mixture was shaken in a separatory funnel. The aqueous layer was separated and concentrated under reduced pressure. The residue was purified by chromatography on a Cosmosil column using distilled water—3% acetonitrile; distilled water—6% acetonitrile; distilled water—9% acetonitrile; distilled water—12% acetonitrile; distilled water—15% acetonitrile and distilled water as the eluant. The eluate was lyophilized to afford the desired compound (1R,5S,6S)-2-[1-(4-morpholinocarbonyl-1,3-thiazol-2-yl)azetidin-3-yl]thio-6-[(R)-1-hydroxyethyl]-1-methylcarbapen-2-em-3-carboxylic acid sodium salt (236 mg, yield 60%) as a white solid.

$^1$H-NMR (400 MHz, D$_2$O, TSP): δ (ppm) 7.15 (1H, s), 4.56 (2H, dt, J=8.4, 0.9 Hz), 4.42–4.32 (1H, m), 4.25 (1H, quintet, J=6.3 Hz), 4.21 (1H, dd, J=9.0, 2.3 Hz), 4.05 (2H, m), 3.90–3.60 (8H, m), 3.44 (1H, dd, J=6.3, 2.3 Hz), 3.25 (1H, dq, J=9.0, 7.3 Hz), 1.30 (3H, d, J=6.3 Hz), 1.20 (3H, d, J=7.3 Hz).

IR (KBr): 1799, 1608, 1536, 1392, 1311, 1236, 1113 cm$^{-1}$.

Mass spectrum (FAB$^+$): 517 [M+H]$^+$.

High-resolution mass spectrum (FAB$^+$): calculated for C$_{21}$H$_{26}$O$_6$N$_4$S$_2$Na: 517.1192, Found: 517.1186 [M+H]$^+$.

EXAMPLE 12

(1R,5S,6S)-2-[1-(4-Ethoxycarbonyl-1,3-thiazol-2-yl) piperidin-4-yl]thio-6-[(R)-1-hydroxyethyl]-1-methylcarbapen-2-em-3-carboxylic acid sodium salt

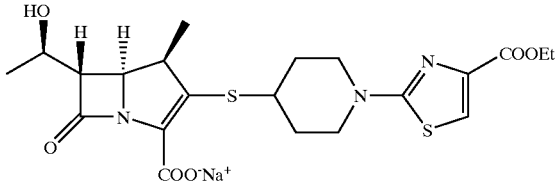

(1) p-Nitrobenzyl (1R,5S,6S)-2-[1-(4-ethoxycarbonyl-3-thiazol-2-yl)piperidin-4-yl]thio-6-[(R)-1-hydroxyethyl]-1-methylcarbapen-2-em-3-carboxylate To a solution of 4-acetylthio-1-(4-ethoxycarbonyl-1,3-thiazol-2-yl)piperidine (400 mg, 1.27 mmol) (obtained as described in Reference Example 13) in dimethylformamide (12 ml) was added hydrazine acetate (152 mg, 1.65 mmol) at room temperature under an atmosphere of nitrogen and the mixture was stirred for 2.5 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (755 mg, 1.27 mmol) in acetonitrile (21 ml) was added dropwise to the resulting mixture in an ice bath under an atmosphere of nitrogen, followed by the addition of diisopropylethylamine (1.11 ml, 6.37 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using n-hexane: ethyl acetate (1:2) and ethyl acetate as the eluant to afford p-nitrobenzyl (1R,5S,6S)-2-[1-(4-ethoxycarbonyl-1,3-thiazol-2-yl)piperidin-4-yl]thio-6-[(R)-1-hydroxyethyl]-1-methylcarbapen-2-em-3-carboxylate as a pale yellow solid (296 mg, yield 38%).

$^1$H-NMR (400 MHz, CDCl$_3$): δ (ppm) 8.27 (2H, d, J=8.7 Hz), 7.71 (2H, d, J=8.7 Hz), 7.51 (1H, s), 5.56 (1H, d, J=13.7 Hz), 5.28 (1H, d, J=13.7 Hz), 4.40 (2H, q, J=7.1 Hz), 4.39–4.30 (2H, m), 4.10–4.00 (2H, m), 3.60–3.20 (5H, m), 2.20–2.00 (2H, m), 1.90–1.70 (3H, m), 1.43 (3H, d, J=6.5 Hz), 1.41 (3H, t, J=7.1 Hz), 1.36 (7.2 Hz).

(2) (1R,5S,6S)-2-[1-(4-Ethoxycarbonyl-1,3-thiazol-2-yl)piperidin-4-yl]thio-6-[(R)-1-hydroxyethyl]-1-methylcarbapen-2-em-3-carboxylic acid sodium salt p-Nitrobenzyl (1R,5S,6S)-2-[1-(4-ethoxycarbonyl-1,3-thiazol-2-yl)piperidin-4-yl]thio-6-[(R)-1-hydroxyethyl]-1-methylcarbapen-2-em-3-carboxylate (291 mg, 0.578 mmol) (obtained as described in Example 12(1)) in a mixture of tetrahydrofuran (14 ml) and distilled water (7 ml) was subjected to catalytic hydrogenation in the presence of 20% palladium hydroxide (291 mg) in a water bath (30° C.) for 1.5 hours. After checking the completion of the reaction, the reaction mixture was filtered and to the filtrate were added sodium hydrogencarbonate (42 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water—5% acetonitrile; distilled water—7% acetonitrile and distilled water as the eluant. The eluate was lyophilized to afford the desired compound (1R,5S,6S)-2-[1-(4-ethoxycarbonyl-1,3-thiazol-2-yl)piperidin4-yl]thio-6-[(R)-1-hydroxyethyl]-1-methylcarbapen-2-em-3-carboxylic acid sodium salt (69 mg, yield 29%) as a white solid.

$^1$H-NMR (400 MHz, D$_2$O, TSP): δ (ppm) 7.69 (1H, s), 4.35 (2H, q, J=7.1 Hz), 4.30–4.20 (2H, m including dd at 4.23, J=9.2, 2.5 Hz), 4.00–3.85 (2H, m), 3.55–3.20 (5H, m), 2.20–2.05 (2H, m), 1.75–1.60 (2H, m), 1.36 (3H, t, J=7.1 Hz), 1.31 (3H, d, J=6.4 Hz), 1.23 (3H, d, J=7.2 Hz).

IR (KBr): 1750, 1729, 1603, 1540, 1448, 1385, 1337, 1265, 1223, 1210 cm$^{-1}$.

Mass spectrum (FAB$^+$): 504 [M+H]$^+$.

High-resolution mass spectrum (FAB$^+$): calculated for C$_{21}$H$_{27}$O$_6$N$_3$S$_2$Na: 504.1239, Found: 504.1246 [M+H]$^+$.

EXAMPLE 13

(1R,5S,6S)-2-[1-(4-Carboxyl-1,3-thiazol-2-yl) piperidin-4-yl]thio-6-[(R)-1-hydroxyethyl]-1-methylcarbapen-2-em-3-carboxylic acid disodium salt

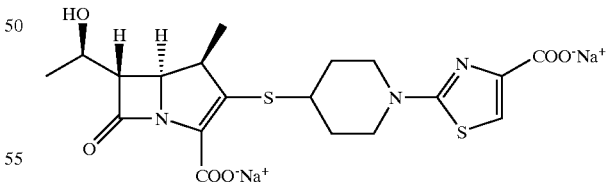

(1) p-Nitrobenzyl (1R,5S,6S)-2-[1-(4-p-nitrobenzyloxycarbonyl-3-thiazol-2-yl)piperidin-4-yl]thio-6-[(R)-1-hydroxyethyl]-1-methylcarbapen-2-em-3-carboxylate To a solution of 4-acetylthio-1-(4-p-nitrobenzylcarbonyl-1,3-thiazol-2-yl)piperidine (150 mg, 0.353 mmol) (obtained as described in Reference Example 14) in dimethylformamide (7.5 ml) was added hydrazine acetate (46 mg, 0.49 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (200 mg, 0.353 mmol) in acetonitrile (3.0 ml) was added dropwise to the resulting mixture in an ice bath under an atmosphere of nitrogen, followed by the addition of diisopropylethylamine (0.09 ml, 0.517 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column to afford p-nitrobenzyl (1R,5S,6S)-2-[1-(4-p-nitrobenzyloxycarbonyl-1,3-thiazol-2-yl)piperidin-4-yl]thio-6-[(R)-1-hydroxyethyl]-1-methylcarbapen-2-em-3-carboxylate as a pale yellow solid (220 mg, yield 89%).

¹H-NMR (400 MHz, CDCl₃): δ (ppm) 8.23 (2H, d, J=8.6 Hz), 8.22 (2H, d, J=8.6 Hz), 7.66 (2H, d, J=8.6 Hz), 7.59 (2H, d, J=8.6 Hz), 7.53 (1H, s), 5.51 (1H, d, J=13.8 Hz), 5.43 (2H, s), 5.22 (1H, d, J=13.8 Hz), 4.35–4.20 (2H, m), 4.05–3.90 (2H, m), 3.50–3.10 (6H, m), 2.20–1.95 (2H, m), 1.90–1.50 (3H, m), 1.38 (3H, d, J=6.2 Hz), 1.31 (3H, d, J=7.2 Hz).

Mass spectrum (FAB⁺): 724 [M+H]⁺.

(2) (1R,5S,6S)-2-[1-(4-Carboxyl-1,3-thiazol-2-yl)piperidin-4-yl]thio-6-[(R)-1-hydroxyethyl]-1-methylcarbapen-2-em-3-carboxylic acid disodium salt p-Nitrobenzyl (1R,5S,6S)-2-[1-(4-p-nitrobenzyloxycarbonyl-1,3-thiazol-2-yl)piperidin-4-yl]thio-6-[(R)-1-hydroxyethyl]-1-methylcarbapen-2-em-3-carboxylate (570 mg, 0.788 mmol) (obtained as described in Example 13(1)) in a mixture of tetrahydrofuran (38 ml) and distilled water (19 ml) was subjected to catalytic hydrogenation in the presence of 20% palladium hydroxide (572 mg) in a water bath (30° C.) for 2 hours. After checking the completion of the reaction, the reaction mixture was filtered and to the filtrate were added sodium hydrogencarbonate (132 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water—3% acetonitrile and distilled water as the eluant. The eluate was lyophilized to afford the desired compound (1R,5S,6S)-2-[1-(4-carboxyl-1,3-thiazol-2-yl)piperidin-4-yl]thio-6-[(R)-1-hydroxyethyl]-1-methylcarbapen-2-em-3-carboxylic acid disodium salt (285 mg, yield 76%) as a white solid.

¹H-NMR (400 MHz, D₂O): δ (ppm) 7.22 (1H, s), 4.30–4.10 (2H, m), 4.00–3.78 (2H, m), 3.60–3.05 (5H, m), 2.15–2.00 (2H, m), 1.80–1.55 (2H, m), 1.26 (3H, d, J=6.4 Hz), 1.18 (3H, d, J=7.2 Hz).

IR (KBr): 1747, 1597, 1532, 1397, 1289 cm⁻¹.

EXAMPLE 14

(1R,5S,6S)-2-[1-(4-Carbamoyl-1,3-thiazol-2-yl)piperidin-4-yl]thio-6-[(R)-1-hydroxyethyl]-1-methylcarbapen-2-em-3-carboxylic acid sodium salt

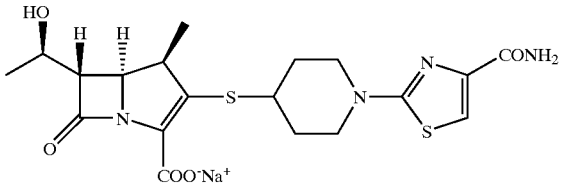

(1) p-Nitrobenzyl (1R,5S,6S)-2-[1-(4-carbamoyl-1,3-thiazol-2-yl)piperidin-4-yl]thio-6-[(R)-1-hydroxyethyl]-1-methylcarbapen-2-em-3-carboxylate To a solution of 4-acetylthio-1-(4-carbamoyl-1,3-thiazol-2-yl)piperidine (400 mg, 1.40 mmol) (obtained as described in Reference Example 15) in dimethylformamide (20 ml) was added hydrazine acetate (142 mg, 1.54 mmol) at room temperature under an atmosphere of nitrogen and the mixture was stirred for 2 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (1.25 g, 2.10 mmol) in acetonitrile (37 ml) was added dropwise to the resulting mixture in an ice bath under an atmosphere of nitrogen, followed by the addition of diisopropylethylamine (0.61 ml, 3.50 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate and ethyl acetate:methanol (10:1) as the eluant to afford p-nitrobenzyl (1R,5S,6S)-2-[1-(4-carbamoyl-1,3-thiazol-2-yl)piperidin4-yl]thio-6-[(R)-1-hydroxyethyl]-1-methylcarbapen-2-em-3-carboxylate as a pale yellow solid (348 mg, yield 42%).

¹H-NMR (400 MHz, CDCl₃): δ (ppm) 8.22 (2H, d, J=8.6 Hz), 7.66 (2H, d, J=8.6 Hz), 7.44 (1H, s), 6.99 (1H, br s), 5.56 (1H, br s), 5.51 (1H, d, J=13.8 Hz), 5.24 (1H, d, J=13.8 Hz), 4.35–4.20 (2H, m including dd at 4.28, J=9.7, 2.9 Hz), 4.04–3.85 (3H, m), 3.50–3.10 (6H, m), 2.20–2.00 (2H, m), 1.95–1.70 (3H, m), 1.39 (3H, d, J=6.3 Hz), 1.31 (3H, d, J=7.3 Hz).

Mass spectrum (FAB⁺): 587 [M+H]⁺.

(2) (1R,5S,6S)-2-[1-(4-Carbamoyl-1,3-thiazol-2-yl)piperidin-4-yl]thio-6-[(R)-1-hydroxyethyol]-1-methylcarbapen-2-em-3-carboxylic acid sodium salt p-Nitrobenzyl (1R,5S,6S)-2-[1-(4-carbamoyl-1,3-thiazol-2-yl)piperidin-4-yl]thio-6-[(R)-1-hydroxyethyl]-1-methylcarbapen-2-em-3-carboxylate (493 mg, 0.839 mmol) (obtained as described in Example 14(1)) in a mixture of tetrahydrofuran (30 ml) and distilled water (15 ml) was subjected to catalytic hydrogenation in the presence of 20% palladium hydroxide (0.50 g) in a water bath (30° C.) for 2 hours. After checking the completion of the reaction, the reaction mixture was filtered and to the filtrate were added sodium hydrogencarbonate (71 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water—3% acetonitrile; distilled water—5% acetonitrile and distilled water as the eluant. The eluate was lyophilized to afford the desired compound (1R,5S,6S)-2-[1-(4-carbamoyl-1,3-thiazol-2-yl)piperidin-4-yl]thio-6-[(R)-1-hydroxyethyl]-1-methylcarbapen-2-em-3-carboxylic acid sodium salt (127 mg, yield 32%) as a white solid.

$^1$H-NMR (400 MHz, D$_2$O): δ (ppm) 7.70 (1H, s), 4.50–4.35 (2H, m including dd at 4.18, J=9.2, 2.8 Hz), 4.00–3.80 (2H, m), 3.50–3.10 (5H, m), 2.15–1.95 (2H, m), 1.75–1.55 (2H, m), 1.26 (3H, d, J=6.5 Hz), 1.19 (3H, d, J=9.0 Hz).

IR (KBr): 1749, 1667, 1594, 1547, 1386 cm$^{-1}$.

Mass spectrum (FAB$^+$): 475 [M+H]$^+$.

High-resolution mass spectrum (FAB$^+$): calculated for C$_{19}$H$_{24}$O$_5$N$_4$S$_2$Na: 475.1086, Found: 475.1070 [M+H]$^+$.

EXAMPLE 15

(1R,5S,6S)-2-[1-(4-N-Methylcarbamoyl-1,3-thiazol-2-yl)piperidin-4-yl]thio-6-[(R)-1-hydroxyethyl]-1-methylcarbapen-2-em-3-carboxylic acid sodium salt

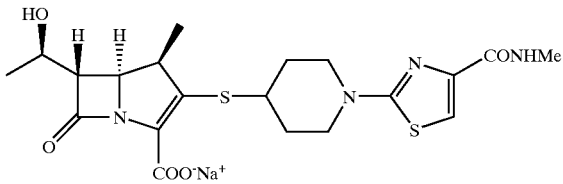

(1) p-Nitrobenzyl (1R,5S,6S)-2-[1-(4-N-methylcarbamoyl-1,3-thiazol-2-yl)piperidin-4yl]thio-6-[(R)-1-hydroxyethyl]-1-methylcarbapen-2-em-3-carboxylate To a solution of 4-acetylthio-1-(4-N-methylcarbamoyl-1,3-thiazol-2-yl)piperidine (1.21 g, 4.04 mmol) (obtained as described in Reference Example 16) in dimethylformamide (36 ml) was added hydrazine acetate (408 mg, 4.43 mmol) at room temperature under an atmosphere of nitrogen and the mixture was stirred for 1.5 hours. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (3.12 g, 5.25 mmol) in acetonitrile (72 ml) was added dropwise to the resulting mixture in an ice bath under an atmosphere of nitrogen, followed by the addition of diisopropylethylamine (1.76 ml, 10.1 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate:methanol (20:1) as the eluant to afford p-nitrobenzyl (1R,5S,6S)-2-[1-(4-N-methylcarbamoyl-1,3-thiazol-2-yl)piperidin-4-yl]thio-6-[(R)-1-hydroxyethyl]-1-methylcarbapen-2-em-3-carboxylate as a pale yellow solid (1.336 g, yield 55%).

$^1$H-NMR (400 MHz, CDCl$_3$): δ (ppm) 8.21 (2H, d, J=8.0 Hz), 7.64 (2H, d, J=8.0 Hz), 7.40 (1H, s), 7.19 (1H, br s), 5.50 (1H, d, J=12.8 Hz), 5.22 (1H, d, J=12.8 Hz), 4.40–4.20 (2H, m), 4.00–3.80 (2H, m), 3.50–3.10 (5H, m), 2.95 (3H, d, J=6.4 Hz), 2.15–1.90 (3H, m), 1.90–1.70 (2H, m), 1.39 (3H, d, J=6.4 Hz), 1.20 (3H, d, J=9.6 Hz).

Mass spectrum (FAB$^+$): 602 [M+H]$^+$.

(2) (1R,5S,6S)-2-[1-(4-N-Methylcarbamoyl-1,3-thiazol-2-yl)piperidin-4-yl]thio-6-[(R)-1-hydroxyethyl]-1-methylcarbapen-2-em-3-carboxylic acid sodium salt p-Nitrobenzyl (1R,5S,6S)-2-[1-(4-N-methylcarbamoyl-1,3-thiazol-2-yl)piperidin-4-yl]thio-6-[(R)-1-hydroxyethyl]-1-methylcarbapen-2-em-3-carboxylate (857 mg, 1.424 mmol) (obtained as described in Example 15(1)) in a mixture of tetrahydrofuran (40 ml) and distilled water (20 ml) was subjected to catalytic hydrogenation in the presence of 20% palladium hydroxide (853 mg) in a water bath (30° C.) for 2 hours. After checking the completion of the reaction, the reaction mixture was filtered and to the filtrate were added sodium hydrogencarbonate (120 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water—3% acetonitrile; distilled water—5% acetonitrile; distilled water—7% acetonitrile; distilled water—9% acetonitrile and distilled water as the eluant. The eluate was lyophilized to afford the desired compound (1R,5S,6S)-2-[1-(4-N-methylcarbamoyl-1,3-thiazol-2-yl)piperidin-4-yl]thio-6-[(R)-1-hydroxyethyl]-1-methylcarbapen-2-em-3-carboxylic acid sodium salt (317 mg, yield 46%) as a white solid.

$^1$H-NMR (400 MHz, D$_2$O): δ (ppm) 7.34 (1H, s), 4.25–4.10 (2H, m including dd at 4.16, J=9.2, 2.2 Hz), 3.95–3.80 (2H, m), 3.50–3.10 (5H, m), 2.84 (3H, s), 2.15–1.95 (2H, m), 1.75–1.50 (2H, m), 1.24 (3H, d, J=6.3 Hz), 1.17 (3H, d, J=7.3 Hz).

IR (KBr): 1750, 1654, 1602, 1553, 1385, 1266 cm$^{-1}$.

Mass spectrum (FAB$^+$): 489 [M+H]$^+$.

High-resolution mass spectrum (FAB$^+$): calculated for C$_{20}$H$_{26}$O$_5$N$_4$S$_2$Na: 489.1242, Found: 489.1255 [M+H]$^+$.

EXAMPLE 16

(1R,5S,6S)-2-[1-(4-N,N-Dimethylcarbamoyl-1,3-thiazol-2-yl)piperidin-4-yl]thio-6-[(R)-1-hydroxyethyl]-1-methylcarbapen-2-em-3-carboxylic acid sodium salt

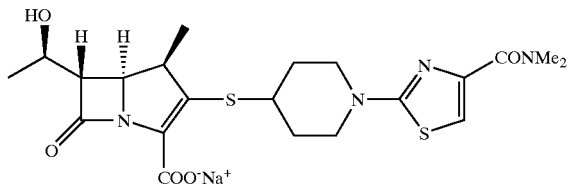

(1) p-Nitrobenzyl (1R,5S,6S)-2-[1-(4-N,N-dimethylcarbamoyl-1,3-thiazol-2-yl)piperidin-4-yl]thio-6-[(R)-1-hydroxyethyl]-1-methylcarbapen-2-em-3-carboxylate To a solution of 4-acetylthio-1-(4-N,N-dimethylcarbamoyl-1,3-thiazol-2-yl)piperidine (620 mg, 1.98 mmol) (obtained as described in Reference Example 17) in dimethylformamide (35 ml) was added hydrazine acetate (201 mg, 2.18 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (2.35 g, 3.96 mmol) in acetonitrile (65 ml) was added dropwise to the resulting mixture in an ice bath under an atmosphere of nitrogen, followed by the addition of diisopropylethylamine (1.40 ml, 8.04 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate and ethyl acetate:methanol (10:1) as the eluant to afford p-nitrobenzyl (1R,5S,6S)-2-[1-(4-N,N-dimethylcarbamoyl-1,3-thiazol-2-yl)piperidin-4-yl]thio-6-[(R)-1-hydroxyethyl]-1-methylcarbapen-2-em-3-carboxylate as a pale yellow solid (495 mg, yield 41%).

$^1$H-NMR (400 MHz, CDCl$_3$): δ (ppm) 8.22 (2H, d, J=8.7 Hz), 7.66 (2H, d, J=8.7 Hz), 7.09 (1H, s), 5.51 (1H, d, J=13.8 Hz), 5.23 (1H, d, J=13.8 Hz), 4.35–4.20 (2H, m), 4.00–3.85 (2H, m), 3.50–3.00 (12H, m including 3H ×2, each br s at 3.22 and 3.07), 2.20–1.95 (2H, m), 1.93–1.70 (3H, m), 1.38 (3H, d, J=6.2 Hz), 1.31 (3H, d, J=7.3 Hz).

Mass spectrum (FAB$^+$): 616 [M+H]$^+$.

(2) (1R,5S,6S)-2-[1-(4-N,N-Dimethylcarbamoyl-1,3-thiazol-2-yl)piperidin-4-yl]thio[(R)-1-hydroxyethyl]-1-methylcarbapen-2-em-3-carboxylic acid sodium salt p-Nitrobenzyl (1R,5S,6S)-2-[1-(4-N,N-dimethylcarbamoyl-1,3-thiazol-2-yl)piperidin4-yl]thio-6-[(R)-1-hydroxyethyl]-1-methylcarbapen-2-em-3-carboxylate (487 mg, 0.791 mmol) (obtained as described in Example 16(1)) in a mixture of tetrahydrofuran (22 ml) and distilled water (11 ml) was subjected to catalytic hydrogenation in the presence of 20% palladium hydroxide (485 mg) in a water bath (30° C.) for 1.5 hours. After checking the completion of the reaction, the reaction mixture was filtered and to the filtrate were added sodium hydrogencarbonate (67 mg), a mixture of ethyl acetate and tetrahydrofuran (1:1) and distilled water. The mixture was shaken in a separatory funnel. The aqueous layer was separated, washed with a mixture of ethyl acetate and tetrahydrofuran (1:1) and concentrated under reduced pressure. The residue was purified by chromatography on a Cosmosil column using distilled water—5% acetonitrile; distilled water—7% acetonitrile; distilled water—9% acetonitrile and distilled water as the eluant. The eluate was lyophilized to afford the desired compound (1R,5S,6S)-2-[1-(4-N,N-dimethylcarbamoyl-1,3-thiazol-2-yl)piperidin-4-yl]thio-6-[(R)-1-hydroxyethyl]-1-methylcarbapen-2-em-3-carboxylic acid sodium salt (183 mg, yield 46%) as a white solid.

$^1$H-NMR (400 MHz, D$_2$O): δ (ppm) 7.00 (1H, s), 4.30–4.10 (2H, m including dd at 4.17, J=9.0, 2.3 Hz), 3.95–3.75 (2H, m), 3.50–3.10 (5H, m), 3.07 (3H, s), 3.00 (3H, s), 2.15–1.95 (2H, m), 1.80–1.50 (2H, m), 1.25 (3H, d, J=6.3 Hz), 1.18 (3H, d, J=7.2 Hz).

IR (KBr): 1750, 1612, 1538, 1395 cm$^{-1}$.

Mass spectrum (FAB$^+$): 503 [M+H]$^+$.

EXAMPLE 17

(1R,5S,6S)-2-[(3S)-1-(4-Carbamoyl-1,3-thiazol-2-yl)pyrrolidin-3-yl]thio-6-[(R)-1-hydroxyethyl]-1-methylcarbapen-2-em-3-carboxylic acid sodium salt

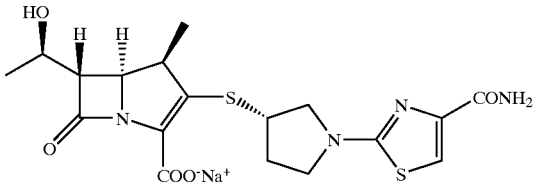

(1) p-Nitrobenzyl (1R,5S,6S)-2-[(3S)-1-(4-carbamoyl-1,3-thiazol-2-yl)pyrrolidin-3-yl]thio-6-[(R)-1-hydroxyethyl]-1-methylcarbapen-2-em-3-carboxylate To a solution of (3S)-3-acetylthio-1-(4-carbamoyl-1,3-thiazol-2-yl)pyrrolidine (210 mg, 0.721 mmol) (obtained as described in Reference Example 18) in dimethylformamide (10 ml) was added hydrazine acetate (80 mg, 0.865 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (429 mg, 0.721 mmol) in acetonitrile (20 ml) was added dropwise to the resulting mixture in an ice bath under an atmosphere of nitrogen, followed by the addition of diisopropylethylamine (0.502 ml, 2.88 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using methylene chloride—10% methanol and methylene chloride as the eluant to afford p-nitrobenzyl (1R,5S,6S)-2-[(3S)-1-(4-carbamoyl-1,3-thiazol-2-yl)pyrrolidin-3-yl]thio-6-[(R)-1-hydroxyethyl]-1-methylcarbapen-2-em-3-carboxylate as a pale yellow solid (412 mg, yield 100%).

$^1$H-NMR (400 MHz, CDCl$_3$): δ (ppm) 8.22 (2H, d, J=8.8 Hz), 7.65 (2H, d, J=8.8 Hz), 7.40 (1H, s), 7.03 (1H, br s), 5.50 (1H, d, J=13.6 Hz), 5.48 (1H, br s), 5.22 (1H, d, J=13.6 Hz), 4.36–4.25 (2H, m including dd at 4.32, J=9.5, 2.2 Hz), 3.71–3.60 (1H, m), 3.60–3.49 (2H, m), 3.40 (1H, dq, J=9.5, 7.3 Hz), 3.30 (1H, dd, J=6.6, 2.2 Hz), 2.60–2.45 (1H, m), 2.40–2.05 (1H, m), 1.77 (1H, d, J=4.4 Hz), 1.39 (3H, d, J=6.6 Hz), 1.31 (3H, d, J=7.3 Hz).

Mass spectrum (FAB$^+$): 574 [M+H]$^+$.

(2) (1R,5S,6S)-2-[(3S)-1-(4-Carbamoyl-1,3-thiazol-2-yl)pyrrolidin-3-yl]thio-6-[(R)-1-hydroxyethyl]-1-methylcarbapen-2-em-3-carboxylic acid sodium salt p-Nitrobenzyl (1R,5S,6S)-2-[(3S)-1-(4-carbamoyl-1,3-thiazol-2-yl)pyrrolidin-3-yl]thio-6-[(R)-1-hydroxyethyl]-1-methylcarbapen-2-em-3-carboxylate (410 mg, 0.715 mmol) (obtained as described in Example 17(1)) in a mixture of tetrahydrofuran (15 ml) and distilled water (15 ml) was subjected to catalytic hydrogenation in the presence of 10% palladium on charcoal (410 mg) at room temperature for 1.7 hours. After checking the completion of the reaction, the reaction mixture was filtered and to the filtrate were added sodium hydrogencarbonate (60 mg), ethyl acetate and distilled water. The mixture was shaken in a separatory funnel. The aqueous layer was separated and concentrated under reduced pressure. The residue was purified by chromatography on a Cosmosil column using distilled water—3% acetonitrile; distilled water—6% acetonitrile; distilled water—9% acetonitrile; distilled water—12% acetonitrile and distilled water as the eluant. The eluate was lyophilized to afford the desired compound (1R,5S,6S)-2-[(3S)-1-(4-carbamoyl-1,3-thiazol-2-yl)pyrrolidin-3-yl]thio-6-[(R)-1-hydroxyethyl]-1-methylcarbapen-2-em-3-carboxylic acid sodium salt (150 mg, yield 46%) as a white solid.

$^1$H-NMR (400 MHz, D$_2$O): δ (ppm) 7.41 (1H, s), 4.35–4.20 (2H, m), 4.05 (1H, quintet, J=5.2 Hz), 3.90 (1H, dd, J=10.8, 5.9 Hz), 3.75–3.65 (1H, m), 3.60–3.40 (4H, m), 2.60–2.45 (1H, m), 2.20–2.15 (1H, m), 1.31 (3H, d, J=6.4 Hz), 1.25 (3H, d, J=8.9 Hz).

IR (KBr): 1749, 1669, 1599, 1557, 1391, 1289 cm$^{-1}$.

Mass spectrum (FAB$^+$): 461 [M+H]$^+$.

High-resolution mass spectrum (FAB$^+$): calculated for C$_{18}$H$_{22}$O$_5$N$_4$S$_2$Na: 461.0929, Found: 461.0926 [M+H]$^+$.

EXAMPLE 18

(1R,5S,6S)-2-[(3S)-1-(4-Cyano-1,3-thiazol-2-yl)pyrrolidin-3-yl]thio-6-[(R)-1-hydroxyethyl]-1-methylcarbapen-2-em-3-carboxylic acid sodium salt

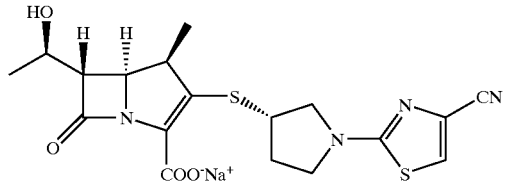

(1) p-Nitrobenzyl (1R,5S,6S)-2-[(3S)-1-(4-cyano-1,3-thiazol-2-yl)pyrrolidin-3-yl]thio-6-[(R)-1-hydroxyethyl]-1-methylcarbapen-2-em-3-carboxylate To a solution of (3S)-3-acetylthio-1-(4-cyano-1,3-thiazol-2-yl)pyrrolidine (137 mg, 0.541 mmol) (obtained as described in Reference Example 19) in dimethylformamide (7 ml) was added hydrazine acetate (60 mg, 0.649 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (322 mg, 0.541 mmol) in acetonitrile (16 ml) was added dropwise to the resulting mixture in an ice bath under an atmosphere of nitrogen, followed by the addition of diisopropylethylamine (0.376 ml, 2.16 mmol). The mixture was stirred for 2 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane: ethyl acetate (1:3) and ethyl acetate as the eluant to afford p-nitrobenzyl (1R,5S,6S)-2-[(3S)-1-(4-cyano-1,3-thiazol-2-yl)pyrrolidin-3-yl]thio-6-[(R)-1-hydroxyethyl]-1-methylcarbapen-2-em-3-carboxylate as a pale yellow solid (251 mg, yield 84%).

$^1$H-NMR (400 MHz, CDCl$_3$): δ (ppm) 8.22 (2H, d, J=8.8 Hz), 7.65 (2H, d, J=8.8 Hz), 7.21 (1H, s), 5.50 (1H, d, J=13.6 Hz), 5.22 (1H, d, J=13.9 Hz), 4.35–4.24 (2H, m), 3.90 (2H, m), 3.74–3.45 (3H, m), 3.38 (1H, dq, J=9.4, 4.7 Hz), 3.30 (1H, dd, J=7.3, 2.9 Hz), 2.60–2.48 (1H, m), 2.24–2.10 (1H, m), 1.62–1.50 (1H, br s), 1.38 (3H, d, J=5.9 Hz), 1.31 (3H, d, J=7.3 Hz).

Mass spectrum (FAB$^+$): 556 [M+H]$^+$.

(2) (1R,5S,6S)-2-[(3S)-1-(4-Cyano-1,3-thiazol-2-yl)pyrrolidin-3-yl]thio-6-[(R)-1-hydroxyethyl]-1-methylcarbapen-2-em-3-carboxylic acid sodium salt p-Nitrobenzyl (1R,5S,6S)-2-[(3S)-1-(4-cyano-1,3-thiazol-2-yl)pyrrolidin-3-yl]thio-6-[(R)-1-hydroxyethyl]-1-methylcarbapen-2-em-3-carboxylate (250 mg, 0.450 mmol) (obtained as described in Example 18(1)) in a mixture of tetrahydrofuran (12 ml) and distilled water (12 ml) was subjected to catalytic hydrogenation in the presence of 10% palladium on charcoal (250 mg) at room temperature for 2 hours. After checking the completion of the reaction, the reaction mixture was filtered and to the filtrate were added sodium hydrogencarbonate (38 mg), ethyl acetate and distilled water. The mixture was shaken in a separatory funnel. The aqueous layer was separated and concentrated under reduced pressure. The residue was purified by chromatography on a Cosmosil column using distilled water—3% acetonitrile; distilled water—6% acetonitrile; distilled water—9% acetonitrile; distilled water—12% acetonitrile; distilled water—15% acetonitrile and distilled water as the eluant. The eluate was lyophilized to afford the desired compound (1R,5S,6S)-2-[(3S)-1-(4-cyano-1,3-thiazol-2-yl)pyrrolidin-3-yl]thio-6-[(R)-1-hydroxyethyl]-1-methylcarbapen-2-em-3-carboxylic acid sodium salt (128 mg, yield 64%) as a white solid.

$^1$H-NMR (400 MHz, D$_2$O): δ (ppm) 7.56 (1H, s), 4.32–4.22 (2H, m), 4.10–4.00 (1H, m), 3.88 (1H, dd, J=10.8, 5.9 Hz), 3.74–3.62 (1H, m), 3.62–3.53 (1H, m), 3.52–3.38 (3H, m), 2.60–2.48 (1H, m), 2.19–2.08 (1H, m), 1.31 (3H, d, J=6.4 Hz), 1.24 (3H, d, J=7.3 Hz).

IR (KBr): 2229, 1751, 1604, 1560, 1391, 1310 cm$^{-1}$.

Mass spectrum (FAB$^+$): 443 [M+H]$^+$.

High-resolution mass spectrum (FAB$^+$): calculated for C$_{18}$H$_{20}$O$_4$N$_4$S$_2$Na: 443.0824, Found: 443.0799 [M+H]$^+$.

EXAMPLE 19

(1R,5S,6S)-2-[(3R)-1-(4-Carbamoyl-1,3-thiazol-2-yl)pyrrolidin-3-yl]thio-6-[(R)-1-hydroxyethyl]-1-methylcarbapen-2-em-3-carboxylic acid sodium salt

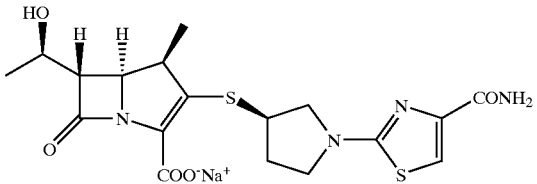

(1) p-Nitrobenzyl (1R,5S,6S)-2-[(3R)-1-(4-carbamoyl-1,3-thiazol-2-yl)pyrrolidin-3-yl]thio-6-[(R)-1-hydroxyethyl]-1-methylcarbapen-2-em-3-carboxylate To a solution of (3R)-3-acetylthio-1-(4-carbamoyl-1,3-thiazol-2-yl)pyrrolidine (500 mg, 1.84 mmol) (obtained as described in Reference Example 20) in dimethylformamide (25 ml) was added hydrazine acetate (204 mg, 2.21 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (1.09 g, 1.84 mmol) in acetonitrile (55 ml) was added dropwise to the resulting mixture in an ice bath under an atmosphere of nitrogen, followed by the addition of diisopropylethylamine (1.28 ml, 7.36 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using methylene chloride—9% methanol and methylene chloride as the eluant to afford p-nitrobenzyl (1R,5S,6S)-2-[(3R)-1-(4-carbamoyl-1,3-thiazol-2-yl)pyrrolidin-3-yl]thio-6-[(R)-1-hydroxyethyl]-1-methylcarbapen-2-em-3-carboxylate as a pale yellow solid (917 mg, yield 87%).

$^1$H-NMR (400 MHz, CDCl$_3$): δ (ppm) 8.22 (2H, d, J=8.2 Hz), 7.66 (2H, d, J=8.2 Hz), 7.40 (1H, s), 7.05 (1H, br s), 5.55 (1H, br s), 5.51 (1H, d, J=14.1 Hz), 5.24 (1H, d, J=14.1 Hz), 4.35–4.25 (2H, m), 4.05–3.90 (2H, m), 3.70–3.60 (1H, m), 3.60–3.40 (4H, m), 3.31 (1H, dd, J=6.9, 2.9 Hz), 2.60–2.40 (1H, m), 2.20–2.05 (1H, m), 1.95 (1H, br s), 1.39 (3H, d, J=5.9 Hz), 1.33 (3H, d, J=6.8 Hz).

Mass spectrum (FAB$^+$): 574 [M+H]$^+$.

(2) (1R,5S,6S)-2-[(3R)-1-(4-Carbamoyl-1,3-thiazol-2-yl)pyrrolidin-3-yl]thio-6-[(R)-1-hydroxyethyl]-1-methylcarbapen-2-em-3-carboxylic acid sodium salt p-Nitrobenzyl (1R,5S,6S)-2-[(3R)-1-(4-carbamoyl-1,3-thiazol-2-yl)pyrrolidin-3-yl]thio-6-[(R)-1-hydroxyethyl]-1-methylcarbapen-2-em-3-carboxylate (917 mg, 1.60 mmol) (obtained as described in Example 19(1)) in a mixture of tetrahydrofuran (45 ml) and distilled water (45 ml) was subjected to catalytic hydrogenation in the presence of 10% palladium on charcoal (917 mg) at room temperature for 1.7 hours. After checking the completion of the reaction, the reaction mixture was filtered and to the filtrate were added sodium hydrogencarbonate (134 mg), ethyl acetate and distilled water. The mixture was shaken in a separatory funnel. The aqueous layer was separated and concentrated under reduced pressure. The residue was purified by chromatography on a Cosmosil column using distilled water—2% acetonitrile; distilled water—4% acetonitrile; distilled water—6% acetonitrile; distilled water—8% acetonitrile; distilled water—10% acetonitrile; distilled water—12% acetonitrile; distilled water—14% acetonitrile; distilled water—16% acetonitrile and distilled water as the eluant. The eluate was lyophilized to afford the desired compound (1R,5S,6S)-2-[(3R)-1-(4-carbamoyl-1,3-thiazol-2-yl)pyrrolidin-3-yl]thio-6-[(R)-1-hydroxyethyl]-1-methylcarbapen-2-em-3-carboxylic acid sodium salt (338 mg, yield 46%) as a white solid.

$^1$H-NMR (400 MHz, D$_2$O): δ (ppm) 7.41 (1H, s), 4.35–4.20 (2H, m), 4.10–4.00 (1H, dd, J=11.2, 6.7 Hz), 3.70–3.60 (1H, m), 3.58–3.40 (4H, m), 2.60–2.45 (1H, m), 2.20–2.10 (1H, m), 1.31 (3H, d, J=6.3 Hz), 1.25 (3H, d, J=7.3 Hz).

IR (KBr): 1748, 1608, 1597, 1559, 1391, 1289 cm$^{-1}$.

Mass spectrum (FAB$^+$): 461 [M+H]$^+$.

High-resolution mass spectrum (FAB$^+$): calculated for C$_{18}$H$_{22}$O$_5$N$_4$S$_2$Na: 461.0929 Found: 461.0938 [M+H]$^+$.

EXAMPLE 20

(1R,5S,6S)-2-[1-(4-Hydroxymethyl-1,3-thiazol-2-yl)azetidin-3-yl]thio-6-[(R)-1-hydroxyethyl]-1-methylcarbapen-2-em-3-carboxylic acid sodium salt

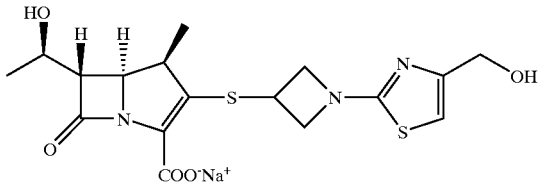

(1) p-Nitrobenzyl (1R,5S,6S)-2-[1-(4-t-butyldimethylsilyloxymethyl-1,3-thiazol-2-yl)azetidin-3-yl]thio-6-[(R)-1-hydroxyethyl]-1-methylcarbapen-2-em-3-carboxylate To a solution of 3-acetylthio-1-(4-t-butyldimethylsilyloxymethyl-1,3-thiazol-2-yl)azetidine (415 mg, 1.16 mmol) (obtained as described in Reference Example 12) in dimethylformamide (20.8 ml) was added hydrazine acetate (137.0 mg, 1.39 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (690 mg, 1.16 mmol) in acetonitrile (34.4 ml) was added dropwise to the resulting mixture in an ice bath under an atmosphere of nitrogen, followed by the addition of diisopropylethylamine (1.34 ml, 7.69 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate as the eluant to afford p-nitrobenzyl (1R,5S,6S)-2-[1-(4-t-butyldimethylsilyloxymethyl-1,3-thiazol-2-yl)azetidin-3-yl]thio-6-[(R)-1-hydroxyethyl]-1-methylcarbapen-2-em-3-carboxylate as a pale yellow syrup (719 mg, yield 94%).

$^1$H-NMR (400 MHz, CDCl$_3$): δ (ppm) 8.22 (2H, d, J=8.3 Hz), 7.66 (2H, d, J=8.8 Hz), 6.48 (1H, s), 5.50 (1H, d, J=13.9 Hz), 5.25 (1H, d, J=13.9 Hz), 4.66 (2H, s), 4.46 (2H, dd, J=15.4, 8.1 Hz), 4.32–4.20 (3H, m), 4.08–4.00 (2H, m), 3.28 (1H, dd, J=6.6, 2.2 Hz), 3.21 (1H, d, dq, J=9.1, 7.3 Hz), 1.95 (1H, br s), 1.37 (3H, d, J=5.9 Hz), 1.26 (3H, d, J=7.3 Hz), 0.94 (9H, s), 0.10 (6H, s).

(2) p-Nitrobenzyl (1R,5S,6S)-2-[1-(4-hydroxymethyl-1,3-thiazol-2-yl)azetidin-3-yl]thio-6-[(R)-1-hydroxyethyl]-1-methylcarbapen-2-em-3-carboxylate To a solution of p-nitrobenzyl (1R,5S,6S)-2-[1-(4-t-butyldimethylsilyloxymethyl-1,3-thiazol-2-yl)azetidin-3-yl]thio-6-[(R)-1-hydroxyethyl]-1-methylcarbapen-2-em-3-carboxylate (719 mg, 1.09 mmol) (obtained as described in Example 20(1)) in anhydrous tetrahydrofuran (36 ml) were added sequentially acetic acid (0.19 ml, 3.3 mmol) and a solution of tetra-n-butylammonium fluoride in tetrahydrofuran (3.3 ml, 3.3 mmol) in an ice bath. The resulting mixture was stirred at room temperature overnight. After checking the completion of the reaction, the reaction mixture was partitioned between ethyl acetate and saturated aqueous sodium hydrogencarbonate and the aqueous layer was further extracted with ethyl acetate. The organic layers were washed with saturated aqueous sodium chloride solution, dried over anhydrous magnesium sulfate, filtered and the filtrate was concentrated under reduced pressure. The residue was purified by chromatography on a silica gel column using ethyl acetate: methanol (15:1) as the eluant to afford the desired compound p-nitrobenzyl (1R,5S,6S)-2-[1-(4-hydroxymethyl-1,3-thiazol-2-yl)azetidin-3-yl]thio-6-[(R)-1-hydroxyethyl]-1-methylcarbapen-2-em-3-carboxylate (426.2 mg, yield 72%) as a yellow syrup.

$^1$H-NMR (400 MHz, CDCl$_3$): δ (ppm) 8.20 (2H, d, J=8.1 Hz), 7.66 (2H, d, J=8.1 Hz), 6.50 (1H, s), 5.54 (1H, d, J=13.6 Hz), 5.27 (1H, d, J=13.6 Hz), 4.56 (1H, d, J=13.6 Hz), 4.53 (1H, d, J=13.6 Hz), 4.47 (1H, t, J=8.5 Hz), 4.41 (1H, t, J=8.5 Hz), 4.32 (1H, quintet, J=6.4 Hz), 4.28–4.20 (2H, m), 4.08 (1H, dd, J=8.5, 5.4 Hz), 3.88 (1H, dd, J=5.4, 8.5 Hz), 3.304 (1H, dd, J=6.2, 2.7 Hz), 3.204 (1H, dq, J=9.2, 7.3 Hz), 1.35 (3H, d, J=6.2 Hz), 1.25 (3H, d, J=7.3 Hz).

(3) (1R,5S,6S)-2-[1-(4-Hydroxymethyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-hydroxymethyl-1,3-thiazol-2-yl)azetidin-3-yl]thio-6-[(R)-1-hydroxyethyl]-1-methylcarbapen-2-em-3-carboxylate (426.2 mg, 0.78 mmol) (obtained as described in Example 20(2)) in a mixture of tetrahydrofuran (20 ml) and distilled water (10 ml) was subjected to catalytic hydrogenation in the presence of 20% palladium hydroxide (530 mg) at room temperature for 1.5 hours. After checking the completion of the reaction, the reaction mixture was filtered and to the filtrate were added sodium hydrogencarbonate (65.5 mg), ethyl acetate and distilled water. The mixture was shaken in a separatory funnel. The aqueous layer was separated and concentrated under reduced pressure. The residue was purified by chromatography on a Cosmosil column using distilled water—3% acetonitrile and distilled water as the eluant. The eluate was lyophilized to afford the desired compound (1R,5S,6S)-2-[1-(4-hydroxymethyl-1,3-thiazol-2-yl)azetidin-3-yl]thio-6-[(R)-1-hydroxyethyl]-1-methylcarbapen-2-em-3-carboxylic acid sodium salt (156 mg, yield 46%) as a white solid.

$^1$H-NMR (400 MHz, D$_2$O): δ (ppm) 6.50 (1H, s), 4.36–4.28 (4H, m), 4.19–4.10 (1H, m), 4.10–3.98 (2H, m including 1H, dd at 4.01, J=8.0, 3.0 Hz), 3.88–3.68 (2H, m), 3.24 (1H, dd, J=6.6, 2.9 Hz), 3.12–3.00 (1H, m), 1.11 (3H, d, J=5.9 Hz), 1.00 (3H, d, J=7.3 Hz).

IR (KBr): 3357, 1748, 1600, 1528, 1470, 1396, 1311 cm$^{-1}$.

Mass spectrum (FAB$^+$): 434 [M+H]$^+$.

High-resolution mass spectrum (FAB$^+$): calculated for C$_{17}$H$_{21}$O$_5$N$_3$S$_2$Na: 434.0820, Found: 434.0796 [M+H]$^+$.

EXAMPLE 21

(1R,5S,6S)-2-[1-(4-N-Methylcarbamoyl-1,3-oxazol-2-yl)azetidin-3-yl]thio-6-[(R)-1-hydroxyethyl]-1-methylcarbapen-2-em-3-carboxylic acid sodium salt

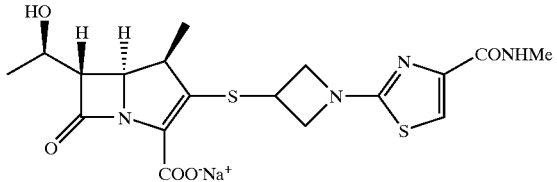

(1) p-Nitrobenzyl (1R,5S,6S)-2-[1-(4-N-Methylcarbamoyl-1,3-oxazol-2-yl)azetidin-3-yl]thio-6-[(R)-1-hydroxyethyl]-1-methylcarbapen-2-em-3-carboxylate To a solution of 3-acetylthio-1-(4-N-methylcarbamoyl-1,3-oxazol-2-yl)azetidine (142 mg, 0.56 mmol) (obtained as described in Reference Example 21) in dimethylformamide (7 ml) was added hydrazine acetate (62 mg, 0.67 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (333 mg, 0.56 mmol) in acetonitrile (7 ml) was added dropwise to the resulting mixture in an ice bath under an atmosphere of nitrogen, followed by the addition of diisopropylethylamine (0.39 ml, 2.24 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford p-nitrobenzyl (1R,5S,6S)-2-[1-(4-N-methylcarbamoyl-1,3-oxazol-2-yl)azetidin-3-yl]thio-6-[(R)-1-hydroxyethyl]-1-methylcarbapen-2-em-3-carboxylate (274 mg, yield 88%) as a pale yellow solid.

$^1$H-NMR (400 MHz, CDCl$_3$): δ (ppm) 8.23 (2H, d, J=8.8 Hz), 7.77 (1H, s), 7.66 (2H, d, J=8.8 Hz), 6.78 (1H, br s), 5.51 (1H, d, J=13.9 Hz), 5.25 (1H, d, J=13.2 Hz), 4.51 (2H, q, J=8.1 Hz), 4.30–4.21 (3H, m), 4.08 (2H, dd, J=5.9, 8.1 Hz), 3.30 (1H, dd, J=2.9, 7.3 Hz), 3.24–3.16 (1H, m), 2.94 (3H, d, J=5.1 Hz), 1.38 (3H, d, J=5.9 Hz), 1.26 (3H, d, J=7.4 Hz).

(2) (1R,5S,6S)-2-[1-(4-N-Methylcarbamoyl-1,3-oxazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-methylcarbamoyl-1,3-oxazol-2-yl)azetidin-3-yl]thio-6-[(R)-1-hydroxyethyl]-1-methylcarbapen-2-em-3-carboxylate (344 mg, 0.62 mmol) (obtained as described in Example 21(1)) in a mixture of tetrahydrofuran (17 ml) and distilled water (9 ml) was subjected to catalytic hydrogenation in the presence of 20% palladium hydroxide (344 mg) in a water bath (30° C.) for 2 hours. After checking the completion of the reaction, the reaction mixture was filtered, and to the filtrate were added sodium hydrogencarbonate (52 mg), a mixture of ethyl acetate and tetrahydrofuran (1:1) and distilled water. The mixture was shaken in a separatory funnel. The aqueous layer was washed with a mixture of ethyl acetate and tetrahydrofuran (1:1), separated and concentrated under reduced pressure. The residue was purified by chromatography on a Cosmosil column using distilled water—5% acetonitrile as the eluant. The eluate was lyophilized to afford the desired compound (1R,5S,6S)-2-[1-(4-N-methylcarbamoyl-1,3-oxazol-2-yl)azetidin-3-yl]thio-6-[(R)-1-hydroxyethyl]-1-methylcarbapen-2-em-3-carboxylic acid sodium salt (166 mg, yield 60%) as a white solid.

$^1$H-NMR (400 MHz, D$_2$O): δ (ppm) 7.73 (1H, s), 4.44 (2H, t, J=8.1 Hz), 4.20–4.13 (1H, m), 4.10 (1H, t, J=6.6 Hz), 4.05 (1H, d, J=9.5 Hz), 3.94 (2H, quint., J=4.4 Hz), 3.28 (1H, dd, J=2.2, 5.9 Hz), 3.09 (1H, quint., J=7.3 Hz), 2.73 (3H, s), 1.15 (3H, d, J=6.6 Hz), 1.04 (3H, d, J=7.3 Hz).

IR (KBr): 3415, 1750, 1625, 1531, 1388 cm$^{-1}$.

High-resolution mass spectrum (FAB$^+$): calculated for C$_{18}$H$_{22}$O$_6$N$_4$SNa: 445.1157, Found: 445.1162 [M+H]$^+$.

EXAMPLE 22

(1R,5S,6S)-2-[1-(4-Carbamoyl-1,3-oxazol-2-yl) azetidin-3-yl]thio-6-[(R)-1-hydroxyethyl]-1-methylcarbapen-2-em-3-carboxylic acid sodium salt

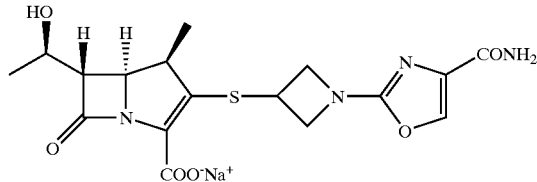

(1) p-Nitrobenzyl (1R,5S,6S)-2-[1-(4-carbamoyl-1,3-oxazol-2-yl)azetidin-3-yl]thio-6-[(R)-1-hydroxyethyl]-1-methylcarbapen-2-em-3-carboxylate To a solution of 3-acetylthio-1-(4-carbamoyl-1,3-oxazol-2-yl)azetidine (275 mg, 1.14 mmol) (obtained as described in Reference Example 22) in dimethylformamide (14 ml) was added hydrazine acetate (126 mg, 1.37 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (677 mg, 1.14 mmol) in acetonitrile (14 ml) was added dropwise to the resulting mixture in an ice bath under an atmosphere of nitrogen, followed by the addition of diisopropylethylamine (0.79 ml, 4.56 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column using toluene: acetonitrile: methanol (10:10:1) as the eluant to afford p-nitrobenzyl (1R,5S,6S)-2-[1-(4-carbamoyl-1,3-oxazol-2-yl)azetidin-3-yl]thio-6-[(R)-1-hydroxyethyl]-1-methylcarbapen-2-em-3-carboxylate (313 mg, yield 51%) as a pale yellow solid.

$^1$H-NMR (400 MHz, CD$_3$OD): δ (ppm) 8.08 (2H, d, J=8.8 Hz), 7.77 (1H, s), 7.55 (2H, d, J=8.8 Hz), 5.32 (1H, d, J=13.9 Hz), 5.14 (1H, d, J=13.9 Hz), 4.43 (2H, t, J=8.8 Hz), 4.28–4.20 (1H, m), 4.13 (1H, dd, J=2.9, 9.5 Hz), 4.00 (1H, t, J=6.6 Hz), 3.90 (2H, dt, J=4.4, 9.5 Hz), 3.23–3.18 (2H, m), 1.18 (3H, d, J=5.9 Hz), 1.09 (3H, d, J=7.3 Hz).

(2) (1R,5S,6S)-2-[1-(4-Carbamoyl-1,3-oxazol-2-yl) azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-carbamoyl-1,3-oxazol-2-yl)azetidin-3-yl]thio-6-[(R)-1-hydroxyethyl]-1-methylcarbapen-2-em-3-carboxylate (313 mg, 0.582 mmol) (obtained as described in Example 22(1)) in a mixture of tetrahydrofuran (16 ml) and distilled water (8 ml) was subjected to catalytic hydrogenation in the presence of 20% palladium hydroxide (313 mg) in a water bath (30° C.) for 2 hours. After checking the completion of the reaction, the reaction mixture was filtered and to the filtrate were added sodium hydrogencarbonate (49 mg), a mixture of ethyl acetate and tetrahydrofuran (1:1) and distilled water. The mixture was shaken in a separatory funnel. The aqueous layer was washed with a mixture of ethyl acetate and tetrahydrofuran (1:1), separated and concentrated under reduced pressure. The residue was purified by chromatography on a Cosmosil column using distilled water—5% acetonitrile as the eluant. The eluate was lyophilized to afford the desired compound (1R,5S,6S)-2-[1-(4-carbamoyl-1,3-oxazol-2-yl)azetidin-3-yl]thio-6-[(R)-1-hydroxyethyl]-1-methylcarbapen-2-em-3-carboxylic acid sodium salt (110 mg, yield 44%) as a white solid.

$^1$H-NMR (400 MHz, D$_2$O): δ (ppm) 7.79 (1H, s), 4.46 (2H, t, J=8.1 Hz), 4.20–4.16 (1H, m), 4.10 (1H, t, J=5.9 Hz), 4.06 (1H, dd, J=2.9, 9.5 Hz), 3.95 (2H, quint., J=4.4 Hz), 3.28 (1H, dd, J=2.9, 5.9 Hz), 3.12–3.08 (1H, m), 1.15 (3H, d, J=6.6 Hz), 1.05 (3H, d, J=7.3 Hz).

IR (KBr): 3360, 1749, 1671, 1625, 1384, 1275 cm$^{-1}$.

High-resolution mass spectrum (FAB$^+$): calculated: 431.0992, Found: 431.1008 [M+H]$^+$.

EXAMPLE 23

(1R,5S,6S)-2-[1-(4-Cyano-1,3-oxazol-2-yl)azetidin-3-yl]thio-6-[(R)-1-hydroxyethyl]-1-methylcarbapen-2-em-3-carboxylic acid sodium salt

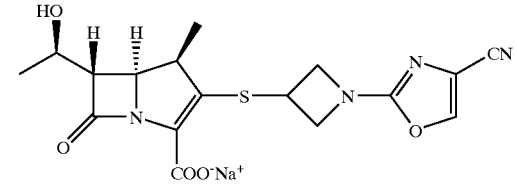

(1) p-Nitrobenzyl (1R,5S,6S)-2-[1-(4-cyano-1,3-oxazol-2-yl)azetidin-3-yl]thio-6-[(R)-1-hydroxyethyl]-1-methylcarbapen-2-em-3-carboxylate To a solution of 3-acetylthio-1-(4-cyano-1,3-oxazol-2-yl) azetidine (156 mg, 0.70 mmol) (obtained as described in Reference Example 23) in dimethylformamide (8 ml) was added hydrazine acetate (77 mg, 0.84 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (416 mg, 0.70 mmol) in acetonitrile (8 ml) was added dropwise to the resulting mixture in an ice bath under an atmosphere of nitrogen, followed by the addition of diisopropylethylamine (0.49 ml, 2.80 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column using ethyl acetate as the eluant to afford p-nitrobenzyl (1R,5S,6S)-2-[1-(4-cyano-1,3-oxazol-2-yl)azetidin-3-yl]thio-6-[(R)-1-hydroxyethyl]-1-methylcarbapen-2-em-3-carboxylate (309 m yield 84%) as a pale yellow solid.

$^1$H-NMR (400 MHz, CDCl$_3$): δ (ppm) 8.22 (2H, d, J=8.8 Hz), 7.74 (1H, s), 7.66 (2H, d, J=8.8 Hz), 5.51 (1H, d, J=13.9 Hz), 5.25 (1H, d, J=13.2 Hz), 4.56 (2H, q, J=8.1 Hz), 4.29–4.22 (3H, m), 4.15–4.10 (2H, m), 3.30 (1H, dd, J=2.9, 7.3 Hz), 3.19 (1H, dt, J=7.3, 9.5 Hz), 1.37 (3H, d, J=6.6 Hz), 1.26 (3H, d, J=7.3 Hz).

(2) (1R,5S,6S)-2-[1-(4-Cyano-1,3-oxazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-cyano-1,3-oxazol-2-yl)azetidin-3-yl]thio-6-[(R)-1-hydroxyethyl]-1-methylcarbapen-2-em-3-carboxylate (309 mg, 0.59 mmol) (obtained as described in Example 23(1)) in a mixture of tetrahydrofuran (16 ml) and distilled water (8 ml) was subjected to catalytic hydrogenation in the presence of 20% palladium hydroxide (309 mg) in a water bath (30° C.) for 2 hours. After checking the completion of the reaction, the reaction mixture was filtered and to the filtrate were added sodium hydrogencarbonate (50 mg), a mixture of ethyl acetate and tetrahydrofuran (1:1) and distilled water. The mixture was shaken in a separatory funnel. The aqueous layer was washed with a mixture of ethyl acetate and tetrahydrofuran (1:1), separated and concentrated under reduced pressure. The residue was purified by chromatography on a Cosmosil column using distilled water—5% acetonitrile as the eluant. The eluate was lyophilized to afford the desired compound (1R,5S,6S)-2-[1-(4-cyano-1,3-oxazol-2-yl)azetidin-3-yl]thio-6-[(R)-1-hydroxyethyl]-1-methylcarbapen-2-em-3-carboxylic acid sodium salt (150 mg, yield 60%) as a white solid.

$^1$H-NMR (400 MHz, D$_2$O): δ (ppm) 7.92 (1H, s), 4.45 (2H, t, J=8.8 Hz), 4.20–4.16 (1H, m), 4.09 (1H, t, J=6.6 Hz), 4.05 (1H, d, J=8.8 Hz), 3.95 (2H, quint., J=4.4 Hz), 3.28 (1H, d, J=6.6 Hz), 3.08 (1H, quint., J=8.1 Hz), 1.14 (3H, d, J=6.6 Hz), 1.03 (3H, d, J=7.3 Hz).

IR (KBr): 3372, 1750, 1628, 1394, 1283 cm$^{-1}$.

High-resolution mass spectrum (FAB$^+$): calculated: 413.0860, Found: 413.0921 [M+H]$^+$.

EXAMPLE 24

(1R,5S,6S)-2-[1-(4-Azetidinocarbonyl-1,3-thiazol-2-yl)azetidin-3-yl]thio-6-[(R)-1-hydroxyethyl]-1-methylcarbapen-2-em-3-carboxylic acid sodium salt

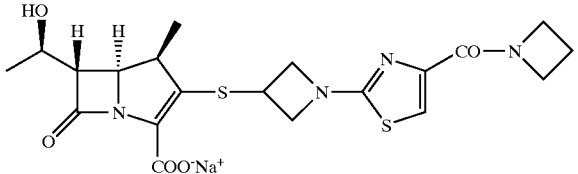

(1) p-Nitrobenzyl (1R,5S,6S)-2-[1-(4-azetidinocarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-azetidinocarbonyl-1,3-thiazol-2-yl)azetidine (247 mg, 0.83 mmol) (obtained as described in Reference Example 24) in dimethylformamide (12 ml) was added hydrazine acetate (92 mg, 1.0 mmol) at room temperature under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (493 mg, 0.83 mmol) in acetonitrile (25 ml) was added dropwise to the resulting mixture in an ice bath under an atmosphere of nitrogen, followed by the addition of diisopropylethylamine (0.58 ml, 3.32 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate and saturated aqueous sodium chloride solution, dried over anhydrous sodium sulfate, filtered and concentrated under reduced pressure. The residue was purified by chromatography on a silica gel column using 10% methanol-ethyl acetate as the eluant to afford p-nitrobenzyl (1R,5S,6S)-2-[1-(4-azetidinocarbonyl-1,3-thiazol-2-yl)azetidin-3-yl]thio-6-[(R)-1-hydroxyethyl]-1-methylcarbapen-2-em-3-carboxylate (321 mg, yield 65%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.41 (1H, s), 5.51 (1H, d, J=13.7 Hz), 5.25 (1H, d, J=13.7 Hz), 4.56 (2H, t, J=7.4 Hz), 4.50–4.40 (2H, m), 4.35–4.10 (5H, m including 2H, t at 4.17, J=7.4 Hz), 4.04 (1H, t, J=5.4 Hz), 4.02 (1H, t, J=5.4 Hz), 3.29 (1H, dd, J=7.0, 2.5 Hz), 3.18 (1H, dq, J=8.9, 7.3 Hz), 2.30 (2H, quintet, J=7.4 Hz), 1.95–1.50 (dull s including 1H of OH group), 1.38 (3H, d, J=6.3 Hz), 1.26 (3H, d, J=7.3 Hz).

Mass spectrum (FAB$^+$): 600 [M+H]$^+$.

(2) (1R,5S,6S)-2-[1-(4-Azetidinocarbonyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-azetidinocarbonyl-1,3-thiazol-2-yl)azetidin-3-yl]thio-6-[(R)-1-hydroxyethyl]-1-methylcarbapen-2-em-3-carboxylate (321 mg, 0.54 mmol) (obtained as described in Example 24(1)) in a mixture of tetrahydrofuran (15 ml) and distilled water (15 ml) was subjected to catalytic hydrogenation in the presence of 10% palladium on charcoal (321 mg) at room temperature for 2 hours. After checking the completion of the reaction, the reaction mixture was filtered and to the filtrate were added sodium hydrogencarbonate (45 mg), ethyl acetate and distilled water. The mixture was shaken in a separatory funnel. The aqueous layer was washed with the mixture of solvents described above, separated and concentrated under reduced pressure. The residue was purified by chromatography on a Cosmosil column using distilled water—5% acetonitrile; distilled water—10% acetonitrile; distilled water—15% acetonitrile and distilled water as the eluant. The eluate was lyophilized to afford the desired compound (1R,5S,6S)-2-[1-(4-azetidinocarbonyl-1,3-thiazol-2-yl)azetidin-3-yl]thio-6-[(R)-1-hydroxyethyl]-1-methylcarbapen-2-em-3-carboxylic acid sodium salt (162 mg, yield 65%) as a white solid.

$^1$H-NMR (400 MHz, D$_2$O, TSP): δ (ppm) 7.34 (1H, s), 4.95–4.65 (4H, m), 4.40–4.30 (1H, m), 4.30–4.13 (4H, m including 1H, quintet at 4.25, J=6.3 Hz, and 1H, dd, at 4.19, J=14.4, 7.2 Hz), 4.10–4.00 (2H, m), 3.43 (1H, dd, J=6.3, 2.5 Hz), 3.26 (1H, quintet, J=7.2 Hz), 2.37 (2H, quintet, J=7.9 Hz), 1.30 (3H, d, J=6.4 Hz), 1.20 (3H, d, J=7.2 Hz).

IR (KBr): 1750, 1607, 1538, 1455, 1435, 1393, 1308, 1292 cm$^{-1}$.

Mass spectrum (FAB$^+$): 487 [M+H]$^+$.

EXAMPLE 25

(1R,5S,6S)-2-[1-(4-Thiomorpholinocarbonyl-1,3-thiazol-2-yl)azetidin-3-yl]thio-6-[(R)-1-hydroxyethyl]-1-methylcarbapen-2-em-3-carboxylic acid sodium salt

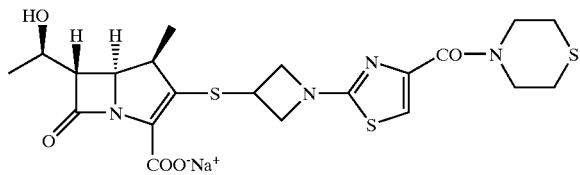

(1) p-Nitrobenzyl (1R,5S,6S)-2-[1-(4-thiomorpholinocarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-thiomorpholinocarbonyl-1,3-thiazol-2-yl)azetidine (207 mg, 0.62 mmol) (obtained as described in Reference Example 25) in dimethylformamide (8 ml) was added hydrazine acetate (68.4 mg, 0.74 mmol) at 0° C. under an atmosphere of nitrogen and the mixture was stirred for 1 hour. After checking the completion of the reaction, a solution of p-nitrobenzyl (1R,5S,6S)-2-diphenylphosphoryloxy-6-[(R)-1-hydroxyethyl]-1-methylcarbapen-2-em-3-carboxylate (370.5 mg, 0.62 mmol) in acetonitrile (16 ml) was added dropwise to the resulting mixture in an ice bath under an atmosphere of nitrogen, followed by the addition of diisopropylethylamine (0.43 ml, 2.48 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate and saturated aqueous sodium chloride solution, dried over anhydrous magnesium sulfate, filtered and concentrated under reduced pressure. The residue was purified by chromatography on a silica gel column using 5% methanol-ethyl acetate as the eluant to afford p-nitrobenzyl (1R,5S,6S)-2-[1-(1-(1,3-thiazol-4-thiomorpholinocarbonyl-2-yl)azetidin-3-yl)thio-6-[(R)-1-hydroxyethyl]-1-methylcarbapen-2-em-3-carboxylate (246 mg, yield 61%) as a pale yellow solid.

$^1$H-NMR (400 MHz, CDCl$_3$): δ (ppm) 8.23 (2H, d, J=8.7 Hz), 7.67 (2H, d, J=8.7 Hz), 7.12 (1H, s), 5.51 (1H, d, J=13.8 Hz), 5.25 (1H, d, J=13.8 Hz), 4.60–4.40 (2H, m), 4.35–4.22 (3H, m), 4.10–4.00 (2H, m), 4.00–3.90 (4H, m), 3.29 (1H, dd, J=6.4, 2.6 Hz), 3.21 (1H, dq, J=9.2, 7.3 Hz), 2.80–2.60 (4H, m), 1.80–1.50 (dull s including 1H of OH group), 1.38 (3H, d, J=6.4 Hz), 1.27 (3H, d, J=7.3 Hz).

Mass spectrum (FAB$^+$): 646 [M+H]$^+$.

(2) (1R,5S,6S)-2-[1-(4-Thiomorpholinocarbonyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-thiomorpholinocarbonyl-1,3-thiazol-2-yl)azetidin-3-yl]thio-6-[(R)-1-hydroxyethyl]-1-methylcarbapen-2-em-3-carboxylate (543 mg, 0.84 mmol) (obtained as described in Example 25(1)) in a mixture of tetrahydrofuran (30 ml) and distilled water (30 ml) was subjected to catalytic hydrogenation in the presence of 10% palladium on charcoal (543 mg) at room temperature for 2 hours. After checking the completion of the reaction, the reaction mixture was filtered and to the filtrate were added sodium hydrogencarbonate (70.6 mg), ethyl acetate and distilled water. The mixture was shaken in a separatory funnel. The aqueous layer was separated and concentrated under reduced pressure. The residue was purified by chromatography on a Cosmosil column using distilled water—5% acetonitrile; distilled water—10% acetonitrile; distilled water—15% acetonitrile; distilled water—20% acetonitrile and distilled water as the eluant. The eluate was lyophilized to afford the desired compound (1R,5S,6S)-2-[1-(4-thiomorpholinocarbonyl-1,3-thiazol-2-yl)azetidin-3-yl]thio-6-[(R)-1-hydroxyethyl]-1-methylcarbapen-2-em-3-carboxylic acid sodium salt (277 mg, yield 62%) as a white solid.

$^1$H-NMR (400 MHz, D$_2$O, TSP): δ (ppm) 7.10 (1H, s), 4.56 (2H, t, J=8.0 Hz), 4.42–4.30 (1H, m), 4.25 (1H, quintet, J=6.3 Hz), 4.21 (2H, dd, J=7.8, 2.4 Hz), 4.12–4.02 (2H, m), 3.96–3.85 (2H, m), 3.85–3.75 (2H, m), 3.44 (1H, dd, J=6.3, 2.4 Hz), 3.26 (1H, dq, J=8.9, 7.8 Hz), 2.86–2.70 (2H, m), 2.70–2.60 (2H, m), 1.30 (3H, d, J=6.3 Hz), 1.20 (3H, d, J=7.8 Hz).

IR (KBr): 1749, 1608, 1535, 1454 cm$^{-1}$.

Mass spectrum (FAB$^+$): 533 [M+H]$^+$.

EXAMPLE 26

Ethyl (1R,5S,6S)-2-[1-(4-Carbamoyl-1,3-thiazol-2-yl)azetidin-3-yl]thio-6-[(R)-1-hydroxyethyl]-1-methylcarbapen-2-em-3-carboxylate

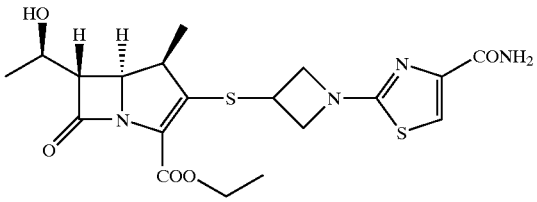

To a solution of (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylic acid sodium salt (357 mg, 0.80 mmol) (obtained as described in Example 3) in dimethylformamide (5 ml) was added ethyl iodide (357 mg, 2.40 mmol) at 0° C. under an atmosphere of nitrogen and the mixture was stirred for 1 hour. The mixture was further stirred for 2 hours while gradually raising the temperature to room temperature. At the end of this time, to the reaction mixture was added ethyl acetate and the organic layer was washed sequentially with 10% aqueous sodium chloride solution, 10% aqueous sodium thiosulfate solution saturated aqueous sodium hydrogencarbonate solution, and saturated aqueous sodium chloride solution, dried over anhydrous sodium sulfate, filtered and concentrated under reduced pressure. The residue was purified by chromatography on a silica gel column using ethyl acetate—20% acetonitrile; ethyl acetate—40% acetonitrile; ethyl acetate—60% acetonitrile and ethyl acetate to give a purified product, which was dissolved in methylene chloride and diethyl ether and hexane were sequentially added to the solution to afford ethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate (387 mg, yield 95%) as a colorless powder.

$^1$H-NMR (400 MHz, CDCl$_3$): δ (ppm) 7.48 (1H, s), 6.99 (1H, br s), 5.61 (1H, br s), 4.48 (2H, q, J=8.5 Hz), 4.19–4.43

(4H, m), 4.02–4.13 (2H, m), 3.26 (2H, dd, J=7.1, 2.7 Hz), 3.10 (1H, dq, J=9.0, 7.3 Hz), 2.07 (1H, d, J=4.8 Hz), 1.37 (3H, d, J=6.9 Hz), 1.36 (3H, t, J=7.5 Hz), 1.25 (3H, d, J=7.2 Hz).

IR (KBr): 1770, 1669, 1602, 1543, 1324, 1283 cm$^{-1}$.

Mass spectrum (FAB$^+$): 453 [M+H]$^+$.

High-resolution mass spectrum (FAB$^+$): calculated for $C_{19}H_{25}O_5N_4S_2$ 453.1267, Found 453.1235 [M+H]$^+$.

EXAMPLE 27

Phenyl (1R,5S,6S)-2-[1-(4-Carbamoyl-1,3-thiazol-2-yl)azetidin-3-yl]thio-6-[(R)-1-hydroxyethyl]-1-methylcarbapen-2-em-3-carboxylate

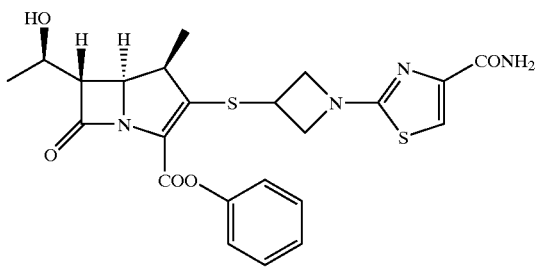

To a solution of (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylic acid sodium salt (162 mg, 0.36 mmol) (obtained as described in Example 3) in a mixture of water (1-ml) and tetrahydrofuran (1 ml) was added 1 M hydrochloric acid (0.33 ml, 0.36 mmol) at 0° C. The mixture was concentrated under reduced pressure. To a solution of the residue in acetonitrile (10 ml) were added phenol (102 mg, 1.1 mmol), dimethylaminopyridine (22 mg, 0.18 mmol) and 1-ethyl-3-(3-dimethylaminopropyl)carbodiimide hydrochloride (139 mg, 0.73 mmol) at room temperature. After stirring the mixture for 30 minutes, further 1-ethyl-3-(3-dimethylaminopropyl)carbodiimide hydrochloride (139 mg, 0.73 mmol) was added thereto and the resulting mixture was stirred for 30 minutes. At the end of this time, to the reaction mixture was added ethyl acetate and the organic layer was washed sequentially with dilute hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate—20% acetonitrile; ethyl acetate—40% acetonitrile; ethyl acetate—60% acetonitrile and ethyl acetate to afford phenyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate (66 mg, yield 36%) as a colorless powder.

$^1$H-NMR (400 MHz, CDCl$_3$): δ (ppm) 7.48 (1H, s), 7.38–7.43 (2H, m), 7.23–7.28 (3H, m), 6.99 (1H, br s), 5.60 (1H, br s), 4.40–4.55 (2H, m), 4.24–4.36 (3H, m), 4.03–4.13 (2H, m), 3.32 (1H, dd, J=7.0, 2.6 Hz), 3.25 (1H, dq, J=9.2, 7.3 Hz), 2.09 (1H, br), 1.39 (3H, d, J=6.4 Hz), 1.30 (3H, d, J=7.3 Hz).

IR (KBr): 1771, 1668, 1542, 1195 cm$^{-1}$.

Mass spectrum (FAB$^+$): 501 [M+H]$^+$.

High-resolution mass spectrum (FAB$^+$): calculated for $C_{23}H_{25}O_5N_4S_2$ 501.1266, Found 501.1266 [M+H]$^+$.

EXAMPLE 28

Pivaloyloxymethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate

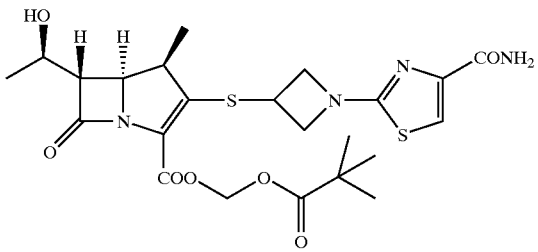

To a solution of (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylic acid sodium salt (402 mg, 0.90 mmol) (obtained as described in Example 3) in dimethylacetamide (5 ml) was added iodomethyl pivalate (261 mg, 1.08 mmol) at 0° C. under an atmosphere of nitrogen and the mixture was stirred for 1 hour. At the end of this time, to the reaction mixture was added ethyl acetate and the organic layer was washed sequentially with 10% aqueous sodium chloride solution 10% aqueous sodium thiosulfate solution, saturated aqueous sodium hydrogencarbonate solution and saturated aqueous sodium chloride solution, dried over anhydrous sodium sulfate, filtered and concentrated under reduced pressure. To the residue was added diethyl ether to afford pivaloyloxymethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate (450 mg, yield 93%) as a colorless powder.

$^1$H-NMR (400 MHz, DMSO-d$_6$): δ (ppm) 7.47 (1H, s), 7.43 (1H, br s), 7.32 (1H, br s), 5.89 (1H, d, J=5.9 Hz), 5.74 (1H, d, J=5.9 Hz), 5.09 (1H, d, J=5.2 Hz), 4.42–4.58 (3H, m), 4.20 (1H, dd, J=9.4, 2.4 Hz), 3.89–4.02 (3H, m), 3.37 (1H, dq, J=9.1, 7.4 Hz), 3.26 (1H, dd, J=6.3, 2.6 Hz), 1.14 (3H, d, J=7.4 Hz), 1.13 (9H, s), 1.11 (3H, d, J=6.5 Hz).

IR (KBr): 1778, 1754, 1602, 1545, 1282, 1118 cm$^{-1}$.

Mass spectrum (FAB$^+$): 539 [M+H]$^+$.

High-resolution mass spectrum (FAB$^+$): calculated for $C_{23}H_{31}O_7N_4S_2$ 539.1634, Found 539.1634 [M+H]$^+$.

EXAMPLE 29

1-(Isopropoxycarbonyloxy)ethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate

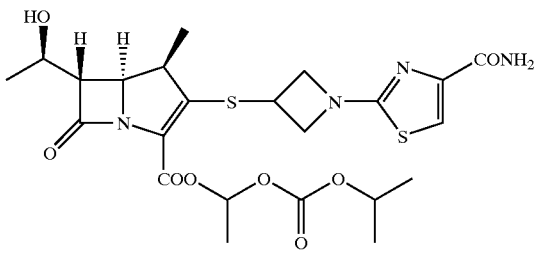

To a solution of (1R,5S,6S)-2-[1-(4-carbamoyl-1,3-thiazol-2-yl)azetidin-3-yl]thio-6-[(R)-1-hydroxyethyl]-1- methylcarbapen-2-em-3-carboxylic acid sodium salt (245 mg, 0.55 mmol) obtained as described in Example 3 in dimethylacetamide (5 ml) was added 1-iodoethyl isopropyl carbonate (317 mg, 1.21 mmol) at 0° C. under an atmosphere of nitrogen and the mixture was stirred for 1.5 hours. The resulting mixture was further stirred for 1.5 hours while gradually raising the temperature to room temperature. At the end of this time, to the reaction mixture was added ethyl acetate and the organic layer was washed sequentially with 10% aqueous sodium chloride solution, 0.1 M hydrochloric acid, 10% aqueous sodium thiosulfate solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate—20% acetonitrile; ethyl acetate—40% acetonitrile; ethyl acetate—60% acetonitrile and ethyl acetate to give a purified product, which was dissolved in methylene chloride and diethyl ether and hexane were sequentially added to the solution to afford 1-(isopropoxycarbonyloxy)ethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate (266 mg, yield 88%) as a colorless powder.

$^1$H-NMR (400 MHz, CDCl$_3$): δ (ppm) 7.48 (1H, s), 7.00 (1H, br s), 6.82–6.92 (1H, m), 5.65 (1H, br s), 4.84–4.97 (1H, m), 4.43–4.52 (2H, m), 4.18–4.39 (3H, m), 4.02–4.07 (2H, m), 3.25 (1H, dd, J=7.0, 2.5 Hz), 3.17 (1H, dq, J=9.3, 7.3 Hz), 2.16 (1H, br s), 1.61 (3/2H, d, J=5.5 Hz), 1.59 (3/2H, d, J=5.5 Hz), 1.18–1.39 (12H, m).

IR (KBr): 1763, 1669, 1542, 1276, 1074 cm$^{-1}$.

Mass spectrum (FAB$^+$): 555 [M+H]$^+$.

High-resolution mass spectrum (FAB$^+$): calculated for C$_{23}$H$_{31}$O$_8$N$_4$S$_2$ 555.1584, Found 555.1570 [M+H]$^+$.

EXAMPLE 30

1-(3-Pentyloxycarbonyloxy)ethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate

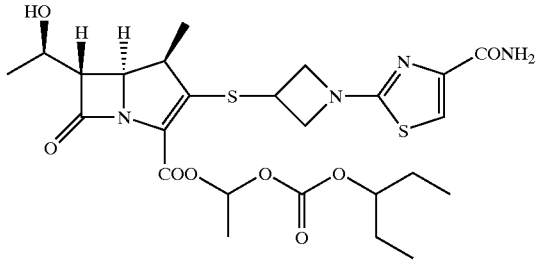

To a solution of (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylic acid sodium salt (402 mg, 0.90 mmol) (obtained as described in Example 3) in dimethylacetamide (8 ml) was added 1-iodoethyl 3-pentyl carbonate (568 mg, 1.98 mmol) at 0° C. under an atmosphere of nitrogen and the mixture was stirred for 1 hour. The resulting mixture was further stirred for 2 hours while gradually raising the temperature to room temperature. At the end of this time, to the reaction mixture was added ethyl acetate and the organic layer was washed sequentially with 10% aqueous sodium chloride solution, 0.1 M hydrochloric acid, 10% aqueous sodium thiosulfate solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate—20% acetonitrile; ethyl acetate—40% acetonitrile; ethyl acetate—60% acetonitrile and ethyl acetate to afford 1-(3-pentyloxycarbonyloxy)ethyl (1R,5S,6S)-2-[1-(4-carbamoyl-1,3-thiazol-2-yl)azetidin-3-yl]thio-6-[(R)-1-hydroxyethyl]-1-methylcarbapen-2-em-3-carboxylate (506 mg, yield 96%) as a colorless amorphous.

$^1$H-NMR (400 MHz, CDCl$_3$): δ (ppm) 7.48 (1H, s), 7.00 (1H, br s), 6.85–6.93 (1H, m), 5.58 (1H, br s), 4.57–4.66 (1H, m), 4.42–4.52 (2H, m), 4.15–4.32 (3H, m), 4.02–4.10 (2H, m), 3.24 (1H, dd, J=7.1, 2.6 Hz), 3.17 (1H, dq, J=9.3, 7.4 Hz), 2.00 (1H, br s), 1.50–1.72 (7H, m), 1.34 (3/2H, d, J=6.5 Hz), 1.36 (3/2H, J=6.5 Hz), 1.24, (3/2H, d, J=7.3 Hz), 0.84–0.98 (6H, m).

IR (KBr): 1761, 1671, 1542, 1268, 1074 cm$^{-1}$.

Mass spectrum (FAB$^+$): 583 [M+H]$^+$.

High-resolution mass spectrum (FAB$^+$): calculated for C$_{25}$H$_{35}$O$_8$N$_4$S$_2$ 583.1896, Found 583.1907 [M+H]$^+$.

EXAMPLE 31

(1R,5S,6S)-2-[1-(4-Pyrrolidinocarbonyl-1,3-thiazol-2-yl)azetidin-3-yl]thio-6-[(R)-1-hydroxyethyl]-1-methylcarbapen-2-em-3-carboxylic acid sodium salt

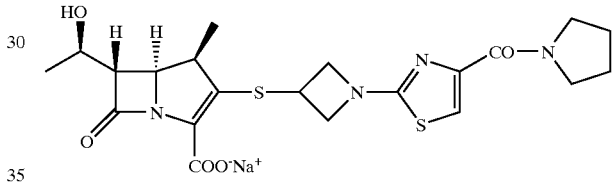

(1) p-Nitrobenzyl (1R,5S,6S)-2-[1-(4-pyrrolidinocarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-pyrrolidinocarbonyl-1,3-thiazol-2-yl)azetidine (235 mg, 0.84 mmol) (obtained as described in Reference Example 26) in dimethylformamide (12 ml) was added hydrazine acetate (103 mg, 110 mmol) at room temperature under an atmosphere of nitrogen and the mixture was stirred for 3 hours. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (499 mg, 0.84 mmol) in acetonitrile (25 ml) was added dropwise to the resulting mixture in an ice bath under an atmosphere of nitrogen, followed by the addition of diisopropylethylamine (0.56 ml, 3.36 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate and ethyl acetate:methanol (9:1) as the eluant to afford p-nitrobenzyl (1R,5S,6S)-2-[1-(4-pyrrolidinocarbonyl-1,3-thiazol-2-yl)azetidin-3-yl]thio-6-[(R)-1-hydroxyethyl]-1-methylcarbapen-2-em-3-carboxylate (240 mg, yield 46%) as a pale yellow solid.

¹H-NMR (400 MHz, CDCl₃): δ (ppm) 8.23 (2H, d, J=8.7 Hz), 7.66 (2H, d, J=8.7 Hz), 7.28 (1H, s), 5.51 (1H, d, J=13.8 Hz), 5.25 (1H, d, J=13.8 Hz), 4.49 (2H, dd, J=14.6, 8.5 Hz), 4.35–4.20 (3H, m), 4.05 (1H, t, J=6.1 Hz), 4.04 (1H, t, J=6.1 Hz), 3.78 (2H, t, J=6.5 Hz), 3.62 (2H, t, J=6.5 Hz), 3.29 (1H, dd, J=7.2, 2.5 Hz), 3.20 (1H, dq, J=9.0, 7.3 Hz), 1.82–1.98 (4H, m), 1.38 (3H, d, J=6.1 Hz), 1.27 (3H, d, J=7.2 Hz).

(2) (1R,5S,6S)-2-[1-(4-Pyrrolidinocarbonyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-pyrrolidinocarbonyl-1,3-thiazol-2-yl)azetidin-3-yl]thio-6-[(R)-1-hydroxyethyl]-1-methylcarbapen-2-em-3-carboxylate (240 mg, 0.39 mmol) (obtained as described in Example 31(1)) in a mixture of tetrahydrofuran (12 ml) and distilled water (12 ml) was subjected to catalytic hydrogenation in the presence of 7.5% palladium on charcoal (240 mg) in a water bath (30° C.) for 1.5 hours. After checking the completion of the reaction, the reaction mixture was filtered and to the filtrate were added sodium hydrogencarbonate (33 mg), acetic acid and distilled water. The mixture was shaken in a separatory funnel. The aqueous layer was separated and concentrated under reduced pressure. The residue was purified by chromatography on a Cosmosil column using distilled water—3% acetonitrile; distilled water—6% acetonitrile and distilled water as the eluant. The eluate was lyophilized to afford the desired compound (1R,5S,6S)-2-[1-(4-pyrrolidinocarbonyl-1,3-thiazol-2-yl)azetidin-3-yl]thio-6-[(R)-1-hydroxyethyl]-1-methylcarbapen-2-em-3-carboxylic acid sodium salt (113 mg, yield 60%) as a white solid.

¹H-NMR (400 MHz, D₂O): δ (ppm) 7.40 (1H, s), 4.56 (2H, t, J=8.6 Hz), 4.43–4.30 (1H, m), 4.25 (1H, quint., J=6.4 Hz), 4.20 (1H, dd, J=8.9, 2.4 Hz), 4.10–3.98 (2H, m), 3.62 (2H, t, J=6.6 Hz), 3.54 (2H, t, J=6.6 Hz), 3.26 (1H, dq, J=8.9, 7.4 Hz), 3.43 (1H, dd, J=8.9, 2.4 Hz), 2.05–1.85 (4H, m), 1.30 (3H, d, J=6.4 Hz), 1.27 (3H, d, J=7.4 Hz).

IR (KBr): 3375.7, 1605.9, 1537.4, 1468.9, 1423.6, 1396.6, 1298.2 cm⁻¹.

Mass spectrum (FAB⁺): m/z: 501 [M+H]⁺.

EXAMPLE 32

(1R,5S,6S)-2-[1-(4-Piperidinocarbonyl-1,3-thiazol-2-yl)azetidin-3-yl]thio-6-[(R)-1-hydroxyethyl]-1-methylcarbapen-2-em-3-carboxylic acid sodium salt

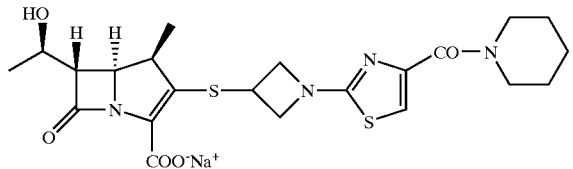

(1) p-Nitrobenzyl (1R,5S,6S)-2-[1-(4-piperidinocarbonyl-1,3-thiazol-2-yl)azetidin-3-yl]thio-6-[(R)-1-hydroxyethyl]-1-methylcarbapen-2-em-3-carboxylate To a solution of 3-acetylthio-1-(4-piperidinocarbonyl-1,3-thiazol-2-yl)azetidine (276 mg, 0.85 mmol) (obtained as described in Reference Example 27) in dimethylformamide (20 ml) was added hydrazine acetate (94 mg, 1.02 mmol) at room temperature under an atmosphere of nitrogen and the mixture was stirred for 2 hours. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (505 mg, 0.85 mmol) in acetonitrile (20 ml) was added dropwise to the resulting mixture in an ice bath under an atmosphere of nitrogen, followed by the addition of diisopropylethylamine (0.59 ml, 3.40 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate and ethyl acetate:methanol (9:1) as the eluant to afford p-nitrobenzyl (1R,5S,6S)-2-[1-(4-piperidinocarbonyl-1,3-thiazol-2-yl)azetidin-3-yl]thio-6-[(R)-1-hydroxyethyl]-1-methylcarbapen-2-em-3-carboxylate (464 mg, yield 87%) as a pale yellow solid.

¹H-NMR (400 MHz, CDCl₃): δ (ppm) 8.23 (2H, d, J=8.7 Hz), 7.66 (2H, d, J=8.7 Hz), 7.02 (1H, s), 5.51 (1H, d, J=13.7 Hz), 5.26 (1H, d, J=13.7 Hz), 4.51 (1H, t, J=8.1 Hz), 4.50 (1H, t, J=8.1 Hz), 4.32–4.20 (3H, m including 4.25 (1H, dd, J=8.0, 2.5 Hz)), 4.07 (1H, t, J=5.7 Hz), 4.05 (1H, t, J=5.7 Hz), 3.72–3.58 (4H, m), 3.28 (1H, dd, J=6.8, 2.5 Hz), 3.20 (1H, dq, J=8.4, 7.3 Hz), 1.80–1.45 (6H, m), 1.38 (3H, d, J=6.8 Hz), 1.26 (3H, d, J=7.1 Hz).

(2) (1R,5S,6S)-2-[1-(4-Piperidinocarbonyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-piperidinocarbonyl-1,3-thiazol-2-yl)azetidin-3-yl]thio-6-[(R)-1-hydroxyethyl]-1-methylcarbapen-2-em-3-carboxylate (464 mg, 0.74 mmol) (obtained as described in Example 32(1)) in a mixture of tetrahydrofuran (20 ml) and distilled water (20 ml) was subjected to catalytic hydrogenation in the presence of 7.5% palladium on charcoal (464 mg) in a water bath (35° C.) for 2 hours. After checking the completion of the reaction, the reaction mixture was filtered and to the filtrate were added sodium hydrogencarbonate (62 mg), acetic acid and distilled water. The mixture was shaken in a separatory funnel. The aqueous layer was separated and concentrated under reduced pressure. The residue was purified by chromatography on a Cosmosil column using distilled water—2% acetonitrile; distilled water—5% acetonitrile; distilled water—10% acetonitrile; distilled water—20% acetonitrile; distilled water—30% acetonitrile and distilled water as the eluant. The eluate was lyophilized to afford the desired compound (1R,5S,6S)-2-[1-(4-piperidinocarbonyl-1,3-thiazol-2-yl)azetidin-3-yl]thio-6-[(R)-1-hydroxyethyl]-1-methylcarbapen-2-em-3-carboxylic acid sodium salt (171 mg, yield 45%) as a white solid.

¹H-NMR (400 MHz, D₂O): δ (ppm) 7.04 (1H, s), 4.10–4.00 (2H, m), 4.42–4.30 (1H, m), 4.25 (1H quint., J=6.2 Hz), 4.21 (1H, dd, J=9.0, 2.4 Hz), 4.05 (2H, ddd, J=8.3, 5.4 2.7 Hz), 3.62 (2H, t, J=5.3 Hz), 3.49 (2H, t, J=5.3 Hz), 3.44 (1H, dd, J=6.2, 2.4 Hz), 3.26 (1H, dq, J=7.7, 7.4 Hz), 1.70–1.60 (4H, m), 1.60–1.50 (2H, m), 1.30 (3H, d, J=6.4 Hz), 1.27 (3H, d, J=7.2 Hz).

IR (KBr): 3382.5, 1747.7, 1605.9, 1538.4, 1400.4, 1310.7, 1249.0 cm⁻¹.

Mass spectrum (FAB⁺): m/z: 515 [M+H]⁺.

EXAMPLE 33

(1R,5S,6S)-2-[1-(4-N-cyclopropylcarbamoyl-1,3-thiazol-2-yl)azetidin-3-yl]thio-6-[(R)-1-hydroxyethyl]-1-methylcarbapen-2-em-3-carboxylic acid sodium salt

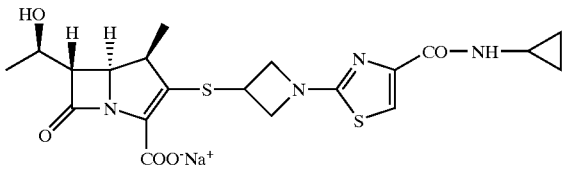

(1) p-Nitrobenzyl (1R,5S,6S)-2-[1-(4-N-cyclopropylcarbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-N-cyclopropylcarbamoyl-1,3-thiazol-2-yl)azetidine (342 mg, 1.15 mmol) (obtained as described in Reference Example 28) in dimethylformamide (12 ml) was added hydrazine acetate (127 mg, 1.38 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (684 mg, 1.15 mmol) in acetonitrile (25 ml) was added dropwise to the resulting mixture in an ice bath under an atmosphere of nitrogen, followed by the addition of diisopropylethylamine (0.80 ml, 4.60 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M aqueous sodium chloride solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate: methanol (9:1) as the eluant to afford p-nitrobenzyl (1R,5S,6S)-2-[1-(4-N-cyclopropylcarbamoyl-1,3-thiazol-2-yl)azetidin-3-yl]thio-6-[(R)-1-hydroxyethyl]-1-methylcarbapen-2-em-3-carboxylate (606 m yield 88%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.44 (1H, s), 7.23 (1H, br s), 5.51 (1H, d, J=13.7 Hz), 5.25 (1H, d, J=13.7 Hz), 4.49 (2H, dd, J=14.3, 7.6 Hz), 4.37–4.19 (3H, m), 3.98–4.12 (3H, m), 3.30 (1H, dd, J=9.2, 7.3 Hz), 3.20 (1H, dq, J=9.2, 7.3 Hz), 2.80–2.94 (1H, m), 1.38 (3H, d, J=6.4 Hz), 1.27 (3H, d, J=7.3 Hz), 0.85 (1H, t, J=5.5 Hz), 0.83 (1H, t, J=5.5 Hz), 0.58–0.70 (2H, m).

(2) (1R,5S,6S)-2-[1-(4-N-Cyclopropylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-cyclopropylcarbamoyl-1,3-thiazol-2-yl)azetidin-3-yl]thio-6-[(R)-1-hydroxyethyl]-1-methylcarbapen-2-em-3-carboxylate (606 mg, 1.01 mmol) (obtained as described in Example 33(1)) in a mixture of tetrahydrofuran (30 ml) and distilled water (30 ml) was subjected to catalytic hydrogenation in the presence of 7.5% palladium on charcoal (606 mg) in a water bath (35° C.) for 2.5 hours. After checking the completion of the reaction, the reaction mixture was filtered and to the filtrate were added sodium hydrogencarbonate (85 mg), ethyl acetate and distilled water. The mixture was shaken in a separatory funnel. The aqueous layer was separated and concentrated under reduced pressure. The residue was purified by chromatography on a Cosmosil column using distilled water—5% acetonitrile; distilled water—10% acetonitrile and distilled water as the eluant. The eluate was lyophilized to afford the desired compound (1R,5S,6S)-2-[1-(4-N-cyclopropylcarbamoyl-1,3-thiazol-2-yl)azetidin-3-yl]thio-6-[(R)-1-hydroxyethyl]-1-methylcarbapen-2-em-3-carboxylic acid sodium salt (275 mg, yield 56%) as a white solid.

$^1$H-NMR (400 MHz, D$_2$O): δ (ppm) 7.46 (1H, s), 4.54 (2H, t, J=8.2 Hz), 4.38–4.30 (1H, m), 4.25 (1H, quint., J=6.3 Hz), 4.19 (1H, dd, J=8.9, 2.4 Hz), 4.10–4.19 (1H, dd, J=8.9, 2.4 Hz), 3.43 (1H, dd, J=6.3, 2.4 Hz), 3.24 (1H, dq, J=8.9, 7.3 Hz), 2.78–2.70 (1H, m), 1.30 (3H, d, J=6.4 Hz), 1.19 (3H, d, J=7.2 Hz), 0.85 (1H, t, J=5.2 Hz), 0.84 (1H, t, J=5.2 Hz), 0.73–0.61 (2H, m).

IR (KBr): 3397.0, 1750.1, 1603.5, 1545.7, 1489.7, 1470.5, 1393.3, 1312.3 cm$^{-1}$.

Mass spectrum (FAB$^+$): m/z: 465 [M+H]$^+$.

EXAMPLE 34

(1R,5S,6S)-2-[1-(4-N-Cyclobutylcarbamoyl-1,3-thiazol-2-yl)azetidin-3-yl]thio-6-[(R)-1-hydroxyethyl]-1-methylcarbapen-2-em-3-carboxylic acid sodium salt

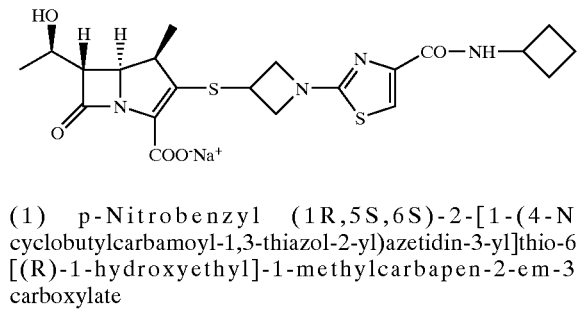

(1) p-Nitrobenzyl (1R,5S,6S)-2-[1-(4-N-cyclobutylcarbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-N-cyclobutylcarbamoyl-1,3-thiazol-2-yl)azetidine (398 mg, 1.28 mmol) (obtained as described in Reference Example 29) in dimethylformamide (15 ml) was added hydrazine acetate (141 mg, 1.53 mmol) at room temperature under an atmosphere of nitrogen and the mixture was stirred for 2.5 hours. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (761 mg, 1.28 mmol) in acetonitrile (30 ml) was added dropwise to the resulting mixture in an ice bath under an atmosphere of nitrogen, followed by the addition of diisopropylethylamine (0.88 ml, 5.12 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5M aqueous sodium chloride solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate: methanol (9:1) as the eluant to afford p-nitrobenzyl (1R,5S,6S)-2-[1-(4-N-cyclbutylcarbamoyl-1,3-thiazol-2-yl)azetidin-3-yl]thio-6-[(R)-1-hydroxyethyl]-1-methylcarbapen-2-em-3-carboxylate (578 mg, yield 74%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.41 (1H, s), 5.51 (1H, d, J=13.7 Hz), 5.25 (1H, d, J=13.7 Hz), 4.60–4.42 (3H, m including 4.52 (2H, quint., J=7.8 Hz)), 4.36–4.20 (3H, m), 3.30 (1H, dd, J=6.9, 2.5 Hz), 3.21 (1H, dq, J=9.2, 7.4 Hz), 2.47–2.33 (2H, m), 2.10–1.92 (2H, m), 1.85–1.65 (2H, m), 1.39 (3h, d, J=6.4 Hz), 1.28 (3H, d, J=7.3 Hz).

(2) (1R,5S,6S)-2-[1-(4-N-Cyclobutylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-N-cyclobutylcarbamoyl-1,3-thiazol-2-yl)azetidin-3-yl]thio-6-[(R)-1-hydroxyethyl]-1-methylcarbapen-2-em-3-carboxylate (578 mg, 0.94 mmol) (obtained as described in Example 34(1)) in a mixture of tetrahydrofuran (30 ml) and distilled water (30 ml) was subjected to catalytic hydrogenation in the presence of 7.5% palladium on charcoal (578 mg) in a water bath (35° C.) for 2.5 hours. After checking the completion of the reaction, the reaction mixture was filtered and to the filtrate were added sodium hydrogencarbonate (79 mg), ethyl acetate and distilled water. The mixture was shaken in a separatory funnel. The aqueous layer was separated and concentrated under reduced pressure. The residue was purified by chromatography on a Cosmosil column using distilled water—5% acetonitrile; distilled water—10% acetonitrile and distilled water as the eluant. The eluate was lyophilized to afford the desired compound (1R,5S,6S)-2-[1-(4-N-cyclobutylcarbamoyl-1,3-thiazol-2-yl)azetidin-3-yl]thio-6-[(R)-1-hydroxyethyl]-1-methylcarbapen-2-em-3-carboxylic acid sodium salt (322 mg, yield 68%) as a white solid.

$^1$H-NMR (400 MHz, D$_2$O): δ (ppm) 7.45 (1H, s), 4.56 (2H, t, J=8.0 Hz), 4.44–4.29 (2H, m), 4.25 (1H, quint., J=6.3 Hz), 4.20 (1H, dd, J=8.8, 2.4 Hz), 4.12–4.00 (2H, m), 3.44 (1H, dd, J=6.3, 2.5 Hz), 3.26 (1H, dq, J=8.8, 7.4 Hz), 2.41–2.28 (2H, m), 2.15–2.00 (2H, m), 1.87–1.72 (2H, m), 1.31 (3H, d, J=6.2 Hz), 1.20 (3H, d, J=7.2 Hz).

IR (KBr): 3395.1, 1750.1, 1659.4, 1604.5, 1545.7, 1490.7, 1470.5, 1393.8, 1310.4, 1251.6 cm$^{-1}$.

Mass spectrum (FAB$^+$): m/z: 501 [M+H]$^+$.

EXAMPLE 35

(1R,5S,6S)-2-{1-[4-(4-Methylpiperazine-1-carbonyl)-1,3-thiazol-2-yl]azetidin-3-yl}thio-6-[(R)-1-hydroxyethyl]-1-methylcarbapen-2-em-3-carboxylic acid sodium salt

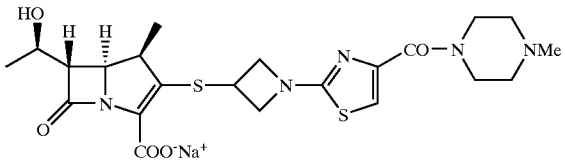

(1) p-Nitrobenzyl (1R,5S,6S)-2-{1-[4-(4-methylpiperazine-1-carbonyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(4-methylpiperazine-1-carbonyl)-1,3-thiazol-2-yl]azetidine (1.35 g, 3.97 mmol) (obtained as described in Reference Example 30) in dimethylformamide (40 ml) was added hydrazine acetate (438 mg, 4.76 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (2.36 g, 3.97 mmol) in acetonitrile (40 ml) was added dropwise to the resulting mixture in an ice bath under an atmosphere of nitrogen, followed by the addition of diisopropylethylamine (2.77 ml, 15.9 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate and ethyl acetate: methanol (1:5) as the eluant to afford p-nitrobenzyl (1R,5S,6S)-2-{1-[4-(4-methylpiperazine-1-carbonyl)-1,3-thiazol-2-yl]azetidin-3-yl}thio-6-[(R)-1-hydroxyethyl]-1-methylcarbapen-2-em-3-carboxylate (828 mg, yield 60%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.16 (1H, s), 5.51 (1H, d, J=13.8 Hz), 5.25 (1H, d, J=13.8 Hz), 4.50 (1H, t, J=4.9 Hz), 4.49 (1H, t, J=4.9 Hz), 4.33–4.20 (3H, m), 4.06 (1H, t, J=4.9 Hz), 4.05 (1H, t, J=4.9 Hz), 3.99–3.73 (4H, m), 3.29 (1H, dd, J=7.0, 2.5 Hz), 3.20 (1H, dq, J=9.1, 7.3 Hz), 2.74–2.48 (4H, m), 1.38 (3H, d, J=6.3 Hz), 1.27 (3H, d, J=7.3 Hz).

(2) (1R,5S,6S)-2-{1-[4-(4-Methylpiperazine-1-carbonyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1l-[4-(4-methylpiperazine-1-carbonyl)-1,3-thiazol-2-yl]azetidin-3-yl}thio-6-[(R)-1-hydroxyethyl]-1-methylcarbapen-2-em-3-carboxylate (500 mg, 0.78 mmol (obtained as described in Example 35(1)) in a mixture of tetrahydrofuran (25 ml) and distilled water (25 ml) was subjected to catalytic hydrogenation in the presence of 7.5% palladium on charcoal (500 mg) in a water bath (35° C.) for 2 hours. After checking the completion of the reaction, the reaction mixture was filtered and to the filtrate were added acetic acid and distilled water. The mixture was shaken in a separatory funnel. The aqueous layer was separated, washed with the mixture of solvents described above and concentrated under reduced pressure. The residue was purified by chromatography on a Cosmosil column using distilled water—2% acetonitrile; distilled water—4% acetonitrile; distilled water—6% acetonitrile; distilled water—8% acetonitrile; distilled water—10% acetonitrile; distilled water—12% acetonitrile and distilled water as the eluant. The eluate was lyophilized to afford the desired compound (1R,5S,6S)-2-{1-[4-(4-methylpiperazine-1-carbonyl)-1,3-thiazol-2-yl]azetidin-3-yl}thio-6-[(R)-1-hydroxyethyl]-1-methylcarbapen-2-em-3-carboxylic acid sodium salt (192 mg, yield 49%) as a white solid.

$^1$H-NMR (400 MHz, D$_2$O): δ (ppm) 7.24 (1H, s), 4.57 (2H, t, J=8.4 Hz), 4.39–4.30 (1H, m), 4.25 (1H, quint., J=6.3 Hz), 4.20 (1H, dd, J=9.0, 2.4 Hz), 4.15–3.05 (12H, m including 4.04 (2H, dd, J=8.4, 4.9 Hz), 3.44 (1H, dd, J=6.3, 2.6 Hz), 3.25 (1H, dq, J=9.0, 7.0 Hz)), 2.88 (3H, s), 1.30 (3H, d, J=6.4 Hz), 1.20 (3H, d, J=7.1 Hz).

IR (KBr): 3397.0, 1757.8, 1606.4, 1536.0, 1457.9, 1429.0, 1383.7, 1312.3 cm$^{-1}$.

Mass spectrum (FAB$^+$): m/z: 508 [M+H]$^+$.

EXAMPLE 36

(1R,5S,6S)-2-{1-[4-(3-Methoxyazetidine-1-carbonyl)-1,3-thiazol-2-yl]azetidin-3-yl}thio-6-[(R)-1-hydroxyethyl]-1-methylcarbapen-2-em-3-carboxylic acid sodium salt

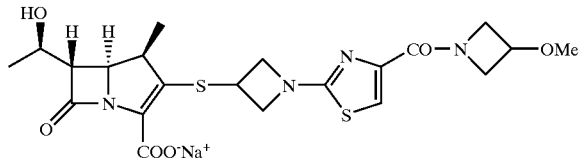

(1) p-Nitrobenzyl (1R,5S,6S)-2-{1-[4-(3-methoxyazetidine-1-carbonyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(3-methoxyazetidine-1-carbonyl)-1,3-thiazol-2-yl]azetidine (350 mg, 1.07 mmol) (obtained as described in Reference Example 31) in dimethylformamide (18 ml) was added hydrazine acetate (118 mg, 1.28 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (636 mg, 1.07 mmol) in acetonitrile (32 ml) was added dropwise to the resulting mixture in an ice bath under an atmosphere of nitrogen, followed by the addition of diisopropylethylamine (746 µl, 4.28 mmol). The mixture was stirred for 6 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% aqueous sodium chloride solution and saturated aqueous sodium chloride solution, dried over anhydrous sodium sulfate, filtered and concentrated under reduced pressure. The residue was purified by chromatography on a silica gel column using ethyl acetate: methanol (95:5 and 9:1) as the eluant to afford p-nitrobenzyl (1R,5S,6S)-2-{1-[4-(3-methoxyazetidine-1-carbonyl)-1,3-thiazol-2-yl]azetidin-3-yl}thio-6-[(R)-1-hydroxyethyl]-1-methylcarbapen-2-em-3-carboxylate (636 mg, yield 94%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.44 (1H, s), 5.51 (1H, d, J=13.9 Hz), 5.25 (1H, d, J=13.2 Hz), 4.75–4.69 (1H, m), 4.51–4.43 (2H, m), 4.42–4.37 (1H, m), 4.32–4.20 (5H, m), 4.04 (2H, dt, J=8.1, 5.1 Hz), 3.33 (3H, s), 3.39 (1H, dd, J=2.2, 6.6 Hz), 3.20 (1H, dq, J=9.2, 7.3 Hz), 1.38 (3H, d, J=6.6 Hz), 1.27 (3H, d, J=7.3 Hz).

(2) (1R,5S,6S)-2-{1-[4-(3-Methoxyazetidine-1-carbonyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(3-methoxyazetidine-1-carbonyl)-1,3-thiazol-2-yl]azetidin-3-yl}thio-6-[(R)-1-hydroxyethyl]-1-methylcarbapen-2-em-3-carboxylate (630 mg, 1.00 mm (obtained as described in Example 36(1)) in a mixture of tetrahydrofuran (32 ml) and distilled water (32 ml) was subjected to catalytic hydrogenation in the presence of 10% palladium on charcoal (630 mg) at room temperature for 2 hours. After checking the completion of the reaction, the reaction mixture was filtered and to the filtrate were added sodium hydrogencarbonate (84 mg), ethyl acetate and distilled water. The mixture was shaken in a separatory funnel. The aqueous layer was separated and concentrated under reduced pressure. The residue was purified by chromatography on a Cosmosil column using distilled water and distilled water: acetonitrile (92:8) as the eluant. The eluate was lyophilized to afford the desired compound (1R,5S,6S)-2-{1-[4-(3-methoxyazetidine-1-carbonyl)-1,3-thiazol-2-yl]azetidin-3-yl}thio-6-[(R)-1-hydroxyethyl]-1-methylcarbapen-2-em-3-carboxylic acid sodium salt (239 mg, yield 46%) as a white solid.

$^1$H-NMR (400 MHz, D$_2$O): δ (ppm) 7.39 (1H, s), 4.76–4.69 (1H, m), 4.56 (2H, d, J=8.1 Hz), 4.44–4.31 (4H, m), 4.25 (1H, dq, J=6.1, 6.4 Hz), 4.20 (1H, dd, J=2.4, 9.1 Hz), 4.09–3.99 (3H, m), 3.43 (1H, dd, J=2.4, 6.1 Hz), 3.37 (3H, s), 3.26 (1H, dq, J=9.1, 7.2 Hz), 1.30 (3H, d, J=6.4 Hz), 1.20 (3H, d, J=7.2 Hz).

IR (KBr): 1750, 1607, 1538, 1449, 1395, 1306 cm$^{-1}$.

Mass spectrum (FAB$^+$): m/z: 539 [M+Na]$^+$.

High-resolution mass spectrum (ESI$^+$): calculated for C$_{21}$H$_{25}$O$_6$N$_4$S$_2$Na$_2$ 539.0111, Found 539.1026 [M+Na]$^+$.

Elemental analysis calculated for C$_{21}$H$_{25}$O$_6$N$_4$S$_2$Na.3/2H$_2$O. C: 46.40%; H: 5.19%; N: 10.31%; S: 11.80%. Found C: 46.48%; H: 5.53%; N: 10.60%; S: 11.66%.

EXAMPLE 37

(1R,5S,6S)-2-[1-(4-Phenylcarbamoyl-1,3-thiazol-2-yl)azetidin-3-yl]thio-6-[(R)-1-hydroxyethyl]-1-methylcarbapen-2-em-3-carboxylic acid sodium salt

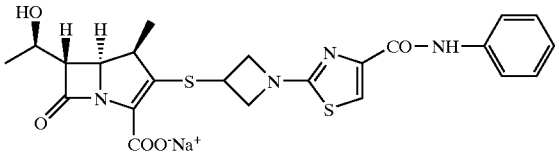

(1) p-Nitrobenzyl (1R,5S,6S)-2-[1-(4-phenylcarbamoyl-1,3-thiazol-2-yl)azetidin-3-yl]thio-6-[(R)-1-hydroxyethyl]-1-methylcarbapen-2-em-3-carboxylate To a solution of 3-acetylthio-1-(4-phenylcarbamoyl-1,3-thiazol-2-yl)azetidine (893 mg, 2.68 mmol) (obtained as described in Reference Example 32) in dimethylformamide (40 ml) was added hydrazine acetate (296 mg, 3.21 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.59 g, 3.21 mmol) in acetonitrile (53 ml) was added dropwise to the resulting mixture in an ice bath under an atmosphere of nitrogen, followed by the addition of diisopropylethylamine (1.87 ml, 10.7 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate: methanol (9:1) as the eluant to afford p-nitrobenzyl (1R,5S,6S)-2-[1-(4-phenylcarbamoyl-1,3-thiazol-2-yl)azetidin-3-yl]thio-6-[(R)-1-hydroxyethyl]-1-methylcarbapen-2-em-3-carboxylate (1.2 g, yield 71%) as a pale yellow solid.

$^1$H-NMR (400 MHz, CDCl$_3$): δ (ppm) 8.29–8.18 (2H, m), 7.73–7.62 (4H, m), 7.62–7.50 (1H, m), 7.42–7.82 (2H, m), 7.18–7.09 (1H, m), 5.51 (1H, d, J=13.8 Hz), 5.25 (1H, d, J=13.8 Hz), 4.54 (2H, dd, J=15.6, 7.8 Hz), 4.40–4.21 (3H, m), 4.21–4.08 (2H, m), 3.31 (1H, dd, J=6.9, 2.5 Hz), 3.23 (1H, dq, J=9.1, 7.3 Hz), 1.39 (3H, d, J=6.4 Hz), 1.29 (3H, d, J=7.3 Hz).

(2) (1R,5S,6S)-2-[1-(4-Phenylcarbamoyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-phenylcarbamoyl-1,3-thiazol-2-yl)azetidin-3-yl]thio-6-[(R)-1-hydroxyethyl]-1-methylcarbapen-2-em-3-carboxylate (400 mg, 0.63 mmol) (obtained as described in Example 37(1)) in a mixture of tetrahydrofuran (120 ml) and distilled water (120 ml) was subjected to catalytic hydrogenation in the presence of 7.5% palladium on charcoal (400 mg) at room temperature for 2 hours. After checking the completion of the reaction, the reaction mixture was filtered and to the filtrate were added sodium hydrogencarbonate (53 mg), ethyl acetate and distilled water. The mixture was shaken in a separatory funnel. The aqueous layer was separated and concentrated under reduced pressure. The residue was purified by chromatography on a Cosmosil column using distilled water—4% acetonitrile; distilled water—8% acetonitrile; distilled water—12% acetonitrile; distilled water—16% acetonitrile and distilled water as the eluant. The eluate was lyophilized to afford the desired compound (1R,5S,6S)-2-[1-(4-phenylcarbamoyl-1,3-thiazol-2-yl)azetidin-3-yl]thio-6-[(R)-1-hydroxyethyl]-1-methylcarbapen-2-em-3-carboxylic acid sodium salt (211 mg, yield 64%) as a white solid.

$^1$H-NMR (400 MHz, D$_2$O): δ (ppm) 7.60–7.51 (3H, m), 7.54–7.42 (2H, m), 7.36–7.27 (1H, m), 4.63–4.52 (2H, m), 4.29–4.39 (1H, m), 4.25 (1H, quint., J=6.3 Hz), 4.20 (1H, dd, J=9.0, 2.3 Hz), 4.09 (1H, t, J=8.8 Hz), 4.08 (1H, t, J=8.8 Hz), 3.44 (1H, dd, J=6.6, 1.9 Hz), 3.25 (1H, dq, J=6.3, 5.9 Hz), 1.3 (3H, d, J=6.4 Hz), 1.20 (3H, dd, J=7.2, 2.4 Hz).

IR (KBr): 3368.1, 1750.1, 1676.8, 1598.7, 1538.9, 1506.1, 1470.5, 1440.6, 1394.3, 1324.9, 1295.9, 1245.8 cm$^{-1}$.

Mass spectrum (FAB$^+$): m/z: 501 [M+H]$^+$.

EXAMPLE 38

(1R,5S,6S)-2-{1-[4-(2-Hydroxyethylcarbamoyl)-1,3-thiazol-2-yl]azetidin-3-yl}thio-6-[(R)-1-hydroxyethyl]-1-methylcarbapen-2-em-3-carboxylic acid sodium salt

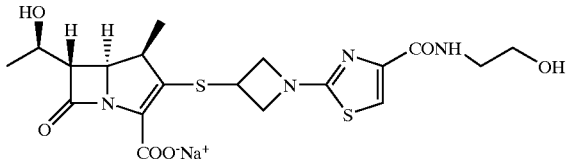

(1) p-Nitrobenzyl (1R,5S,6S)-2-(1-{4-[2-(t-Butyldimethylsilyloxy)ethylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[2-(t-butyldimethylsilyloxy)ethylcarbamoyl]-1,3-thiazol-2-yl}azetidine (398.2 mg, 0.96 mmol) (obtained as described in Reference Example 33) in dimethylformamide (20 ml) was added hydrazine acetate (110 mg, 1.19 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (561.4 mg, 0.94 mmol) in acetonitrile (38 ml) was added dropwise to the resulting mixture in an ice bath under an atmosphere of nitrogen, followed by the addition of diisopropylethylamine (0.7 ml, 4.02 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using toluene: acetonitrile (2:1) as the eluant to afford p-nitrobenzyl (1R,5S,6S)-2-(1-{4-[2-(t-butyldimethylsilyloxy)ethylcarbamoyl]-1,3-thiazol-2-yl}azetidin-3-yl)thio-6-[(R)-1-hydroxyethyl]-1-methylcarbapen-2-em-3-carboxylate (605.3 mg, yield 80%) as a pale yellow syrup.

$^1$H-NMR (500 MHz, CDCl$_3$): δ (ppm) 8.79 (2H, d, J=8.8 Hz), 7.66 (2H, d, J=8.8 Hz), 7.54 (1H, t, J=5.8 Hz), 7.42 (1H, s), 5.51 (1H, d, J=13.7 Hz), 5.26 (1H, d, J=13.7 Hz), 4.48 (1H, dd, J=8.3, 7.3 Hz), 4.45 (1H, dd, J=8.3, 7.3 Hz), 4.32–4.23 (3H, m), 4.06 (1H, dd, J=8.3, 5.9 Hz), 4.03 (1H, dd, J=8.3, 5.9 Hz), 3.76 (2H, t, J=5.8 Hz), 3.52 (2H, q, J=5.8 Hz), 3.30 (1H, dd, J=6.8, 2.0 Hz), 3.208 (1H, dq, J=9.0, 7.4 Hz), 1.95 (1H, br s), 1.38 (3H, d, J=5.7 Hz), 1.27 (3H, d, J=6.8 Hz), 0.91 (9H, s), 0.07 (6H, s).

(2) p-Nitrobenzyl (1R,5S,6S)-2-{1-[4-(2-hydroxyethylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-(1-{4-[2-(t-butyldimethylsilyloxy)ethylcarbamoyl]-1,3-thiazol-2-yl}azetidin-3-yl)thio-6-[(R)-1-hydroxyethyl]-1-methylcarbapen-2-em-3-carboxylate (605.3 mg, 0.84 mmol) in tetrahydrofuran (30 ml) were added acetic acid (0.15 ml, 2.6 mmol) and a solution of 1 M tetrabutylammonium fluoride in tetrahydrofuran (2.5 ml, 2.5 mmol) in an ice bath and the mixture was stirred for 1 hour at room temperature. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using toluene: acetonitrile (2:3) as the eluant to afford p-nitrobenzyl (1R,5S,6S)-2-{1-[4-(2-hydroxyethylcarbamoyl)-1,3-thiazol-2-yl]azetidin-3-yl}thio-6-[(R)-1-hydroxyethyl]-1-methylcarbapen-2-em-3-carboxylate (383.7 mg, yield 75%) as a pale yellow solid.

$^1$H-NMR (500 MHz, CDCl$_3$): δ (ppm) 8.23 (2H, d, J=7.9 Hz), 7.66 (2H, d, J=7.9 Hz), 7.53 (1H, t, J=5.3 Hz), 7.45 (1H, s), 5.508 (1H, d, J=13.7 Hz), 5.255 (1H, d, J=13.7 Hz), 4.50 (1H, t, J=8.6 Hz), 4.48 (1H, t, J=8.6 Hz), 4.32–4.24 (3H, m), 4.07 (1H, dd, J=8.6, 5.3 Hz), 4.05 (1H, dd, J=8.6, 5.3 Hz), 3.807 (2H, t, J=5.3 Hz), 3.58 (2H, q, J=5.3 Hz), 3.295 (1H, dd, J=7.6, 2.3 Hz), 3.21 (1H, dq, J=9.1, 7.6 Hz), 2.78 (1H, br s), 1.92 (1H, br s), 1.38 (3H, d, J=6.3 Hz), 1.24 (3H, d, J=7.6 Hz).

(3) (1R,5S,6S)-2-{1-[4-(2-Hydroxyethylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(2-hydroxylethylcarbamoyl)-1,3-thiazol-2-yl]azetidin-3-yl}thio-6-[(R)-1-hydroxyethyl]-1-methylcarbapen-2-em-3-carboxylate (383.7 mg, 0.64 mmol) (obtained as described in Example 38(2)) in a mixture of tetrahydrofuran (20 ml) and distilled water (9.6 ml) was subjected to catalytic hydrogenation in the presence of 20% palladium hydroxide on charcoal (400 mg) in a water bath (30° C.) for 1 hour. After checking the completion of the reaction, the reaction mixture was filtered and to the filtrate were added sodium hydrogencarbonate (53.4 mg), ethyl acetate and distilled water. The mixture was shaken in a separatory funnel. The aqueous layer was separated and concentrated under reduced pressure. The residue was purified by chromatography on a Cosmosil column using distilled water—3% acetonitrile; distilled water—5% acetonitrile; distilled water—10% acetonitrile and distilled water as the eluant. The eluate was lyophilized to afford the desired compound (1R,5S,6S)-2-{1-[4-(2-hydroxyethylcarbamoyl)-1,3-thiazol-2-yl]azetidin-3-yl}thio-6-[(R)-1-hydroxyethyl]-1-methylcarbapen-2-em-3-carboxylic acid sodium salt (152.2 mg, yield 49%) as a white solid.

$^1$H-NMR (400 MHz, D$_2$O): δ (ppm) 7.29 (1H, s), 4.36 (2H, t, J=8.4 Hz), 4.20–4.10 (1H, m), 4.05 (1H, quintet, J=6.6 Hz), 4.00 (1H, dd, J=10.9, 2.2 Hz), 3.90–3.83 (2H, m), 3.55 (2H, t, J=5.5 Hz), 3.32 (2H, t, J=5.5 Hz), 3.24 (1H, dd, J=6.6, 2.2 Hz), 3.06 (1H, dq, J=10.9, 8.6 Hz), 1.11 (3H, d, J=6.6 Hz), 1.00 (3H, d, J=8.6 Hz).

IR (KBr): 3396, 1748, 1649, 1599, 1551, 1395, 1315, 1265 cm$^{-1}$.

Mass spectrum (FAB$^+$): m/z: 491 [M+H]$^+$.

High-resolution mass spectrum (FAB$^+$): calculated for C$_{19}$H$_{23}$O$_6$N$_4$S$_2$Na 491.1035, Found 491.1024 [M+H]$^+$.

EXAMPLE 39

(1R,5S,6S)-2-{1-[4-((1S)-1-Hydroxymethyl-propylcarbamoyl)-1,3-thiazol-2-yl]azetidin-3-yl}thio-6-[(R)-1-hydroxyethyl]-1-methylcarbapen-2-em-3-carboxylic acid sodium salt

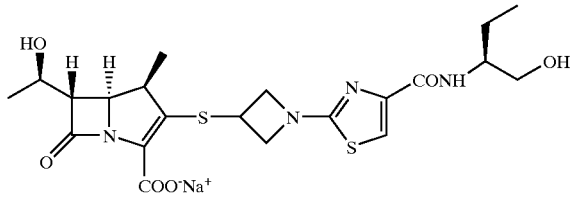

(1) p-Nitrobenzyl (1R,5S,6S)-2-(1-{4-[(1S)-1-(t-Butyidimethylsilyloxymethyl)-propylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(1S)-1-(t-butyidimethylsilyloxymethyl)-propylcarbamoyl]-1,3-thiazol-2-yl}azetidine (610 mg, 1.37 mmol) (obtained as described in Reference Example 34) in dimethylformamide (30 ml) was added hydrazine acetate (152 mg, 1.65 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (814 mg, 1.37 mmol) in acetonitrile (40 ml) was added dropwise to the resulting mixture in an ice bath under an atmosphere of nitrogen, followed by the addition of diisopropylethylamine (955 µl, 5.48 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% aqueous sodium chloride solution and saturated aqueous sodium chloride solution, dried over anhydrous sodium sulfate, filtered and concentrated under reduced pressure. The residue was purified by chromatography on a silica gel column using n-hexane: ethyl acetate (1:2) and ethyl acetate as the eluant to afford p-nitrobenzyl (1R,5S,6S)-2-(1-{4-[(1S)-1-(t-butyidimethylsilyloxymethyl)-propylcarbamoyl]-1,3-thiazol-2-yl}azetidin-3-yl)thio-6-[(R)-1-hydroxyethyl]-1-methylcarbapen-2-em-3-carboxylate (928 mg, yield 89%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.42 (1H, s), 7.42–7.38 (1H, br d, J=9.5 Hz), 5.51 (1H, d, J=13.9 Hz), 5.25 (1H, d, J=13.9 Hz), 4.50 (1H, t, J=8.1 Hz), 4.45 (1H, t, J=8.1 Hz), 4.31–4.23 (2H, m), 4.27 (1H, dd, J=8.8, 2.6 Hz), 4.07–4.01 (2H, m), 4.00–3.94 (1H, m), 3.72 (1H, dd, J=10.3, 2.6 Hz), 3.65 (1H, dd, J=10.3, 4.0 Hz), 3.30 (1H, dd, J=7.3, 2.6 Hz), 3.21 (1H, dq, J=8.8, 6.6 Hz), 1.72–1.56 (2H, m), 1.38 (3H, d, J=5.7 Hz), 1.27 (3H, d, J=6.6 Hz), 0.95 (3H, t, J=7.3 Hz), 0.90 (9H, s), 0.06 (6H, s).

(2) p-Nitrobenzyl (1R,5S,6S)-2-{1-[4-((1S)-1-hydroxymethyl-propylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-(1-{4-[(1S)-1-(t-butyldimethylsilyloxymethyl)-propylcarbamoyl]-1,3-thiazol-2-yl}azetidin-3-yl)thio-6-[(R)-1-hydroxyethyl]-1-methylcarbapen-2-em-3-carboxylate (920 mg, 1.23 mmol) (obtained as described in Example 39(1)) in tetrahydrofuran (46 ml) were added acetic acid (208 µl, 3.63 mmol) and a solution of 1 M tetrabutylammonium fluoride in tetrahydrofuran (3.63 ml, 3.63 mmol) in an ice bath and the mixture was stirred for 2 days at room temperature. After checking the completion of the reaction, the reaction mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate:methanol (95:5) as the eluant to afford p-nitrobenzyl (1R,5S,6S)-2-{1-[4-((1S)-1-hydroxymethyl-propylcarbamoyl)-1,3-thiazol-2-yl]azetidin-3-yl}thio-6-[(R)-1-hydroxyethyl]-1-methylcarbapen-2-em-3-carboxylate (437 mg, yield 56%) as a pale yellow solid.

$^1$H-NMR (500 MHz, CDCl$_3$): δ (ppm) 8.23 (2H, d, J=8.8 Hz), 7.66 (2H, d, J=8.8 Hz), 7.44 (1H, s), 7.24–7.19 (1H, br d, J=7.8 Hz), 5.51 (1H, d, J=13.7 Hz), 5.26 (1H, d, J=13.7 Hz), 4.50 (2H, dt, J=8.8, 4.9 Hz), 4.32–4.24 (3H, m), 4.07 (2H, dt, J=8.8, 5.9 Hz), 4.01–3.93 (1H, m), 3.81–3.75 (1H, m), 3.71–3.64 (1H, m), 3.30 (1H, dd, J=6.8, 2.9 Hz), 3.21 (1H, dq, J=9.0, 6.8 Hz), 1.75–1.66 (1H, m), 1.65–1.55 (1H, m), 1.38 (3H, d, J=6.8 Hz), 1.28 (3H, d, J=7.8 Hz), 1.00 (3H, t, J=7.8 Hz).

(3) (1R,5S,6S)-2-{1-[4-((1S)-1-Hydroxymethyl-propylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-((1S)-1-hydroxymethyl-propylcarbamoyl )-1,3-thiazol-2-yl]azetidin-3-yl}thio-6-[(R)-1-hydroxyethyl]-1-methylcarbapen-2-em-3-carboxylate (430 mg, 0.681 mmol) (obtained as described in Example 39(2)) in a mixture of tetrahydrofuran (22 ml) and distilled water (22 ml) was subjected to catalytic hydrogenation in the presence of 10% palladium on charcoal (430 mg) at room temperature for 4 hours. After checking the completion of the reaction, the reaction mixture was filtered and to the filtrate were added sodium hydrogencarbonate (57 mg), ethyl acetate and distilled water. The mixture was shaken in a separatory funnel. The aqueous layer was separated and concentrated under reduced pressure. The residue was purified by chromatography on a Cosmosil column using distilled water and distilled water: acetonitrile (94:6) as the eluant. The eluate was lyophilized to afford the desired compound (1R,5S,6S)-2-{1-[4-((1S)-1-hydroxymethyl-propylcarbamoyl)-1,3-thiazol-2-yl]azetidin-3-yl}thio-6-[(R)-1-hydroxyethyl]-1-methylcarbapen-2-em-3-carboxylic acid sodium salt (212 mg, yield 60%) as a white solid.

$^1$H-NMR (400 MHz, D$_2$O, TSP): δ (ppm) 7.49 (1H, s), 4.59–4.52 (2H, m), 4.39–4.31 (1H, m), 4.25 (1H, dq, J=6.8, 6.3 Hz), 4.21 (1H, dd, J=9.0, 2.4 Hz), 4.10–4.03 (2H, m), 4.01–3.93 (1H, m), 3.71 (1H, dd, J=11.7, 4.5 Hz), 3.64 (1H, dd, J=11.7, 6.8 Hz), 3.43 (1H, dd, J=6.3, 2.4 Hz), 3.26 (1H, dq, J=8.8, 7.2 Hz), 1.73–1.62 (1H, m), 1.57–1.44 (1H, m), 1.30 (3H, d, J=6.4 Hz), 1.20 (3H, d, J=7.2 Hz), 0.93 (3H, t, J=7.4 Hz).

IR (KBr): 1750, 1650, 1602, 1547, 1393, 1313 cm$^{-1}$.

Mass spectrum (FAB$^+$): m/z: 519 [M+H]$^+$.

High-resolution mass spectrum (FAB$^+$): calculated 519.1348, Found 519.1339 [M+H]$^+$.

Elemental analysis calculated for C$_{21}$H$_{27}$O$_6$N$_4$S$_2$Na.7/4H$_2$O. C: 45.85%; H: 5.79%; N: 10.18%; S: 11.66%. Found C: 46.07%; H: 5.78%; N: 10.29%; S: 11.61%.

EXAMPLE 40

(1R,5S,6S)-2-{1-[4-((1S)-1-Hydroxymethyl-ethylcarbamoyl)-1,3-thiazol-2-yl]azetidin-3-yl}thio-6-[(R)-1-hydroxyethyl]-1-methylcarbapen-2-em-3-carboxylic acid sodium salt

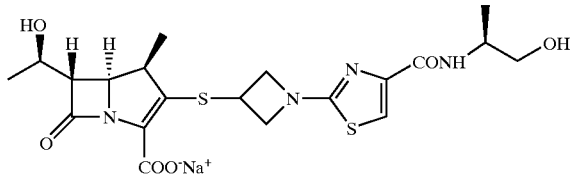

(1) p-Nitrobenzyl (1R,5S,6S)-2-(1-{4-[(1S)-2-(t-Butyldimethylsilyloxy)-1-methyl-ethylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(1S)-2-(t-butyldimethylsilyloxy)-1-methyl-ethylcarbamoyl]-1,3-thiazol-2-yl}azetidine (645 mg, 1.50 mmol) (obtained as described in Reference Example 35) in dimethylformamide (32 ml) was added hydrazine acetate (166 mg, 1.80 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (892 mg, 1.50 mmol) in acetonitrile (45 ml) was added dropwise to the resulting mixture in an ice bath under an atmosphere of nitrogen, followed by the addition of diisopropylethylamine (1.05 ml, 6.0 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% aqueous sodium chloride solution and saturated aqueous sodium chloride solution, dried over anhydrous sodium sulfate, filtered and concentrated under reduced pressure. The residue was purified by chromatography on a silica gel column using n-hexane:ethyl acetate (1:2) and ethyl acetate as the eluant to afford p-nitrobenzyl (1R,5S,6S)-2-(1-{4-[(1 S)-2-(t-butyldimethylsilyloxy)-1-methyl]-ethylcarbamoyl}-1,3-thiazol-2-yl)azetidin-3-yl)thio-6-[(R)-1-hydroxyethyl]-1-methylcarbapen-2-em-3-carboxylate (949 mg, yield 86%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.44–7.38 (1H, br d, J=5.9 Hz), 7.42 (1H, s), 5.51 (1H, d, J=13.9 Hz), 5.25 (1H, d, J=13.9 Hz), 4.52–4.42 (2H, m), 4.33–4.22 (3H, m), 4.22–4.14 (1H, m), 4.04 (2H, ddd, J=14.0, 5.9, 2.9 Hz), 3.67 (1H, dd, J=10.3, 4.4 Hz), 3.62 (1H, dd, J=10.3, 2.9 Hz), 3.30 (1H, dd, J=6.6, 2.2 Hz), 3.21 (1H, dq, J=7.3, 6.6 Hz), 1.38 (3H, d, J=5.9 Hz), 1.27 (3H, d, J=7.3 Hz), 1.25 (3H, d, J=6.6 Hz), 0.92 (9H, s), 0.07 (6H, s).

(2) p-Nitrobenzyl (1R,5S,6S)-2-{1-[4-((1S)-2-hydroxy-1-methylethylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-(1-{4-[(1S)-2-(t-butyldimethylsilyloxy)-1-methyl-ethylcarbamoyl]-1,3-thiazol-2-yl}azetidin-3-yl)thio-6-[(R)-1-hydroxyethyl]-1-methylcarbapen-2-em-3-carboxylate (940 mg, 1.28 mmol) (obtained as described in Example 40(1)) in tetrahydrofuran (47 ml) were added acetic acid (221 μl, 3.85 mmol) and a solution of 1 M tetrabutylammonium fluoride in tetrahydrofuran (3.85 ml, 3.85 mmol) in an ice bath and the mixture was stirred for 3 days at room temperature. After checking the completion of the reaction, the reaction mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate: methanol (99:1 and 9:1) as the eluant to afford p-nitrobenzyl (1R,5S,6S)-2-{1-[4-((1S)-2-hydroxy-1-methylethylcarbamoyl)-1,3-thiazol-2-yl]azetidin-3-yl}thio-6-[(R)-1-hydroxyethyl]-1-methylcarbapen-2-em-3-carboxylate (462 mg, yield 58%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.44 (1H, s), 7.23–7.19 (1H, br d, J=7.3 Hz), 5.51 (1H, d, J=13.9 Hz), 5.25 (1H, d, J=13.9 Hz), 4.52–4.46 (2H, m), 4.31–4.24 (2H, m), 4.27 (1H, dd, J=9.5, 2.0 Hz), 4.22–4.15 (1H, m), 4.06 (2H, dt, J=8.1, 5.1 Hz), 3.79–3.71 (1H, m), 3.66–3.59 (1H, m), 3.30 (1H, dd, J=6.6, 2.2 Hz), 3.21 (1H, dq, J=9.5, 7.3 Hz), 1.38 (3H, d, J=5.9 Hz), 1.28 (6H, d, J=7.3 Hz).

(3) (1R,5S,6S)-2-{1-[4-((1S)-2-Hydroxy-1-methylethylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-((1S)-2-hydroxy-1-methylethylcarbamoyl)-1,3-thiazol-2-yl]azetidin-3-yl}thio-6-[(R)-1-hydroxyethyl]-1-methylcarbapen-2-em-3- carboxylate (460 mg, 0.745 mmol) (obtained as described in Example 40(2)) in a mixture of tetrahydrofuran (23 ml) and distilled water (23 ml) was subjected to catalytic hydrogenation in the presence of 10% palladium on charcoal (460 mg) at room temperature for 3 hours. After checking the completion of the reaction, the reaction mixture was filtered and to the filtrate were added sodium hydrogencarbonate (63 mg), ethyl acetate and distilled water. The mixture was shaken in a separatory funnel. The aqueous layer was separated and concentrated under reduced pressure. The residue was purified by chromatography on a Cosmosil column using distilled water and distilled water: acetonitrile (82:12) as the eluant. The eluate was lyophilized to afford the desired compound (1R,5S,6S)-2-{1-[4-((1S)-2-hydroxy-1-methylethylcarbamoyl)-1,3-thiazol-2-yl]azetidin-3-yl}thio-6-[(R)-1-hydroxyethyl]-1-methylcarbapen-2-em-3-carboxylic acid sodium salt (179 mg, yield 48%) as a white solid.

$^1$H-NMR (400 MHz, D$_2$O, TSP): δ (ppm) 7.48 (1H, s), 4.56 (2H, dd, J=8.3, 8.3 Hz), 4.39–4.32 (1H, m), 4.25 (1H, dq, J=6.3, 6.4 Hz), 4.20 (1H, dd, J=9.1, 2.4 Hz), 4.18–4.11 (1H, m), 4.10–4.03 (2H, m), 3.68 (1H, dd, J=11.6, 4.8 Hz), 3.61 (1H, dd, J=11.6, 6.7 Hz), 3.44 (1H, dd, J=6.3, 2.4 Hz), 3.26 (1H, dq, J=9.1, 6.6 Hz), 1.30 (3H, d, J=6.4 Hz), 1.22 (3H, d, J=6.7 Hz), 1.20 (3H, d, J=6.6 Hz).

IR (KBr): 1749, 1650, 1602, 1547, 1393, 1313, 1295 cm$^{-1}$.

Mass spectrum (FAB$^+$): m/z: 505 [M+H]$^+$.

High-resolution mass spectrum (FAB$^+$): calculated for C$_{20}$H$_{26}$O$_6$N$_4$S$_2$Na 505.1191, Found 505.1196 [M+H]$^+$.

Elemental analysis calculated for C$_{20}$H$_{25}$O$_6$N$_4$S$_2$Na.4/3H$_2$O. C: 45.45%; H: 5.28%; N: 10.60%; S: 12.13%. Found C: 45.63%; H: 5.35%; N: 10.66%; S: 11.91%.

EXAMPLE 41

(1R,5S,6S)-2-{1-[4-((1S)-1-Hydroxymethyl-2-methylpropylcarbamoyl)-1,3-thiazol-2-yl]azetidin-3-yl}thio-6-[(R)-1-hydroxyethyl]-1-methylcarbapen-2-em-3-carboxylic acid sodium salt

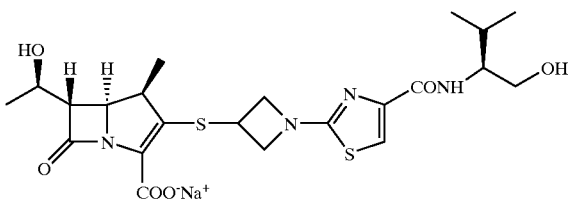

(1) p-Nitrobenzyl (1R,5S,6S)-2-(1-{4-[(1S)-1-(t-butyldimethylsilyloxymethyl)-2-methyl-propylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(1S)-1-(t-butyldimethylsilyloxymethyl)-2-methyl-propylcarbamoyl]-1,3-thiazol-2-yl}azetidine (500 mg, 1.09 mmol) (obtained as described in Reference Example 36) in dimethylformamide (25 ml) was added hydrazine acetate (121 mg, 1.31 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (648 mg, 1.09 mmol) in acetonitrile (33 ml) was added dropwise to the resulting mixture in an ice bath under an atmosphere of nitrogen, followed by the addition of diisopropylethylamine (759 µl, 4.36 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% aqueous sodium chloride solution and saturated aqueous sodium chloride solution, dried over anhydrous sodium sulfate, filtered and concentrated under reduced pressure. The residue was purified by chromatography on a silica gel column using n-hexane: ethyl acetate (1:2 and 1:4) as the eluant to afford p-nitrobenzyl (1R,5S,6S)-2-(1-{4-[(1S)-1-(t-butyldimethylsilyloxymethyl)-2-methyl-propylcarbamoyl]-1,3-thiazol-2-yl}azetidin-3-yl)thio-6-[(R)-1-hydroxyethyl]-1-methylcarbapen-2-em-3-carboxylate (649 mg, yield 84%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.47–7.52 (1H, br d, J=9.8 Hz), 7.43 (1H, s), 5.52 (1H, d, J=13.7 Hz), 5.25 (1H, d, J=13.7 Hz), 4.51 (1H, t, J=7.8 Hz), 4.45 (1H, t, J=7.8 Hz), 4.28 (1H, dd, J=9.3, 2.0 Hz), 4.31–4.25 (2H, m), 4.05 (2H, ddd, J=7.8, 5.6, 1.2 Hz), 3.86–3.80 (2H, m), 3.62 (1H, dd, J=9.8, 3.9 Hz), 3.30 (1H, dd, J=6.8, 2.0 Hz), 3.22 (1H, dq, J=9.3, 6.8 Hz), 2.05–1.95 (1H, m), 1.39 (3H, d, J=5.9 Hz), 1.28 (3H, d, J=6.8 Hz), 0.99 (3H, d, J=6.8 Hz), 0.97 (3H, d, J=6.8 Hz), 0.91 (9H, s), 0.06 (6H, s).

(2) p-Nitrobenzyl (1R,5S,6S)-2-{1-[4-((1S)-1-hydroxymethyl-2-methylpropylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-(1-(4-[(1S)-1-(t-butyldimethylsilyloxymethyl)-2-methylpropylcarbamoyl]-1,3-thiazol-2-yl}azetidin-3-yl)thio-6-[(R)-1-hydroxyethyl]-1-methylcarbapen-2-em-3-carboxylate (690 mg, 0.914 mmol) (obtained as described in Example 41(1)) in tetrahydrofuran (35 ml) were added acetic acid (157 µl, 2.74 mmol) and a solution of 1 M tetrabutylammonium fluoride in tetrahydrofuran (2.74 ml, 2.74 mmol) in an ice bath and the mixture was stirred for 2 days at room temperature. After checking the completion of the reaction, the reaction mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate: methanol (9:1) as the eluant to afford p-nitrobenzyl (1R,5S,6S)-2-{1-[4-((1S)-1-hydroxymethyl-2-methylpropylcarbamoyl)-1,3-thiazol-2-yl]azetidin-3-yl}thio-6-[(R)-1-hydroxyethyl]-1-methylcarbapen-2-em-3-carboxylate (388 mg, yield 66%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.44 (1H, s), 7.33–7.28 (1H, br d, J=8.8 Hz), 5.51 (1H, d, J=13.9 Hz), 5.25 (1H, d, J=13.9 Hz), 4.50 (2H, ddd, J=8.1, 8.1, 3.7 Hz), 4.32–4.24 (2H, m), 4.27 (1H, dd, J=9.2, 2.5 Hz), 3.88–3.76 (2H, m), 3.74 (1H, dd, J=11.0, 6.6 Hz), 3.30 (1H, dd, J=7.0, 2.5 Hz), 3.22 (1H, dq, J=7.2, 7.3 Hz), 2.06–1.95 (1H, m), 1.38 (3H, d, J=6.6 Hz), 1.28 (3H, d, J=7.3 Hz), 1.02 (3H, d, J=7.3 Hz), 0.99 (3H, d, J=6.6 Hz).

(3) (1R,5S,6S)-2-{1-[4-((1S)-1-Hydroxymethyl-2-methylpropylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-((1S)-1-hydroxymethyl-2-methylpropylcarbamoyl)-1,3-thiazol-2- yl]azetidin-3-yl}thio-6-[(R)-1-hydroxyethyl]-1-methylcarbapen-2-em-3-carboxylate (380 mg, 0.588 mmol) obtained as described in Example 41(2) in a mixture of tetrahydrofuran (19 ml) and distilled water (19 ml) was subjected to catalytic hydrogenation in the presence of 10% palladium on charcoal (380 mg) at room temperature for 2 hours. After checking the completion of the reaction, the reaction mixture was filtered and to the filtrate were added sodium hydrogencarbonate (49 mg), ethyl acetate and distilled water. The mixture was shaken in a separatory funnel. The aqueous layer was separated and concentrated under reduced pressure. The residue was purified by chromatography on a Cosmosil column using distilled water and distilled water: acetonitrile (76:24) as the eluant. The eluate was lyophilized to afford the desired compound (1R,5S,6S)-2-{1-[4-((1S)-1-hydroxymethyl-2-methylpropylcarbamoyl)-1,3-thiazol-2-yl]azetidin-3-yl}thio-6-[(R)-1-hydroxyethyl]-1-methylcarbapen-2-em-3-carboxylic acid sodium salt (164 mg, yield 52%) as a white solid.

$^1$H-NMR (400 MHz, D$_2$O, TSP): δ (ppm) 7.49 (1H, s), 4.61–4.53 (2H, m), 4.39–4.31 (1H, m), 4.25 (1H, dq, J=6.2, 6.3 Hz), 4.20 (1H, dd, J=2.4, 9.1 Hz), 4.11–4.04 (2H, m), 3.87–3.83 (1H, m), 3.80 (1H, dd, J=3.8, 11.7 Hz), 3.71 (1H, dd, J=7.5, 11.7 Hz), 3.43 (1H, dd, J=2.4, 6.2 Hz), 3.26 (1H, dq, J=9.1, 7.2 Hz), 1.97–1.84 (1H, m), 1.30 (3H, d, J=6.3 Hz), 1.20 (3H, d, J=7.2 Hz), 0.97 (3H, d, J=6.8 Hz), 0.93 (3H, d, J=6.9 Hz).

IR (KBr): 1749, 1651, 1600, 1547, 1493, 1470, 1393, 1315 cm$^{-1}$.

Mass spectrum (FAB$^+$): m/z: 555 [M+Na]$^+$.

High-resolution mass spectrum (FAB$^+$): calculated for C$_{22}$H$_{30}$O$_6$N$_4$S$_2$Na 533.1505, Found 533.1497 [M+H]$^+$.

Elemental analysis calculated for C$_{22}$H$_{29}$O$_6$N$_4$S$_2$Na.5/3H$_2$O. C: 46.96%; H: 5.79%; N: 9.96%; S: 1.40%. Found C: 46.89%; H: 5.86%; N: 10.41%; S: 11.15%.

EXAMPLE 42

(1R,5S,6S)-2-{1-[4-((1S)-1-Hydroxymethyl-3-methylbutylcarbamoyl)-1,3-thiazol-2-yl]azetidin-3-yl}thio-6-[(R)-1-hydroxyethyl]-1-methylcarbapen-2-em-3-carboxylic acid sodium salt

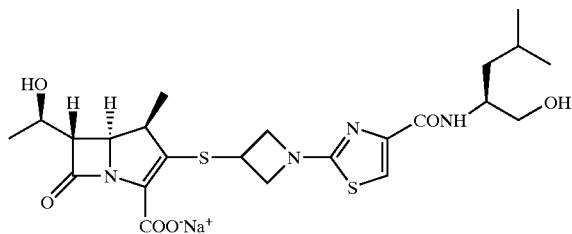

(1) p-Nitrobenzyl (1R,5S,6S)-2-(1-{4-[(1S)-1-(t-Butyldimethylsilyloxymethyl)-3-methyl-butylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(1S)-1-(t-butyldimethylsilyloxymethyl)-3-methyl-butylcarbamoyl]-1,3-thiazol-2-yl}azetidine (450 mg, 0.954 mmol) (obtained as described in Reference Example 37) in dimethylformamide (23 ml) was added hydrazine acetate (105 mg, 1.14 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (567 mg, 0.954 mmol) in acetonitrile (28 ml) was added dropwise to the resulting mixture in an ice bath under an atmosphere of nitrogen, followed by the addition of diisopropylethylamine (665 µl, 3.82 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% aqueous sodium chloride solution and saturated aqueous sodium chloride solution, dried over anhydrous sodium sulfate, filtered and concentrated under reduced pressure. The residue was purified by chromatography on a silica gel column using n-hexane:ethyl acetate (1:2 and 1:4) as the eluant to afford p-nitrobenzyl (1R,5S,6S)-2-(1-{4-[(1S)-1-(t-butyldiphenylsilyloxy)-3-methylbutylcarbamoyl]-1,3-thiazol-2-yl}azetidin-3-yl)thio-6-[(R)-1-hydroxyethyl]-1-methylcarbapen-2-em-3-carboxylate (645 mg, yield 87%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.41 (1H, s), 7.35–7.30 (1H, br d, J=9.5 Hz), 5.51 (1H, d, J=13.9 Hz), 5.25 (1H, d, J=13.9 Hz), 4.50 (1H, dd, J=8.1 Hz), 4.45 (1H, dd, J=8.1 Hz), 4.31–4.24 (3H, m), 4.21–4.13 (1H, m), 4.06 (1H, dd, J=5.9, 2.9 Hz), 4.03 (1H, dd, J=5.9, 2.2 Hz), 3.66 (2H, d, J=2.9 Hz), 3.30 (1H, dd, J=7.3, 2.9 Hz), 3.21 (1H, dq, J=6.6, 7.3 Hz), 1.68–1.57 (1H, m), 1.52 (1H, ddd, J=14.6, 8.8, 5.9 Hz), 1.44 (1H, ddd, J=14.6, 8.8, 5.9 Hz), 1.38 (3H, d, J=5.9 Hz), 1.28 (3H, d, J=7.3 Hz), 0.95 (6H, t, J=6.6 Hz), 0.91 (9H, s), 0.05 (6H, s).

(2) p-Nitrobenzyl (1R,5S,6S)-2-{1-[4-((1S)-1-Hydroxymethyl-3-methylbutylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-(1-{4-[(1S)-1-(t-butyldimethylsilyloxymethyl)-3-methylbutylcarbamoyl]-1,3-thiazol-2-yl}azetidin-3-yl)thio-6-[(R)-1-hydroxyethyl]-1-methylcarbapen-2-em-3-carboxylate (640 mg, 0.827 mmol) (obtained as described in Example 42(1)) in tetrahydrofuran (32 ml) were added acetic acid (142 µl, 2.48mmol) and a solution of 1 M tetrabutylammonium fluoride in tetrahydrofuran (2.48 ml, 2.48 mmol) in an ice bath and the mixture was stirred for 2 days at room temperature. After checking the completion of the reaction, the reaction mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate:methanol (9:1) as the eluant to afford p-nitrobenzyl (1R,5S,6S)-2-{1-[4-((1S)-1-hydroxymethyl-3-methylbutylcarbamoyl)-1,3-thiazol-2-yl]azetidin-3-yl}thio-6-[(R)-1-hydroxyethyl]-1-methylcarbapen-2-em-3-carboxylate (302 mg, yield 55%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.44 (1H, s), 7.18–7.14 (1H, br d, J=7.8 Hz), 5.51 (1H, d, J=13.7 Hz), 5.26 (1H, d, J=13.7 Hz), 4.53–4.47 (2H, m), 4.31–4.25 (3H, m), 4.20–4.13 (1H, m), 4.07 (2H, ddd, J=8.8, 4.9, 4.9 Hz), 3.80–3.74 (1H, m), 3.66–3.60 (1H, m), 3.30 (1H, dd, J=6.8, 2.9 Hz), 3.22 (1H, dq, J=6.8, 6.8 Hz), 2.79–2.74 (1H, bt, J=5.9 Hz), 1.74–1.65 (1H, m), 1.51 (1H, ddd, J=14.7, 8.8, 5.9 Hz), 1.43 (1H, ddd, J=14.7, 8.8, 5.9 Hz), 1.38 (3H, d, J=6.8 Hz), 1.28 (3H, d, J=6.8 Hz), 0.96 (3H, d, J=4.9 Hz), 0.95 (3H, d, J=4.9 Hz).

(3) (1R,5S,6S)-2-{1-[4-((1S)-1-Hydroxymethyl-3-methylbutylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-((1S)-1-hydroxymethyl-3-methylbutylcarbamoyl)-1,3-thiazol-2-yl]azetidin-3-yl}thio-6-[(R)-1-hydroxyethyl]-1-methylcarbapen-2-em-3-carboxylate (300 mg, 0.455 mmol) obtained as described in Example 42(2) in a mixture of tetrahydrofuran (15 ml) and distilled water (15 ml) was subjected to catalytic hydrogenation in the presence of 10% palladium on charcoal (380 mg) at room temperature for 2.5 hours. After checking the completion of the reaction, the reaction mixture was filtered and to the filtrate were added sodium hydrogencarbonate (38 mg), ethyl acetate and distilled water. The mixture was shaken in a separatory funnel. The aqueous layer was separated and concentrated under reduced pressure. The residue was purified by chromatography on a Cosmosil column using distilled water and distilled water: acetonitrile (76:24) as the eluant. The eluate was lyophilized to afford the desired compound (1R,5S,6S)-2-{1-[4-((1S)-1-hydroxymethyl-3-methylbutylcarbamoyl)-1,3-thiazol-2-yl]azetidin-3-yl}thio-6-[(R)-1-hydroxyethyl]-1-methylcarbapen-2-em-3-carboxylic acid sodium salt (131 mg, yield 53%) as a white solid.

$^1$H-NMR (400 MHz, D$_2$O, TSP): δ (ppm) 7.45 (1H, s), 4.60–4.53 (2H, m), 4.39–4.31 (1H, m), 4.25 (1H, dq, J=6.0, 6.4 Hz), 4.19 (1H, dd, J=2.0, 9.1 Hz), 4.19–4.13 (1H, m), 4.06 (2H, dd, J=4.9, 8.4 Hz), 3.68 (1H, dd, J=4.7, 11.6 Hz), 3.59 (1H, dd, J=6.7, 11.6 Hz), 3.43 (1H, dd, J=2.0, 6.0 Hz), 3.26 (1H, dq, J=9.1, 7.2 Hz), 1.69–1.57 (1H, m), 1.50 (1H, ddd, J=4.5, 9.2, 14.1 Hz), 1.39 (1H, ddd, J=4.5, 9.2, 14.1 Hz), 1.39 (3H, d, J=6.4 Hz), 1.20 (3H, d, J=7.2 Hz), 0.91 (6H, t, J=6.2 Hz).

IR (KBr): 1750, 1651, 1604, 1547, 1492, 1470, 1390, 1311 cm$^{-1}$.

Mass spectrum (FAB$^+$): m/z: 547 [M+H]$^+$.

High-resolution mass spectrum (FAB$^+$): calculated for C$_{23}$H$_{32}$O$_6$N$_4$S$_2$Na 547.1661, Found 547.1674 [M+H]$^+$.

EXAMPLE 43

(1R,5S,6S)-2-{1-[4-((1S,2S)-1-hydroxymethyl-2-methylbutylcarbamoyl)-1,3-thiazol-2-yl]azetidin-3-yl}thio-6-[(R)-1-hydroxyethyl]-1-methylcarbapen-2-em-3-carboxylic acid sodium salt

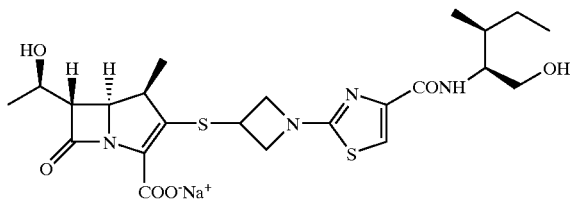

(1) p-Nitrobenzyl (1R,5S,6S)-2-(1-{4-[(1S,2S)-1-(t-butyldimethylsilyloxymethyl)-2-methylbutylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(1S,2S)-1-(t-butyldimethylsilyloxymethyl)-2-methylbutylcarbamoyl]-1,3-thiazol-2-yl}azetidine (910 mg, 1.93 mmol) (obtained as described in Reference Example 38) in dimethylformamide (46 ml) was added hydrazine acetate (213 mg, 2.31 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.15 g, 1.93 mmol) in acetonitrile (58 ml) was added dropwise into the resulting mixture in an ice bath under an atmosphere of nitrogen, followed by the addition of diisopropylethylamine (1.34 ml, 7.72 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride and saturated aqueous sodium chloride solution, dried over anhydrous sodium sulfate, filtered and concentrated under reduced pressure. The residue was purified by chromatography on a silica gel column (eluant: n-hexane:ethyl acetate (1:1→1:4)) to afford p-nitrobenzyl (1R,5S,6S)-2-(1-{4-[(1S,2S)-1-(t-butyldimethylsilyloxymethyl)-2-methylbutylcarbamoyl]-1,3-thiazol-2-yl}azetidin-3-yl)thio-6-[(R)-1-hydroxyethyl]-1-methylcarbapen-2-em-3-carboxylate (765 mg, yield 51%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.50–7.45 (1H, br d, J=9.5 Hz), 7.42 (1H, s), 5.66 (1H, d, J=13.9 Hz), 5.25 (1H, d, J=13.9 Hz), 4.50 (1H, t, J=8.1 Hz), 4.44 (1H, t, J=8.1 Hz), 4.32–4.24 (2H, m), 4.27 (1H, dd, J=2.6, 9.7 Hz), 4.07–4.02 (2H, m), 3.91–3.85 (1H, m), 3.83 (1H, dd, J=2.9, 10.3 Hz), 3.63 (1H, dd, J=3.7, 10.3 Hz), 3.30 (1H, dd, J=2.6, 7.0 Hz), 3.21 (1H, dq, J=9.7, 6.6 Hz), 1.88–1.84 (1H, br s), 1.80–1.70 (1H, m), 1.58–1.50 (1H, m), 1.38 (3H, d, J=6.6 Hz), 1.27 (3H, d, J=7.3 Hz), 1.22–1.10 (1H, m), 0.95 (3H, d, J=7.3 Hz), 0.90 (3H, t, J=7.4 Hz), 0.91 (9H, s), 0.05 (6H, s).

(2) p-Nitrobenzyl (1R,5S,6S)-2-{1-[4-((1S,2S)-1-hydroxymethyl-2-methylbutylcarbamoyl-1,3-thiazol-2-yl]azetidin-3-yl}thio-6-[(R)-1-hydroxyethyl]-1-methylcarbapen-2-em-3-carboxylate p-Nitrobenzyl (1R,5S,6S)-2-(1-{4-[(1S,2S)-1-(t-butyldimethylsilyloxymethyl)-2-methyl-butylcarbamoyl]-1,3-thiazol-2-yl}azetidin-3-yl)thio-6-[(R)-1-hydroxyethyl]-1-methylcarbapen-2-em-3-carboxylate (760 mg, 0.982 mmol) (obtained as described in Example 43(1)) in tetrahydrofuran (38ml) was added to acetic acid (169 µl, 2.95 mmol) and 1 M tetrabutylammonium fluoride in tetrahydrofuran solution (2.95 ml, 2.95 mmol) and the mixture was stirred at room temperature for 3 days. After checking the completion of the reaction, ethyl acetate and water were added to the reaction mixture. The resulting mixture was shaken in a separatory funnel and the ethyl acetate layer was separated, washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate→ethyl acetate: methanol (9:1)) to afford p-nitrobenzyl (1R,5S,6S)-2-{1-[4-((1S,2S)-1-hydroxymethyl-2-methylbutylcarbamoyl)-1,3-thiazol-2-yl]azetidin-3-yl}thio-6-[(R)-1-hydroxyethyl]-1-methylcarbapen-2-em-3-carboxylate (390 mg, yield 60%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.44 (1H, s), 7.33–7.29 (1H, br d, J=8.8 Hz), 5.51 (1H, d, J=13.8 Hz), 5.25 (1H, d, J=13.8 Hz), 4.53–4.46 (2H, m), 4.31–4.28 (2H, m), 4.28 (1H, dd, J=9.5, 2.2 Hz), 4.10–4.03 (2H, m), 3.94–3.87 (1H, m), 3.85–3.79 (1H, m), 3.78–3.72 (1H, m), 3.30 (1H, dd, J=7.0, 2.2 Hz), 3.21 (1H, dq, J=9.5, 7.3 Hz), 1.83–1.72 (1H, m), 1.61–1.48 (1H, m), 1.38 (3H, d, J=6.6 Hz), 1.28 (3H, d, J=7.3 Hz), 1.26–1.14 (1H, m), 0.99 (3H, d, J=6.6 Hz), 0.93 (3H, t, J=7.3 Hz).

(3) (1R,5S,6S)-2-{1-[4-((1S,2S)-1-hydroxymethyl-2-methylbutylcarbamoyl-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-((1S,2S)-1-hydroxymethyl-2-methylbutylcarbamoyl-1,3-thiazol-2-yl]azetidin-3-yl}thio-6-[(R)-1-hydroxyethyl]-1-methylcarbapen-2-em-3-carboxylate (390 mg, 0.591 mmol) (obtained as described in Example 43(2)) in a mixture of tetrahydrofuran (20 ml) and distilled water (20 ml) was subjected to catalytic hydrogenation in the presence of 10% palladium on charcoal (390 mg) at room temperature for 2 hours. After checking the completion of the reaction, the reaction mixture was filtered and to the filtrate were added sodium hydrogencarbonate (50 mg), ethyl acetate and distilled water. The mixture was shaken in a separatory funnel. The aqueous layer was separated and concentrated under reduced pressure. The residue was purified by chromatography on a Cosmosil column (eluant: distilled water→distilled water:acetonitrile (76:24)) and the eluate was lyophilized to afford the desired compound (1R,5S,6S)-2-{1-[4-((1S,2S)-1-hydroxymethyl-2-methylbutylcarbamoyl)-1,3-thiazol-2-yl]azetidin-3-yl}thio-6-[(R)-1-hydroxyethyl]-1-methylcarbapen-2-em-3-carboxylic acid sodium salt (136 mg, yield 42%) as a white solid.

$^1$H-NMR (400 MHz, D$_2$O, TSP): δ (ppm) 7.49 (1H, s), 4.61–4.53 (2H, m), 4.39–4.31 (1H, m), 4.25 (1H, dq, J=6.2, 6.3 Hz), 4.20 (1H, dd, J=9.0, 2.3 Hz), 4.11–4.04 (2H, m), 3.91 (1H, ddd, J=7.4, 3.6, 3.6 Hz), 3.81 (1H, dd, J=11.8, 3.6 Hz), 3.72 (1H, dd, J=11.8, 7.4 Hz), 3.43 (1H, dd, J=6.2, 2.3 Hz), 3.25 (1H, dq, J=9.0, 7.2 Hz), 1.76–1.64 (1H, m), 1.55–1.44 (1H, m), 1.30 (3H, d, J=6.3 Hz), 1.20 (3H, d, J=7.2 Hz), 1.22–1.11 (1H, m), 0.95 (3H, d, J=6.9 Hz), 0.88 (3H, t, J=7.4 Hz).

IR (KBr): 1750, 1651, 1602, 1547, 1493, 1470, 1394, 1311 cm$^{-1}$.

Mass spectrum (FAB$^+$): m/z: 547 [M+H]$^+$.

High-resolution mass spectrum (FAB$^+$): calculated for C$_{23}$H$_{32}$O$_6$N$_4$S$_2$Na 547.1661; Found: 547.1647 [M+H]$^+$.

EXAMPLE 44

(1R,5S,6S)-2-{1-[4-(2-hydroxy-1-(hydroxymethyl)ethylcarbamoyl)-1,3-thiazol-2-yl]azetidin-3-yl}thio-6-[(R)-1-hydroxyethyl]-1-methylcarbapen-2-em-3-carboxylic acid sodium salt

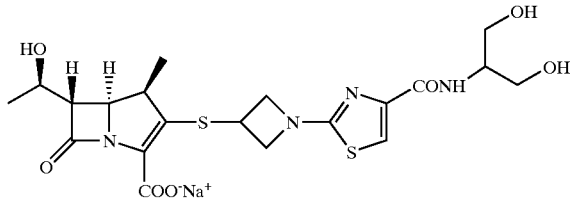

(1) p-Nitrobenzyl (1R,5S,6S)-2-(1-{4-[(2-t-butyldimethylsilyloxy)-(1-t-butyldiphenylsilyloxymethyl)ethylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(2-t-butyldimethylsilyloxy)-(1-t-butyldiphenylsilyloxymethyl)ethylcarbamoyl]-1,3-thiazol-2-yl}azetidine (770 mg, 1.45 mmol) (obtained as described in Reference Example 39) in dimethylformamide (39 ml) was added hydrazine acetate (160 mg, 1.74 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (862 mg, 1.45 mmol) in acetonitrile (43 ml) was added dropwise into the resulting mixture in an ice bath under an atmosphere of nitrogen, followed by the addition of diisopropylethylamine (1.01 ml, 5.79 mmol). The mixture was stirred overnight while gradually raising the temperature to room temperature. After checking the completion of the reaction, ethyl acetate and saturated aqueous sodium hydrogencarbonate were added to the reaction mixture. The resulting mixture was shaken in a separatory funnel and the ethyl acetate layer was separated, washed with 10% sodium chloride and saturated aqueous sodium chloride solution, dried over anhydrous sodium sulfate, filtered and concentrated under reduced pressure. The residue was purified by chromatography on a silica gel column (eluant: n-hexane: ethyl acetate (1:2→1:4)) to afford p-nitrobenzyl (1R,5S,6S)-2-(1-{4-[(2-t-butyldimethylsilyloxy)-(1-t-butyldimethylsilyloxymethyl)ethylcarbamoyl]-1,3-thiazol-2-yl}azetidin-3-yl)thio-6-[(R)-1-hydroxyethyl]-1-methylcarbapen-2-em-3-carboxylate (951 mg, yield 76%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.57–7.52 (1H, br d, J=8.8 Hz), 7.42 (1H, s), 5.52 (1H, d, J=13.9 Hz), 5.25 (1H, d, J=13.9 Hz), 4.47 (1H, t, J=8.1 Hz), 4.44 (1H, t, J=8.1 Hz), 4.26 (1H, dd, J=3.6, 9.2 Hz), 4.31–4.23 (2H, m), 4.09–3.99 (3H, m), 3.86–3.81 (1H, m), 3.61 (1H, dd, J=6.6, 9.5 Hz), 3.30 (1H, dd, J=2.6, 7.0 Hz), 3.21 (1H, dq, J=9.2, 6.6 Hz), 1.38 (3H, d, J=5.9 Hz), 1.27 (3H, d, J=6.6 Hz), 0.91 (9H, s), 0.07 (6H, s).

(2) p-Nitrobenzyl (1R,5S,6S)-2-{1-[4-(2-hydroxy-1-hydroxymethyl)ethylcarbamoyl)-1,3-thiazol-2-yl]azetidin-3-yl}thio-6-[(R)-1-hydroxyethyl]-1-methylcarbapen-2-em-3-carboxylate p-Nitrobenzyl (1R,5S,6S)-2-(1-{4-[(2-t-butyldimethylsilyloxy)-(1-t-butyldimethylsilyloxymethyl)ethylcarbamoyl]-1,3-thiazol-2-yl}azetidin-3-yl)thio-6-[(R)-1-hydroxyethyl]-1-methylcarbapen-2-em-3-carboxylate (950 mg, 1.10 mmol) (obtained as described in Example 44(1)) in tetrahydrofuran (48ml) was added to acetic acid (378 μl, 6.60 mmol)and 1 M tetrabutylammonium fluoride in tetrahydrofuran solution (6.60 ml, 6.60 mmol) and the mixture was stirred at room temperature for 3 days. After checking the completion of the reaction, ethyl acetate and water were added to the reaction mixture. The resulting mixture was shaken in a separatory funnel and the ethyl acetate layer was separated, washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate: methanol (9:1→85:15)) to afford p-nitrobenzyl (1R,5S,6S)-2-{1-[4-(2-hydroxy-1-(hydroxymethyl)ethylcarbamoyl)-1,3-thiazol-2-yl]azetidin-3-yl}thio-6-[(R)-1-hydroxyethyl]-1-methylcarbapen-2-em-3-carboxylate (499 mg, yield 72%) as a pale yellow solid.

$^1$H-NMR (400 MHz, CDCl$_3$): δ (ppm) 8.23 (2H, d, J=8.8 Hz), 7.73 (2H, d, J=8.8 Hz), 7.49 (1H, s), 7.45 (1H, d, J=8.1 Hz), 5.46 (1H, d, J=13.9 Hz), 5.31 (1H, d, J=13.9 Hz), 5.09 (1H, d, J=4.4 Hz), 4.85–4.77 (2H, m), 4.57–4.42 (3H, m), 4.22 (1H, dd, J=1.7, 8.8 Hz), 4.01–3.95 (2H, m), 3.89–3.82 (1H, m), 3.56–3.50 (2H, m), 3.49–3.41 (2H, m), 3.41–3.27 (2H, m), 1.16 (3H, d, J=6.6 Hz), 1.14 (3H, d, J=6.6 Hz).

(3) (1R,5S,6S)-2-{1-[4-(2-hydroxy-1-(hydroxymethyl)ethylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(2-hydroxy-1-(hydroxymethyl)ethylcarbamoyl)-1,3-thiazol-2-yl]azetidin-3-yl}thio-6-[(R)-1-hydroxyethyl]-1-methylcarbapen-2-em-3-carboxylate (490 mg, 0.773 mmol) (obtained as described in Example 44(2)) in a mixture of tetrahydrofuran (25 ml) and distilled water (25 ml) was subjected to catalytic hydrogenation in the presence of 10% palladium on charcoal (490 mg) at room temperature for 2 hours. After checking the completion of the reaction, the reaction mixture was filtered and to the filtrate were added sodium hydrogencarbonate (65 mg), ethyl acetate and distilled water. The mixture was shaken in a separatory funnel. The aqueous layer was separated and concentrated under reduced pressure. The residue was purified by chromatography on a Cosmosil column (eluant: distilled water→distilled water: acetonitrile (9:1), and the eluate was lyophilized to afford the desired compound (1R,5S,6S)-2-{1-[4-(2-hydroxy-1-(hydroxymethyl)ethylcarbamoyl)-1,3-thiazol-2-yl]azetidin-3-yl}thio-6-[(R)-1-hydroxyethyl]-1-methylcarbapen-2-em-3-carboxylic acid sodium salt (187 mg, yield 47%) as a white solid.

$^1$H-NMR (400 MHz, D$_2$O, TSP): δ (ppm) 7.51 (1H, s), 4.56 (2H, t, J=8.2 Hz), 4.39–4.31 (1H, m), 4.25 (1H, dq, J=6.3, 6.4 Hz), 4.20 (1H, dd, J=2.4, 9.0 Hz), 4.19–4.14 (1H, m), 4.06 (2H, ddd, J=3.6, 4.9, 8.6 Hz), 3.78 (2H, dd, J=5.1, 11.7 Hz), 3.72 (2H, dd, J=6.6, 11.7 Hz), 3.43 (1H, dd, J=2.4, 6.3 Hz), 3.25 (1H, dq, J=9.0, 7.2 Hz), 1.30 (3H, d, J=6.4 Hz), 1.20 (3H, d, J=7.2 Hz).

IR (KBr): 1748, 1649, 1599, 1547, 1393, 1313 cm$^{-1}$.

Mass spectrum (FAB$^+$): m/z: 521 [M+H]$^+$.

High-resolution mass spectrum (FAB$^+$): calculated for C$_{20}$H$_{26}$N$_4$O$_7$S$_2$Na: 521.1141, Found: 521.1155 [M+H]$^+$.

Elemental analysis: C$_{20}$H$_{25}$N$_4$O$_7$S$_2$Na.4/3H$_2$O. Calculated for: C, 44.11%; H, 5.12%; N, 10.29%; S, 11.78%. Found: C, 44.21%; H, 5.12%; N, 10.31%; S, 11.46%.

EXAMPLE 45

(1R,5S,6S)-2-(1-{4-[N-(2-hydroxyethyl)-N-methyl-carbamoyl]-1,3-thiazol-2-yl)azetidin-3-yl)thio-6-[(R)-1-hydroxyethyl]-1-methylcarbapen-2-em-3-carboxylic acid sodium salt

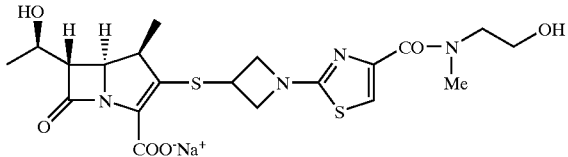

(1) p-Nitrobenzyl (1R,5S,6S)-2-[1-(4-{2-[N-(t-butyldimethylsilyloxy)ethyl]-N-methyl-carbamoyl}-1,3-thiazol-2-yl)azetidin-3-yl]thio-6-[(R)-1-hydroxyethyl]-1-methylcarbapen-2-em-3-carboxylate To a solution of 3-acetylthio-1-(4-{2-[N-(t-butyldimethylsilyloxy)ethyl]-N-methyl-carbamoyl}-1,3-thiazol-2-yl)azetidine (384 mg, 0.89 mmol) (obtained as described in Reference Example 40) in dimethylformamide (11 ml) was added hydrazine acetate (99mg, 1.07 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (5.29 mg, 0.89 mmol) in acetonitrile (22 ml) was added dropwise into the resulting mixture in an ice bath under an atmosphere of nitrogen, followed by the addition of diisopropylethylamine (0.62 ml, 3.56 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate: methanol (9:1)) to afford p-nitrobenzyl (1R,5S,6S)-2-[1-(4-{2-[N-(t-butyldimethylsilyloxy)ethyl]-N-methyl-carbamoyl}-1,3-thiazol-2-yl)azetidin-3-yl]thio-6-[(R)-1-hydroxyethyl]-1-methylcarbapen-2-em-3-carboxylate (263 mg, yield 50%) as a pale yellow solid.

$^1$H-NMR (400 MHz, CDCl$_3$): δ (ppm) 8.21 (2H, d, J=8.7 Hz), 7.63 (2H, d, J=8.7 Hz), 7.14 (0.6H, s), 7.03 (0.4H, s), 5.48 (1H, d, J=1.3 Hz), 5.25 (1H, d, J=1.3 Hz), 4.50 (1H, t, J=8.0 Hz), 4.23 (2H, t, J=9.0 Hz), 4.31–4.18 (3H, m), 4.05 (1H, dd, J=8.3, 5.4 Hz), 3.89–3.80 (1H, m), 3.80–3.72 (1H, m), 3.72–3.63 (1H, m), 3.63–3.51 (1H, m), 3.26 (1H, dd, J=7.1, 2.5 Hz), 3.26 (1.8H, s), 3.18 (1H, dq, J=8.3, 7.5 Hz), 3.07 (1.2H, s), 1.35 (3H, d, J=6.4 Hz), 1.22 (3H, d, J=6.9 Hz), 0.86 (9H, dd, J=7.8, 1.4 Hz), 0.27 (6H, dd, J=12.4, 3.2 Hz).

(2) p-Nitrobenzyl (1R,5S,6S)-2-(1-{4-[N-(2-hydroxyethyl)-N-methyl-carbamoyl]-1,3-thiazol-2-yl}azetidin-3-yl)thio-6-[(R)-1-hydroxyethyl]-1-methylcarbapen-2-em-3-carboxylate p-Nitrobenzyl (1R,5S,6S)-2-[1-(4-{2-[N-(t-butyldimethylsilyloxy)ethyl]-N-methyl-carbamoyl}-1,3-thiazol-2-yl)azetidin-3-yl]thio-6-[(R)-1-hydroxyethyl]-1-methylcarbapen-2-em-3-carboxylate (622 mg, 0.85 mmol) (obtained as described in Example 45(1)) in tetrahydrofuran (30 ml) was added to acetic acid (0.15 ml, 2.55 mmol) and 1 M tetrabutylammonium fluoride in tetrahydrofuran solution (2.55 ml, 2.55 mmol) in an ice bath and the mixture was stirred at room temperature overnight. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with saturated aqueous sodium chloride solution, dried over anhydrous sodium sulfate, filtered and concentrated under reduced pressure. The residue was purified by chromatography on a silica gel column (eluant: ethyl acetate→ethyl acetate: methanol (9:1)) to afford p-nitrobenzyl (1R,5S,6S)-2-(1-{4-[N-(2-hydroxyethyl)-N-methyl-carbamoyl]-1,3-thiazol-2-yl}azetidin-3-yl)thio-6-[(R)-1-hydroxyethyl]-1-methylcarbapen-2-em-3-carboxylate (263 mg, yield 50%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.25 (1H, s), 5.50 (1H, d, J=1.4 Hz), 5.26 (1H, d, J=1.4 Hz), 4.62–4.40 (2H, m), 4.36–4.20 (3H, m ), 4.08 (1H, t., J=9.1 Hz), 4.06 (1H, t., J=9.1 Hz), 3.84 (2H, t, J=4.9 Hz), 3.63 (2H, dd, J=4.9 Hz), 3.29 (1H, dd, J=6.4, 2.6 Hz), 3.21 (1H, quint., J=7.5 Hz), 3.08 (3H, s), 1.38 (3H, d, J=6.2 Hz), 1.26 (3H, d, J=7.3 Hz).

(3) (1R,5S,6S)-2-(1-{4-[N-(2-hydroxyethyl)-N-methyl-carbamoyl]-1,3-thiazol-2-yl}azetidin-3-yl)thio-6-[(R)-1-hydroxyethyl]-1-methylcarbapen-2-em-3-carboxylic acid sodium salt p-Nitrobenzyl (1R,5S,6S)-2-(1-{4-[N-(2-hydroxyethyl)-N-methyl-carbamoyl]-1,3-thiazol-2-yl}azetidin-3-yl)thio-6-[(R)-1-hydroxyethyl]-1-methylcarbapen-2-em-3- carboxylate (401 mg, 0.65 mmol) (obtained as described in Example 45(2)) in a mixture of tetrahydrofuran (20 ml) and distilled water (20 ml) was subjected to catalytic hydrogenation in the presence of 7.5% palladium on charcoal (401 mg) in a water bath (35° C.) for 2 hours. After checking the completion of the reaction, the reaction mixture was filtered and to the filtrate were added sodium hydrogencarbonate (5 mg), ethyl acetate and distilled water. The mixture was shaken in a separatory funnel. The aqueous layer was separated and concentrated under reduced pressure. The residue was purified by chromatography on a Cosmosil column (eluant: distilled water→2% acetonitrile in distilled water→4% acetonitrile in distilled water), and the eluate was lyophilized to afford the desired compound (1R,5S,6S)-2-(1-{4-[(2-hydroxyethyl)-methyl-carbamoyl]-1,3-thiazol-2-yl}azetidin-3-yl)thio-6-[(R)-1-hydroxyethyl]-1-methylcarbapen-2-em-3-carboxylic acid sodium salt (134 mg, yield 41%) as a white solid.

$^1$H-NMR (400 MHz, D$_2$O, TSP): δ (ppm) 7.31 (0.6H, s), 7.11 (0.4H, s), 4.56 (2H, t, J=8.2 Hz), 4.41–4.31 (2H, m), 4.25 (1H, quint., J=6.2 Hz), 4.21 (1H, dd, J=9.1, 2.4 Hz), 4.12–4.00 (2H, m), 3.85 (1H, t, J=5.4 Hz), 3.74 (1H, t, J=5.4 Hz), 3.70–3.60 (2H, m), 3.44 (1H, dd, J=6.2, 2.4 Hz), 3.26 (1H, dq, J=9.1, 7.4 Hz), 3.07 (1.2H, s), 3.08 (1.8H, s), 1.30 (3H, d, J=6.5 Hz), 1.20 (3H, d, J=7.3 Hz).

IR (KBr): 3397.0, 1749.1, 1606.4, 1538.9, 1469.5, 1398.1, 1311.4, 1266:0 cm$^{-1}$.

Mass spectrum (FAB$^+$): m/z: 505 [M+H]$^+$.

High-resolution mass spectrum (ESI$^+$): calculated for C$_{20}$H$_{25}$N$_4$O$_6$S$_2$Na$_2$: 505.1191, Found: 505.1185 [M+Na]$^+$.

Elemental analysis: C$_{20}$H$_{25}$N$_4$O$_7$S$_2$Na.4/3H$_2$O. Calculated for: C, 44.11%; H, 5.12%; N, 10.29%; S, 11.78%.

EXAMPLE 46

(1R,5S,6S)-2-{1-[4-(carboxymethylcarbamoyl)-1,3-thiazol-2-yl]azetidin-3-yl}thio-6-[(R)-1-hydroxyethyl]-1-methylcarbapen-2-em-3-carboxylic acid disodium salt

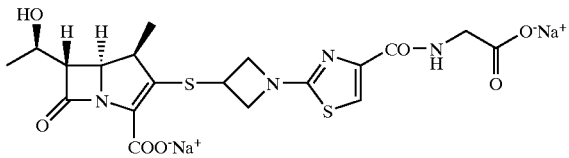

(1) p-Nitrobenzyl (1R,5S,6S)-2-{1-[4-(p-nitrobenzyloxycarbonylmethylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-{1-[4-(p-nitrobenzyloxycarbonylmethyl-carbamoyl)-1,3-thiazol-2-yl]azetidin-3-yl}thio-6-[(R)-1-t-butyldimethylsilyloxyethyl]-1-methylcarbapen-2-em-3-carboxylate (209.7 mg, 0.24 mmol) (obtained as described in Reference Example 41(10)) in tetrahydrofuran (10 ml) was added acetic acid (0.042 ml, 0.7 mmol) and 1 M tetrabutylammonium fluoride in tetrahydrofuran solution (0.72 ml, 0.72 mmol) in an ice bath and the mixture was stirred at room temperature for 4 days. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column (eluant: toluene:acetonitrile (2:1)) to afford p-nitrobenzyl (1R,5S,6S)-2-{1-[4-(p-nitrobenzyloxycarbonylmethyl-carbamoyl)-1,3-thiazol-2-yl]azetidin-3-yl}thio-6-[(R)-1-hydroxyethyl]-1-methylcarbapen-2-em-3-carboxylate (94.5 mg, yield 53%) as a pale yellow solid.

$^1$H-NMR (400 MHz, CDCl$_3$): δ (ppm) 8.23 (2H, d, J=7.9 Hz), 8.22 (2H, d, J=7.9 Hz), 7.66 (2H, d, J=7.9 Hz), 7.60 (1H, t, J=6.6 Hz), 7.54 (2H, d, J=7.9 Hz), 7.47 (1H, s), 5.505 (1H, d, J=13.8 Hz), 5.30 (2H, s), 5.255 (1H, d, J=13.8 Hz), 4.50 (1H, t, J=8.3 Hz), 4.40 (1H, t, J=8.3 Hz), 4.32–4.24 (4H, m), 4.06 (1H, dd, J=8.3, 6.2 Hz), 4.05 (1H, dd, J=8.3, 6.2 Hz), 3.30 (1H, dd, J=7.0, 3.1 Hz), 3.21 (1H, dq, J=9.0, 7.4 Hz), 1.98 (1H, br s), 1.38 (3H, J=5.7 Hz), 1.27 (3H, d, J=7.4 Hz).

(2) (1R,5S,6S)-2-{1-[4-(carboxymethylcarbamoyl)-1,3-thiazol-2-yl]azetidin-3-yl}thio-6-[(R)-1-hydroxyethyl]-1-methylcarbapen-2-em-3-carboxylic acid disodium salt p-Nitrobenzyl (1R,5S,6S)-2-{1-[4-(p-nitrobenzyloxycarbonylmethylcarbamoyl)-1,3-thiazol-2-yl]azetidin-3-yl}thio-6-[(R)-1-hydroxyethyl]-1-methylcarbapen-2-em-3-carboxylate (330.4 mg 0.38 mmol) obtained as described in Example 46(1) in a mixture of tetrahydrofuran (16.5 ml) and distilled water (8.3 ml) was subjected to catalytic hydrogenation in the presence of 20% palladium hydroxide on charcoal (350 mg) at room temperature for 2 hours. After checking the completion of the reaction, the reaction mixture was filtered and to the filtrate were added sodium hydrogencarbonate (63.9 mg), ethyl acetate and distilled water. The mixture was shaken in a separatory funnel. The aqueous layer was separated and concentrated under reduced pressure. The residue was purified by chromatography on a Cosmosil column (eluant: distilled water), and the eluate was lyophilized to afford the desired compound (1R,5S,6S)-2-{1-[4-(carboxymethylcarbamoyl)-1,3-thiazol-2-yl]azetidin-3-yl}thio-6-[(R)-1-hydroxyethyl]-1-methylcarbapen-2-em-3-carboxylic acid disodium salt (158.7 mg, yield 79%) as a white solid.

$^1$H-NMR (400 MHz, D$_2$O): δ (ppm) 7.83 (1H, s), 4.45 (1H, t, J=8.3 Hz), 4.43 (1H, t, J=8.3 Hz), 4.28–4.21 (1H, m), 4.124 (1H, quintet, J=5.8 Hz), 4.08 (1H, dd, J=8.8, 2.0 Hz), 3.99–3.92 (2H, m), 3.80 (2H, s), 3.31 (1H, dd, J=5.9, 2.0 Hz), 3.14 (1H, dq, J=8.8, 6.8 Hz), 1.18 (3H, d, J=5.9 Hz), 1.08 (3H, d, J=6.8 Hz).

IR (KBr): 3388, 1748, 1602, 1550, 1398, 1314, 1267 cm$^{-1}$.

Mass spectrum (FAB$^+$): 527 [M+H]$^+$.

High-resolution mass spectrum (FAB$^+$): calculated for C$_{19}$H$_{21}$N$_4$O$_7$S$_2$Na: Found: [M+H]$^+$.

EXAMPLE 47

(1R,5S,6S)-2-{1-[4-(3-hydroxyazetidine-1-carbonyl)-1,3-thiazol-2-yl]azetidin-3-yl}thio-6-[(R)-1-hydroxyethyl]-1-methylcarbapen-2-em-3-carboxylic acid sodium salt

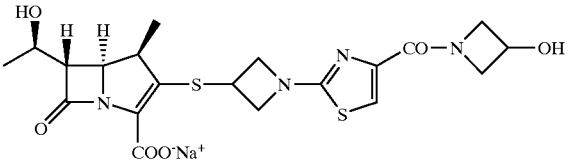

(1) p-Nitrobenzyl (1R,5S,6S)-2-{1-[4-(3-hydroxyazetidine-1-carbonyl)-1,3-thiazol-2-yl]azetidin-3-yl}thio-6-[(R)-1-t-butyldimethylsilyloxyethyl]-1-methylcarbapen-2-em-3-carboxylate To a solution of p-nitrobenzyl (1R,5S,6S)-2-(1-{4-[3-(t-butyldiphenylsilyloxy)azetidine-1-carbonyl]-1,3-thiazol-2-yl}azetidin-3-yl)thio-6-[(R)-1-t-butyldimethylsilyloxyethyl]-1-methylcarbapen-2-em-3-carboxylate (850 mg, 0.878 mmol) obtained as described in Reference Example 42(2) in tetrahydrofuran (43 ml) was added acetic acid (301 μl, 5.27 mmol) and 1 M tetrabutylammonium fluoride in tetrahydrofuran solution (5.27 ml, 5.27 mmol) in an ice bath and the mixture was stirred at room temperature for 1 day. After checking the completion of the reaction, ethyl acetate and water were added to the reaction mixture. The resulting mixture was shaken in a separatory funnel and the ethyl acetate layer was separated, washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate: methanol (95:5)→methylene chloride:methanol (9:1) to afford p-nitrobenzyl (1R,5S,6S)-2-{1-[4-(3-hydroxyazetidine-1-carbonyl)-1,3-thiazol-2-yl]azetidin-3-yl}thio-6-[(R)-1-t-butyldimethylsilyloxyethyl]-1-methylcarbapen-2-em-3-carboxylate (355 mg, yield 66%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.44 (1H, s), 5.51 (1H, d, J=13.7 Hz), 5.25 (1H, d, J=13.7 Hz), 4.82–4.77 (1H, m), 4.71–4.65 (1H, m), 4.51–4.36 (4H, m), 4.31–4.23 (3H, m), 4.07–3.96 (3H, m), 3.29 (1H, dd, J=2.4, 7.0 Hz), 3.20 (1H, dq, J=9.2, 7.1 Hz), 1.38 (3H, d, J=6.3 Hz), 1.27 (3H, d, J=7.1 Hz).

(2) (1R,5S,6S)-2-{1-[4-(3-hydroxyazetidine-1-carbonyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(3-hydroxyazetidine-1-carbonyl)-1,3-thiazol-2-yl]azetidin-3-yl}thio-6-[(R)-1-t-butyldimethylsilyloxyethyl]-1-methylcarbapen-2-em-3-carboxylate (350 mg, 0.568 mmol) (obtained as described in Example 47(1)) in a mixture of tetrahydrofuran (18 ml) and distilled water (18 ml) was subjected to catalytic hydrogenation in the presence of 10% palladium on charcoal (350 mg) at room temperature for 2 hours. After checking the completion of the reaction, the reaction mixture was filtered and to the filtrate were added sodium hydrogencarbonate (48 mg), ethyl acetate and distilled water. The mixture was shaken in a separatory funnel. The aqueous layer was separated and concentrated under reduced pressure. The residue was purified by chromatography on a Cosmosil column (eluant: distilled water→distilled water: acetonitrile (9:1)),and the eluate was lyophilized to afford the desired compound (1R,5S,6S)-2-{1-[4-(3-hydroxyazetidine-1-carbonyl)-1,3-thiazol-2-yl]azetidin-3-yl}thio-6-[(R)-1-hydroxyethyl]-1-methylcarbapen-2-em-3-carboxylic acid sodium salt (118 mg, yield 42%) as a white solid.

$^1$H-NMR (400 MHz, D$_2$O, TSP): δ (ppm) 7.33 (1H, s), 4.78–4.67 (2H, m), 4.56 (2H, t, J=8.0 Hz), 4.45–4.31 (3H, m), 4.25 (1H, dq, J=6.3, 6.3 Hz), 4.20 (1H, dd, J=2.3, 9.0 Hz), 4.10–4.03 (2H, m), 3.97 (1H, dd, J=3.7, 11.5 Hz), 3.44 (1H, dd, J=2.3, 6.3 Hz), 3.25 (1H, dq, J=9.0, 7.2 Hz), 1.30 (3H, d, J=6.3 Hz), 1.20 (3H, d, J=7.2 Hz).

IR (KBr): 1749, 1603, 1540, 1452, 1394, 1306 cm$^{-1}$.

Mass spectrum (FAB$^+$): m/z: 503 [M+H]$^+$.

High-resolution mass spectrum (FAB$^+$): calculated for C$_{20}$H$_{24}$N$_4$O$_6$S$_2$Na: 503.1035, Found: 503.1040 [M+H]$^+$.

Elemental analysis: C$_{20}$H$_{23}$N$_4$O$_6$S$_2$Na.8/3H$_2$O. Calculated for: C, 43.63%; H, 5.19%; N, 10.18%; S, 11.65%. Found: C, 44.04%; H, 4.93%; N, 9.86%; S, 11.30%.

EXAMPLE 48

(1R,5S,6S)-2-{1-[4-(N-carboxymethyl-N-methyl-carbamoyl)-1,3-thiazol-2-yl]azetidin-3-yl}thio-6-[(R)-1-hydroxyethyl]-1-methylcarbapen-2-em-3-carboxylic acid disodium salt

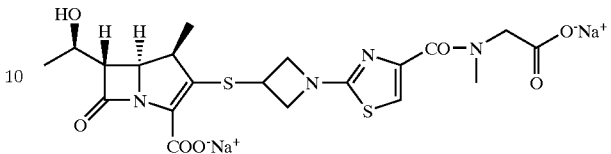

(1) p-Nitrobenzyl (1R,5S,6S)-2-{1-[4-(N-methyl-N-p-nitrobenzyloxycarbonylmethyl-carbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-{1-[4-(N-methyl-p-N-nitrobenzyloxycarbonylmethyl-carbamoyl)-1,3-thiazol-2-yl]azetidin-3-yl}thio-6-[(R)-1-t-butyldimethylsilyloxyethyl]-1-methylcarbapen-2-em-3-carboxylate (997 mg, 1.15 mmol) (obtained as described in Reference Example 43(3)) in tetrahydrofuran (50 ml) was added acetic acid (0.2 ml, 3.44 mmol)and 1 M tetrabutylammonium fluoride in tetrahydrofuran solution (3.44 ml, 3.44 mmol) in an ice bath and the mixture was stirred at room temperature for 2 days. After checking the completion of the reaction, ethyl acetate and saturated aqueous sodium hydrogencarbonate were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column (eluant: ethyl acetate→ethyl acetate: methanol (19:1)) to afford p-nitrobenzyl (1R,5S,6S)-2-{1-[4-(N-methyl-N-p-nitrobenzyloxycarbonylmethyl-carbamoyl)-1,3-thiazol-2-yl]azetidin-3-yl}thio-6-[(R)-1-hydroxyethyl]-1-methylcarbapen-2-em-3-carboxylate (413 mg, yield 47%) as a pale yellow solid.

$^1$H-NMR (400 MHz, CDCl$_3$): δ (ppm) 8.32–8.10 (4H, m), 7.75–7.60 (2H, m), 7.60–7.45 (2H, m), 7.75 (0.5H, s), 7.41 (0.5H, s), 5.51 (1H, d, J=13.6 Hz), 5.38–5.20 (3H, m including 5.26 (1H, d, J=13.6 Hz)), 4.75–3.71 (9H, m including 4.36 (1H, s), 4.56–4.46 (1H, m), 3.93–3.83 (1H, m)), 3.45–3.05 (4H, m including 3.36 (0.9H, s), 3.16 (2.1H, s)), 3.29 (1H, d, J=6.3 Hz), 1.38 (3H, d, J=6.1 Hz), 1.33–1.20 (3H, m).

(2) (1R,5S,6S)-2-{1-[4-(N-carboxymethyl-N-methyl-carbamoyl)-1,3-thiazol-2-yl]azetidin-3-yl)thio-6-[(R)-1-hydroxyethyl]-1-methylcarbapen-2-em-3-carboxylic acid disodium salt p-Nitrobenzyl (1R,5S,6S)-2-{1-(4-(N-methyl-N-p-nitrobenzyloxycarbonylmethyl-carbamoyl)-1,3-thiazol-2-yl]azetidin-3-yl}thio-6-[(R)-1-hydroxyethyl]-1-methylcarbapen-2-em-3-carboxylate (413 mg, 0.54 mmol) (obtained as described in Example 48(1)) in a mixture of tetrahydrofuran (20 ml) and distilled water (20 ml) was subjected to catalytic hydrogenation in the presence of 7.5% palladium on charcoal (413 mg) at room temperature for 2 hours. After checking the completion of the reaction, the reaction mixture was filtered and to the filtrate were added sodium hydrogencarbonate (91 mg), ethyl acetate and distilled water. The mixture was shaken in a separatory funnel. The aqueous layer was separated and concentrated under reduced pressure. The residue was purified by chromatography on a Cosmosil column (eluant: distilled water), and the eluate was lyophilized to afford the desired compound (1R,5S,6S)-2-{1-[4-(N-carboxymethyl-N-methyl-carbamoyl)-1,3-thiazol-2-yl]azetidin-3-yl}thio-6-[(R)-1-hydroxyethyl]-1-methylcarbapen-2-em-3-carboxylic acid disodium salt (126 mg, yield 43%) as a white solid.

$^1$H-NMR (400 MHz, D$_2$O, TSP): δ (ppm) 7.18 (0.6H, s), 7.03 (0.4H, s), 4.41–4.32 (0.2H, m), 4.25 (1H, quint., J=6.3 Hz), 4.15–3.98 (4H, m), 3.43 (1H, dd, J=6.3, 2.2 Hz), 3.26 (1H, quint., J=8.2 Hz), 3.11 (1.2H, s), 3.06 (1.8H, s), 1.30 (3H, d, J=6.4 Hz), 1.20 (3H, d, 7.1 Hz).

IR (KBr): 3389.3, 1748.2, 1605.4, 1541.8, 1469.5, 1394.3 cm$^{-1}$.

Mass spectrum (ESI$^+$): m/z: 519 [M−Na+2H]$^+$.

High-resolution mass spectrum (ESI$^+$): calculated for C$_{20}$H$_{24}$N$_4$O$_7$S$_2$Na: 519.0984, Found: 519.0956 [M−Na+2H]$^+$.

EXAMPLE 49

(1R,5S,6S)-2-[1-(4-N-carbamoylmethyl-N-methyl-carbamoyl-1,3-thiazol-2-yl)azetidin-3-yl]thio-6-[(R)-1-hydroxyethyl]-1-methylcarbapen-2-em-3-carboxylic acid sodium salt

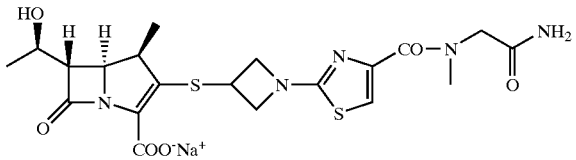

(1) p-Nitrobenzyl (1R,5S,6S)-2-{1-[4-(carbamoylmethyl-methyl-carbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-{1-[4-(carbamoylmethyl-methyl-carbamoyl)-1,3-thiazol-2-yl]azetidin-3-yl)thio-6-[(R)-1-t-butyidimethylsilyloxyethyl]-1-methylcarbapen-2-em-3-carboxylate (932 mg, 1.27 mmol) (obtained as described in Reference Example 44(2)) in tetrahydrofuran (50 ml) were added acetic acid (0.22 ml, 3.81 mmol) and 1 M tetrabutylammonium fluoride in tetrahydrofuran solution (3.81 ml, 3.81 mmol) in an ice bath and the mixture was stirred at room temperature for 2 days. After checking the completion of the reaction, ethyl acetate and saturated aqueous sodium hydrogencarbonate were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column (eluant: ethyl acetate→ethyl acetate: methanol (10:1)) to afford p-nitrobenzyl (1R,5S,6S)-2-{1-[4-(carbamoylmethyl-methyl-carbamoyl)-1,3-thiazol-2-yl]azetidin-3-yl}thio-6-[(R)-1-hydroxyethyl]-1-methylcarbapen-2-em-3-carboxylate (424 mg, yield 53%) as a pale yellow solid.

$^1$H-NMR (400 MHz, CDCl$_3$): δ (ppm) 8.23 (2H, d, J=7.8 Hz), 7.66 (2H, d, J=7.8 Hz), 7.36 (0.2H, s), 7.24 (0.8H, s), 5.51 (1H, d, J=13.7 Hz), 5.25 (1H, d, J=13.7 Hz), 4.59–4.39 (2H, m), 4.39–3.94 (7H, m), 3.36 (0.6H, s), 3.29 (1H, dd, J=6.9, 3.3 Hz), 3.25–3.14 (1H, m), 3.11 (2.4H, s), 1.38 (3H, d, J=6.1 Hz), 1.26 (3H, d, J=7.1 Hz).

(2) (1R,5S,6S)-2-{1-[4-(carbamoylmethyl-methyl-carbamoyl)-1,3-thiazol-2-yl]azetidin-3-yl}thio-6-[(R)-1-hydroxyethyl]-1-methylcarbapen-2-em-3-carboxylic acid disodium salt p-Nitrobenzyl (1R,5S,6S)-2-{1-[4-(carbamoylmethyl-methyl-carbamoyl)-1,3-thiazol-2-yl]azetidin-3-yl}thio-6-[(R)-1-hydroxyethyl]-1-methylcarbapen-2-em-3-carboxylate (424 mg, 0.67 mmol) (obtained as described in Example 49(1)) in a mixture of tetrahydrofuran (20 ml) and distilled water (20 ml) was subjected to catalytic hydrogenation in the presence of 7.5% palladium on charcoal (424 mg) at room temperature for 2 hours. After checking the completion of the reaction, the-reaction mixture was filtered and to the filtrate were added sodium hydrogencarbonate (57 mg), ethyl acetate and distilled water. The mixture was shaken in a separatory funnel. The aqueous layer was separated and concentrated under reduced pressure. The residue was purified by chromatography on a Cosmosil column (eluant: distilled water→2% acetonitrile in distilled water→4% acetonitrile in distilled water) and the eluate was lyophilized to afford the desired compound (1R,5S,6S)-2-{1-[4-(carbamoylmethyl-methyl-carbamoyl)-1,3-thiazol-2-yl]azetidin-3-yl}thio-6-[(R)-1-hydroxyethyl]-1-methylcarbapen-2-em-3-carboxylic acid sodium salt (115 mg, yield 33%) as a white solid.

$^1$H-NMR (400 MHz, D$_2$O, TSP): δ (ppm) 7.22 (0.5H, s), 7.20 (0.5H, s), 4.55 (2H, dd, J=17.4, 8.4 Hz), 4.41–4.32 (1H, m), 4.25 (1H, quint., J=6.3 Hz), 4.23–4.18 (3H, m including 4.22 (2H, s)), 4.05 (2H, ddd, J=17.3, 8.8, 4.9 Hz), 3.44 (1H, dd, J=6.2, 2.4 Hz), 3.31–3.20 (1H, m), 3.18 (1.5H, s), 3.09 (1.5H, s), 1.30 (3H, d, J=6.4 Hz), 1.20 (3H, d, 7.1 Hz IR (KBr): 3384.5, 1748.2, 1681.6, 1603.5, 1539.9, 1469.5, 1397.2, 1310.4 cm$^{-1}$.

Mass spectrum (FAB$^+$): m/z: 518 [M+H]$^+$.

High-resolution mass spectrum (ESI$^+$): calculated for C$_{20}$H$_{25}$N$_5$O$_6$S$_2$Na: 518.1144, Found: 518.1168 [M+H]$^+$.

EXAMPLE 50

(1R,5S,6S)-2-{1-[4-(carbamoylmethyl-carbamoyl)-1,3-thiazol-2-yl]azetidin-3-yl}thio-6-[(R)-1-hydroxyethyl]-1-methylcarbapen-2-em-3-carboxylic acid sodium salt

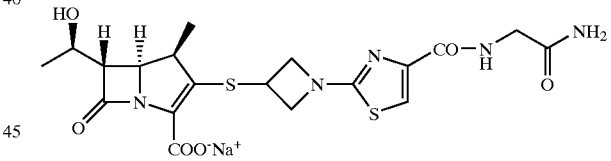

(1) p-Nitrobenzyl (1R,5S,6S)-2-{1-[4-(carbamoylmethyl-carbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-{1-[4-(carbamoylmethyl-carbamoyl)-1,3-thiazol-2-yl]azetidin-3-yl}thio-6-[(R)-1-t-butyldimethylsilyloxyethyl]-1-methylcarbapen-2-em-3-carboxylate (428.6 mg, 0.6 mmol) (obtained as described in Reference Example 45(2)) in tetrahydrofuran (21 ml) were added acetic acid (0.11 ml, 1.9 mmol) and 1 M tetrabutylammonium fluoride in tetrahydrofuran solution (1.8 ml, 1.8 mmol) in an ice bath and the mixture was stirred at room temperature for 3 days. After checking the completion of the reaction, ethyl acetate and saturated aqueous sodium hydrogencarbonate were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column (eluant: ethyl acetate: methanol (8:1)) to afford p-nitrobenzyl (1R,5S,6S)-2-{1-[4-(carbamoylmethyl-carbamoyl)-1,3-thiazol-2-yl]azetidin-3-yl}thio-6-[(R)-1-hydroxyethyl]-1-methylcarbapen-2-em-3-carboxylate (310.5 mg, yield 85%) as a pale yellow solid.

$^1$H-NMR (400 MHz, DMSO-d$_6$): δ (ppm) 8.24 (2H, d, J=8.8 Hz), 7.96 (1H, t, J=5.7 Hz), 7.72 (2H, d, J=8.8 Hz), 7.50 (1H, s), 7.40 (1H, br s), 7.08 (1H, br s), 5.46 (1H, d, J=13.9 Hz), 5.32 (1H, d, J=13.9 Hz), 5.09 (1H, d, J=5.1 Hz), 4.58–4.40 (3H, m), 4.22 (1H, dd, J=9.2, 2.7 Hz), 4.01–3.96 (3H, m), 3.81 (2H, d, J=5.7 Hz), 3.44–3.30 (2H, m), 1.16 (3H, d, J=6.6 Hz), 1.14 (3H, d, J=7.3 Hz).

(2) (1R,5S,6S)-2-{1-[4-(carbamoylmethyl-carbamoyl)-1,3-thiazol-2-yl]azetidin-3yl}thio-6-[(R)-1-hydroxyethyl]-1-methylcarbapen-2-em-3-carboxylic acid sodium salt p-Nitrobenzyl (1R,5S,6S)-2-{1-[4-(carbamoylmethyl-carbamoyl)-1,3-thiazol-2-yl]azetidin-3-yl}thio-6-[(R)-1-hydroxyethyl]-1-methylcarbapen-2-em-3-carboxylate (310.5 mg, 0.5 mmol) (obtained as described in Example 50(1)) in a mixture of tetrahydrofuran (15.5 ml) and distilled water (7.8 ml) was subjected to catalytic hydrogenation in the presence of 20% palladium hydroxide on charcoal (360 mg) in a water bath (35° C.) for 2 hours. After checking the completion of the reaction, the reaction mixture was filtered and to the filtrate were added sodium hydrogencarbonate (42.3 mg), ethyl acetate and distilled water. The mixture was shaken in a separatory funnel. The aqueous layer was separated and concentrated under reduced pressure. The residue was purified by chromatography on a Cosmosil column (eluant: distilled water→5% acetonitrile in distilled water→10% acetonitrile in distilled water),and the eluate was lyophilized to afford the desired compound (1R,5S,6S)-2-{1-[4-(carbamoylmethyl-carbamoyl)-1,3-thiazol-2-yl]azetidin-3-yl}thio-6-[(R)-1-hydroxyethyl]-1-methylcarbapen-2-em-3-carboxylic acid sodium salt (157 mg, yield 62%) as a white solid.

$^1$H-NMR (400 MHz, D$_2$O): δ (ppm) 7.43 (1H, s), 4.45 (2H, t, J=7.8 Hz), 4.28–4.18 (1H, m), 4.13 (1H, quintet, J=5.9 Hz), 4.08 (1H, dd, J=9.3, 2.3 Hz), 4.00–3.92 (4H, m), 3.31 (1H, dd, J=5.9, 2.3 Hz), 3.14 (1H, dq, J=9.3, 7.8 Hz), 1.13 (3H, d, J=5.9 Hz), 1.08 (3H, d, J=7.8 Hz).

IR (KBr): 3384, 1748, 1660, 1600, 1549, 1492, 1471, 1394, 1315, 1264 cm$^{-1}$.

Mass spectrum (FAB$^+$): 504 [M+H]$^+$.

High-resolution mass spectrum (FAB$^+$): calculated for C$_{19}$H$_{23}$O$_6$N$_5$S$_2$Na: 504.0988, Found: 504.1018 [M+H]$^+$.

EXAMPLE 51

(1R,5S,6S)-2-{1-[4-((1S)-1-carboxyl-2-methylpropylcarbamoyl)-1,3-thiazol-2-yl]azetidin-3-yl}thio-6-[(R)-1-hydroxyethyl]-1-methylcarbapen-2-em-3-carboxylic acid disodium salt

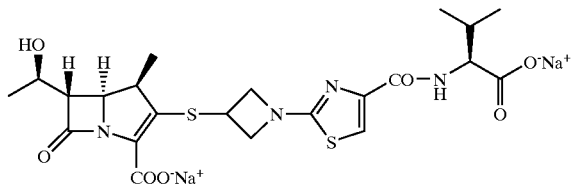

(1) p-Nitrobenzyl (1R,5S,6S)-2-(1-{4-[(1S)-2-methyl-1-(p-nitrobenzyloxycarbonyl)-propylcarbamoyl]-1,3-thiazol-2-yl}azetidin-3-yl)thio-6-[(R)-1-hydroxyethyl]-1-methylcarbapen-2-em-3-carboxylate To a solution of p-nitrobenzyl (1R,5S,6S)-2-(1-{4-[(1S)-2-methyl-1-(p-nitrobenzyloxycarbonyl)propylcarbamoyl]-1,3-thiazol-2-yl}azetidin-3-yl)thio-6-[(R)-1-t-butyldimethylsilyloxyethyl]-1-methylcarbapen-2-em-3-carboxylate (1.1 5g, 1.29 mmol) (obtained as described in Reference Example 46(3)) in tetrahydrofuran (58 ml) was added acetic acid (222 µl, 3.87 mmol) and 1 M tetrabutylammonium fluoride in tetrahydrofuran solution (3.87 ml, 3.87 mmol) in an ice bath and the mixture was stirred at room temperature for 2 days. After checking the completion of the reaction, ethyl acetate and saturated aqueous sodium chloride were added to the reaction mixture. The resulting mixture was shaken in a separatory funnel and the ethyl acetate layer was separated, washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: n-hexane: ethyl acetate (1:2)→ethyl acetate) to afford p-nitrobenzyl (1R,5S,6S)-2-(1-{4-[(1S)-2-methyl-1-(p-nitrobenzyloxycarboxyl)propylcarbamoyl]-1,3-thiazol-2-yl}azetidin-3-yl)thio-6-[(R)-1-hydroxyethyl]-1-methylcarbapen-2-em-3-carboxylate (377 mg, yield 37%) as a pale yellow solid.

$^1$H-NMR (400 MHz, CDCl$_3$): δ (ppm) 8.23 (2H, d, J=8.8 Hz), 8.22 (2H, d, J=8.8 Hz), 7.66 (2H, d, J=8.8 Hz), 7.58–7.55 (1H, br s), 7.54 (2H, d, J=8.8 Hz), 7.45 (1H, s), 5.51 (1H, d, J=13.5 Hz), 5.28 (2H, s), 5.26 (1H, d, J=13.5 Hz), 4.74 (1H, dd, J=5.1, 8.8 Hz), 4.53–4.47 (2H, m), 4.32–4.26 (3H, m), 4.10–4.05 (2H, m), 3.30 (1H, dd, J=2.9, 6.6 Hz), 3.22 (1H, dq, J=9.5, 6.6 Hz), 2.32–2.24 (1H, m), 1.39 (3H, d, J=5.8 Hz), 1.28 (3H, d, J=6.6 Hz), 1.00 (3H, d, J=7.32 Hz), 0.97 (3H, d, J=7.3 Hz).

(2) (1R,5S,6S)-2-{1-[4-((1S)-1-carboxyl-2-methylpropylcarbamoyl)-1,3-thiazol-2-yl]azetidin-3-yl}thio-6-[(R)-1-hydroxyethyl]-1-methylcarbapen-2-em-3-carboxylic acid disodium salt p-Nitrobenzyl (1R,5S,6S)-2-(1-{4-[(1S)-2-methyl-1-(p-nitrobenzyloxycarbonyl)-propylcarbamoyl]-1,3-thiazol-2-yl}azetidin-3-yl)thio-6-[(R)-1-hydroxyethyl]-1-methylcarbapen-2-em-3-carboxylate (370 mg, 0.465 mmol) (obtained as described in Example 51(1)) in a mixture of tetrahydrofuran (19 ml) and distilled water (19 ml) was subjected to catalytic hydrogenation in the presence of 10% palladium on charcoal (370 mg) at room temperature for 3 hours. After checking the completion of the reaction, the reaction mixture was filtered and to the filtrate were added sodium hydrogencarbonate (80 mg), ethyl acetate and distilled water. The mixture was shaken in a separatory funnel. The aqueous layer was separated and concentrated under reduced pressure. The residue was purified by chromatography on a Cosmosil column (eluant: distilled water→distilled water:acetonitrile (96:4)),and the eluate was lyophilized to afford the desired compound (1R,5S,6S)-2-{1-[4-((1S)-1-carboxyl-2-methyl-propylcarbamoyl)-1,3-thiazol-2-yl]azetidin-3-yl}thio-6-[(R)-1-hydroxyethyl]-1-methylcarbapen-2-em-3-carboxylic acid disodium salt (165 mg, yield 63%) as a white solid.

$^1$H-NMR (400 MHz, D$_2$O, TSP): δ (ppm) 7.51 (1H, s), 4.59 (2H, dt, J=8.0, 5.6 Hz), 4.40–4.34 (1H, m), 4.29–4.23 (2H, m), 4.20 (1H, dd, J=2.4, 9.0 Hz), 4.10 (2H, dt, J=9.0, 5.2 Hz), 3.44 (1H, dd, J=2.4, 6.4 Hz), 3.27 (1H, dq, J=9.0, 7.2 Hz), 2.28–2.16 (1H, m), 1.30 (3H, d, J=6.2 Hz), 1.20 (3H, d, J=7.2 Hz), 0.98 (3H, d, J=6.8 Hz), 0.95 (3H, d, J=6.8 Hz).

IR (KBr): 1749, 1599, 1547, 1491, 1471, 1400, 1314, 1292, 1264 cm$^{-1}$.

Mass spectrum (ESI$^+$): m/z: 591 [M+Na]$^+$.

High-resolution mass spectrum (ESI$^+$): calculated for C$_{22}$H$_{26}$N$_4$O$_7$S$_2$Na$_2$: 591.0936, Found: 591.0952 [M+Na]$^+$.

EXAMPLE 52

(1R,5S,6S)-2-{1-[4-((1S)-1-carbamoyl-2-methyl-propylcarbamoyl)-1,3-thiazol-2-yl]azetidin-3-yl}thio-6-[(R)-1-hydroxyethyl]-1-methylcarbapen-2-em-3-carboxylic acid sodium salt

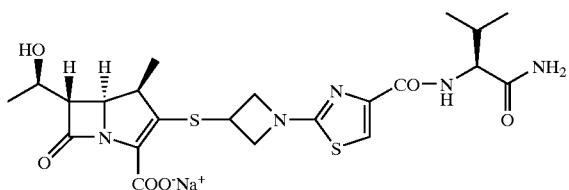

(1) p-Nitrobenzyl (1R,5S,6S)-2-{1-[4-((1S)-1-carbamoyl-2-methyl-propylcarbamoyl)-1,3-thiazol-2-yl]azetidin-3-yl}thio-6-[(R)-1-hydroxyethyl]-1-methylcarbapen-2-em-3-carboxylate To a solution of p-nitrobenzyl (1R,5S,6S)-2-{1-[4-((1S)-1-carbamoyl-2-methyl-propylcarbamoyl)-1,3-thiazol-2-yl]azetidin-3-yl}thio-6-[(R)-1-t-butyldimethylsilyloxyethyl]-1-methylcarbapen-2-em-3-carboxylate (930 mg, 1.20 mmol) (obtained as described in Reference Example 47(3)) in tetrahydrofuran (47 ml) was added acetic acid (206 μl, 3.60 mmol) and 1 M tetrabutylammonium fluoride in tetrahydrofuran solution (3.60 ml, 3.60 mmol) in an ice bath and the mixture was stirred at room temperature for 2 days. After checking the completion of the reaction, ethyl acetate and water were added to the reaction mixture. The resulting mixture was shaken in a separatory funnel and the ethyl acetate layer was separated, washed with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate: methanol (95:5)) to afford p-nitrobenzyl (1R,5S,6S)-2-{1-[4-((1S)-1-carbamoyl-2-methyl-propylcarbamoyl)-1,3-thiazol-2-yl]azetidin-3-yl}thio-6-[(R)-1-hydroxyethyl]-1-methylcarbapen-2-em-3-carboxylate (383 mg, yield 48%) as a pale yellow solid.

$^1$H-NMR (400 MHz, CDCl$_3$): δ (ppm) 8.23 (2H, d, J=8.8 Hz), 7.66 (2H, d, J=8.8 Hz), 7.61–7.56 (1H, br d, J=9.5 Hz), 6.05–6.01 (1H, br s), 5.51 (1H, d, J=13.5 Hz), 5.43–5.39 (1H, br s), 5.26 (1H, d, J=13.5 Hz), 4.54–4.47 (2H, m), 4.38–4.33 (1H, m), 4.32–4.25 (2H, m), 4.10–4.04 (2H, m), 3.30 (1H, dd, J=6.6, 2.9 Hz), 3.22 (1H, dq, J=9.5, 7.3 Hz), 2.33–2.24 (1H, m), 1.38 (3H, d, J=5.9 Hz), 1.28 (3H, d, J=7.3 Hz), 1.03 (3H, d, J=6.6 Hz), 10.1 (3H, d, J=6.6 Hz).

(2) (1R,5S,6S)-2-{1-[4-((1S)-1-carbamoyl-2-methyl-propylcarbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-((1S)-1-carbamoyl-2-methyl-propylcarbamoyl)-1,3-thiazol-2-yl]azetidin-3-yl}thio-6-[(R)-1-hydroxyethyl]-1-methylcarbapen-2-em-3-carboxylate (380 mg, 0.577 mmol) (obtained as described in Example 52(1)) in a mixture of tetrahydrofuran (19 ml) and distilled water (19 ml) was subjected to catalytic hydrogenation in the presence of 10% palladium on charcoal (380 mg) at room temperature for 3 hours. After checking the completion of the reaction, the reaction mixture was filtered and to the filtrate were added sodium hydrogencarbonate (48 mg), ethyl acetate and distilled water. The mixture was shaken in a separatory funnel. The aqueous layer was separated and concentrated under reduced pressure. The residue was purified by chromatography on a Cosmosil column (eluant: distilled water→distilled water:acetonitrile (81:9)),and the eluate was lyophilized to afford the desired compound (1R,5S,6S)-2-{1-[4-((1S)-1-carbamoyl-2-methyl-propylcarbamoyl)-1,3-thiazol-2-yl]azetidin-3-yl}thio-6-[(R)-1-hydroxyethyl]-1-methylcarbapen-2-em-3-carboxylic acid sodium salt (170 mg, yield 54%) as a white solid.

$^1$H-NMR (400 MHz, D$_2$O, TSP): δ (ppm) 7.55 (1H, s), 4.58 (2H, t, J=8.2 Hz), 4.40–4.34 (1H, m), 4.29 (1H, d, J=6.9 Hz), 4.25 (1H, dq, J=6.2, 6.4 Hz), 4.20 (1H, dd, J=2.4, 9.0 Hz), 4.09 (2H, dt, J=9.0, 4.6 Hz), 3.43 (1H, dd, J=2.4, 6.2 Hz), 3.26 (1H, dq, J=9.0, 7.2 Hz), 2.26–2.16 (1H, m), 1.30 (3H, d, J=6.4 Hz), 0.20 (3H, d, J=7.2 Hz), 1.02 (6H, d, J=6.8 Hz).

IR (KBr): 1749, 1662, 1603, 1545, 1490, 1471, 1394, 1316, 1293, 1260 cm$^{-1}$.

Mass spectrum (FAB$^+$): m/z: 546 [M+H]$^+$.

High-resolution mass spectrum (ESI$^+$): calculated for C$_{22}$H$_{28}$N$_5$O$_6$SNa$_2$: 568.1276, Found: 568.1271 [M+Na]$^+$.

Elemental analysis: C$_{22}$H$_{28}$N$_5$O$_6$SNa.3H$_2$O. Calculated for: C, 44.07%; H, 5.72%; N, 11.68%; S, 10.69%. Found: C, 44.17%; H, 6.18%; N, 11.84%; S, 10.67%.

EXAMPLE 53

(1R,5S,6S)-2-{1-[4-(N-carboxymethyl-N-isopropyl-carbamoyl)-1,3-thiazol-2-yl]azetidin-3-yl}thio-6-[(R)-1-hydroxyethyl]-1-methylcarbapen-2-em-3-carboxylic acid disodium salt

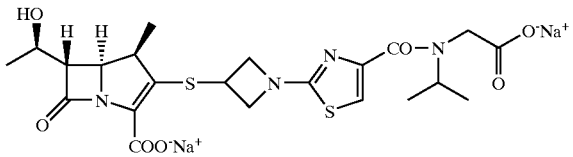

(1) To a solution of 3-acetylthio-1-{4-[N-isopropyl-N-(p-nitrobenzyloxycarbonylmethyl)-carbamoyl]-1,3-thiazol-2-yl}azetidine (312 mg, Q.63 mmol) (obtained as described in Reference Example 48) in dimethylformamide (9 ml) was added hydrazine acetate (70 mg, 0.76 mmol) at room temperature under an atmosphere of nitrogen and the mixture was stirred for 1 hour.

After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (452 mg, 0.76 mmol) in acetonitrile (20 ml) was added dropwise into the resulting mixture in an ice bath under an atmosphere of nitrogen, followed by the addition of diisopropylethylamine (0.44 ml, 2.52 mmol). The mixture was stirred for 4 hours. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate: methanol (20:1)) to afford Elemental analysis: C$_{22}$H$_{26}$N$_4$O$_7$S$_2$Na$_2$.8/3H$_2$O . Calculated for: C, 42.85%; H, 5.12%; N, 9.09%; S, 10.40%. Found: C, 42.78%; H, 5.33%; N, 9.14%; S, 10.12%.

p-nitrobenzyl (1R,5S,6S)-2-(1-{4-[N-isopropyl-N-(p-nitrobenzyloxycarbonylmethyl)-carbamoyl]-1,3-thiazol-2-yl}azetidin-3-yl)thio-6-[(R)-1-hydroxyethyl]-1-methylcarbapen-2-em-3-carboxylate (193 mg, yield 39%) as a pale yellow solid.

¹H-NMR (400 MHz, CDCl₃): δ (ppm) 8.23 (4H, d, J=8.9 Hz), 7.66 (2H, d, J=8.9 Hz), 7.56 (1H, d, J=8.0 Hz), 7.43–7.32 (1.4H, m), 7.15 (0.6H, br s), 5.51 (1H, d, J=13.8 Hz), 5.28 (1.2H, br s), 5.25 (1H, d, J=13.8 Hz), 5.20 (0.8H, br s), 5.05–4.65 (0.4H, m), 4.85–4.65 (0.6H, m), 4.65–3.95 (8H, m including 4.50 (2H, t, J=7.4 Hz), 4.11 (2H, t, J=7.4 Hz)), 3.93–3.75 (1H, m), 3.29 (1H, dd, J=6.6, 2.0 Hz), 3.25–3.08 (1H, m), 1.38 (3H, d, J=6.4 Hz), 1.35 (3H, d, J=7.2 Hz), 1.20 (6H, br s).

(2) (1R,5S,6S)-2-{1-[4-(N-carboxymethyl-N-isopropyl-carbamoyl)-1,3-thiazol-2-yl]azetidin-3-yl}thio-6-[(R)-1-hydroxyethyl]-1-methylcarbapen-2-em-3-carboxylic acid disodium salt p-Nitrobenzyl (1R,5S,6S)-2-1-{4-[N-isopropyl-N-(p-nitrobenzyloxycarbonylmethyl)-carbamoyl]-1,3-thiazol-2-yl}azetidin-3-yl)thio-6-[(R)-1-hydroxyethyl]-1-methylcarbapen-2-em-3-carboxylate (193 mg, 0.24 mmol) (obtained as described in Example 53(1)) in a mixture of tetrahydrofuran (9 ml) and distilled water (9 ml) was subjected to catalytic hydrogenation in the presence of 7.5% palladium on charcoal (193 mg) in a water bath (35° C.) for 3 hours. After checking the completion of the reaction, the reaction mixture was filtered and to the filtrate were added sodium hydrogencarbonate (40 mg), ethyl acetate and distilled water. The mixture was shaken in a separatory funnel. The aqueous layer was separated, washed with the above-mentioned mixed solvents, and concentrated under reduced pressure. The residue was purified by chromatography on a Cosmosil column (eluant: distilled water),and the eluate was lyophilized to afford the desired compound (1R,5S,6S)-2-{1-[4-(N-carboxymethyl-N-isopropyl-carbamoyl)-1,3-thiazol-2-yl]azetidin-3-yl}thio-6-[(R)-1-hydroxyethyl]-1-methylcarbapen-2-em-3-carboxylic acid disodium salt (63 mg, yield 45%) as a white solid.

¹H-NMR (400 MHz, D₂O): δ (ppm) 7.08 (0.6H, br s), 7.04 (0.4H, br s), 4.70–4.69 (0.2H, m), 4.53 (2H, d, J=8.0 Hz), 4.42–4.31 (1H, m), 4.18–4.09 (0.8H, m), 4.25 (1H, quint., J=6.4 Hz), 4.20 (1H, d, J=9.1 Hz), 4.09–4.02 (2H, m), 3.95 (2H, d, J=5.8 Hz), 3.43 (1H, dd, J=6.4, 0.8 Hz), 3.26 (1H, quint., J=7.6 Hz), 1.31 (3H, d, J=6.4 Hz), 1.26–1.10 (9H, m).

IR (KBr): 3398.0, 1749.1, 1603.5, 1539.9, 1467., 1453.1, 1392.4, 1310.4, 1277.6 cm⁻¹.

Mass spectrum (FAB⁺): m/z: 569 [M+H]⁺.

High-resolution mass spectrum (FAB⁺): calculated for C₂₂H₂₇O₇N₄S₂Na₂: 569.1116, Found: 569.1119 [M+H]⁺.

EXAMPLE 54

(1R,5S,6S)-2-{1-[4-(N-carbamoylmethyl-N-isopropyl-carbamoyl)-1,3-thiazol-2-yl]azetidin-3-yl}thio-6-[(R)-1-hydroxyethyl]-1-methylcarbapen-2-em-3-carboxylic acid sodium salt

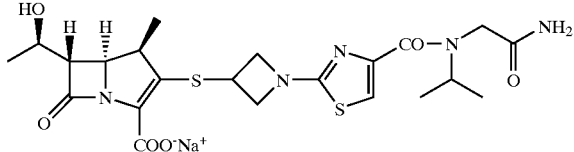

(1) p-Nitrobenzyl (1R,5S,6S)-2-{1-[4-(N-carbamoylmethyl-N-isopropyl-carbamoyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(N-carbamoylmethyl-N-isopropyl-carbamoyl)-1,3-thiazol-2-yl]azetidine (347 mg, 0.97 mmol) (obtained as described in Reference Example 49) in dimethylformamide (10 ml) was added hydrazine acetate (108 mg, 1.17 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (696 mg,1.17 mmol) in acetonitrile (20 ml) was added dropwise into the resulting mixture in an ice bath under an atmosphere of nitrogen, followed by the addition of diisopropylethylamine (0.68 ml, 3.88 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate: methanol (10:1) to afford p-nitrobenzyl (1R,5S,6S)-2-{1-[4-(N-carbamoylmethyl-N-isopropyl-carbamoyl)-1,3-thiazol-2-yl]azetidin-3-yl}thio-6-[(R)-1-hydroxyethyl]-1-methylcarbapen-2-em-3-carboxylate (359 mg, yield 56%) as a pale yellow solid.

¹H-NMR (400 MHz, CDCl₃): δ (ppm) 8.22 (2H, d, J=8.6 Hz), 7.66 (2H, d, J=8.6 Hz), 7.05–6.72 (1H, m), 5.51 (1H, d, J=13.8 Hz), 5.25 (11H, d, J=13.8 Hz), 4.80–4.45 (1H, m), 4.45–4.35 (2H, m), 4.35–4.17 (3H, m), 4.03 (4H, m), 3.29 (1H, dd, J=7.0, 2.5 Hz), 3.25–3.05 (1H, m), 1.38 (3H, d, J=6.3 Hz), 1.33–0.98 (9H, m including 1.25 (3H, d, J=7.1 Hz)).

(2) (1R,5S,6S)-2-{1-[4-(N-carbamoylmethyl-N-isopropyl-carbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(N-carbamoylmethyl-N-isopropyl-carbamoyl)-1,3-thiazol-2-yl]azetidin-3-yl}thio-6-[(R)-1-hydroxyethyl]-1-methylcarbapen-2-em-3-carboxylate (359 mg, 0.55 mmol) (obtained as described in Example 54(1)) in a mixture of tetrahydrofuran (12 ml) and distilled water (12 ml) was subjected to catalytic hydrogenation in the presence of 7.5% palladium hydroxide (359 mg) in a water bath (35° C.) for 3 hours. After checking the completion of the reaction, the reaction mixture was filtered and to the filtrate were added sodium hydrogencarbonate (46 mg), acetic acid and distilled water. The mixture was shaken in a separatory funnel. The aqueous layer was separated and concentrated under reduced pressure. The residue was purified by chromatography on a Cosmosil column (eluant: distilled water→2% acetonitrile in distilled water) and the eluate was lyophilized to afford the desired compound (1R,5S,6S)-2-{1-[4-(N-carbamoylmethyl-N-isopropyl-carbamoyl)-1,3-thiazol-2-yl]azetidin-3-yl}thio-6-[(R)-1-hydroxyethyl]-1-methylcarbapen-2-em-3-carboxylic acid sodium salt (195 mg, yield 65%) as a white solid.

¹H-NMR (400 MHz, D₂O): δ (ppm) 7.17 (0.2H, br s), 7.12 (0.8H, br s), 4.56 (2H, dd, J=17.4, 9.0 Hz), 4.42–4.16 (4H, m including 4.25 (1H, quint., J=6.3 Hz), 4.21 (1H, dd, J=8.4, 2.3 Hz), 4.09–3.97 (2H, m), 3.44 (1H, dd, J=6.3, 2.5 Hz), 3.26 (1H, quint., J=8.4 Hz), 1.30 (3H, d, J=6.4 Hz), 1.25–1.08 (9H, m including 1.19 (3H, d, J=6.7 Hz)).

IR (KBr): 3404.7, 1749.1, 1681.6, 1605.4, 1538.0, 1468.5, 1448.3, 1395.2, 1306.5, 1277.6 cm$^{-1}$.

Mass spectrum (FAB$^+$): m/z: 546 [M+H]$^+$.

High-resolution mass spectrum (FAB$^+$): calculated for $C_{22}H_{29}N_5O_6S_2Na$: 546.1457, Found: 546.1458 [M+H]$^+$.

EXAMPLE 55

(1R,5S,6S)-2-{1-[4-(N-cyanomethyl-N-isopropyl-carbamoyl)-1,3-thiazol-2-yl]azetidin-3-yl}thio-6-[(R)-1-hydroxyethyl]-1-methylcarbapen-2-em-3-carboxylic acid sodium salt

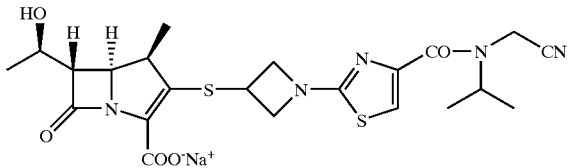

(1) p-Nitrobenzyl (1R,5S,6S)-2-{1-[4-(N-cyanomethyl-N-isopropyl-carbamoyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(N-cyanomethyl-N-isopropyl-carbamoyl)-1,3-thiazol-2-yl]azetidine (344 mg, 1.01 mmol) (obtained as described in Reference Example 50) in dimethylformamide (1 0 ml) was added hydrazine acetate (112 mg, 1.22 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (725 mg, 1.22 mmol) in acetonitrile (20 ml) was added dropwise into the resulting mixture in an ice bath under an atmosphere of nitrogen, followed by the addition of diisopropylethylamine (0.70 ml, 4.04 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate-:methanol (10:1) to afford p-nitrobenzyl (1R,5S,6S)-2-{1-[4-(N-cyanomethyl-N-isopropyl-carbamoyl)-1,3-thiazol-2-yl]azetidin-3-yl}thio-6-[(R)-1-hydroxyethyl]-1-methylcarbapen-2-em-3-carboxylate (245 mg, yield 39%) as a pale yellow solid.

$^1$H-NMR (400 MHz, CDCl$_3$): δ (ppm) 8.23 (2H, d, J=8.7 Hz), 7.6 (2H, d, J=8.7 Hz), 7.48–7.15 (1H, m), 5.51 (1H, d, J=14.0 Hz), 5.26 (1H, d, J=14.0 Hz), 4.86 (1H, quint, J=6.5 Hz), 4.72–3.76 (9H, m including 4.52 (2H, t, J=8.1 Hz), 4.27 (2H, dd, J=6.6, 2.5 Hz)), 3.29 (1H, dd, J=6.9, 2.5 Hz), 3.21 (1H, quint., J=9.3, 7.3 Hz), 1.38 (3H, d, J=6.2 Hz), 1.35–1.20 (9H, m including 1.25 (3H, d, J=7.3 Hz)).

(2) (1R,5S,6S)-2-{1-[4-(N-cyanomethyl-N-isopropyl-carbamoyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(N-cyanomethyl-N-isopropyl-carbamoyl)-1,3-thiazol-2-yl]azetidin-3-yl}thio-6-[(R)-1-hydroxyethyl]-1-methylcarbapen-2-em-3-carboxylate (245 mg, 0.39 mmol) (obtained as described in Example 55(1)) in a mixture of tetrahydrofuran (12 ml) and distilled water (12 ml) was subjected to catalytic hydrogenation in the presence of 7.5% palladium on charcoal (245 mg) in a water bath (35° C.) for 2 hours. After checking the completion of the reaction, the reaction mixture was filtered and to the filtrate were added sodium hydrogencarbonate (33 mg), ethyl acetate and distilled water. The mixture was shaken in a separatory funnel. The aqueous layer was separated, washed with the above-mentioned mixed solvent, and concentrated under reduced pressure. The residue was purified by chromatography on a Cosmosil column (eluant: distilled water→2% acetonitrile in distilled water→4% acetonitrile in distilled water→6% acetonitrile in distilled water) and the eluate was lyophilized to afford the desired compound (1R,5S,6S)-2-{1-[4-(N-cyanomethyl-N-isopropyl-carbamoyl)-1,3-thiazol-2-yl]azetidin-3-yl}thio-6-[(R)-1-hydroxyethyl]-1-methylcarbapen-2-em-3-carboxylic acid sodium salt (87 mg, yield 42%) as a white solid.

$^1$H-NMR (400 MHz, D$_2$O): δ (ppm) 7.20 (1H, br s), 4.58 (2H, t, J=8.0 Hz), 4.49–4.31 (3H, m including 4.41 (2H, s)), 4.25 (1H, quint., J=6.3 Hz), 4.21 (1H, dd, J=9.0, 2.3 Hz), 4.19–3.80 (3H, m including 4.07 (2H, dd, J=8.6, 4.9 Hz), 3.44 (1H, dd, J=6.3, 2.4 Hz), 3.26 (1H, dq, J=9.0, 7.2 Hz), 1.43–1.25 (9H, m including 1.31 (3H, d, J=6.4 Hz), 1.20 (3H, d, J=7.2 Hz)).

IR (KBr): 3398.0, 1750.1, 1606.4, 1537.0, 1468.5, 1426.1, 1401.0, 1373.1, 1332.6, 1311.4, 1274.7 cm$^{-1}$.

Mass spectrum (FAB$^+$): m/z: 550 [M+Na]$^+$.

High-resolution mass spectrum (FAB$^+$): calculated for $C_{22}H_{26}N_5O_5S_2Na_2$: 550.1171, Found: 550.1179 [M+Na]$^+$.

EXAMPLE 56

(1R,5S,6S)-2-{1-[4-(piperidin-4-ylcarbamoyl)-1,3-thiazol-2-yl]azetidin-3-yl}thio-6-[(R)-1-hydroxyethyl]-1-methylcarbapen-2-em-3-carboxylic acid

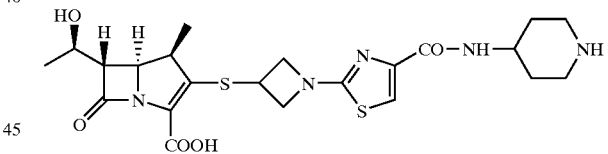

(1) p-Nitrobenzyl (1R,5S,6S)-2-(1-{4-[1-(p-nitrobenzyloxycarbonyl)-piperidin-4-ylcarbamoyl]-1,3-thiazo(-2-yl}azetidin-3-yl)thio-6-[(R)-1-hydroxyethyl]-1-methylcarbapen-2-em-3-carboxylate To a solution of 3-acetylthio-1-{4-[1-(p-nitrobenzyloxycarbonyl)-piperidin-4-ylcarbamoyl]-1,3-thiazol-2-yl}azetidine (260 mg, 0.500 mmol) (obtained as described in Reference Example 51) in dimethylformamide (13 ml) was added hydrazine acetate (55 mg, 0.600 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (297 mg, 0.500 mmol) in acetonitrile (15 ml) was added dropwise into the resulting mixture in an ice bath under an atmosphere of nitrogen, followed by the addition of diisopropylethylamine (348 μl, 2.00 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (9:1) to afford p-nitrobenzyl (1R,5S,6S)-2-(1-{4-[1-(p-nitrobenzyloxycarbonyl)-piperidin-4-ylcarbamoyl]-1,3-thiazol-2-yl}azetidin-3-yl)thio-6-[(R)-1-hydroxyethyl]-1-methylcarbapen-2-em-3-carboxylate (348 mg, yield 85%) as a pale yellow solid.

$^1$H-NMR (400 MHz, CDCl$_3$): δ (ppm) 8.23 (4H, d, J=8.8 Hz), 7.66 (2H, d, J=8.8 Hz), 7.52 (2H, d, J=8.8 Hz), 7.43 (1H, s), 7.05–7.01 (1H, br d, J=8.8 Hz), 5.51 (1H, d, J=13.7 Hz), 5.25 (1H, d, J=13.7 Hz), 5.23 (2H, s), 4.52–4.46 (2H, m), 4.31–4.25 (3H, m), 4.23–4.04 (3H, m), 4.05 (2H, dt, J=8.8, 5.9 Hz), 3.30 (1H, dd, J=2.4, 7.3 Hz), 3.21 (1H, dq, J=6.8, 8.8 Hz), 3.11–2.95 (2H, m), 2.07–2.00 (2H, m), 1.55–1.41 (2H, m), 1.38 (3H, d, J=6.8 Hz), 1.28 (3H, d, J=5.9 Hz).

(2) (1R,5S,6S)-2-{1-[4-(piperidin-4-ylcarbamoyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-(1-{4-[1-(p-nitrobenzyloxycarbonyl)-piperidin-4-ylcarbamoyl]-1,3-thiazol-2-yl}azetidin-3-yl)thio-6-[(R)-1-hydroxyethyl]-1-methylcarbapen-2-em-3-carboxylate (340 mg, 0.414 mmol) (obtained as described in Example 56(1)) in a mixture of tetrahydrofuran (17 ml) and distilled water (17 ml) was subjected to catalytic hydrogenation in the presence of 10% palladium on charcoal (340 mg) at room temperature for 4.5 hours. After checking the completion of the reaction, the reaction mixture was filtered and to the filtrate were added ethyl acetate and distilled water. The mixture was shaken in a separatory funnel. The aqueous layer was separated and concentrated under reduced pressure. The residue was purified by chromatography on a Cosmosil column (eluant: distilled water→distilled water:acetonitrile (8:2)) and the eluate was lyophilized to afford the desired compound (1R,5S,6S)-2-{1-[4-(piperidin-4-ylcarbamoyl)-1,3-thiazol-2-yl]azetidin-3-yl}thio-6-[(R)-1-hydroxyethyl]-1-methylcarbapen-2-em-3-carboxylic acid (70 mg, yield 33%) as a white solid.

$^1$H-NMR (400 MHz, D$_2$O): δ (ppm) 7.50 (1H, s), 4.55 (2H, t, J=8.2 Hz), 4.36–4.29 (1H, m), 4.24 (1H, dq, J=6.2, 6.4 Hz), 4.17 (1H, dd, J=2.2, 9.1 Hz), 4.17–4.08 (1H, m), 4.03 (1H, dd, J=5.0, 8.3 Hz), 3.53 (2H, dt, J=13.3, 3.1 Hz), 3.43 (1H, dd, J=2.2, 6.2 Hz), 3.25 (1H, dq, J=9.1, 7.2 Hz), 3.17 (2H, dt, J=12.8, 2.9 Hz), 2.20 (1H, dd, J=2.9, 14.2 Hz), 1.93–1.80 (2H, m), 1.30 (3H, d, J=6.4 Hz), 1.19 (3H, d, J=7.2 Hz).

IR (KBr): 1754, 1658, 1602, 1545, 1385, 1315 cm$^{-1}$.

Mass spectrum (FAB$^+$): m/z: 508 [M+H]$^+$.

High-resolution mass spectrum (FAB$^+$): calculated for C$_{22}$H$_{30}$N$_5$O$_5$S$_2$: 508.1688, Found: 508.1693 [M+H]$^+$.

Elemental analysis: C$_{22}$H$_{29}$N$_5$O$_5$S$_2$.3H$_2$O. Calculated for: C, 47.05%; H, 6.28%; N, 12.47%; S, 11.42%. Found: C, 47.07%; H, 6.38%; N, 12.37%; S, 11.14%.

EXAMPLE 57

(1R,5S,6S)-2-{1-[4-((3S)-pyrrolidin-3-ylcarbamoyl)-1,3-thiazol-2-yl]azetidin-3-yl}thio-6-[(R)-1-hydroxyethyl]-1-methylcarbapen-2-em-3-carboxylic acid

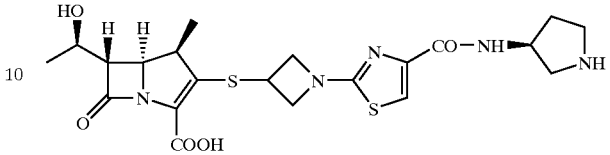

(1) p-Nitrobenzyl (1R,5S,6S)-2-(1-{4-[(3S)-1-(p-nitrobenzyloxycarbonyl)-pyrrolidin-3-ylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(3S)-1-(p-nitrobenzyloxycarbonyl)-pyrrolidin-3-ylcarbamoyl]-1,3-thiazol-2-yl}azetidine (280 mg, 0.554 mmol) (obtained as described in Reference Example 52) in dimethylformamide (14 ml) was added hydrazine acetate (61 mg, 0.665 mmol) at room temperature under an atmosphere of nitrogen and the mixture was stirred for 2 hours. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (329 mg, 0.554 mmol) in acetonitrile (16 ml) was added dropwise into the resulting mixture in an ice bath under an atmosphere of nitrogen, followed by the addition of diisopropylethylamine (356 μl, 2.22 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (9:1)) to afford p-nitrobenzyl (1R,5S,6S)-2-(1-{4-[(3S)-1-(p-nitrobenzyloxycarbonyl)-pyrrolidin-3-ylcarbamoyl]-1,3-thiazol-2-yl}azetidin-3-yl)thio-6-[(R)-1-hydroxyethyl]-1-methylcarbapen-2-em-3-carboxylate (399 mg, yield 89%) as a pale yellow solid.

$^1$H-NMR (400 MHz, CDCl$_3$): δ (ppm) 8.23 (2H, d, J=8.8 Hz), 8.20 (2H, d, J=8.8 Hz), 7.66 (2H, d, J=8.8 Hz), 7.53 (2H, dd, J=8.8, 13.7 Hz), 7.45 (1H, s), 7.17–7.12 (1H, br t, J=7.8 Hz), 5.51 (1H, d, J=13.7 Hz), 5.25 (1H, d, J=13.7 Hz), 5.30–5.18 (2H, m), 4.68–4.59 (1H, m), 4.54–4.46 (2H, m), 4.32–4.24 (3H, m), 4.09–4.00 (2H, m), 3.84–3.76 (1H, m), 3.65–3.53 (2H, m), 3.46–3.40 (1H, m), 3.30 (1H, dd, J=2.9, 6.8 Hz), 3.22 (1H, dq, J=8.8, 6.6 Hz), 2.32–2.22 (1H, m), 2.09–1.94 (1H, m), 1.38 (3H, d, J=6.8 Hz), 1.28 (3H, d, J=6.8 Hz).

(2) (1R,5S,6S)-2-{1-[4-((3S)-pyrrolidin-3-ylcarbamoyl)-1,3-thiazol-2-yl]azetidin-3yl}thio-6-[(R)-1-hydroxyethyl]-1-methylcarbapen-2-em-3-carboxylic acid p-Nitrobenzyl (1R,5S,6S)-2-(1-{4-[(3S)-1-(p-nitrobenzyloxycarbonyl)-pyrrolidin-3-ylcarbamoyl]-1,3-thiazol-2-yl}azetidin-3-yl)thio-6-[(R)-1-hydroxyethyl]-1-methylcarbapen-2-em-3-carboxylate (390 mg, 0.483 mmol) (obtained as described in Example 57(1)) in a mixture of tetrahydrofuran (20 ml) and distilled water (20 ml) was subjected to catalytic hydrogenation in the presence of 20% palladium hydroxide on charcoal (390 mg) at room temperature for 4.5 hours. After checking the completion of the reaction, the reaction mixture was filtered and to the filtrate were added ethyl acetate and distilled water. The mixture was shaken in a separatory funnel. The aqueous layer was separated and concentrated under reduced pressure. The residue was purified by chromatography on a Cosmosil column (eluant: distilled water→distilled water:acetonitrile (76:24)) and the eluate was lyophilized to afford the desired compound (1R,5S,6S)-2-{1-[4-((3S)-pyrrolidin-3-ylcarbamoyl)-1,3-thiazol-2-yl]azetidin-3-yl}thio-6-[(R)-1-hydroxyethyl]-1-methylcarbapen-2-em-3-carboxylic acid (90 mg, yield 38%) as a white solid.

$^1$H-NMR (400 MHz, D$_2$O): δ (ppm) 7.52 (1H, s), 4.69–4.62 (1H, m), 4.59–4.50 (2H, m), 4.37–4.39 (1H, m), 4.22 (1H, dq, J=6.4, 6.4 Hz), 4.11 (1H, dd, J=2.4, 9.0 Hz), 4.07–4.01 (2H, m), 3.65–3.55 (2H, m), 3.48–3.39 (3H, m), 3.21 (1H, dq, J=9.0, 7.2 Hz), 2.50–2.40 (1H, m), 2.23–2.14 (1H, m), 1.30 (3H, d, J=6.4 Hz), 1.18 (3H, d, J=7.2 Hz).

IR (KBr): 1754, 1654, 1597, 1545, 1386,1313 cm$^{-1}$.

Mass spectrum (FAB$^+$): m/z: 494 [M+H]$^+$.

High-resolution mass spectrum (FAB$^+$): calculated for C$_{21}$H$_{28}$N$_5$O$_5$S$_2$: 494.1532, Found: 494.1529 [M+H]$^+$.

Elemental analysis: C$_{21}$H$_{27}$N$_5$O$_5$S$_2$.7/3H$_2$O. Calculated for: C, 47.09%; H, 5.96%; N, 13.08%; S, 11.97%. Found: C, 47.04%; H, 5.95%; N, 13.04%; S, 11.83%.

EXAMPLE 58

(1R,5S,6S)-2-{1-[4-((3R)-pyrrolidin-3-ylcarbamoyl)-1,3-thiazol-2-yl]azetidin-3-yl}thio-6-[(R)-1-hydroxyethyl]-1-methylcarbapen-2-em-3-carboxylic acid

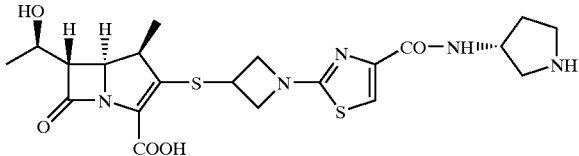

(1) p-Nitrobenzyl (1R,5S,6S)-2-(1-{4-[(3R)-1-(p-nitrobenzyloxycarbonyl)-pyrrolidin-3-ylcarbamoyl]-1,3-thiazol-2-yl}azetidin-3-yl}thio-6-[(R)-1-hydroxyethyl]-1-methylcarbapen-2-em-3-carboxylate To a solution of 3-acetylthio-1-{4-[(3R)-1-(p-nitrobenzyloxycarbonyl)-pyrrolidin-3-ylcarbamoyl]-1,3-thiazol-2-yl}azetidine (280 mg, 0.554 mmol) (obtained as described in Reference Example 53) in dimethylformamide (14 ml) was added hydrazine acetate (61 mg, 0.665 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (329 mg, 0.554 mmol) in acetonitrile (16 ml) was added dropwise into the resulting mixture in an ice bath under an atmosphere of nitrogen, followed by the addition of diisopropylethylamine (386 µl, 2.22 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (9:1)) to afford p-nitrobenzyl (1R,5S,6S)-2-(1-{4-[(3R)-1-(p-nitrobenzyloxycarbonyl)-pyrrolidin-3-ylcarbamoyl]-1,3-thiazol-2-yl}azetidin-3-yl}thio-6-[(R)-1-hydroxyethyl]-1-methylcarbapen-2-em-3-carboxylate (416 mg, yield 93%) as a pale yellow solid.

$^1$H-NMR (400 MHz, CDCl$_3$): δ (ppm) 8.23 (2H, d, J=8.8 Hz), 8.19 (2H, d, J=8.8 Hz), 7.66 (2H, d, J=8.8 Hz), 7.53 (2H, dd, J=8.8, 15.6 Hz), 7.45 (1H, s), 7.17–7.11 (1H, br s), 5.51 (1H, d, J=13.8 Hz), 5.30–5.18 (3H, m), 4.67–4.58 (1H, m), 4.53–4.47 (2H, m), 4.32–4.23 (3H, m), 4.06 (2H, dt, J=8.8, 5.9 Hz), 3.81–3.76 (1H, m), 3.65–3.53 (2H, m), 3.47–3.40 (1H, m), 3.30 (1H, dd, J=2.9, 6.8 Hz), 3.22 (1H, dq, J=8.8, 7.8 Hz), 2.32–2.25 (1H, m), 2.09–1.95 (1H, m), 1.39 (3H, d, J=5.9 Hz), 1.28 (3H, d, J=7.8 Hz).

(2) (1R,5S,6S)-2-{1-[4-((3R)-pyrrolidin-3-ylcarbamoyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-(1-{4-[(3R)-1-(p-nitrobenzyloxycarbonyl)-pyrrolidin-3-ylcarbamoyl]-1,3-thiazol-2-yl}azetidin-3-yl)thio-6-[(R)-1-hydroxyethyl]-1-methylcarbapen-2-em-3-carboxylate (410 mg, 0.508 mmol) (obtained as described in Example 58(1)) in a mixture of tetrahydrofuran (21 ml) and distilled water (21 ml) was subjected to catalytic hydrogenation in the presence of 20% palladium hydroxide on charcoal (410 mg) at room temperature for 4.5 hours. After checking the completion of the reaction, the reaction mixture was filtered and to the filtrate were added ethyl acetate and distilled water. The mixture was shaken in a separatory funnel. The aqueous layer was separated, washed with the above-mentioned mixed solvent and concentrated under reduced pressure. The residue was purified by chromatography on a Cosmosil column (eluant: distilled water→distilled water:acetonitrile (76:24)) and the eluate was lyophilized to afford the desired compound (1R,5S,6S)-2-{1-[4-((3R)-pyrrolidin-3-ylcarbamoyl)-1,3-thiazol-2-yl]azetidin-3yl}thio-6-[(R)-1-hydroxyethyl]-1-methylcarbapen-2-em-3-carboxylic acid (101 mg, yield 41%) as a white solid.

$^1$H-NMR (400 MHz, D$_2$O): δ (ppm) 7.52 (1H, s), 4.69–4.62 (1H, m), 4.60–4.52 (2H, m), 4.38–4.30 (1H, m), 4.24 (1H, dq, J=6.3, 6.3 Hz), 4.16 (1H, dd, J=2.3, 8.9 Hz), 4.09–4.02 (2H, m), 3.67–3.54 (2H, m), 3.49–3.40 (3H, m), 3.24 (1H, dq, J=8.9, 7.2 Hz), 2.49–2.40 (1H, m), 2.24–2.14 (1H, m), 1.30 (3H, d, J=6.3 Hz), 1.20 (3H, d, J=7.2 Hz).

IR (KBr): 1756, 1656, 1598, 1544, 1384, 1313 cm$^{-1}$.

Mass spectrum (FAB$^+$): m/z: 494 [M+H]$^+$.

High-resolution mass spectrum (FAB$^+$): calculated for C$_{21}$H$_{28}$N$_5$O$_5$S$_2$: 494.1532, Found: 494.1519 [M+H]$^+$.

Elemental analysis: C$_{21}$H$_{27}$N$_5$O$_5$S$_2$.3H$_2$O. Calculated for: C, 46.06%; H, 6.07%; N, 12.79%; S, 11.71%. Found: C, 46.35%; H, 5.75%; N, 12.82%; S, 11.68%.

EXAMPLE 59

(1R,5S,6S)-2-{1-[4-(azetidin-3-ylcarbamoyl)-1,3-thiazol-2-yl]azetidin-3-yl}thio-6-[(R)-1-hydroxyethyl]-1-methylcarbapen-2-em-3-carboxylic acid

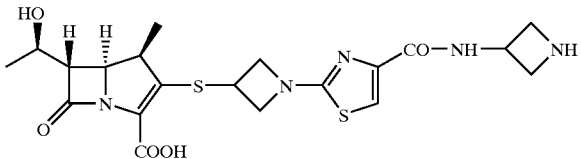

(1) p-Nitrobenzyl (1R,5S,6S)-2-(1-{4-[1-(p-nitrobenzyloxycarbonyl)-azetidin-3-ylcarbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[1-(p-nitrobenzyloxycarbonyl)-azetidin-3-ylcarbamoyl]-1,3-thiazol-2-yl}azetidine (400 mg, 0.814 mmol) (obtained as described in Reference Example 54) in dimethylformamide (20 ml) was added hydrazine acetate (90 mg, 0.977 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (484 mg, 0.814 mmol) in acetonitrile (25 ml) was added dropwise into the resulting mixture in an ice bath under an atmosphere of nitrogen, followed by the addition of diisopropylethylamine (568 μl, 3.26 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (9:1)) to afford p-nitrobenzyl (1R,5S,6S)-2-(1-{4-[1-(p-nitrobenzyloxycarbonyl)-azetidin-3-ylcarbamoyl]-1,3-thiazol-2-yl}azetidin-3-yl)thio-6-[(R)-1-hydroxyethyl]-1-methylcarbapen-2-em-3-carboxylate (496 mg, yield 77%) as a pale yellow solid.

$^1$H-NMR (400 MHz, CDCl$_3$): δ (ppm) 7.54 (1H, s), 8.23 (4H, d, J=8.8 Hz), 8.22 (2H, d, J=8.8 Hz), 7.66 (2H, d, J=8.8 Hz), 7.52 (2H, d, J=8.8 Hz), 7.52–7.47 (1H, m), 7.45 (1H, s), 5.51 (1H, d, J=13.9 Hz), 5.25 (1H, d, J=13.9 Hz), 4.90–4.80 (1H, m), 4.54–4.47 (2H, m), 4.47–4.38 (2H, m), 4.42 (2H, dd, J=8.8, 8.8 Hz), 4.13–4.25 (2H, m), 4.27 (1H, dd, J=2.2, 9.5 Hz), 4.09–3.96 (4H, m), 3.30 (1H, dd, J=2.2, 7.0 Hz), 3.21 (1H, dq, J=9.5, 6.6 Hz), 1.38 (3H, d, J=6.6 Hz). 1.28 (3H, d, J=5.9 Hz).

(2) (1R,5S,6S)-2-{1-[4-(azetidin-3-ylcarbamoyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-(1-{4-[1-(p-nitrobenzyloxycarbonyl)-azetidin-3-ylcarbamoyl]-1,3-thiazol-2-yl}azetidin-3-yl)thio-6-[(R)-1-hydroxyethyl]-1-methylcarbapen-2-em-3-carboxylate (490 mg, 0.617 mmol) (obtained as described in Example 59(1)) in a mixture of tetrahydrofuran (25 ml) and distilled water (25 ml) was subjected to catalytic hydrogenation in the presence of 20% palladium hydroxide on charcoal (490 mg) at room temperature for 4.5 hours. After checking the completion of the reaction, the reaction mixture was filtered and to the filtrate were added ethyl acetate and distilled water. The mixture was shaken in a separatory funnel. The aqueous layer was separated and concentrated under reduced pressure. The residue was purified by chromatography on a Cosmosil column (eluant: distilled water→distilled water:acetonitrile (76:24)) and the eluate was lyophilized to afford the desired compound (1R,5S,6S)-2-{1-[4-(azetidin-3-ylcarbamoyl)-1,3-thiazol-2-yl]azetidin-3-yl}thio-6-[(R)-1-hydroxyethyl]-1-methylcarbapen-2-em-3-carboxylic acid (143 mg, yield 49%) as a white solid.

$^1$H-NMR (400 MHz, D$_2$O): δ (ppm) 7.54 (1H, s), 4.97–4.87 (1H, m), 4.60–4.54 (2H, m), 4.44 (2H, dd, J=11.9, 8.4 Hz), 4.39–4.30 (3H, m), 4.23 (1H, qd, J=6.4, 6.2 Hz), 4.15 (1H, dd, J=9.0, 2.4 Hz), 4.10–4.03 (2H, m), 3.43 (1H, dd, J=6.3, 2.4 Hz), 3.23 (1H, dq, J=9.0, 7.2 Hz), 1.30 (3H, d, J=6.4 Hz), 1.19 (3H, d, J=7.2 Hz).

IR (KBr): 1753, 1655, 1600, 1545, 1387, 1314 cm$^{-1}$.
Mass spectrum (FAB$^+$): m/z: 480 [M+H]$^+$.
High-resolution mass spectrum (FAB$^+$): calculated for C$_{20}$H$_{26}$N$_5$O$_5$S$_2$: 480.1375, Found: 480.1391 [M+H]$^+$.
Elemental analysis: C$_{20}$H$_{25}$N$_5$O$_5$S$_2$.9/4H$_2$O . Calculated for: C, 46.19%; H, 5.72%; N, 13.47%; S, 12.33%. Found: C, 46.06%; H, 5.38%; N, 13.70%; S, 12.33%.

EXAMPLE 60

(1R,5S,6S)-2-{1-[4-(piperazine-1-carbonyl)-1,3-thiazol-2-yl]azetidin-3-yl}thio-6-[(R)-1-hydroxyethyl]-1-methylcarbapen-2-em-3-carboxylic acid

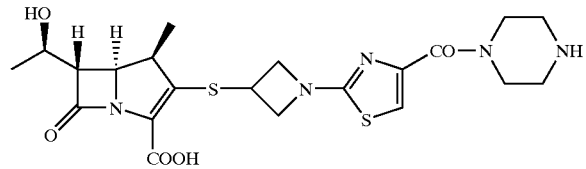

(1) p-Nitrobenzyl (1R,5S,6S)-2-(1-{4-[(4-p-nitrobenzyloxycarbonyl)-piperazine-1-carbonyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(4-p-nitrobenzyloxycarbonyl)-piperazine-1-carbonyl]-1,3-thiazol-2-yl}azetidine (546 mg, 1.07 mmol) (obtained as described in Reference Example 55) in dimethylformamide (15 ml) was added hydrazine acetate (118 mg, 1.29 mmol) in an ice bath under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (636 mg, 1.07 mmol) in acetonitrile (30 ml) was added dropwise into the resulting mixture in an ice bath under an atmosphere of nitrogen, followed by the addition of diisopropylethylamine (0.22 ml, 1.29 mmol). The mixture was stirred for 1 hour while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate-:methanol (20:1)) to afford p-nitrobenzyl (1R,5S,6S)-2-(1-{4-[(4-p-nitrobenzyloxycarbonyl)-piperazine-1-carbonyl]-1,3-thiazol-2-yl}azetidin-3-yl)thio-6-[(R)-1-hydroxyethyl]-1-methylcarbapen-2-em-3-carboxylate (215 mg, yield 29%) as a pale yellow solid.

$^1$H-NMR (400 MHz, CDCl$_3$): δ (ppm) 8.22 (4H, dd, J=8.5, 5.2 Hz), 7.66 (2H, d, J=8.7 Hz), 7.52 (2H, d, J=8.7 Hz), 7.22 (1H, s), 5.51 (1H, d, J=13.8 Hz), 5.25 (1H, d, J=13.8 Hz), 5.25 (2H, s), 4.50 (1H, t, J=8.0 Hz), 4.49 (1H, t, J=8.0 Hz), 4.35–4.20 (3H, m), 4.04 (1H, t, J=8.5 Hz), 4.31 (1H, t, J=8.5 Hz), 3.98–3.69 (4H, m), 3.69–3.48 (4H, m), 3.29 (1H, dd, J=6.8, 2.6 Hz), 3.20 (1H, dq, J=9.2, 7.2 Hz), 1.36 (3H, d, J=6.3 Hz), 1.26 (3H, d, J=7.5 Hz).

(2) (1R,5S,6S)-2-{1-[4-(piperazine-1-carbonyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-(1-{4-[(4-p-nitrobenzyloxycarbonyl)-piperazine-1-carbonyl]-1,3-thiazol-2-yl}azetidin-3-yl)thio-6-[(R)-1-hydroxyethyl]-1-methylcarbapen-2-em-3-carboxylate (539 mg, 0.79 mmol) (obtained as described in Example 60(1)) in a mixture of tetrahydrofuran (30 ml) and distilled water (30 ml) was subjected to catalytic hydrogenation in the presence of 7.5% palladium on charcoal (539 mg) in a water bath (35° C.) for 2 hours. After checking the completion of the reaction, the reaction mixture was filtered and to the filtrate were added ethyl acetate and distilled water. The mixture was shaken in a separatory funnel. The aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water→8% acetonitrile in distilled water→10% acetonitrile in distilled water→13% acetonitrile in distilled water→16% acetonitrile in distilled water→20% acetonitrile in distilled water) and the eluate was lyophilized to afford the desired compound (1R,5S,6S)-2-{1-[4-(piperazine-1-carbonyl)-1,3-thiazol-2-yl]azetidin-3-yl}thio-6-[(R)-1-hydroxyethyl]-1-methylcarbapen-2-em-3-carboxylic acid (107 mg, yield 27%) as a white solid.

$^1$H-NMR (400 MHz, D$_2$O): δ (ppm) 7.23 (1H, s), 4.56 (2H, t, J=8.4 Hz), 4.40–4.30 (1H, m), 4.24 (1H, quint., J=6.2 Hz), 4.20 (1H, dd, J=8.7, 2.2 Hz), 4.03 (2H, dd, J=8.7, 2.2 Hz), 3.95 (4H, t, J=5.2 Hz), 3.43 (1H, dd, J=6.2, 2.4 Hz), 3.40–3.29 (4H, m), 3.24 (1H, dq, J=8.7, 7.3 Hz), 1.29 (3H, d, J=6.3 Hz), 1.19 (3H, d, J=7.9 Hz).

IR (KBr): 3415.3, 1759.7, 1620.9, 1536.0, 1456.0, 1431.9, 1384.6, 1313.3, 1246.8 cm$^{-1}$.

Mass spectrum (FAB$^+$): m/z: 494 [M+H]$^+$.

High-resolution mass spectrum (ESI$^+$): calculated for C$_{21}$H$_{28}$N$_5$O$_5$S$_2$: 494.2532, Found: 494.1529 [M+H]$^+$.

EXAMPLE 61

(1R,5S,6S)-2-{1-[4-((2-aminoethyl)carbamoyl)-1,3-thiazol-2-yl]azetidin-3-yl}thio-6-[(R)-1-hydroxyethyl]-1-methylcarbapen-2-em-3-carboxylic acid

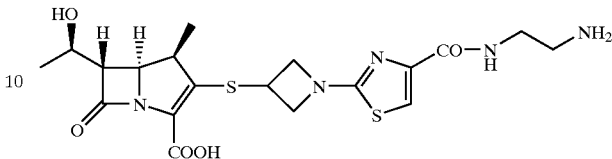

(1) p-Nitrobenzyl (1R,5S,6S)-2-(1-{4-[(2-(p-nitrobenzyloxycarbonylamino)ethyl)carbamoyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(2-(p-nitrobenzyloxycarbonylamino)ethyl)carbamoyl]-1,3-thiazol-2-yl}azetidine (330.6 mg, 0.68 mmol) (obtained as described in Reference Example 56) in dimethylformamide (17 ml) was added hydrazine acetate (82 mg, 0.89 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (426 mg, 0.72 mmol) in acetonitrile (21 ml) was added dropwise into the resulting mixture in an ice bath under an atmosphere of nitrogen, followed by the addition of diisopropylethylamine (0.5 ml, 2.9 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: toluene:acetonitrile (1:2)) to afford p-nitrobenzyl (1R,5S,6S)-2-(1-{4-[(2-(p-nitrobenzyloxycarbonylamino)ethyl)carbamoyl]-1,3-thiazol-2-yl}azetidin-3-yl)thio-6-[(R)-1-hydroxyethyl]-1-methylcarbapen-2-em-3-carboxylate (348.1 mg, yield 66%) as a pale yellow solid.

$^1$H-NMR (500 MHz, CDCl$_3$): δ (ppm) 8.23 (2H, d, J=7.8 Hz), 8.14 (2H, d, J=8.8 Hz), 7.66 (2H, d, J=7.8 Hz), 7.47 (2H, d, J=8.8 Hz), 7.43 (1H, s), 7.38 (1H, t, J=6.3 Hz), 5.51 (1H, d, J=13.7 Hz), 5.51 (1H, t, J=6.3 Hz), 5.25 (1H, d, J=13.7 Hz), 5.18.(2H, s), 4.48 (1H, t, J=8.3 Hz), 4.46 (1H, t, J=8.3 Hz), 4.32–4.24 (3H, m), 4.05 (1H, dd, J=8.3, 5.6 Hz), 4.03 (1H, dd, J=8.3, 5.6 Hz), 3.55 (2H, d, 6.3 Hz), 3.44 (2H, q, 6.3 Hz), 3.30 (1H, dd, J=6.9, 1.9 Hz), 3.22 (1H, dq, J=8.8, 6.5 Hz), 1.73 (1H, br s), 1.38 (3H, d, J=6.5 Hz), 1.28 (3H, d, J=6.5 Hz).

(2) (1R,5S,6S)-2-{1-[4-((2-aminoethyl)carbamoyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-(1-{4-[(2-(p-nitrobenzyloxycarbonylamino)ethyl)carbamoyl]-1,3-thiazol-2-yl}azetidin-3-yl)thio-6-[(R)-1-hydroxyethyl]-1-methylcarbapen-2-em-3-carboxylate (328.4 mg, 0.42 mmol) (obtained as described in Example 61(1)) in a mixture of tetrahydrofuran (16.4 ml) and distilled water (8.2 ml) was subjected to catalytic hydrogenation in the presence of 20% palladium hydroxide on charcoal (328.4 mg) in a water bath (30° C.) for 2 hours. After checking the completion of the reaction, the reaction mixture was filtered and to the filtrate were added ethyl acetate-tetrahydrofuran (1:1) and distilled water. The mixture was shaken in a separatory funnel. The aqueous layer was separated, washed with the above-mentioned mixed solvent, and concentrated under reduced pressure. The residue was purified by chromatography on a Cosmosil column (eluant: distilled water→5% acetonitrile in distilled water→10% acetonitrile in distilled water→15% acetonitrile in distilled water) and the eluate was lyophilized to afford the desired compound (1R,5S,6S)-2-{1-[4-((2-aminoethyl)carbamoyl)-1,3-thiazol-2-yl]azetidin-3-yl}thio-6-[(R)-1-hydroxyethyl]-1-methylcarbapen-2-em-3-carboxylic acid (96.4 mg, yield 49%) as a white solid.

$^1$H-NMR (400 MHz, D$_2$O): δ (ppm) 7.37 (1H, s), 4.42 (1H, t, J=8.4 Hz), 4.42 (1H, t, J=8.4 Hz), 4.24–4.16 (1H, m), 4.10 (1H, quintet, J=6.6 Hz), 4.00 (1H, dd, J=8.9, 2.4 Hz), 3.94 (1H, dd, J=8.4, 4.8 Hz), 3.90 (1H, dd, J=8.4, 4.8 Hz), 3.57 (2H, t, J=5.9 Hz), 3.26 (1H, dd, J=6.6, 2.4 Hz), 3.12 (2H, t, J=5.9 Hz), 3.08 (1H, dq, J=8.9, 7.3 Hz), 1.16 (3H, d, J=6.6 Hz), 1.05 (3H, d, J=7.3 Hz).

IR (KBr): 3383, 1755, 1652, 1599, 1547, 1387, 1314 cm$^{-1}$.

Mass spectrum (FAB$^+$): m/z: 468 [M+H]$^+$.

High-resolution mass spectrum (FAB$^+$): calculated for C$_{19}$H$_{26}$O$_5$N$_5$S$_2$: 468.1366, Found: 468.1365 [M+H]$^+$.

EXAMPLE 62

(1R,5S,6S)-2-{1-[4-(3-aminoazetidine-1-carbonyl)-1,3-thiazol-2-yl]azetidin-3-yl}thio-6-[(R)-1-hydroxyethyl]-1-methylcarbapen-2-em-3-carboxylic acid

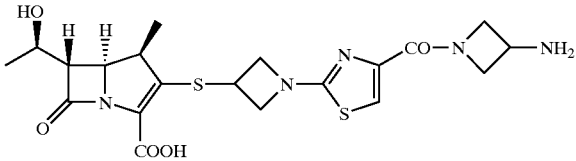

(1) p-Nitrobenzyl (1R,5S,6S)-2-(1-{4-[3-(p-nitrobenzyloxycarbonylamino)azetidine-1-carbonyl]-1,3-thiazol-2-yl}azetidin-3-yl}thio-6-[(R)-1-hydroxyethyl]-1-methylcarbapen-2-em-3-carboxylate To a solution of 3-acetylthio-1-{4-[3-(p-nitrobenzyloxycarbonylamino)azetidine-1-carbonyl]-1,3-thiazol-2-yl}azetidine (390 mg, 0.793 mmol) (obtained as described in Reference Example 57) in dimethylformamide (20 ml) was added hydrazine acetate (88 mg, 0.952 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (471 mg, 0.793 mmol) in acetonitrile (24 ml) was added dropwise into the resulting mixture in an ice bath under an atmosphere of nitrogen, followed by the addition of diisopropylethylamine (552 μl, 3.17 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate:methanol (93:7)) to afford p-nitrobenzyl (1R,5S,6S)-2-(1-{4-[3-(p-nitrobenzyloxycarbonylamino)-azetidine-1-carbonyl]-1,3-thiazol-2-yl}azetidin-3-yl}thio-6-[(R)-1-hydroxyethyl]-1-methylcarbapen-2-em-3-carboxylate (587 mg, yield 93%) as a pale yellow solid.

$^1$H-NMR (400 MHz, CDCl$_3$): δ (ppm) 8.23 (4H, d, J=8.8 Hz), 7.66 (2H, d, J=8.8 Hz), 7.51 (2H, d, J=8.8 Hz), 7.46 (2H, s), 5.51 (1H, d, J=13.9 Hz), 5.40–5.37 (1H, m), 5.25 (1H, d, J=13.9 Hz), 5.21 (2H, s), 4.92–4.86 (1H, m), 4.59–4.42 (4H, m), 4.40–4.32 (1H, m), 4.30–4.23 (3H, m), 4.04–3.92 (3H, m), 3.30 (1H, dd, J=2.2, 6.6 Hz), 3.21 (1H, dq, J=7.3, 9.0 Hz), 1.38 (3H, d, J=6.6 Hz), 1.27 (3H, d, J=7.3 Hz).

(2) (1R,5S,6S)-2-{1-[4-(3-aminoazetidino-1-carbonyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-{1-{4-[3-(p-nitrobenzyloxycarbonyl)azetidine-1-carbonyl]-1,3-thiazol-2-yl}azetidin-3-yl}thio-6-[(R)-1-hydroxyethyl]-1-methylcarbapen-2-em-3-carboxylate (580 mg, 0.731 mmol) (obtained as described in Example 62(1)) in a mixture of tetrahydrofuran (30 ml) and distilled water (30 ml) was subjected to catalytic hydrogenation in the presence of 10% palladium on charcoal (580 mg) at room temperature for 5 hours. After checking the completion of the reaction, the reaction mixture was filtered and to the filtrate were added ethyl acetate and distilled water. The mixture was shaken in a separatory funnel. The aqueous layer was separated, washed with the above-mentioned mixed solvents, and concentrated under reduced pressure. The residue was purified by chromatography on a Cosmosil column (eluant: distilled water→distilled water:acetonitrile (8:2)) and the eluate was lyophilized to afford the desired compound (1R,5S,6S)-2-{1-[4-(3-aminoazetidine-1-carbonyl)-1,3-thiazol-2-yl]azetidin-3-yl}thio-6-[(R)-1-hydroxyethyl]-1-methylcarbapen-2-em-3-carboxylic acid (135 mg, yield 39%) as a white solid.

$^1$H-NMR (400 MHz, D$_2$O): δ (ppm) 7.45 (1H, s), 4.98–4.85 (1H, m), 4.64–4.49 (4H, m), 4.38–4.30 (1H, m), 4.31–4.17 (4H, m), 4.07–4.00 (2H, m), 3.44 (1H, dd, J=2.0, 5.9 Hz), 3.24 (1H, qd, J=7.2, 8.5 Hz), 1.30 (3H, d, J=6.4 Hz), 1.20 (3H, d, J=7.2 Hz).

IR (KBr): 1756, 1607, 1537, 1449, 1387, 1309, 1291, 1261 cm$^{-1}$.

Mass spectrum (FAB$^+$): m/z: 502 [M+Na]$^+$.

High-resolution mass spectrum (ESI$^+$): calculated for C$_{20}$H$_{25}$N$_5$O$_5$S$_2$Na: 502.1195, Found: 502.1179 [M+Na]$^+$.

Elemental analysis: C$_{20}$H$_{25}$N$_5$O$_5$S$_2$.3H$_2$O. Calculated for: C, 45.02%; H, 5.86%; N, 13.12%; S, 12.02%. Found: C, 44.27%; H, 5.28%; N, 13.26%; S, 12.68%.

EXAMPLE 63

(1R,5S,6S)-2-(1-{4-[N-(2-aminoethyl)-N-methyl-carbamoyl]-1,3-thiazol-2-yl}azetidin-3-yl)thio-6-[(R)-1-hydroxyethyl]-1-methylcarbapen-2-em-3-carboxylic acid

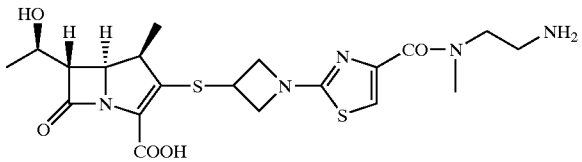

(1) p-Nitrobenzyl (1R,5S,6S)-2-[1-(4-{N-methyl-N-[2-(p-nitrobenzyloxycarbonylamino)ethyl]carbamoyl}-1,3-thiazol-2-yl)azetidin-3-yl]thio-6-[(R)-1-hydroxyethyl]-1-methylcarbapen-2-em-3-carboxylate To a solution of 3-acetylthio-1-(4-{N-methyl-N-[2-(p-nitrobenzyloxycarbonylamino)-ethyl]carbamoyl}-1,3-thiazol-2-yl)azetidine (348.9 mg, 0.71 mmol) (obtained as described in Reference Example 58) in dimethylformamide (17.5 ml) was added hydrazine acetate (85.2 mg, 0.93 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (420.3 mg, 0.71 mmol) in acetonitrile (21 ml) was added dropwise into the resulting mixture in an ice bath under an atmosphere of nitrogen, followed by the addition of diisopropylethylamine (0.49 ml, 2.8 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: toluene:acetonitrile (1:2)) to afford p-nitrobenzyl (1R,5S,6S)-2-[1-(4-{N-methyl-N-[2-(p-nitrobenzyloxycarbonylamino)ethyl]carbamoyl}-1,3-thiazol-2-yl)azetidin-3-yl]thio-6-[(R)-1-hydroxyethyl]-1-methylcarbapen-2-em-3-carboxylate (267.5 mg, yield 47%) as a pale yellow solid.

$^1$H-NMR (400 MHz, CDCl$_3$): δ (ppm) 8.23 (4H, d, J=8.8 Hz), 7.66 (2H, d, J=8.8 Hz), 7.56–7.46 (3H, m including 2H, d, at 7.49 ppm, J=8.8 Hz), 7.22 (0.7H, s), 7.21 (0.3H, s), 5.52 (1H, d, J=13.9 Hz), 5.25 (1H, d, J=13.9 Hz), 5.172 (2H, s), 4.52–4.38 (2H, m), 4.32–4.10 (3H, m), 4.10–3.98 (2H, m), 3.74–3.58 (2H, m), 3.56–3.40 (2H, m), 3.30–3.26 (1H, m), 3.16–3.06 (1H, m), 3.24 (0.9H, s), 3.04 (2.1H, s), 1.77 (1H, d, J=4.4 Hz), 1.38 (3H, d, J=5.9 Hz), 1.22 (3H, J=7.3 Hz).

(2) (1R,5S,6S)-2-(1-{4-[N-(2-aminoethyl)-N-methyl-carbamoyl]-1,3-thiazol-2-yl}azetidin-3-yl)thio-6-[(R)-1-hydroxyethyl]-1-methylcarbapen-2-em-3-carboxylic acid p-Nitrobenzyl (1R,5S,6S)-2-[1-(4-{N-methyl-N-[2-(p-nitrobenzyloxycarbonylamino)ethyl]carbamoyl}-1,3-thiazol-2-yl)azetidin-3-yl]thio-6-[(R)-1-hydroxyethyl]-1-methylcarbapen-2-em-3-carboxylate (267.5 mg, 0.33 mmol) (obtained as described in Example 63(1)) in a mixture of tetrahydrofuran (14 ml) and distilled water (6.7 ml) was subjected to catalytic hydrogenation in the presence of 20% palladium hydroxide on charcoal (300 mg) at 30° C. in a water bath for 1.5 hours. After checking the completion of the reaction, the reaction mixture was filtered and to the filtrate were added ethyl acetate-tetrahydrofuran (1:1) and distilled water. The mixture was shaken in a separatory funnel. The aqueous layer was separated, washed with the above-mentioned mixed solvent, and concentrated under reduced pressure. The residue was purified by chromatography on a Cosmosil column (eluant: distilled water→5% acetonitrile in distilled water→10% acetonitrile in distilled water→15% acetonitrile in distilled water), and the eluate was lyophilized to afford the desired compound (1R,5S,6S)-2-(1-{4-[N-(2-aminoethyl)-N-methyl-carbamoyl]-1,3-thiazol-2-yl}azetidin-3-yl)thio-6-[(R)-1-hydroxyethyl]-1-methylcarbapen-2-em-3-carboxylic acid (81.6 mg, yield 51%) as a white solid.

$^1$H-NMR (400 MHz, D$_2$O): δ (ppm) 7.11 (0.4H, s), 7.05 (0.6H, s), 4.43 (2H, t, J=8.8 Hz), 4.26–4.18 (1H, m), 4.12 (1H, quintet, J=5.9 Hz), 4.08 (1H, dd, J=8.8, 2.3 Hz), 3.91 (2H, dd, J=8.8, 4.9 Hz), 3.70 (2H, t, 5.9 Hz), 3.31 (1H, dd, J=5.9, 2.3 Hz), 3.23–3.16 (2H, m), 3.12 (1H, dq, J=8.8, 7.8 Hz), 3.00 (1.8H, s), 2.94 (1.2H, s), 1.17 (3H, d, J=5.9 Hz), 1.07 (3H, d, J=7.8 Hz).

IR (KBr): 3419, 2966, 1754, 1607, 1540, 1470, 1391, 1315 cm$^{-1}$.

Mass spectrum (FAB$^+$): m/z: 482 [M+H]$^+$.

EXAMPLE 64

(1R,5S,6S)-2-(1-{4-[N-(2-hydroxyethyl)-N-isopropyl-carbamoyl]-1,3-thiazol-2-yl}azetidin-3-yl)thio-6-[(R)-1-hydroxyethyl]-1-methylcarbapen-2-em-3-carboxylic acid sodium salt

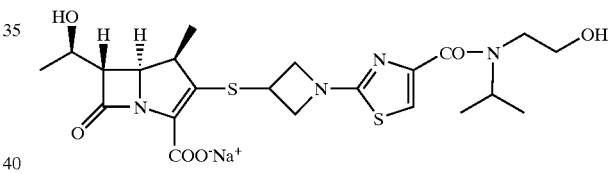

(1) p-Nitrobenzyl (1R,5S ,6S)-2-[1-(4-{N-[2-(t-butyldimethylsilyloxy)ethyl]-N-isopropyl-carbamoyl}-1,3-thiazol-2-yl)azetidin-3-yl]thio-6-[(R)-1-hydroxyethyl]-1-methylcarbapen-2-em-3-carboxylate To a solution of 3-acetylthio-1-(4-{N-[2-(t-butyldimethylsilyloxy)-ethyl]-N-isopropyl-carbamoyl}-1,3-thiazol-2-yl)azetidine (618 mg, 1.35 mmol) (obtained as described in Reference Example 59) in dimethylformamide (30 ml) was added hydrazine acetate (149 mg, 1.62 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (963 mg, 1.62 mmol) in acetonitrile (60 ml) was added dropwise into the resulting mixture in an ice bath under an atmosphere of nitrogen, followed by the addition of diisopropylethylamine (0.94 ml, 5.40 mmol). The mixture was stirred for 8 hours gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate:methanol (10:1)) to afford p-nitrobenzyl (1R,5S,6S)-2-{[1-(4-{N-[2-(t-butyidimethylsilyloxy)ethyl]-N-isopropyl-carbamoyl}-1,3-thiazol-2-yl)azetidin-3-yl]thio-6-[(R)-1-hydroxyethyl]-1-methylcarbapen-2-em-3-carboxylate (310 mg, yield 30%) as a pale yellow solid.

$^1$H-NMR (400 MHz, CDCl$_3$): δ (ppm) 8.21 (2H, d, J=8.4 Hz), 7.64 (2H, d, J=8.4 Hz), 7.12–6.90 (1H, m), 5.45 (1H, d, J=13.7 Hz), 5.25 (1H, d, J=13.7 Hz), 4.69–4.18 (6H, m including 4.45 (2H, dd, J=7.9, 6.5 Hz), 4.24 (1H, quint., J=6.3 Hz), 4.22 (1H, dd, J=9.0, 2.5 Hz)), 3.89–3.72 (1H, m), 3.72–3.46 (2H, m), 3.46–3.32 (1H, m), 3.26 (1H, dd, J=6.3, 2.5 Hz), 3.17 (1H, dq, J=9.0, 7.3 Hz), 1.36 (3H, d, J=6.3 Hz), 1.31–1.09 (9H, m including 1.25 (3H, d, J=7.2 Hz)), 0.87 (9H, s), 0.06 (6H, d, J=2.9 Hz).

(2) p-Nitrobenzyl (1R,5S,6S)-2-(1-{4-[N-(2-hydroxyethyl)-N-isopropyl-carbamoyl]-1,3-thiazol-2-yl}azetidin-3-yl)thio-6-[(R)-1-hydroxyethyl]-1-methylcarbapen-2-em-3-carboxylate p-Nitrobenzyl (1R,5S,6S)-2-[1-(4-{N-[2-(t-butyldimethylsilyloxy)ethyl]-N-isopropyl-carbamoyl}-1,3-thiazol-2-yl)azetidin-3-yl]thio-6-[(R)-1-hydroxyethyl]-1-methylcarbapen-2-em-3-carboxylate (4.47 g, 5.88 mmol) (obtained as described in Example 64(1)) in a mixture of tetrahydrofuran (220 ml) was added to acetic acid (0.40 ml, 7.06 mmol) and 1M tetrabutylammonium fluoride in tetrahydrofuran solution (7.06 ml, 7.06 mmol) and the mixture was stirred at room temperature for 1 day. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with saturated aqueous sodium chloride solution, dried over anhydrous magnesium sulfate, filtered and concentrated under reduced pressure. The residue was purified by chromatography on a silica gel column (eluant: ethyl acetate→ethyl acetate:methanol (10:1)) to afford p-nitrobenzyl (1R,5S,6S)-2-(1-{4-[(2-hydroxyethyl)-isopropyl-carbamoyl]-1,3-thiazol-2-yl}azetidin-3-yl)thio-6-[(R)-1-hydroxyethyl]-1-methylcarbapen-2-em-3-carboxylate (1.79 g, yield 47%) as a pale yellow solid.

$^1$H-NMR (400 MHz, CDCl$_3$): δ (ppm) 8.23 (2H, d, J=8.7 Hz), 7.66 (2H, d, J=8.7 Hz), 7.20 (0.6H, br s), 7.09 (0.4H, br s), 5.50 (1H, d, J=13.8 Hz), 5.26 (1H, d, J=13.8 Hz), 4.62–4.18 (6H, m including 4.49 (2H, t, J=8.4 Hz), 4.26 (1H, dd, J=9.3, 2.6 Hz)), 4.04 (2H, dd, J=8.4, 5.4 Hz), 3.80 (2H, br s), 3.56 (2H, br s), 3.28 (1H, dd, J=7.5, 2.5 Hz), 3.19 (1H, br s), 1.38 (3H, d, J=6.2 Hz), 1.35 (3.6H, br s), 1.26 (3H, d, J=7.3 Hz), 1.21 (2.4H, br s).

(3) (1R,5S,6S)-2-(1-{4-[N-(2-hydroxyethyl)-N-isopropyl-carbamoyl]-1,3-thiazol-2yl}azetidin-3-yl)thio-6-[(R)-1-hydroxyethyl]-1-methylcarbapen-2-em-3-carboxylic acid sodium salt p-Nitrobenzyl (1R,5S,6S)-2-(1-{4-[(2-hydroxyethyl)-isopropyl-carbamoyl]-1,3-thiazol-2-yl}azetidin-3-yl)thio-6-[(R)-1-hydroxyethyl]-1-methylcarbapen-2-em-3-carboxylate (1.79 g, 2.77 mmol) (obtained as described in Example 64(2)) in a mixture of tetrahydrofuran (90 ml) and distilled water (90 ml) was subjected to catalytic hydrogenation in the presence of 7.5% palladium on charcoal (1.79 g) in a water bath (35° C.) for 2 hours. After checking the completion of the reaction, the reaction mixture was filtered and to the filtrate were added sodium hydrogencarbonate (233 mg), ethyl acetate and distilled water. The mixture was shaken in a separatory funnel. The aqueous layer was separated and concentrated under reduced pressure. The residue was purified by chromatography on a Cosmosil column (eluant: distilled water→2% acetonitrile in distilled water→4% acetonitrile in distilled water) and the eluate was lyophilized to afford the desired compound (1R,5S,6S)-2-(1-{4-[(2-hydroxyethyl)-isopropyl-carbamoyl]-1,3-thiazol-2-yl}azetidin-3-yl)thio-6-[(R)-1-hydroxyethyl]-1-methylcarbapen-2-em-3-carboxylic acid sodium salt (897 mg, yield 61%) as a white solid.

$^1$H-NMR (400 MHz, D$_2$O): δ (ppm) 7.08 (0.2H, s), 7.02 (0.8H, s), 4.56 (2H, t, J=8.0 Hz), 4.50–4.40 (0.3H, m), 4.40–4.30 (1H, m), 4.25 (1H, quint., J=6.5 Hz), 4.21 (1H, dd, J=8.4, 2,2 Hz), 4.16–4.06 (0.7H, m), 4.05 (2H, dd, J=8.0, 4.8 Hz), 3.84–3.76 (1H, m), 3.69–3.60 (0.5H, m), 3.60–3.52 (0.5H, m), 3.52 (2H, t, J=6.3 Hz), 3.43 (1H, dd, J=6.5, 2.4 Hz), 3.25 (1H, quint., J=8.4 Hz), 1.42–1.07 (6H, m), 1.30 (3H, d, J=6.3 Hz), 1.20 (3H, d, J=7.1 Hz)).

IR (KBr): 3382.5, 1750.1, 1603.5, 1537.0, 1468.5, 1452.1, 1396.2, 1312.3, 1284.4 cm$^{-1}$.

Mass spectrum (FAB$^+$): m/z: 533 [M+H]$^+$.

High-resolution mass spectrum (ESI$^+$): calculated for C$_{22}$H$_{29}$N$_4$O$_5$S$_2$Na: 533.1504, Found: 533.1489 [M+H]$^+$.

EXAMPLE 65

(1R,5S,6S)-2-(1-{4-[N-(2-aminoethyl)-N-isopropyl-carbamoyl]-1,3-thiazol-2-yl}azetidin-3-yl)thio-6-[(R)-1-hydroxyethyl]-1-methylcarbapen-2-em-3-carboxylic acid

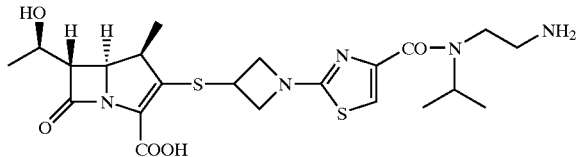

(1) p-Nitrobenzyl (1R,5S,6S)-2-[1-(4-{N-isopropyl-N-[2-(p-nitrobenzyloxycarbonylamino)-ethyl]-carbamoyl}-1,3-thiazol-2-yl)azetidin-3-yl]thio-6-[(R)-1-hydroxyethyl]-1-methylcarbapen-2-em-3-carboxylate To a solution of 3-acetylthio-1-(4-{N-isopropyl-N-[2-(p-nitrobenzyloxycarbonylamino)-ethyl]-carbamoyl}-1,3-thiazol-2-yl)azetidine (746 mg, 1.43 mmol) (obtained as described in Reference Example 60) in dimethylformamide (22 ml) was added hydrazine acetate (158 mg, 1.72 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.02 g, 1.72 mmol) in acetonitrile (45 ml) was added dropwise into the resulting mixture in an ice bath under an atmosphere of nitrogen, followed by the addition of diisopropylethylamine (1.00 ml, 5.72 mmol). The mixture was stirred for 3 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant:

ethyl acetate→ethyl acetate:methanol (10:1)) to afford p-nitrobenzyl (1R,5S,6S)-2-[1-(4-{N-isopropyl-N-[2-(p-nitrobenzyloxycarbonylamino)ethyl]-carbamoyl}-1,3-thiazol-2-yl)azetidin-3-yl]thio-6-[(R)-1-hydroxyethyl]-1-methylcarbapen-2-em-3-carboxylate (610 mg, yield 52%) as a pale yellow solid.

¹H-NMR (400 MHz, CDCl₃): δ (ppm) 8.21 (4H, dd, J=11.0, 8.6 Hz), 7.66 (2H, d, J=8.6 Hz), 7.50 (2H, d, J=8.6 Hz), 7.25–6.95 (1H, m), 5.51 (1H, d, J=13.7 Hz), 5.25 (1H, d, J=13.7 Hz), 5.19 (2H, s), 4.63–3.88 (8H, m), 3.91–3.35 (4H, m), 3.29 (1H, dd, J=6.8, 2.2 Hz), 3.25–3.08 (1H, m), 1.38 (3H, d, J=6.2 Hz), 1.31 (3H, br s), 1.25 (3H, d, J=7.3 Hz), 1.21 (3H, br s).

(2) (1R,5S,6S)-2-(1-{4-[N-(2-aminoethyl)-N-isopropyl-carbamoyl]-1,3-thiazol-2-yl}azetidin-3-yl)thio-6-[(R)-1-hydroxyethyl]-1-methylcarbapen-2-em-3-carboxylic acid p-Nitrobenzyl (1R,5S,6S)-2-[1-(4-{N-isopropyl-N-[2-(p-nitrobenzyloxycarbonylamino)ethyl]-carbamoyl}-1,3-thiazol-2-yl)azetidin-3-yl]thio-6-[(R)-1-hydroxyethyl]-1-methylcarbapen-2-em-3-carboxylate (610 mg, 0.74 mmol) (obtained as described in Example 65(1)) in a mixture of tetrahydrofuran (30 ml) and distilled water (30 ml) was subjected to catalytic hydrogenation in the presence of 7.5% palladium on charcoal (610 mg) in a water bath (35° C.) for 2 hours. After checking the completion of the reaction, ethyl acetate and distilled water were added to the reaction mixture. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water→8% acetonitrile in distilled water→10% acetonitrile in distilled water→12% acetonitrile in distilled water→14% acetonitrile in distilled water→16% acetonitrile in distilled water→18% acetonitrile in distilled water) and the eluate was lyophilized to afford the desired compound (1R,5S,6S)-2-(1-{4-[N-(2-aminoethyl)-N-isopropyl-carbamoyl]-1,3-thiazol-2-yl}azetidin-3-yl)thio-6-[(R)-1-hydroxyethyl]-1-methylcarbapen-2-em-3-carboxylic acid (104 mg, yield 28%) as a white solid.

¹H-NMR (400 MHz, D₂O): δ (ppm) 7.06 (1H, s), 4.56 (2H, t, J=8.4 Hz), 4.41–4.31 (1H, m), 4.29–4.09 (3H, m including 4.24 (1H, quint., J=6.3 Hz), 4.20 (1H, dd, J=8.9, 2.4 Hz)), 4.03 (2H, dd, J=8.4, 4.8 Hz), 3.43 (1H, dd, J=6.3, 2.4 Hz), 3.37–3.16 (3H, m including 3.25 (1H, dq, J=8.9, 7.4 Hz)), 1.29 (3H, d, J=6.4 Hz), 1.25–1.15 (9H, m including 1.19 (3H, d, J=7.0 Hz))

IR (KBr): 3381.6, 1759.7, 1597.7, 1537.0, 1469.5, 1424.2, 1388.5, 1371.1, 1314.3, 1282.4 cm⁻¹.

Mass spectrum (FAB⁺): m/z: 510 [M+H]⁺.

High-resolution mass spectrum (ESI⁺): calculated for C₂₂H₃₂N₅O₅S₂Na: 510.1845, Found: 510.1826 [M+H]⁺.

EXAMPLE 66

(1R,5S,6S)-2-{1-[4-((1S)-1-aminomethyl-2-methylpropylcarbamoyl)-1,3-thiazol-2-yl]azetidin-3-yl}thio-6-[(R)-1-hydroxyethyl]-1-methylcarbapen-2-em-3-carboxylic acid

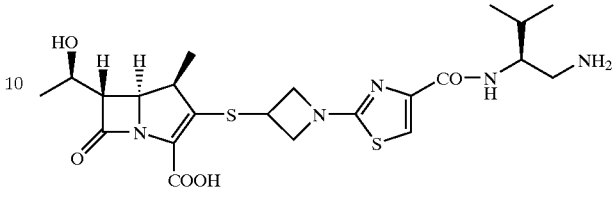

(1) p-Nitrobenzyl (1R,5S,6S)-2-[1-(4-{(1S)-2-methyl-[1-(p-nitrobenzyloxycarbonylamino)methyl]propylcarbamoyl}-1,3-thiazol-2-yl)azetidin-3-yl]thio-6-[(R)-1-hydroxyethyl]-1-methylcarbapen-2-em-3-carboxylate To a solution of 3-acetylthio-1-(4-{(1S)-2-methyl-[1-(p-nitrobenzyloxycarbonylamino)methyl]-propylcarbamoyl}-1,3-thiazol-2-yl)azetidine (780 mg, 1.50 mmol) (obtained as described in Reference Example 61) in dimethylformamide (40 ml) was added hydrazine acetate (166 mg, 1.80 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (892 mg, 1.50 mmol) in acetonitrile (45 ml) was added dropwise into the resulting mixture in an ice bath under an atmosphere of nitrogen, followed by the addition of diisopropylethylamine (1.05 ml, 6.00 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate→ethyl acetate: methanol (98:2)) to afford p-nitrobenzyl (1R,5S,6S)-2-[1-(4-{(1S)-2-methyl-[1-(p-nitrobenzyloxycarbonylamino)methyl]propylcarbamoyl}-1,3-thiazol-2-yl)azetidin-3-yl]thio-6-[(R)-1-hydroxyethyl]-1-methylcarbapen-2-em-3-carboxylate (950 mg, yield 77%) as a pale yellow solid.

¹H-NMR (400 MHz, CDCl₃): δ (ppm) 8.23 (2H, d, J=8.8 Hz), 8.09 (2H, d, J=8.8 Hz), 7.66 (2H, d, J=8.8 Hz), 7.43 (1H, s), 7.40 (2H, d, J=8.8 Hz), 7.12 (1H, br d, J=8.8 Hz), 5.51 (1H, d, J=13.2 Hz), 5.25 (1H, d, J=13.2 Hz), 5.23 (1H, d, J=13.2 Hz), 5.05 (1H, d, J=13.2 Hz), 4.51 (1H, t, J=8.1 Hz), 4.44 (1H, t, J=8.1 Hz), 4.32–4.25 (3H, m), 4.06–3.96 (3H, m), 3.45–3.32 (2H, m), 3.30 (1H, dd, J=2.2, 6.6 Hz), 3.21 (1H, dq, J=7.3, 9.5 Hz), 1.93–1.84 (1H, m), 1.38 (3H, d, J=5.9 Hz), 1.28 (3H, d, J=7.3 Hz), 1.00 (3H, d, J=6.6 Hz), 0.98 (3H, d, J=7.3 Hz).

(2) (1R,5S,6S)-2-{1-[4-((1 S)-1-aminomethyl-2-methylpropylcarbamoyl)-1,3-thiazol-2-yl]azetidin-3-yl}thio-6-[(R)-1-hydroxyethyl]-1-methylcarbapen-2-em-3-carboxylic acid p-Nitrobenzyl (1R,5S,6S)-2-[1-(4-{(1 S)-2-methyl-[1-(p-nitrobenzyloxycarbonylamino)methyl]propylcarbamoyl}-1,3-thiazol-2-yl)azetidin-3-yl]thio-6-[(R)-1-hydroxyethyl]-1-methylcarbapen-2-em-3-carboxylate (950 mg, 1.15 mmol)

(obtained as described in Example 66(1)) in a mixture of tetrahydrofuran (48 ml) and distilled water (48 ml) was subjected to catalytic hydrogenation in the presence of 10% palladium on charcoal (950 mg) at room temperature for 3 hours. After checking the completion of the reaction, the reaction mixture was filtered and to the filtrate were added ethyl acetate and distilled water. The resulting mixture was shaken in a separatory funnel and the aqueous layer was separated, washed with the above-mentioned mixed solvent and concentrated under reduced pressure. The residue was purified by chromatography on a Cosmosil column (eluant: distilled water→distilled water:acetonitrile (76:24)) and the eluate was lyophilized to afford the desired compound (1R,5S,6S)-2-{1-[4-((1S)-1-aminomethyl-2-methylpropylcarbamoyl)-1,3-thiazol-2-yl]azetidin-3-yl}thio-6-[(R)-1-hydroxyethyl]-1-methylcarbapen-2-em-3-carboxylic acid (103 mg, yield 18%) as a white solid.

$^1$H-NMR (400 MHz, $D_2O$): δ (ppm) 8.18–8.03 (1H, m), 7.51 (1H, s), 4.47 (2H, t, J=8.1 Hz), 4.24–4.14 (1H, m), 3.99–3.85 (4H, m), 3.84–3.77 (1H, m), 3.09–2.88 (4H, m), 1.94–1.84 (1H, m), 1.14 (3H, d, J=6.2 Hz), 1.03 (3H, d, J=7.0 Hz), 0.89 (3H, d, J=6.6 Hz), 0.84 (3H, d, J=6.6 Hz).

IR (KBr): 1752, 1660, 1605, 1545, 1494, 1471 cm$^{-1}$.

Mass spectrum (FAB$^+$): m/z: 510 [M+H]$^+$.

High-resolution mass spectrum (FAB$^+$): calculated for $C_{22}H_{32}N_5O_6S_2$: 510.1845, Found: 510.1846 [M+H]$^+$.

Elemental analysis: $C_{22}H_{31}N_5O_6S_2$ 13/7$H_2O$. Calculated for: C, 48.65%; H, 6.44%; N, 12.90%; S, 11.81%. Found: C, 48.92%; H, 6.29%; N, 12.60%; S, 12.04%.

EXAMPLE 67

(1R,5S,6S)-2-[1-(4-aminomethyl-1,3-thiazol-2-yl) azetidin-3-yl]thio-6-[(R)-1-hydroxyethyl]-1-methylcarbapen-2-em-3-carboxylic acid

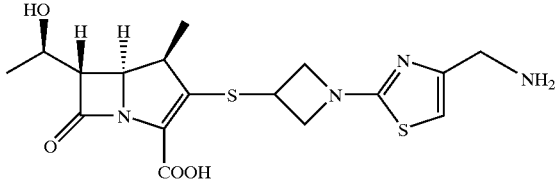

(1) p-Nitrobenzyl (1R,5S,6S)-2-{1-[4-(p-nitrobenzylcarbonylaminomethyl)-1,3-thiazol-2-yl] azetidin-3-yl}thio-6-[(R)-1-hydroxyethyl]-1-methylcarbapen-2-em-3-carboxylate To a solution of 3-acetylthio-1-[4-(p-nitrobenzylcarbonylaminomethyl)-1,3-thiazol-2-yl] azetidine (265.2 mg, 0.63 mmol) (obtained as described in Reference Example 62) in dimethylformamide (14 ml) was added hydrazine acetate (76.4 mg, 0.5 mmol) at room temperature under an atmosphere of nitrogen and the mixture was stirred for 0.5 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (390 mg, 0.66 mmol) in acetonitrile (19 ml) was added dropwise into the resulting mixture in an ice bath under an atmosphere of nitrogen, followed by the addition of diisopropylethylamine (0.44 ml, 2.5 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: toluene:acetonitrile (2:3)) to afford p-nitrobenzyl (1R,5S,6S)-2-{1-[4-(p-nitrobenzylcarbonylaminomethyl)-1,3-thiazol-2-yl] azetidin-3-yl}thio-6-[(R)-1-hydroxyethyl]-1-methylcarbapen-2-em-3-carboxylate (268.4 mg, yield 59%) as a pale yellow solid.

$^1$H-NMR (400 MHz, CDCl$_3$): δ (ppm) 8.22 (4H, d, J=8.8 Hz), 7.66 (2H, d, J=8.8 Hz), 7.51 (2H, d, J=8.8 Hz), 6.45 (1H, s), 5.51 (1H, d, J=13.9 Hz), 5.37 (1H, br s), 5.25 (1H, d, J=13.9 Hz), 5.21 (2H, s), 4.48 (1H, t, J=7.8 Hz), 4.46 (1H, t, J=7.8 Hz), 4.35–4.20 (5H, m), 4.03 (2H, dd, J=7.8, 4.9 Hz), 3.29 (1H, dd, J=6.2, 2.5 Hz), 3.22 (1H, dq, J=8.9, 7.3 Hz), 1.80 (1H, d, J=4.4 Hz), 1.38 (3H, d, J=5.9 Hz), 1.27 (3H, d, J=7.3 Hz).

(2) (1R,5S,6S)-2-[1-(4-aminomethyl-1,3-thiazol-2-yl) azetidin-3-yl]thio-6 [(R)-1-hydroxyethyl]-1-methylcarbapen-2-em-3-carboxylic acid p-Nitrobenzyl (1R,5S,6S)-2-1-[4-(p-nitrobenzylcarbonylaminomethyl)-1,3-thiazol-2-yl] azetidin-3-yl}thio-6-[(R)-1-hydroxyethyl]-1-methylcarbapen-2-em-3-carboxylate (660 mg, 0.89 mmol) (obtained as described in Example 67(1)) in a mixture of tetrahydrofuran (30 ml) and distilled water (30 ml) was subjected to catalytic hydrogenation in the presence of 7.5% palladium on charcoal (606 mg) in a water bath (35° C.) for 2 hours. After checking the completion of the reaction, the reaction mixture was filtered and to the filtrate were added ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water→8% acetonitrile in distilled water→10% acetonitrile in distilled water→13% acetonitrile in distilled water→15% acetonitrile in distilled water), and the eluate was lyophilized to afford the desired compound (1R,5S,6S)-2-[1-(4-aminomethyl-1,3-thiazol-2-yl)azetidin-3-yl]thio-6-[(R)-1-hydroxyethyl]-1-methylcarbapen-2-em-3-carboxylic acid (123 mg, yield 34%) as a white solid.

$^1$H-NMR (400 MHz, $D_2O$): δ (ppm) 6.85 (1H, s), 4.54 (2H, t, J=8.1 Hz), 4.38–4.30 (1H, m), 4.25 (1H, quint., J=6.3 Hz), 4.25 (1H, dd, J=8.9, 2.5 Hz), 4.07 (2H, s), 4.02 (2H, dd, J=8.1, 4.0 Hz), 3.44 (1H, dd, J=6.3, 2.5 Hz), 3.25 (1H, dq, J=8.9, 7.3 Hz), 1.30 (3H, d, J=6.4 Hz), 1.20 (3H, d, J=7.2 Hz).

IR (KBr): 3362.3, 1756.8, 1589.1, 1527.3, 1469.5, 1386.6, 1309.4, 1286.3, 1259.3 cm$^{-1}$.

Mass spectrum (FAB$^+$): m/z: 411 [M+H]$^+$.

High-resolution mass spectrum (ESI$^+$): calculated for $C_{17}H_{23}N_4O_4S_2$: 411.4161, Found: 411.1173 [M+H]$^+$.

EXAMPLE 68

(1R,5S,6S)-2-{1-[4-(methoxycarbonylaminomethyl)-1,3-thiazol-2-yl]azetidin-3-yl}thio-6-[(R)-1-hydroxyethyl]-1-methylcarbapen-2-em-3-carboxylic acid sodium salt

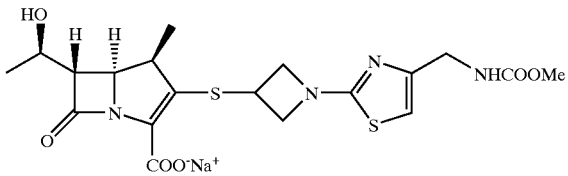

(1) p-Nitrobenzyl (1R,5S,6S)-2-{1-[4-(methoxycarbonylaminomethyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(methoxycarbonylamino-methyl)-1,3-thiazol-2-yl]azetidine (441 mg, 1.39 mmol) (obtained as described in Reference Example 63) in dimethylformamide (13 ml) was added hydrazine acetate (154 mg, 1.67 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (993 mg, 1.67 mmol) in acetonitrile (26 ml) was added dropwise into the resulting mixture in an ice bath under an atmosphere of nitrogen, followed by the addition of diisopropylethylamine (0.97 ml, 5.56 mmol). The mixture was stirred for 30 minutes while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate) to afford p-nitrobenzyl (1R,5S,6S)-2-{1-[4-(methoxycarbonylaminomethyl)-1,3-thiazol-2-yl]azetidin-3-yl}thio-6-[(R)-1-hydroxyethyl]-1-methylcarbapen-2-em-3-carboxylate (307 mg, yield 53%) as a pale yellow solid.

$^1$H-NMR (400 MHz, CDCl$_3$): δ (ppm) 8.22 (2H, d, J=8.7 Hz), 7.66 (2H, d, J=8.7 Hz), 6.45 (1H, s), 5.51 (1H, d, J=13.7 Hz), 5.26 (1H, d, J=13.7 Hz), 4.48 (2H, t, J=8.0 Hz), 4.43–4.16 (5H, m), 4.09–3.99 (2H, m), 4.09–3.99 (2H, m), 3.69 (3H, s), 3.29 (1H, dd, J=6.7, 2.7 Hz), 3.21 (1H, dq, J=9.0, 7.3 Hz), 1.38 (3H, d, J=6.1 Hz), 1.25 (3H, d, J=7.3 Hz).

(2) (1R,5S,6S)-2-{1-[4-(methoxycarbonylaminomethyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(methoxycarbonylaminomethyl)-1,3-thiazol-2-yl]azetidin-3-yl}thio-6-[(R)-1-hydroxyethyl]-1-methylcarbapen-2-em-3-carboxylate (307 mg, 0.52 mmol) (obtained as described in Example 68(1)) in a mixture of tetrahydrofuran (15 ml) and distilled water (15 ml) was subjected to catalytic hydrogenation in the presence of 7.5% palladium on charcoal (307 mg) in a water bath (35° C.) for 2 hours. After checking the completion of the reaction, the reaction mixture was filtered and to the filtrate were added sodium hydrogencarbonate (44 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water) and the eluate was lyophilized to afford the desired compound (1R,5S,6S)-2-{1-[4-(methoxycarbonylaminomethyl)-1,3-thiazol-2-yl]azetidin-3-yl}thio-6-[(R)-1-hydroxyethyl]-1-methylcarbapen-2-em-3-carboxylic acid sodium salt (135 mg, yield 53%) as a white solid.

$^1$H-NMR (400 MHz, D$_2$O): δ (ppm) 6.59 (1H, s), 4.51 (2H, t, J=8.1 Hz), 4.38–4.29 (1H, m), 4.25 (1H, quint., J=6.2 Hz), 4.20 (1H, dd, J=9.1, 2.5 Hz), 4.19 (2H, s), 4.05–3.98 (2H, m), 3.68 (3H, s), 3.43 (1H, dd, J=6.2, 2.4 Hz), 3.25 (1H, dq, J=9.1, 7.4 Hz), 1.30 (3H, d, J=6.2 Hz), 1.20 (3H, d, J=7.2 Hz).

IR (KBr): 3355.5, 1748.2, 1725.1, 1600.6, 1525.4, 1470.5, 1395.2, 1311.4, 1290.1, 1254.5 cm$^{-1}$.

Mass spectrum (FAB$^+$): m/z: 513 [M+Na]$^+$.

High-resolution mass spectrum (FAB$^+$): calculated for C$_{19}$H$_{23}$N$_4$O$_5$S$_2$Na$_2$: 513.0855, Found: 513.0850 [M+Na]$^+$.

EXAMPLE 69

(1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylic acid sodium salt

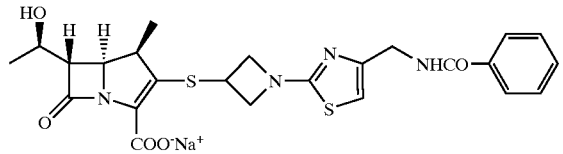

(1) p-Nitrobenzyl (1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(benzoylaminomethyl)-1,3-thiazol-2-yl]azetidine (698 mg, 2.01 mmol) (obtained as described in Reference Example 64) in dimethylformamide (20 ml) was added hydrazine acetate (222 mg, 2.41 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.43 g, 2.41 mmol) in acetonitrile (40 ml) was added dropwise into the resulting mixture in an ice bath under an atmosphere of nitrogen, followed by the addition of diisopropylethylamine (1.40 ml, 8.94 mmol). The mixture was stirred for 2.5 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate:methanol (20:1)) to afford p-nitrobenzyl (1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylate (851 mg, yield 65%) as a pale yellow solid.

$^1$H-NMR (400 MHz, CDCl$_3$): δ (ppm) 8.21 (2H, d, J=8.7 Hz), 7.81 (2H, d, J=7.3 Hz), 7.66 (2H, d, J=8.7 Hz), 7.56–7.38 (3H, m), 6.79 (1H, bs), 6.52 (1H, s), 5.51 (1H, d, J=13.7 Hz), 5.25 (1H, d, J=13.7 Hz), 4.53 (2H, dd, J=5.3, 2.9 Hz), 4.47 (2H, t, J=8.3 Hz), 4.33–4.22 (3H, m), 4.10–3.95 (2H, m), 3.28 (1H, dd, J=6.7, 2.6 Hz), 3.19 (1H, dq, J=7.9, 6.4 Hz), 1.37 (3H, d, J=6.4 Hz), 1.26 (3H, d, J=7.3 Hz).

(2) (1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylate (851 mg, 1.31 mmol) (obtained as described in Example 69(1)) in a mixture of tetrahydrofuran (40 ml) and distilled water (40 ml) was subjected to catalytic hydrogenation in the presence of 7.5% palladium on charcoal (851 mg) in a water bath (35° C.) for 2 hours. After checking the completion of the reaction, the reaction mixture was filtered and to the filtrate were added sodium hydrogencarbonate (110 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water→8% acetonitrile in distilled water→10% acetonitrile in distilled water→15% acetonitrile in distilled water) and the eluate was lyophilized to afford the desired compound (1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylic acid sodium salt (144 mg, yield 20%) as a white solid.

$^1$H-NMR (400 MHz, D$_2$O): δ (ppm) 7.81 (2H, d, J=7.4 Hz), 7.70–7.55 (3H, m), 1H, d, J=8.6 Hz), 4.52 (2H, t, J=7.9 Hz), 4.47 (2H, s), 4.37–4.28 (1H, m), 4.24 (1H, quint., J=6.2 Hz), 4.19 (1H, dd, J=8.8, 2.2 Hz), 4.05–3.97 (2H, m), 3.43 (1H, dd, J=6.2, 2.2 Hz), 3.26 (1H, dq, J=8.8, 7.2 Hz), 1.29 (3H, d, J=6.4 Hz), 1.19 (3H, d, J=7.2 Hz).

IR (KBr): 3336.2, 1750.2, 1645.9, 1601.6, 1526.4, 1488.8, 1470.5, 1396.2, 1308.5, 1294.0 cm$^{-1}$.

Mass spectrum (FAB$^+$): m/z: 537 [M+H]$^+$.

High-resolution mass spectrum (FAB$^+$): calculated for C$_{24}$H$_{26}$N$_4$O$_5$S$_2$Na: 537.1243, Found: 537.1246 [M+H]$^+$.

EXAMPLE 70

(1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylic acid sodium salt

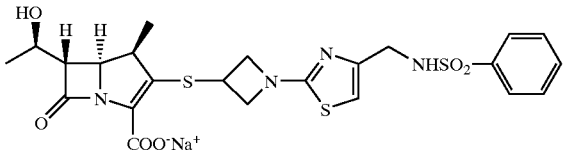

(1) p-Nitrobenzyl (1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylate To a solution of 3-acetylthio-1-[4-(benzenesulfonylaminomethyl)-1,3-thiazol-2-yl]azetidine (1.00 g, 2.68 mmol) (obtained as described in Reference Example 65) in dimethylformamide (30 ml) was added hydrazine acetate (296 mg, 3.21 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.75 g, 2.94 mmol) in acetonitrile (60 ml) was added dropwise into the resulting mixture in an ice bath under an atmosphere of nitrogen, followed by the addition of diisopropylethylamine (1.87 ml, 10.7 mmol). The mixture was stirred for 3 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: hexane:ethyl acetate (1:1)) to afford p-nitrobenzyl (1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylate (1.13 g, yield 61%) as a pale yellow solid.

$^1$H-NMR (400 MHz, CDCl$_3$): δ (ppm) 8.21 (2H, d, J=8.7 Hz), 7.83 (2H, d, J=7.5 Hz), 7.66 (2H, d, J=8.7 Hz), 7.60–7.43 (3H, m), 6.33 (1H, s), 5.58 (1H, br s), 5.51 (1H, d, J=13.7 Hz), 5.26 (1H, d, J=13.7 Hz), 4.48 (2H, t, J=7.8 Hz), 4.44 (2H, t, J=7.8 Hz), 4.36–4.18 (3H, m), 4.13 (1H, quint., J=7.2 Hz), 4.08 (1H, dd, J=12.7, 6.0 Hz), 4.01 (1H, dd, J=8.6, 5.6 Hz), 3.94 (1H, dd, J=8.6, 5.6 Hz), 3.30 (1H, dd, J=6.7, 2.6 Hz), 3.21 (1H, dq, J=8.9, 7.9 Hz), 1.37 (3H, d, J=6.2 Hz), 1.23 (3H, dd, J=7.2, 1.2 Hz).

(2) (1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylate (1.13 g, 1.65 mmol) (obtained as described in Example 70(1)) in a mixture of tetrahydrofuran (55 ml) and distilled water (55 ml) was subjected to catalytic hydrogenation in the presence of 7.5% palladium on charcoal (1.13 g) in a water bath (35° C.) for 2 hours. After checking the completion of the reaction, the reaction mixture was filtered and to the filtrate were added sodium hydrogencarbonate (139 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→8% acetonitrile in distilled water→12% acetonitrile in distilled water→16% acetonitrile in distilled water→20% acetonitrile in distilled water) and the eluate was lyophilized to afford the desired compound (1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylic acid sodium salt (627 mg, yield 66%) as a white solid.

$^1$H-NMR (400 MHz, D$_2$O): δ (ppm) 7.71–7.68 (3H, m), 7.61–7.52 (2H, m), 6.52 (1H, s), 4.35–4.18 (5H, m including 4.22 (1H, dd, J=9.1, 2.4 Hz)), 4.12 (2H, s), 3.78–3.65 (2H, m), 3.36 (1H, dd, J=6.2, 2.4 Hz), 3.23 (1H, dq, J=8.8, 7.2 Hz), 1.31 (3H, d, J=6.4 Hz), 1.21 (3H, d, J=7.2 Hz).

IR (KBr): 3293.8, 1748.2, 1597.7, 1528.3, 1470.5, 1447.3, 1397.2, 1314.3 cm$^{-1}$.

Mass spectrum (FAB$^+$): m/z: 573 [M+H]$^+$.

High-resolution mass spectrum (FAB$^+$): calculated for $C_{23}H_{26}N_4O_5S_2Na$: 573.0093, Found: 573.0911 [M+H]$^+$.

EXAMPLE 71

(1R,5S,6S)-2-(1-{4-[(Thiophene-2-carbonylamino)methyl]-1,3-thiazol-2-yl}azetidin-3-yl)thio-6-[(R)-1-hydroxyethyl]-1-methylcarbapen-2-em-3-carboxylic acid sodium salt

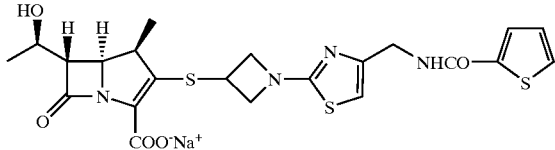

(1) p-Nitrobenzyl (1R,5S,6S)-2-(1-{4-[(thiophene-2-carbonylamino)methyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(thiophene-2-carbonylamino)methyl]-1,3-thiazol-2-yl}azetidine (490 mg, 1.52 mmol) (obtained as described in Reference Example 66) in dimethylformamide (15 ml) was added hydrazine acetate (169 mg, 1.83 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.09 g, 1.83 mmol) in acetonitrile (30 ml) was added dropwise into the resulting mixture in an ice bath under an atmosphere of nitrogen, followed by the addition of diisopropylethylamine (1.06 ml, 0.68 mmol). The mixture was stirred for 2.5 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate) to afford p-nitrobenzyl (1R,5S,6S)-2-(1-{4-[(thiophene-2-carbonylamino)methyl]-1,3-thiazol-2-yl}azetidin-3-yl)thio-6-[(R)-1-hydroxyethyl]-1-methylcarbapen-2-em-3-carboxylate (997 mg, yield 100%) as a pale yellow solid.

$^1$H-NMR (400 MHz, CDCl$_3$): δ (ppm) 8.22 (2H, d, J=8.0 Hz), 8.02 (2H, s), 7.66 (2H, d, J=8.0 Hz), 7.47 (1H, d, J=5.2 Hz), 7.07 (1H, d, J=4.2 Hz), 6.55 (1H, s), 5.50 (1H, d, J=13.7 Hz), 5.26 (1H, d, J=13.7 Hz), 4.67–4.55 (2H, m), 4.51 (2H, d, J=5.3 Hz), 4.35–4.22 (2H, m), 4.22–4.03 (3H, m), 3.29 (1H, dd, J=6.8, 2.6 Hz), 3.18 (1H, dq, J=9.0, 7.5 Hz), 1.37 (3H, d, J=6.3 Hz), 1.25 (3H, d, J=7.3 Hz).

(2) (1R,5S,6S)-2-(1-{4-[(thiophene-2-carbonylamino)methyl]-1,3-thiazol-2-yl}azetidin-3-yl)thio-6-[(R)-1-hydroxyethyl]-1-methylcarbapen-2-em-3-carboxylic acid sodium salt p-Nitrobenzyl (1R,5S,6S)-2-(1-{4-[(thiophene-2-carbonylamino)methyl]-1,3-thiazol-2-yl}azetidin-3-yl)thio-6-[(R)-1-hydroxyethyl]-1-methylcarbapen-2-em-3-carboxylate (997 mg, 1.52 mmol) (obtained as described in Example 71(1)) in a mixture of tetrahydrofuran (35 ml) and distilled water (35 ml) was subjected to catalytic hydrogenation in the presence of 7.5% palladium on charcoal (997 mg) in a water bath (35° C.) for 2 hours. After checking the completion of the reaction, the reaction mixture was filtered and to the filtrate were added sodium hydrogencarbonate (128 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→4% acetonitrile in distilled water→8% acetonitrile in distilled water→12% acetonitrile in distilled water→15% acetonitrile in distilled water→20% acetonitrile in distilled water) and the eluate was lyophilized to afford the desired compound (1R,5S,6S)-2-(1-{4-[(thiophene-2-carbonylamino)methyl]-1,3-thiazol-2-yl}azetidin-3-yl)thio-6-[(R)-1-hydroxyethyl]-1-methylcarbapen-2-em-3-carboxylic acid sodium salt (287 mg, yield 35%) as a white solid.

$^1$H-NMR (400 MHz, D$_2$O): δ (ppm) 7.73 (2H, d, J=2.7 Hz), 7.19 (1H, t, J=4.4 Hz), 6.59 (1H, d, J=0.7 Hz), 4.49 (2H, t, J=7.5 Hz), 4.43 (2H, s), 4.35–4.27 (1H, m), 4.24(1H, quint, J=6.3 Hz), 4.18 (1H, dd, J=8.3, 2.4 Hz), 3.99 (1H, t, J=4.7 Hz), 3.97 (1H, t, J=4.7 Hz), 3.42 (1H, dd, J=6.3, 2.4 Hz), 3.22 (1H, quint., J=8.3 Hz), 1.30 (3H, d, J=6.4 Hz), 1.18 (3H, d, J=7.1 Hz).

IR (KBr): 3324.7, 1749.1, 1599.7, 1530.2, 1469.5, 1418.4, 1396.2 cm$^{-1}$.

Mass spectrum (FAB$^+$): m/z: 521 [M−Na+2H]$^+$.

High-resolution mass spectrum (ESI$^+$): calculated for $C_{22}H_{25}N_4O_5S_3$: 521.0942, Found: 521.0992 [M−Na+2H]$^+$.

EXAMPLE 72

(1R,5S,6S)-2-(1-{4-[(furan-2-carbonylamino)methyl]-1,3-thiazol-2-yl}azetidin-3-yl)thio-6-[(R)-1-hydroxyethyl]-1-methylcarbapen-2-em-3-carboxylic acid sodium salt

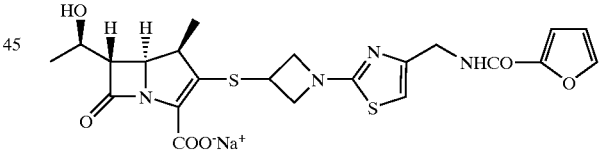

(1) p-Nitrobenzyl (1R,5S,6S)-2-(1-{4-[(furan-2-carbonylamino)methyl]-1,3-thiazol-2-yl}azetidin-3-yl)thio-6-[(R)-1-hydroxyethyl]-1-methylcarbapen-2-em-3-carboxylate To a solution of 3-acetylthio-1-{4-[(furan-2-carbonylamino)methyl]-1,3-thiazol-2-yl}azetidine (341 mg, 1.12 mmol) (obtained as described in Reference Example 67) in dimethylformamide (10 ml) was added hydrazine acetate (123 mg, 1.34 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (797 mg, 1.34 mmol) in acetonitrile (20 ml) was added dropwise into the resulting mixture in an ice bath under an atmosphere of nitrogen, followed by the addition of diisopropylethylamine (0.78 ml, 4.48 mmol). The mixture was stirred for 3 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate) to afford p-nitrobenzyl (1R,5S,6S)-2-(1-{4-[(furan-2-carbonylamino) methyl]-1,3-thiazol-2-yl}azetidin-3-yl)thio-6-[(R)-1-hydroxyethyl]-1-methylcarbapen-2-em-3-carboxylate (641 mg, yield 89%) as a pale yellow solid.

$^1$H-NMR (400 MHz, CDCl$_3$): δ (ppm) 8.22 (2H, d, J=7.8 Hz), 7.66 (2H, d, J=7.8 Hz), 7.45 (1H, s), 7.13 (1H, d, J=3.5 Hz), 6.53 (1H, s), 6.49 (1H, d, J=5.1 Hz), 5.48 (1H, d, J=13.7 Hz), 5.26 (1H, d, J=13.7 Hz), 4.60–4.40 (4H, m including 4.51 (2H, d, J=5.6 Hz), 4.35–4.20 (2H, m), 4.20–4.00 (3H, m), 3.29 (1H, dd, J=6.9, 2.5 Hz), 3.19 (1H, dq, J=9.3, 7.3 Hz), 1.37 (3H, d, J=6.4 Hz), 1.26 (3H, d, J=7.3 Hz).

(2) (1R,5S,6S)-2-(1-{4-[(furan-2-carbonylamino)methyl]-1,3-thiazol-2-yl}azetidin-3-yl)thio-6-[(R)-1-hydroxyethyl]-1-methylcarbapen-2-em-3-carboxylic acid sodium salt p-Nitrobenzyl (1R,5S,6S)-2-(1-{4-[(furan-2-carbonylamino)methyl]-1,3-thiazol-2-yl}azetidin-3-yl)thio-6-[(R)-1-hydroxyethyl]-1-methylcarbapen-2-em-3-carboxylate (640 mg,1.00 mmol) (obtained as described in Example 72(1)) in a mixture of tetrahydrofuran (32 ml) and distilled water (32 ml) was subjected to catalytic hydrogenation in the presence of 7.5% palladium on charcoal (640 mg) in a water bath (35° C.) for 2 hours. After checking the completion of the reaction, the reaction mixture was filtered and to the filtrate were added sodium hydrogencarbonate (84 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water→8% acetonitrile in distilled water→10% acetonitrile in distilled water→15% acetonitrile in distilled water) and the eluate was lyophilized to afford the desired compound (1R,5S,6S)-2-(1-{4-[(furan-2-carbonylamino)methyl]-1,3-thiazol-2-yl}azetidin-3-yl)thio-6-[(R)-1-hydroxyethyl]-1-methylcarbapen-2-em-3-carboxylic acid sodium salt (218 mg, yield 41%) as a white solid.

$^1$H-NMR (400 MHz, D$_2$O): δ (ppm) 7.69 (1H, dd, J=1.7, 0.8 Hz), 7.19 (1H, dd, J=3.6, 0.7 Hz), 6.64 (1H, dd, J=3.6, 1.7 Hz), 4.51 (2H, t, J=8.2 Hz), 4.44 (2H, s), 4.38–4.28 (1H, m), 4.25 (1H, quint., J=6.3 Hz), 4.19 (1H, dd, J=8.9, 2.2 Hz), 4.02 (1H, dd, J=5.0, 3.2 Hz), 4.00 (1H, dd, J=5.0, 2.9 Hz), 3.43 (1H, dd, J=6.3, 2.5 Hz), 3.24 (1H, dq, J=8.9, 7.1 Hz), 1.30 (3H, d, J=6.4 Hz), 1.19 (3H, d, J=7.1 Hz).

IR (KBr): 3367.1, 1749.1, 1653.7, 1594.8, 1524.5, 1472.4, 1395.2 cm$^{-1}$.

Mass spectrum (FAB$^+$): m/z: 505 [M–Na+2H]$^+$.

High-resolution mass spectrum (ESI$^+$): calculated for C$_{22}$H$_{25}$N$_4$O$_6$S$_2$: 505.1216, Found: 505.1208 [M–Na+2H]$^+$.

EXAMPLE 73

(1R,5S,6S)-2-[1-(4-phthalimidomethyl-1,3-thiazol-2-yl)azetidin-3-yl]thio-6-[(R)-1-hydroxyethyl]-1-methylcarbapen-2-em-3-carboxylic acid sodium salt

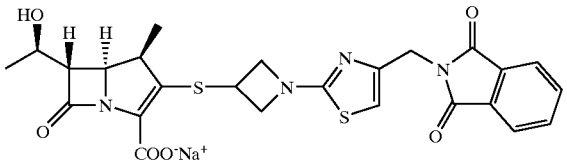

(1) p-Nitrobenzyl (1R,5S,6S)-2-[1-(4-phthalimidomethyl-1,3-thiazol-2-yl)azetidin-3-yl]thio-6-[(R)-1-hydroxyethyl]-1-methylcarbapen-2-em-3-carboxylate To a solution of 3-acetylthio-1-(4-phthalimidomethyl-1,3-thiazol-2-yl)azetidine (599 mg, 1.60 mmol) obtained as described in Reference Example 68 in dimethylformamide (18 ml) was added hydrazine acetate (177 mg, 1.92 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (1.14 g, 1.92 mmol) in acetonitrile (36 ml) was added dropwise into the resulting mixture in an ice bath under an atmosphere of nitrogen, followed by the addition of diisopropylethylamine (1.11 ml, 6.40 mmol). The mixture was stirred for 30 minutes while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate) to afford p-nitrobenzyl (1R,5S,6S)-2-[1-(4-phthalimidomethyl-1,3-thiazol-2-yl)azetidin-3-yl]thio-6-[(R)-1-hydroxyethyl]-1-methylcarbapen-2-em-3-carboxylate (640 mg, yield 59%) as a pale yellow solid.

$^1$H-NMR (400 MHz, CDCl$_3$): δ (ppm) 8.22 (2H, d, J=8.7 Hz), 7.88 (2H, dd, J=5.5, 3.1 Hz), 7.73 (2H, dd, J=5.5, 3.1 Hz), 7.65 (2H, d, J=8.7 Hz), 6.41 (1H, s), 5.49 (1H, d, J=13.7 Hz), 5.25 (1H, d, J=13.7 Hz), 4.80 (2H, s), 4.46 (1H, t, J=8.1 Hz), 4.43 (1H, t, J=8.1 Hz), 4.32–4.18 (3H, m, including 4.24 (1H, dd, J=9.2, 2.4 Hz)), 4.02 (1H, dd, J=5.5, 2.8 Hz), 4.00 (1H, dd, J=5.5, 2.8 Hz), 3.26 (1H, dd, J=6.9, 2.5 Hz), 3.19 (1H, dq, J=9.2, 7.3 Hz), 1.38 (3H, d, J=6.2 Hz), 1.25 (3H, dd, J=7.3, 2.1 Hz).

(2) (1R,5S,6S)-2-[1-(4-phthalimidomethyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-phthalimidomethyl-1,3-thiazol-2-yl)azetidin-3-yl]thio-6-[(R)-1-hydroxyethyl]-1-methylcarbapen-2-em-3-carboxylate (640 mg, 0.95 mmol) (obtained as described in Example 73(1)) in a mixture of tetrahydrofuran (32 ml) and distilled water (32 ml) was subjected to catalytic hydrogenation in the presence of 7.5% palladium on charcoal (640 mg) in a water bath (35° C.) for 2 hours. After checking the completion of the reaction, the reaction mixture was filtered and to the filtrate were added sodium hydrogencarbonate (80 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water→6% acetonitrile in distilled water→8% acetonitrile in distilled water→10% acetonitrile in distilled water→15% acetonitrile in distilled water→20% acetonitrile in distilled water) and the eluate was lyophilized to afford the desired compound (1R,5S,6S)-2-[1-(4-phthalimidomethyl-1,3-thiazol-2-yl)azetidin-3-yl]thio-6-[(R)-1-hydroxyethyl]-1-methylcarbapen-2-em-3-carboxylic acid sodium salt (202 mg, yield 38%) as a white solid.

$^1$H-NMR (400 MHz, D$_2$O): δ (ppm) 7.90–7.78 (4H, m), 6.56 (1H, d, J=2.7 Hz), 4.70 (2H, s), 4.43 (1H, t, J=7.9 Hz), 4.42 (1H, t, J=7.9 Hz), 4.31–4.19 (2H, m including 4.24 (1H, quint, J=6.3 Hz)), 4.17 (1H, dd, J=8.7, 2.0 Hz), 3.94 (1H, t, J=7.9 Hz), 3.92 (1H, t, J=7.9 Hz), 3.18 (1H, dq, J=8.7, 7.2 Hz), 1.29 (3H, d, J=6.4 Hz), 1.15 (3H, d, J=7.2 Hz).

IR (KBr): 3409.5, 1768.4, 1750.1, 1717.3, 1601.6, 1528.3, 1425.1, 1393.3, 1313.3 cm$^{-1}$.

Mass spectrum (FAB$^+$): m/z: 563 [M+H]$^+$.

High-resolution mass spectrum (FAB$^+$): calculated for C$_{25}$H$_{23}$N$_4$O$_6$S$_2$Na$_2$: 585.0864, Found: 585.0865 [M+Na]$^+$.

EXAMPLE 74

(1R,5S,6S)-2-[1-(4-succinimidomethyl-1,3-thiazol-2-yl)azetidin-3-yl]thio-6-[(R)-1-hydroxyethyl]-1-methylcarbapen-2-em-3-carboxylic acid sodium salt

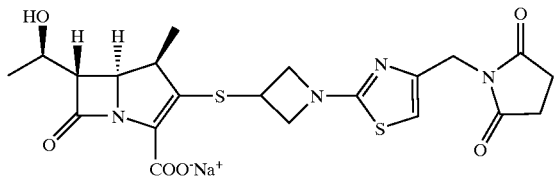

(1) p-Nitrobenzyl (1R,5S,6S)-2-[1-(4-succinimidomethyl-1,3-thiazol-2-yl)azetidin-3-yl]thio-6-[(R)-1-hydroxyethyl]-1-methylcarbapen-2-em-3-carboxylate To a solution of 3-acetylthio-1-(4-succinimidomethyl-1,3-thiazol-2-yl)azetidine (238 mg, 0.73 mmol) (obtained as described in Reference Example 69) in dimethylformamide (7 ml) was added hydrazine acetate (81 mg, 0.88 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (523 mg, 0.88 mmol) in acetonitrile (14 ml) was added dropwise into the resulting mixture in an ice bath under an atmosphere of nitrogen, followed by the addition of diisopropylethylamine (0.51 ml, 2.92 mmol). The mixture was stirred for 2 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 0.5 M hydrochloric acid, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column (eluant: ethyl acetate→ethyl acetate:methanol (20:1)) to afford p-nitrobenzyl (1R,5S,6S)-2-[1-(4-succinimidomethyl-1,3-thiazol-2-yl)azetidin-3-yl]thio-6-[(R)-1-hydroxyethyl]-1-methylcarbapen-2-em-3-carboxylate (211 mg, yield 46%) as a pale yellow solid.

$^1$H-NMR (400 MHz, CDCl$_3$): δ (ppm) 8.23 (2H, d, J=8.7 Hz), 7.66 (2H, d, J=8.7 Hz), 6.42 (1H, s), 5.50 (1H, d, J=13.8 Hz), 5.25 (1H, d, J=13.8 Hz), 4.61 (2H, s), 4.46 (1H, t, J=8.0 Hz), 4.45 (1H, t, J=8.0 Hz), 4.32–4.18 (3H, m, including 4.25 (1H, dd, J=9.1, 2.3 Hz)), 4.02 (1H, t, J=4.8 Hz), 4.00 (1H, dd, J=4.8, 3.7 Hz), 3.28 (1H, dd, J=6.9, 2.5 Hz), 3.20 (1H, dq, J=9.1, 7.3 Hz), 2.76 (4H, s), 1.38 (3H, d, J=6.2 Hz), 1.27 (3H, d, J=7.3 Hz).

(2) (1R,5S,6S)-2-[1-(4-succinimidomethyl-1,3-thiazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-succinimidomethyl-1,3-thiazol-2-yl)azetidin-3-yl]thio-6-[(R)-1-hydroxyethyl]-1-methylcarbapen-2-em-3-carboxylate (211 mg, 0.34 mmol) (obtained as described in Example 74(1)) in a mixture of tetrahydrofuran (10 ml) and distilled water (10 ml) was subjected to catalytic hydrogenation in the presence of 7.5% palladium on charcoal (211 mg) in a water bath (35° C.) for 2 hours. After checking the completion of the reaction, the reaction mixture was filtered and to the filtrate were added sodium hydrogencarbonate (29 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→2% acetonitrile in distilled water→4% acetonitrile in distilled water) and the eluate was lyophilized to afford the desired compound (1R,5S,6S)-2-[1-(4-succinimidomethyl-1,3-thiazol-2-yl)azetidin-3-yl]thio-6-[(R)-1-hydroxyethyl]-1-methylcarbapen-2-em-3-carboxylic acid sodium salt (115 mg, yield 66%) as a white solid.

$^1$H-NMR (400 MHz, D$_2$O): δ (ppm) 6.59 (1H, s), 4.57 (2H, s), 4.50 (2H, t, J=8.1 Hz), 4.38–4.29 (1H, m), 4.25 (1H, quint., J=6.3 Hz), 4.20 (1H, dd, J=8.7, 2.3 Hz), 4.01 (1H, t, J=4.2 Hz), 3.99 (1H, t, J=4.2 Hz), 3.43 (1H, dd, J=6.3, 2.4 Hz), 3.24 (1H, dq, J=8.7, 7.4 Hz), 2.48 (4H, s), 1.30 (3H, d, J=6.4 Hz), 1.19 (3H, d, J=7.2 Hz).

IR (KBr): 3381.6, 1749.1, 1794.8, 1601.6, 1526.4, 1470.5, 1424.2, 1399.1, 1312.3, 1295.0, 1168.7 cm$^{-1}$.

Mass spectrum (FAB$^+$): m/z: 515 [M+H]$^+$.

High-resolution mass spectrum (FAB$^+$): calculated for C$_{21}$H$_{24}$N$_4$O$_6$S$_2$Na: 515.1035, Found: 515.1034 [M+H]$^+$.

EXAMPLE 75

(1R,5S,6S)-2-[1-(4-azetidinocarbonyl-1,3-oxazol-2-yl)azetidin-3-yl]thio-6-[(R)-1-hydroxyethyl]-1-methylcarbapen-2-em-3-carboxylic acid sodium salt

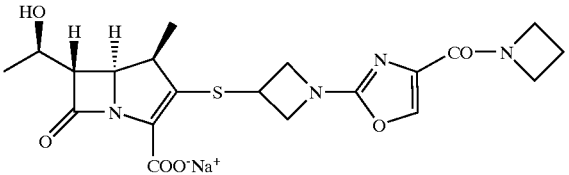

(1) p-Nitrobenzyl (1R,5S,6S)-2-[1-(4-azetidinocarbonyl-1,3-oxazol-2-yl)azetidin-3yl]thio-6-[(R)-1-hydroxyethyl]-1-methylcarbapen-2-em-3-carboxylate To a solution of 3-acetylthio-1-(4-azetidinocarbonyl-1,3-oxazol-2-yl)azetidine (330 mg, 1.17 mmol) (obtained as described in Reference Example 71) in dimethylformamide (17 ml) was added hydrazine acetate (130 mg, 1.41 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (696 mg, 1.17 mmol) in acetonitrile (35 ml) was added dropwise into the resulting mixture in an ice bath under an atmosphere of nitrogen, followed by the addition of diisopropylethylamine (815 µl, 4.68 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate:methanol (9:1)) to afford p-nitrobenzyl (1R,5S,6S)-2-[1-(4-azetidinocarbonyl-1,3-oxazol-2-yl)azetidin-3-yl]thio-6-[(R)-1-hydroxyethyl]-1-methylcarbapen-2-em-3-carboxylate (605 mg, yield 89%) as a pale yellow solid.

$^1$H-NMR (400 MHz, CDCl$_3$): δ (ppm) 8.23 (2H, d, J=8.8 Hz), 7.71 (1H, s), 7.66 (2H, d, J=8.8 Hz), 5.51 (1H, d, J=13.9 Hz), 5.25 (1H, d, J=13.9 Hz), 4.54–4.47 (4H, m), 4.29–4.12 (2H, m), 4.26 (1H, dd, J=2.2, 9.5 Hz), 4.09 (2H, t, J=8.8 Hz), 4.07 (2H, t, J=8.8 Hz), 3.29 (1H, dd, J=2.2, 6.6 Hz), 3.19 (1H, dq, J=9.5, 7.3 Hz), 2.37–2.27 (2H, m), 1.38 (3H, d, J=5.9 Hz), 1.26 (3H, d, J=7.3 Hz).

(2) (1R,5S,6S)-2-[1-(4-azetidinocarbonyl-1,3-oxazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-azetidinocarbonyl-1,3-oxazol-2-yl)azetidin-3-yl]thio-6-[(R)-1-hydroxyethyl]-1-methylcarbapen-2-em-3-carboxylate (600 mg, 1.03 mmol) (obtained as described in Example 75(1)) in a mixture of tetrahydrofuran (30 ml) and distilled water (30 ml) was subjected to catalytic hydrogenation in the presence of 10% palladium on charcoal (600 mg) at room temperature for 2 hours. After checking the completion of the reaction, the reaction mixture was filtered and to the filtrate were added sodium hydrogencarbonate (86 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→distilled water:acetonitrile (9:1)),and the eluate was lyophilized to afford the desired compound (1R,5S,6S)-2-[1-(4-azetidinocarbonyl-1,3-oxazol-2-yl)azetidin-3-yl]thio-6-[(R)-1-hydroxyethyl]-1-methylcarbapen-2-em-3-carboxylic acid sodium salt (278 mg, yield 58%) as a white solid.

$^1$H-NMR (400 MHz, D$_2$O, TSP): δ (ppm) 7.80 (1H, s), 4.59 (2H, t, J=8.3 Hz), 4.45 (2H, t, J=7.8 Hz), 4.35–4.27 (1H, m), 4.25 (1H, dq, J=6.2, 6.4 Hz), 4.20 (1H, dd, J=2.4, 9.1 Hz), 4.16 (2H, t, J=7.8 Hz), 4.08 (2H, dt, J=9.2, 4.6 Hz), 3.43 (1H, dd, J=2.4, 6.2 Hz), 3.24 (1H, dq, J=9.1, 7.2 Hz), 2.39 (1H, quintet, J=7.8 Hz), 1.30 (3H, d, J=6.4 Hz), 1.19 (3H, d, J=7.2 Hz).

IR (KBr): 1750, 1619, 1468, 1443, 1383 cm$^{-1}$.

Mass spectrum (FAB$^+$): m/z: 493 [M+Na]$^+$.

High-resolution mass spectrum (ESI$^+$): calculated for C$_{20}$H$_{23}$N$_4$O$_6$SNa$_2$: 493.1133, Found: 493.11 67 [M+Na]$^+$.

Elemental analysis: C$_{20}$H$_{23}$N$_4$O$_6$SNa.H$_2$O. Calculated for: C, 49.18%; H, 5.16%; N, 11.47%; S, 6.56%. Found: C, 49.04%; H, 5.46%; N, 11.57%; S, 6.29%.

EXAMPLE 76

(1R,5S,6S)-2-[1-(4-morpholinocarbonyl-1,3-oxazol-2-yl)azetidin-3-yl]thio-6-[(R)-1-hydroxyethyl]-1-methylcarbapen-2-em-3-carboxylic acid sodium salt

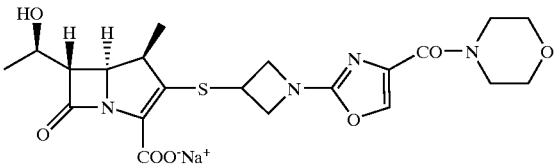

(1) p-Nitrobenzyl (1R,5S,6S)-2-[1-(4-morpholinocarbonyl-1,3-oxazol-2-yl)azetidin-3-yl]thio-6-[(R)-1-hydroxyethyl]-1-methylcarbapen-2-em-3-carboxylate To a solution of 3-acetylthio-1-(4-morpholinocarbonyl-1,3-oxazol-2-yl)azetidine (260 mg, 0.835 mmol) (obtained as described in Reference Example 72) in dimethylformamide (13 ml) was added hydrazine acetate (92 mg, 1.00 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (496 mg, 0.835 mmol) in acetonitrile (25 ml) was added dropwise into the resulting mixture in an ice bath under an atmosphere of nitrogen, followed by the addition of diisopropylethylamine (582 µl, 3.34 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate:methanol (9:1)) to afford p-nitrobenzyl (1R,5S,6S)-2-[1-(4-morpholinocarbonyl-1,3-oxazol-2-yl)azetidin-3-yl]thio-6-[(R)-1-hydroxyethyl]-1-methylcarbapen-2-em-3-carboxylate (552 mg, yield 100%) as a pale yellow solid.

$^1$H-NMR (400 MHz, CDCl$_3$): δ (ppm) 8.23 (2H, d, J=8.8 Hz), 7.73 (1H, s), 7.66 (2H, d, J=8.8 Hz), 5.51 (1H, d, J=13.2 Hz), 5.25 (1H, d, J=13.2 Hz), 4.52 (2H, q, J=8.1 Hz), 4.31–4.20 (3H, m), 4.13–4.06 (2H, m), 3.76–3.65 (8H, br s), 3.29 (1H, dd, J=2.5, 7.0 Hz), 3.19 (1H, dq, J=9.5, 7.3 Hz), 1.38 (3H, d, J=5.9 Hz), 1.26 (3H, d, J=7.3 Hz).

(2) (1R,5S,6S)-2-[1-(4-morpholinocarbonyl-1,3-oxazol-2-yl)azetidin-3-yl]thio-6-[(R)-1-hydroxyethyl]-1-methylcarbapen-2-em-3-carboxylic acid sodium salt p-Nitrobenzyl (1R,5S,6S)-2-[1-(4-morpholinocarbonyl-1,3-oxazol-2-yl)azetidin-3-yl]thio-6-[(R)-1-hydroxyethyl]-1-methylcarbapen-2-em-3-carboxylate (550 mg, 0.835 mmol) (obtained as described in Example 76(1)) in a mixture of tetrahydrofuran (28 ml) and distilled water (28 ml) was subjected to catalytic hydrogenation in the presence of 10% palladium on charcoal (550 mg) at room temperature for 2.5 hours. After checking the completion of the reaction, the reaction mixture was filtered and to the filtrate were added sodium hydrogencarbonate (70 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→distilled water:acetonitrile (9:1)) and the eluate was lyophilized to afford the desired compound (1R,5S,6S)-2-[1-(4-morpholinocarbonyl-1,3-oxazol-2-yl)azetidin-3-yl]thio-6-[(R)-1-hydroxyethyl]-1-methylcarbapen-2-em-3-carboxylic acid sodium salt (193 mg, yield 46%) as a white solid.

¹H-NMR (400 MHz, D₂O, TSP): δ (ppm) 7.77 (1H, s), 4.60 (2H, t, J=8.2 Hz), 4.36–4.28 (1H, m), 4.25 (1H, dq, J=6.1, 6.3 Hz), 4.21 (1H, dd, J=2.2, 9.0 Hz), 4.09 (1H, dt, J=8.9, 4.5 Hz), 3.90–3.66 (8H, m), 3.43 (1H, dd, J=2.2, 6.1 Hz), 3.25 (1H, dq, J=9.0, 7.2 Hz), 1.30 (3H, d, J=6.3 Hz), 1.19 (3H, d, J=7.2 Hz).

IR (KBr): 1750, 1618, 1459, 1443, 1385, 1304 cm⁻¹.

Mass spectrum (FAB⁺): m/z: 523 [M+Na]⁺.

High-resolution mass spectrum (ESI⁺): calculated for C₂₁H₂₅N₄O₇SNa₂: 523.1240, Found: 523.1238 [M+Na]⁺.

Elemental analysis: C₂₁H₂₅N₄O₇SNa/H₂O. Calculated for: C, 48.64%; H, 5.25%; N, 10.81%; S, 6.18%. Found: C, 48.45%; H, 5.41%; N, 10.45%; S, 5.55%.

EXAMPLE 77

(1R,5S,6S)-2-{1-[4-(3-methoxyazetidine-1-carbonyl)-1,3-oxazol-2-yl]azetidin-3-yl}thio-6-[(R)-1-hydroxyethyl]-1-methylcarbapen-2-em-3-carboxylic acid sodium salt

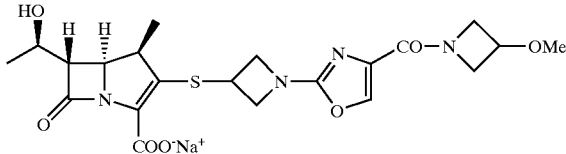

(1) p-Nitrobenzyl (1R,5S,6S)-2-{1-[4-(3-methoxyazetidine-1-carbonyl)-1,3-oxazol-2-yl]azetidin-3-yl}thio-6-[(R)-1-hydroxyethyl]-1-methylcarbapen-2-em-3-carboxylate To a solution of 3-acetylthio-1-(4-(3-methoxyazetidine-I-carbonyl)-1,3-oxazol-2-yl)azetidine (330 mg, 1.06 mmol) (obtained as described in Reference Example 73) in dimethylformamide (17 ml) was added hydrazine acetate (117 mg, 1.27 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (630 mg, 1.06 mmol) in acetonitrile (32 ml) was added dropwise into the resulting mixture in an ice bath under an atmosphere of nitrogen, followed by the addition of diisopropylethylamine (739 μl, 4.24 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate:methanol (95:5→9:1)) to afford p-nitrobenzyl (1R,5S,6S)-2-{1-[4-(3-methoxyazetidine-1-carbonyl)-1,3-oxazol-2-yl]azetidin-3-yl}thio-6-[(R)-1-hydroxyethyl]-1-methylcarbapen-2-em-3-carboxylate (550 mg, yield 85%) as a pale yellow solid.

¹H-NMR (400 MHz, CDCl₃): δ (ppm) 8.23 (2H, d, J=8.8 Hz), 7.74 (1H, s), 7.66 (2H, d, J=8.8 Hz), 5.55 (1H, d, J=13.2 Hz), 5.25 (1H, d, J=13.2 Hz), 4.71–4.63 (1H, m), 4.51 (2H, q, J=8.1 Hz), 4.38–4.20 (6H, m), 4.10–4.05 (2H, m), 4.04–3.98 (1H, m), 3.32 (3H, s), 3.29 (1H, dd, J=2.2, 6.6 Hz), 3.20 (1H, dq, J=9.2, 7.3 Hz), 1.38 (3H, d, J=5.9 Hz), 1.26 (3H, d, J=7.3 Hz).

(2) (1R,5S,6S)-2-{1-[4-(3-methoxyazetidine-1-carbonyl)-1,3-oxazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(3-methoxyazetidine-1-carbonyl)-1,3-oxazol-2-yl]azetidin-3-yl}thio-6-[(R)-1-hydroxyethyl]-1-methylcarbapen-2-em-3-carboxylate (550 mg, 0.896 mmol) (obtained as described in Example 77(1)) in a mixture of tetrahydrofuran (28 ml) and distilled water (28 ml) was subjected to catalytic hydrogenation in the presence of 10% palladium on charcoal (550 mg) at room temperature for 2 hours. After checking the completion of the reaction, the reaction mixture was filtered and to the filtrate were added sodium hydrogencarbonate (75 mg), acetic acid and distilled water. The resulting mixture was shaken in a separatory funnel and the aqueous layer was separated and concentrated under reduced pressure. The residue was purified by chromatography on a Cosmosil column (eluant: distilled water→distilled water:acetonitrile (92:8)) and the eluate was lyophilized to afford the desired compound (1R,5S,6S)-2-{1-[4-(3-methoxyazetidine-1-carbonyl)-1,3-oxazol-2-yl]azetidin-3-yl}thio-6-[(R)-1-hydroxyethyl]-1-methylcarbapen-2-em-3-carboxylic acid sodium salt (276 mg, yield 62%) as a white solid.

H-NMR (400 MHz, D₂O): δ (ppm) 7.84 (1H, s), 4.66 (1H, dd, J=6.4, 10.3 Hz), 4.60 (2H, t, J=8.3 Hz), 4.46–4.30 (4H, m), 4.25 (1H, dq, J=6.2, 6.4 Hz), 4.20 (1H, dd, J=2.4, 9.0 Hz), 4.09 (2H, quintet, J=4.5 Hz), 4.04–3.98 (1H, m), 3.43 (1H, dd, J=2.4, 6.2 Hz), 3.37 (3H, s), 3.25 (1H, dq, J=9.0, 7.2 Hz), 1.30 (3H, d, J=6.4 Hz), 1.19 (3H, d, J=7.2 Hz).

IR (KBr): 1750, 1622, 1457, 1385 cm⁻¹.

Mass spectrum (FAB⁺): m/z: 523 [M+Na]⁺.

High-resolution mass spectrum (ESI⁺): calculated for C₂₁H₂₅N₄O₇SNa₂: 523.1239, Found: 523.1227 [M+Na]⁺.

Elemental analysis: C₂₁H₂₅N₄O₇SNa.4/3H₂O. Calculated for: C, 48.09%; H, 5.32%; N, 10.68%; S, 6.11%. Found: C, 48.07%; H, 5.61%; N, 10.78%; S, 6.03%.

EXAMPLE 78

(1R,5S,6S)-2-{1-[4-(3-hydroxyazetidine-1-carbonyl)-1,3-oxazol-2-yl]azetidin-3-yl}thio-6-[(R)-1-hydroxyethyl]-1-methylcarbapen-2-em-3-carboxylic acid sodium salt

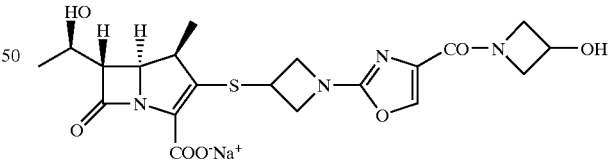

(1) p-Nitrobenzyl (1R,5S,6S)-2-(1-{4-[3-(t-butyldiphenylsilyloxy)-azetidin-1-ylcarbonyl]-1,3-oxazol-2-yl}azetidin-3-yl)thio-6-[(R)-1-hydroxyethyl]-1-methylcarbapen-2-em-3-carboxylate To a solution of 3-acetylthio-1-{4-[3-(t-butyldiphenylsilyloxy)-azetidin-1-ylcarbonyl]-1,3-oxazol-2-yl}azetidine (860 mg, 1.61 mmol) (obtained as described in Reference Example 74) in dimethylformamide (43 ml) was added hydrazine acetate (178 mg, 1.93 mmol) at room temperature under an atmosphere of nitrogen and the mixture was stirred for 1 hour. After checking the completion of the reaction, a solution of p-nitrobenzyl (1R,5S,6S)-2-

(diphenylphosphoryloxy)-6-[(R)-1-hydroxyethyl]-1-methylcarbapen-2-em-3-carboxylate (957 mg, 1.61 mmol) in acetonitrile (48 ml) was added dropwise into the resulting mixture in an ice bath under an atmosphere of nitrogen, followed by the addition of diisopropylethylamine (1.12 ml, 6.44 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (95:5)) to afford p-nitrobenzyl (1R,5S,6S)-2-(1-{4-[3-(t-butyldiphenylsilyloxy)-azetidin-1-ylcarbonyl]-1,3-oxazol-2-yl}azetidin-3-yl)thio-6-[(R)-1-hydroxyethyl]-1-methylcarbapen-2-em-3-carboxylate (1.20 g, yield 89%) as a pale yellow solid.

$^1$H-NMR (400 MHz, CDCl$_3$): δ (ppm) 8.23 (2H, d, J=8.8 Hz), 7.69 (1H, s), 7.66 (2H, d, J=8.8 Hz), 7.64–7.59 (4H, m), 7.47–7.36 (6H, m), 5.51 (1H, d, J=13.5 Hz), 5.25 (1H, d, J=13.5 Hz), 4.65–4.59 (1H, m), 4.69–4.50 (1H, m), 4.50 (2H, q, J=8.1 Hz), 4.39–4.32 (1H, m), 4.30–4.20 (2H, m), 4.26 (1H, dd, J=2.9, 9.5 Hz), 4.18–3.99 (4H, m), 3.29 (1H, dd, J=2.9, 7.3 Hz), 3.20 (1H, dq, J=9.5, 7.3 Hz), 1.38 (3H, d, J=6.5 Hz), 1.27 (3H, d, J=7.3 Hz), 1.06 (9H, s).

(2) p-Nitrobenzyl (1R,5S,6S)-2-{1-[4-(3-hydroxyazetidine-1-carbonyl)-1,3-oxazol-2-yl]azetidin-3-yl}thio-6-[(R)-1-hydroxyethyl]-1-methylcarbapen-2-em-3-carboxylate p-Nitrobenzyl (1R,5S,6S)-2-(1-{4-[3-(t-butyldiphenylsilyloxy)-azetidin-1-ylcarbonyl]-1,3-oxazol-2-yl}azetidin-3-yl)thio-6-[(R)-1-hydroxyethyl]-1-methylcarbapen-2-em-3-carboxylate (1.20 g, 1.43 mmol) (obtained as described in Example 78(1)) in tetrahydrofuran (60 ml) was added to acetic acid (240 μl, 4.30 mmol) and 1 M tetrabutylammonium fluoride in tetrahydrofuran solution (4.30 ml, 4.30 mmol) and the mixture was stirred at room temperature for 4 days. After checking the completion of the reaction, ethyl acetate and saturated aqueous sodium chloride solution were added to the reaction mixture. The resulting mixture was shaken in a separatory funnel and the ethyl acetate layer was separated, washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column (eluant: ethyl acetate:methanol (95:5→9:1)) to afford p-nitrobenzyl (1R,5S,6S)-2-{1-[4-(3-hydroxyazetidine-1-carbonyl)-1,3-oxazol-2-yl]azetidin-3-yl}thio-6-[(R)-1-hydroxyethyl]-1-methylcarbapen-2-em-3-carboxylate (325 mg, yield 38%) as a pale yellow solid.

$^1$H-NMR (400 MHz, CDCl$_3$): δ (ppm) 8.23 (2H, d, J=8.8 Hz), 7.74 (1H, s), 7.66 (2H, d, J=8.8 Hz), 5.51 (1H, d, J=13.7 Hz), 5.25 (1H, d, J=13.7 Hz), 4.80–4.68 (2H, m), 4.50 (2H, q, J=8.0 Hz), 4.431 4.29 (2H, m), 4.29–4.20 (3H, m), 4.13–4.05 (2H, m), 4.02–3.95 (1H, m), 3.29 (1H, dd, J=2.7, 6.9 Hz), 3.20 (1H, dq, J=9.3, 7.3 Hz), 1.38 (3H, d, J=6.3 Hz), 1.26 (3H, d, J=7.3 Hz).

(3) (1R,5S,6S)-2-{1-[4-(3-hydroxyazetidine-l1-carbonyl)-1,3-oxazol-2-yl]azetidin-3-yl}thio-6-[(R)-1-hydroxyethyl]-1-methylcarbapen-2-em-3-carboxylic acid sodium salt p-Nitrobenzyl (1R,5S,6S)-2-{1-[4-(3-hydroxyazetidine-1-carbonyl)-1,3-oxazol-2-yl]azetidin-3-yl}thio-6-[(R)-1-hydroxyethyl]-1-methylcarbapen-2-em-3-carboxylate (320 mg, 0.534 mmol (obtained as described in Example 78(2)) in a mixture of tetrahydrofuran (16 ml) and distilled water (16 ml) was subjected to catalytic hydrogenation in the presence of 10% palladium on charcoal (320 mg) at room temperature for 5 hours. After checking the completion of the reaction, the reaction mixture was filtered and to the filtrate were added sodium hydrogencarbonate (45 mg), ethyl acetate and distilled water. The resulting mixture was shaken in a separatory funnel and the aqueous layer was separated and concentrated under reduced pressure. The residue was purified by chromatography on a Cosmosil column (eluant: distilled water→distilled water:acetonitrile (9:1)) and the eluate was lyophilized to afford the desired compound (1R,5S,6S)-2-{1-[4-(3-hydroxyazetidine-1-carbonyl)-1,3-oxazol-2-yl]azetidin-3-yl}thio-6-[(R)-1-hydroxyethyl]-1-methylcarbapen-2-em-3-carboxylic acid sodium salt (144 mg, yield 56%) as a white solid.

$^1$H-NMR (400 MHz, D$_2$O, TSP): δ (ppm) 7.84 (1H, s), 4.75–4.66 (2H, m), 4.60 (2H, t, J=8.2 Hz), 4.44–4.38 (1H, m), 4.35–4.23 (3H, m), 4.20 (1H, dd, J=2.4, 9.0 Hz), 4.09 (2H, dt, J=8.9, 4.5 Hz), 3.98–3.93 (1H, m), 3.43 (1H, dd, J=2.4, 6.2 Hz), 3.24 (1H, dq, J=9.0, 7.2 Hz), 1.30 (3H, d, J=6.4 Hz), 1.19 (3H, d, J=7.2 Hz).

IR (KBr): 1750, 1621, 1470, 1385, 1294, 1277 cm$^{-1}$.

Mass spectrum (FAB$^+$): m/z: 509 [M+Na]$^+$.

High-resolution mass spectrum (ESI$^+$): calculated for 509.1083, Found: 509.1102 [M+Na]$^+$.

Elemental analysis: Calculated for: C, 49.38%; H, 4.77%; N, 11.52%; S, 6.59%. Found: C, 46.25%; H, 6.23%; N, 11.07%; S, 5.90%.

EXAMPLE 79

(1R,5S,6S)-2-{1-[4-(3-aminoazetidine-1-carbonyl)-1,3-oxazol-2-yl]azetidin-3-yl}thio-6-[(R)-1-hydroxyethyl]-1-methylcarbapen-2-em-3-carboxylic acid

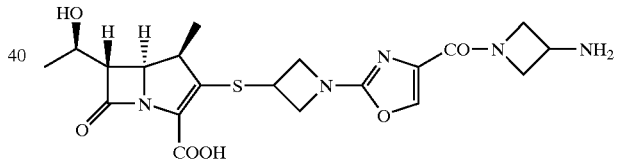

(1) p-Nitrobenzyl (1R,5S,6S)-2-{1-{4-[3-(p-nitrobenzyloxycarbonylamino)azetidin-1-ylcarbonyl]-1,3-oxazol-2-yl}azetidin-3-yl}thio-6-[(R)-1-hydroxyethyl]-1-methylcarbapen-2-em-3-carboxylate To a solution of 3-acetylthio-1-{4-[3-(p-nitrobenzyloxycarbonylamino)azetidin-1-ylcarbonyl]-1,3-oxazol-2-ylazetidine (190 mg, 0.383 mmol) (obtained as described in Reference Example 75) in dimethylformamide (10 ml) was added hydrazine acetate (42 mg, 0.460 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (228 mg, 0.383 mmol) in acetonitrile (11 ml) was added dropwise into the resulting mixture in an ice bath under an atmosphere of nitrogen, followed by the addition of diisopropylethylamine (268 μl, 1.53 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate:methanol (93:7)) to afford p-nitrobenzyl (1R,5S,6S)-2-{1-{4-[3-(p-nitrobenzyloxycarbonylamino)azetidin-1-ylcarbonyl]-1,3-oxazol-2-yl}azetidin-3-yl}thio-6-[(R)-1-hydroxyethyl]-1-methylcarbapen-2-em-3-carboxylate (257 mg, yield 86%) as a pale yellow solid.

$^1$H-NMR (400 MHz, CDCl$_3$): δ (ppm) 8.22 (4H, d, J=8.8 Hz), 7.75 (1H, s), 7.66 (2H, d, J=8.8 Hz), 7.51 (2H, d, J=8.8 Hz), 5.51 (1H, d, J=13.7 Hz), 5.34–5.31 (1H, m), 5.25 (1H, d, J=13.7 Hz), 5.21 (2H, s), 4.87–4.82 (1H, m), 4.60–4.42 (2H, m), 4.49 (2H, q, J=8.8 Hz), 4.38–4.30 (1H, m), 4.28–4.20 (3H, m), 4.06 (2H, dt, J=8.8, 4.9 Hz), 4.00–3.93 (1H, m), 3.29 (1H, dd, J=2.9, 6.8 Hz), 3.18 (1H, dq, J=9.0, 6.8 Hz), 1.38 (3H, d, J=5.9 Hz), 1.26 (3H, d, J=6.8 Hz).

(2) (1R,5S,6S)-2-{1-[4-(3-aminoazetidine-1-carbonyl)-1,3-oxazol-2-yl]azetidin-3-yl}thio-6-[(R)-1-hydroxyethyl]-1-methylcarbapen-2-em-3-carboxylic acid p-Nitrobenzyl (1R,5S,6S)-2-{1-{4-[3-(p-nitrobenzyloxycarbonylamino)azetidin-1-ylcarbonyl]-1,3-oxazol-2-yl}azetidin-3-yl}thio-6-[(R)-1-hydroxyethyl]-1-methylcarbapen-2-em-3-carboxylate (250 mg, 0.321 mmol) (obtained as described in Example 79(1)) in a mixture of tetrahydrofuran (13 ml) and distilled water (13 ml) was subjected to catalytic hydrogenation in the presence of 10% palladium on charcoal (250 mg) at room temperature for 3.5 hours. After checking the completion of the reaction, the reaction mixture was filtered and to the filtrate were added ethyl acetate and distilled water. The resulting mixture was shaken in a separatory funnel and the aqueous layer was separated and concentrated under reduced pressure. The residue was purified by chromatography on a Cosmosil column (eluant: distilled water→distilled water:acetonitrile (82:18)) and the eluate was lyophilized to afford the desired compound (1R,5S,6S)-2-{1-[4-(3-aminoazetidine-1-carbonyl)-1,3-oxazol-2-yl]azetidin-3-yl}thio-6-[(R)-1-hydroxyethyl]-1-methylcarbapen-2-em-3-carboxylic acid (68 mg, yield 46%) as a white solid.

$^1$H-NMR (400 MHz, D$_2$O): δ (ppm) 7.88 (1H, s), 4.60 (2H, t, J=8.2 Hz), 4.57–4.49 (2H, m), 4.35–4.16 (6H, m), 4.08 (2H, dt, J=8.6, 4.5 Hz), 3.44 (1H, dd, J=2.5, 6.2 Hz), 3.24 (1H, dq, J=9.0, 7.2 Hz), 1.30 (3H, d, J=6.4 Hz), 1.19 (3H, d, J=7.2 Hz).

IR (KBr): 1754, 1624, 1457, 1380 cm$^{-1}$.

Mass spectrum (ESI$^+$): m/z: 486 [M+Na]$^+$.

High-resolution mass spectrum (ESI$^+$): calculated for C$_{20}$H$_{26}$N$_5$O$_6$S: 464.1603, Found: 464.1609 [M+H]$^+$.

Elemental analysis: C$_{20}$H$_{25}$N$_5$O$_6$S.10/3H$_2$O. Calculated for: C, 45.85%; H, 5.69%; N, 13.62%; S, 6.18%. Found: C, 45.88%; H, 6.10%; N, 13.38%; S, 6.12%.

EXAMPLE 80

(1R,5S,6S)-2-{1-[4-((3S)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid

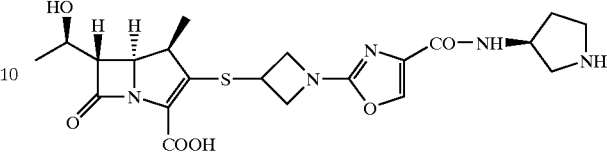

(1) p-Nitrobenzyl (1R,5S,6S)-2-(1-{4-[(3S)-1-(p-nitrobenzyloxycarbonyl)-pyrrolidin-3-ylcarbamoyl]-1,3-oxazol-2-yl}azetidin-3-yl)thio-6-[(R)-1-hydroxyethyl]-1-methylcarbapen-2-em-3-carboxylate To a solution of 3-acetylthio-1-{4-[(3S)-1-(p-nitrobenzyloxycarbonyl)-pyrrolidin-3-ylcarbamoyl]-1,3-oxazol-2-yl}azetidine (530 mg, 1.08 mmol) (obtained as described in Reference Example 76) in dimethylformamide (27 ml) was added hydrazine acetate (120 mg, 1.30 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (642 mg, 1.08 mmol) in acetonitrile (32 ml) was added dropwise into the resulting mixture in an ice bath under an atmosphere of nitrogen, followed by the addition of diisopropylethylamine (753 μl, 4.32 mmol). The mixture was stirred overnight while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (95:5)) to afford p-nitrobenzyl (1R,5S,6S)-2-(1-{4-[(3S)-1-(p-nitrobenzyloxycarbonyl)-pyrrolidin-3-ylcarbamoyl]-1,3-oxazol-2-yl}azetidin-3-yl)thio-6-[(R)-1-hydroxyethyl]-1-methylcarbapen-2-em-3-carboxylate (652 mg, yield 76%) as a pale yellow solid.

$^1$H-NMR (400 MHz, CDCl$_3$): δ (ppm) 8.23 (4H, d, J=8.8 Hz), 7.77 (1H, s), 7.66 (2H, d, J=8.8 Hz), 7.53 (2H, t, J=8.8 Hz), 6.82–6.78 (1H, m), 5.51 (1H, d, J=13.6 Hz), 5.25 (1H, d, J=13.6 Hz), 5.30–5.18 (2H, m), 4.66–4.58 (1H, m), 4.57–4.46 (2H, m), 4.11–4.20 (2H, m), 4.26 (1H, dd, J=2.2, 8.8 Hz), 4.14–4.04 (2H, m), 3.82–3.74 (1H, m), 3.64–3.55 (2H, m), 3.46–3.40 (1H, m), 3.29 (1H, dd, J=2.2, 6.6 Hz), 3.20 (1H, dq, J=8.8, 7.2 Hz), 2.30–2.20 (1H, m), 2.10–1.92 (1H, m), 1.38 (3H, d, J=6.6 Hz), 1.27 (3H, d, J=7.2 Hz).

(2) (1R,5S,6S)-2-{1-[4-((3S)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid p-Nitrobenzyl (1R,5S,6S)-2-(1-{4-[(3S)-1-(p-nitrobenzyloxycarbonyl)-pyrrolidin-3-ylcarbamoyl]-1,3-oxazol-2-yl}azetidin-3-yl)thio-6-[(R)-1-hydroxyethyl]-1-methylcarbapen-2-em-3-carboxylate (650 mg, 0.821 mmol) (obtained as described in Example 80(1)) in a mixture of tetrahydrofuran (33 ml) and distilled water (33 ml) was subjected to catalytic hydrogenation in the presence of 10% palladium on charcoal (650 mg) at room temperature for 4.5 hours. After checking the completion of the reaction, the reaction mixture was filtered and to the filtrate were added ethyl acetate and distilled water. The resulting mixture was shaken in a separatory funnel and the aqueous layer was separated and concentrated under reduced pressure. The residue was purified by chromatography on a Cosmosil column (eluant: distilled water distilled water:acetonitrile (76:24)), and the eluate was lyophilized to afford the desired compound (1R,5S,6S)-2-{1-[4-((3S)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid (129 mg, yield 33%) as a white solid.

$^1$H-NMR (400 MHz, D$_2$O): δ (ppm) 7.94 (1H, s), 4.68–4.60 (1H, m), 4.60 (2H, t, J=8.2 Hz), 4.35–4.28 (1H, m), 4.25 (1H, dq, J=6.2, 6.4 Hz), 4.19 (1H, dd, J=2.4, 9.1 Hz), 4.09 (2H, dt, J=8.9, 4.4 Hz), 3.63 (1H, dd, J=7.0, 12.6 Hz), 3.58 (1H, dt, J=12.0, 7.6 Hz), 3.50–2.98 (3H, m), 3.24 (1H, dq, J=9.1, 7.2 Hz), 2.49–2.39 (1H, m), 2.22–2.13 (1H, m), 1.30 (3H, d, J=6.4 Hz), 1.19 (3H, d, J=7.2 Hz).

IR (KBr): 1755, 1626, 1543, 1386 cm$^{-1}$.

Mass spectrum (FAB$^+$): m/z: 478 [M+H]$^+$.

High-resolution mass spectrum (FAB$^+$): calculated for C$_{21}$H$_{28}$N$_5$O$_6$S: 478.1761, Found: 478.1768 [M+H]$^+$.

Elemental analysis: C$_{21}$H$_{27}$N$_5$O$_6$S.3H$_2$O. Calculated for: C, 47.45%; H, 6.26%; N, 13.17%; S, 6.06%. Found: C, 47.33%; H, 5.52%; N, 12.9%; S, 5.97%.

EXAMPLE 81

(1R,5S,6S)-2-{1-[4-((3R)-1-(p-nitrobenzyloxycarbonyl)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid

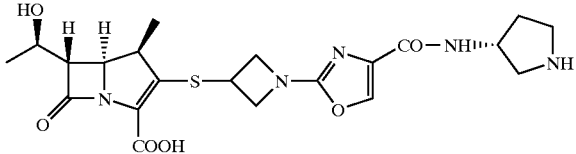

(1) p-Nitrobenzyl (1R,5S,6S)-2-{1-[4-((3R)-1-(p-nitrobenzyloxycarbonyl)-pyrrolidin-3-ylcarbamoyl)-1,3-oxazol-2-yl]azetidin-3-yl}thio-6-[(R)-1-hydroxyethyl]-1-methylcarbapen-2-em-3-carboxylate To a solution of 3-acetylthio-1-[4-((3R)-1-(p-nitrobenzyloxycarbonyl)-pyrrolidin-3-ylcarbamoyl)-1,3-oxazol-2-yl]azetidine (280 mg, 0.572 mmol) (obtained as described in Reference Example 77) in dimethylformamide (14 ml) was added hydrazine acetate (63 mg, 0.686 mmol) at room temperature under an atmosphere of nitrogen and the mixture was stirred for 1 hour. After checking the completion of the reaction, a solution of p-nitrobenzyl (1R,5S,6S)-2-(diphenylphosphoryloxy)-6-[(R)-1-hydroxyethyl]-1-methylcarbapen-2-em-3-carboxylate (340 mg, 0.572 mmol) in acetonitrile (17 ml) was added dropwise into the resulting mixture in an ice bath under an atmosphere of nitrogen, followed by the addition of diisopropylethylamine (399 μl, 2.29 mmol). The mixture was stirred for 4.5 hours while gradually raising the temperature to room temperature. After checking the completion of the reaction, ethyl acetate and saturated aqueous sodium hydrogencarbonate solution were added to the reaction mixture. The resulting mixture was shaken in a separatory funnel and the ethyl acetate layer was separated, washed with 10% sodium chloride solution and saturated aqueous sodium chloride solution, dried over anhydrous sodium sulfate, filtered and concentrated under reduced pressure. The residue was purified by chromatography on a silica gel column (eluant: ethyl acetate→ethyl acetate:methanol (95:5)) to afford p-nitrobenzyl (1R,5S,6S)-2-1-[4-((3R)-1-(p-nitrobenzyloxycarbonyl)-pyrrolidin-3-ylcarbamoyl)-1,3-oxazol-2-yl]azetidin-3-yl}thio-6-[(R)-1-hydroxyethyl]-1-methylcarbapen-2-em-3-carboxylate (323 mg, yield 73%) as a pale yellow solid.

$^1$H-NMR (400 MHz, CDCl$_3$): δ (ppm) 8.23 (2H, d, J=8.8 Hz), 8.22 (2H, dd, J=8.8, 12.7 Hz), 7.77 (1H, s), 7.66 (2H, d, J=8.8 Hz), 7.52 (2H, dd, J=8.8, 12.7 Hz), 6.82–6.78 (1H, bt, J=6.8 Hz), 5.51 (1H, d, J=13.7 Hz), 5.23 (1H, d, J=13.7 Hz), 5.25–5.19 (2H, m), 4.66–4.58 (1H, m), 4.56–4.49 (2H, m), 4.30–4.21 (3H, m), 4.13–4.04 (2H, m), 3.80–3.74 (1H, m), 3.64–3.53 (2H, m), 3.44–3.39 (1H, m), 3.29 (1H, dd, J=2.9, 6.8 Hz), 3.20 (1H, dq, J=7.8, 7.8 Hz), 2.30–2.20 (1H, m), 2.10–1.94 (1H, m), 1.38 (3H, d, J=5.9 Hz), 1.27 (3H, d, J=7.8 Hz).

(2) (1R,5S,6S)-2-{1-[4-((3R)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid p-Nitrobenzyl (1R,5S,6S)-2-{1-[4-((3R)-1-(p-nitrobenzyloxycarbonyl)-pyrrolidin-3-ylcarbamoyl)-1,3-oxazol-2-yl]azetidin-3-yl}thio-6-[(R)-1-hydroxyethyl]-1-methylcarbapen-2-em-3-carboxylate (320 mg, 0.404 mmol) (obtained as described in Example 81(1)) in a mixture of tetrahydrofuran (16 ml) and distilled water (16 ml) was subjected to catalytic hydrogenation in the presence of 10% palladium on charcoal (320 mg) at room temperature for 4 hours. After checking the completion of the reaction, the reaction mixture was filtered and to the filtrate were added ethyl acetate and distilled water. The resulting mixture was shaken in a separatory funnel and the aqueous layer was separated and concentrated under reduced pressure. The residue was purified by chromatography on a Cosmosil column (eluant: distilled water→distilled water:acetonitrile (79:21)) and the eluate was lyophilized to afford the desired compound (1R,5S,6S)-2-{1-[4-((3R)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid (88 mg, yield 46%) as a white solid.

$^1$H-NMR (400 MHz, D$_2$O): δ (ppm) 7.94 (1H, s), 4.67–4.60 (1H, m), 4.60 (2H, t, J=8.3 Hz), 4.35–4.28 (1H, m), 4.25 (1H, dq, J=6.2, 6.4 Hz), 4.20 (1H, dd, J=2.4, 9.1 Hz), 4.08 (2H, dt, J=8.8, 4.5 Hz), 3.63 (1H, dd, J=7.0, 12.6 Hz), 3.57 (1H, dt, J=12.0, 7.6 Hz), 3.49–3.37 (3H, m), 3.24 (1H, dq, J=9.1, 7.2 Hz), 2.49–2.38 (1H, m), 2.22–2.13 (1H, m), 1.30 (3H, d, J=6.4 Hz), 1.19 (3H, d, J=7.2 Hz).

IR (KBr): 1758, 1625, 1543, 1385 cm$^{-1}$.

Mass spectrum (ESI$^+$): m/z: 478 [M+H]$^+$.

High-resolution mass spectrum (ESI$^+$): calculated for C$_{21}$H$_{28}$N$_5$O$_6$S: 478.1760, Found: 478.1739 [M+H]$^+$.

Elemental analysis: C$_{21}$H$_{27}$N$_5$O$_6$S.3H$_2$O. Calculated for: C, 47.45%; H, 6.26%; N, 13.17%; S, 6.03%. Found: C, 47.30%; H, 5.88%; N, 13.14%; S, 6.01%.

REFERENCE EXAMPLE 1

3-Acetylthio-1-(4-ethoxycarbonyl-1,3-thiazol-2-yl)azetidine

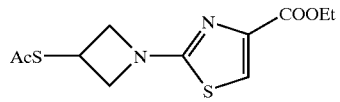

(1) (3-Hydroxyazetidine-1-carbothioyl)carbamic acid ethyl ester

A solution of N-benzhydryl-3-hydroxyazetidine (20 g, 83.6 mmol) in methanol (600 ml) was subjected to catalytic hydrogenation in the presence of 10% palladium on charcoal (20 g) in a water bath (50° C.) under 1 atmosphere hydrogen pressure for 2 hours. After checking the completion of the reaction, the reaction mixture was filtered in order to remove the catalyst and the filtrate was concentrated under reduced pressure. The residue was partitioned between ethyl acetate and distilled water. The organic layer was separated and further extracted with distilled water. The aqueous layers were concentrated under reduced pressure and dried in vacuo to give a product as a brown oil. To a solution of the product in a mixture of tetrahydrofuran (180 ml) and distilled water (60 ml) was added ethoxycarbonyl isothiocyanate (19.7 ml, 167 mmol) in an ice bath. After stirring the mixture for 10 minutes in the ice bath, the resulting mixture was stirred at room temperature overnight. After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using n-hexane:ethyl acetate (1:1)→ethyl acetate as the eluant to afford (3-hydroxyazetidine-1-carbothioyl)carbamic acid ethyl ester (7.4 g, yield 43%) as a yellow oil.

$^1$H-NMR (400 MHz, CDCl$_3$): δ 7.63 (1H, br s), 4.80–4.50 (3H, m), 4.40–4.00 (4H, m including 2H, q, at 4.18, J=7.3 Hz), 2.28 (1H, br s), 1.29 (3H, t, 7.3 Hz).

(2) 1-(4-Ethoxycarbonyl-1,3-thiazol-2-yl)-3-hydroxyazetidine

To a solution of (3-hydroxyazetidine-1-carbothioyl)carbamic acid ethyl ester (14.4 g, 70.5 mmol) (obtained as described in Reference Example 1(1)) in a mixture of ethanol (72 ml) and distilled water (72 ml) was added sodium hydroxide (14.1 g, 353 mmol). The mixture was heated under reflux for 16 hours. After checking the completion of the reaction, the reaction mixture was cooled to room temperature. To the reaction mixture was added 4N hydrogen chloride gas in dioxane (88 ml) in an ice bath, followed by the addition of ethyl 2-bromopyruvate (17.7 ml, 141 mmol) and triethylamine (19.8 ml, 141 mmol). The resulting mixture was heated under reflux for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using toluene:acetonitrile (3:1→1:1) as the eluant to afford 1-(4-ethoxycarbonyl-1,3-thiazol-2-yl)-3-hydroxyazetidine (8.5 g, yield 53%) as a pale brown solid.

$^1$H-NMR (400 MHz, CDCl$_3$): δ 7.46 (1H, s), 4.88–4.78 (1H, m), 4.42–4.32 (4H, m), 4.02 (2H, ddd, J=10.3, 5.6, 1.5 Hz), 2.05 (1H, br s), 1.37 (3H, t, 7.3 Hz).

(3) 1-(4-Ethoxycarbonyl-1,3-thiazol-2-yl)-3-methanesulfonyloxyazetidine

To a solution of 1-(4-ethoxycarbonyl-1,3-thiazol-2-yl)-3-hydroxyazetidine (676 mg, 2.96 mmol) (obtained as described in Reference Example 1(2)) in methylene chloride (20.5 ml) were added methanesulfonyl chloride (0.28 ml, 3.63 mmol) and triethylamine (0.495 ml, 3.56 mmol) in an ice bath. After stirring the mixture in the ice bath for 10 minutes, the mixture was stirred at room temperature for 2 hours. After checking the completion of the reaction, ethanol was added to the reaction mixture in an ice bath and the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:2) as the eluant to afford 1-(4-ethoxycarbonyl-1,3-thiazol-2-yl)-3-methanesulfonyloxyazetidine (748 mg, yield 82%) as a pale brown solid.

$^1$H-NMR (400 MHz, CDCl$_3$): δ (ppm) 7.52 (1H, s), 5.50–5.30 (1H, m), 4.51 (2H, dd, J=9.9, 6.7 Hz), 4.37 (2H, q, J=7.1 Hz), 4.32 (2H, dd, J=10.1, 3.7 Hz), 3.09 (3H, s), 1.37 (3H, t, J=7.1 Hz).

(4) 3-Acetylthio-1-(4-ethoxycarbonyl-1,3-thiazol-2-yl)azetidine

To a solution of 1-(4-ethoxycarbonyl-1,3-thiazol-2-yl)-3-methanesulfonyloxyazetidine (742 mg, 2.42 mmol) (obtained as described in Reference Example 1(3)) in dimethylformamide (37 ml) was added potassium thioacetate (1.11 g, 9.72 mmol) at room temperature. The mixture was stirred in an oil bath (80° C.) for 6 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:1) as the eluant to afford 3-acetylthio-1-(4-ethoxycarbonyl-1,3-thiazol-2-yl)azetidine (494 mg, yield 71%) as a pale brown solid.

$^1$H-NMR (400 MHz, CDCl$_3$): δ (ppm) 7.49 (1H, s), 4.58 (2H, t, J=8.3 Hz), 4.50–4.30 (3H, m, including 2H, q, at 4.36, J=7.2 Hz), 4.03 (2H, dd, J=8.3, 5.7 Hz), 2.36 (3H, s), 1.37 (3H, t, J=7.2 Hz).

Mass spectrum (FAB$^+$): 287 [M+H]$^+$.

REFERENCE EXAMPLE 2

3-Acetylthio-1-(4-p-nitrobenzyloxycarbonyl-1,3-thiazol-2-yl)azetidine

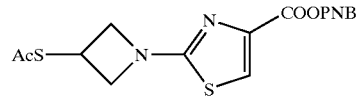

(1) 3-t-Butyldiphenylsilyloxy-1-(4-ethoxycarbonyl-1,3-thiazol-2-yl)azetidine

To a solution of 1-(4-ethoxycarbonyl-1,3-thiazol-2-yl)-3-hydroxyazetidine (8.5 g, 37.2 mmol) (obtained as described in Reference Example 1(2)) in dimethylformamide (255 ml) were added t-butyldiphenylsilyl chloride (19.4 ml, 74.5 mmol) and imidazole (5.07 g, 74.5 mmol) in an ice bath.

After stirring the mixture in an ice bath for 10 minutes, the resulting mixture was stirred at room temperature for 2.5 hours. After checking the completion of the reaction, ethanol (2.59 ml) was added to the reaction mixture in an ice bath and the resulting mixture was stirred at room temperature for 30 minutes. The reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→2:1) as the eluant to afford 3-t-butyldiphenylsilyloxy-1-(4-ethoxycarbonyl-1,3-thiazol-2-yl)azetidine (14.85 g, yield 86%) as a pale brown solid.

$^1$H-NMR (400 MHz, CDCl$_3$): δ (ppm) 7.64–7.58 (4H, m), 7.50–7.36 (6H, m), 7.43 (1H, s), 4.79–4.50 (1H, m), 4.35 (2H, q, J=7.3 Hz), 4.13 (2H, dd, J=9.0, 6.6 Hz), 4.06 (2H, dd, J=9.0, 5.1 Hz), 1.36 (3H, t, J=7.1 Hz), 1.06 (9H, s).

(2) 3-t-Butyldiphenylsilyloxy-1-(4-hydroxymethyl-1,3-thiazol-2-yl)azetidine

A solution of 3-t-butyldiphenylsilyloxy-1-(4-ethoxycarbonyl-1,3-thiazol-2-yl)azetidine (5.0 g, 10.7 mmol) (obtained as described in Reference Example 2(1)) in anhydrous tetrahydrofuran (100 ml) was added dropwise to a solution of lithium aluminum hydride (1.22 g, 32.1 mmol) in anhydrous tetrahydrofuran (250 ml) in an ice bath under an atmosphere of nitrogen and the mixture was stirred for 1.5 hours under the same conditions. After checking the completion of the reaction, magnesium sulfate decahydrate was gradually added to the reaction mixture in an ice bath. After termination of foaming, the resulting mixture was stirred at room temperature for 1 hour. Ethyl acetate was gradually added to the reaction mixture. The resulting mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using n-hexane:ethyl acetate (3:1→1:2) as the eluant to afford 3-t-butyldiphenylsilyloxy-1-(4-hydroxymethyl-1,3-thiazol-2-yl)azetidine (3.88 g, yield 86%) as a white solid.

$^1$H-NMR (400 MHz, CDCl$_3$): δ (ppm) 7.66–7.58 (4H, m), 7.50–7.38 (6H, m), 6.40 (1H, s), 4.78–4.70 (1H, m), 4.53 (2H, s), 4.10 (2H, dd, J=9.2, 6.6 Hz), 4.01 (2H, ddd, J=9.2, 5.1, 1.3 Hz), 2.24 (1H, br s), 1.06 (9H, s).

(3) 3-t-Butyldiphenylsilyloxy-1-(4-formyl-1,3-thiazol-2-yl)azetidine

To a solution of 3-t-butyldiphenylsilyloxy-1-(4-hydroxymethyl-1,3-thiazol-2-yl)azetidine (3.88 g, 9.15 mmol) (obtained as described in Reference Example 2(2)) in anhydrous methylene chloride (194 ml) were added activated manganese dioxide (19.4 g) and the mixture was stirred at room temperature for 7 hours. After checking the completion of the reaction, the reaction mixture was filtered and the filtrate concentrated under reduced pressure. The residue was purified by chromatography on a silica gel column using n-hexane:ethyl acetate (3:1→1:1) as the eluant to afford 3-t-butyldiphenylsilyloxy-1-(4-formyl-1,3-thiazol-2-yl)azetidine (3.54 g, yield 92%) as a white solid.

$^1$H-NMR (400 MHz, CDCl$_3$): δ (ppm) 9.69 (1H, s), 7.64–7.59 (4H, m), 7.50–7.36 (7H, m), 4.80–4.72 (1H, m), 4.16 (2H, dd, J=9.5, 6.6 Hz), 4.08 (2H, ddd, J=9.5, 5.1, 1.5 Hz), 1.06 (9H, s).

(4) 3-t-Butyldiphenylsilyloxy-1-(4-carboxyl-1,3-thiazol-2-yl)azetidine

To a solution of 3-t-butyldiphenylsilyloxy-1-(4-formyl-1,3-thiazol-2-yl)azetidine (3.5 g, 8.28 mmol) (obtained as described in Reference Example 2(3)) in anhydrous methylene chloride (21 ml) were added t-butanol (105 ml) and a solution of 2M 2-methyl-2-butene in tetrahydrofuran (41.4 ml), followed by dropwise addition of a solution of sodium chlorite (1.88 g, 16.6 mmol) and sodium dihydrogenphosphate (1.99 g, 16.6 mmol) in water (21 ml) in an ice bath and the mixture was stirred for 1 hour. After checking the completion of the reaction, to the reaction mixture was added 1 M hydrochloric acid to a pH of from 2 to 3. The resulting mixture was extracted with ethyl acetate. The organic layer was separated, washed with saturated aqueous sodium chloride solution, dried over anhydrous sodium sulfate, filtered and concentrated under reduced pressure. The residue was purified by chromatography on a silica gel column using ethyl acetate→5% methanol in ethyl acetate as the eluant to afford 3-t-butyldiphenylsilyloxy-1-(4-carboxyl-1,3-thiazol-2-yl)azetidine (2.34 g, yield 67%) as a brown syrup.

$^1$H-NMR (400 MHz, CDCl$_3$): δ (ppm) 7.62–7.56 (4H, m), 7.50 (1H, s), 7.49–7.36 (6H, m), 4.81–4.72 (1H, m), 4.16–4.08 (2H, m), 4.04 (2H, dd, J=9.5, 5.1 Hz), 2.00 (1H, br s), 1.07 (9H, s).

(5) 3-t-Butyldiphenylsilyloxy-1-(4-p-nitrobenzyloxycarbonyl-1,3-thiazol-2-yl)azetidine To a solution of 3-t-butyldiphenylsilyloxy-1-(4-carboxyl-1,3-thiazol-2-yl)azetidine (224.8 mg, 0.51 mmol) (obtained as described in Reference Example 2(4)) in anhydrous methylene chloride (11.2 ml) were added oxalyl chloride (0.067 ml, 0.76 mmol) and a catalytic amount of dimethylformamide (0.022 ml) in an ice bath. The mixture was stirred for 2 hours and then concentrated under reduced pressure. The residue was dried in vacuo to give a product. To a solution of the product in anhydrous dichloromethane (11.2 ml) were added p-nitrobenzyl alcohol (157 mg, 1.0 mmol) and triethylamine (0.14 ml, 1.0 mmol) in an ice bath. The mixture was stirred for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (3:1) as the eluant to afford 3-t-butyldiphenylsilyloxy-1-(4-p-nitrobenzyloxycarbonyl-1,3-thiazol-2-yl)azetidine (93 mg, yield 32%) as a pale yellow syrup.

$^1$H-NMR (400 MHz, CDCl$_3$): δ (ppm) 8.22 (2H, d, J=8.8 Hz), 7.64–7.56 (4H, m), 7.50 (1H, s), 7.48–7.36 (6H, m), 5.42 (2H, s), 4.79–4.72 (1H, m), 4.16 (2H, dd, J=8.8, 6.8 Hz), 4.07 (2H, dd, J=8.8, 4.8 Hz), 1.06 (9H, s).

(6) 1-(4-p-Nitrobenzyloxycarbonyl-1,3-thiazol-2-yl)-3-hydroxyazetidine

To a solution of 3-t-butyldiphenylsilyloxy-1-(4-p-nitrobenzyloxycarbonyl-1,3-thiazol-2-yl)azetidine (93 mg, 0.16 mmol) (obtained as described in Reference Example 2(5)) in anhydrous tetrahydrofuran (4.7 ml) were added acetic acid (0.028 ml, 0.49 mmol) and a solution of 1 M tetrabutylammonium fluoride in tetrahydrofuran (0.48 ml, 0.48 mmol) in an ice bath. The mixture was stirred for 2 hours. After checking the completion of the reaction, reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using toluene:acetonitrile (2:1) as the eluant to afford 1-(4-p-nitrobenzyloxycarbonyl-1,3-thiazol-2-yl)-3-hydroxyazetidine (42.4 mg, yield 81%) as a pale yellow solid.

¹H-NMR (400 MHz, CDCl₃): δ (ppm) 8.23 (2H, d, J=8.8 Hz), 7.59 (2H, d, J=8.8 Hz), 7.53 (1H, s), 5.40 (2H, s), 4.90–4.78 (1H, m), 4.39-(2H, dd, J=9.7, 7.2 Hz), 4.03 (2H, dd, J=9.7, 5.1 Hz), 2.28 (1H, d, J=6.2 Hz).

(7) 1-(4-p-Nitrobenzyloxycarbonyl-1,3-thiazol-2-yl)-3-methanesulfonyloxyazetidine To a solution of 1-(4-p-nitrobenzyloxycarbonyl-1,3-thiazol-2-yl)-3-hydroxyazetidine (648 mg, 1.93 mmol) (obtained as described in Reference Example 2(6)) in methylene chloride (20 ml) were added methanesulfonyl chloride (0.31 ml, 3.95 mmol) and triethylamine (0.55 ml, 3.95 mmol) in an ice bath. After stirring the mixture in the ice bath for 10 minutes, the mixture was stirred at room temperature for 3 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was recrystallized from a mixture of n-hexane and ethyl acetate to afford 1-(4-p-nitrobenzyloxycarbonyl-1,3-thiazol-2-yl)-3-methanesulfonyloxyazetidine (789 mg, yield 99%) as a white solid.

¹H-NMR (400 MHz, CDCl₃): δ (ppm) 8.23 (2H, d, J=8.7 Hz), 7.59 (1H, s), 7.59 (2H, d, J=8,7 Hz), 5.50–5.40 (3H, m including 1H, s at 5.44), 4.52 (2H, dd, J=10.3, 6.6 Hz), 4.32 92H, dd, J=10.3, 4.1 Hz), 3.10 (3H, s).

(8) 3-Acetylthio-1-(4-p-nitrobenzyloxycarbonyl-1,3-thiazol-2-yl)azetidine

To a solution of 1-(4-p-nitrobenzyloxycarbonyl-1,3-thiazol-2-yl)-3-methanesulfonyloxyazetidine (776 mg, 1.88 mmol) (obtained as described in Reference Example 2(7)) in dimethylformamide (35 ml) was added potassium thioacetate (860 mg, 7.53 mmol) at room temperature. The mixture was stirred in an oil bath (90° C.) for 4 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:1) as the eluant to afford 3-acetylthio-1-(4-p-nitrobenzyloxycarbonyl-1,3-thiazol-2-yl)azetidine (73.8 mg, yield 11%) as a pale brown solid.

¹H-NMR (400 MHz, CDCl₃): δ (ppm) 8.23 (2H, d, J=8.6 Hz), 7.59 (2H, d, J=8.6 Hz), 7.55 (1H, s), 5.43 (2H, s), 4.59 (2H, t, J=8.5 Hz), 4.50–4.40 (1H, m), 4.04 (2H, dd, J=8.5, 5.7 Hz), 2.36 (3H, s).

REFERENCE EXAMPLE 3

3-Acetylthio-1-(4-carbamoyl-1,3-thiazol-2-yl)azetidine

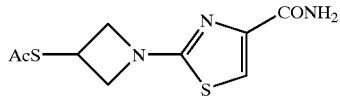

(1) 3-t-Butyldiphenylsilyloxy-1-(4-carbamoyl-1,3-thiazol-2-yl)azetidine

To a solution of 3-t-butyldiphenylsilyloxy-1-(4-ethoxycarbonyl-1,3-thiazol-2-yl)azetidine (5.85 g, 12.5 mmol) (obtained as described in Reference Example 2(1)) in benzene (290 ml) was added a solution of 0.67M ammonium chloride-trimethylaluminium in benzene (56.4 ml) at room temperature under an atmosphere of nitrogen. The mixture was stirred in a water bath (40° C.) for 17 hours. After checking the completion of the reaction, 10% aqueous acetic acid solution (100 ml) and ethyl acetate (50 ml) were added to the reaction mixture in an ice bath and the resulting mixture was stirred at room temperature for 2 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using toluene:acetonitrile (3:1→1:2) as the eluant to afford 3-t-butyldiphenylsilyloxy-1-(4-carbamoyl-1,3-thiazol-2-yl) azetidine (4.97 g, yield 91%) as a pale brown solid.

¹H-NMR (400 MHz, CDCl₃): δ (ppm) 7.66–7.58 (4H, m), 7.50–7.38 (7H, m), 6.99 (1H, bs), 5.48 (1H, br s), 4.80–4.72 (1H, m), 4.10 (2H, dd, J=8.8, 6.6 Hz), 4.01 (2H, dd, J=8.8, 5.1 Hz), 1.07 (9H, s).

(2) 1-(4-Carbamoyl-1,3-thiazol-2-yl)-3-hydroxyazetidine

To a solution of 3-t-butyldiphenylsilyloxy-1-(4-carbamoyl-1,3-thiazol-2-yl)azetidine (6.7 g, 15.3 mmol) (obtained as described in Reference Example 3(1)) in anhydrous tetrahydrofuran (200 ml) was added a solution of 1.0M tetra-n-butylammonium fluoride in tetrahydrofuran (18.4 ml) in an ice bath. The mixture was stirred for 1 hour. After checking the completion of the reaction, the reaction mixture was concentrated under reduced pressure. The residue was purified by chromatography on a silica gel column using ethyl acetate→10% methanol in ethyl acetate as the eluant to afford 1-(4-carbamoyl-1,3-thiazol-2-yl)-3-hydroxyazetidine (2.78 g, yield 91%) as a pale yellow solid.

¹H-NMR (400 MHz, CDCl₃): δ (ppm) 7.43 (1H, s), 7.05 (1H, br s), 5.47 (1H, br s), 4.90–4.80 (1H, m), 4.35 (2H, dd, J=9.5, 6.6 Hz), 3.97 (2H, dd, J=9.5, 4.4 Hz), 2.31 (1H, d, J=9.6 Hz).

(3) 1-(4-Carbamoyl-1,3-thiazol-2-yl)-3-methanesulfonyloxyazetidine

To a solution of 1-(4-carbamoyl-1,3-thiazol-2-yl)-3-hydroxyazetidine (1.0 g, 5.02 mmol) (obtained as described in Reference Example 3(2)) in a mixture of methylene chloride (30 ml) and pyridine (5 ml) were added methanesulfonyl chloride (0.967 ml, 12.5 mmol) and triethylamine (1.75 ml, 12.5 mmol) in an ice bath. After stirring the mixture in the ice bath for 10 minutes, the mixture was stirred at room temperature for 2.5 hours. After checking the completion of the reaction, methanol (0.405 ml) was added to the reaction mixture in an ice bath and then the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. To the residue was added isopropyl ether, and the mixture was filtered to afford 1-(4-carbamoyl-1,3-thiazol-2-yl)-3-methanesulfonyloxyazetidine (1.30 g, yield 94%) as a pale yellow solid.

$^1$H-NMR (400 MHz, CDCl$_3$): δ (ppm) 7.50 (1H, s), 6.99 (1H, br s), 5.60–5.40 (2H, m), 4.46 (2H, ddd, J=9.5, 6.6, 1.5 Hz), 4.28 (2H, ddd, J=9.5, 4.4, 1.5 Hz), 3.11 (1H, s).

(4) 3-Acetylthio-1-(4-carbamoyl-1,3-thiazol-2-yl)azetidine

To a solution of 1-(4-carbamoyl-1,3-thiazol-2-yl)-3-methanesulfonyloxyazetidine (3.04 g, 11.0 mmol) (obtained as described in Reference Example 3(3)) in dimethylformamide (152 ml) was added potassium thioacetate (7.5 g, 65.8 mmol) at room temperature. The mixture was stirred in an oil bath (80° C.) for 10 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate→4% methanol in ethyl acetate as the eluant to afford 3-acetylthio-1-(4-carbamoyl-1,3-thiazol-2-yl)azetidine (1.97 g, yield 70%) as a pale brown solid.

$^1$H-NMR (400 MHz, CDCl$_3$): δ (ppm) 7.46 (1H, s), 7.00 (1H, br s), 5.55 (1H, br s), 4.53 (2H, t, J=8.1 Hz), 4.50–4.40 (1H, m), 3.99 (2H, dd, J=8.1, 5.1 Hz), 2.37 (3H, s).

REFERENCE EXAMPLE 4

3-Acetylthio-1-(4-cyano-1,3-thiazol-2-yl)azetidine

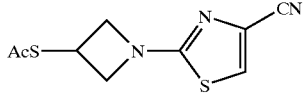

(1) 3-t-Butyldiphenylsilyloxy-1-(4-cyano-1,3-thiazol-2-yl)azetidine

To a solution of 3-t-butyldiphenylsilyloxy-1-(4-ethoxycarbonyl-1,3-thiazol-2-yl)azetidine (7.73 g, 16.6 mmol) (obtained as described in Reference Example 2(1)) in benzene (370 ml) was added a solution of 0.67M ammonium chloride-trimethylaluminium in benzene (75 ml) at room temperature under an atmosphere of nitrogen. The mixture was stirred in a water bath (50° C.) for 17 hours. After checking the completion of the reaction, 10% aqueous acetic acid solution (100 ml) and ethyl acetate (50 ml) were added to the reaction mixture in an ice bath and the resulting mixture was stirred at room temperature for 30 minutes. The reaction mixture was extracted with ethyl acetate. The organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using n-hexane:ethyl acetate (3:1) as the eluant to afford 3-t-butyldiphenylsilyloxy-1-(4-cyano-1,3-thiazol-2-yl)azetidine (6.98 g, yield 76%) as a pale brown solid.

$^1$H-NMR (400 MHz, CDCl$_3$): δ 7.64 (4H, m), 7.50–7.37 (6H, m), 7.20 (1H, s), 4.80–4.74 (1H, m), 4.13 (2H, dd, J=8.8, 6.8 Hz), 4.04 (2H, dd, J=8.8, 4.9 Hz), 1.07 (9H, s).

IR (KBr): 2230, 1535, 1465, 1310, 1114 cm$^{-1}$.

Mass spectrum (FAB$^+$): 420 [M+H]$^+$.

(2) 1-(4-Cyano-1,3-thiazol-2-yl)-3-hydroxyazetidine

To a solution of 3-t-butyldiphenylsilyloxy-1-(4-cyano-1,3-thiazol-2-yl)azetidine (2.36 g, 5.62 mmol) (obtained as described in Reference Example 4(1)) in anhydrous tetrahydrofuran (115 ml) was added a solution of 1.0M tetra-n-butylammonium fluoride in tetrahydrofuran (6.7 ml, 6.7 mmol) in an ice bath. The mixture was stirred in the ice bath for 1 hour. After checking the completion of the reaction, the reaction mixture was concentrated under reduced pressure. The residue was purified by chromatography on a silica gel column using toluene:ethyl acetate (1:2) as the eluant to afford 1-(4-cyano-1,3-thiazol-2-yl)-3-hydroxyazetidine (0.78 g, yield 77%) as a white solid.

$^1$H-NMR (400 MHz, CDCl$_3$): δ (ppm) 7.26 (1H, s), 4.92–4.86 (1H, m), 4.37 (2H, dd, J=9.8, 6.8 Hz), 4.02 (2H, dd, J=9.8, 4.9 Hz), 2.34 (1H, d, J=5.9 Hz).

(3) 1-(4-Cyano-1,3-thiazol-2-yl)-3-methanesulfonyloxyazetidine

To a solution of 1-(4-cyano-1,3-thiazol-2-yl)-3-hydroxyazetidine (0.78 g, 4.3 mmol) (obtained as described in Reference Example 4(2)) in methylene chloride (40 ml) were added methanesulfonyl chloride (1.0 ml, 12.9 mmol) and triethylamine (1.8 ml, 12.9 mmol) in an ice bath. After stirring the mixture in the ice bath for 10 minutes, the mixture was stirred at room temperature for 40 minutes. After checking the completion of the reaction, methanol was added to the reaction mixture in an ice bath and then the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using toluene:ethyl acetate (1:1) as the eluant to afford 1-(4-cyano-1,3-thiazol-2-yl)-3-methanesulfonyloxyazetidine (1.12 g, yield 100%) as a white solid.

$^1$H-NMR (400 MHz, CDCl$_3$): δ (ppm) 7.31 (1H, s), 5.50–5.40 (1H, m), 4.50 (2H, dd, J=9.9, 6.6 Hz), 4.31 (2H, dd, J=9.9, 4.4 Hz), 3.11 (3H, s).

(4) 3-Acetylthio-1-(4-cyano-1,3-thiazol-2-yl)azetidine

To a solution of 1-(4-cyano-1,3-thiazol-2-yl)-3-methanesulfonyloxyazetidine (1.12 g, 4.32 mmol) (obtained as described in Reference Example 4(3)) in dimethylformamide (56 ml) was added potassium thioacetate (3.89 g, 27.0 mmol) at room temperature. The mixture was stirred in an oil bath (80° C.) for 4 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (2:1) as the eluant to afford 3-acetylthio-1-(4-cyano-1,3-thiazol-2-yl)azetidine (0.767 g, yield 75%) as a pale brown solid.

$^1$H-NMR (400 MHz, CDCl$_3$): δ (ppm) 7.28 (1H, s), 4.57 (2H, t, J=8.3 Hz), 4.50–4.40 (1H, m), 4.03 (2H, dd, J=8.3, 5.5 Hz), 2.39 (3H, s).

REFERENCE EXAMPLE 5

3-Acetylthio-1-(4-N-methylcarbamoyl-1,3-thiazol-2-yl)azetidine

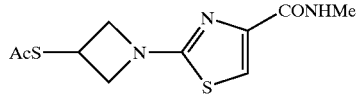

(1) 3-t-Butyldiphenylsilyloxy-1-(4-N-methylcarbamoyl-1,3-thiazol-2-yl)azetidine

To a solution of 3-t-butyldiphenylsilyloxy-1-(4-ethoxycarbonyl-1,3-thiazol-2-yl)azetidine (500 mg, 1.07 mmol) (obtained as described in Reference Example 2(1)) in benzene (25 ml) was added a solution of 0.67M methylamine hydrochloride-trimethylaluminium in benzene (3.21 ml) at room temperature under an atmosphere of nitrogen. The mixture was heated under reflux for 1.5 hours. After checking the completion of the reaction, 10% aqueous acetic acid solution (25 ml) and ethyl acetate (50 ml) were added to the reaction mixture in an ice bath and the resulting mixture was stirred at room temperature for 30 minutes. The reaction mixture was extracted with ethyl acetate. The organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using n-hexane:ethyl acetate (1:1) as the eluant to afford 3-t-butyldiphenylsilyloxy-1-(4-N-methylcarbamoyl-1,3-thiazol-2-yl)azetidine (479 mg, yield 99%) as a pale brown solid.

$^1$H-NMR (400 MHz, CDCl$_3$): δ (ppm) 7.65–7.59 (4H, m), 7.50–7.34 (7H, m), 7.14 (1H, br s), 4.80–4.70 (1H, m), 4.09 (2H, t, J=8.8 Hz), 4.00 (2H, dd, J=8.8, 5.1 Hz), 2.95 (3H, d, J=5.1 Hz), 1.06 (9H, s).

(2) 1-(4-N-Methylcarbamoyl-1,3-thiazol-2-yl)-3-hydroxyazetidine

To a solution of 3-t-butyldiphenylsilyloxy-1-(4-N-methylcarbamoyl-1,3-thiazol-2-yl)azetidine (4.74 g, 10.5 mmol) (obtained as described in Reference Example 5(1)) in anhydrous tetrahydrofuran (240 ml) was added a solution of 1.0M tetra-n-butylammonium fluoride in tetrahydrofuran (12.6 ml, 12.6 mmol) in an ice bath. The mixture was stirred for 30 minutes. After checking the completion of the reaction, the reaction mixture was concentrated under reduced pressure. The residue was purified by chromatography on a silica gel column using ethyl acetate:methanol (10:1) as the eluant to afford 1-(4-N-methylcarbamoyl-1,3-thiazol-2-yl)-3-hydroxyazetidine (2.10 g, yield 96%) as a white solid.

$^1$H-NMR (400 MHz, CDCl$_3$): δ (ppm) 7.34 (2H, s), 7.20 (1H, br s), 4.85–4.75 (1H, m), 4.31 (2H, dd, J=9.7, 6.4 Hz), 3.94 (2H, dd, J=9.7, 5.5 Hz), 3.10 (1H, br s), 2.96 (3H, d, J=5.1 Hz).

Mass spectrum: 213 [M$^+$].

(3) 1-(4-N-Methylcarbamoyl-1,3-thiazol-2-yl)-3-methanesulfonyloxyazetidine

To a solution of 1-(4-N-methylcarbamoyl-1,3-thiazol-2-yl)-3-hydroxyazetidine (2.15 g, 10.1 mmol) (obtained as described in Reference Example 5(2)) in methylene chloride (45 ml) were added methanesulfonyl chloride (3.12 ml, 40.3 mmol) and triethylamine (7.04 ml, 50.5 mmol) in an ice bath. After stirring the mixture in the ice bath for 10 minutes, the mixture was stirred at room temperature for 1.5 hours. After checking the completion of the reaction, methanol was added to the reaction mixture in an ice bath and then the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford 1-(4-N-methylcarbamoyl-1,3-thiazol-2-yl)-3-methanesulfonyloxyazetidine (2.95 g, yield 100%) as a pale yellow foaming-solid. $^1$H-NMR (400 MHz, CDCl$_3$): δ (ppm) 7.44 (1H, s), 7.18 (1H, br s), 5.50–5.39 (1H, m), 4.45 (2H, dd, J=9.7, 6.6 Hz), 4.26 (2H, dd, J=9.7, 4.3 Hz), 3.11 (3H, s), 2.97 (3H, d, J=5.1 Hz).

Mass spectrum (FAB$^+$): 292 [M+H]$^+$.

(4) 3-Acetylthio-1-(4-N-methylcarbamoyl-1,3-thiazol-2-yl)azetidine

To a solution of 1-(4-N-methylcarbamoyl-1,3-thiazol-2-yl)-3-methanesulfonyloxyazetidine (3.0 g, 10.3 mmol) (obtained as described in Reference Example 5(3)) in dimethylformamide (150 ml) was added potassium thioacetate (7.07 g, 61.9 mmol) at room temperature. The mixture was stirred in an oil bath (80° C.) for 3 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:4→1:10) as the eluant to afford 3-acetylthio-1-(4-N-methylcarbamoyl-1,3-thiazol-2-yl)azetidine (2.41 g, yield 86%) as a pale brown solid.

$^1$H-NMR (400 MHz, CDCl$_3$): δ (ppm) 7.44 (1H, s), 7.18 (1H, br s), 4.53 (2H, t, J=8.0 Hz), 4.50–4.40 (1H, m), 4.50–3.95 (2H, m), 2.95 (3H, d, J=6.0 Hz), 2.38 (3H, s).

Mass spectrum (FAB$^+$): 272 [M+H]$^+$.

REFERENCE EXAMPLE 6

3-Acetylthio-1-(4-N,N-dimethylcarbamoyl-1,3-thiazol-2-yl )azetidine

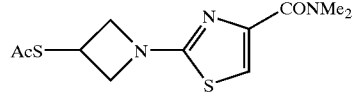

(1) 3-t-Butyldiphenylsilyloxy-1-(4-N,N-dimethylcarbamoyl-1,3-thiazol-2-yl)azetidine To a solution of 3-t-butyldiphenylsilyloxy-1-(4-ethoxycarbonyl-1,3-thiazol-2-yl)azetidine (500 mg, 1.07 mmol) (obtained as described in Reference Example 2(1)) in benzene (25 ml) was added a solution of 0.67M dimethylamine hydrochloride-trimethylaluminium in benzene (3.21 ml) at room temperature under an atmosphere of nitrogen. The mixture was heated under reflux for 2 hours. After checking the completion of the reaction, 10% aqueous acetic acid solution (50 ml) and ethyl acetate (50 ml) were added to the reaction mixture in an ice bath and the resulting mixture was stirred at room temperature for 30 minutes. The reaction mixture was extracted with ethyl acetate. The organic layer was washed successively with saturated aqueous sodium hydrogencarbonate solution and saturated aqueous sodium chloride solution, dried over anhydrous sodium sulfate, filtered and concentrated under reduced pressure.

The residue was purified by chromatography on a silica gel column using n-hexane:ethyl acetate (3:1→1:3) as the eluant to afford 3-t-butyldiphenylsilyloxy-1-(4-N,N-dimethylcarbamoyl-1,3-thiazol-2-yl)azetidine (500 mg, yield 100%) as a pale brown solid.

$^1$H-NMR (400 MHz, CDCl$_3$): δ (ppm) 7.70–7.60 (4H, m), 7.52–7.40 (6H, m), 7.00 (1H, s), 4.69–4.70 (1H, m), 4.11 (2H, dd, J=9.5, 7.5 Hz), 4.02 (2H, dd, J=9.5, 5.0 Hz), 3.19 (3H, s), 3.05 (3H, s), 1.06 (9H, s).

(2) 1-(4-N,N-dimethylcarbamoyl-1,3-thiazol-2-yl)-3-hydroxyazetidine

To a solution of 3-t-butyldiphenylsilyloxy-1-(4-N,N-dimethylcarbamoyl-1,3-thiazol-2-yl)azetidine (5.13 g, 10.7 mmol) (obtained as described in Reference Example 6(1)) in anhydrous tetrahydrofuran (250 ml) was added a solution of 1.0M tetra-n-butylammonium fluoride in tetrahydrofuran (12.0 ml, 12.0 mmol) in an ice bath. The mixture was stirred for 30 minutes. After checking the completion of the reaction, the reaction mixture was concentrated under reduced pressure. The residue was purified by chromatography on a silica gel column using ethyl acetate:methanol (10:1) as the eluant to afford 1-(4-N,N-dimethylcarbamoyl-1,3-thiazol-2-yl)-3-hydroxyazetidine (2.42 g, yield 100%) as a clear syrup.

$^1$H-NMR (400 MHz, CDCl$_3$): δ (ppm) 7.03 (1H, s), 4.90–4.70 (1H, m), 4.32 (2H, t, J=8.2 Hz), 3.95 (2H, dd, J=8.2, 4.5 Hz), 3.20 (3H, br s), 3.05 (3H, br s), 2.85 (1H, br s).

Mass spectrum: 227 [M$^+$].

(3) 1-(4-N,N-Dimethylcarbamoyl-1,3-thiazol-2-yl)-3-methanesulfonyloxyazetidine

To a solution of 1-(4-N,N-dimethylcarbamoyl-1,3-thiazol-2-yl)-3-hydroxyazetidine (2.56 g, 10.7 mmol) (obtained as described in Reference Example 6(2)) in methylene chloride (50 ml) were added methanesulfonyl chloride (2.4 ml, 31.0 mmol) and triethylamine (7.4 ml, 53.1 mmol) in an ice bath. After stirring the mixture in the ice bath for 10 minutes, the mixture was stirred at room temperature for 2.5 hours. After checking the completion of the reaction, methanol was added to the reaction mixture in an ice bath and then the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate and ethyl acetate:methanol (10:1) as the eluant to afford 1-(4-N,N-dimethylcarbamoyl-1,3-thiazol-2-yl)-3-methanesulfonyloxyazetidine (3.28 g, yield 100%) as a pale brown oil.

$^1$H-NMR (400 MHz, CDCl$_3$): δ (ppm) 7.13 (1H, s), 5.50–5.38 (1H, m), 4.46 (2H, dd, J=9.7, 6.6 Hz), 4.26 (2H, dd, J=9.7, 4.3 Hz), 3.21 (3H, br s), 3.10 (3H, s), 3.07 (3H, br s).

Mass spectrum (FAB$^+$): 306 [M+H]$^+$.

(4) 3-Acetylthio-1-(4-N,N-dimethylcarbamoyl-1,3-thiazol-2-yl)azetidine

To a solution of 1-(4-N,N-dimethylcarbamoyl-1,3-thiazol-2-yl)-3-methanesulfonyloxyazetidine (3.40 g, 11.1 mmol) (obtained as described in Reference Example 6(3)) in dimethylformamide (170 ml) was added potassium thioacetate (7.62 g, 66.7 mmol) at room temperature. The mixture was stirred in an oil bath (80° C.) for 3 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:n-hexane (4:1→5:1→7:1) as the eluant to afford 3-acetylthio-1-(4-N,N-dimethylcarbamoyl-1,3-thiazol-2-yl)azetidine (2.71 g, yield 85%) as a brown syrup.

$^1$H-NMR (400 MHz, CDCl$_3$): δ (ppm) 7.09 (1H, s), 4.53 (2H, dd, J=9.0, 7.9 Hz), 4.50–4.40 (1H, m), 3.99 (2H, dd, J=9.0, 5.5 Hz), 3.20 (3H, br s), 3.06 (3H, br s), 2.36 (3H, s).

REFERENCE EXAMPLE 7

3-Acetylthio-1-(4-N-ethylcarbamoyl-1,3-thiazol-2-yl)azetidine

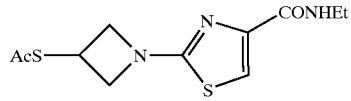

(1) 3-t-Butyldiphenylsilyloxy-1-(4-N-ethylcarbamoyl-1,3-thiazol-2-yl)azetidine

To a solution of 3-t-butyldiphenylsilyloxy-1-(4-ethoxycarbonyl-1,3-thiazol-2-yl)azetidine (1.0 g, 2.14 mmol) (obtained as described in Reference Example 2(1)) in benzene (50 ml) was added a solution of 0.67M ethylamine hydrochloride-trimethylaluminium in benzene (6.42 ml) at room temperature under an atmosphere of nitrogen. The mixture was heated under reflux for 2 hours. After checking the completion of the reaction, 10% aqueous acetic acid solution (50 ml) and ethyl acetate (100 ml) were added to the reaction mixture, and the resulting mixture was stirred at room temperature for 30 minutes. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (5:1→1:1) as the eluant to afford 3-t-butyldiphenylsilyloxy-1-(4-N-ethylcarbamoyl-1,3-thiazol-2-yl)azetidine (997 mg, yield 100%) as a pale brown solid.

$^1$H-NMR (400 MHz, CDCl$_3$): δ (ppm) 7.66–7.58 (4H, m), 7.50–7.37 (6H, m), 7.35 (1H, s), 7.14 (1H, br s), 4.80–4.76 (1H, m), 4.16–4.06 (2H, m), 4.01 (2H, dd, J=8.8, 5.1 Hz), 3.43 (2H, dq, J=7.3, 5.6 Hz), 1.22 (3H, t, J=7.3 Hz), 1.07 (9H, s).

(2) 1-(4-N-Ethylcarbamoyl-1,3-thiazol-2-yl)-3-hydroxyazetidine

To a solution of 3-t-butyldiphenylsilyloxy-1-(4-N-ethylcarbamoyl-1,3-thiazol-2-yl)azetidine (990 mg, 2.14 mmol) (obtained as described in Reference Example 7(1)) in anhydrous tetrahydrofuran (30 ml) was added a solution of 1.0M tetra-n-butylammoniumfluoride in tetrahydrofuran (2.56 ml, 2.56 mmol) in an ice bath. The mixture was stirred in the ice bath for 1.3 hours. After checking the completion of the reaction, ethyl acetate was added thereto and the reaction mixture was partitioned between ethyl acetate and water. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate→5% methanol in ethyl acetate as the eluant to afford 1-(4-N-ethylcarbamoyl-1,3-thiazol-2-yl)-3-hydroxyazetidine (461 mg, yield 95%) as a white solid.

$^1$H-NMR (400 MHz, CDCl$_3$): δ (ppm) 7.36 (1H, s), 7.20 (1H, br s), 4.90–4.78 (1H, m), 4.32 (2H, dd, J=9.0, 7.3 Hz), 3.96 (2H, dd, J=9.0, 4.3 Hz), 3.44 (2H, dq, J=7.2, 5.4 Hz), 2.61 (1H, d, J=6.6 Hz), 1.22 (3H, t, J=7.2 Hz).

(3) 1-(4-N-Ethylcarbamoyl-1,3-thiazol-2-yl)-3-methanesulfonyloxyazetidine

To a solution of 1-(4-N-methylcarbamoyl-1,3-thiazol-2-yl)-3-hydroxyazetidine (460 mg, 2.02 mmol) (obtained as described in Reference Example 7(2)) in methylene chloride (23 ml) were added methanesulfonyl chloride (0.469 ml, 6.06 mmol) and triethylamine (0.849 ml, 6.06 mmol) in an ice bath. The reaction mixture was brought to room temperature in 10 minutes and stirred for 1.3 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:3)→ethyl acetate as the eluant to afford 1-(4-N-ethylcarbamoyl-1,3-thiazol-2-yl)-3-methanesulfonyloxyazetidine (598 mg, yield 97%) as a pale yellow solid.

$^1$H-NMR (400 MHz, CDCl$_3$): δ (ppm) 7.44 (1H, s), 7.13 (1H, br s), 5.48–5.38 (1H, m), 4.46 (2H, ddd, J=9.5, 6.6, 1.5 Hz), 4.27 (2H, ddd, J=9.5, 4.4, 1.5 Hz), 3.45 (2H, dq, J=7.3, 5.0 Hz), 3.10 (3H, s), 1.24 (3H, t, J=7.3 Hz).

(4) 3-Acetylthio-1-(4-N-ethylcarbamoyl-1,3-thiazol-2-yl)azetidine

To a solution of 1-(4-N-ethylcarbamoyl-1,3-thiazol-2-yl)-3-methanesulfonylazetidine (590 mg, 1.93 mmol) (obtained as described in Reference Example 7(3)) in dimethylformamide (30 ml) was added potassium thioacetate (1.32 g, 11.6 mmol) at room temperature. The reaction mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The obtained residue was purified by chromatography on a silica gel column using n-hexane:ethyl acetate (1:3→1:2) as the eluant to afford 3-acetylthio-1-(4-N-ethylcarbamoyl-1,3-thiazol-2-yl)azetidine (453 mg, yield 82%) as a pale brown solid.

$^1$H-NMR (400 MHz, CDCl$_3$): δ (ppm) 7.40 (1H, s), 7.14 (1H, br s), 4.53 (2H, t, J=8.8 Hz), 4.48–4.38 (1H, m), 3.98 (2H, dd, J=8.8, 5.6 Hz), 3.44 (2H, dq, J=7.3, 5.9 Hz), 2.37 (3H, s), 1.23 (3H, t, J=7.3 Hz).

REFERENCE EXAMPLE 8

3-Acetylthio-1-(4-N-isopropylcarbamoyl-1,3-thiazol-2-yl)azetidine

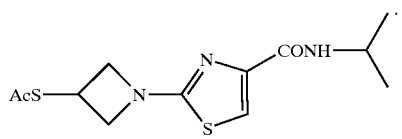

(1) 3-t-Butyldiphenylsilyloxy-1-(4-N-isopropylcarbamoyl-1,3-thiazol-2-yl)azetidine To a solution of 3-t-butyldiphenylsilyloxy-1-(4-ethoxycarbamoyl-1,3-thiazol-2-yl)azetidine (1.0 g, 2.14 mmol) (obtained as described in Reference Example 2(1)) in benzene (50 ml) was added a solution of 0.67M isopropylamine hydrochloride-trimethylaluminium in benzene (6.42 ml) at room temperature under an atmosphere of nitrogen. The mixture was heated under reflux for 2.5 hours. After checking the completion of the reaction, 10% aqueous acetic acid solution (50 ml) and ethyl acetate (100 ml) were added to the reaction mixture in an ice bath and the resulting mixture was stirred at room temperature for 30 minutes. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column to afford 3-t-butyldiphenylsilyloxy-1-(4-N-isopropylcarbamoyl-1,3-thiazol-2-yl)azetidine (1.01 g, yield 99%) as a pale brown solid.

$^1$H-NMR (400 MHz, CDCl$_3$): δ (ppm) 7.66–7.58 (4H, m), 7.50–7.36 (6H, m), 7.34 (1H, s), 6.98 (1H, br d, J=8.1 Hz), 4.80–4.70 (1H, m), 4.26–4.16 (1H, m), 4.11 (2H, dd, J=8.8, 7.3 Hz), 4.02 (2H, dd, J=8.8, 4.4 Hz), 1.24 (6H, d, J=6.6 Hz), 1.07 (9H, s).

(2) 1-(4-N-Isopropylcarbamoyl-1,3-thiazol-2-yl)-3-hydroxyazetidine

To a solution of 3-t-butyldiphenylsilyloxy-1-(4-N-isopropylcarbamoyl-1,3-thiazol-2-yl)azetidine (1.01 g, 2.11 mmol) (obtained as described in Reference Example 8(1)) in anhydrous tetrahydrofuran (30 ml) was added a solution of 1.0M tetra-n-butylammonium fluoride-tetrahydrofuran (2.53 ml) in an ice bath. The mixture was stirred for 30 minutes. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:3)→ethyl acetate as the eluant to afford 1-(4-N-isopropylcarbamoyl-1,3-thiazol-2-yl)-3-hydroxyazetidine (681 mg, yield 100%) as a white solid.

$^1$H-NMR (400 MHz, CDCl$_3$): δ (ppm) 7.36 (1H, s), 7.00 (1H, br d, J=8.0 Hz), 4.90–4.78 (1H, m), 4.32 (2H, dd, J=9.9, 8.7 Hz), 3.97 (2H, ddd, J=9.9, 7.3, 1.7 Hz), 2.55 (1H, d, J=8.0 Hz), 1.25 (6H, d, J=6.6 Hz).

(3) 1-(4-N-Isopropylcarbamoyl-1,3-thiazol-2-yl)-3-methanesulfonyloxyazetidine

To a solution of 1-(4-N-isopropylcarbamoyl-1,3-thiazol-2-yl)-3-hydroxyazetidine (490 mg, 2.03 mmol) (obtained as described in Reference Example 8(2)) in methylene chloride (15 ml) were added methanesulfonyl chloride (0.471 ml, 6.09 mmol) and triethylamine (0.854 ml, 6.09 mmol) in an ice bath. The reaction mixture was brought to room temperature in 10 minutes and stirred for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:3)→ethyl acetate as the eluant to afford 1-(4-N-isopropylcarbamoyl-1,3-thiazol-2-yl)-3- methanesulfonyloxyazetidine (681 mg, yield 100%) as a pale yellow solid.

¹H-NMR (400 MHz, CDCl₃): δ (ppm) 7.44 (1H, s), 7.00 (1H, br d, J=8.0 Hz), 5.48–5.38 (1H, m), 4.46 (2H, dd, J=9.5, 6.6 Hz), 4.32–4.18 (3H, m including 2H, dd, at 4.28, J=9.5, 5.1 Hz), 3.11 (3H, s), 1.25 (6H, d, J=6.6 Hz).

(4) 3-Acetylthio-1-(4-N-isopropylcarbamoyl-1,3-thiazol-2-yl)azetidine

To a solution of 1-(4-N-isopropylcarbamoyl-1,3-thiazol-2-yl)-3-methanesulfonyloxyazetidine (680 mg, 2.03 mmol) (obtained as described in Reference Example 8(3)) in dimethylformamide (35 ml) was added potassium thioacetate (1.39 g, 12.2 mmol) at room temperature. The reaction mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column to afford 3-acetylthio-1-(4-N-isopropylcarbamoyl-1,3-thiazol-2-yl)azetidine (461 mg, yield 81%) as a pale brown solid.

¹H-NMR (400 MHz, CDCl₃): δ (ppm) 7.40 (1H, s), 6.98 (1H, br s), 4.54 (2H, t, J=8.8 Hz), 4.50–4.40 (1H, m), 4.26–4.16 (1H, m), 3.99 (2H, dd, J=8.8, 5.9 Hz), 2.37 (3H, s), 1.24 (6H, d, J=5.9 Hz).

REFERENCE EXAMPLE 9

3-Acetylthio-1-(4-N-cyclopentylcarbamoyl-1,3-thiazol-2-yl)azetidine

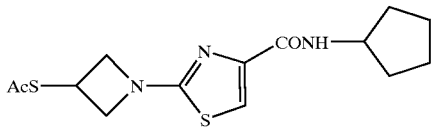

(1) 3-t-Butyldiphenylsilyloxy-1-(4-N-cyclopentylcarbamoyl-1,3-thiazol-2-yl)azetidine To a solution of 3-t-butyldiphenylsilyloxy-1-(4-ethoxycarbonyl-1,3-thiazol-2-yl)azetidine (1.0 g, 2.14 mmol) (obtained as described in Reference Example 2(1)) in benzene (50 ml) was added a solution of 0.67M cyclopentylamine-trimethylaluminium in benzene (6.42 ml) at room temperature under an atmosphere of nitrogen. The mixture was heated under reflux for 5 hours. After checking the completion of the reaction, 10% aqueous acetic acid solution (50 ml) and ethyl acetate (100 ml) were added to the reaction mixture in an ice bath, and the resulting mixture was stirred at room temperature for 30 minutes. After adding ethyl acetate thereto, the reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column to afford 3-t-butyldiphenylsilyloxy-1-(4-N-cyclopentylcarbamoyl-1,3-thiazol-2-yl)azetidine (1.07 g, yield 99%) as a pale brown solid.

¹H-NMR (400 MHz, CDCl₃): δ (ppm) 7.66–7.60 (4H, m), 7.50–7.38 (6H, m), 7.34 (1H, s), 7.08 (1H, br d, J=8.1 Hz), 4.80–4.70 (1H, m), 4.38–4.26 (1H, m), 4.11 (2H, dd, J=8.8, 5.6 Hz), 4.02 (2H, dd, J=8.8, 4.4 Hz), 2.12–2.20 (2H, m), 1.80–1.40 (6H, m), 1.07 (9H, s).

(2) 1-(4-N-Cyclopentylcarbamoyl-1,3-thiazol-2-yl)-3-hydroxyazetidine

To a solution of 3-t-butyldiphenylsilyloxy-1-(4-N-cyclopentylcarbonyl-1,3-thiazol-2-yl)azetidine (1.07 g, 2.12 mmol) (obtained as described in Reference Example 9(1)) in anhydrous tetrahydrofuran (32 ml) was added a solution of 1.0M tetra-n-butylammonium fluoride in tetrahydrofuran (2.54 ml, 2.54 mmol) in an ice bath. The mixture was stirred in the ice bath for 40 minutes. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column to afford 1-(4-N-cyclopentylcarbamoyl-1,3-thiazol-2-yl)-3-hydroxyazetidine (528 mg, yield 93%) as a white solid.

¹H-NMR (400 MHz, CDCl₃): δ (ppm) 7.36 (1H, s), 7.11 (1H, d, J=4.4 Hz), 4.88–4.78 (1H, m), 4.40–4.25 (3H, m), 3.96 (2H, dd, J=9.5, 4.4 Hz), 2.54 (1H, d, J=6.0 Hz), 2.12–2.00 (2H, m), 1.80–1.44 (6H, m).

(3) 1-(4-N-Cyclopentylcarbamoyl-1,3-thiazol-2-yl)-3-methanesulfonyloxyazetidine

To a solution of 1-(4-N-cyclopentylcarbamoyl-1,3-thiazol-2-yl)-3-hydroxyazetidine (520 mg, 1.95 mmol) (obtained as described in Reference Example 9(2)) in methylene chloride (16 ml) were added methanesulfonyl chloride (0.452 ml, 5.84 mmol) and triethylamine (0.818 ml, 5.84 mmol) in an ice bath. The reaction mixture was brought to room temperature in 10 minutes and stirred overnight. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:2)→ethyl acetate as the eluant to afford 1-(4-N-cyclopentylcarbamoyl-1,3-thiazol-2-yl)-3-methanesulfonyloxyazetidine (691 mg, yield 100%) as a pale yellow solid.

¹H-NMR (400 MHz, CDCl₃): δ (ppm) 7.43 (1H, s), 7.07 (1H, br d, J=8.1 Hz), 5.48–5.38 (1H, m), 4.46 (2H, ddd, J=9.9, 6.6, 1.5 Hz), 4.40–4.20 (3H, m including 2H, ddd, J=9.9, 4.9, 1.5 Hz), 3.11 (3H, s), 2.15–1.98 (2H, m), 1.80–1.40 (6H, m).

(4) 3-Acetylthio-1-(4-N-cyclopentylcarbamoyl-1,3-thiazol-2-yl)azetidine

To a solution of 1-(4-N-cyclopentylcarbamoyl-1,3-thiazol-2-yl)-3-methanesulfonyloxyazetidine (670 mg, 1.95 mmol) (obtained as described in Reference Example 9(3)) in dimethylformamide (34 ml) was added potassium thioacetate (1.34 g, 11.7 mmol) at room temperature. The reaction mixture was stirred in an oil bath (80° C.) overnight. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 3-acetylthio-1-(4-N-cyclopentylcarbamoyl-1,3-thiazol-2-yl)azetidine (550 mg, yield 87%) as a pale brown solid.

¹H-NMR (400 MHz, CDCl₃): δ (ppm) 7.40 (1H, s), 7.10 (1H, d, J=8.0 Hz), 4.53 (2H, dd, J=9.2, 6.9 Hz), 4.48–4.38

(1H, m), 4.38–4.26 (1H, m), 3.99 (2H, dd, J=9.2, 4.6 Hz), 2.36 (3H, s), 2.12–2.06 (2H, m), 1.80–1.40 (6H, m).

REFERENCE EXAMPLE 10

3-Acetylthio-1-(4-N-cyclohexylcarbamoyl-1,3-thiazol-2-yl)azetidine

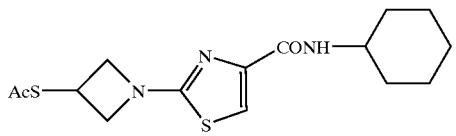

(1) 3-t-Butyldiphenylsilyloxy-1-(4-N-cyclohexylcarbamoyl-1,3-thiazol-2-yl)azetidine To a solution of 3-t-butyldiphenylsilyloxy-1-(4-ethoxycarbonyl-1,3-thiazol-2-yl)azetidine (1.0 g, 2.14 mmol) (obtained as described in Reference Example 2(1)) in benzene (50 ml) was added a solution of 0.67M cyclohexylamine-trimethylaluminium in benzene (6.42 ml) at room temperature under an atmosphere of nitrogen and then the mixture was heated under reflux for 2 hours. After checking the completion of the reaction, 10% aqueous acetic acid solution (50 ml) and ethyl acetate (100 ml) were added to the reaction mixture in an ice bath, and the reaction mixture was then stirred at room temperature for 30 minutes. Ethyl acetate was gradually added to the reaction mixture, and the resulting mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (5:1→1:1) as the eluant to afford 3-t-butyldiphenylsilyloxy-1-(4-N-cyclohexylcarbamoyl-1,3-thiazol-2-yl)azetidine (1.09 g, yield 99%) as a pale brown solid.

$^1$H-NMR (400 MHz, CDCl$_3$): δ (ppm) 7.66–7.58 (4H, m), 7.50–7.38 (6H, m), 7.34 (1H, s), 7.04 (1H, br d, J=8.8 Hz), 4.80–4.70 (1H, m), 4.11 (2H, dd, J=8.8, 6.6 Hz), 4.02 (2H, dd, J=8.8, 5.1 Hz), 3.98–3.80 (1H, m), 2.02–1.94 (2H, m), 1.80–1.70 (2H, m), 1.70–1.10 (6H, m), 1.07 (9H, s).

(2) 1-(4-N-Cyclohexylcarbamoyl-1,3-thiazol-2-yl)-3-hydroxyazetidine

To a solution of 3-t-butyldiphenylsilyloxy-1-(4-N-cyclohexylcarbonyl-1,3-thiazol-2-yl)azetidine (1.09 g, 2.10 mmol) (obtained as described in Reference Example 10(1)) in anhydrous tetrahydrofuran (55 ml) was added a solution of 1.0M tetra-n-butylammonium fluoride in tetrahydrofuran (2.52 ml) in an ice bath and then the mixture was stirred in the ice bath for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1)→ethyl acetate as the eluant to afford 1-(4-N-cyclohexylcarbamoyl-1,3-thiazol-2-yl)-3-hydroxyazetidine (570 mg, yield 97%) as a white solid.

$^1$H-NMR (400 MHz, CDCl$_3$): δ (ppm) 7.36 (1H, s), 7.07 (1H, d, J=8.1 Hz), 4.99–4.78 (1H, m), 4.33 (2H, dd, J=9.0, 7.3 Hz), 4.00–3.80 (3H, m including 2H, dd, J=9.0, 4.4 Hz), 2.56 (1H, d, J=8.3 Hz), 2.02–1.92 (2H, m), 1.80–1.70 (2H, m), 1.70–1.10 (6H, m).

(3) 1-(4-N-Cyclohexylcarbamoyl-1,3-thiazol-2-yl)-3-methanesulfonyloxyazetidine

To a solution of 1-(4-N-cyclohexylcarbamoyl-1,3-thiazol-2-yl)-3-hydroxyazetidine (570 mg, 2.03 mmol) (obtained as described in Reference Example 10(2)) in methylene chloride (17 ml) were added methanesulfonyl chloride (0.471 ml, 6.08 mmol) and triethylamine (0.852 ml, 6.08 mmol) in an ice bath. The reaction mixture was brought to room temperature in 10 minutes, and then stirred at room temperature for 17 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. To the obtained residue was added isopropyl ether, and the resulting mixture was filtered to afford 1-(4-N-cyclohexylcarbamoyl-1,3-thiazol-2-yl)-3-methanesulfonyloxyazetidine (739 mg, yield 100%) as a pale yellow solid.

$^1$H-NMR (400 MHz, CDCl$_3$): δ (ppm) 7.43 (1H, s), 7.02 (1H, br d, J=8.1 Hz), 5.48–5.39 (1H, m), 4.46 (2H, ddd, J=9.5, 6.6, 1.5 Hz), 4.27 (2H, dd, J=9.5, 5.1 Hz), 3.98–3.84 (1H, m), 3.11 (3H, s), 2.01–1.94 (2H, m), 1.80–1.70 (2H, m), 1.70–1.10 (6H, m).

(4) 3-Acetylthio-1-(4-N-cyclohexylcarbamoyl-1,3-thiazol-2-yl)azetidine

To a solution of 1-(4-N-cyclohexylcarbamoyl-1,3-thiazol-2-yl)-3-methanesulfonyloxyazetidine (730 mg, 2.03 mmol) (obtained as described in Reference Example 10(3)) in dimethylformamide (37 ml) was added potassium thioacetate (1.39 g, 12.2 mmol) at room temperature, and then the reaction mixture was stirred in an oil bath (80° C.) for 15 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The obtained residue was purified by chromatography on a silica gel column using n-hexane:ethyl acetate (2:1→1:2) as the eluant to afford 3-acetylthio-1-(4-N-cyclohexylcarbamoyl-1,3-thiazol-2-yl)azetidine (372 mg, yield 54%) as a pale brown solid.

$^1$H-NMR (400 MHz, CDCl$_3$): δ (ppm) 7.40 (1H, s), 7.06 (1H, br d, J=8.0 Hz), 4.53 (1H, dd, J=9.5, 8.2 Hz), 4.48–4.40 (1H, m), 3.99 (2H, dd, J=9.5, 3.7 Hz), 3.95–3.85 (1H, m), 2.37 (3H, s), 2.01–1.96 (2H, m), 1.80–1.10 (8H, m).

REFERENCE EXAMPLE 11

3-Acetylthio-1-(4-morpholinocarbonyl-1,3-thiazol-2-yl)azetidine

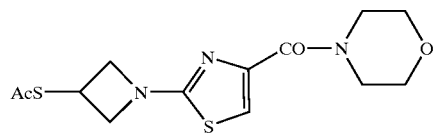

(1) 3-t-Butyldiphenylsilyloxy-1-(4-N-morpholinocarbonyl-1,3-thiazol-2-yl)azetidine To a solution of 3-t-butyldiphenylsilyloxy-1-(4-ethoxycarbonyl-1,3-thiazol-2-yl)azetidine (1.0 g, 2.14 mmol) (obtained as described in Reference Example 2(1)) in benzene (50 ml) was added a solution of 0.67M morpholine-trimethylaluminium in benzene (6.42 ml) at room temperature under an atmosphere of nitrogen. The reaction mixture was heated under reflux for 2 hours. After checking the completion of the reaction, 10% aqueous acetic acid solution (50 ml) and ethyl acetate (100 ml) were added to the reaction mixture in an ice bath, and then the resulting mixture was stirred at room temperature for 30 minutes. The reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (3:1→1:3) as the eluant to afford 3-t-butyldiphenylsilyloxy-1-(4-morpholinocarbonyl-1,3-thiazol-2-yl)azetidine (1.05 g, yield 97%) as a pale brown solid.

$^1$H-NMR (400 MHz, CDCl$_3$): δ (ppm) 7.64–7.58 (4H, m), 7.50–7.36 (6H, m), 7.12 (1H, s), 4.80–4.70 (1H, m), 4.10 (2H, dd, J=9.6, 8.0 Hz), 4.00 (2H, dd, J=9.6, 4.8 Hz), 3.96–3.60 (8H, m), 1.06 (9H, s).

(2) 1-(4-N-Morpholinocarbonyl-1,3-thiazol-2-yl)-3-hydroxyazetidine

To a solution of 3-t-butyldiphenylsilyloxy-1-(4-morpholinocarbonyl-1,3-thiazol-2-yl)azetidine (1.05 g, 2.07 mmol) (obtained as described in Reference Example 11(1)) in anhydrous tetrahydrofuran (32 ml) was added a solution of 1.0M tetra-n-butylammonium fluoride in tetrahydrofuran (2.48 ml, 2.48 mmol) and the reaction mixture was stirred for 1 hour. After checking the completion of the reaction, the reaction mixture was concentrated under reduced pressure and the residue was purified by chromatography on a silica gel column using ethyl acetate→10% methanol in ethyl acetate as the eluant to afford 1-(4-morpholinocarbonyl-1,3-thiazol-2-yl)-3-hydroxyazetidine (542 mg, yield 97%) as a white solid.

$^1$H-NMR (400 MHz, CDCl$_3$): δ (ppm) 7.15 (1H, s), 4.90 (1H, m), 4.32 (2H, dd, J=8.8, 7.3 Hz), 3.95 (2H, dd, J=8.8, 4.4 Hz), 4.00–3.60 (8H, m), 2.45 (1H, br s).

(3) 1-(4-N-Morpholinocarbonyl-1,3-thiazol-2-yl)-3-methanesulfonyloxyazetidine

To a solution of 1-(4-morpholinocarbonyl-1,3-thiazol-2-yl)-3-hydroxyazetidine (540 mg, 2.01 mmol) (obtained as described in Reference Example 11(2)) in methylene chloride (27 ml) were added methanesulfonyl chloride (0.467 ml, 6.03 mmol) and triethylamine (0.845 ml, 6.03 mmol) in an ice bath. The reaction mixture was brought to room temperature in 10 minutes, and stirred for 1 hour. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using 5% methanol in ethyl acetate as the eluant to afford 1-(4-morpholinocarbonyl-1,3-thiazol-2-yl)-3-methanesulfonyloxyazetidine (688 mg, yield 99%) as a pale yellow solid.

$^1$H-NMR (400 MHz, CDCl$_3$): δ (ppm) 7.23 (1H, s), 5.45–5.40 (1H, m), 4.45 (2H, dd, J=9.5, 6.6 Hz), 4.26 (2H, ddd, J=9.5, 4.4, 1.5 Hz), 4.00–3.60 (8H, m), 3.10 (3H, s).

(4) 3-Acetylthio-1-(4-N-morpholinocarbonyl-1,3-thiazol-2-yl)azetidine

To a solution of 1-(4-morpholinocarbonyl-1,3-thiazol-2-yl)-3-methanesulfonyloxyazetidine (680 mg, 1.96 mmol) (obtained as described in Reference Example 11(3)) in dimethylformamide (20 ml) was added potassium thioacetate (671 mg, 5.87 mmol) at room temperature, and then the reaction mixture was stirred in an oil bath (80° C.) for 18 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:3)→ethyl acetate as the eluant to afford 3-acetylthio-1-(4-morpholinocarbonyl-1,3-thiazol-2-yl)azetidine (411 mg, yield 64%) as a pale brown solid.

$^1$H-NMR (400 MHz, CDCl$_3$): δ (ppm) 7.20 (1H, s), 4.52 (2H, t, J=8.8 Hz), 4.48–4.38 (1H, m), 3.98 (2H, dd, J=8.8, 5.1 Hz), 4.00–3.60 (8H, m), 2.36 (3H, s).

REFERENCE EXAMPLE 12

3-Acetylthio-1-(4-t-butyldimethylsilyloxymethyl-1,3-thiazol-2-yl)azetidine

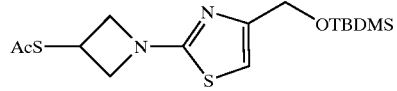

(1) 1-(4-Hydroxymethyl-1,3-thiazol-2-yl)-3-hydroxyazetidine

To a solution of 3-t-butyldiphenylsilyloxy-1-(4-hydroxymethyl-1,3-thiazol-2-yl)azetidine (548.5 mg, 1.29 mmol) (obtained as described in Reference Example 2(2)) in anhydrous tetrahydrofuran (28 ml) was added a solution of 1.0M tetra-n-butylammonium fluoride in tetrahydrofuran (1.56 ml, 1.56 mmol) in an ice bath, and the mixture was then stirred in the ice bath for 1 hour. After checking the completion of the reaction, the reaction mixture was concentrated under reduced pressure. The residue was purified by chromatography on a silica gel column using ethyl acetate:methanol (10:1) as the eluant to afford 1-(4-hydroxymethyl-1,3-thiazol-2-yl)-3-hydroxyazetidine (230 mg, yield 96%) as a white solid.

$^1$H-NMR (400 MHz, CD$_3$OD): δ (ppm) 6.54 (1H, s), 4.76–4.68 (1H, m), 4.46 (2H, s), 4.32–4.24 (2H, m), 3.88–3.82 (2H, m).

(2) 1-(4-t-Butyldimethylsilyloxymethyl-1,3-thiazol-2-yl)-3-hydroxyazetidine

To a solution of 1-(4-hydroxymethyl-1,3-thiazol-2-yl)-3-hydroxyazetidine (226.5 mg, 1.22 mmol) (obtained as described in Reference Example 12(1)) in dimethylformamide (11.5 ml) were added t-butyldimethylsilyl chloride (220 mg, 1.46 mmol) and imidazole (120 mg, 1.76 mmol) in an ice bath. The reaction mixture was then brought to room temperature in 10 minutes, and stirred for 5 hours. After checking the completion of the reaction, methanol (2 ml) was added thereto in an ice bath, and then the reaction mixture was stirred at room temperature for 30 minutes. The reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1) as the eluant to afford 1-(4-t-butyldimethylsilyloxymethyl-1,3-thiazol-2-yl)-3-hydroxyazetidine (300.4 mg, yield 82%) as a white solid.

$^1$H-NMR (400 MHz, CDCl$_3$): δ (ppm) 6.43 (1H, s), 4.86–4.78 (1H, m), 4.66 (2H, s), 4.30 (2H, dd, J=9.5, 7.0 Hz), 3.93 (2H, dd, J=9.5, 4.4 Hz), 2.80 (1H, br s), 0.94 (9H, s), 0.10 (6H, s).

(3) 1-(4-t-Butyldimethylsilyloxymethyl-1,3-thiazol-2-yl)-3-methanesulfonyloxyazetidine To a solution of 1-(4-t-butyldimethylsilyloxymethyl-1,3-thiazol-2-yl)-3-methanesulfonyloxyazetidine (300.4 mg, 1.00 mmol) (obtained as described in Reference Example 12(2)) in methylene chloride (15 ml) were added methanesulfonyl chloride (0.2 ml, 2.49 mmol) and triethylamine (0.35 ml, 2.51 mmol) in an ice bath, and the reaction mixture was then stirred for 1 hour. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:1) as the eluant to afford 1-(4-t-butyldimethylsilyloxymethyl-1,3-thiazol-2-yl)-3-methanesulfonyloxyazetidine (326.5 mg, yield 86%) as a yellow syrup.

$^1$H-NMR (400 MHz, CDCl$_3$): δ (ppm) 6.50 (1H, s), 5.44–5.38 (1H, m), 4.43 (2H, dd, J=9.9, 5.5 Hz), 4.23 (2H, dd, J=9.9, 4.1 Hz), 3.10 (3H, s), 0.90 (9H, s), 0.10 (6H, s).

(4) 3-Acetylthio-1-(4-t-butyldimethylsilyloxymethyl-1,3-thiazol-2-yl)azetidine

To a solution of 1-(4-t-butyldimethylsilyloxymethyl-1,3-thiazol-2-yl)-3-methanesulfonyloxyazetidine (326.5 mg, 0.86 mmol) (obtained as described in Reference Example 12(3)) in dimethylformamide (16 ml) was added potassium thioacetate (780 mg, 5.41 mmol) at room temperature, and the reaction mixture was then stirred in an oil bath (80° C.) for 2 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (4:1) as the eluant to afford 3-acetylthio-1-(4-t-butyldimethylsilyloxymethyl-1,3-thiazol-2-yl)azetidine (191 mg, yield 62%) as a brown syrup.

$^1$H-NMR (400 MHz, CDCl$_3$): δ (ppm) 6.45 (1H, s), 4.66 (2H, s), 4.50 (2H, t, J=8.6 Hz), 3.95 (2H, dd, J=8.6, 5.1 Hz), 2.35 (3H, s), 0.93 (9H, s), 0.10 (6H, s).

REFERENCE EXAMPLE 13

4-Acetylthio-1-(4-ethoxycarbonyl-1,3-thiazol-2-yl)piperidine

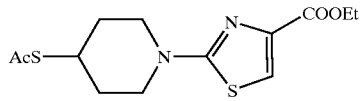

(1) (4-Hydroxypiperidine-1-carbothioyl)carbamic acid ethyl ester

To a solution of 3-hydroxypiperidine (1.0 g, 9.89 mmol) in tetrahydrofuran (50 ml) was added ethoxycarbonyl isothiocyanate (1.4 ml, 11.9 mmol) in an ice bath. The reaction mixture was brought to room temperature in 10 minutes and then stirred overnight. After checking the completion of the reaction, the reaction mixture was partitioned between ethyl acetate and saturated aqueous sodium chloride solution. The organic layer was dried over anhydrous magnesium sulfate, filtered and concentrated under reduced pressure. The obtained residue was purified by chromatography on a silica gel column using toluene:ethyl acetate (1:2) as the eluant to afford (4-hydroxypiperidine-1-carbothioyl)carbamic acid ethyl ester (2.3 g, yield 100%) as a yellow oil.

$^1$H-NMR (400 MHz, CDCl$_3$): δ (ppm) 4.26 (1H, br s), 4.19 (2H, q, J=8.3 Hz), 4.06 (1H, m), 4.0–3.4 (3H, dull s), 2.10 (2H, m), 1.80–1.60 (4H, m), 1.29 (3H, t, J=8.3 Hz).

(2) 1-(4-Ethoxycarbonyl-1,3-thiazol-2-yl)-4-hydroxypiperidine

To a solution of (4-hydroxypiperidine-1-carbothioyl)carbamic acid ethyl ester (2.3 g, 9.89 mmol) (obtained as described in Reference Example 13(1)) in ethanol (23 ml) and distilled water (23 ml) was added sodium hydroxide (1.98 g, 49.5 mmol), and the mixture was then heated under reflux for 15 hours. After checking the completion of the reaction, the reaction mixture was brought to room temperature and a solution of 4N hydrogen chloride in dioxane (12.4 ml) was added to the reaction mixture in an ice bath, ethyl 2-bromopyruvate (2.5 ml, 19.8 mmol) and triethylamine (2.8 ml, 20.1 mmol) were added thereto, and then the reaction mixture was heated under reflux for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using toluene ethyl acetate (2:1) as the eluant to afford 1-(4-ethoxycarbonyl-1,3-thiazol-2-yl)-4-hydroxypiperidine (0.99 g, yield 39%) as a pale yellow syrup.

$^1$H-NMR (400 MHz, CDCl$_3$): δ (ppm) 7.46 (1H, s), 4.35 (2H, q, J=7.8 Hz), 3.96 (1H, m), 3.88 (2H, dt, J=13.5, 3.0 Hz), 3.31 (2H, ddd, J=13.5, 9.0, 3.0 Hz), 2.04–1.96 (2H, m), 1.74–1.56 (3H, m), 1.37 (3H, t, J=7.8 Hz).

Mass spectrum: 256 [M$^+$].

(3) 1-(4-Ethoxycarbonyl-1,3-thiazol-2-yl)-4-methanesulfonyloxypiperidine

To a solution of 1-(4-ethoxycarbonyl-1,3-thiazol-2-yl)-4-hydroxypiperidine (128 mg, 0.50 mmol) (obtained as described in Reference Example 13(2)) in methylene chloride (6.5 ml) was added methanesulfonyl chloride (0.043 ml, 0.56 mmol) and triethylamine (0.084 ml, 0.60 mmol) in an ice bath. The reaction mixture was brought to room temperature in 10 minutes and then stirred for 30 minutes. After checking the completion of the reaction, ethanol (1 ml) was added thereto in an ice bath and then the reaction mixture was stirred for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was recrystallized from a solution of ethyl acetate:n-hexane (5:1) to afford 1-(4-ethoxycarbonyl-1,3-thiazol-2-yl)4-methanesulfonyloxypiperidine (81.0 mg, yield 49%) as a white solid.

$^1$H-NMR (400 MHz, CDCl$_3$): δ (ppm) 7.49 (1H, s), 5.01–4.90 (1H, m), 4.45 (2H, q, J=8.0 Hz), 3.80 (2H, ddd, J=12.6, 8.4, 4.2 Hz), 3.52 (2H, ddd, J=12.6, 8.4, 4.2 Hz), 3.05 (3H, s), 2.20–1.90 (4H, m), 1.36 (3H, t, J=8.0 Hz).

Mass spectrum: 334 [M$^+$].

(4) 4-Acetylthio-1-(4-ethoxycarbonyl-1,3-thiazol-2-yl)piperidine

To a solution of 1-(4-ethoxycarbonyl-1,3-thiazol-2-yl)-4-methanesulfonyloxypiperidine (76 mg, 0.23 mmol) (obtained as described in Reference Example 13(3)) in dimethylformamide (4.0 ml) was added potassium thioacetate (145 mg, 1.3 mmol) at room temperature, and the reaction mixture was then stirred in an oil bath (80° C.) for 8 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using n-hexane:ethyl acetate (1:1) as the eluant to afford 4-acetylthio-1-(4-ethoxycarbonyl-1,3-thiazol-2-yl)piperidine (67 mg, yield 94%) as a pale brown solid.

$^1$H-NMR (400 MHz, CDCl$_3$): δ (ppm) 7.45 (1H, s), 4.34 (2H, q, J=7.1 Hz), 3.88 (2H, dt, J=13.4, 3.2 Hz), 3.80–3.60 (1H, m), 3.33 (ddd, J=13.6, 8.5, 3.2 Hz), 2.33 (3H, s), 2.15–1.95 (2H, m), 1.85–1.65 (2H, m), 1.37 (3H, t, J=7.1 Hz).

Mass spectrum: 314 [M$^+$].

REFERENCE EXAMPLE 14

4-Acetylthio-1-(4-p-nitrobenzylcarbonyl-1,3-thiazol-2-yl)piperidine

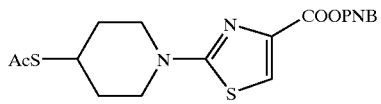

(1) 4-t-Butyidimethylsilyloxy-1-(4-ethoxycarbonyl-1,3-thiazol-2-yl)piperidine

To a solution of 1-(4-ethoxycarbonyl-1,3-thiazol-2-yl)-4-hydroxypiperidine (1.00 g, 3.90 mmol) (obtained as described in Reference Example 13(2)) in dimethylformamide (50 ml) were added t-butyldimethylsilyl chloride (1.2 g, 7.96 mmol) and imidazole (0.6 g, 8.8 mmol) in an ice bath. The reaction mixture was brought to room temperature in 10 minutes and then stirred for 18 hours. After checking the completion of the reaction, ethanol was added thereto in an ice bath, and the reaction mixture was then stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using n-hexane:ethyl acetate (4:1) as the eluant to afford 4-t-butyidimethylsilyloxy-1-(4-ethoxycarbonyl-1,3-thiazol-2-yl)azetidine (1.38 g, yield 95%) as a pale yellow oil.

$^1$H-NMR (400 MHz, CDCl$_3$): δ (ppm) 7.42 (1H, s), 4.35 (2H, q, J=7.1 Hz), 4.03–3.89 (1H, m), 3.70 (2H, ddd, J=12.4, 8.5, 3.7 Hz), 3.46 (2H, ddd, 12.4, 8.5, 3.7 Hz), 1.90–1.77 (2H, m), 1.71–1.59 (2H, m), 1.37 (3H, t, J=7.1 Hz), 0.90 (9H, s), 0.08 (6H, s).

Mass spectrum: 370 [M$^+$].

(2) 4-t-Butyldimethylsilyloxy-1-(4-carboxyl-1,3-thiazol-2-yl)piperidine

To a solution of 4-t-butyidimethylsilyloxy-1-(4-ethoxycarbonyl-1,3-thiazol-2-yl)piperidine (1.00 g, 2.7 mmol) (obtained as described in Reference Example 14(1)) in ethanol (20 ml) was added 1N aqueous sodium hydroxide solution (5.4 ml, 5.4 mmol) in an ice bath, and the reaction mixture was then stirred at room temperature for 3.5 hours. After checking the completion of the reaction, 2N aqueous hydrochloric acid solution (1.8 ml) was added thereto in an ice bath. The reaction mixture was partitioned between ethyl acetate and saturated aqueous sodium chloride solution. The organic layer was dried over anhydrous magnesium sulfate, filtered and concentrated under reduced pressure. The obtained residue was recrystallized from a solution of methanol in ethyl acetate to give a white crystal (471 mg) as a primary crystal. Subsequently, the residue obtained by concentration of the mother liquor was purified by chromatography on a silica gel column using ethyl acetate:2-propanol:water (10:4:1→5:2:1) as the eluant to afford 4-t-butyldimethylsilyloxy-1-(4-carboxyl-1,3-thiazol-2-yl)piperidine (440 mg, total amount 911 mg, yield 99%) as a white solid.

$^1$H-NMR (400 MHz, CDCl$_3$+D$_2$O): δ (ppm) 7.35 (1H, s), 4.10–3.85 (1H, m), 3.75–3.50 (2H, m), 3.50–3.25 (2H, m), 1.90–1.70 (2H, m), 1.70–1.50 (2H, m), 0.90 (9H, s), 0.07 (6H m).

Mass spectrum (FAB$^+$): 343 [M+H]$^+$.

(3) 4-t-Butyidimethylsilyloxy-1-(4-p-nitrobenzyloxycarboxyl-1,3-thiazol-2-yl )piperidine To a solution of 4-t-butyldimethylsilyloxy-1-(4-carboxyl-1,3-thiazol-2-yl)piperidine (902 mg, 2.63 mmol) (obtained as described in Reference Example 14(2)) in anhydrous methylene chloride (40 ml) were added hydroxybenzotriazole (710 mg, 5.3 mmol), 1-ethyl-3-(3-dimethylaminopropyl)carbodiimide hydrochloride (WSC) (1.254 g, 6.6 mmol) and p-nitrobenzyl alcohol (788 mg, 5.2 mmol) in an ice bath under an atmosphere of nitrogen, and the mixture was then stirred at room temperature for 4 hours. After checking the completion of the reaction, the reaction mixture was partitioned between ethyl acetate and saturated aqueous sodium hydrogencarbonate solution. The organic layer was washed with saturated aqueous sodium hydrogencarbonate solution, dried over anhydrous magnesium sulfate, filtered and concentrated under reduced pressure. The obtained residue was purified by chromatography on a silica gel column using n-hexane:ethyl acetate (1:1) as the eluant to afford 4-t-butyldimethylsilyloxy-1-(4-p-nitrobenzyloxycarbonyl-1,3-thiazol-2-yl)piperidine (916 mg, yield 73%) as a yellow solid.

$^1$H-NMR (400 MHz, CDCl$_3$): δ (ppm) 8.23 (2H, d, J=8.5 Hz), 7.60 (2H, d, J=8.5 Hz), 7.49 (1H, s), 5.42 (2H, s), 4.05–3.95 (1H, m), 3.70 (2H, ddd, J=12.6, 8.6, 3.9 Hz), 3.48 (2H, ddd, J=12.6, 6.2, 4.2 Hz), 1.92–1.76 (2H, m), 1.75–1.50 (2H, m), 0.90 (9H, s), 0.07 (6H, s).

Mass spectrum (FAB$^+$): 478 [M+H]$^+$.

(4) 1-(4-p-Nitrobenzyloxycarbonyl-1,3-thiazol-2-yl)-4-hydroxypiperidine

To a solution of 4-t-butyldimethylsilyloxy-1-(4-p-nitrobenzyloxycarbonyl-1,3-thiazol-2-yl)piperidine (300 mg, 0.628 mmol) (obtained as described in Reference Example 14(3)) in anhydrous tetrahydrofuran (15 ml) were added acetic acid (0.22 ml, 0.628 mmol) and a solution of 1M tetrabutylammonium fluoride in tetrahydrofuran (3.76 ml, 3.76 mmol) in an ice bath, and the mixture was then stirred at room temperature for 21 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using ethyl acetate:methanol (10:1) as the eluant to afford 1-(4-p-nitrobenzyloxycarbonyl-1,3-thiazol-2-yl)-4-hydroxypiperidine (123 mg, yield 54%) as a pale yellow solid.

¹H-NMR (400 MHz, CDCl₃+D₂O): δ (ppm) 8.22 (2H, d, J=8.0 Hz), 7.60 (2H, d, J=8.0 Hz), 7.50 (1H, s), 5.42 (2H, s), 4.02–3.94 (1H, m), 3.89 (2H, dt, J=12.0, 4.0 Hz), 3.33 (2H, ddd, J=12.0, 8.0, 4.0 Hz), 2.05–1.94 (2H, m), 1.75–1.55 (2H, m).

Mass spectrum: 363 [M⁺].

(5) 4-Methanesulfonyloxy-1-(4-p-nitrobenzyloxycarbonyl-1,3-thiazol-2-yl)piperidine To a solution of 1-(4-p-nitrobenzyloxycarbonyl-1,3-thiazol-2-yl)-4-hydroxypiperidine (0.75 g, 2.06 mmol) (obtained as described in Reference Example 14(4)) in anhydrous methylene chloride (38 ml) were added methanesulfonyl chloride (0.18 ml, 2.33 mmol) and triethylamine (0.35 ml, 2.51 mmol) in an ice bath. The mixture was brought to room temperature in 10 minutes, and then stirred for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using n-hexane:ethyl acetate (2:1) as the eluant to afford 4-methanesulfonyloxy-1-(4-p-nitrobenzyloxycarbonyl-1,3-thiazol-2-yl)piperidine (0.87 g, yield 96%) as a colorless solid.

¹H-NMR (400 MHz, CDCl₃): δ (ppm) 8.23 (2H, d, J=8.5 Hz), 7.59 (2H, d, J=8.5 Hz), 7.54 (1H, s), 5.42 (2H, s), 5.05–4.95 (1H, m), 3.79 (2H, ddd, J=12.2, 7.6, 4.0 Hz), 3.55 (2H, ddd, J=12.2, 7.2, 4.0 Hz), 3.07 (3H, s), 2.18–2.06 (2H, m), 2.00–1.80 (2H, m).

Mass spectrum (FAB⁺): 441 [M+H]⁺.

(6) 4-Acetylthio-1-(4-p-nitrobenzyloxycarbonyl-1,3-thiazol-2-yl)piperidine

To a solution of 4-methanesulfonyloxy-1-(4-p-nitrobenzyloxycarbonyl-1,3-thiazol-2-yl)piperidine (1.2 g, 2.72 mmol) (obtained as described in Reference Example 14(5)) in dimethylformamide (60 ml) was added potassium thioacetate (625 mg, 5.47 mmol) at room temperature, and the reaction mixture was stirred in an oil bath (90° C.) for 3.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using n-hexane:ethyl acetate (1:1) as the eluant to afford 4-acetylthio-1-(4-p-nitrobenzyloxycarbonyl-1,3-thiazol-2-yl)piperidine (769 mg, yield 88%) as a pale brown solid.

¹H-NMR (400 MHz, CDCl₃): δ (ppm) 8.23 (2H, d, J=8.4 Hz), 7.59 (2H, d, J=8.4 Hz), 7.51 (1H, s), 5.42 (2H, s), 3.95–3.80 (2H, m), 3.80–3.60 (1H, m), 3.34 (2H, ddd, J=13.1, 9.9, 3.1 Hz), 2.34 (3H, s), 2.25–1.95 (2H, m), 1.85–1.65 (2H, m).

Mass spectrum (FAB⁺): 422 [M+H]⁺.

REFERENCE EXAMPLE 15

4-Acetylthio-1-(4-carbamoyl-1,3-thiazol-2-yl)piperidine

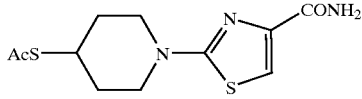

(1) 4-t-Butyldimethylsilyloxy-1-(4-carbamoyl-1,3-thiazol-2-yl)piperidine

To a solution of 4-t-butyldimethylsilyloxy-1-(4-carboxyl-1,3-thiazol-2-yl)piperidine (4.99 g, 14.6 mmol) (obtained as described in Reference Example 14(2)) in methylene chloride (150 ml) was added carbonyldiimidazole (2.80 g, 17.3 mmol) at room temperature under an atmosphere of nitrogen, and the reaction mixture was stirred for 1.5 hours under the same conditions. After checking the completion of the reaction, 28% aqueous ammonia solution was added thereto and the reaction mixture was stirred at room temperature for 30 minutes.

Subsequently, the reaction mixture was concentrated under reduced pressure. The obtained residue was partitioned between ethyl acetate and saturated aqueous sodium chloride solution. The organic layer was dried over anhydrous magnesium sulfate, filtered and concentrated under reduced pressure. The residue was purified by chromatography on a silica gel column using n-hexane:ethyl acetate (1:1) as the eluant to afford 4-t-butyldimethylsilyloxy-1-(4-carbamoyl-1,3-thiazol-2-yl)piperidine (2.90 g, yield 59%) as a pale yellow solid.

¹H-NMR (400 MHz, CDCl₃): δ (ppm) 7.39 (1H, s), 7.03 (1H, br s), 5.50 (1H, br s), 4.05–3.95 (1H, m), 3.66 (2H, ddd, J=12.5, 8.6, 3.7 Hz), 3.43 (2H, ddd, J=12.5, 6.5, 4.2 Hz), 1.92–1.75 (2H, m), 1.75–1.55 (2H, m), 0.90 (9H, s), 0.08 (6H, s).

Mass spectrum (FAB⁺): 342 [M+H]⁺.

(2) 1-(4-Carbamoyl-1,3-thiazol-2-yl)-4-hydroxypiperidine

To a solution of 4-t-butyldimethylsilyloxy-1-(4-carbamoyl-1,3-thiazol-2-yl)piperidine (1.226 g, 3.59 mmol) (obtained as described in Reference Example 15(1)) in anhydrous tetrahydrofuran (30 ml) were added acetic acid (1.85 ml) and a solution of 1.0M tetra-n-butylammonium fluoride in tetrahydrofuran (32.3 ml, 32.3 mmol) in an ice bath, and the mixture was stirred for 24 hours. After checking the completion of the reaction, the reaction mixture was concentrated under reduced pressure. The residue was purified by chromatography on a silica gel column to afford 1-(4-carbamoyl-1,3-thiazol-2-yl)-4-hydroxypiperidine (0.82 g, yield 100%) as a white solid.

¹H-NMR (400 MHz, CD₃OD): δ (ppm) 7.38 (1H, s), 3.95–3.80 (1H, m), 3.40–3.20 (2H, m), 2.00–1.85 (2H, m), 1.75–1.50 (2H, m).

Mass spectrum (FAB⁺): 228 [M+H]⁺.

(3) 1-(4-Carbamoyl-1,3-thiazol-2-yl)-4-methanesulfonyloxypiperidine

To a solution of 1-(4-carbamoyl-1,3-thiazol-2-yl)-4-hydroxypiperidine (1.93 g, 8.49 mmol) (obtained as described in Reference Example 15(2)) in methylene chloride (100 ml) were added methanesulfonyl chloride (10.0 ml, 129 mmol) and triethylamine (18.0 ml, 129 mmol) in an ice bath. After stirring the mixture in the ice bath for 10 minutes, the mixture was stirred at room temperature for 24 hours. After checking the completion of the reaction, methanol was added to the reaction mixture in an ice bath and the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford 1-(4-carbamoyl-1,3-thiazol-2-yl)-4-methanesulfonyloxypiperidine (1.59 g, yield 61%) as a pale yellow solid.

$^1$H-NMR (400 MHz, CD$_3$OD): δ (ppm) 7.42 (1H, s), 5.10–4.90 (1H, m), 3.77 (2H, ddd, J=13.0, 7.4, 4.0 Hz), 3.53 (2H, ddd, J=13.0, 7.7, 4.0 Hz), 3.12 (3H, s), 2.18–2.07 (2H, m), 2.00–1.89 (2H, m).

Mass spectrum: 305 [M$^+$].

(4) 4-Acetylthio-1-(4-carbamoyl-1,3-thiazol-2-yl)piperidine

To a solution of 1-(4-carbamoyl-1,3-thiazol-2-yl)-4-methanesulfonyloxypiperidine (1.59 g, 5.21 mmol) (obtained as described in Reference Example 15(3)) in dimethylformamide (80 ml) was added potassium thioacetate (1.19 g, 10.4 mmol) at room temperature, and the reaction mixture was stirred in an oil bath (90° C.) for 2.5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using ethyl acetate:n-hexane (10:1) as the eluant to afford 4-acetylthio-1-(4-carbamoyl-1,3-thiazol-2-yl) piperidine (1.01 g, yield 68%) as a brown solid.

$^1$H-NMR (400 MHz, CDCl$_3$): δ (ppm) 7.41 (1H, s), 7.00 (1H, br s), 5.55 (1H, br s), 3.90–3.78 (2H, m), 3.78–3.64 (1H, m), 3.35–3.25 (2H, m), 2.32 (3H, s), 2.10–2.00 (2H, m), 1.80–1.65 (2H, m).

Mass spectrum (FAB$^+$): 285 [M+H]$^+$.

REFERENCE EXAMPLE 16

4-Acetylthio-1-(4-N-methylcarbamoyl-1,3-thiazol-2-yl)piperidine

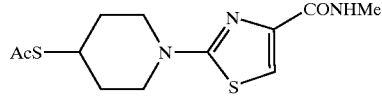

(1) 4-t-Butyldimethylsilyloxy-1-(4-N-methylcarbamoyl-1,3-thiazol-2-yl)piperidine To a solution of 4-t-butyldimethylsilyloxy-1-(4-carboxyl-1,3-thiazol-2-yl)piperidine (200 mg, 0.584 mmol) (obtained as described in Reference Example 14(2)) in dimethylformamide (6.0 ml) was added carbonyldiimidazole (114 mg, 0.703 mmol) at room temperature under an atmosphere of nitrogen, and the reaction mixture was then stirred in an oil bath (50° C.) for 3 hours. After checking the completion of the reaction, 40% aqueous methylamine solution (0.23 ml) was added thereto and the reaction mixture was stirred at room temperature for 30 minutes.

Subsequently, the reaction mixture was partitioned between ethyl acetate and saturated aqueous sodium chloride solution. The obtained organic layer was dried over anhydrous magnesium sulfate, filtered and concentrated under reduced pressure. The residue was purified by chromatography on a silica gel column using n-hexane:ethyl acetate (5:4) as the eluant to afford 4-t-butyldimethylsilyloxy-1-(4-N-methylcarbamoyl-1,3-thiazol-2-yl)piperidine (202.5 mg, yield 97%) as a pale brown solid.

$^1$H-NMR (400 MHz, CDCl$_3$): δ (ppm) 7.36 (1H, s), 7.20 (1H, br s), 4.10–3.98 (1H, m), 3.68 (2H, ddd, J=12.6, 8.5, 3.7 Hz), 3.45 (2H, ddd, J=12.6, 6.4, 4.2 Hz), 2.99 (3H, d, J=4.8 Hz), 1.95–1.78 (2H, m), 1.78–1.60 (2H, m), 0.93 (H, s), 0.11 (6H, s).

Mass spectrum (FAB$^+$): 356 [M+H]$^+$.

(2) 1-(4-N-Methylcarbamoyl-1,3-thiazol-2-yl)-4-hydroxypiperidine

To a solution of 4-t-butyldimethylsilyloxy-1-(4-N-methylcarbamoyl-1,3-thiazol-2-yl)piperidine (1.69 g, 4.75 mmol) (obtained as described in Reference Example 16(1)) in anhydrous tetrahydrofuran (85 ml) was added a solution of 1.0M tetra-n-butylammonium fluoride in tetrahydrofuran (23.8 ml, 23.8 mmol) in an ice bath, and then the mixture was stirred in an oil bath (50° C.) for 14.5 hours. After checking the completion of the reaction, the reaction mixture was concentrated under reduced pressure. The residue was purified by chromatography on a silica gel column using ethyl acetate:methanol (10:1) as the eluant to afford 1-(4-N-methylcarbamoyl-1,3-thiazol-2-yl)-4-hydroxypiperidine (1.48 g, yield 97%) as a white solid.

$^1$H-NMR (400 MHz, CDCl$_3$): δ 7.35 (1H, s), 7.18 (1H, br s), 4.05–3.90 (1H, m), 3.74 (2H, ddd, J=12.7, 4.7 Hz), 3.28 (2H, ddd, J=12.7, 9.0, 3.6 Hz), 2.10–1.90 (2H, m), 1.80–1.50 (3H, m).

Mass spectrum: 241 [M$^+$].

(3) 4-Methanesulfonyloxy-1-(4-N-methylcarbamoyl-1,3-thiazol-2-yl)piperidine

To a solution of 1-(4-N-methylcarbamoyl-1,3-thiazol-2-yl)-4-hydroxypiperidine (1.143 g, 4.74 mmol) (obtained as described in Reference Example 16(2)) in methylene chloride (35 ml) were added methanesulfonyl chloride (0.44 ml, 5.63 mmol) and triethylamine (0.86 ml, 5.68 mmol) in an ice bath. After stirring the mixture in the ice bath for 10 minutes, the mixture was stirred at room temperature for 4 hours. After checking the completion of the reaction, methanol was added to the reaction mixture in an ice bath and the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. To the residue was added ethyl acetate, and the mixture was filtered to afford 4-methanesulfonyloxy-1-(4-N-methylcarbamoyl-1,3-thiazol-2-yl)piperidine (1.438 g, yield 95%) as a pale yellow solid.

$^1$H-NMR (400 MHz, CDCl$_3$): δ (ppm) 7.38 (1H, s), 7.14 (1H, br s), 5.06–4.93 (1H, m), 3.74 (2H, ddd, J=13.2, 7.5, 4.2 Hz), 3.48 (2H, ddd, J=13.2, 7.2, 4.2 Hz), 3.07 (3H, s), 2.97 (3H, d, J=5.1 Hz), 2.20–1.90 (4H, m).

Mass spectrum (FAB$^+$): 320 [M+H]$^+$.

(4) 4-Acetylthio-1-(4-N-methylcarbamoyl-1,3-thiazol-2-yl)piperidine

To a solution of 4-methanesulfonyloxy-1-(4-N-methylcarbamoyl-1,3-thiazol-2-yl)piperidine (1.438 g, 4.50 mmol) (obtained as described in Reference Example 16(3)) in dimethylformamide (72 ml) was added potassium thioacetate (1.03 g, 9.00 mmol) at room temperature. The reaction mixture was stirred in an oil bath (90° C.) for 2.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using ethyl acetate:n-hexane (10:1)→ethyl acetate as the eluant to afford 4-acetylthio-1-(4-N-methylcarbamoyl-1,3-thiazol-2-yl)piperidine (1.22 g, yield 91%) as a pale brown solid.

$^1$H-NMR (400 MHz, CDCl$_3$): δ (ppm) 7.38 (1H, s), 7.15 (1H, br s), 3.82 (2H, dt, J=12.7, 4.8 Hz), 3.78–3.63 (1H, m), 3.30 (2H, ddd, J=12.7, 11.1, 4.7 Hz), 2.95 (3H, d, J=6.4 Hz), 2.35 (3H, s), 2.15–1.95 (2H, m), 1.85–1.35 (2H, m).

Mass spectrum (FAB$^+$): 300 [M+H]$^+$.

REFERENCE EXAMPLE 17

4-Acetylthio-1-(4-N,N-dimethylcarbamoyl-1,3-thiazol-2-yl)piperidine

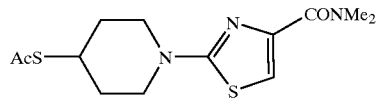

(1) 4-t-Butyldimethylsilyloxy-1-(4-N,N-dimethylcarbamoyl-1,3-thiazol-2-yl)piperidine To a solution of 4-t-butyldimethylsilyloxy-1-(4-carboxyl-1,3-thiazol-2-yl)piperidine (0.98 g, 2.86 mmol) (obtained as described in Reference Example 14(2)) in dimethylformamide (30 ml) was added carbonyldiimidazole (559 mg, 3.45 mmol) at room temperature under an atmosphere of nitrogen, and the reaction mixture was then stirred in an oil bath (50° C.) for 3 hours. After checking the completion of the reaction, 50% aqueous dimethylamine solution (100 ml) was added thereto and the reaction mixture was stirred at room temperature for 30 minutes.

Subsequently, the reaction mixture was partitioned between ethyl acetate and an aqueous solution. The obtained organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (2:3) as the eluant to 4-t-butyidimethylsilyloxy-1-(4-N,N-dimethylcarbamoyl-1,3-thiazol-2-yl)piperidine (440 mg, total amount 995 mg, yield 94%) as a pale yellow oil.

$^1$H-NMR (400 MHz, CDCl$_3$): δ (ppm) 7.04 (1H, s), 4.05–3.95 (1H, m), 3.67 (2H, ddd, J=12.6, 8.4, 4.3 Hz), 3.41 (2H, ddd, J=12.6, 7.0, 4.3 Hz), 3.26 (3H, br s), 3.07 (3H, br s), 1.92–1.75 (2H, m), 1.72–1.50 (2H, m), 0.90 (9H, s), 0.08 (6H, s).

Mass spectrum (FAB$^+$): 370 [M+H]$^+$.

(2) 1-(4-N,N-Dimethylcarbamoyl-1,3-thiazol-2-yl)-4-hydroxypiperidine

To a solution of 4-t-butyidimethylsilyloxy-1-(4-N,N-dimethylcarbamoyl-1,3-thiazol-2-yl)piperidine (2.13 g, 5.76 mmol) (obtained as described in Reference Example 17(1)) in anhydrous tetrahydrofuran (85 ml) were added acetic acid (1.65 ml, 28.8 mmol) and a solution of 1.0M tetra-n-butylammonium fluoride in tetrahydrofuran (28.8 ml, 28.8 mmol) in an ice bath, and the mixture was then stirred in an oil bath (50° C.) for 1.5 hours. After checking the completion of the reaction, the reaction mixture was concentrated under reduced pressure. The residue was purified by chromatography on a silica gel column using ethyl acetate:methanol (10:1) as the eluant to afford 1-(4-N,N-dimethylcarbamoyl-1,3-thiazol-2-yl)-4-hydroxypiperidine (1.47 g, yield 100%) as a white solid.

$^1$H-NMR (400 MHz, CDCl$_3$): δ (ppm) 7.07 (1H, s), 4.03–3.89 (1H, m), 3.83 (2H, ddd, J=12.0, 5.0 Hz), 3.35–3.20 (5H, m), 3.08 (3H, br s), 2.05–1.90 (2H, m), 1.90–1.55 (3H, m).

Mass spectrum: 255 [M$^+$].

(3) 1-(4-N,N-Dimethylcarbamoyl-1,3-thiazol-2-yl)-4-methanesulfonyloxypiperidine

To a solution of 1-(4-N,N-dimethylcarbamoyl-1,3-thiazol-2-yl)-4-hydroxypiperidine (1.47 g, 5.76 mmol) (obtained as described in Reference Example 17(2)) in methylene chloride (60 ml) were added methanesulfonyl chloride (0.82 ml, 10.6 mmol) and triethylamine (1.48 ml, 10.6 mmol) in an ice bath. After stirring the mixture in the ice bath for 10 minutes, the mixture was stirred at room temperature for 2 hours. After checking the completion of the reaction, methanol was added to the reaction mixture in an ice bath and the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford 1-(4-N,N-dimethylcarbamoyl-1,3-thiazol-2-yl)-4-methanesulfonyloxypiperidine (1.38 g, yield 72%) as a pale yellow solid.

$^1$H-NMR (400 MHz, CDCl$_3$): δ (ppm) 7.12 (1H, s), 5.05–4.90 (1H, m), 3.85–3.65 (2H, m), 3.60–3.40 (2H, m), 3.23 (3H, br s), 3.08 (6H, br s), 2.20–1.90 (4H, m).

Mass spectrum (FAB$^+$): 334 [M+H]$^+$.

(4) 4-Acetylthio-1-(4-N,N-dimethylcarbamoyl-1,3-thiazol-2-yl)piperidine

To a solution of 1-(4-N,N-dimethylcarbamoyl-1,3-thiazol-2-yl)-4-methanesulfonyloxypiperidine (1.33 g, 3.99 mmol) (obtained as described in Reference Example 17(3)) in dimethylformamide (66 ml) was added potassium thioacetate (940 mg, 8.23 mmol) at room temperature. The mixture was stirred in an oil bath (90° C.) for 3.0 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:n-hexane (5:1→7:1) as the eluant to afford 4-acetylthio-1-(4-N,N-dimethylcarbamoyl-1,3-thiazol-2-yl)piperidine (629 mg, yield 50%) as a pale brown solid.

$^1$H-NMR (400 MHz, CDCl$_3$): δ (ppm) 7.07 (1H, s), 3.90–3.78 (3H, m), 3.75–3.60 (2H, m), 3.40–3.15 (5H, m), 3.08 (3H, br s), 2.32 (3H, s), 2.12–1.98 (2H, m), 1.82–1.60 (2H, m).

Mass spectrum (FAB$^+$): 314 [M+H]$^+$.

REFERENCE EXAMPLE 18

(3S)-3-Acetylthio-1-(4-carbamoyl-1,3-thiazol-2-yl)pyrrolidine

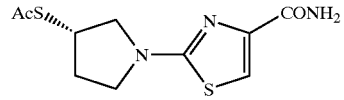

(1) [(3R)-3-Hydroxypyrrolidine-1-carbothioyl]carbamic acid ethyl ester (3R)-3-hydroxypyrrolidine hydrochloride (15 g, 121.4 mmol) was dissolved in tetrahydrofuran (450 ml), and ethoxycarbonyl isothiocyanate (15.7 ml) was added thereto in an ice bath. The mixture solution was brought to room temperature in 10 minutes and then stirred overnight. After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was recrystallized from a mixture of ethyl acetate and n-hexane to afford [(3R)-3-hydroxypyrrolidine-1-carbothioyl]carbamic acid ethyl ester (24.62 g, yield 93%) as a yellow crystal.

$^1$H-NMR (400 MHz, CDCl$_3$): δ (ppm) 7.38–7.25 (1H, br s), 4.35–3.63 (5H, m), 4.16 (2H, q, J=6.8 Hz), 2.19–2.05 (2H, m), 1.30 (3H, t, J=6.8 Hz).

(2) (3R)-1-(4-Ethoxycarbonyl-1,3-thiazol-2-yl)-3-hydroxypyrrolidine

To a solution of [(3R)-3-hydroxypyrrolidine-1-carbothioyl]carbamic acid hydrochloride (24.6 g, 113 mmol) (obtained as described in Reference Example 18(1)) in ethanol (125 ml) and distilled water (125 ml) was added sodium hydroxide (31.6 g, 789 mmol), and the mixture was heated under reflux overnight. After checking the completion of the reaction, the reaction mixture was cooled to room temperature. To the reaction mixture was added a solution of 4N hydrogen chloride in dioxane was added in an ice bath until the pH of the reaction mixture became 7, ethyl 2-bromopyruvate (28.4 ml, 226 mmol) and triethylamine (31.7 ml, 226 mmol) were added thereto, and the reaction mixture was heated under reflux for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The obtained residue was purified by chromatography on a silica gel column using toluene:acetonitrile (1:1→1:2) as the eluant to afford (3R)-1-(4-ethoxycarbonyl-1,3-thiazol-2-yl)-3-hydroxypyrrolidine (19.26 g, yield 70%) as a pale brown solid.

$^1$H-NMR (400 MHz, CDCl$_3$): δ (ppm) 7.39 (1H, s), 4.66–4.61 (1H, m), 4.36 (2H, q, J=7.3 Hz), 3.72–3.65 (2H, m), 3.62–3.56 (2H, m), 2.23–2.15 (1H, m), 2.14–2.07 (1H, m), 1.37 (3H, t, J=7.3 Hz).

(3) (3R)-3-t-Butyldiphenylsilyloxy-1-(4-ethoxycarbonyl-1,3-thiazol-2-yl)pyrrolidine To a solution of (3R)-1-(4-ethoxycarbonyl-1,3-thiazol-2-yl)-3-hydroxypyrrolidine (3.0 g, 12.4 mmol) (obtained as described in Reference Example 18(2)) in dimethylformamide (90 ml) were added t-butyldiphenylsilyl chloride (6.45 ml, 24.8 mmol) and imidazole (1.69 g, 24.8 mmol) in an ice bath. After stirring the mixture in an ice bath for 10 minutes, the resulting mixture was stirred at room temperature overnight. After checking the completion of the reaction, ethanol (2.59 ml) was added to the reaction mixture in an ice bath and the resulting mixture was stirred at room temperature for 2 hours. The reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:1→1:1) as the eluant to afford (3R)-3-t-butyldiphenylsilyloxy-1-(4-ethoxycarbonyl-1,3-thiazol-2-yl)pyrrolidine (5.85 g, yield 90%) as a pale brown solid.

$^1$H-NMR (400 MHz, CDCl$_3$): δ (ppm) 7.69–7.60 (4H, m), 7.48–7.35 (6H, m), 7.39 (1H, s), 4.56–4.50 (1H, m), 4.12 (2H, q, J=7.3 Hz), 3.77–3.70 (1H, m), 3.56–3.46 (3H, m), 2.06–1.90 (2H, m), 1.38 (3H, t, J=7.3 Hz), 1.05 (9H, s).

(4) (3R)-3-t-Butyldiphenylsilyloxy-1-(4-carboxyl-1,3-thiazol-2-yl)pyrrolidine

To a solution of (3R)-3-t-butyldiphenylsilyloxy-1-(4-ethoxycarbonyl-1,3-thiazol-2-yl)pyrrolidine (300 mg, 0.624 mmol) (obtained as described in Reference Example 18(3)) in the mixture of ethanol (12 ml) and distilled water (3 ml) was added 1N aqueous sodium hydroxide solution (1.56 ml, 1.56 mmol) at room temperature, and the reaction mixture was stirred at room temperature for 6 hours. After checking the completion of the reaction, 1N aqueous hydrochloric acid solution (1.8 ml) was added thereto in an ice bath until the pH of the reaction mixture reached 4 to 5. The reaction mixture was partitioned between ethyl acetate and saturated, aqueous sodium chloride solution. The organic layer was dried over anhydrous sodium sulfate, filtered and concentrated under reduced pressure to afford (3R)-3-t-butyldiphenylsilyloxy-1-(4-carboxyl-1,3-thiazol-2-yl)pyrrolidine (305 mg, yield 97%) as a white solid.

$^1$H-NMR (400 MHz, CDCl$_3$): δ (ppm) 7.68–7.60 (4H, m), 7.48–7.35 (6H, m), 7.40 (1H, s), 4.57–4.50 (1H, m), 3.72–3.62 (1H, m), 3.50–3.36 (3H, m), 2.10–1.92 (2H, m), 1.05 (9H, s).

(5) (3R)-3-t-Butyldiphenylsilyloxy-1-(4-carbamoyl-1,3-thiazol-2-yl)pyrrolidine

To a solution of (3R)-3-t-butyldiphenylsilyloxy-1-(4-carboxyl-1,3-thiazol-2-yl)pyrrolidine (910 mg, 2.01 mmol) (obtained as described in Reference Example 18(4)) in dimethylformamide (30 ml) was added carbonyldiimidazole (652 mg, 4.02 mmol) at room temperature under an atmosphere of nitrogen, and the reaction mixture was then stirred in an oil bath (50° C.) for 4 hours. After checking the completion of the reaction, 28% aqueous ammonia solution was added thereto and the reaction mixture was stirred at room temperature for 30 minutes.

Subsequently, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column to afford (3R)-3-t-butyldiphenylsilyloxy-1-(4-N-carbamoyl-1,3-thiazol-2-yl)pyrrolidine (730 mg, yield 80%) as a pale brown solid.

$^1$H-NMR (400 MHz, CDCl$_3$): δ (ppm) 7.71–7.64 (4H, m), 7.48–7.38 (6H, m), 7.09–7.05 (1H, br s), 5.50–5.44 (1H, br s), 4.57–4.52 (1H, m), 3.72–3.66 (1H, m), 3.51–3.45 (1H, m), 3.45–3.43 (2H, m), 2.09–2.02 (1H, m), 2.08–1.93 (1H, m), 1.08 (9H, s).

(6) (3R)-1-(4-Carbamoyl-1,3-thiazol-2-yl)-3-hydroxypyrrolidine

To a solution of (3R)-3-t-butyldiphenylsilyloxy-1-(4-carbamoyl-1,3-thiazol-2-yl)pyrrolidine (950 mg, 2.10 mmol) (obtained as described in Reference Example 18(5)) in anhydrous tetrahydrofuran (20 ml) was added a solution of 1.0M tetra-n-butylammonium fluoride in tetrahydrofuran (2.52 ml, 2.52 mmol) in an ice bath. The mixture was stirred at room temperature for 1 hour. After checking the completion of the reaction, the reaction mixture was concentrated under reduced pressure. The residue was purified by chromatography on a silica gel column using n-hexane:ethyl acetate (1:1)→10% methanol in ethyl acetate as the eluant to afford (3R)-1-(4-carbamoyl-1,3-thiazol-2-yl)-3-hydroxypyrrolidine (428 mg, yield 96%) as a white solid.

¹H-NMR (400 MHz, DMSO-d₆): δ (ppm) 7.42–7.36 (1H, br s), 7.30–7.23 (1H, br s), 7.27 (1H, s), 5.08 (1H, d, J=3.7 Hz), 4.42–4.37 (1H, m), 3.51 (1H, dd, J=11.0, 4.4 Hz), 3.90–3.43 (2H, m), 3.30–3.27 (1H, m), 2.14–2.01 (1H, m), 1.99–1.86 (1H, m).

(7) (3R)-1-(4-Carbamoyl-1,3-thiazol-2-yl)-3-methanesulfonyloxypyrrolidine and (3R)-1-(4-cyano-1,3-thiazol-2-yl)-3-methanesulfonyloxypyrrolidine To a solution of (3R)-1-(4-carbamoyl-1,3-thiazol-2-yl)-3-hydroxypyrrolidine (290 mg, 1.36 mmol) (obtained as described in Reference Example 18(6)) suspended in methylene chloride (9 ml) were added methanesulfonyl chloride (0.684 ml, 8.85 mmol) and triethylamine (1.24 ml, 8.85 mmol) in an ice bath. After stirring the mixture in the ice bath for 10 minutes, the mixture was stirred at room temperature overnight. After checking the completion of the reaction, methanol (0.33 ml) was added to the reaction mixture in an ice bath, and then the resulting mixture was stirred at room temperature for 30 minutes. The reaction mixture was concentrated under reduced pressure. The residue was purified by chromatography on a silica gel column using 5% methanol in ethyl acetate→10% methanol in ethyl acetate as the eluant to afford (3R)-1-(4-carbamoyl-1,3-thiazol-2-yl)-3-methanesulfonyloxypyrrolidine (148 mg, yield 40%) as a pale yellow solid.

(3R)-1-(4-Carbamoyl-1,3-thiazol-2-yl)-3-methanesulfonyloxypyrrolidine (a)

¹H-NMR (400 MHz, CDCl₃): δ (ppm) 7.41 (1H, s), 7.10–6.98 (1H, bs), 5.60–5.52 (1H, br s), 5.50–5.40 (1H, m), 3.88–3.76 (2H, m), 3.65–3.60 (2H, m), 3.08 (3H, s), 2.50–2.41 (1H, m). 2.39–2.32 (1H, m).

(3R)-1-(4-Cyano-1,3-thiazol-2-yl)-3-methanesulfonyloxypyrrolidine (b)

¹H-NMR (400 MHz, CDCl₃): δ (ppm) 7.23 (1H, s), 5.45–5.42 (1H, m), 3.88–3.76 (2H, m), 3.69–3.62 (2H, m), 3.08 (3H, s), 2.55–2.47 (1H, m), 2.43–2.32 (1H, m).

(8) (3S)-3-Acetylthio-1-(4-carbamoyl-1,3-thiazol-2-yl)pyrrolidine

To a solution of (3R)-1-(4-carbamoyl-1,3-thiazol-2-yl)-3-methanesulfonyloxypyrrolidine (190 mg, 0.652 mmol) (obtained as described in Reference Example 18(7)) in acetonitrile (6 ml) was added potassium thioacetate (223 mg, 1.96 mmol) at room temperature. The mixture was heated under reflux for 4 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1)→ethyl acetate→2% methanol in ethyl acetate as the eluant to afford (3S)-3-acetylthio-1-(4-carbamoyl-1,3-thiazol-2-yl)pyrrolidine (135 mg, yield 77%) as a pale brown solid.

¹H-NMR (400 MHz, CDCl₃): δ (ppm) 7.37 (1H, s), 7.08–7.02 (1H, br s), 5.50–5.44 (1H, br s), 4.26–4.12 (1H, m), 3.94 (1H, dd, J=11.0, 6.6 Hz), 3.62–3.50 (2H, m), 3.44 (1H, dd, J=11.0, 5.1 Hz), 2.54–2.45 (1H, m), 2.36 (3H, s), 2.13–2.04 (1H, m).

REFERENCE EXAMPLE 19

(3S)-3-Acetylthio-1-(4-cyano-1,3-thiazol-2-yl)pyrrolidine

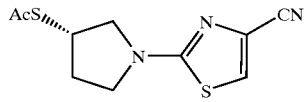

To a solution of (3R)-1-(4-cyano-1,3-thiazol-2-yl)-3-methanesulfonyloxypyrrolidine (300 mg, 1.10 mmol) (obtained as described in Reference Example 18(7)) in acetonitrile (9 ml) was added potassium thioacetate (376 mg, 3.30 mmol) at room temperature. The mixture was heated under reflux for 5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (5:1→1:1) as the eluant to afford (3S)-3-acetylthio-1-(4-cyano-1,3-thiazol-2-yl)pyrrolidine (137 mg, yield 50%) as a pale brown solid.

¹H-NMR (400 MHz, CDCl₃): δ (ppm) 7.19 (1H, s), 4.19–4.12 (1H, m), 3.94 (1H, dd, J=11.0, 6.6 Hz), 3.64–3.53 (2H, m), 3.43 (1H, dd, J=11.0, 5.1 Hz), 2.55–2.48 (1H, m), 2.36 (3H, s), 2.15–2.06 (1H, m).

REFERENCE EXAMPLE 20

(3R)-3-Acetylthio-1-(4-carbamoyl-1,3-thiazol-2-yl)pyrrolidine

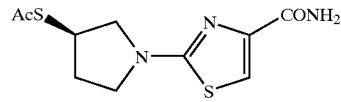

(1) (3R)-1-(4-Ethoxycarbonyl-1,3-thiazol-2-yl)-3-methanesulfonyloxypyrrolidine

To a solution of (3R)-1-(4-ethoxycarbonyl-1,3-thiazol-2-yl)-3-hydroxypyrrolidine (970 mg, 4.00 mmol) (obtained as described in Reference Example 18(2)) in methylene chloride (30 ml) were added methanesulfonyl chloride (1.24 ml, 16.0 mmol) and triethylamine (2.24 ml, 16.0 mmol) in an ice bath, and then the mixture was stirred for 1 hour. After checking the completion of the reaction, ethanol (0.81 ml) was added thereto and then the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using toluene:acetonitrile (4:1→1:1) as the eluant to afford (3R)-1-(4-ethoxycarbonyl-1,3-thiazol-2-yl)-3-methanesulfonyloxypyrrolidine (1.00 g, yield 78%) as a pale yellow solid.

¹H-NMR (400 MHz, CDCl₃): δ (ppm) 7.43 (1H, s), 5.44–5.41 (1H, m), 4.36 (2H, q, J=7.0 Hz), 3.92 (1H, dd, J=12.5, 1.5 Hz), 3.85 (1H, dd, J=12.5, 3.7 Hz), 3.72–3.65 (2H, m), 3.06 (3H, s), 2.52–2.46 (1H, m), 2.40–2.31(1H ,m), 1.38 (3H, t, J=7.0 Hz).

(2) (3S)-3-Acetyl-1-(4-ethoxycarbonyl-1,3-thiazol-2-yl)pyrrolidine

To a solution of (3R)-1-(4-ethoxycarbonyl-1,3-thiazol-2-yl)-3-methanesulfonyloxypyrrolidine (1.0 g, 3.12 mmol) (obtained as described in Reference Example 20(1)) in dimethylformamide (30 ml) was added potassium thioacetate (919 mg, 9.36 mmol) at room temperature. The mixture was stirred in an oil bath (80° C.) for 5.5 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using toluene:acetonitrile (3:1→1:1) as the eluant to afford (3S)-3-acetyl-1-(4-ethoxycarbonyl-1,3-thiazol-2-yl)pyrrolidine (877 mg, yield 99%) as a pale brown solid.

$^1$H-NMR (400 MHz, CDCl$_3$): δ (ppm) 7.41 (1H, s), 5.45–5.41 (1H, m), 4.36 (2H, q, J=7.3 Hz), 3.44 (1H, dd, J=11.7, 5.1 Hz), 3.70–3.60 (3H, m), 2.35–2.17 (2H, m), 2.05 (3H, s), 1.38 (3H, t, 7.3 Hz).

(3) (3S)-1-(4-Ethoxycarbonyl-1,3-thiazol-2-yl)-3-hydroxypyrrolidine

To a solution of (3S)-3-acetyl-1-(4-ethoxycarbonyl-1,3-thiazol-2-yl)pyrrolidine (5.0 g, 17.6 mmol) (obtained as described in Reference Example 20(2)) in ethanol (150 ml) was added sodium ethoxide (60 mg, 0.879 mmol) at room temperature, and the mixture was stirred overnight under the same conditions. After checking the completion of the reaction, a solution of 4N hydrogen chloride in 1,4-dioxane (0.22 ml) was added thereto to neutralize the reaction mixture. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The obtained residue was purified by chromatography on a silica gel column using toluene:acetonitrile (1:1→1:2) as the eluant to afford (3S)-1-(4-ethoxycarbonyl-1,3-thiazol-2-yl)-3-hydroxypyrrolidine (4.16 g, yield 98%) as a white solid.

$^1$H-NMR (400 MHz, CDCl$_3$): δ (ppm) 7.39 (1H, s), 4.67–4.61 (1H, m), 4.36 (2H, q, J=7.3 Hz), 3.72–3.56 (4H, m), 2.24–2.07 (2H, m), 1.37 (3H, t, J=7.3 Hz).

(4) (3S)-3-t-Butyldiphenylsilyloxy-1-(4-ethoxycarbonyl-1,3-thiazol-2-yl)pyrrolidine To a solution of (3S)-1-(4-ethoxycarbonyl-1,3-thiazol-2-yl)-3-hydroxypyrrolidine (4.1 g, 16.9 mmol) (obtained as described in Reference Example 20(3)) in dimethylformamide (120 ml) were added t-butyldiphenylsilyl chloride (8.8 ml, 33.8 mmol) and imidazole (2.3 g, 33.8 mmol) in an ice bath, and then the reaction mixture was brought to room temperature in 10 minutes, and stirred for overnight. After checking the completion of the reaction, ethanol (1.18 ml) was added thereto in an ice bath, and then the reaction mixture was stirred at room temperature for 30 minutes. The reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:1→1:1) as the eluant to afford (3S)-3-t-butyldiphenylsilyloxy-1-(4-ethoxycarbonyl-1,3-thiazol-2-yl)pyrrolidine (7.60 g, yield 94%) as a pale brown solid.

$^1$H-NMR (400 MHz, CDCl$_3$): δ (ppm) 7.68–7.61 (4H, m), 7.52–7.35 (6H, m), 7.37 (1H, s), 4.56–4.51 (1H, m), 4.36 (2H, q, J=7.0 Hz), 3.77–3.69 (1H, m), 3.58–3.48 (3H, m), 2.05–1.88 (2H, m), 1.38 (3H, t, J=7.0 Hz), 1.05 (9H, s).

(5) (3S)-3-t-Butyldiphenylsilyloxy-1-(4-carboxyl-1,3-thiazol-2-yl)pyrrolidine

To a solution of (3S)-3-t-butyldiphenylsilyloxy-1-(4-ethoxycarbonyl-1,3-thiazol-2-yl)pyrrolidine (5.0 g, 10.4 mmol) (obtained as described in Reference Example 20(4)) in a mixture of ethanol (200 ml) and distilled water (50 ml) was added 1N aqueous sodium hydroxide solution (26.0 ml, 26.0 mmol) at room temperature, and the reaction mixture was stirred at room temperature for 7.5 hours. After checking the completion of the reaction, 1N aqueous hydrochloric acid solution was added thereto in an ice bath until the pH of the reaction mixture reached 4 to 5. The reaction mixture was partitioned between ethyl acetate and saturated aqueous sodium chloride solution. The organic layer was dried over anhydrous sodium sulfate, filtered and concentrated under reduced pressure to afford (3S)-3-t-butyldiphenylsilyloxy-1-(4-carboxyl-1,3-thiazol-2-yl)pyrrolidine (4.71 g, yield 100%) as a white solid.

$^1$H-NMR (400 MHz, CDCl$_3$): δ (ppm) 7.70–7.52 (4H, m), 7.52–7.25 (6H, m), 7.40 (1H, s), 4.57–4.40 (1H, m), 3.68–3.55 (1H, m), 3.48–3.24 (3H, m), 2.04–1.86 (2H, m), 1.07 (9H, s).

(6) (3S)-3-t-Butyldiphenylsilyloxy-1-(4-carbamoyl-1,3-thiazol-2-yl)pyrrolidine

To a solution of (3S)-3-t-butyldiphenylsilyloxy-1-(4-carboxyl-1,3-thiazol-2-yl)pyrrolidine (4.7 g, 10.4 mmol) (obtained as described in Reference Example 20(5)) in dimethylformamide (140 ml) was added carbonyldiimidazole (3.37 g, 20.8 mmol) at room temperature under an atmosphere of nitrogen, and then the reaction mixture was stirred in an oil bath (50° C.) for 3.5 hours. After checking the completion of the reaction, 28% aqueous ammonia solution was added thereto and the reaction mixture was stirred at room temperature for 1 hour. The reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using toluene:acetonitrile (4:1→2:1) as the eluant to afford (3S)-3-t-butyldiphenylsilyloxy-1-(4-N-carbamoyl-1,3-thiazol-2-yl)pyrrolidine (3.14 g, yield 67%) as a pale brown solid.

$^1$H-NMR (400 MHz, CDCl$_3$): δ (ppm) 7.68–7.62 (4H, m), 7.48–7.36 (6H, m), 7.34 (1H, s), 7.08–7.05 (1H, br s), 5.49–5.44 (1H, br s), 4.57–4.51 (1H, m), 2.10–1.93 (2H, m), 1.06 (9H, s).

(7) (3S)-1-(4-Carbamoyl-1,3-thiazol-2-yl)-3-hydroxypyrrolidine

To a solution of (3S)-3-t-butyldiphenylsilyloxy-1-(4-carbamoyl-1,3-thiazol-2-yl)pyrrolidine (3.1 g, 6.86 mmol) (obtained as described in Reference Example 20(6)) in anhydrous tetrahydrofuran (90 ml) was added a solution of 1.0M tetra-n-butylammonium fluoride in tetrahydrofuran (8.24 ml, 8.24 mmol) in an ice bath, and the mixture was stirred for 1.5 hours. After checking the completion of the reaction, the reaction mixture was concentrated under reduced pressure. The residue was purified by chromatography on a silica gel column using ethyl acetate→10% methanol in ethyl acetate as the eluant to afford (3S)-1-(4- carbamoyl-1,3-thiazol-2-yl)-3-hydroxypyrrolidine (1.42 g, yield 98%) as a white solid.

$^1$H-NMR (400 MHz, DMSO-d$_6$): δ (ppm) 7.43–7.36 (1H, br s), 7.74–7.22 (1H, br s), 7.27 (1H, s), 5.09 (1H, d, J=3.7 Hz), 4.44–4.38 (1H, m), 3.51 (1H, dd, J=11.0, 4.4 Hz), 3.49–3.42 (2H, m), 3.33–3.28 (1H, m), 2.15–2.02 (1H, m), 1.97–1.89 (1H, m).

(8) (3S)-1-(4-Carbamoyl-1,3-thiazol-2-yl)-3-methanesulfonyloxypyrrolidine

To a solution of (3S)-1-(4-carbamoyl-1,3-thiazol-2-yl)-3-hydroxypyrrolidine (1.42 g, 6.66 mmol) (obtained as described in Reference Example 20(7)) suspended in a mixture of methylene chloride (40 ml) and pyridine (9 ml) were added methanesulfonyl chloride (2.58 ml, 33.3 mmol) and triethylamine (4.67 ml, 33.3 mmol) in an ice bath, and the mixture was stirred for 1 hour. After checking the completion of the reaction, methanol (1.2 ml) was added thereto in an ice bath and the resulting mixture was stirred at room temperature for 30 minutes. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using 5% methanol in ethyl acetate→10% methanol in ethyl acetate as the eluant to afford (3S)-1-(4-carbamoyl-1,3-thiazol-2-yl)-3-methanesulfonyloxypyrrolidine (1.15 g, yield 60%) as a pale yellow solid.

$^1$H-NMR (400 MHz, CDCl$_3$): δ (ppm) 7.41 (1H, s), 7.08–7.02 (1H, br s), 5.57–5.46 (1H, br s), 5.45–5.43 (1H, m), 3.86 (1H, dd, J=12.5 Hz), 3.80 (1H, dd, J=12.5, 4.4 Hz), 3.68–3.60 (2H, m), 3.08 (3H, s), 2.52–2.40 (1H, m), 2.39–2.31 (1H, m).

(9) (3R)-3-Acetylthio-1-(4-carbamoyl-1,3-thiazol-2-yl)pyrrolidine

To a solution of (3S)-1-(4-carbamoyl-1,3-thiazol-2-yl)-3-methanesulfonyloxypyrrolidine (1.15 g) (obtained as described in Reference Example 20(8)) in acetonitrile (35 ml) was added potassium thioacetate (1.35 g, 11.8 mmol) at room temperature, and the mixture was heated under reflux for 6 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate→2% methanol in ethyl acetate as the eluant to afford (3R)-3-acetylthio-1-(4-carbamoyl-1,3-thiazol-2-yl)pyrrolidine (962 mg, yield 90%) as a pale brown solid.

$^1$H-NMR (400 MHz, CDCl$_3$): δ (ppm) 7.37 (1H, s), 7.13–6.99 (1H, br s), 5.59–5.45 (1H, br s), 4.19–4.09 (1H, m), 3.94 (1H, dd, J=11.0, 6.6 Hz), 3.61–3.50 (2H, m), 3.44 (1H, dd, J=11.0, 5.1 Hz), 2.54–2.45 (1H, m), 2.37 (3H, s), 2.14–2.05 (1H, m).

REFERENCE EXAMPLE 21

3-Acetylthio-1-(4-N-methylcarbamoyl-1,3-thiazol-2-yl)azetidine

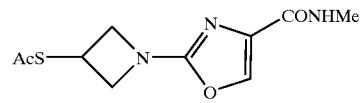

(1) 1-Carbamoyl-3-hydroxyazetidine

A solution of N-benzhydryl-3-hydroxyazetidine (5.36 g, 22.4 mmol) in methanol (250 ml) underwent catalytic hydrogenation in the presence of 10% palladium hydroxide (5.36 g) a water bath (50° C.) at 1 atmosphere hydrogen pressure. After checking the completion of the reaction, the reaction mixture was filtered to remove the catalyst. The filtrate was concentrated under reduced pressure. The residue was partitioned between ethyl acetate and distilled water. The organic layer was extracted with distilled water. The obtained aqueous layer was concentrated under reduced pressure to give a reddish brown oily product.

Subsequently, the product was dried under reduced pressure and dissolved in a mixture of acetic acid (10 ml) and distilled water (20 ml), an aqueous solution (20 ml) of sodium cyanide (2.91 g) was added thereto at room temperature and the reaction mixture was stirred for 2 hours. After checking the completion of the reaction, the reaction mixture was concentrated. The obtained residue was purified by chromatography on a silica gel column using methylene chloride:methanol (5:1) as the eluant to afford 1-carbamoyl-3-hydroxyazetidine as a colorless oil.

$^1$H-NMR (500 MHz, CD$_3$OD): δ (ppm) 4.54–4.50 (1H, m), 4.16–4.12 (2H, m), 3.74 (2H, dd, J=4.4, 9.7 Hz).

(2) 3-t-Butyldiphenylsilyloxy-1-carbamoylazetidine

To a solution of 1-carbamoyl-3-hydroxyazetidine (obtained as described in Reference Example 21(1)) in dimethylformamide (100 ml) were added t-butyldiphenylsilyl chloride (18.0 ml, 66.9 mmol) and imidazole (4.55 g, 66.9 mmol) in an ice bath. After stirring the mixture in an ice bath for 10 minutes, the resulting mixture was stirred at room temperature overnight. After checking the completion of the reaction, ethanol (1 ml) was added to the reaction mixture in an ice bath and the resulting mixture was stirred at room temperature for 30 minutes. The reaction mixture was partitioned between ethyl acetate and aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford 3-t-butyldiphenylsilyloxy-1-carbamoylazetidine (1.45 g, total yield 18%) as a white solid.

$^1$H-NMR (400 MHz, CDCl$_3$): δ (ppm) 7.60 (4H, d, J=8.1 Hz), 7.46–7.36 (6H, m), 4.59–4.54 (1H, m), 4.26 (2H, br s), 3.96 (2H, t, J=8.8 Hz), 3.91 (2H, dd, J=5.1, 8.8 Hz), 1.06 (9H, s).

(3) 3-t-Butyldiphenylsilyloxy-1-(4-ethoxycarbonyl-1,3-oxazol-2-yl)azetidine

To a solution of 3-t-butyldiphenylsilyloxy-1-carbamoylazetidine (3.47 g, 9.79 mmol) (obtained as described in Reference Example 21(2)) in tetrahydrofuran (170 ml) were added sodium hydrogencarbonate (4.11 g, 48.95 mmol) and ethyl-2-bromopyruvate (2.5 ml, 19.58 mmol), and the reaction mixture was heated under reflux for 8 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The obtained residue was purified by chromatography on a silica gel column using hexane:ethyl acetate (5:1) as the eluant to afford 3-t-butyldiphenylsilyloxy-1-(4-ethoxycarbonyl-1,3-oxazol-2-yl)azetidine (2.96 g, yield 45%) as a white solid.

$^1$H-NMR (400 MHz, CDCl$_3$): δ (ppm) 7.76 (1H, s), 7.60 (4H, d, J=7.8 Hz), 7.46–7.37 (6H, m), 4.71–4.67 (1H, m), 4.34 (2H, q, J=6.8 Hz), 4.14 (2H, t, J=8.8 Hz), 4.09 (2H, dd, J=5.9, 9.8 Hz), 1.34 (3H, t, J=6.8 Hz), 1.05 (9H, s).

(4) 3-t-Butyldiphenylsilyloxy-1-(4-N-methylcarbamoyl-1,3-oxazol-2-yl)azetidine

To a solution of 3-t-butyldiphenylsilyloxy-1-(4-ethoxycarbonyl-1,3-oxazol-2-yl)azetidine (325 mg, 0.72 mmol) (obtained as described in Reference Example 21(3)) in benzene (7 ml) was added a solution of 0.67M methylamine-trimethylaluminium in benzene (2.7 ml) at room temperature under an atmosphere of nitrogen. The mixture was heated under reflux for 1 hour. After checking the completion of the reaction, 10% aqueous acetic acid solution (20 ml) was added to the reaction mixture in an ice bath, and the resulting mixture was stirred at room temperature for 30 minutes. The reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using hexane:ethyl acetate (1:1) as the eluant to afford 3-t-butyldiphenylsilyloxy-1-(4-N-methylcarbamoyl-1,3-oxazol-2-yl)azetidine (236 mg, yield 75%) as a white solid.

$^1$H-NMR (400 MHz, CDCl$_3$): δ (ppm) 7.72 (1H, s), 7.61 (4H, d, J=7.8 Hz), 7.47–7.38 (6H, m), 6.88 (1H, br s), 4.74–4.68 (1H, m), 4.10 (2H, t, J=8.7 Hz), 4.04 (2H, dd, J=5.6, 8.8 Hz), 2.92 (3H, d, J=5.0 Hz), 1.06 (9H, s).

(5) 1-(4-N-Methylcarbamoyl-1,3-oxazol-2-yl)azetidine

To a solution of 3-t-butyldiphenylsilyloxy-1-(4-N-methylcarbamoyl-1,3-oxazol-2-yl)azetidine (662 mg, 1.52 mmol) (obtained as described in Reference Example 21(4)) in tetrahydrofuran (33 ml) was added a solution of 1.0M tetra-n-butylammonium fluoride in tetrahydrofuran (1.5 ml, 1.5 mmol) in an ice bath, and the mixture was stirred for 1 hour. After checking the completion of the reaction, the reaction mixture was concentrated under reduced pressure. The residue was purified by chromatography on a silica gel column using ethyl acetate:methanol (10:1) as the eluant to afford 1-(4-N-methylcarbamoyl-1,3-oxazol-2-yl)azetidine (210 mg, yield 70%) as a white solid.

$^1$H-NMR (400 MHz, CD$_3$OD): δ (ppm) 7.83 (1H, s), 4.86–4.66 (1H, m), 4.33 (2H, dd, J=6.6, 8.1 Hz), 3.93 (2H, dd, J=5.1, 8.8 Hz), 2.85 (3H, s).

(6) 1-(4-N-Methylcarbamoyl-1,3-oxazol-2-yl)-3-methanesulfonyloxyazetidine

To a solution of 1-(4-N-methylcarbamoyl-1,3-oxazol-2-yl)azetidine (209 mg, 1.06 mmol) (obtained as described in Reference Example 21(5)) in a mixture of methylene chloride (5 ml) and pyridine (15 ml) were added methanesulfonyl chloride (0.41 ml, 5.30 mmol) and triethylamine (0.74 ml, 5.30 mmol) in an ice bath. After stirring the mixture in the ice bath for 10 minutes, the mixture was stirred at room temperature for 2 hours. After checking the completion of the reaction, methanol (1 ml) was added thereto and the reaction mixture was stirred at room temperature for 30 minutes. After checking the completion of the reaction, the reaction mixture was concentrated under reduced pressure. The residue was purified by chromatography on a silica gel column using ethyl acetate:methanol (10:1) as the eluant to afford 1-(4-N-methylcarbamoyl-1,3-oxazol-2-yl)-3-methanesulfonyloxyazetidine (253 mg, yield 86%) as a white solid.

$^1$H-NMR (400 MHz, CDCl$_3$): δ (ppm) 7.78 (1H, s), 6.80 (1H, br s), 5.41–5.35 (1H, m), 4.48 (2H, dd, J=6.6, 10.3 Hz), 4.30 (2H, dd, J=4.4, 10.3 Hz), 3.10 (3H, s), 2.94 (3H, d, J=5.1 Hz).

(7) 3-Acetylthio-1-(4-N-methylcarbamoyl-1,3-oxazol-2-yl)azetidine

To a solution of 1-(4-N-methylcarbamoyl-1,3-oxazol-2-yl)-3-methanesulfonyloxyazetidine (252 mg, 0.92 mmol) (obtained as described in Reference Example 21(6)) in dimethylformamide (12 ml) was added potassium thioacetate (0.63 g, 5.52 mmol) at room temperature. The mixture was stirred in an oil bath (80° C.) for 8 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate as the eluant to afford 3-acetylthio-1-(4-N-methylcarbamoyl-1,3-oxazol-2-yl)azetidine (136 mg, yield 58%) as a white solid.

$^1$H-NMR (500 MHz, CDCl$_3$): δ (ppm) 7.75 (1H, s), 6.79 (1H, br s), 4.55 (2H, t, J=8.4 Hz), 4.43–4.37 (1H, m), 4.02 (2H, dd, J=5.8, 8.9 Hz), 2.94 (3H, d, J=5.1 Hz), 2.36 (3H, s).

REFERENCE EXAMPLE 22

3-Acetylthio-1-(4-N-carbamoyl-1,3-oxazol-2-yl)azetidine

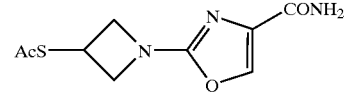

(1) 3-t-Butyldiphenylsilyloxy-1-(4-carbamoyl-1,3-oxazol-2-yl)azetidine

To a solution of 3-t-butyldiphenylsilyloxy-1-(4-ethoxycarbonyl-1,3-oxazol-2-yl)azetidine (1.70 g, 3.77 mmol) (obtained as described in Reference Example 21(3)) in benzene (38 ml) was added a solution of 0.67M methylamine-trimethylaluminium in benzene (13.7 ml) at room temperature under an atmosphere of nitrogen, and then the mixture was stirred in water bath (50° C.) for 4 hour. After checking the completion of the reaction, 10% aqueous acetic acid solution (100 ml) was added to the reaction mixture in an ice bath, and the resulting mixture was stirred at room temperature for 30 minutes. The reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate as the eluant to afford 3-t-butyldiphenylsilyloxy-1-(4-carbamoyl-1,3-oxazol-2-yl)azetidine (0.83 g, yield 52%) as a white solid.

$^1$H-NMR (500 MHz, CDCl$_3$): δ (ppm) 7.75 (1H, s), 7.61 (4H, d, J=6.7 Hz), 7.47–7.36 (6H, m), 6.72 (1H, br s), 5.69

(1H, br s), 4.74–4.69 (1H, m), 4.12 (2H, t, J=6.7 Hz), 4.05 (2H, dd, J=5.0, 7.8 Hz), 1.06 (9H, s).

(2) 1-(4-Carbamoyl-1,3-oxazol-2-yl)-3-hydroxyazetidine

To a solution of 3-t-butyldiphenylsilyloxy-1-(4-carbamoyl-1,3-oxazol-2-yl)azetidine (1.30 g, 3.08 mmol) in tetrahydrofuran (60 ml) was added a solution of 1.0M tetra-n-butylammonium fluoride in tetrahydrofuran (3.1 ml) in an ice bath, and the mixture was stirred for 1 hour. After checking the completion of the reaction, the reaction mixture was concentrated under reduced pressure. The residue was purified by chromatography on a silica gel column using ethyl acetate:methanol (10:1) as the eluant to afford 1-(4-carbamoyl-1,3-oxazol-2-yl)-3-hydroxyazetidine (0.43 g, yield 75%) as a white solid.

$^1$H-NMR (400 MHz, CD$_3$OD): δ (ppm) 7.87 (1H, s), 4.70–4.65 (1H, m), 4.34 (2H, dd, J=6.6, 9.5 Hz), 3.94 (2H, dd, J=5.9, 9.5 Hz).

(3) 1-(4-Carbamoyl-1,3-oxazol-2-yl)-3-methanesulfonyloxyazetidine

To a solution of 1-(4-carbamoyl-1,3-oxazol-2-yl)-3-hydroxyazetidine (423 mg, 2.31 mmol) (obtained as described in Reference Example 22(2)) in a mixture of methylene chloride (10 ml) and pyridine (30 ml) were added methanesulfonyl chloride (0.90 ml,11.55 mmol) and triethylamine (1.60 ml, 11.55 mmol) in an ice bath. After stirring the mixture in the ice bath for 10 minutes, the mixture was stirred at room temperature for 2 hours. After checking the completion of the reaction, methanol (1 ml) was added to the reaction mixture in an ice bath and then the resulting mixture was stirred at room temperature for 30 minutes. After checking the completion of the reaction, the reaction mixture was concentrated under reduced pressure. The residue was purified by chromatography on a silica gel column using ethyl acetate:methanol (10:1) as the eluant to afford 1-(4-carbamoyl-1,3-oxazol-2-yl)-3-methanesulfonyloxyazetidine (470 mg, yield 78%) as a white solid.

$^1$H-NMR (400 MHz, CD$_3$OD): δ (ppm) 7.91 (1H, s), 5.45–5.42 (1H, m), 4.51 (2H, dd, J=6.6, 9.5 Hz), 4.28 (2H, dd, J=4.4, 9.5 Hz), 3.16 (3H, s).

(4) 3-Acetylthio-1-(4-carbamoyl-1,3-oxazol-2-yl)azetidine

To a solution of 1-(4-carbamoyl-1,3-oxazol-2-yl)-3-methanesulfonyloxyazetidine (469 mg, 1.80 mmol) (obtained as described in Reference Example 22(3)) in dimethylformamide (23 ml) was added potassium thioacetate (1.23 g, 10.80 mmol) at room temperature, and the mixture was stirred in an oil bath (80° C.) for 8 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate: methanol (10:1) as the eluant to afford 3-acetylthio-1-(4-carbamoyl-1,3-oxazol-2-yl)azetidine (275 mg, yield 63%) as a white solid.

$^1$H-NMR (400 MHz, CDCl$_3$): δ (ppm) 7.79 (1H, s), 6.69 (1H, br s), 5.60 (1H, br s), 4.56 (2H, t, J=8.8 Hz), 4.44–4.37 (1H, m), 4.03 (2H, dd, J=5.1, 8.8 Hz), 2.36 (3H, s).

REFERENCE EXAMPLE 23

3-Acetylthio-1-(4-cyano-1,3-oxazol-2-yl)azetidine

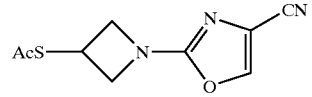

(1) 3-t-Butyldiphenylsilyloxy-1-(4-cyano-1,3-oxazol-2-yl)azetidine

To a solution of 3-t-butyldiphenylsilyloxy-1-(4-ethoxycarbonyl-1,3-oxazol-2-yl)azetidine (357 g, 0.79 mmol) (obtained as described in Reference Example 21(3)) in benzene (8 ml) was added a solution of 0.67M methylamine-trimethylaluminium in benzene (2.8 ml) at room temperature under an atmosphere of nitrogen. The mixture was stirred in a water bath (60° C.) for 7 hours. After checking the completion of the reaction, 10% aqueous acetic acid solution (10 ml) was added to the reaction mixture in an ice bath, and the resulting mixture was stirred at room temperature for 30 minutes. The reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using hexane:ethyl acetate (5:1) as the eluant to afford 3-t-butyldiphenylsilyloxy-1-(4-cyano-1,3-oxazol-2-yl)azetidine (130 mg, yield 41%) as a colorless oil.

$^1$H-NMR (400 MHz, CDCl$_3$): δ (ppm) 7.66 (1H, s), 7.60 (4H, d, J=8.1 Hz), 7.48–7.38 (6H, m), 4.73–4.70 (1H, m), 4.14 (2H, dd, J=6.6, 8.8 Hz), 4.08 (2H, dd, J=5.1, 9.5 Hz), 1.06 (9H, s).

(2) 1-(4-Cyano-1,3-oxazol-2-yl)-3-hydroxyazetidine

To a solution of 3-t-butyldiphenylsilyloxy-1-(4-cyano-1,3-oxazol-2-yl)azetidine (0.61 g, 1.51 mmol) (obtained as described in Reference Example 23(1)) in tetrahydrofuran (30 ml) was added a solution of 1.0M tetra-n-butylammonium fluoride in tetrahydrofuran (1.5 ml) in an ice bath, and the mixture was stirred for 1 hour. After checking the completion of the reaction, the reaction mixture was concentrated under reduced pressure. The residue was purified by chromatography on a silica gel column using ethyl acetate as the eluant to afford 1-(4-cyano-1,3-oxazol-2-yl)-3-hydroxyazetidine (0.21 g, yield 86%) as a white solid.

$^1$H-NMR (400 MHz, CDCl$_3$): δ (ppm) 7.70 (1H, s), 4.83–4.81 (1H, m), 4.40 (2H, dd, J=6.6, 9.5 Hz), 4.06 (2H, dd, J=4.4, 8.8 Hz), 2.26 (1H, d, J=5.9 Hz).

(3) 1-(4-Cyano-1,3-oxazol-2-yl)-3-methanesulfonyloxyazetidine

To a solution of 1-(4-cyano-1,3-oxazol-2-yl)-3-hydroxyazetidine (214 mg, 1.30 mmol) (obtained as described in Reference Example 23(2)) in a mixture of methylene chloride (10 ml) and pyridine (5 ml) were added methanesulfonyl chloride (0.50 ml, 6.50 mmol) and triethylamine (0.90 ml, 6.50 mmol) in an ice bath. After stirring the mixture in the ice bath for 10 minutes, the resulting mixture was stirred at room temperature for 2 hours. After checking the completion of the reaction, methanol (1 ml) was added thereto in an ice bath and then the resulting mixture was stirred at room temperature for 30 minutes. After checking the completion of the reaction, the reaction mixture was concentrated under reduced pressure. The residue was purified by chromatography on a silica gel column using ethyl acetate as the eluant to afford 1-(4-cyano-1,3-oxazol-2-yl)-3-methanesulfonyloxyazetidine (310 mg, yield 98%) as a colorless oil.

$^1$H-NMR (400 MHz, CDCl$_3$): δ (ppm) 7.76 (1H, s), 5.42–5.36 (1H, m), 4.53 (2H, dd, J=6.6, 11.0 Hz), 4.34 (2H, dd, J=4.4, 11.0 Hz), 3.11 (3H, s).

(4) 3-Acetylthio-1-(4-cyano-1,3-oxazol-2-yl)azetidine

To a solution of 1-(4-cyano-1,3-oxazol-2-yl)-3-methanesulfonyloxyazetidine (309 mg, 1.27 mmol) (obtained as described in Reference Example 23(3)) in dimethylformamide (15 ml) was added potassium thioacetate (0.87 g, 7.62 mmol) at room temperature. The reaction mixture was stirred in an oil bath (80° C.) for 5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using hexane:ethyl acetate (2:1) as the eluant to afford 3-acetylthio-1-(4-cyano-1,3-oxazol-2-yl)azetidine (157 mg, yield 55%) as a colorless oil.

$^1$H-NMR (400 MHz, CDCl$_3$): δ (ppm) 7.72 (1H, s), 4.60 (2H, t, J=8.8 Hz), 4.45–4.38 (1H, m), 4.07 (2H, dd, J=5.9, 8.8 Hz), 2.37 (3H, s).

REFERENCE EXAMPLE 24

3-t-Acetylthio-1-(4-cyano-1,3-oxazol-2-yl)azetidine

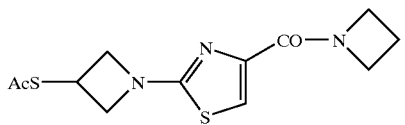

(1) 3-t-Butyldiphenylsilyloxy-1-(4-azetidinocarbonyl-1,3-thiazol-2-yl)azetidine

To a solution of 3-t-butyldiphenylsilyloxy-1-(4-ethoxycarbonyl-1,3-thiazol-2-yl)azetidine (1.0 g, 2.14 mmol) (obtained as described in Reference Example 2(1)) in benzene (50 ml) was added a solution of 0.67M azetidine-trimethylaluminium in benzene (4.6 ml) at room temperature under an atmosphere of nitrogen. The mixture was heated under reflux for 4 hours. After checking the completion of the reaction, 10% aqueous acetic acid solution (50 ml) and ethyl acetate (100 ml) were added to the reaction mixture in an ice bath and the resulting mixture was stirred at room temperature for 30 minutes. The reaction mixture was extracted with ethyl acetate. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1) as the eluant to afford 3-t-butyldiphenylsilyloxy-1-(4-azetidinocarbonyl-1,3-thiazol-2-yl)azetidine (0.60 g, yield 55%) as a pale brown solid.

$^1$H-NMR (400 MHz, CDCl$_3$): δ (ppm) 7.62 (4H, dd, J=8.0, 1.4 Hz), 7.51–7.36 (6H, m), 7.42 (1H, s), 4.80–4.68 (1H, m), 4.56 (2H, t, J=7.7 Hz), 4.16 (2H, t, J=7.7 Hz), 4.09 (2H, t, J=8.7 Hz), 4.00 (2H, dd, J=8.7, 4.9 Hz), 2.28 (2H, quintet, J=7.7 Hz), 1.06 (9H, s).

(2) 1-(4-Azetidinocarbonyl-1,3-thiazol-2-yl)-3-hydroxyazetidine

To a solution of 3-t-butyldiphenylsilyloxy-1-(4-azetidinocarbonyl-1,3-thiazol-2-yl)azetidine (0.60 g, 1.18 mmol) (obtained as described in Reference Example 24(1)) in anhydrous tetrahydrofuran (25 ml) was added a solution of 1.0M tetra-n-butylammonium fluoride in tetrahydrofuran (1.42 ml, 1.42 mmol) in an ice bath, and then the mixture was stirred for 30 minutes. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using 5% methanol in ethyl acetate as the eluant to afford 1-(4-azetidinocarbonyl-1,3-thiazol-2-yl)-3-hydroxyazetidine (242 mg, yield 86%) as a white solid.

$^1$H-NMR (400 MHz, CDCl$_3$): δ (ppm) 7.35 (1H, s), 4.86–4.78 (2H, t, J=7.7 Hz), 4.30 (2H, dd, J=9.5, 6.6 Hz), 4.16 (2H, t, J=7.7 Hz), 3.93 (2H, dd, J=9.5, 5.0 Hz), 2.29 (2H, quintet, J=7.7 Hz), 1.95–1.5 (dull s including 1H of OH group).

(3) 1-(4-Azetidinocarbonyl-1,3-thiazol-2-yl)-3-methanesulfonyloxyazetidine

To a solution of 1-(4-azetidinocarbonyl-1,3-thiazol-2-yl)-3-hydroxyazetidine (242 mg, 1.01 mmol) (obtained as described in Reference Example 24(2)) in methylene chloride (10 ml) were added methanesulfonyl chloride (0.43 ml, 3.04 mmol) and triethylamine (0.24 ml, 3.04 mmol) in an ice bath. After stirring the mixture in the ice bath for 10 minutes, the mixture was stirred at room temperature for 30 minutes. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. To the residue was added isopropyl ether and the resulting mixture was filtered to afford 1-(4-azetidinocarbonyl-1,3-thiazol-2-yl)-3-methanesulfonyloxyazetidine (302 mg, yield 94%) as a pale yellow solid.

$^1$H-NMR (400 MHz, CDCl$_3$): δ (ppm) 7.44 (1H, s), 5.46–5.38 (1H, m), 4.58 (2H, t, J=7.8 Hz), 4.43 (2H, ddd, J=9.6, 6.6, 1.0 Hz), 4.24 (1H, ddd, J=9.6, 4.6, 1.0 Hz), 4.17 (2H, t, J=7.8 Hz), 3.10 (3H, s), 2.30 (2H, quintet, J=7.8 Hz).

(4) 3-Acetylthio-1-(4-azetidinocarbonyl-1,3-thiazol-2-yl)azetidine

To a solution of 1-(4-azetidinocarbonyl-1,3-thiazol-2-yl)-3-methanesulfonyloxyazetidine (302 mg, 0.95 mmol) (obtained as described in Reference Example 24(3)) in dimethylformamide (10 ml) was added potassium thioacetate (0.65 g, 5.70 mmol) at room temperature, and the reaction mixture was stirred in an oil bath (80° C.) for 6 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1) as the eluant to afford 3-acetylthio-1-(4-azetidinocarbonyl-1,3-thiazol-2-yl)azetidine (247 mg, yield 87%) as a pale brown solid.

$^1$H-NMR (400 MHz, CDCl$_3$): δ (ppm) 7.40 (1H, s), 4.57 (2H, t, J=7.8 Hz), 4.51 (2H, t, J=8.4 Hz), 4.46–4.36 (1H, m), 4.16 (2H, t, J=7.8 Hz), 3.96 (2H, dd, J=8.4, 5.3 Hz), 2.36 (3H, s), 2.29 (2H, quintet, J=7.8 Hz).

REFERENCE EXAMPLE 25

3-Acetylthio-1-(4-thiomorpholinocarbonyl-1,3-thiazol-2-yl)azetidine

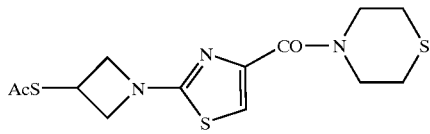

(1) 3-t-Butyldiphenylsilyloxy-1-(4-thiomorpholinocarbonyl-1,3-thiazol-2-yl)azetidine To a solution of 3-t-butyldiphenylsilyloxy-1-(4-ethoxycarbonyl-1,3-thiazol-2-yl)azetidine (1.0 g, 2.14 mmol) (obtained as described in Reference Example 2(1)) in benzene (50 ml) was added a solution of 0.67M thiomorphopline-trimethylaluminium in benzene (4.6 ml) at room temperature under an atmosphere of nitrogen. The mixture was heated under reflux for 4 hours. After checking the completion of the reaction, 10% aqueous acetic acid solution (50 ml) and ethyl acetate (100 ml) were added to the reaction mixture in an ice bath and the resulting mixture was stirred at room temperature for 30 minutes. The reaction mixture was extracted with ethyl acetate. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1) as the eluant to afford 3-t-butyldiphenylsilyloxy-1-(4-thiomorpholinocarbonyl-1,3-thiazol-2-yl)azetidine (1.16 g, yield 98%) as a pale brown solid.

$^1$H-NMR (400 MHz, CDCl$_3$): δ (ppm) 7.32 (4H, dd, J=7.9, 1.4 Hz), 7.54–7.35 (6H, m), 7.07 (1H, s), 4.80–4.70 (1H, m), 4.10 (2H, dd, J=8.8, 6.5 Hz), 4.10–3.86 (6H, m including 2H, dd at 4.00, J=8.8, 4.8 Hz), 2.80–2.55 (4H, m), 1.06 (9H, s).

(2) 1-(4-Thiomorpholinocarbonyl-1,3-thiazol-2-yl)-3-hydroxyazetidine

To a solution of 3-t-butyldiphenylsilyloxy-1-(4-thiomorpholinocarbonyl-1,3-thiazol-2-yl)azetidine (1.16 g, 2.10 mmol) (obtained as described in Reference Example 25(1)) in anhydrous tetrahydrofuran (35 ml) was added a solution of 1.0M tetra-n-butylammonium fluoride in tetrahydrofuran (2.52 ml, 2.52 mmol), and the reaction mixture was stirred for 30 minutes. After checking the completion of the reaction, the reaction mixture was concentrated under reduced pressure, and the residue was purified by chromatography on a silica gel column using ethyl acetate as the eluant to afford 1-(4-thiomorpholinocarbonyl-1,3-thiazol-2-yl)-3-hydroxyazetidine (599 mg, yield 100%) as a white solid.

$^1$H-NMR (400 MHz, CDCl$_3$): δ (ppm) 7.09 (1H, s), 4.89–4.77 (1H, m), 4.32 (2H, dd, J=9.1, 6.7 Hz), 4.10–3.90 (6H, m including 2H, dd at 3.96, J=9.1, 4.3 Hz), 2.80–2.58 (4H, m), 2.50 (1H, br s).

(3) 1-(4-Thiomorpholinocarbonyl-1,3-thiazol-2-yl)-3-methanesulfonyloxyazetidine

To a solution of 1-(4-thiomorpholinocarbonyl-1,3-thiazol-2-yl)-3-hydroxyazetidine (599 g, 2.50 mmol) (obtained as described in Reference Example 25(2)) in methylene chloride (30 ml) were added methanesulfonyl chloride (0.49 ml, 6.30 mmol) and triethylamine (0.88 ml, 6.30 mmol) in an ice bath. After stirring the mixture in the ice bath for 10 minutes, the mixture was stirred at room temperature for 40 minutes. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using 5% methanol in ethyl acetate as the eluant to afford 1-(4-thiomorpholinocarbonyl-1,3-thiazol-2-yl)-3-methanesulfonyloxyazetidine (709 mg, yield 93%) as a pale yellow solid.

$^1$H-NMR (400 MHz, CDCl$_3$): δ (ppm) 7.17 (1H, s), 5.46–5.38 (1H, m), 4.45 (2H, dd, J=9.8, 6.7 Hz), 4.26 (2H, ddd, J=9.8, 4.4, 1.1 Hz), 4.08–3.93 (4H, m), 3.11 (3H, s), 2.80–2.60 (4H, m).

(4) 3-Acetylthio-1-(4-thiomorpholinocarbonyl-1,3-thiazol-2-yl)azetidine

To a solution of 1-(4-thiomorpholinocarbonyl-1,3-thiazol-2-yl)-3-methanesulfonyloxyazetidine (709 g, 1.95 mmol) (obtained as described in Reference Example 25(3)) in dimethylformamide (20 ml) was added potassium thioacetate (1.34 g, 11.7 mmol) at room temperature. The mixture was stirred in an oil bath (80° C.) for 5 hours. After checking the completion of the reaction, the reaction mixture was partitioned between ethyl acetate and saturated aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate:n-hexane:methylene chloride (1:1:1) as the eluant to afford 3-acetylthio-1-(4-thiomorpholinocarbonyl-1,3-thiazol-2-yl)azetidine (413 mg, yield 64%) as a pale brown solid.

$^1$H-NMR (400 MHz, CDCl$_3$): δ (ppm) 7.13 (1H, s), 4.53 (2H, t, J=8.4 Hz), 4.48–4.40 (1H, m), 4.13–3.86 (6H, m including 2H, dd at 3.98, J=8.4, 5.2 Hz), 2.80–2.60 (4H, m), 2.36 (3H, s).

REFERENCE EXAMPLE 26

3-Acetylthio-1-(4-pyrrolidinocarbonyl-1,3-thiazol-2-yl)azetidine

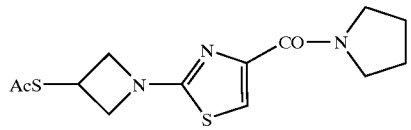

(1) 3-t-Butyldiphenylsilyloxy-1-(4-pyrrolidinocarbonyl-1,3-thiazol-2-yl)azetidine To a solution of 3-t-butyldiphenylsilyloxy-1-(4-ethoxycarbonyl-1,3-thiazol-2-yl)azetidine (1.00 g, 2.14 mmol) (obtained as described in Reference Example 2(1)) in benzene (50 ml) was added a solution of 0.67M pyrrolidine-trimethylaluminium in benzene (7.6 ml) at room temperature under an atmosphere of nitrogen. The mixture was heated under reflux for 6 hours. After checking the completion of the reaction, 10% aqueous acetic acid solution (50 ml) and ethyl acetate (100 ml) were added to the reaction mixture in an ice bath and the resulting mixture was stirred at room temperature for 2 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-t-butyldiphenylsilyloxy-1-(4-pyrrolidinocarbonyl-1,3-thiazol-2-yl)azetidine (775 mg, yield 78%) as a pale brown solid.

$^1$H-NMR (400 MHz, CDCl$_3$): δ (ppm) 7.70–7.56 (4H, m), 7.35–7.50 (6H, m), 7.21 (1H, s), 4.80–4.70 (1H, m), 4.18–4.06 (2H, m), 4.00 (2H, dd, J=8.6. 5.1 Hz), 3.80 (2H, t, J=6.5 Hz), 3.60 (2H, t, J=6.5 Hz), 1.83–1.98 (4H, m), 1.06 (9H, s).

(2) 3-Hydroxy-1-(4-pyrrolidinocarbonyl-1,3-thiazol-2-yl)azetidine

To a solution of 3-t-butyldiphenylsilyloxy-1-(4-pyrrolidinocarbonyl-1,3-thiazol-2-yl)azetidine (775 mg, 1.58 mmol) (obtained as described in Reference Example 26(1)) in anhydrous tetrahydrofuran (30 ml) was added a solution of 1.0M tetra-n-butylammonium fluoride in tetrahydrofuran (2.01 ml, 2.01 mmol) in an ice bath, and then the mixture was stirred at room temperature for 1 hour. After checking the completion of the reaction, the reaction mixture was concentrated under reduced pressure. The residue was purified by chromatography on a silica gel column using ethyl acetate→ethyl acetate:methanol (20:1) as the eluant to afford 3-hydroxy-1-(4-pyrrolidinocarbonyl-1,3-thiazol-2-yl)azetidine (290 mg, yield 72%) as a white solid.

$^1$H-NMR (400 MHz, CDCl$_3$): δ (ppm) 7.42 (1H, s), 4.88–4.78 (1H, m), 4.32 (2H, dd, J=9.0, 6.8 Hz), 3.95 (2H, dd, J=9.0, 4.3 Hz), 3.82 (2H, t, J=6.5 Hz), 3.61 (2H, t, J=6.5 Hz), 2.43 (1H, d, J=6.8 Hz), 1.83–1.97 (4H, m).

(3) 3-Methanesulfonyloxy-1-(4-pyrrolidinocarbonyl-1,3-thiazol-2-yl)azetidine

To a solution of 3-hydroxy-1-(4-pyrrolidinocarbonyl-1,3-thiazol-2-yl)azetidine (290 mg, 1.14 mmol) (obtained as described in Reference Example 26(2)) in methylene chloride (9 ml) were added methanesulfonyl chloride (0.30 ml, 5.12 mmol) and triethylamine (0.70 ml, 5.12 mmol) in an ice bath, and the mixture was stirred for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using methylene chloride:ethyl acetate (1:1)→ethyl acetate as the eluant to afford 3-methanesulfonyloxy-1-(4-pyrrolidinocarbonyl-1,3-thiazol-2-yl)azetidine (335 mg, yield 89%) as a pale yellow solid.

$^1$H-NMR (400 MHz, CDCl$_3$): δ (ppm) 7.33 (1H, s), 5.48–5.38 (1H, m), 4.45 (2H, ddd, J=10.1, 6.6, 1.2 Hz), 4.26 (2H, ddd, J=10.1, 4.4, 1.1 Hz), 3.82 (2H, t, J=6.6 Hz), 3.62 (2H, t, J=6.6 Hz), 3.10 (3H, s), 2.00–1.83 (4H, m).

(4) 3-Acetylthio-1-(4-pyrrolidinocarbonyl-1,3-thiazol-2-yl)azetidine

To a solution of 3-methanesulfonyloxy-1-(4-pyrrolidinocarbonyl-1,3-thiazol-2-yl)azetidine (335 mg, 1.01 mmol) (obtained as described in Reference Example 26(3)) in dimethylformamide (15 ml) was added potassium thioacetate (1.10 g, 8.80 mmol) at room temperature, and the reaction mixture was stirred in an oil bath (80° C.) for 5 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The obtained residue was purified by chromatography on a silica gel column using ethyl acetate as the eluant to afford 3-acetylthio-1-(4-pyrrolidinocarbonyl-1,3-thiazol-2-yl)azetidine (235 mg, yield 75%) as a pale brown solid.

$^1$H-NMR (400 MHz, CDCl$_3$): δ (ppm) 7.28 (1H, s), 4.52 (2H, dd, J=8.4, 8.4 Hz), 4.39–4.48 (1H, m), 3.98 (2H, dd, J=8.4, 5.2 Hz), 3.82 (2H, t, J=6.5 Hz), 3.61 (2H, t, J=6.5 Hz), 2.36 (3H, s), 1.98–1.82 (4H, m).

REFERENCE EXAMPLE 27

3-Acetylthio-1-(4-piperidinocarbonyl-1,3-thiazol-2-yl)azetidine

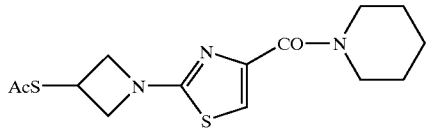

(1) 3-t-Butyldiphenylsilyloxy-1-(4-piperidinocarbonyl-1,3-thiazol-2-yl)azetidine To a solution of 3-t-butyldiphenylsilyloxy-1-(4-ethoxycarbonyl-1,3-thiazol-2-yl)azetidine (1.00 g, 2.14 mmol) (obtained as described in Reference Example 2(1)) in benzene (50 ml) was added a solution of 0.67M piperidine-trimethylaluminium in benzene (7.3 ml) at room temperature under an atmosphere of nitrogen. The mixture was heated under reflux for 5 hours. After checking the completion of the reaction, 10% aqueous acetic acid solution (50 ml) and ethyl acetate (100 ml) were added to the reaction mixture in an ice bath and the resulting mixture was stirred at room temperature for 2 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:2) as the eluant to afford 3-t-butyldiphenylsilyloxy-1-(4-piperidinocarbonyl-1,3-thiazol-2-yl)azetidine (607 mg, yield 56%) as a pale brown solid.

$^1$H-NMR (400 MHz, CDCl$_3$): δ (ppm) 7.61 (4H, dd, J=6.2 Hz), 7.35–7.50 (6H, m), 6.95 (1H, s), 4.78–4.70 (1H, m), 4.17–4.05 (2H, m), 4.01 (2H, dd, J=8.6. 4.9 Hz), 3.64 (4H, t, J=5.4 Hz), 1.75–1.48 (6H, m), 1.06 (9H, s).

(2) 3-Hydroxy-1-(4-piperidinocarbonyl-1,3-thiazol-2-yl)azetidine

To a solution of 3-t-butyldiphenylsilyloxy-1-(4-piperidinocarbonyl-1,3-thiazol-2-yl)azetidine (607 mg, 1.20 mmol) (obtained as described in Reference Example 27(1)) in anhydrous tetrahydrofuran (25 ml) was added a solution of 1.0M tetra-n-butylammonium fluoride in tetrahydrofuran (1.40 ml, 1.40 mmol) in an ice bath, and the mixture was stirred at room temperature for 1 hour. After checking the completion of the reaction, the reaction mixture was concentrated under reduced pressure. The residue was purified by chromatography on a silica gel column using ethyl acetate→ethyl acetate:methanol (9:1) as the eluant to afford 3-hydroxy-1-(4-piperidinocarbonyl-1,3-thiazol-2-yl)azetidine (310 mg, yield 97%) as a white solid.

$^1$H-NMR (400 MHz, CDCl$_3$): δ (ppm) 6.97 (1H, s), 4.87–4.77 (1H, m), 4.33 (2H, ddd, J=9.8, 6.6, 1.1 Hz), 3.96

(2H, dd, J=9.8, 4.4 Hz), 3.57–3.72 (4H, t, J=5.4 Hz), 1.81–1.45 (6H, m).

(3) 3-Methanesulfonyloxy-1-(4-piperidinocarbonyl-1,3-thiazol-2-yl)azetidine

To a solution of 3-hydroxy-1-(4-piperidinocarbonyl-1,3-thiazol-2-yl)azetidine (310 mg, 1.16 mmol) (obtained as described in Reference Example 27(2)) in methylene chloride (10 ml) were added methanesulfonyl chloride (0.27 ml, 3.48 mmol) and triethylamine (0.49 ml, 3.48 mmol) in an ice bath, and then the mixture was stirred for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 3-methanesulfonyloxy-1-(4-piperidinocarbonyl-1,3-thiazol-2-yl)azetidine (346 mg, yield 86%) as a pale yellow solid.

$^1$H-NMR (400 MHz, CDCl$_3$): δ (ppm) 7.06 (1H, s), 5.37–5.47 (1H, m), 4.46 (2H, dd, J=9.8, 6.7 Hz), 4.27 (2H, dd, J=9.8, 4.3 Hz), 3.65 (4H, t, J=5.2 Hz), 3.10 (3H, t, J=5.2 Hz), 1.78–1.47 (6H, m).

(4) 3-Acetylthio-1-(4-piperidinocarbonyl-1,3-thiazol-2-yl)azetidine

To a solution of 3-methanesulfonyloxy-1-(4-piperidinocarbonyl-1,3-thiazol-2-yl)azetidine (346 mg, 1.00 mmol) (obtained as described in Reference Example 27(3)) in dimethylformamide (15 ml) was added potassium thioacetate (687 g, 6.01 mmol) at room temperature. The reaction mixture was stirred in an oil bath (90° C.) for 4 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3-acetylthio-1-(4-piperidinocarbonyl-1,3-thiazol-2-yl)azetidine (276 mg, yield 85%) as a pale brown solid.

$^1$H-NMR (400 MHz, CDCl$_3$): δ (ppm) 7.02 (1H, s), 4.54 (2H, dd, J=8.5 Hz), 4.39–4.49 (1H, m), 3.99 (2H, dd, J=8.5, 5.4 Hz), 3.65 (4H, t, J=5.4 Hz), 2.36 (3H, s), 1.90–1.40 (6H, m).

REFERENCE EXAMPLE 28

3-Acetylthio-1-(4-N-cyclopentylcarbamoyl-1,3-thiazol-2-yl)azetidine

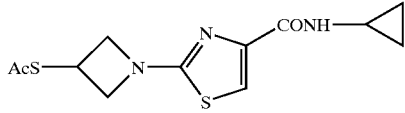

(1) 3-t-Butyldiphenylsilyloxy-1-(4-N-cyclopropylcarbamoyl-1,3-thiazol-2-yl)azetidine To a solution of 3-t-butyldiphenylsilyloxy-1-(4-ethoxycarbonyl-1,3-thiazol-2-yl)azetidine (1.00 g, 2.14 mmol) (obtained as described in Reference Example 2(1)) in benzene (50 ml) was added a solution of 0.67M cyclopropylamine-trimethylaluminium in benzene (7.20 ml) at room temperature under an atmosphere of nitrogen. The mixture was heated under reflux for 2 hours. After checking the completion of the reaction, 10% aqueous acetic acid solution (50 ml) and ethyl acetate (100 ml) were added to the reaction mixture in an ice bath, and the resulting mixture was stirred at room temperature for 2 hours. After adding ethyl acetate thereto, the reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using hexane:ethyl acetate (1:2) as the eluant to afford 3-t-butyldiphenylsilyloxy-1-(4-N-cyclopropylcarbamoyl-1,3-thiazol-2-yl)azetidine (979 mg, yield 90%) as a pale brown solid.

$^1$H-NMR (400 MHz, CDCl$_3$): δ (ppm) 7.70–7.60 (4H, m), 7.33–7.50 (6H, m), 7.36 (1H, s), 4.80–4.68 (1H, m), 4.18–4.06 (3H, m), 4.02 (2H, dd, J=8.2, 5.8 Hz), 3.80–3.70 (1H, m), 1.06 (9H, s), 0.83 (1H, t, J=6.9 Hz), 0.82 (1H, t, J=6.9 Hz), 0.70–0.58 (2H, m).

(2) 1-(4-N-Cyclopropylcarbamoyl-1,3-thiazol-2-yl)-3-hydroxyazetidine

To a solution of 3-t-butyldiphenylsilyloxy-1-(4-N-cyclopropylcarbamoyl-1,3-thiazol-2-yl)azetidine (907 mg, 1.94 mmol) (obtained as described in Reference Example 28(1)) in anhydrous tetrahydrofuran (40 ml) was added a solution of 1.0M tetra-n-butylammonium fluoride in tetrahydrofuran (2.30 ml, 2.30 mmol) in an ice bath, and then the mixture was stirred for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate as the eluant to afford 1-(4-N-cyclopropylcarbamoyl-1,3-thiazol-2-yl)-3-hydroxyazetidine (367 mg, yield 81%) as a white solid.

$^1$H-NMR (400 MHz, CDCl$_3$): δ (ppm) 7.37 (1H, s), 7.23 (1H, s), 4.67–4.80 (1H, m), 4.32 (2H, dd, J=9.0, 6.7 Hz), 3.96 (2H, dd, J=9.0, 4.3 Hz), 2.82–2.70 (1H, m), 0.84 (1H, t, J=7.1 Hz), 0.83 (1H, t, J=7.1 Hz), 0.55–0.70 (2H, m).

(3) 1-(4-N-Cyclopropylcarbamoyl-1,3-thiazol-2-yl)-3-methanesulfonyloxyazetidine

To a solution of 1-(4-N-cyclopropylcarbamoyl-1,3-thiazol-2-yl)-3-hydroxyazetidine (376 mg, 1.57 mmol) (obtained as described in Reference Example 28(2)) in methylene chloride (10 ml) were added methanesulfonyl chloride (0.36 ml, 4.71 mmol) and triethylamine (0.66 ml, 4.71 mmol) in an ice bath, and then the reaction mixture was stirred for 2 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using hexane:ethyl acetate (1:1) as the eluant to afford 1-(4-N-cyclopropylcarbamoyl-1,3-thiazol-2-yl)-3-methanesulfonyloxyazetidine (343 mg, yield 88%) as a pale yellow solid.

$^1$H-NMR (400 MHz, CDCl$_3$): δ (ppm) 7.45 (1H, s), 7.18 (1H, s), 5.48–5.36 (1H, m), 4.44 (2H, dd, J=10.2, 6.6 Hz), 4.26 (2H, dd, J=10.2, 4.4 Hz), 3.11 (3H, s), 2.91–2.79 (1H, m), 0.85 (1H, d, J=6.9 Hz), 0.84 (1H, d, J=6.9 Hz), 0.72–0.66 (2H, m).

(4) 3-Acetylthio-1-(4-N-cyclopropylcarbamoyl-1,3-thiazol-2-yl)azetidine

To a solution of 1-(4-N-cyclopropylcarbamoyl-1,3-thiazol-2-yl)-3-methanesulfonyloxyazetidine (433 mg, 1.31 mmol) (obtained as described in Reference Example 28(3)) in dimethylformamide (20 ml) was added potassium thioacetate (895 mg, 7.84 mmol) at room temperature. The mixture was stirred in an oil bath (90° C.) for 5 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-acetylthio-1-(4-N-cyclopropylcarbamoyl-1,3-thiazol-2-yl)azetidine (343 mg, yield 88%) as a pale brown solid.

$^1$H-NMR (400 MHz, CDCl$_3$): δ (ppm) 7.14 (1H, s), 7.20 (1H, br s), 4.52 (2H, t, J=8.6 Hz), 4.49–4.38 (1H, m), 3.98 (2H, dd, J=8.6, 5.9 Hz), 2,90–2.82 (1H, m), 2.36 (3H, s), 0.84 (1H, t, J=7.0 Hz), 0.83 (1H, t, J=7.0 Hz), 0.70–0.56 (2H, m).

REFERENCE EXAMPLE 29

3-Acetylthio-1-(4-N-cyclobutylcarbamoyl-1,3-thiazol-2-yl)azetidine

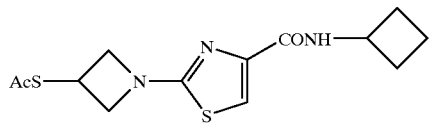

(1) 3-t-Butyldiphenylsilyloxy-1-(4-N-cyclobutylcarbamoyl-1,3-thiazol-2-yl)azetidine To a solution of 3-t-butyldiphenylsilyloxy-1-(4-N-ethoxycarbonyl-1,3-thiazol-2-yl)azetidine (1.00 g, 2.14 mmol) (obtained as described in Reference Example 2(1)) in benzene (50 ml) was added a solution of 0.67M cyclobutylamine-trimethylaluminium in benzene (7.30 ml) at room temperature under an atmosphere of nitrogen. The mixture was heated under reflux for 2 hours. After checking the completion of the reaction, 10% aqueous acetic acid solution (50 ml) and ethyl acetate (100 ml) were added to the reaction mixture in an ice bath, and the resulting mixture was stirred at room temperature for 2 hours. After adding ethyl acetate thereto, the reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using hexane:ethyl acetate (1:1) as the eluant to afford 3-t-butyldiphenylsilyloxy-1-(4-N-cyclobutylcarbamoyl-1,3-thiazol-2-yl)azetidine (965 mg, yield 87%) as a pale brown solid.

$^1$H-NMR (400 MHz, CDCl$_3$): δ (ppm) 7.62 (4H, d, J=8.0 Hz), 7.28–7.39 (6H, m), 7.34 (1H, s), 4.70–4.80 (1H, m), 4.58–4.46 (1H, m), 4.11 (2H, dd, J=8.8, 6.5 Hz), 4.02 (2H, dd, J=8.8, 4.0 Hz), 2.35–2.20 (2H, m), 2.05–1.92 (2H, m), 1.69–1.80 (2H, m), 1.07 (9H, s).

(2) 1-(4-N-Cyclobutylcarbamoyl-1,3-thiazol-2-yl)-3-hydroxyazetidine

To a solution of 3-t-butyldiphenylsilyloxy-1-(4-N-cyclobutylcarbamoyl-1,3-thiazol-2-yl)azetidine (966 mg, 1.86 mmol) (obtained as described in Reference Example 29(1)) in anhydrous tetrahydrofuran (40 ml) was added a solution of 1.0M tetra-n-butylammonium fluoride in tetrahydrofuran (2.20 ml, 2.20 mmol) in an ice bath, and the mixture was stirred for 1 hour. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using hexane-:ethyl acetate (1:1)→ethyl acetate as the eluant to afford 1-(4-N-cyclobutylcarbamoyl-1,3-thiazol-2-yl)-3-hydroxyazetidine (433 mg, yield 95%) as a white solid.

$^1$H-NMR (400 MHz, CDCl$_3$): δ (ppm) 7.35 (1H, s), 4.89–4.78 (1H, m), 4.60–4.45 (1H, m), 4.34 (2H, dd, J=9.3, 6.7 Hz), 3.96 (2H, dd, J=9.3, 6.7 Hz), 2.32–2.48 (2H, m), 2.48–2.32 (1H, m), 1.72–1.68 (2H, m).

(3) 1-(4-N-Cyclobutylcarbamoyl-1,3-thiazol-2-yl)-3-methanesulfonyloxyazetidine

To a solution of 1-(4-N-cyclobutylcarbamoyl-1,3-thiazol-2-yl)-3-hydroxyazetidine (433 mg, 1.71 mmol) (obtained as described in Reference Example 29(2)) in methylene chloride (10 ml) were added methanesulfonyl chloride (0.30 ml, 5.12 mmol) and triethylamine (0.70 ml, 5.12 mmol) in an ice bath, and the reaction mixture was stirred for 1 hour. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using ethyl acetate as the eluant to afford 1-(4-N-cyclobutylcarbamoyl-1,3-thiazol-2-yl)-3-methanesulfonyloxyazetidine (567 mg, yield 100%) as a pale yellow solid.

$^1$H-NMR (400 MHz, CDCl$_3$): δ (ppm) 7.43 (1H, s), 5.48–5.38 (1H, m), 4.60–4.38 (3H, m including 4.47 (2H, dd, J=9.6, 6.6 Hz)), 4.28 (2H, dd, J=9.6, 4.6 Hz), 3.11 (3H, s), 2.48–2.33 (2H, m), 2.07–1.92 (2H, m), 1.85–1.68 (2H, m).

(4) 3-Acetylthio-1-(4-N-cyclobutylcarbamoyl-1,3-thiazol-2-yl)azetidine

To a solution of 1-(4-N-cyclobutylcarbamoyl-1,3-thiazol-2-yl)-3-methanesulfonyloxyazetidine (567 mg, 1.71 mmol) (obtained as described in Reference Example 29(3)) in dimethylformamide (10 ml) was added potassium thioacetate (1.17 g, 10.3 mmol) at room temperature. The mixture was stirred in an oil bath (90° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:3) as the eluant to afford 3-acetylthio-1-(4-N-cyclobutylcarbamoyl-1,3-thiazol-2-yl)azetidine (318 mg, yield 75%) as a pale brown solid.

$^1$H-NMR (400 MHz, CDCl$_3$): δ (ppm) 7.33 (1H, s), 4.62–4.37 (4H, m including 4.54 (2H, t, J=8.6 Hz), 4.00 (2H, dd, J=8.6, 2.5 Hz)), 2,31–2.48 (5H, m including 2.37 (3H, s)), 2.07–1.93 (2H, m), 1.84–1.67 (2H, m).

REFERENCE EXAMPLE 30

3-Acetylthio-1-[4-(4-methylpiperazine-1-carbonyl)-1,3-thiazol-2-yl]azetidine

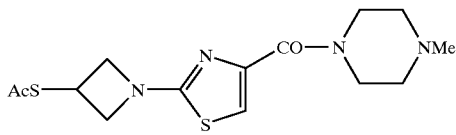

(1) 3-t-Butyldiphenylsilyloxy-1-[4-(4-methylpiperazine-1-carbonyl)-1,3-thiazol-2-yl]azetidine To a solution of 3-t-butyldiphenylsilyloxy-1-(4-ethoxycarbonyl-1,3-thiazol-2-yl)azetidine (1.00 g, 2.14 mmol) (obtained as described in Reference Example 2(1)) in toluene (50 ml) was added a solution of 0.67M 1-methylpiperazine-trimethylaluminium in toluene (7.40 ml) at room temperature under an atmosphere of nitrogen. The mixture was heated under reflux for 3 hours. After checking the completion of the reaction, 10% aqueous acetic acid solution (50 ml) and ethyl acetate (100 ml) were added to the reaction mixture in an ice bath, and the resulting mixture was stirred at room temperature for 2 hours. After adding ethyl acetate thereto, the reaction mixture was partitioned between ethyl acetate and water. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate:methanol (10:1) as the eluant to afford 3-t-butyldiphenylsilyloxy-1-[4-(4-methylpiperazine-1-carbonyl)-1,3-thiazol-2-yl]azetidine (941 mg, yield 85%) as a pale brown solid.

$^1$H-NMR (400 MHz, CDCl$_3$): δ (ppm) 7.62 (4H, dd, J=8.0, 1.4 Hz), 7.50–7.36 (6H, m), 7.08 (1H, s), 4.10 (2H, dd, J=10.3, 6.9 Hz), 4.00 (2H, dd, J=10.3, 5.0 Hz)), 3.98–3.65 (4H, m), 2.63–2.42 (4H, m), 2.37 (3H, m), 1.06 (9H, s).

(2) 3-Hydroxy-1-[4-(4-methylpiperazine-1-carbonyl)-1,3-thiazol-2-yl]azetidine

To a solution of 3-t-butyldiphenylsilyloxy-1-[4-(4-methylpiperazine-1-carbonyl)-1,3-thiazol-2-yl]azetidine (941 mg, 1.81 mmol) (obtained as described in Reference Example 30(1)) in anhydrous tetrahydrofuran (47 ml) was added a solution of 1.0M tetra-n-butylammonium fluoride in tetrahydrofuran (2.17 ml, 2.17 mmol) in an ice bath, and the mixture was stirred for 1 hour. After checking the completion of the reaction, the reaction mixture was concentrated under reduced pressure. The residue was purified by chromatography on a silica gel column using ethyl acetate-:methanol (3:1) as the eluant to afford 3-hydroxy-1-[4-(4-methylpiperazine-1-carbonyl)-1,3-thiazol-2-yl]azetidine (422 mg, yield 83%) as a white solid.

$^1$H-NMR (400 MHz, CDCl$_3$): δ (ppm) 7.01 (1H, s), 4.88–4.80 (1H, m), 4.26 (2H, dd, J=8.6, 7.1 Hz), 3.96 (2H, dd, J=8.6, 4.8 Hz), 3.89–3.68 (4H, m), 2.80–2.58 (4H, m), 2.31 (3H, s).

(3) 3-Methanesulfonyloxy-1-[4-(4-methylpiperazine-1-carbonyl)-1,3-thiazol-2-yl]azetidine To a solution of 3-hydroxy-1-[4-(4-methylpiperazine-1-carbonyl)-1,3-thiazol-2-yl]azetidine (422 mg, 1.49 mmol) (obtained as described in Reference Example 30(2)) in methylene chloride (21 ml) were added methanesulfonyl chloride (0.14 ml, 1.79 mmol) and triethylamine (0.25 ml, 1.79 mmol) in an ice bath, and then the mixture was stirred for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using toluene:methanol (3:1) as the eluant to afford 3-methanesulfonyloxy-1-[4-(4-methylpiperazine-1-carbonyl)-1,3-thiazol-2-yl]azetidine (537 mg, yield 100%) as a pale yellow solid.

$^1$H-NMR (400 MHz, CDCl$_3$): δ (ppm) 7.36 (1H, s), 5.47–5.40 (1H, m), 4.46 (2H, dd, J=10.0, 6.6 Hz), 4.27 (2H, dd, J=10.0, 4.3 Hz), 3.56–3.47 (4H, m), 3.11 (3H, s), 2.96–2.86 (4H, m), 2.81 (3H, s).

(4) 3-Acetylthio-1-[4-(4-methylpiperazine-1-carbonyl)-1,3-thiazol-2-yl]azetidine To a solution of 3-methanesulfonyloxy-1-[4-(4-methylpiperazine-1-carbonyl)-1,3-thiazol-2-yl]azetidine (537 mg, 1.49 mmol) (obtained as described in Reference Example 20(3)) in dimethylformamide (16 ml) was added potassium thioacetate (1.02 g, 8.94 mmol) at room temperature. The mixture was stirred in an oil bath (90° C.) for 4 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate:methanol (10:1) as the eluant to afford 3-acetylthio-1-[4-(4-methylpiperazine-1-carbonyl)-1,3-thiazol-2-yl]azetidine (261 mg, yield 51%) as a pale brown solid.

$^1$H-NMR (400 MHz, CDCl$_3$): δ (ppm) 7.15 (1H, s), 4.53 (2H, t, J=8.5 Hz), 4.48–4.38 (1H, m), 3.98 (2H, dd, J=8.5, 5.4 Hz), 3.96–3.74 (4H, m), 2.63–2.42 (4H, m), 3.49 (6H, s).

REFERENCE EXAMPLE 31

3-Acetylthio-1-[4-(3-methoxyazetidine-1-carbonyl)-1,3-thiazol-2-yl]azetidine

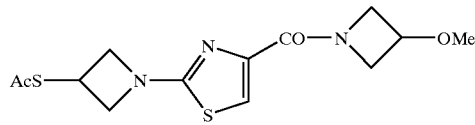

(1) 1-t-Butoxycarbonyl-3-methoxyazetidine

A solution of 1-benzhydryl-3-hydroxyazetidine (10.0 g, 41.8 mmol) in methanol (300 ml) was subjected to catalytic hydrogenation in the presence of 10% palladium (10.0 g) on charcoal at room temperature for 3 hours. After checking the completion of the reaction, the reaction mixture was filtered in order to remove the catalyst. To the filtrate was added di-t-butoxycarbonic anhydride (18.2 g, 83.6 mmol), and the reaction mixture was stirred at room temperature for 1 hour. After checking the completion of the reaction, the reaction mixture was concentrated under reduced pressure. The residue was purified by chromatography on a silica gel column using n-hexane:ethyl acetate (1:1→1:2) as the eluant to afford 1-t-butoxycarbonyl-3-hydroxyazetidine (7.05 g, yield 97%).

Subsequently, to a solution of 1-t-butoxycarbonyl-3-hydroxyazetidine (2.5 g, 14.4 mmol) in dimethylformamide (125 ml) was added sodium hydride (55% oil dispersion) in an ice bath. After stirring the mixture for 10 minutes in the ice bath, the resulting mixture was stirred at room temperature for 30 minutes. To the reaction mixture was added methyl iodide (1.79 ml, 28 mmol) in an ice bath. After stirring the mixture in an ice bath for 10 minutes, the reaction mixture was stirred at room temperature for 1 hour. After checking the completion of the reaction, 10% aqueous acetic acid solution was added thereto in an ice bath and the reaction mixture was stirred in the ice bath for 30 minutes. The reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1) as the eluant to afford 1-t-butoxycarbonyl-3-methoxyazetidine (2.18 g, yield 81%) as a colorless oil.

$^1$H-NMR (400 MHz, CDCl$_3$): δ (ppm) 4.16–4.10 (1H, m), 4.09–4.03 (2H, m), 3.82 (2H, dd, J=10.2, 4.4 Hz), 3.28 (3H, s), 1.44 (9H, s).

(2) 3-t-Butyldiphenylsilyloxy-1-[4-(3-methoxyazetidine-1-carbonyl)-1,3-thiazol-2-yl]azetidine To a solution of 1-t-butoxycarbonyl-3-methoxyazetidine (2.60 g, 13.9 mmol) (obtained as described in Reference Example 31(1)) in 1,4-dioxane (26 ml) was added a solution of 4N hydrogen chloride in 1,4-dioxane (26 ml) in an ice bath, and the mixture was stirred at room temperature overnight. After checking the completion of the reaction, the reaction mixture was filtered, and to the residue was added ethyl acetate and diisopropyl ether. The resulting mixture was filtered, and the residue was washed with diisopropyl ether and then dried under reduced pressure to give 3-methoxyazetidine hydrochloride (1.84 g, yield 100%) as white crystals.

Subsequently, to a solution of 3-t-butyldiphenylsilyloxy-1-(4-ethoxycarbonyl-1,3-thiazol-2-yl)azetidine (500 mg, 1.07 mmol) in toluene (25 ml) was added a solution of 0.67M 3-methoxyazetidine-trimethylaluminium in benzene (3.21 ml) at room temperature under an atmosphere of nitrogen. The mixture was stirred in a water bath (80° C.) for 1 hour. After checking the completion of the reaction, 10% aqueous acetic acid solution (20 ml) and ethyl acetate (50 ml) were added to the reaction mixture in an ice bath, and the resulting mixture was stirred at room temperature for 1 hour. After adding ethyl acetate thereto, the reaction mixture was partitioned between ethyl acetate and water. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3-t-butyldiphenylsilyloxy-1-[4-(3-methoxyazetidine-1-carbonyl)-1,3-thiazol-2-yl]azetidine (366 mg, yield 67%) as a pale brown solid.

$^1$H-NMR (400 MHz, CDCl$_3$): δ (ppm) 7.64–7.60 (4H, m), 7.49–7.38 (6H, m), 7.36 (1H, s), 4.78–4.70 (2H, m), 4.42–4.36 (1H, m), 4.32–4.25 (1H, m), 4.24–4.18 (1H, m), 4.09 (2H, t, J=7.3 Hz), 4.03–3.96 (3H, m), 3.33 (3H, s), 1.07 (9H, s).

(3) 3-Hydroxy-1-[4-(3-methoxyazetidine-1-carbonyl)-1,3-thiazol-2-yl]azetidine

To a solution of 3-t-butyldiphenylsilyloxy-1-[4-(3-methoxyazetidine-1-carbonyl)-1,3-thiazol-2-yl]azetidine (870 mg, 1.71 mmol) (obtained as described in Reference Example 31(2)) in anhydrous tetrahydrofuran (45 ml) was added a solution of 1.0M tetra-n-butylammonium fluoride in tetrahydrofuran (2.06 ml, 2.06 mmol) in an ice bath, and then the mixture was stirred for 30 minutes. After checking the completion of the reaction, the reaction mixture was concentrated under reduced pressure. The residue was purified by chromatography on a silica gel column using ethyl acetate:methanol (9:1) as the eluant to afford 3-hydroxy-1-[4-(3-methoxyazetidine-1-carbonyl)-1,3-thiazol-2-yl]azetidine (481 mg, yield 100%) as a white solid.

$^1$H-NMR (400 MHz, CDCl$_3$): δ (ppm) 7.38 (1H, s), 4.85–4.79 (1H, m), 4.75 (1H, dd, J=10.3, 5.9 Hz), 4.41 (1H, dd, J=11.0, 2.9 Hz), 4.34–4.25 (3H, m), 4.22 (1H, tt, J=6.6, 4.4 Hz), 4.01 (1H, dd, J=10.3, 2.9 Hz), 3.93 (2H, dd, J=8.8, 4.4 Hz), 3.32 (3H, s).

(4) 3-Methanesulfonyloxy-1-[4-(3-methoxyazetidine-1-carbonyl)-1,3-thiazol-2-yl]azetidine To a solution of 3-hydroxy-1-[4-(3-methoxyazetidine-1-carbonyl)-1,3-thiazol-2-yl]azetidine (480 mg, 1.71 mmol) (obtained as described in Reference Example 31(3)) in methylene chloride (25 ml) were added methanesulfonyl chloride (397 μl, 5.13 mmol) and triethylamine (719 μl, 5.13 mmol) in an ice bath. After stirring the mixture in the ice bath for 10 minutes, the mixture was stirred at room temperature for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate:methanol (95:5) as the eluant to afford 3-methanesulfonyloxy-1-[4-(3-methoxyazetidine-1-carbonyl)-1,3-thiazol-2-yl]azetidine (568 mg, yield 96%) as a pale yellow solid.

$^1$H-NMR (400 MHz, CDCl$_3$): δ (ppm) 7.46 (1H, s), 5.45–5.39 (1H, m), 4.74 (1H, dd, J=10.6, 6.2 Hz), 4.47–4.37 (3H, m), 4.33–4.19 (4H, m), 4.04–3.99 (1H, m), 3.33 (3H, s), 3.10 (3H, s).

(5) 3-Acetylthio-1-[4-(3-methoxyazetidine-1-carbonyl)-1,3-thiazol-2-yl]azetidine To a solution of 3-methanesulfonyloxy-1-[4-(3-methoxyazetidine-1-carbonyl)-1,3-thiazol-2-yl]azetidine (560 mg, 1.61 mmol) (obtained as described in Reference Example 31(4)) in dimethylformamide (28 ml) was added potassium thioacetate (1.10 g, 9.67 mmol) at room temperature. The mixture was stirred in an oil bath (80° C.) for 4.5 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate→ethyl acetate:methanol (97:3) as the eluant to afford 3-acetylthio-1-[4-(3-methoxy-azetidine-1-carbonyl)-1,3-thiazol-2-yl]azetidine (356 mg, yield 68%) as a pale brown solid.

$^1$H-NMR (400 MHz, CDCl$_3$): δ (ppm) 7.43 (1H, s), 4.73 (1H, dd, J=10.3, 5.1 Hz), 4.51 (2H, t, J=8.1 Hz), 4.46–4.37 (2H, m), 4.32–4.26 (1H, m), 4.21 (1H, tt, J=6.6, 4.4 Hz), 4.00–3.93 (2H, m), 3.78–3.72 (1H, m), 3.32 (3H, s), 2.36 (3H, s).

REFERENCE EXAMPLE 32

3-Acetylthio-1-(4-phenylcarbamoyl-1,3-thiazol-2-yl)azetidine

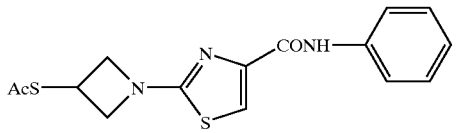

(1) 3-t-Butyldiphenylsilyloxy-1-(4-phenylcarbamoyl-1,3-thiazol-2-yl)azetidine

To a solution of 3-t-butyldiphenylsilyloxy-1-(4-ethoxycarbonyl-1,3-thiazol-2-yl)azetidine (2.00 g, 4.29 mmol) (obtained as described in Reference Example 2(1)) in toluene (100 ml) was added a solution of 0.67M anilinetrimethylaluminium in benzene (14.6 ml) at room temperature under an atmosphere of nitrogen. The mixture was heated under reflux for 3 hours. After checking the completion of the reaction, 10% aqueous acetic acid solution (100 ml) and ethyl acetate (200 ml) were added to the reaction mixture in an ice bath and the resulting mixture was stirred at room temperature for 3 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (2:1) as the eluant to afford 3-t-butyldiphenylsilyloxy-1-(4-phenylcarbamoyl-1,3-thiazol-2-yl)azetidine (2.20 g, yield 100%) as a pale brown solid.

$^1$H-NMR (400 MHz, CDCl$_3$): δ (ppm) 7.73–7.61 (6H, m), 7.51–7.30 (9H, m), 7.14–7.08 (1H, m), 4.82–4.76 (1H, m), 4.14 (2H, dd, J=15.2, 8.2 Hz), 4.06 (2H, dd, J=8.9, 4.6 Hz), 1.08 (9H, s).

(2) 3-Hydroxy-1-(4-phenylcarbamoyl-1,3-thiazol-2-yl)azetidine

To a solution of 3-t-butyldiphenylsilyloxy-1-(4-phenylcarbamoyl-1,3-thiazol-2-yl)azetidine (2.20 g, 4.29 mmol) (obtained as described in Reference Example 32(1)) in anhydrous tetrahydrofuran (110 ml) was added a solution of 1.0M tetra-n-butylammonium fluoride in tetrahydrofuran (5.15 ml, 5.15 mmol) in an ice bath, and then the mixture was stirred for 2 hours. After checking the completion of the reaction, the reaction mixture was concentrated under reduced pressure. The residue was purified by chromatography on a silica gel column using ethyl acetate as the eluant to afford 3-hydroxy-1-(4-phenylcarbamoyl-1,3-thiazol-2-yl)azetidine (1.18 g, yield 100%) as a white solid.

$^1$H-NMR (400 MHz, CDCl$_3$): δ (ppm) 9.04 (1H, br s), 7.76–7.65 (2H, m), 7.51–7.37 (3H, m), 7.18–7.08 (1H, m), 4.90–4.80 (1H, m), 4.36 (2H, dd, J=9.1, 6.6 Hz), 3.99 (2H, dd, J=9.1, 4.3 Hz).

(3) 3-Methanesulfonyloxy-1-(4-phenylcarbamoyl-1,3-thiazol-2-yl)azetidine

To a solution of 3-hydroxy-1-(4-phenylcarbamoyl-1,3-thiazol-2-yl)azetidine (1.18 g, 4.29 mmol) (obtained as described in Reference Example 32(2)) in methylene chloride (60 ml) were added methanesulfonyl chloride (0.50 ml, 6.44 mmol) and triethylamine (0.90 ml, 6.44 mmol) in an ice bath, and then the mixture was stirred in the ice bath for 2 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using methylene chloride:ethyl acetate (9:1) as the eluant to afford 3-methanesulfonyloxy-1-(4-phenylcarbamoyl-1,3-thiazol-2-yl)azetidine (1.36 g, yield 89%) as a pale yellow solid.

$^1$H-NMR (400 MHz, CDCl$_3$): δ (ppm) 8.98 (1H, br s), 7.68 (2H, d, J=7.6 Hz), 7.55 (1H, s), 7.36 (2H, d, J=8.0 Hz), 7.18–7.08 (1H, m), 5.50–5.40 (1H, m), 4.51 (2H, ddd, J=9.6, 6.6, 1.0 Hz), 4.32 (2H, ddd, J=9.6, 4.3, 1.0 Hz), 3.12 (3H, s).

(4) 3-Acetylthio-1-(4-phenylcarbamoyl-1,3-thiazol-2-yl)azetidine

To a solution of 3-methanesulfonyloxy-1-(4-phenylcarbamoyl-1,3-thiazol-2-yl)azetidine (1.28 g, 3.85 mmol) (obtained as described in Reference Example 32(3)) in dimethylformamide (40 ml) was added potassium thioacetate (2.60 g, 23.1 mmol) at room temperature. The mixture was stirred in an oil bath (90° C.) for 3 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:2) as the eluant to afford 3-acetylthio-1-(4-phenylcarbamoyl-1,3-thiazol-2-yl)azetidine (893 mg, yield 70%) as a pale brown solid.

$^1$H-NMR (400 MHz, CDCl$_3$): δ (ppm) 9.01 (1H, br s), 7.68 (2H, d, J=8.6 Hz), 7.35 (2H, t, J=7.5 Hz), 7.20–7.28 (1H, m), 4.58 (2H, t, J=8.5 Hz), 4.52–4.02 (1H, m), 4.04 (2H, dd, J=8.5, 5.3 Hz), 2.83 (3H, s).

REFERENCE EXAMPLE 33

3-Acetylthio-1-{4-[2-(t-butyldimethylsilyloxy)ethylcarbamoyl]-1,3-thiazol-2-yl}azetidine

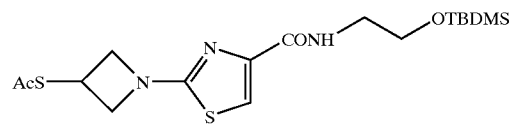

(1) [2-(t-Butyldiphenylsilyloxy)ethyl]carbamic acid benzyl ester

To a solution of aminoethanol (2.0 g, 32.7 mmol) in methylene chloride (60 ml) were added chloroformic acid benzyl ester (5.6 ml, 41.3 mmol) and triethylamine (5.5 ml, 39.5 mmol) in an ice bath. The mixture was stirred at room temperature for 1 hour. After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using toluene:acetonitrile (3:2) as the eluant to afford (2-hydroxyethyl)carbamic acid benzyl ester (5.37 g, yield 840%) as a white solid.

Subsequently, to a solution of (2-hydroxyethyl)carbamic acid benzyl ester (5.37 g, 27.5 mmol) in dimethylformamide (160 ml) were added t-butyldiphenylsilyl chloride (8.6 ml, 33.0 mmol) and imidazole (2.3 g, 33.8 mmol) in an ice bath, and the mixture was stirred at room temperature overnight. After checking the completion of the reaction, ethanol was added thereto and the reaction mixture was stirred for 2 hours. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (5:1) as the eluant to afford [2-(t-butyldiphenylsilyloxy)ethyl]carbamic acid benzyl ester (11.93 g, yield 100%) as a colorless and transparent syrup.

$^1$H-NMR (400 MHz, CDCl$_3$): δ (ppm) 7.64 (4H, d, J=6.8 Hz), 7.46–7.28 (12H, m), 5.10 (2H, s), 3.73 (2H, t, J=4.9 Hz), 3.35 (2H, q, J=4.9 Hz), 1.05 (9H, s).

(2) 3-t-Butyldiphenylsilyloxy-1-{4-[2-(t-butyldiphenylsilyloxy)ethylcarbamoyl]-1,3-thiazol-2-yl}azetidine A solution of [2-(t-butyldiphenylsilyloxy)ethyl]carbamic acid benzyl ester (3.01 g, 6.9 mmol) (obtained as described in Reference Example 33(1)) in methanol (150 ml) was subjected to catalytic hydrogenation in the presence of 20% palladium hydroxide on charcoal (3.0 g) at room temperature. After checking the completion of the reaction, the reaction mixture was filtered in order to remove the catalyst and the filtrate concentrated under reduced pressure. The residue was purified by chromatography on a silica gel column using methylene chloride:methanol (10:1) as the eluant to afford 2-(t-butyldiphenylsilyloxy)ethylamine (1.49 g, yield 72%) as a pale brown syrup.

Subsequently, to a solution of 3-t-butyldiphenylsilyloxy-1-(4-ethoxycarbonyl-1,3-thiazol-2-yl)azetidine (1.16 g, 2.49 mmol) (obtained as described in Reference Example 2(1)) in benzene (8.5 ml) was added a solution of 0.67M 2-(t-butyldiphenylsilyloxy)ethylamine-trimethylaluminium in benzene (6.42 ml) at room temperature under an atmosphere of nitrogen. The mixture was heated under reflux for 5 hours. After checking the completion of the reaction, 10% aqueous acetic acid solution (50 ml) and ethyl acetate (200 ml) were added to the reaction mixture, and the resulting mixture was stirred at room temperature for 1 hour. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (3:1) as the eluant to afford 3-t-butyldiphenylsilyloxy-1-{4-[2-(t-butyldiphenylsilyloxy)ethylcarbamoyl]-1,3-thiazol-2-yl}azetidine (1.68 g, yield 94%) as a pale brown solid.

$^1$H-NMR (400 MHz, CDCl$_3$): δ (ppm) 7.74 (1H, br t, J=4.6 Hz), 7.67 (4H, d, J=7.5 Hz), 7.60 (4H, d, J=7.5 Hz), 7.42–7.32 (13H, m), 4.78–4.68 (1H, m), 4.08 (2H, t, J=7.8 Hz), 4.03–3.98 (2H, m), 3.79 (2H, t, J=4.6 Hz), 3.56 (2H, t, J=4.6 Hz), 1.08 (9H, s), 1.06 (9H, s).

(3) 3-Hydroxy-1-(4-hydroxyethylcarbamoyl-1,3-thiazol-2-yl)azetidine

To a solution of 3-t-butyldiphenylsilyloxy-1-{4-[2-(t-butyldiphenylsilyloxy)ethylcarbamoyl]-1,3-thiazol-2-yl}azetidine (1.68 g, 2.33 mmol) (obtained as described in Reference Example 33(2)) in anhydrous tetrahydrofuran (75 ml) was added a solution of 1.0M tetra-n-butylammonium fluoride in tetrahydrofuran (5.6 ml, 5.6 mmol) in an ice bath, and the mixture was stirred in the ice bath for 1 hour. After checking the completion of the reaction, the reaction mixture was concentrated under reduced pressure. The residue was purified by chromatography on a silica gel column using ethyl acetate:methanol (10:1) as the eluant to afford 3-hydroxy-1-(4-hydroxyethylcarbamoyl-1,3-thiazol-2-yl)azetidine (481.2 mg, yield 85%) as a white solid.

$^1$H-NMR (400 MHz, CD$_3$OD): δ (ppm) 7.39 (1H, s), 4.78 (1H, m), 4.31 (2H, dd, J=8.4, 7.0 Hz), 3.89 (2H, dd, J=8.4, 4.8 Hz), 3.67 (2H, t, J=5.9 Hz), 3.46 (2H, t, J=5.9 Hz).

(4) 1-{4-[2-(t-Butyldimethylsilyloxy)ethylcarbamoyl]-1,3-thiazol-2-yl}-3-hydroxyazetidine To a solution of 3-hydroxy-1-(4-hydroxyethylcarbamoyl-1,3-thiazol-2-yl)azetidine (481.2 mg, 1.98 mmol) (obtained as described in Reference Example 33(3)) in dimethylformamide (24.0 ml) were added t-butyldimethylsilyl chloride (352 mg, 2.3 mmol) and imidazole (116.3 mg, 2.4 mmol) in an ice bath, and the mixture was stirred in the ice bath for 4 hours. After checking the completion of the reaction, methanol was added thereto and the reaction mixture was stirred for 30 minutes. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (2:3) as the eluant to afford 1-{4-[2-(t-butyldimethylsilyloxy)ethylcarbamoyl]-1,3-thiazol-2-yl}-3-hydroxyazetidine (531.1 mg, yield 75%) as a colorless and transparent syrup.

$^1$H-NMR (400 MHz, CDCl$_3$): δ (ppm) 7.60 (1H, t, J=5.9 Hz), 7.35 (1H, s), 4.88–4.76 (1H, m), 4.30 (2H, dd, J=9.8, 7.8 Hz), 3.93 (2H, dd, J=9.8, 4.9 Hz), 3.75 (2H, t, J=5.9 Hz), 3.52 (2H, q, J=5.9 Hz), 2.85 (1H, d, J=6.8 Hz), 0.92 (9H, s), 0.08 (6H, s).

(5) 1-{4-[2-(t-Butyldimethylsilyloxy)ethylcarbamoyl]-1,3-thiazol-2-yl}-3-methanesulfonyloxyazetidine To a solution of 1-{4-[2-(t-butyldimethylsilyloxy)ethylcarbamoyl]-1,3-thiazol-2-yl}-3-hydroxyazetidine (531.1 mg, 1.49 mmol) (obtained as described in Reference Example 33(4)) in methylene chloride (26.6 ml) were added methanesulfonyl chloride (0.3 ml, 3.9 mmol) and triethylamine (0.52 ml, 3.7 mmol) in an ice bath, and the mixture was stirred in the ice bath for 2 hours. After checking the completion of the reaction, methanol was added to the reaction mixture and the resulting mixture was stirred for 30 minutes. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using toluene:ethyl acetate (1:1) as the eluant to afford 1-{4-[2-(t-butyldimethylsilyloxy)ethylcarbamoyl]-1,3-thiazol-2-yl}-3-methanesulfonyloxyazetidine (647.1 mg, yield 100%) as a pale yellow solid.

$^1$H-NMR (400 MHz, CDCl$_3$): δ (ppm) 7.54 (1H, br t, J=5.9 Hz), 7.44 (1H, s), 5.46–5.39 (1H, m), 4.43 (2H, dd, J=9.7, 6.8 Hz), 4.24 (2H, dd, J=9.7, 3.9 Hz), 3.76 (2H, t, J=5.9 Hz), 3.53 (2H, t, J=5.9 Hz), 3.11 (3H, s), 0.93 (9H, s), 0.08 (6H, s).

(6) 3-Acetylthio-1-{4-[2-(t-butyldimethylsilyloxy)ethylcarbamoyl]-1,3-thiazol-2-yl}azetidine To a solution of 1-{4-[2-(t-butyldimethylsilyloxy)ethylcarbamoyl]-1,3-thiazol-2-yl}-3-methanesulfonyloxyazetidine (647.1 mg, 1.49 mmol) (obtained as described in Reference Example 33(5)) in dimethylformamide (32.0 ml) was added potassium thioacetate (1.28 mg, 8.9 mmol) at room temperature. The mixture was stirred in an oil bath (80° C.) for 4 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (3:2) as the eluant to afford 3-acetylthio-1-{4-[2-(t-butyldimethylsilyloxy)ethylcarbamoyl]-1,3-thiazol-2-yl}azetidine (398.2 mg, yield 65%) as a pale brown solid.

¹H-NMR (400 MHz, CDCl₃): δ (ppm) 7.55 (1H, br t, J=5.4 Hz), 7.40 (1H, s), 4.51 (2H, dd, J=8.8, 7.8 Hz), 4.48–4.40 (1H, m), 3.96 (2H, dd, J=8.8, 4.9 Hz), 3.75 (2H, t, J=5.4 Hz), 3.52 (2H, q, J=5.4 Hz), 2.37 (3H, s), 0.92 (9H, s), 0.08 (6H, s).

REFERENCE EXAMPLE 34

3-Acetylthio-1-{4-[(1S)-1-(t-butyldimethylsilyloxymethyl)propylcarbamoyl]-1,3-thiazol-2-yl}azetidine

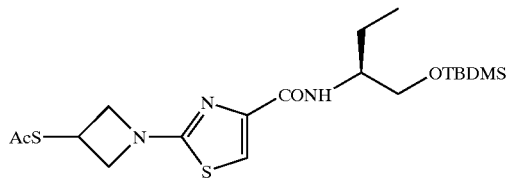

(1) [(1S)-1-(t-butyldiphenylsilyloxymethyl)propyl]carbamic acid benzyl ester

To a solution of L-ethylglycinol (2.00 g, 22.4 mmol) in methylene chloride (60 ml) were added chloroformic acid benzyl ester (3.84 ml, 26.9 mmol) and triethylamine (3.77 ml, 26.9 mmol) in an ice bath, and the mixture was stirred at room temperature for 2 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford [(1S)-1-(hydroxymethyl)propyl]carbamic acid benzyl ester (4.27 g, 85%) as a colorless oil.

Subsequently, to a solution of [(1S)-1-(hydroxymethyl)propyl]carbamic acid benzyl ester (4.27 g, 19.1 mmol) in dimethylformamide (128 ml) were added t-butyldiphenylsilyl chloride (5.97 ml, 22.9 mmol) and imidazole (1.56 g, 22.9 mmol) in an ice bath. The mixture was stirred at room temperature overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→4:1) as the eluant to afford [(1S)-1-(t-butyldiphenylsilyloxymethyl)propyl]carbamic acid benzyl ester (9.48 g, yield 100%) as a white solid.

¹H-NMR (400 MHz, CDCl₃): δ (ppm) 7.65–7.60 (4H, m), 7.44–7.29 (11H, m), 5.09 (2H, s), 4.92–4.86 (1H, br d, J=8.8 Hz), 3.71–3.47 (3H, m), 1.68–1.60 (2H, m), 1.05 (9H, s), 0.88 (3H, t, J=7.3 Hz).

(2) 3-t-Butyldiphenylsilyloxy-1-{4-[(1S)-1-(t-butyldiphenylsilyloxymethyl)propylcarbamoyl]-1,3-thiazol-2-yl}azetidine A solution of [(1S)-1-(t-butyldiphenylsilyloxymethyl)propyl]carbamic acid benzyl ester (3.70 g, 8.00 mmol) (obtained as described in Reference Example 34(1)) in methanol (185 ml) was subjected to catalytic hydrogenation in the presence of 10% palladium on charcoal (3.70 g) at room temperature for 4 hours. After checking the completion of the reaction, the reaction mixture was filtered in order to remove the catalyst and the filtrate concentrated under reduced pressure. The residue was purified by chromatography on a silica gel column using methylene chloride:methanol (9:1) as the eluant to afford (1S)-1-(t-butyldiphenylsilyloxymethyl)propylamine (2.32 g, yield 88%) as a colorless oil.

Subsequently, to a solution of 3-t-butyldiphenylsilyloxy-1-(4-ethoxycarbonyl-1,3-thiazol-2-yl)azetidine (2.00 g, 4.29 mmol) (obtained as described in Reference Example 2(1)) in benzene (100 ml) was added a solution of 0.67M (1S)-1-(t-butyldiphenylsilyloxymethyl)propylamine-trimethylaluminium in benzene (12.9 ml) at room temperature under an atmosphere of nitrogen. The mixture was heated under reflux overnight. After checking the completion of the reaction, 10% aqueous acetic acid solution (100 ml) and ethyl acetate (200 ml) were added to the reaction mixture in an ice bath and the resulting mixture was stirred at room temperature for 1 hour. The reaction mixture was extracted with ethyl acetate. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→2:1) as the eluant to afford 3-t-butyldiphenylsilyloxy-1-{4-[(1S)-1-(t-butyldiphenylsilyloxymethyl)-propylcarbamoyl]-1,3-thiazol-2-yl}azetidine (2.52 g, yield 79%) as a pale brown solid.

¹H-NMR (400 MHz, CDCl₃): δ (ppm) 7.57–7.69 (8H, m), 7.28–7.46 (12H, m), 7.36 (1H, s), 4.69–4.74 (1H, m), 3.76–4.11 (5H, m), 3.74 (1H, dd, J=10.3, 2.9 Hz), 3.70 (1H, dd, J=10.3, 4.1 Hz), 1.08 (9H, s), 1.05 (9H, s), 0.93 (3H, t, J=7.3 Hz).

(3) 3-Hydroxy-1-{4-[(1S)-1-(hydroxymethyl)-propylcarbamoyl]-1,3-thiazol-2-yl}azetidine To a solution of 3-t-butyldiphenylsilyloxy-1-{4-[(1S)-1-(t-butyldiphenylsilyloxymethyl)-propylcarbamoyl]-1,3-thiazol-2-yl}azetidine (2.52 g, 3.50 mmol) (obtained as described in Reference Example 34(2)) in anhydrous tetrahydrofuran (126 ml) was added a solution of 1.0M tetra-n-butylammonium fluoride in tetrahydrofuran (8.40 ml, 8.40 mmol) in an ice bath. The mixture was stirred overnight. After checking the completion of the reaction, the reaction mixture was concentrated under reduced pressure. The residue was purified by chromatography on a silica gel column using ethyl acetate→ethyl acetate:methanol (9:1) as the eluant to afford 3-hydroxy-1-{4-[(1S)-1-(hydroxymethyl)-propylcarbamoyl]-1,3-thiazol-2-yl}azetidine (947 mg, yield 100%) as a pale yellow oil.

¹H-NMR (400 MHz, CDCl₃): δ (ppm) 7.36 (1H, s), 4.86–4.75 (1H, m), 4.33 (2H, dd, J=8.1, 6.6 Hz), 4.02–3.91 (3H, m), 3.79 (1H, dd, J=11.0, 1.2 Hz), 3.67 (1H, dd, J=11.0, 6.6 Hz), 3.19–3.10 (1H, br s), 3.02–2.97 (1H, br s), 1.73–1.64 (2H, m), 1.00 (3H, t, J=7.3 Hz).

(4) 1-{4-[(1S)-1-(t-Butyldimethylsilyloxymethyl)-propylcarbamoyl]-1,3-thiazol-2-yl}-3-hydroxyazetidine To a solution of 3-hydroxy-1-{4-[(1S)-1-(hydroxymethyl)-propylcarbamoyl]-1,3-thiazol-2-yl}azetidine (940 mg, 3.50 mmol) (obtained as described in Reference Example 34(3)) in dimethylformamide (47 ml) were added t-butyldimethylsilyl chloride (633 mg, 4.20 mmol) and imidazole (286 mg, 4.20 mmol) in an ice bath, and the reaction mixture was stirred at room temperature for 3 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1→1:3) as the eluant to afford 1-{4-[(1S)-1-(t-butyldimethylsilyloxymethyl) propylcarbamoyl]-1,3-thiazol-2-yl}-3-hydroxyazetidine (1.00 g, yield 74%) as a pale yellow oil.

$^1$H-NMR (400 MHz, CDCl$_3$): δ (ppm) 7.50–7.44 (1H, m), 7.36 (1H, s), 4.86–4.79 (1H, m), 4.33–4.27 (2H, m), 4.01–3.92 (3H, m), 3.72 (1H, dd, J=9.9, 2.6 Hz), 3.65 (1H, dd, J=9.9, 4.0 Hz), 1.70–1.60 (2H, m), 0.95 (3H, t, J=7.3 Hz), 0.92 (9H, s), 0.06 (6H, s).

(5) 1-{4-[(1S)-1-(t-Butyldimethylsilyloxymethyl) propylcarbamoyl]-1,3-thiazol-2-yl}-3-methanesulfonyloxyazetidine To a solution of 1-{4-[(1S)-1-(t-butyldimethylsilyloxymethyl)propylcarbamoyl]-1,3-thiazol-2-yl}-3-hydroxyazetidine (1.00 mg, 2.59 mmol) (obtained as described in Reference Example 34(4)) in methylene chloride (50 ml) were added methanesulfonyl chloride (602 μl, 7.78 mmol) and triethylamine (1.09 ml, 7.78 mmol) in an ice bath. After stirring the mixture in the ice bath for 10 minutes, the mixture was stirred at room temperature for 3 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 1-{4-[(1S)-1-(t-butyldimethylsilyloxymethyl)propylcarbamoyl]-1,3-thiazol-2-yl}-3-methanesulfonyloxyazetidine (1.02 g, yield 85%) as a pale yellow oil.

$^1$H-NMR (400 MHz, CDCl$_3$): δ (ppm) 7.44 (1H, s), 7.44–7.38 (1H, m), 5.45–5.39 (1H, m), 4.47–4.40 (2H, m), 4.29–4.21 (2H, m), 4.02–3.95 (1H, m), 3.73 (1H, dd, J=10.3, 2.9 Hz), 3.65 (1H, dd, J=10.3, 4.4 Hz), 3.11 (3H, s), 0.95 (3H, t, J=7.3 Hz), 0.92 (9H, s), 0.06 (6H, s).

(6) 3-Acetylthio-1-{4-[(1S)-1-(t-butyldimethylsilyloxymethyl)propylcarbamoyl]-1,3-thiazol-2-yl}azetidine To a solution of 1-{4-[(1S)-1-(t-butyldimethylsilyloxymethyl)propylcarbamoyl]-1,3-thiazol-2-yl}-3-methanesulfonyloxyazetidine (1.02 g, 2.20 mmol) (obtained as described in Reference Example 34(5)) in dimethylformamide (50 ml) was added potassium thioacetate (1.51 mg, 13.2 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:1→2:1) as the eluant to afford 3-acetylthio-1-{4-[(1S)-1-(t-butyldimethylsilyloxymethyl) propylcarbamoyl]-1,3-thiazol-2-yl}azetidine (618 mg, yield 63%) as a pale brown oil.

$^1$H-NMR (400 MHz, CDCl$_3$): δ (ppm) 7.43–7.39 (1H, m), 7.40 (1H, s), 4.53–4.47 (2H, m), 4.46–4.41 (1H, m), 4.00–3.93 (3H, m), 3.74–3.70 (1H, m), 3.67–3.62 (1H, m), 2.37 (3H, s), 1.72–1.56 (2H, m), 0.95 (3H, t, J=7.3 Hz), 0.91 (9H, s), 0.06 (6H, s).

REFERENCE EXAMPLE 35

3-Acetylthio-1-{4-[(1S)-2-(t-butyldimethylsilyloxy)-1-methylethylcarbamoyl]-1,3-thiazol-2-yl}azetidine

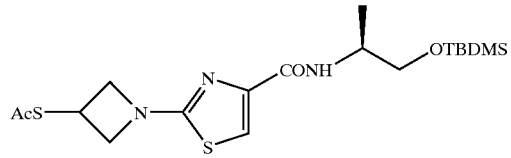

(1) [(1S)-2-(t-Butyldiphenylsilyloxy)-1-methyl-ethyl] carbamic acid benzyl ester To a solution of L-alaninol (2.00 g, 26.6 mmol) in methylene chloride (60 ml) were added chloroformic acid benzyl ester (4.57 ml, 32.0 mmol) and triethylamine (4.48 ml, 32.0 mmol) in an ice bath. The mixture was stirred at room temperature overnight. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford [(1S)-2-hydroxy-1-methylethyl]carbamic acid benzyl ester (4.61 g, yield 83%) as white crystals.

Subsequently, to a solution of [(1S)-1-(hydroxymethyl) ethyl]carbamic acid benzyl ester (4.61 g, 22.0 mmol) in dimethylformamide (140 ml) were added t-butyldiphenylsilyl chloride (6.87 ml, 26.4 mmol) and imidazole (1.80 g, 26.4 mmol) in an ice bath. The resulting mixture was stirred at room temperature for 6 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (8:1→6:1) as the eluant to afford [(1S)-2-(t-butyldiphenylsilyloxy)-1-methylethyl]carbamic acid benzyl ester (10.7 g, yield 100%) as a colorless oil.

$^1$H-NMR (400 MHz, CDCl$_3$): δ (ppm) 7.67–7.60 (4H, m), 7.42–7.29 (11H, m), 5.10 (2H, s), 4.96–4.85 (1H, br s), 3.91–3.80 (1H, m), 3.67 (1H, dd, J=10.3, 2.6 Hz), 3.56 (1H, dd, J=10.3, 3.7 Hz), 1.55 (3H, d, J=11.7 Hz), 1.09 (9H, s).

(2) 3-t-Butyldiphenylsilyloxy-1-{4-[(1S)-2-(t-butyldiphenylsilyloxy)-1-methylethylcarbamoyl]-1,3-thiazol-2-yl}azetidine A solution of [(1S)-2-(t-butyldiphenylsilyloxy)-1-methylethyl]carbamic acid benzyl ester (6.71 g, 15.0 mmol) (obtained as described in Reference Example 35(1)) in methanol (340 ml) was subjected to catalytic hydrogenation in the presence of 10% palladium on charcoal (6.71 g) at room temperature for 2.5 hours. After checking the completion of the reaction, the reaction mixture was filtered in order to remove the catalyst and the filtrate concentrated under reduced pressure. The residue was purified by chromatography on a silica gel column using methylene chloride→methylene chloride:methanol (85:15) as the eluant to afford (1S)-2-(t-butyldiphenylsilyloxy)-1-methylethylamine (3.93 g, yield 84%) as a pale yellow oil.

Subsequently, to a solution of 3-t-butyldiphenylsilyloxy-1-(4-ethoxycarbonyl-1,3-thiazol-2-yl)azetidine (2.0 g, 4.29 mmol) (obtained as described in Reference Example 2(1)) in benzene (100 ml) was added a solution of 0.67M (1S)-2-(t-butyldiphenylsilyloxy)-1-methylethylamine-trimethylaluminium in benzene (12.9 ml) at room temperature under an atmosphere of nitrogen. The mixture was heated under reflux overnight. After checking the completion of the reaction, 10% aqueous acetic acid solution (100 ml) and ethyl acetate (200 ml) were added to the reaction mixture in an ice bath, and the resulting mixture was stirred at room temperature for 1 hour. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→2:1) as the eluant to afford 3-t-butyldiphenylsilyloxy-1-{4-[(1S)-2-(t-butyldiphenylsilyloxy)-1-methylethylcarbamoyl]-1,3-thiazol-2-yl}azetidine (2.77 g, yield 88%) as a pale brown solid.

$^1$H-NMR (400 MHz, CDCl$_3$): δ (ppm) 7.69–7.65 (4H, m), 7.61–7.57 (4H, m), 7.46–7.30 (12H, m), 7.35 (1H, s), 4.75–4.68 (1H, m), 4.28–4.18 (1H, m), 4.10–4.03 (H, m), 4.03–3.97 (2H, m), 3.72 (1H, dd. J=9.9, 4.1 Hz), 3.64 (1H, dd, J=9.9, 3.3 Hz), 1.31 (3H, d, J=6.6 Hz), 1.09 (9H, s), 1.05 (9H, s).

(3) 3-Hydroxy-1-[4-((1S)-2-hydroxy-1-methylethylcarbamoyl)-1,3-thiazol-2-yl]azetidine To a solution of 3-t-butyldiphenylsilyloxy-1-{4-[(1S)-2-(t-butyldiphenylsilyloxy)-1-methylethylcarbamoyl]-1,3-thiazol-2-yl}azetidine (2.77 g, 3.77 mmol) (obtained as described in Reference Example 35(2)) in anhydrous tetrahydrofuran (140 ml) was added a solution of 1.0M tetra-n-butylammonium fluoride in tetrahydrofuran (9.06 ml, 9.06 mmol) in an ice bath. The mixture was stirred in the ice bath for 3.5 hours. After checking the completion of the reaction, the reaction mixture was concentrated under reduced pressure. The residue was purified by chromatography on a silica gel column using ethyl acetate→ethyl acetate:methanol (9:1) as the eluant to afford 3-hydroxy-1-[4-((1S)-2-hydroxy-1-methylethylcarbamoyl)-1,3-thiazol-2-yl]azetidine (911 mg, yield 94%) as a white solid.

$^1$H-NMR (400 MHz, CDCl$_3$): δ (ppm) 7.34 (1H, s), 7.26–7.10 (1H, br s), 4.86–4.77 (1H, m), 4.32 (2H, dd, J=8.8, 6.6 Hz), 4.24–4.12 (1H, m), 3.99–3.92 (2H, m), 3.79–3.71 (1H, m), 3.66–3.58 (1H, m), 3.28–3.21 (1H, br s), 2.99–2.92 (1H, br d, J=5.1 Hz), 1.25 (3H, d, J=7.2 Hz).

(4) 1-{4-[(1S)-2-(t-Butyldimethylsilyloxy)-1-methylethylcarbamoyl]-1,3-thiazol-2-yl}-3-hydroxyazetidine To a solution of 3-hydroxy-1-[4-((1S)-2-hydroxy-1-methylethylcarbamoyl)-1,3-thiazol-2-yl]azetidine (910 mg, 3.54 mmol) (obtained as described in Reference Example 35(3)) in dimethylformamide (46 ml) were added t-butyldimethylsilyl chloride (586 mg, 3.89 mmol) and imidazole (265 mg, 3.89 mmol) in an ice bath, and the reaction mixture was stirred at room temperature for 6 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1→1:4) as the eluant to afford 1-{4-[(1S)-2-(t-butyldimethylsilyloxy)-1-methylethylcarbamoyl]-1,3-thiazol-2-yl}-3-hydroxyazetidine (935 mg, yield 71%) as a pale yellow oil.

$^1$H-NMR (400 MHz, CDCl$_3$): δ (ppm) 7.48–7.42 (1H, br d, J=8.8 Hz), 7.36 (1H, s), 4.86–4.79 (1H, m), 4.30 (2H, ddd, J=15.6, 5.9, 2.9 Hz), 4.34–4.27 (1H, m), 3.97–3.91 (2H, m), 3.68 (1H, dd, J=9.5, 4.4 Hz), 3.63 (1H, dd, J=9.5, 2.9 Hz), 1.25 (3H, d, J=7.3 Hz), 0.93 (9H, s), 0.07 (6H, s).

(5) 1-{4-[(1S)-2-(t-Butyldimethylsilyloxy)-1-methylethylcarbamoyl]-1,3-thiazol-2-yl}-3-methanesulfonyloxyazetidine To a solution of 1-{4-[(1S)-2-(t-butyldimethylsilyloxy)-1-methylethylcarbamoyl]-1,3-thiazol-2-yl}-3-hydroxyazetidine (930 mg, 2.50 mmol) (obtained as described in Reference Example 35(4)) in methylene chloride (47 ml) were added methanesulfonyl chloride (480 μl, 6.20 mmol) (obtained as described in Reference Example 35(4)) and triethylamine (869 μl, 6.20 mmol) in an ice bath. After stirring the mixture in the ice bath for 10 minutes, the mixture was stirred at room temperature for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 1-{4-[(1S)-2-(t-butyldimethylsilyloxy)-1-methylethylcarbamoyl]-1,3-thiazol-2-yl}-3-methanesulfonyloxyazetidine (1.16 g, yield 100%) as a pale yellow oil.

$^1$H-NMR (400 MHz, CDCl$_3$): δ (ppm) 7.43 (1H, s), 7.43–7.39 (1H, br s), 5.44–5.39 (1H, m), 4.43 (2H, ddd, J=6.6, 5.9, 1.5 Hz), 4.27–4.21 (2H, m), 4.21–4.13 (1H, m), 3.68 (1H, dd, J=9.5, 4.4 Hz), 3.63 (1H, dd, J=9.5, 2.9 Hz), 3.11 (3H, s), 1.25 (3H, d, J=6.6 Hz), 0.93 (9H, s), 0.07 (6H, s).

(6) 3-Acetylthio-1-{4-[(1S)-2-(t-butyldimethylsilyloxy)-1-methylethylcarbamoyl]-1,3-thiazol-2-yl}azetidine To a solution of 1-{4-[(1S)-2-(t-butyldimethylsilyloxy)-1-methylethylcarbamoyl]-1,3-thiazol-2-yl}-3-methanesulfonyloxyazetidine (1.16 g, 2.50 mmol) (obtained as described in Reference Example 35(5)) in dimethylformamide (60 ml) was added potassium thioacetate (1.71 mg, 15.0 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:1→2:1) as the eluant to afford 3-acetylthio-1-{4-[(1S)-2-(t-butyldimethylsilyloxy)-1-methylethylcarbamoyl]-1,3-thiazol-2-yl}azetidine (709 mg, yield 60%) as a pale brown oil.

$^1$H-NMR (400 MHz, CDCl$_3$): δ (ppm) 7.45–7.40 (1H, br s), 7.39 (1H, s), 4.54–4.47 (2H, m), 4.46–4.41 (1H, m), 4.20–4.15 (1H, m), 4.00–3.93 (2H, m), 3.67 (1H, dd, J=10.3, 4.4 Hz), 3.62 (1H, dd, J=10.3, 3.7 Hz), 2.37 (3H, s), 1.24 (3H, d, J=6.6 Hz), 0.92 (9H, s), 0.07 (6H, s).

REFERENCE EXAMPLE 36

3-Acetylthio-1-{4-[(1S)-1-(t-butyldimethylsilyloxy)-2-methylpropylcarbamoyl]-1,3-thiazol-2-yl}azetidine

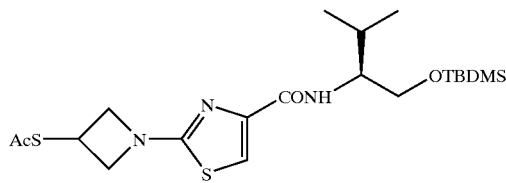

(1) [(1S)-1-(t-Butyldiphenylsilyloxy)-2-methylpropyl]carbamic acid benzyl ester

To a solution of L-valinol (2.00 g, 19.4 mmol) in methylene chloride (60 ml) were added chloroformic acid benzyl ester (3.32 ml, 23.3 mmol) and triethylamine (3.27 ml, 23.3 mmol) in an ice bath, and the mixture was stirred at room temperature for 4.5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford [(1S)-1-(hydroxymethyl)-2-methylpropyl]carbamic acid benzyl ester (4.56 g, yield 99%) as white crystals.

Subsequently, to a solution of [(1S)-1-(hydroxymethyl)-2-methylpropyl]carbamic acid benzyl ester (4.56 g, 19.2 mmol) in dimethylformamide (140 ml) were added t-butyldiphenylsilyl chloride (6.00 ml, 23.1 mmol) and imidazole (1.57 g, 23.1 mmol) in an ice bath, and the resulting mixture was stirred at room temperature for 4 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (8:1→6:1) as the eluant to afford [(1S)-1-(t-butyldiphenylsilyloxy)-2-methyl-propyl]carbamic acid benzyl ester (10.1 g, yield 100%) as white crystals.

$^1$H-NMR (400 MHz, CDCl$_3$): δ (ppm) 7.65–7.60 (4H, m), 7.45–7.29 (11H, m), 5.09 (2H, s), 4.92–4.84 (1H, br d, J=9.5 Hz), 3.71 (1H, dd, J=10.3, 4.4 Hz), 3.66 (1H, dd, J=10.3, 4.4 Hz), 3.55–3.46 (1H, m), 1.99–1.87 (1H, m), 1.05 (9H, s), 0.89 (6H, d, J=7.3 Hz).

(2) 3-t-Butyldiphenylsilyloxy-1-{4-[(1S)-1-(t-butyldiphenylsilyloxy)-2-methylpropylcarbamoyl]-1,3-thiazol-2-yl}azetidine A solution of [(1S)-1-(t-butyldiphenylsilyloxy)-2-methylpropyl]carbamic acid benzyl ester (7.14 g, 15.0 mmol) (obtained as described in Reference Example 36(1)) in methanol (215 ml) was subjected to catalytic hydrogenation in the presence of 10% palladium on charcoal (7.14 g) at room temperature for 3 hours. After checking the completion of the reaction, the reaction mixture was filtered in order to remove the catalyst and the filtrate concentrated under reduced pressure. The residue was purified by chromatography on a silica gel column using methylene chloride:methanol (98:2→9:1) as the eluant to afford (1S)-1-(t-butyldiphenylsilyloxymethyl)-2-methylpropylamine (3.73 g, yield 73%) as a colorless oil.

Subsequently, to a solution of 3-t-butyldiphenylsilyloxy-1-(4-ethoxycarbonyl-1,3-thiazol-2-yl)azetidine (2.0 g, 4.29 mmol) (obtained as described in Reference Example 2(1)) in benzene (100 ml) was added a solution of 0.67M (1S)-1-(t-butyldiphenylsilyloxymethyl)-2-methylpropylamine-trimethylaluminium in benzene (12.9 ml) at room temperature under an atmosphere of nitrogen. The mixture was heated under reflux overnight. After checking the completion of the reaction, 10% aqueous acetic acid solution (100 ml) and ethyl acetate (200 ml) were added to the reaction mixture in an ice bath, and the resulting mixture was stirred at room temperature for 1 hour. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→4:1) as the eluant to afford 3-t-butyldiphenylsilyloxy-1-{4-[(1S)-1-(t-butyldiphenylsilyloxy)-2-methylpropylcarbamoyl]-1,3-thiazol-2-yl}azetidine (1.98 g, yield 61%) as a pale brown solid.

$^1$H-NMR (400 MHz, CDCl$_3$): δ (ppm) 7.69–7.56 (8H, m), 7.44–7.31 (12H, m), 7.37 (1H, s), 4.74–4.67 (1H, m), 4.09–3.94 (4H, m), 3.87–3.78 (1H, m), 3.85 (1H, dd, J=10.3, 2.1 Hz), 3.67 (1H, dd, J=10.3, 3.9 Hz), 2.17–2.05 (1H, m), 1.09 (9H, s), 1.06 (9H, s), 0.99 (3H, d, J=6.9 Hz), 0.97 (3H, d, J=6.8 Hz).

(3) 3-Hydroxy-1-{4-[(1S)-1-(hydroxymethyl)-2-methylpropylcarbamoyl]-1,3-thiazol-2-yl}azetidine To a solution of 3-t-butyldiphenylsilyloxy-1-{4-[(1S)-1-(t-butyldiphenylsilyloxy)-2-methylpropylcarbamoyl]-1,3-thiazol-2-yl}azetidine (1.98 g, 2.60 mmol) (obtained as described in Reference Example 36(2)) in anhydrous tetrahydrofuran (100 ml) was added a solution of 1.0M tetra-n-butylammonium fluoride in tetrahydrofuran (6.23 ml, 6.23 mmol) in an ice bath. The mixture was stirred in the ice bath overnight. After checking the completion of the reaction, the reaction mixture was concentrated under reduced pressure. The residue was purified by chromatography on a silica gel column using ethyl acetate→ethyl acetate:methanol (95:5) as the eluant to afford 3-hydroxy-1-{4-[(1S)-1-(hydroxymethyl)-2-methylpropylcarbamoyl]-1,3-thiazol-2-yl}azetidine (755 mg, yield 100%) as a colorless oil.

$^1$H-NMR (400 MHz, CDCl$_3$): δ (ppm) 7.34 (1H, s), 7.35–7.31 (1H, br s), 4.84–4.75 (1H, m), 4.32 2H, dd, J=8.8, 6.8 Hz), 3.97 (1H, dd, J=8.8, 4.4 Hz), 3.94 (1H, dd, J=8.8, 4.4 Hz), 3.87–3.77 (2H, m), 3.73 (1H, dd, J=10.7, 6.8 Hz), 3.33–3.21 (1H, br s), 3.24–2.94 (1H, br s), 1.98 (1H, septet, J=6.8 Hz), 1.01 (3H, d, J=6.8 Hz), 0.98 (3H, d, J=6.8 Hz).

(4) 1-{4-[(1S)-1-(t-Butyldimethylsilyloxymethyl)-2-methylpropylcarbamoyl]-1,3-thiazol-2-yl}-3-hydroxyazetidine To a solution of 3-hydroxy-1-{4-[(1S)-1-(hydroxymethyl)-2-methylpropylcarbamoyl]-1,3-thiazol-2-yl}azetidine (750 mg, 2.60 mmol) (obtained as described in Reference Example 36(3)) in dimethylformamide (38 ml) were added t-butyldimethylsilyl chloride (470 mg, 3.12 mmol) and imidazole (212 mg, 3.12 mmol) in an ice bath, and then the reaction mixture was stirred in the ice bath for 2 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1→1:3) as the eluant to afford 1-{4-[(1S)-1-(t-butyldimethylsilyloxymethyl)-2-methylpropylcarbamoyl]-1,3-thiazol-2-yl}-3-hydroxyazetidine (700 mg, yield 67%) as a pale yellow oil.

$^1$H-NMR (400 MHz, CDCl$_3$): δ (ppm) 7.54–7.50 (1H, br d, J=9.8 Hz), 7.37 (1H, s), 4.86–4.80 (1H, m), 4.35–4.27 (2H, m), 3.98–3.92 (2H, m), 3.84 (1H, dd, J=9.8, 2.9 Hz), 3.84–3.79 (1H, m), 3.62 (1H, dd, J=9.8, 3.9 Hz), 2.00 (1H, septet, J=6.8 Hz), 0.98 (3H, d, J=6.8 Hz), 0.96 (3H, d, J=6.8 Hz), 0.91 (9H, s), 0.06 (6H, s).

(5) 1-{4-[(1S)-1-(t-Butyldimethylsilyloxymethyl)-2-methylpropylcarbamoyl]-1,3-thiazol-2-yl}-3-methanesulfonyloxyazetidine To a solution of 1-{4-[(1S)-1-(t-butyldimethylsilyloxymethyl)-2-methylpropylcarbamoyl]-1,3-thiazol-2-yl}-3-hydroxyazetidine (700 mg, 1.75 mmol) (obtained as described in Reference Example 36(4)) in methylene chloride (35 ml) were added methanesulfonyl chloride (406 μl, 5.25 mmol) and triethylamine (736 μl, 5.25 mmol) in an ice bath. After stirring the mixture in the ice bath for 10 minutes, the mixture was stirred at room temperature for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 1-{4-[(1S)-1-(t-butyldimethylsilyloxymethyl)-2-methylpropylcarbamoyl]-1,3-thiazol-2-yl}-3-methanesulfonyloxyazetidine (895 mg, yield 100%) as a pale yellow oil.

$^1$H-NMR (400 MHz, CDCl$_3$): δ (ppm) 7.50–7.45 (1H, br d, J=9.5 Hz), 7.44 (1H, s), 5.45–5.39 (1H, m), 4.43 (2H, ddd, J=11.0, 6.6, 1.5 Hz), 4.24 (2H, ddd, J=11.0, 4.4, 1.5 Hz), 3.83 (1H, dd, J=10.7, 2.6 Hz), 3.84–3.79 (1H, m), 3.62 (1H, dd, J=10.7, 4.8 Hz), 3.11 (3H, s), 2.04–1.94 (1H, m), 0.98 (3H, d, J=7.3 Hz), 0.96 (3H, d, J=6.6 Hz), 0.91 (9H, s), 0.06 (6H, s).

(6) 3-Acetylthio-1-{4-[(1S)-1-(t-butyldimethylsilyloxymethyl)-2-methylpropylcarbamoyl]-1,3-thiazol-2-yl}azetidine To a solution of 1-{4-[(1S)-1-(t-butyldimethylsilyloxymethyl)-2-methylpropylcarbamoyl]-1,3-thiazol-2-yl}-3-methanesulfonyloxyazetidine (890 mg, 1.75 mmol) (obtained as described in Reference Example 36(5)) in dimethylformamide (45 ml) was added potassium thioacetate (1.20 g, 10.5 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using n-hexane:ethyl acetate (3:1→1:1) as the eluant to afford 3-acetylthio-1-{4-[(1S)-1-(t-butyldimethylsilyloxymethyl)-2-methylpropylcarbamoyl]-1,3-thiazol-2-yl}azetidine (502 mg, yield 63%) as a pale brown oil.

$^1$H-NMR (400 MHz, CDCl$_3$): δ (ppm) 7.50–7.45 (1H, br d, J=9.5 Hz), 7.40 (1H, s), 4.54–4.43 (2H, m), 4.47–4.40 (1H, m), 4.00–3.93 (2H, m), 3.86–3.78 (2H, m), 3.64–3.59 (1H, m), 2.04–1.94 (1H, m), 0.98 (3H, d, J=6.6 Hz), 0.96 (3H, d, J=6.6 Hz), 0.91 (9H, s), 0.05 (6H, s).

REFERENCE EXAMPLE 37

3-Acetylthio-1-{4-[(1S)-1-(t-butyldimethylsilyloxymethyl)-3-methylbutylcarbamoyl]-1,3-thiazol-2-yl}azetidine

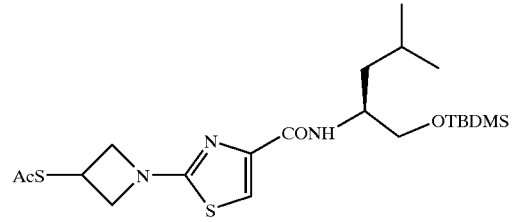

(1) [(1S)-1-(t-Butyldiphenylsilyloxymethyl)-3-methylbutyl]carbamic acid benzyl ester To a solution of L-leucinol (1.00 g, 8.53 mmol) in methylene chloride (30 ml) were added chloroformic acid benzyl ester (1.46 ml, 10.2 mmol) and triethylamine (1.43 ml, 10.2 mmol) in an ice bath, and the mixture was stirred at room temperature for 3 days. After checking the completion of the reaction, the reaction mixture was partitioned between ethyl acetate and saturated aqueous sodium hydrogencarbonate solution. The obtained organic layer was washed With saturated aqueous sodium chloride solution, dried over anhydrous sodium sulfate, filtered and concentrated under reduced pressure. The residue was purified by chromatography on a silica gel column using n-hexane:ethyl acetate (2:1→1:1) as the eluant to afford [(1S)-1-(hydroxymethyl)-3-methylbutyl]carbamic acid benzyl ester (2.31 g, yield 100%) as a colorless oil.

Subsequently, to a solution of [(1S)-1-(hydroxymethyl)-3-methylbutyl]carbamic acid benzyl ester (4.84 g, 19.3 mmol) in dimethylformamide (145 ml) were added t-butyldiphenylsilyl chloride (6.01 ml, 23.1 mmol) and imidazole (1.57 g, 23.1 mmol) in an ice bath, and then the mixture was stirred at room temperature for 8 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (19:1→7:1) as the eluant to afford [(1S)-1-(t-butyldiphenylsilyloxymethyl)-3-methylbutyl] carbamic acid benzyl ester (9.22 g, yield 98%) as a colorless oil.

¹H-NMR (400 MHz, CDCl₃): δ (ppm) 7.65–7.61 (4H, m), 7.45–7.32 (11H, m), 5.09 (2H, d, J=2.9 Hz), 4.85–4.80 (1H, br d, J=8.8 Hz), 3.86–3.77 (1H, m), 3.70 (1H, dd, J=9.8, 2.9 Hz), 3.59 (1H, dd, J=9.8, 2.9 Hz), 1.63–1.54 (1H, m), 1.43–1.37 (2H, m), 1.06 (9H, s), 0.91 (3H, d, J=6.8 Hz), 0.89 (3H, d, J=6.8 Hz).

(2) 3-t-Butyldiphenylsilyloxy-1-{4-[(1S)-1-(t-butyldiphenylsilyloxymethyl)-3-methylbutylcarbamoyl]-1,3-thiazol-2-yl}azetidine A solution of [(1S)-1-(t-butyldiphenylsilyloxymethyl)-3-methylbutyl]carbamic acid benzyl ester (7.35 g, 15.0 mmol) (obtained as described in Reference Example 37(1)) in methanol (220 ml) was subjected to catalytic hydrogenation in the presence of 10% palladium on charcoal (7.35 g) at room temperature for 4 hours. After checking the completion of the reaction, the reaction mixture was filtered in order to remove the catalyst and the filtrate concentrated under reduced pressure. The residue was purified by chromatography on a silica gel column using methylene chloride:methanol (98:2→9:1) as the eluant to afford (1S)-1-(t-butyldiphenylsilyloxymethyl)-3-methylbutylamine (4.50 g, yield 84%) as a colorless oil.

Subsequently, to a solution of 3-t-butyldiphenylsilyloxy-1-(4-ethoxycarbonyl-1,3-thiazol-2-yl)azetidine (2.00 g, 4.29 mmol) (obtained as described in Reference Example 2(1)) in benzene (100 ml) was added a solution of 0.67M (1S)-1-(t-butyldiphenylsilyloxymethyl)-3-methylbutylamine-trimethylaluminium in benzene (12.9 ml) at room temperature under an atmosphere of nitrogen. The mixture was heated under reflux overnight. After checking the completion of the reaction, 10% aqueous acetic acid solution (100 ml) and ethyl acetate (200 ml) were added to the reaction mixture in an ice bath, and the resulting mixture was stirred in the ice bath for 0.5 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→4:1) as the eluant to afford 3-t-butyldiphenylsilyloxy-1-{4-[(1S)-1-(t-butyldiphenylsilyloxymethyl)-3-methylbutylcarbamoyl]-1,3-thiazol-2-yl}azetidine (2.14 g, yield 64%) as a pale brown solid.

¹H-NMR (400 MHz, CDCl₃): δ (ppm) 7.68–7.62 (4H, m), 7.62–7.56 (4H, m), 7.46–7.28 (12H, m), 7.37 (1H, s), 4.74–4.69 (1H, m), 4.24–4.16 (1H, m), 4.11–4.03 (2H, m), 1.00 (1H, dd, J=10.7, 4.9 Hz), 3.98 (1H, dd, J=11.7, 4.9 Hz), 3.72 (1H, dd, J=9.8, 3.9 Hz), 3.67 (1H, dd, J=9.8, 2.9 Hz), 1.65–1.46 (3H, m), 1.08 (9H, s), 1.05 (9H, s), 0.94 (3H, d, J=5.9 Hz), 0.92 (3H, d, J=5.9 Hz).

(3) 3-Hydroxy-1-{4-[(1S)-1-(hydroxymethyl)-3-methylbutylcarbamoyl]-1,3-thiazol-2-yl}azetidine To a solution of 3-t-butyldiphenylsilyloxy-1-{4-[(1S)-1-(t-butyldiphenylsilyloxymethyl)-3-methylbutylcarbamoyl]-1,3-thiazol-2-yl}azetidine (2.14 g, 3.72 mmol) (obtained as described in Reference Example 37(2)) in anhydrous tetrahydrofuran (107 ml) was added a solution of 1.0M tetra-n-butylammonium fluoride in tetrahydrofuran (8.94 ml, 8.94 mmol) in an ice bath. The mixture was stirred in the ice bath for 4 hours. After checking the completion of the reaction, the reaction mixture was concentrated under reduced pressure. The residue was purified by chromatography on a silica gel column using ethyl acetate ethyl acetate:methanol (9:1) as the eluant to afford 3-hydroxy-1-{4-[(1S)-1-(hydroxymethyl)-3-methyl-butylcarbamoyl]-1,3-thiazol-2-yl}azetidine (825 mg, yield 74%) as a pale yellow oil.

¹H-NMR (400 MHz, CDCl₃): δ (ppm) 7.36 (1H, s), 7.24–7.17 (1H, br d, J=8.8 Hz), 4.85–4.77 (1H, m), 4.32 (2H, dd, J=8.8, 7.3 Hz), 4.20–4.12 (1H, m), 3.96 (2H, ddd, J=8.8, 8.8, 4.4 Hz), 3.77 (1H, dd, J=10.9, 1.3 Hz), 3.61 (1H, dd, J=10.9, 5.9 Hz), 3.17–3.08 (1H, br s), 3.08–2.95 (1H, br s), 1.75–1.65 (1H, m), 1.55–1.46 (1H, m), 1.46–1.37 (1H, m), 0.95 (3H, d, J=6.6 Hz), 0.94 (3H, d, J=6.6 Hz).

(4) 1-{4-[(1S)-1-(t-Butyldimethylsilyloxymethyl)-3-methylbutylcarbamoyl]-1,3-thiazol-2-yl}-3-hydroxyazetidine To a solution of 3-hydroxy-1-{4-[(1S)-1-(hydroxymethyl)-3-methylbutylcarbamoyl]-1,3-thiazol-2-yl}azetidine (820 mg, 2.74 mmol) (obtained as described in Reference Example 37(3)) in dimethylformamide (41 ml) were added t-butyldimethylsilyl chloride (495 mg, 3.29 mmol) and imidazole (224 mg, 3.29 mmol) in an ice bath, and then the reaction mixture was stirred in the ice bath overnight. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 1-{4-[(1S)-1-(t-butyldimethylsilyloxymethyl)-3-methylbutylcarbamoyl]-1,3-thiazol-2-yl}-3-hydroxyazetidine (731 mg, yield 65%) as a pale yellow oil.

¹H-NMR (400 MHz, CDCl₃): δ (ppm) 7.40–7.37 (1H, br s), 7.36 (1H, s), 4.87–4.79 (1H, m), 4.31 (2H, dd, J=15.0, 8.4 Hz), 4.21–4.12 (1H, m), 3.98–3.92 (2H, m), 3.68–3.65 (2H, m), 1.68–1.60 (1H, m), 1.56–1.40 (2H, m), 0.95 (3H, d, J=6.6 Hz), 0.94 (3H, d, J=6.6 Hz), 0.92 (9H, s,), 0.06 (6H, s).

(5) 1-{4-[(1S)-1-(t-Butyldimethylsilyloxymethyl)-3-methylbutylcarbamoyl]-1,3-thiazol-2-yl}-3-methanesulfonyloxyazetidine To a solution of 1-{4-[(1S)-1-(t-butyldimethylsilyloxymethyl)-3-methylbutylcarbamoyl]-1,3-thiazol-2-yl}-3-hydroxyazetidine (730 mg, 1.76 mmol) (obtained as described in Reference Example 37(4)) in methylene chloride (37 ml) were added methanesulfonyl chloride (409 μl, 5.29 mmol) and triethylamine (741 μl, 5.29 mmol) in an ice bath. After stirring the mixture in the ice bath for 10 minutes, the mixture was stirred at room temperature for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 1-{4-[(1S)-1-(t-butyldimethylsilyloxymethyl)-3-methylbutylcarbamoyl]-1,3-thiazol-2-yl}-3-methanesulfonyloxyazetidine (846 mg, yield 98%) as a pale yellow oil.

¹H-NMR (400 MHz, CDCl₃): δ (ppm) 7.43 (1H, s), 7.36–7.30 (1H, br d, J=9.5 Hz), 5.45–5.39 (1H, m), 4.47–4.39 (2H, m), 4.28–4.20 (2H, m), 4.20–4.14 (1H, m), 3.66 (2H, d, J=3.7 Hz), 3.11 (3H, s), 1.70–1.58 (1H, m), 1.53 (1H, ddd, J=13.9, 8.8, 5.9 Hz), 1.44 (1H, ddd, J=13.9, 8.8, 5.9 Hz), 0.95 (6H, t, J=6.3 Hz), 0.92 (9H, s), 0.09 (6H, s).

(6) 3-Acetylthio-1-{4-[(1S)-1-(t-butyldimethylsilyloxymethyl)-3-methylbutylcarbamoyl]-1,3-thiazol-2-yl}azetidine To a solution of 1-{4-[(1S)-1-(t-butyldimethylsilyloxymethyl)-3-methylbutylcarbamoyl]-1,3-thiazol-2-yl}-3-methanesulfonyloxyazetidine (840 mg, 1.71 mmol) (obtained as described in Reference Example 37(5)) in dimethylformamide (42 ml) was added potassium thioacetate (1.17 mg, 10.2 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (3:1→1:1) as the eluant to afford 3-acetylthio-1-{4-[(1S)-1-(t-butyldimethylsilyloxymethyl)-3-methyl-butylcarbamoyl]-1,3-thiazol-2-yl}azetidine (452 mg, yield 56%) as a pale brown oil.

¹H-NMR (400 MHz, CDCl₃): δ (ppm) 7.39 (1H, s), 7.36–7.31 (1H, br d, J=9.5 Hz), 4.54–4.39 (3H, m), 4.20–4.12 (1H, m), 3.97 (1H, dd, J=8.8 Hz), 3.96 (1H, dd, J=8.8 Hz), 3.66 (2H, d, J=3.7 Hz), 1.70–1.60 (1H, m), 1.58–1.40 (2H, m), 0.95 (3H, d, J=6.6 Hz), 0.94 (3H, d, J=6.6 Hz), 0.91 (9H, s), 0.05 (6H, s).

REFERENCE EXAMPLE 38

3-Acetylthio-1-{4-[(1S,2S)-1-(t-butyldimethylsilyloxymethyl)-2-methylbutylcarbamoyl]-1,3-thiazol-2-yl}azetidine

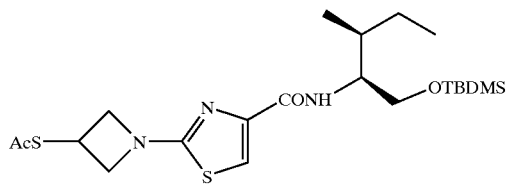

(1) [(1S,2S)-1-(t-Butyldiphenylsilyloxymethyl)-2-methylbutyl]carbamic acid benzyl ester To a solution of L-isoleucinol (2.20 g, 18.8 mmol) in methylene chloride (66 ml) were added chloroformic acid benzyl ester (3.22 ml, 22.5 mmol) and triethylamine (3.15 ml, 22.5 mmol) in an ice bath, and the mixture was stirred at room temperature for 1.5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:1) as the eluant to afford [(1S,2S)-1-(hydroxymethyl)-2-methylbutyl]carbamic acid benzyl ester (4.17 g, yield 88%) as a colorless oil.

Subsequently, to a solution of [(2S)-(N-benzyloxycarbonyl)-2-amino-3-methylbutanol (4.17 g, 16.6 mmol) in dimethylformamide (125 ml) were added t-butyldiphenylsilyl chloride (5.18 ml, 19.9 mmol) and imidazole (1.35 g, 19.9 mmol) in an ice bath, and the mixture was stirred at room temperature for 4 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (19:1→5:1) as the eluant to afford [(1S,2S)-1-(t-butyldiphenylsilyloxymethyl)-2-methylbutyl]carbamic acid benzyl ester (6.72 g, yield 83%) as colorless crystals.

¹H-NMR (400 MHz, CDCl₃): δ (ppm) 7.65–7.60 (4H, m), 7.45–7.30 (11H, m), 5.09 (2H, m), 4.93–4.84 (1H, br d, J=8.8 Hz), 3.74–3.60 (2H, m), 3.60–3.52 (1H, m), 1.74–1.64 (1H, m), 1.53–1.44 (1H, m), 1.14–1.06 (1H, m), 1.04 (9H, s), 0.92–0.8 (6H, m).

(2) 3-t-Butyldiphenylsilyloxy-1-{4-[(1S,2S)-1-(t-butyldiphenylsilyloxymethyl)-2-methylbutylcarbamoyl]-1,3-thiazol-2-yl}azetidine A solution of [(1S,2S)-1-(t-butyldiphenylsilyloxymethyl)-2-methylbutyl]carbamic acid benzyl ester (6.72 g, 13.7 mmol) (obtained as described in Reference Example 38(1)) in methanol (200 ml) was subjected to catalytic hydrogenation in the presence of 10% palladium on charcoal (6.72 g) at room temperature for 2 hours. After checking the completion of the reaction, the reaction mixture was filtered in order to remove the catalyst and the filtrate concentrated under reduced pressure. The residue was purified by chromatography on a silica gel column using methylene chloride:methanol (98:2→9:1) as the eluant to afford (1S,2S)-1-(t-butyldiphenylsilyloxymethyl)-2-methylbutylamine (4.04 g, yield 83%).

Subsequently, to a solution of 3-t-butyldiphenylsilyloxy-1-(4-ethoxycarbonyl-1,3-thiazol-2-yl)azetidine (2.00 g, 4.29 mmol) (obtained as described in Reference Example 2(1)) in benzene (100 ml) was added a solution of 0.67M (1S,2S)-1-(t-butyldiphenylsilyloxymethyl)-2-methylbutylamine-trimethylaluminium in benzene (12.9 ml) at room temperature under an atmosphere of nitrogen. The mixture was heated under reflux overnight. After checking the completion of the reaction, 10% aqueous acetic acid solution (100 ml) and ethyl acetate (200 ml) were added to the reaction mixture in an ice bath, and the resulting mixture was stirred at room temperature for 30 minutes. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→1:3) as the eluant to afford 3-t-butyldiphenylsilyloxy-1-{4-[(1S,2S)-1-(t-butyldiphenylsilyloxymethyl)-2-methylbutylcarbamoyl]-1,3-thiazol-2-yl}azetidine (1.89 g, yield 57%) as a pale brown solid.

¹H-NMR (400 MHz, CDCl₃): δ (ppm) 7.70–7.57 (8H, m), 7.46–7.26 (12H, m), 7.36 (1H, s), 4.73–4.67 (1H, m), 4.09–3.94 (4H, m), 3.93–3.86 (1H, m), 3.84 (1H, dd, J=10.7, 2.0 Hz), 3.67 (1H, dd, J=10.7, 3.4 Hz), 1.90–1.82 (1H, m), 1.22–1.11 (1H, m), 1.07 (9H, s), 1.04 (9H, s), 0.93 (3H, d, J=6.9 Hz), 0.90 (3H, t, J=7.3 Hz).

(3) 3-Hydroxy-1-{4-[(1S,2S)-1-(hydroxymethyl)-2-methylbutylcarbamoyl]-1,3-thiazol-2-yl}azetidine To a solution of 3-t-butyldiphenylsilyloxy-1-{4-[(1S,2S)-1-(t-butyldiphenylsilyloxymethyl)-2-methylbutylcarbamoyl]-1,3-thiazol-2-yl}azetidine (1.89 g, 2.45 mmol) (obtained as described in Reference Example 38(2)) in anhydrous tetrahydrofuran (95 ml) was added a solution of 1.0M tetra-n-butylammonium fluoride in tetrahydrofuran (5.87 ml, 5.87 mmol) in an ice bath. The mixture was stirred in the ice bath overnight. After checking the completion of the reaction, the reaction mixture was concentrated under reduced pressure. The residue was purified by chromatography on a silica gel column using ethyl acetate→ethyl acetate:methanol (9:1) as the eluant to afford 3-hydroxy-1-{4-[(1S,2S)-1-(hydroxymethyl)-2-methylbutylcarbamoyl]-1,3-thiazol-2-yl}azetidine (811 mg, yield 100%) as a pale yellow oil.

$^1$H-NMR (400 MHz, CDCl$_3$): δ (ppm) 7.37 (1H, s), 7.35–7.31 (1H, br s), 4.87–4.78 (1H, m), 4.33 (2H, dd, J=10.3, 6.6 Hz), 4.00–3.93 (2H, m), 3.92–3.86 (1H, m), 3.86–3.78 (1H, m), 3.78–3.70 (1H, m), 3.05–2.98 (1H, br s), 2.75–2.71 (1H, br d, J=7.3 Hz), 1.80–1.70 (1H, m), 1.59–1.50 (1H, m), 1.27–1.13 (1H, m), 0.98 (3H, d, J=7.3 Hz), 0.93 (3H, t, J=7.3 Hz).

(4) 3-Hydroxy-1-{4-[(1S,2S)-1-(t-butyldimethylsilyloxymethyl)-2-methylbutylcarbamoyl]-1,3-thiazol-2-yl}azetidine To a solution of 3-hydroxy-1-{4-[(1S,2S)-1-(hydroxymethyl)-2-methylbutylcarbamoyl]-1,3-thiazol-2-yl}azetidine (1.34 g, 4.48 mmol) (obtained as described in Reference Example 38(3)) in dimethylformamide (67 ml) were added t-butyldimethylsilyl chloride (810 mg, 5.37 mmol) and imidazole (527 mg, 5.37 mmol) in an ice bath, and then the reaction mixture was stirred in the ice bath for 2.5 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using toluene:acetonitrile (5:1→3:1) as the eluant to afford 3-hydroxy-1-{4-[(1S,2S)-1-(t-butyldimethylsilyloxymethyl)-2-methylbutylcarbamoyl]-1,3-thiazol-2-yl}azetidine (1.35 g, yield 97%) as a pale yellow oil.

$^1$H-NMR (400 MHz, CDCl$_3$): δ (ppm) 7.57–7.51 (1H, br d, J=8.8 Hz), 7.36 (1H, s), 4.86–4.79 (1H, m), 4.34–4.26 (2H, m), 3.98–3.91 (2H, m), 3.90–3.84 (1H, m), 3.84 (1H, dd, J=9.8, 2.4 Hz), 3.63 (1H, dd, J=9.8, 3.9 Hz), 2.63–2.59 (1H, br d, J=5.9 Hz), 1.80–1.71 (1H, m), 1.60–1.51 (1H, m), 1.20–1.12 (1H, m), 0.95 (3H, d, J=6.8 Hz), 0.91 (9H, s), 0.90 (2H, t, J=6.8 Hz), 0.05 (6H, s).

(5) 1-{4-[(1S,2S)-1-(t-Butyldimethylsilyloxymethyl)-2-methylbutylcarbamoyl]-1,3-thiazol-2-yl}-3-methanesulfonyloxyazetidine To a solution of 3-hydroxy-1-{4-[(1S,2S)-1-(t-butyldimethylsilyloxymethyl)-2-methylbutylcarbamoyl]-1,3-thiazol-2-yl}azetidine (1.35 g, 3.26 mmol) (obtained as described in Reference Example 38(4)) in methylene chloride (68 ml) were added methanesulfonyl chloride (758 μl, 9.79 mmol) and triethylamine (1.37 ml, 9.79 mmol) in an ice bath. After stirring the mixture in the ice bath for 10 minutes, the mixture was stirred at room temperature for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:2) as the eluant to afford 1-{4-[(1S,2S)-1-(t-butyldimethylsilyloxymethyl)-2-methylbutylcarbamoyl]-1,3-thiazol-2-yl}-3-methanesulfonyloxyazetidine (1.55 g, yield 97%) as a pale yellow oil.

$^1$H-NMR (400 MHz, CDCl$_3$): δ (ppm) 7.50–7.46 (1H, br d, J=9.8 Hz), 7.43 (1H, s), 5.45–5.39 (1H, m), 4.45 (1H, dd, J=8.8, 6.8 Hz), 4.42 (1H, dd, J=8.8, 6.8 Hz), 4.26 (1H, dd, J=9.8, 3.9 Hz), 4.23 (1H, dd, J=9.8, 3.9 Hz), 3.91–3.85 (1H, m), 3.84 (1H, dd, J=10.3, 2.4 Hz), 3.63 (1H, dd, J=10.3, 3.4 Hz), 3.11 (3H, s), 1.80–1.71 (1H, m), 1.59–1.51 (1H, m), 1.22–1.12 (1H, m), 0.95 (3H, d, J=3.8 Hz), 0.91 (9H, s), 0.91 (3H, t, J=6.8 Hz), 0.05 (6H, s).

(6) 3-Acetylthio-1-{4-[(1S,2S)-1-(t-butyldimethylsilyloxymethyl)-2-methylbutylcarbamoyl]-1,3-thiazol-2-yl}azetidine To a solution of 1-{4-[(1S,2S)-1-(t-butyldimethylsilyloxymethyl)-2-methylbutylcarbamoyl]-1,3-thiazol-2-yl}-3-methanesulfonyloxyazetidine (1.55 g, 3.15 mmol) (obtained as described in Reference Example 38(5)) in dimethylformamide (78 ml) was added potassium thioacetate (2.16 g, 18.9 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (3:1→2:1) as the eluant to afford 3-acetylthio-1-{4-[(1S,2S)-1-(t-butyldimethylsilyloxymethyl)-2-methyl-butylcarbamoyl]-1,3-thiazol-2-yl}azetidine (910 mg, yield 61%) as a pale brown oil.

$^1$H-NMR (400 MHz, CDCl$_3$): δ (ppm) 7.52–7.46 (1H, br d, J=9.5 Hz), 7.39 (1H, s), 4.54–4.40 (3H, m), 4.00–3.92 (2H, m), 3.91–3.84 (1H, m), 3.83 (1H, dd, J=10.3, 2.2 Hz), 3.63 (1H, dd, J=10.3, 3.7 Hz), 2.37 (3H, s), 1.81–1.70 (1H, m), 1.58–1.50 (1H, m), 1.20–1.09 (1H, m), 0.95 (3H, d, J=6.6 Hz), 0.91 (9H, s), 0.90 (3H, t, J=7.3 Hz), 0.05 (6H, s).

REFERENCE EXAMPLE 39

3-Acetylthio-1-{4-[2-(t-butyldimethylsilyloxy)-1-(t-butyldimethylsilyloxymethyl)ethylcarbamoyl]-1,3-thiazol-2-yl}azetidine

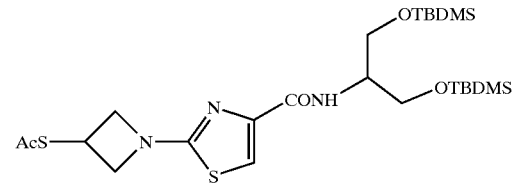

(1) t-Butyldiphenylsilyloxy-N-carbobenzyloxy-L-serine methyl ester

To a solution of N-carbobenzyloxy-L-serine (4.0 g, 16.7 mmol) in benzene (200 ml) and methanol (50 ml) was added a solution of 2M trimethylsilyldiazomethane in hexane (10.9 ml, 21.7 mmol) in an ice bath, and the mixture was stirred at room temperature for 3 hours. After checking the completion of the reaction, the reaction mixture was concentrated under reduced pressure. The residue was purified by chromatography on a silica gel column using n-hexane:ethyl acetate (1:1→1:3) as the eluant to afford N-carbobenzyloxy-L-serine methyl ester (4.40 g, yield 100%) as a colorless oil.

Subsequently, to a solution of N-carbobenzyloxy-L-serine methyl ester (4.40 g, 16.7 mmol) in dimethylformamide (210 ml) were added t-butyldiphenylsilyl chloride (5.20 ml, 20.0 mmol) and imidazole (1.36 g, 20.0 mmol) in an ice bath, and the mixture was stirred at room temperature for 3 days. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (8:1→6:1) as the eluant to afford t-butyldiphenylsilyloxy-N-carbobenzyloxy-L-serine methyl ester (18.8 g, 99%).

$^1$H-NMR (400 MHz, CDCl$_3$): δ (ppm) 7.61–7.56 (4H, m), 7.45–7.31 (11H, m), 5.69–5.62 (1H, br d, J=8.8 Hz), 5.12 (2H, s), 4.45 (1H, dt, J=8.1, 2.9 Hz), 4.09 (1H, dd, J=10.3, 2.9 Hz), 3.90 (1H, dd, J=10.3, 2.9 Hz), 3.74 (3H, s).

(2) [2-(t-Butyldiphenylsilyloxy)-1-(t-butyldiphenylsilyloxymethyl)ethyl]carbamic acid benzyl ester To a solution of t-butyldiphenylsilyloxy-N-carbobenzyloxy-L-serine methyl ester (11.5 g, 24.8 mmol) (obtained as described in Reference Example 39(1)) in a mixture of tetrahydrofuran (115 ml) and ethanol (230 ml) were added sodium borohydride (1.88 g, 49.6 mmol) and lithium chloride (2.10 g, 49.6 mmol) in an ice bath, and then the mixture was stirred at room temperature overnight. After checking the completion of the reaction, the reaction mixture was partitioned between methylene chloride and 10% aqueous acetic acid solution. The organic layer was washed successively with saturated aqueous sodium hydrogencarbonate solution and saturated aqueous sodium chloride solution, dried over anhydrous sodium sulfate, filtered and concentrated under reduced pressure. The obtained residue was purified by chromatography on a silica gel column using n-hexane:ethyl acetate (3:1→1:1) as the eluant to afford [2-(t-butyldiphenylsilyloxy)-1-(hydroxymethyl)ethyl]carbamic acid benzyl ester (9.26 g, yield 81%) as a colorless oil.

Subsequently, to a solution of [2-(t-butyldiphenylsilyloxy)-1-(hydroxymethyl)ethyl]carbamic acid benzyl ester (9.26 g, 20.0 mmol) in dimethylformamide (280 ml) were added t-butyldiphenylsilyl chloride (7.79 ml, 30.0 mmol) and imidazole (2.04 g, 30.0 mmol) in an ice bath, and the mixture was stirred at room temperature for 4 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (19:1→9:1) as the eluant to afford [2-(t-butyldiphenylsilyloxy)-1-(t-butyldiphenylsilyloxymethyl)ethyl]carbamic acid benzyl ester (13.6 g, 97%) as a colorless oil.

$^1$H-NMR (400 MHz, CDCl$_3$): δ (ppm) 7.65–7.60 (8H, m), 7.44–7.29 (17H, m), 5.05 (2H, s), 4.99–4.93 (1H, br d, J=8.8 Hz), 3.94–3.87 (1H, m), 3.85 (2H, dd, J=9.8, 3.9 Hz), 3.76 (2H, dd, J=9.8, 5.9 Hz), 1.02 (18H, s).

(3) 3-t-Butyldiphenyloxy-1-{4-[2-(t-butyldiphenylsilyloxy)-1-(t-butyldiphenylsilyloxymethyl)ethylcarbamoyl]-1,3-thiazol-2-yl}azetidine A solution of [2-(t-butyldiphenylsilyloxy)-1-(t-butyldiphenylsilyloxymethyl)ethyl]carbamic acid benzyl ester (13.6 g, 19.5 mmol) (obtained as described in Reference Example 39(2)) in methanol (410 ml) was subjected to catalytic hydrogenation in the presence of 10% palladium on charcoal (13.6 g) at room temperature for 3.5 hours. After checking the completion of the reaction, the reaction mixture was filtered in order to remove the catalyst and the filtrate concentrated under reduced pressure. The residue was purified by chromatography on a silica gel column using methylene chloride:methanol (98:2→9:1) as the eluant to afford 2-(t-butyldiphenylsilyloxy)-1-(t-butyldiphenylsilyloxymethyl)ethylamine (9.34 g, yield 84%) as a colorless oil.

Subsequently, to a solution of 3-t-butyldiphenylsilyloxy-1-(4-ethoxycarbonyl-1,3-thiazol-2-yl)azetidine (2.00 g, 4.29 mmol) (obtained as described in Reference Example 2(1)) in benzene (100 ml) was added a solution of 0.67M 2-(t-butyldiphenylsilyloxy)-1-(t-butyldiphenylsilyloxymethyl)ethylamine-trimethylaluminium in benzene (12.9 ml) at room temperature under an atmosphere of nitrogen. The mixture was heated under reflux overnight. After checking the completion of the reaction, 10% aqueous acetic acid solution (200 ml) and ethyl acetate (200 ml) were added to the reaction mixture, and the resulting mixture was stirred at room temperature for 3 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1→4:1) as the eluant to afford 3-t-butyldiphenyloxy-1-{4-[2-(t-butyldiphenylsilyloxy)-1-(t-butyldiphenylsilyloxymethyl)ethylcarbamoyl]-1,3-thiazol-2-yl}azetidine (3.19 g, yield 75%) as a pale yellow solid.

$^1$H-NMR (400 MHz, CDCl$_3$): δ (ppm) 7.70–7.65 (8H, m), 7.59–7.55 (4H, m), 7.44–7.28 (18H, m), 7.33 (1H, s), 4.71–4.64 (1H, m), 4.31–4.22 (1H, m), 4.04–3.97 (4H, m), 3.94 (2H, dd, J=9.2, 4.4 Hz), 3.82 (2H, dd, J=9.2, 6.2 Hz).

(4) 3-Hydroxy-1-{4-[2-hydroxy-1-(hydroxymethyl)ethylcarbamoyl]-1,3-thiazol-2-yl}azetidine To a solution of 3-t-butyldiphenyloxy-1-{4-[2-(t-butyldiphenylsilyloxy)-1-(t-butyldiphenylsilyloxymethyl)ethylcarbamoyl]-1,3-thiazol-2-yl}azetidine (3.19 g, 3.23 mmol) (obtained as described in Reference Example 39(3)) in anhydrous tetrahydrofuran (160 ml) was added a solution of 1.0M tetra-n-butylammonium fluoride in tetrahydrofuran (11.6 ml, 11.6 mmol) in an ice bath. The mixture was stirred in the ice bath for 2 hours. After checking the completion of the reaction, the reaction mixture was concentrated under reduced pressure. The residue was purified by chromatography on a silica gel column using ethyl acetate:methanol (9:1→8:2) as the eluant to afford 3-hydroxy-1-{4-[2-hydroxy-1-(hydroxymethyl)-ethylcarbamoyl]-1,3-thiazol-2-yl}azetidine (1.21 g, yield 100%) as a white solid.

$^1$H-NMR (400 MHz, DMSO-d$_6$): δ (ppm) 7.47–7.41 (1H, br d, J=8.8 Hz), 7.42 (1H, s), 5,84 (1H, d, J=6.6 Hz), 4.80 (2H, t, J=5.5 Hz), 4.66–4.58 (1H, m), 4.28–4.21 (2H, m), 3.88–3.81 (1H, m), 3.80 (2H, dd, J=8.8, 4.4 Hz), 3.53 (2H, m), 3.45 (2H, m).

(5) 1-{4-[2-(t-Butyldimethylsilyloxy)-1-(t-butyldimethylsilyloxymethyl)ethylcarbamoyl]-1,3-thiazol-2-yl}-3-hydroxyazetidine To a solution of 3-hydroxy-1-{4-[2-hydroxy-1-(hydroxymethyl)ethylcarbamoyl]-1,3-thiazol-2-yl}azetidine (750 mg, 2.74 mmol) (obtained as described in Reference Example 39(4)) in dimethylformamide (38 ml) were added t-butyldimethylsilyl chloride (951 mg, 6.31 mmol) and imidazole (430 mg, 6.31 mmol) in an ice bath, and the reaction mixture was stirred in the ice bath overnight. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (3:1→1:1) as the eluant to afford 1-{4-[2-(t-butyldimethylsilyloxy)-1-(t-butyldimethylsilyloxymethyl)ethylcarbamoyl]-1,3-thiazol-2-yl}-3-hydroxyazetidine (070 mg, yield 71%) as a pale yellow solid.

$^1$H-NMR (400 MHz, DMSO-d$_6$): δ (ppm) 7.62–7.57 (1H, br d, J=8.1 Hz), 7.38 (1H, s), 4.87–4.78 (1H, m), 4.30 (2H, dd, J=10.3, 6.6 Hz), 4.12–4.04 (1H, m), 3.93 (2H, dd, J=9.5, 4.4 Hz), 3.84 (2H, dd, J=9.5, 3.7 Hz), 3.62 (2H, dd, J=9.5, 6.6 Hz), 2.26–2.22 (1H, br d, J=6.6 Hz), 0.92 (18H, s), 0.08 (12H, s).

(6) 1-{4-[2-(t-Butyldimethylsilyloxy)-1-(t-butyldimethylsilyloxymethyl)ethylcarbamoyl]-1,3-thiazol-2-yl}-3-methanesulfonyloxyazetidine To a solution of 1-{4-[2-(t-butyldimethylsilyloxy)-1-(t-butyldimethylsilyloxymethyl)ethylcarbamoyl]-1,3-thiazol-2-yl}-3-hydroxyazetidine (1.27 g, 2.53 mmol) (obtained as described in Reference Example 39(5)) in methylene chloride (64 ml) were added methanesulfonyl chloride (587 µl, 7.59 mmol) and triethylamine (1.06 ml, 7.59 mmol) in an ice bath. After stirring the mixture in the ice bath for 10 minutes, the mixture was stirred at room temperature for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (3:1→1:2) as the eluant to afford 1-{4-[2-(t-butyldimethylsilyloxy)-1-(t-butyldimethylsilyloxymethyl)ethylcarbamoyl]-1,3-thiazol-2-yl}-3-methanesulfonyloxyazetidine (1.56 g, yield 100%) as a pale yellow solid.

$^1$H-NMR (400 MHz, CDCl$_3$): δ (ppm) 7.58–7.53 (1H, br d, J=8.8 Hz), 7.44 (1H, s), 5.43–5.38 (1H, m), 4.41 (2H, dd, J=9.5, 6.6 Hz), 4.23 (2H, dd, J=9.5, 5.9 Hz), 4.12–4.03 (1H, m), 3.84 (1H, dd, J=9.5, 2.9 Hz), 3.64 (2H, dd, J=9.5, 5.9 Hz), 3.11 (3H, s), 0.91 (18H, s), 0.07 (12H, s).

(7) 3-Acetylthio-1-{4-[2-(t-butyldimethylsilyloxy)-1-(t-butyldimethylsilyloxymethyl)-ethylcarbamoyl]-1,3-thiazol-2-yl}azetidine To a solution of 1-{4-[2-(t-butyldimethylsilyloxy)-1-(t-butyldimethylsilyloxymethyl)-ethylcarbamoyl]-1,3-thiazol-2-yl}-3-methanesulfonyloxyazetidine (1.56 g, 2.53 mmol) (obtained as described in Reference Example 39(6)) in dimethylformamide (78 ml) was added potassium thioacetate (1.73 g, 15.2 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:1→2:1) as the eluant to afford 3-acetylthio-1-{4-[2-(t-butyldimethylsilyloxy)-1-(t-butyldimethylsilyloxymethyl)-ethylcarbamoyl]-1,3-thiazol-2-yl}azetidine (773 mg, yield 57%) as a pale brown solid.

$^1$H-NMR (400 MHz, CDCl$_3$): δ (ppm) 7.59–7.53 (1H, br d, J=8.8 Hz), 7.40 (1H, s), 4.52–4.42 (3H, m), 4.11–4.06 (1H, m), 3.94 (2H, dd, J=8.4, 4.8 Hz), 3.83 (2H, dd, J=9.5, 3.3 Hz), 3.61 (2H, dd, J=9.5, 6.6 Hz), 2.37 (3H, s), 0.91 (18H, s), 0.07 (12H, s).

REFERENCE EXAMPLE 40

3-Acetylthio-1-4-{N-[2-(t-butyldimethylsilyloxy) ethyl]-N-methyl-carbamoyl}-1,3-thiazol-2-yl}azetidine

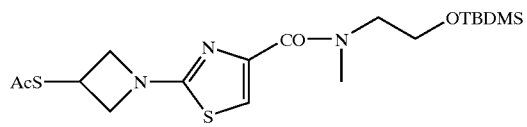

(1) N-[2-(t-Butyldiphenylsilyloxy)ethyl]-N-methyl-carbamic acid benzyl ester

To a solution of N-methylaminoethanol (1.20 ml, 15.0 mmol) in methylene chloride (36 ml) were added chloroformic acid benzyl ester (2.56 ml, 18.0.mmol) and triethylamine (2.52 ml, 18.0 mmol) in an ice bath. The mixture was stirred at room temperature for 3 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford N-(2-hydroxyethyl)-N-methyl-carbamic acid benzyl ester (2.8 g, yield 90%) as a pale yellow oil.

Subsequently, to a solution of N-(2-hydroxyethyl)-N-methylcarbamic acid benzyl ester (2.82 g, 13.5 mmol) in dimethylformamide (85 ml) were added t-butyldiphenylsilyl chloride (4.21 ml, 16.2 mmol) and imidazole (1.10 g, 16.2 mmol) in an ice bath. The resulting mixture was stirred at room temperature for 3 hours. After checking the completion of the reaction, methanol was added thereto and the reaction mixture was stirred for 30 minutes. The reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (9:1) as the eluant to afford N-[2-(t-butyldiphenylsilyloxy)ethyl]-N-methyl-carbamic acid benzyl ester (5.7 g, yield 94%) as a pale yellow solid.

$^1$H-NMR (400 MHz, CDCl$_3$): δ (ppm) 7.72 (1H, dd, J=7.4, 1.6 Hz), 7.47–7.20 (11H, m), 7.64 (4H, t, J=6.1 Hz), 5.12 (1H, s), 5.05 (1H, s), 3.80 (1H, t, J=5.5 Hz), 3.73 (1H, t, J=5.5 Hz), 3.45 (1H, t, J=5.6 Hz), 3.41 (1H, t, J=5.6 Hz), 2.99 (3H, s), 1.03 (9H, s).

(2) 3-t-Butyldiphenylsilyloxy-1-(4-{N-[2-(t-butyldiphenylsilyloxy)ethyl]-N-methyl-carbamoyl}-1,3-thiazol-2-yl)azetidine A solution of N-[2-(t-butyldiphenylsilyloxy)-ethyl]-N-methyl-carbamic acid benzyl ester (5.7 g, 12.7 mmol) (obtained as described in Reference Example 40(1)) in methanol (285 ml) was subjected to catalytic hydrogenation in the presence of 10% palladium on charcoal (5.7 g) at room temperature. After checking the completion of the reaction, the reaction mixture was filtered in order to remove the catalyst and the filtrate concentrated under reduced pressure. The residue was purified by chromatography on a silica gel column using ethyl acetate:methanol (19:2)→ethyl acetate:methanol (1:1) as the eluant to afford [2-(t-butyldiphenylsilyloxy)ethyl]methylamine (2.67 g, yield 69%) as a transparent oil.

Subsequently, to a solution of 3-t-butyldiphenylsilyloxy-1-(4-ethoxycarbonyl-1,3-thiazol-2-yl)azetidine (1,91 g, 4.09 mmol) (obtained as described in Reference Example 2(1)) in benzene (100 ml) was added a solution of 0.67M [2-(t-butyldiphenylsilyloxy)-ethyl]-methyl-amine-trimethylaluminium in benzene (13.6 ml) at room temperature under an atmosphere of nitrogen. The mixture was heated under reflux overnight. After checking the completion of the reaction, 10% aqueous acetic acid solution (100 ml) and ethyl acetate (100 ml) were added to the reaction mixture in an ice bath, and the resulting mixture was stirred at room temperature for 2 hours. After adding ethyl acetate thereto, the reaction mixture was partitioned between ethyl acetate and water. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-t-butyldiphenylsilyloxy-1-(4-{N-[2-(t-butyldiphenylsilyloxy)ethyl]-N-methyl-carbamoyl}-1,3-thiazol-2-yl)azetidine (2.54 g, yield 85%) as a pale yellow solid.

$^1$H-NMR (400 MHz, CDCl$_3$): δ (ppm) 7.74–7.55 (8H, m), 7.50–7.31 (12H, m), 7.00 (1H, s), 4.79–4.64 (1H, m), 4.08–3.59 (7H, m, including 4.80–4.00 (2H, m), 3.85–3.75 (2H, m)), 3.27 (0.3H, s), 3.07 (0.7H, s), 1.06 (9H, s), 1.02 (9H, s).

(3) 3-Hydroxy-1-{4-[N-(2-hydroxyethyl)-N-methyl-carbamoyl]-1,3-thiazol-2-yl}azetidine To a solution of 3-t-butyldiphenylsilyloxy-1-(4-{N-[2-(t-butyldiphenylsilyloxy)ethyl]-N-methyl-carbamoyl}-1,3-thiazol-2-yl)azetidine (2.24 g, 3.05 mmol) (obtained as described in Reference Example 40(2)) in anhydrous tetrahydrofuran (70 ml) was added a solution of 1.0M tetra-n-butylammonium fluoride in tetrahydrofuran (7.32 ml, 7.32 mmol) in an ice bath, and the mixture was stirred in the ice bath for 1 hour. After checking the completion of the reaction, the reaction mixture was concentrated under reduced pressure. The residue was purified by chromatography on a silica gel column using ethyl acetate:methanol (20:1)→ethyl acetate:methanol (15:1) as the eluant to afford 3-hydroxy-1-{4-[N-(2-hydroxyethyl)-N-methyl-carbamoyl]-1,3-thiazol-2-yl}azetidine (833 mg, yield 94%) as a white solid.

$^1$H-NMR (400 MHz, CDCl$_3$): δ (ppm) 7.18 (1H, s), 4.86–4.74 (1H, m), 4.29 (2H, t, J=8.4 Hz), 3.94 (2H, dd, J=8.4, 4.9 Hz), 3.86 (2H, t, J=5.0 Hz), 3.65 (2H, t, J=5.0 Hz), 3.07 (3H, s).

(4) 1-(4-{N-[2-(t-Butyldimethylsilyloxy)ethyl]-N-methyl-carbamoyl}-1,3-thiazol-2-yl)-3-hydroxyazetidine To a solution of 3-hydroxy-1-{4-[N-(2-hydroxyethyl)-N-methyl-carbamoyl]-1,3-thiazol-2-yl}azetidine (576 mg, 2.24 mmol) (obtained as described in Reference Example 40(3)) in dimethylformamide (29 ml) were added t-butyldimethylsilyl chloride (354 mg, 2.35 mmol) and imidazole (160 mg, 2.35 mmol) in an ice bath, and then the reaction mixture was stirred in the ice bath for 2 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using hexane:ethyl acetate (3:1)→ethyl acetate as the eluant to afford 1-(4-{N-[2-(t-butyldimethylsilyloxy)-ethyl]-N-methyl-carbamoyl}-1,3-thiazol-2-yl)-3-hydroxyazetidine (489 mg, yield 60%) as a pale yellow solid.

$^1$H-NMR (400 MHz, CDCl$_3$): δ (ppm) 7.11 (0.7H, s), 7.01 (0.3H, s), 4.87–4.76 (1H, m), 4.31 (2H, t, J=8.3 Hz), 3.96 (2H, dd, J=8.3, 4.5 Hz), 3.91–3.83 (1H, m), 3.79 (1H, d, J=4.5 Hz), 3.74 (1H, d, J=4.5 Hz), 3.66–3.52 (1H, m), 3.28 (0.9H, s), 3.11 (2.1H, s), 0.88 (9H, s), 0.05 (6H, d, J=14.0 Hz).

(5) 1-(4-{N-[2-(t-Butyldimethylsilyloxy)ethyl]-N-methyl-carbamoyl}-1,3-thiazol-2-yl)-3-methanesulfonyloxyazetidine To a solution of 1-(4-{N-[2-(t-butyldimethylsilyloxy)-ethyl]-N-methyl-carbamoyl}-1,3-thiazol-2-yl)-3-hydroxyazetidine (442 mg, 1.19 mmol) (obtained as described in Reference Example 40(4)) in methylene chloride (15 ml) were added methanesulfonyl chloride (0.12 ml, 1.49 mmol) and triethylamine (0.20 ml, 1.49 mmol) in an ice bath. The mixture was stirred in the ice bath for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (1:2) as the eluant to afford 1-(4-{N-[2-(t-butyldimethylsilyloxy)-ethyl]-N-methyl-carbamoyl}-1,3-thiazol-2-yl)-3-methanesulfonyloxyazetidine (517 mg, yield 97%) as a pale yellow solid.

$^1$H-NMR (400 MHz, CDCl$_3$): δ (ppm) 7.18 (0.6H, s), 7.08 (0.4H, s), 5.45–5.35 (1H, m), 4.42 (2H, t, J=8.7 Hz), 4.23 (2H, dd, J=8.7, 3.7 Hz), 3.91–3.81 (1H, m), 3.81–3.74 (1H, m), 3.74–3.67 (1H, m), 3.62–3.53 (1H, m), 3.26 (1.2H, s), 3.09 (1.8H, s), 0.85 (9H, s), 0.01 (6H, s).

(6) 3-Acetylthio-1-(4-{N-[2-(t-butyldimethylsilyloxy)ethyl]-N-methyl-carbamoyl}-1,3-thiazol-2-yl)azetidine To a solution of 1-(4-{N-[2-(t-butyldimethylsilyloxy)ethyl]-N-methyl-carbamoyl}-1,3-thiazol-2-yl)-3-methanesulfonyloxyazetidine (516 mg, 1.14 mmol) (obtained as described in Reference Example 40(5)) in dimethylformamide (15 ml) was added potassium thioacetate (815 mg, 7.14 mmol) at room temperature. The mixture was stirred in an oil bath (90° C.) for 3 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:2) as the eluant to afford 3-acetylthio-1-(4-{N-[2-(t-butyldimethylsilyloxy)ethyl]-N-methyl-carbamoyl}-1,3-thiazol-2-yl)azetidine (279 mg, yield 57%) as a pale brown solid.

$^1$H-NMR (400 MHz, CDCl$_3$): δ (ppm) 7.08 (0.7H, s), 7.16 (0.4H, s), 4.52 (2H, t, J=7.3 Hz), 4.48–4.39 (1H, m), 3.97 (2H, t, J=7.3 Hz), 3.92–3.82 (1H, m), 3.78 (1H, d, J=4.1 Hz), 3.75 (1H, d, J=4.1 Hz), 3.66–3.50 (1H, m), 3.59 (0.9H, s), 3.92 (2.1H, s), 2.39 (3H, s), 0.88 (9H, d, J=4.7 Hz), 0.04 (6H, d, J=1.5 Hz).

REFERENCE EXAMPLE 41 p-Nitrobenzyl (1R,5S,6S)-2-{1-[4-(p-nitrobenzyloxycarbonylmethyl)carbamoyl-1,3-thiazol-2-yl]azetidin-3-yl}thio-6-[(R)-1-t-butyldimethylsilyloxyethyl]-1-methylcarbapen-2-em-3-carboxylate

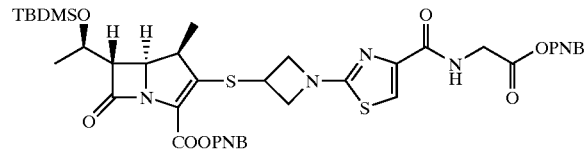

(1) 1-(4-Allyloxycarbonyl-1,3-thiazol-2-yl)-3-t-butyldiphenylsilyloxyazetidine

To a solution of 3-t-butyldiphenylsilyloxy-1-(4-carboxyl-1,3-thiazol-2-yl)azetidine (6.73 g, 15.3 mmol) (obtained as described in Reference Example 2(4)) in dimethylformamide (330 ml) were added allyl bromide (1.59 ml, 18.4 mmol) and diisopropylethylamine (3.21 ml, 18.4 mmol) at room temperature. The mixture was stirred in an oil bath (80° C.) for 10 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (5:1) as the eluant to afford 1-(4-allyloxycarbonyl-1,3-thiazol-2-yl)-3-t-butyldiphenylsilyloxyazetidine (5.31 g, yield 73%) as a brown oil.

$^1$H-NMR (400 MHz, CDCl$_3$): δ (ppm) 7.63–7.59 (4H, m), 7.46 (1H, s), 7.47–7.36 (6H, m), 6.04–5.95 (1H, m), 5.40–5.35 (1H, m), 5.28–5.24 (1H, m), 4.80–4.78 (2H, m), 4.77–4.71 (1H, m), 4.16 (2H, dd, J=8.8, 6.6 Hz), 4.06 (2H, dd, J=8.8, 4.4 Hz), 1.06 (9H, s).

(2) 1-(4-Allyloxycarbonyl-1,3-thiazol-2-yl)-3-hydroxyazetidine

To a solution of 1-(4-allyloxycarbonyl-1,3-thiazol-2-yl)-3-t-butyldiphenylsilyloxyazetidine (5.31 g, 11.1 mmol) (obtained as described in Reference Example 41(1)) in anhydrous tetrahydrofuran (266 ml) was added a solution of 1M tetrabutylammonium fluoride in tetrahydrofuran (13.3 ml, 13.3 mmol) in an ice bath. The mixture was stirred at room temperature overnight. After checking the completion of the reaction, the reaction mixture was concentrated under reduced pressure. The residue was purified by chromatography on a silica gel column using ethyl acetate as the eluant to afford 1-(4-allyloxycarbonyl-1,3-thiazol-2-yl)-3-hydroxyazetidine (2.91 g, yield 100%) as pale brown crystals.

$^1$H-NMR (400 MHz, CDCl$_3$): δ (ppm) 7.49 (1H, s), 6.06–5.96 (1H, m), 5.42–5.35 (1H, m), 5.29–5.24 (1H, m), 4.87–4.80 (1H, m), 4.79 (2H, d, J=5.9 Hz), 4.38 (2H, t, J=8.8 Hz), 4.02 (2H, dd, J=9.8, 3.9 Hz), 2.52–2.37 (1H, br s).

(3) 1-(4-Allyloxycarbonyl-1,3-thiazol-2-yl)-3-methanesulfonyloxyazetidine

To a solution of 1-(4-allyloxycarbonyl-1,3-thiazol-2-yl)-3-hydroxyazetidine (2.91 g, 11.1 mmol) (obtained as described in Reference Example 41(2)) in methylene chloride (146 ml) were added methanesulfonyl chloride (2.58 ml, 33.3 mmol) and triethylamine (4.67 ml, 33.3 mmol) in an ice bath. After stirring the mixture in the ice bath for 10 minutes, the mixture was stirred at room temperature for 2 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. To the residue were added ethyl acetate and diisopropyl ether, and then the mixture was filtered and the resulting residue was washed with diisopropyl ether to give 1-(4-allyloxycarbonyl-1,3-thiazol-2-yl)-3-methanesulfonyloxyazetidine (2.71 g, yield 77%) as pale brown crystals.

$^1$H-NMR (400 MHz, CDCl$_3$): δ (ppm) 7.55 (1H, s), 6.07–5.96 (1H, m), 5.45–5.35 (2H, m), 5.30–5.25 (1H, m), 4.81 (2H, dt, J=5.9, 1.5 Hz), 4.51 (2H, dd, J=11.0, 6.6, 1.5 Hz), 4.31 (2H, ddd, J=11.0, 4.4, 1.5 Hz), 3.10 (3H, s).

(4) 3-Acetylthio-1-(4-allyloxycarbonyl-1,3-thiazol-2-yl)azetidine

To a solution of 1-(4-allyloxycarbonyl-1,3-thiazol-2-yl)-3-methanesulfonyloxyazetidine (2.70 g, 8.51 mmol) (obtained as described in Reference Example 41(3)) in dimethylformamide (135 ml) was added potassium thioacetate (5.83 g, 51.1 mmol) at room temperature. The mixture was stirred in an oil bath (80° C.) for 10 hours. After checking the completion of the reaction, the reaction mixture was partitioned between ethyl acetate and 10% aqueous sodium chloride solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1) as the eluant to afford 3-acetylthio-1-(4-allyloxycarbonyl-1,3-thiazol-2-yl)azetidine (1.61 g, yield 63%) as a pale brown solid.

$^1$H-NMR (400 MHz, CDCl$_3$): δ (ppm) 7.51 (1H, s), 6.06–5.96 (1H, m), 5.41–5.35 (1H, m), 5.29–5.26 (1H, m), 4.58 (2H, t, J=8.1 Hz), 4.47–4.40 (1H, m), 4.04 (2H, dd, J=9.5, 5.9 Hz), 2.36 (3H, s).

(5) p-Nitrobenzyl (1R,5S,6S)-6-[(R)-1-t-butyldimethylsilyloxyethyl]-2-(diphenylphosphoryloxy)-1-methylcarbapen-2-em-3-carboxylate To a solution of p-nitrobenzyl(1R,5S,6S)-2-(diphenylphosphoryloxy)-6-[(R)-1-hydroxyethyl]-1-methylcarbapen-2-em-3-carboxylate (5.00 g, 8.41 mmol) in dimethylformamide (250 ml) were added t-butyldimethylsilyl chloride (2.54 g, 16.8 mmol) and imidazole (1.14 g, 16.8 mmol) in an ice bath, and the reaction mixture was stirred in the ice bath for 7 hours. After checking the completion of the reaction, methanol was added thereto and the resulting mixture was stirred for 30 minutes. The reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (3:1) as the eluant to afford p-nitrobenzyl (1R,5S,6S)-6-[(R)-1-t-butyldimethylsilyloxyethyl]-2-(diphenylphosphoryloxy)-1-methylcarbapen-2-em-3-carboxylate (5.27 g, yield 88%) as a pale yellow oil.

$^1$H-NMR (400 MHz, CDCl$_3$): δ (ppm) 8.14 (2H, d, J=8.8 Hz), 7.56 (2H, d, J=8.8 Hz), 7.39–7.29 (4H, m), 7.28–7.17 (6H, m), 5.34 (1H, d, J=13.9 Hz), 5.23 (1H, d, J=13.9 Hz), 4.24 (1H, dq, J=5.9, 5.9 Hz), 4.20 (1H, dd, J=10.3, 2.9 Hz), 3.43 (1H, dq, J=10.3, 7.3 Hz), 3.28 (1H, dd, J=5.9, 2.9 Hz), 1.23 (3H, d, J=5.9 Hz), 1.20 (3H, d, J=7.3 Hz), 0.86 (9H, s), 0.06 (6H, d, J=3.7 Hz).

(6) p-Nitrobenzyl (1R,5S,6S)-2-[1-(4-allyloxycarbonyl-1,3-thiazol-2-yl)azetidin-3-yl]thio-6-[(R)-1-t-butyldimethylsilyloxyethyl]-1-methylcarbapen-2-em-3-carboxylate To a solution of 3-acetylthio-1-(4-allyloxycarbonyl-1,3-thiazol-2-yl)azetidine (1.61 g, 5.40 mmol) (obtained Reference Example 41(4)) in dimethylformamide (80 ml) was added hydrazine acetate (596 mg, 6.47 mmol) at room temperature under an atmosphere of nitrogen, and the mixture was stirred for 1.5 hours under the same conditions. After checking the completion of the reaction, a solution of p-nitrobenzyl (1R,5S,6S)-6-[(R)-1-t-butyldimethylsilyloxyethyl]-2-(diphenylphosphoryloxy)-1-methylcarbapen-2-em-3-carboxylate (3.83 g, 5.40 mmol) (obtained as described in Reference Example 41(5)) in acetonitrile (190 ml) was added dropwise to the reaction mixture in an ice bath under an atmosphere of nitrogen.

Subsequently, diisopropylethylamine (3.76 ml, 21.6 mmol) was added to the reaction mixture, and the mixture was stirred overnight while gradually raising the temperature of reaction mixture to room temperature. After checking the completion of the reaction, the reaction mixture was partitioned between ethyl acetate and 10% aqueous sodium chloride solution. The obtained organic layer was washed with saturated aqueous sodium hydrogencarbonate solution and then washed with saturated aqueous sodium chloride solution, dried over anhydrous sodium sulfate, filtered and concentrated under reduced pressure. The residue was purified by chromatography on a silica gel column using n-hexane:ethyl acetate (1:1) as the eluant to afford p-nitrobenzyl (1R,5S,6S)-2-[1-(4-allyloxycarbonyl-1,3-thiazol-2-yl)azetidin-3-yl]thio-6-[(R)-1-t-butyldimethylsilyloxyethyl]-1-methyl-carbapen-2-em-3-carboxylate (3.73 g, yield 97%) as a pale yellow solid.

$^1$H-NMR (400 MHz, CDCl$_3$): δ (ppm) 8.21 (2H, d, J=8.8 Hz), 7.65 (2H, d, J=8.8 Hz), 7.53 (1H, s), 6.07–5.96 (1H, m), 5.45 (1H, d, J=13.9 Hz), 5.42–5.35 (1H, m), 5.30–5.25 (1H, m), 5.26 (1H, d, J=13.9 Hz), 4.80 (2H, d, J=5.1 Hz), 4.55 (2H, q, J=8.1 Hz), 4.32–4.22 (3H, m), 4.15–4.09 (3H, m), 3.26 (1H, dd, J=5.1, 2.9 Hz), 3.13 (1H, J=9.5, 7.3 Hz), 1.25 (3H, d, J=5.9 Hz), 1.24 (3H, d, J=7.3 Hz), 0.87 (9H, s), 0.08 (6H, d, J=5.1 Hz).

(7) p-Nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate To a solution of p-nitrobenzyl (1R,5S,6S)-2-[1-(4-allyloxycarbonyl-1,3-thiazol-2-yl)azetidin-3-yl]thio-6-[(R)-1-t-butyldimethylsilyloxyethyl]-1-methylcarbapen-2-em-3-carboxylate (3.73 g, 5.2 mmol) (obtained Reference Example 41(6)) in methylene chloride (180 ml) were added dimedone (1.46 g, 10.4 mmol), tetrakis(triphenylphosphine) palladium(0) (603 mg, 0.522 mmol) and triphenylphosphine (205 mg, 0.783 mmol), and the mixture was stirred at room temperature under an atmosphere of nitrogen for 2 hours. After checking the completion of the reaction, the reaction mixture was partitioned between ethyl acetate and saturated aqueous sodium chloride solution. The obtained organic layer was dried over anhydrous sodium sulfate, filtered and concentrated under reduced pressure. The residue was purified by chromatography on a silica gel column using ethyl acetate:methanol (10:1)→methylene chloride:methanol (10:1) as the eluant to afford p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methyl-carbapen-2-em-3-carboxylate (1.91 g, yield 54%) as a pale brown solid.

Mass spectrum (FAB$^+$): m/z: 675 [M+H]$^+$.

(8) N-(t-Butoxycarbonyl)glycine p-nitrobenzyl ester

To a solution of N-(t-butoxycarbonyl)glycine (1.51 g, 8.62 mmol) in anhydrous methylene chloride (75 ml) were added p-nitrobenzyl alcohol (2.63 ml, 17.2 mmol), 1-ethyl-3-(3-dimethylaminopropyl)carbodiimide hydrochloride (hereinafter referred to as WSC) (3.3 g, 17.2 mmol) and 4-dimethylaminopyridine (106 mg, 0.87 mmol) in an ice bath. The mixture was stirred at room temperature under an atmosphere of nitrogen overnight. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using hexane:ethyl acetate (2:1) as the eluant to afford N-(t-butoxycarbonyl)glycine p-nitrobenzyl ester (2.67 g, yield 100%) as white crystals.

$^1$H-NMR (400 MHz, CDCl$_3$): δ (ppm) 8.23 (2H, d, J=7.5 Hz), 7.53 (2H, d, J=7.5 Hz), 5.28 (2H, s), 5.02 (1H, br t, J=3.3 Hz), 4.00 (2H, d, J=3.3 Hz), 1.46 (9H, s).

(9) p-Nitrobenzyl (1R,5S,6S)-2-{1-[4-(p-nitrobenzyloxycarbonylmethyl)carbamoyl-1,3-thiazol-2-yl]azetidin-3-yl}thio-6-[(R)-1-t-butyldimethylsilyloxyethyl]-1-methyl-carbapen-2-em-3-carboxylate To a solution of N-(t-butoxycarbonyl)glycine nitrobenzyl ester (2.67 g, 8.62 mmol) (obtained as described in Reference Example 41(8)) in 1,4-dioxane (27 ml) was added a solution of 4N hydrogen chloride in 1,4-dioxane (27 ml) in an ice bath. The reaction mixture was stirred at room temperature for 4 hours. After checking the completion of the reaction, diethyl ether was added thereto and the reaction mixture was stirred for 30 minutes. The resulting reaction mixture was filtered, and the obtained residue was washed with diethyl ether and dried to give glycine p-nitrobenzyl ester hydrochloride (1.59 g, yield 75%) as white crystals.

Subsequently, to a suspension of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (207.4 mg, 0.31 mmol) (obtained as described in Reference Example 41(7)) and glycine p-nitrobenzyl ester hydrochloride (116 mg, 0.47 mmol) (obtained as described above) in dimethylformamide (10.5 ml) were added diethylphosphoryl cyanide (0.072 ml, 0.47 mmol) and triethylamine (0.14 ml, 1.00 mmol) in an ice bath under an atmosphere of nitrogen. The mixture was stirred at room temperature for 2 hours. After checking the completion of the reaction, the reaction mixture was partitioned between ethyl acetate and saturated aqueous sodium hydrogencarbonate solution. The obtained organic layer was washed successively with a 0.5M aqueous hydrochloric acid solution, saturated aqueous sodium hydrogencarbonate solution, and saturated aqueous sodium chloride solution, dried over anhydrous magnesium sulfate, filtered and concentrated under reduced pressure. The residue was purified by chromatography on a silica gel column using toluene-:acetonitrile (3:1) as the eluant to afford p-nitrobenzyl (1R,5S,6S)-2-{1-[4-(p-nitrobenzyloxycarbonylmethyl)carbamoyl-1,3-thiazol-2-yl]azetidin-3-yl}thio-6-[(R)-1-t-butyldimethylsilyloxyethyl]-1-methylcarbapen-2-em-3-carboxylate (209.7 mg, yield 77%) as a pale yellow syrup.

$^1$H-NMR (400 MHz, CDCl$_3$): δ (ppm) 8.23 (2H, d, J=8.8 Hz), 8.22 (2H, d, J=8.8 Hz), 7.65 (2H, d, J=8.8 Hz), 7.59 (1H, t, J=3.3 Hz), 7.54 (2H, d, J=8.8 Hz), 7.47 (1H, s), 5.46 (1H, d, J=13.9 Hz), 5.30 (2H, s), 5.27 (1H, d, J=13.9 Hz), 4.51 (1H, t, J=8.3 Hz), 4.47 (1H, t, J=8.3 Hz), 4.37–4.23 (5H, m), 4.08 (1H, dd, J=8.3, 3.3 Hz), 4.06 (1H, dd, J=8.3, 3.3 Hz), 3.27 (1H, dd, J=6.2, 3.6 Hz), 3.16 (1H, dq, J=11.5, 8.8 Hz), 1.27 (3H, d, J=8.8 Hz), 1.25 (3H, d, J=8.8 Hz), 0.87 (9H, s), 0.09 (3H, s), 0.08 (3H, s).

REFERENCE EXAMPLE 42 p-Nitrobenzyl (1R,5S,6S)-2-{1-[4-(3-t-butyldiphenylsilyloxyazetidine-1-carbonyl)-1,3-thiazol-2-yl]azetidin-3-yl}thio-6-[(R)-1-t-butyldimethylsilyloxyethyl]-1-methylcarbapen-2-em-3-carboxylate

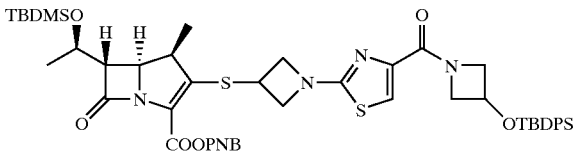

(1) 1-Benzyloxycarbonyl-3-t-butyldiphenylsilyloxyazetidine

A solution of 1-benzhydryl-3-hydroxyazetidine (10 g, 41.8 mmol) in methanol (300 ml) was subjected to catalytic hydrogenation in the presence of 10% palladium (10 g) on charcoal in a water bath (50° C.) for 3 hours. After checking the completion of the reaction, the reaction mixture was filtered and the residue washed with methanol. The combined filtrate was concentrated under reduced pressure. The residue was partitioned between ethyl acetate and distilled water. The organic layer was concentrated under reduced pressure, and the obtained residue dried under reduced pressure. The resulting crude product was dissolved in a mixture of methylene chloride (120 ml) and methanol (120 ml), chloroformic acid benzyl ester (8.95 ml, 62.7 mmol) and triethylamine (8.79 ml, 62,7 mmol) were added thereto, and the mixture was stirred at room temperature overnight. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1)→ethyl acetate as the eluant to afford 1-benzyloxycarbonyl-3-hydroxyazetidine (1.91 g, yield 22%).

Subsequently, to a solution of 1-benzyloxycarbonyl-3-hydroxyazetidine (1.91 g, 9.22 mmol) in dimethylformamide (96 ml) were added t-butyldiphenylsilyl chloride (2.88 ml, 11.1 mmol) and imidazole (756 mg, 11.1 mmol) in an ice bath. The resulting mixture was stirred in the ice bath for 6 hours. After checking the completion of the reaction, the reaction mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (6:1) as the eluant to afford 1-benzyloxycarbonyl-3-t-butyldiphenylsilyloxyazetidine (4.04 g, yield 98%) as a colorless oil.

$^1$H-NMR (400 MHz, CDCl$_3$): δ (ppm) 7.73–7.70 (1H, m), 7.60–7.56 (4H, m), 7.46–7.29 (10H, m), 5.07 (2H, s), 4.58–4.52 (1H, m), 4.01 (2H, m), 3.95 (2H, dd, J=9.8, 4.9 Hz), 1.05 (9H, s).

(2) p-Nitrobenzyl (1R,5S,6S)-2-{1-[4-(3-t-butyldiphenylsilyloxyazetidine-1-carbonyl)-1,3-thiazol-2-yl]azetidin-3-yl}thio-6-[(R)-1-t-butyldimethylsilyloxyethyl]-1-methylcarbapen-2-em-3-carboxylate A solution of 1-benzyloxycarbonyl-3-t-butyldiphenylsilyloxyazetidine (4.04 g, 9.07 mmol) in methanol (200 ml) was subjected to catalytic hydrogenation in the presence of 10% palladium on charcoal (4.04 g) at room temperature for 1.5 hours. After checking the completion of the reaction, the reaction mixture was filtered and the filtrate concentrated under reduced pressure, and the obtained residue was dried under reduced pressure to give 3-t-butyldiphenylsilyloxyazetidine (2.70 g, yield 96%) as a colorless oil.

Subsequently, to a solution of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (1.71 g, 2.53 mmol) and 3-t-butyldiphenylsilyloxyazetidine (947 mg, 3.04 mmol) (obtained as described above) in dimethylformamide (86 ml) were added diethylphosphoryl cyanide (461 μl, 3.04 mmol) and triethylamine (426 μl, 3.04 mmol) in an ice bath under an atmosphere of nitrogen. The mixture was stirred at room temperature for 5.5 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using toluene:acetonitrile (4:1) as the eluant to afford p-nitrobenzyl (1R,5S,6S)-2-{1-[4-(3-t-butyldiphenylsilyloxyazetidine-1-carbonyl)-1,3-thiazol-2-yl]azetidin-3-yl}thio-6-[(R)-1-t-butyldimethylsilyloxyethyl]-1-methylcarbapen-2-em-3-carboxylate (789 mg, yield 32%).

$^1$H-NMR (400 MHz, CDCl$_3$): δ (ppm) 8.22 (2H, d, J=8.8 Hz), 7.66 (2H, d, J=8.8 Hz), 7.62 (2H, d, J=8.8 Hz), 7.47–7.36 (6H, m), 7.39 (1H, s), 5.46 (1H, d, J=13.7 Hz), 5.27 (1H, d, J=13.7 Hz), 4.65–4.52 (2H, m), 4.50–4.42 (2H, m), 4.40–4.34 (1H, m), 4.32–4.26 (3H, m), 4.19–4.11 (1H, m), 4.06–4.00 (3H, m), 3.28 (1H, dd, J=4.9, 2.9 Hz), 3.18 (1H, dq, J=8.8, 7.8 Hz), 1.27 (3H, d, J=7.8 Hz), 1.26 (3H, d, J=5.9 Hz), 1.07 (9H, s), 0.87 (9H, s), 0.09 (6H, d, J=5.9 Hz).

REFERENCE EXAMPLE 43 p-Nitrobenzyl (1R,5S,6S)-2-(1-{4-[N-methyl-N-(p-nitrobenzyloxycarbonyl)methyl-carbamoyl]-1,3-thiazol-2-yl}azetidine-3-yl)thio-6-[(R)-1-t-butyldimethylsilyloxyethyl]-1-methyl-carbapen-2-em-3-carboxylate

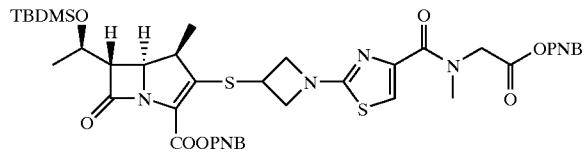

(1) (N-t-Butoxycarbonyl-N-methyl-amino)acetic acid p-nitrobenzyl ester

To a solution of sarcosine (3.56 g, 40 mmol) in a mixture of methanol (180 ml) and distilled water (90 ml) was added 1M aqueous sodium hydroxide solution (80 ml) in an ice bath, and the mixture was stirred at room temperature for 1.5 hours. After checking the completion of the reaction, Dowex-50W was added thereto in the ice bath to adjust the pH of the reaction mixture to 5 to 4. The reaction mixture was filtered and the filtrate concentrated under reduced pressure to give (N-t-butoxycarbonyl-N-methyl-amino) acetic acid (7.57 g) as a crude product.

Subsequently, to a solution of (N-t-butoxycarbonyl-N-methyl-amino)acetic acid (2.52 g, 13.3 mmol) and p-nitrobenzyl alcohol (4.07 g, 26.6 mmol) in methylene chloride (125 ml) were added WSC (5,10 g, 26.6 mmol) and 4-dimethylaminopyridine (252 mg, 1.33 mmol) in an ice bath under an atmosphere of nitrogen, and the mixture was stirred at room temperature overnight. After checking the completion of the reaction, the reaction mixture was partitioned between ethyl acetate and saturated aqueous sodium chloride solution. The organic layer was dried over anhydrous magnesium sulfate, filtered and concentrated under reduced pressure. The residue was purified by chromatography on a silica gel column using hexane:ethyl acetate (1:1) as the eluant to afford (N-t-butoxycarbonyl-N-methyl-amino)acetic acid p-nitrobenzyl ester (4.30 g, yield 88%) as a pale yellow oil.

$^1$H-NMR (400 MHz, CDCl$_3$): δ (ppm) 8.28–8.29 (2H, m), 7.58–7.47 (2H, m), 5.72 (2H, d, J=2.2 Hz), 4.07 (1.2H, s), 3.99 (0.8H, s), 2.95 (3H, d, J=5.8 Hz), 1.47 (5.4H, s), 1.39 (3.6H, s).

(2) Sarcosine p-nitrobenzyl ester hydrochloride

To a solution of (N-t-butoxycarbonyl-N-methyl-amino) acetic acid p-nitrobenzyl ester (4.30 g, 133 mmol) (obtained as described in Reference Example 43(1)) was added a solution of 4N hydrogen chloride in 1,4-dioxane (4.3 ml) in an ice bath, and the mixture was stirred at room temperature for 2.5 hours. After checking the completion of the reaction, diethyl ether was added thereto and the reaction mixture was stirred for 30 minutes. The resulting reaction mixture was filtered and the obtained residue was washed with diethyl ether and dried to give sarcosine p-nitrobenzyl ester hydrochloride (3.04 g, yield 88%).

$^1$H-NMR (400 MHz, CDCl$_3$): δ (ppm) 8.32–8.23 (2H, m), 7.72–7.60 (2H, m), 5.42 (2H, s), 4.08 (2H, s), 2.77 (3H, s).

(3) p-Nitrobenzyl (1R,5S,6S)-2-(1-{4-[N-methyl-N-(p-nitrobenzyloxycarbonyl)methylcarbamoyl]-1,3-thiazol-2-yl}azetidin-3-yl)thio-6-[(R)-1-(t-butyldimethylsilyloxy)ethyl]-1-methylcarbapen-2-em-3-carboxylate To a suspension of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (1.00 g, 1.51 mmol) (obtained as described in Reference Example 41(7)) and sarcosine p-nitrobenzyl ester hydrochloride (590 mg, 2.26 mmol) (obtained as described in Reference Example 43(2)) in dimethylformamide (30 ml) were added diethylphosphoryl cyanide (0.37 ml, 2.26 mmol) and triethylamine (0.95 ml, 6.80 mmol) in an ice bath under an atmosphere of nitrogen. The mixture was stirred at room temperature for 3 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using hexane:ethyl acetate (1:1)→ethyl acetate as the eluant to afford p-nitrobenzyl (1R,5S,6S)-2-(1-{4-[N-methyl-N-(p-nitrobenzyloxycarbonyl)methyl-carbamoyl]-1,3-thiazol-2-yl}azetidin-3-yl)thio-6-[(R)-1-(t-butyldimethylsilyloxy) ethyl]-1-methylcarbapen-2-em-3-carboxylate (997 mg, yield 76%).

$^1$H-NMR (400 MHz, CDCl$_3$): δ (ppm) 8.29–8.15 (4H, m), 7.71–7.62 (2H, m), 7.58–7.42 (2H, m), 7.40 (0.6H, s), 7.25 (0.4H, s), 5.46 (1H, d, J=13.8 Hz), 5.34–5.22 (3H, m including 5.26 (1H, d, J=13.9 Hz)), 4.63 (1H, s), 4.57–4.45 (1H, m), 4.27 (2H, t, J=9.6 Hz), 4.26 (2H, t, J=9.6 Hz), 3.89 (1H, dd, J=7.7, 5.8 Hz), 3.36 (1.2H, s), 3.15 (1.8H, s), 3.26 (1H, dd, J=5.0, 2.6 Hz), 1.25 (6H, d, J=7.2 Hz), 0.86 (9H, s), 0.08 (6H, d, J=5.0 Hz).

REFERENCE EXAMPLE 44 p-Nitrobenzyl (1R,5S,6S)-2-(1-{4-[N-methyl-N-(carbamoyl)methyl-carbamoyl]-1,3-thiazol-2-yl}azetidin-3-yl)thio-6-[(R)-1-t-butyldimethylsilyloxyethyl]-1-methylcarbapen-2-em-3-carboxylate

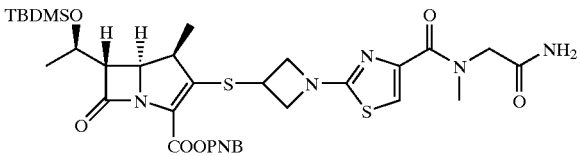

(1) N-Carbamoylmethyl-N-methyl-carbamic acid t-butyl ester

To a solution of N-(t-butoxycarbonyl-N-methyl-amino)-acetic acid (5.03 g, 26.6 mmol) (obtained as described in Reference Example 43(1)) in methylene chloride (250 ml) were added 1-hydroxybenzotriazole (7.19 g, 53.2 mmol), WSC (10.2 g, 53.2 mmol) and 4-dimethylaminopyridine (325 mg, 2.66 mmol) in an ice bath, and the mixture was stirred at room temperature under an atmosphere of nitrogen for 2 days. After checking the completion of the reaction, 28% aqueous ammonia solution was added thereto and the reaction mixture was stirred for 30 minutes. After checking the completion of the reaction, the reaction mixture was partitioned between ethyl acetate and saturated aqueous sodium chloride solution. The organic layer was dried over anhydrous magnesium sulfate, filtered and concentrated under reduced pressure. The residue was purified by chromatography on a silica gel column using methylene chloride:methanol (10:1) as the eluant to afford N-carbamoylmethyl-N-methyl-carbamic acid t-butyl ester (848 mg, yield 17%) as a pale yellow oil.

$^1$H-NMR (400 MHz, CDCl$_3$): δ (ppm) 3.87 (2H, s), 2.96 (3H, s), 1.47 (9H, s).

(2) p-Nitrobenzyl (1R,5S,6S)-2-(1-{4-[N-methyl-N-(carbamoyl)methyl-carbamoyl]-1,3-thiazol-2-yl}azetidin-3-yl)thio-6-[(R)-1-t-butyldimethylsilyloxyethyl]-1-methylcarbapen-2-em-3-carboxylate To a solution of N-carbamoylmethyl-N-methyl-carbamic acid t-butyl ester (848 mg, 4.50 mmol) (obtained as described in Reference Example 44(1)) in 1,4-dioxane (8.50 ml) was added a solution of 4N hydrogen chloride in 1,4-dioxane (8.50 ml) in an ice bath, and the mixture was stirred at room temperature for 2.5 hours. After checking the completion of the reaction, diethyl ether was added thereto, and the reaction mixture was stirred for 30 minutes. The resulting reaction mixture was filtered, and the obtained residue was washed with diethyl ether and dried to give 2-methylaminoacetamide hydrochloride (421 mg, yield 75%).

Subsequently, to a suspension of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (1.00 g, 1.51 mmol) (obtained as described in Reference Example 41(7)) and 2-methylaminoacetamide hydrochloride (282 mg, 2.26 mmol) (obtained as described above) in dimethylformamide (30 ml) were added diethylphosphoryl cyanide (0.37 ml, 2.26 mmol) and triethylamine (0.95 ml, 6.80 mmol) in an ice bath under an atmosphere of nitrogen. The mixture was stirred at room temperature for 3.5 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution, and saturated aqueous sodium chloride solution, dried over anhydrous sodium sulfate, filtered and concentrated under reduced pressure. The residue was purified by chromatography on a silica gel column using ethyl acetate ethyl acetate:methanol (10:1) as the eluant to afford p-nitrobenzyl (1R,5S,6S)-2-(1-{4-[N-methyl-N-(carbamoyl)methyl-carbamoyl]-1,3-thiazol-2-yl}azetidin-3-yl)thio-6-[(R)-1-(t-butyldimethylsilyloxy)ethyl]-1-methylcarbapen-2-em-3-carboxylate (932 mg, yield 84%).

$^1$H-NMR (400 MHz, CDCl$_3$): δ (ppm) 8.22 (2H, d, J=7.9 Hz), 7.65 (2H, d, J=7.9), 7.35 (0.7H, s), 7.23 (0.3H, s), 5.46 (1H, d, J=13.9 Hz), 5.26 (1H, d, J=13:9 Hz), 4.62–4.40 (2H, m), 4.40–4.22 (3H, m), 4.20 (1H, s), 4.12 (2H, dd, J=14.2, 7.1 Hz), 4.07–3.97 (1H, m), 4.04 (0.6H, br s), 3.27 (1H, dd, J=5.0, 2.8 Hz), 3.15 (1H, dq, J=9.5, 7.3 Hz), 3.11 (2.4H, br s), 1.25 (6H, d, J=5.8 Hz), 0.87 (9H, s), 0.08 (6H, d, J=5.0 Hz).

REFERENCE EXAMPLE 45 p-Nitrobenzyl (1R,5S,6S)-2-{1-[4-(carbamoylmethyl)carbamoyl-1,3-thiazol-2-yl]azetidin-3-yl}thio-6-[(R)-1-t-butyldimethylsilyloxyethyl]-1-methylcarbapen-2-em-3-carboxylate

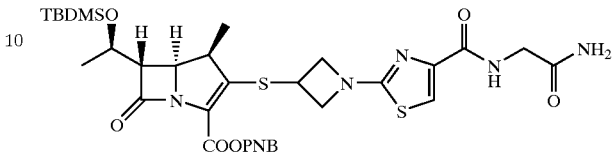

(1) (Carbamoylmethyl)carbamic acid t-butyl ester

To a solution of N-(t-butoxycarbonyl)glycine (3.01 g, 17.2 mmol) in anhydrous methylene chloride (150 ml) were added 1-hydroxybenzotriazole (4.63 g, 34.3 mmol), WSC (6.60 g, 34.4 mmol) and 4-dimethylaminopyridine (210 mg, 1.72 mmol) in an ice bath. The mixture was stirred at room temperature under an atmosphere of nitrogen overnight. After checking the completion of the reaction, 28% aqueous ammonia solution was added thereto and resulting mixture was stirred for 15 minutes. After checking the completion of the reaction, the reaction mixture was partitioned between methylene chloride and saturated aqueous sodium chloride solution. The organic layer was dried over anhydrous magnesium sulfate, filtered and concentrated under reduced pressure. The residue was purified by chromatography on a silica gel column using ethyl acetate:methanol (10:1) as the eluant to afford (carbamoylmethyl)carbamic acid t-butyl ester (717.7 mg, yield 24%) as a colorless and transparent syrup.

$^1$H-NMR (400 MHz, CDCl$_3$): δ (ppm) 6.202 (1H, br s), 5.763 (1H, br s), 5.267 (1H, br t, J=5.1 Hz), 3.820 (2H, d, J=5.1 Hz), 1.456 (9H, s).

(2) p-Nitrobenzyl (1R,5S,6S)-2-{1-[4-(carbamoylmethyl)carbamoyl-1,3-thiazol-2-yl]azetidin-3-yl}thio-6-[(R)-1-t-butyldimethylsilyloxyethyl]-1-methylcarbapen-2-em-3-carboxylate To a solution of (carbamoylmethyl)carbamic acid t-butyl ester (717.2 mg, 4.12 mmol) (obtained as described in Reference Example 45(1)) in 1,4-dioxane (7.2 ml) was added a solution of 4N hydrogen chloride in 1,4-dioxane (7.2 ml) in an ice bath. The reaction mixture was stirred at room temperature overnight. After checking the completion of the reaction, diethyl ether was added thereto, and the reaction mixture was stirred for 30 minutes. The resulting reaction mixture was filtered, and the obtained residue was washed with diethyl ether and dried to give glycinamide hydrochloride (389 mg, yield 86%) as white crystals. Subsequently, to a suspension of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (566.6 mg, 0.85 mmol) (obtained as described in Reference Example 41(7)) and glycinamide hydrochloride (154.3 mg, 1.40 mmol) (obtained as described above) in dimethylformamide (28.0 ml) were added diethylphosphoryl cyanide (0.2 ml, 1.32 mmol) and triethylamine (0.36 ml, 2.6 mmol) in an ice bath under an atmosphere of nitrogen. The mixture was stirred at room temperature for 5 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using toluene:acetonitrile (2:3) as the eluant to afford p-nitrobenzyl (1R,5S,6S)-2-{1-[4-(carbamoylmethyl) carbamoyl-1,3-thiazol-2-yl]azetidin-3-yl}thio-6-[(R)-1-t-butyldimethylsilyloxyethyl]-1-methyl-carbapen-2-em-3-carboxylate (428.6 mg, yield 70%) as a pale yellow solid.

$^1$H-NMR (400 MHz, CDCl$_3$): δ (ppm) 8.21 (2H, d, J=8.4 Hz), 7.70 (1H, t, J=5.3 Hz), 7.65 (2H, d, J=8.4 Hz), 7.46 (1H, s), 6.15 (1H, br s), 5.46 (1H, d, J=13.4 Hz), 5.43 (1H, br s), 5.27 (1H, d, J=13.4 Hz), 4.52 (1H, t, J=8.3 Hz), 4.50 (1H, t, J=8.3 Hz), 4.345–4.24 (3H, m), 4.12–4.04 (4H, m), 3.265 (1H, dd, J=5.1, 2.7 Hz), 3.155 (1H, dq, J=9.4, 7.0 Hz), 1.264 (3H, d, J=7.0 Hz), 1.22 (3H, d, J=4.8 Hz), 0.86 (9H, s), 0.09 (3H, s), 0.08 (3H, s).

REFERENCE EXAMPLE 46 p-Nitrobenzyl (1R,5S,6S)-2-{1-[4-((1S)-2-methyl-1-(p-nitrobenzyloxycarbonyl)-propylcarbamoyl)-1,3-thiazol-2-yl]azetidin-3-yl}thio-6-[(R)-1-t-butyldimethylsilyloxyethyl]-1-methylcarbapen-2-em-3-carboxylate

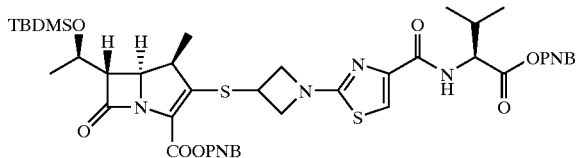

(1) N-(t-Butoxycarbonyl)-L-valine p-nitrobenzyl ester

To a solution of N-(t-butoxycarbonyl)-L-valine (2.50 g, 11.5 mmol) in methylene chloride (125 ml) were added p-nitrobenzyl alcohol (3.52 g, 23.0 mmol), WSC (4.41 g, 23.0 mmol) and 4-dimethylaminopyridine (140 mg, 1.15 mmol) in an ice bath. The mixture was stirred at room temperature under an atmosphere of nitrogen for 4.5 hours. After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using n-hexane:ethyl acetate (2:1) as the eluant to afford N-(t-butoxycarbonyl)-L-valine p-nitrobenzyl ester (3.07 g, yield 76%) as white crystals.

$^1$H-NMR (400 MHz, CDCl$_3$): δ (ppm) 8.23 (2H, d, J=8.8 Hz), 7.53 (2H, d, J=8.8 Hz), 5.26 (2H, d, J=5.1 Hz), 5.00–4.94 (1H, m), 2.21–2.10 (1H, m), 1.45 (9H, s), 0.97 (3H, d, J=7.3 Hz), 0.88 (3H, d, J=6.6 Hz).

(2) L-Valine p-nitrobenzyl alcohol hydrochloride

To a solution of N-(t-butoxycarbonyl)-L-valine p-nitrobenzyl ester (3.07 g, 8.71 mmol) (obtained as described in Reference Example 46(1)) in 1,4-dioxane (31 ml) was added a solution of 4N hydrogen chloride in 1,4-dioxane (31 ml) in an ice bath, and the mixture was stirred at room temperature overnight. After checking the completion of the reaction, the reaction mixture was concentrated under reduced pressure, to the obtained residue was added ethyl acetate, and the mixture was filtered. The resulting residue was washed with ethyl acetate and dried to give L-valine p-nitrobenzyl ester hydrochloride (2.21 g, yield 88%).

Elemental analysis: Observed value: C, 48.77%; H, 5.63%; N, 9.49% Cl, 12.38%. Calculated value: C, 49.92%; H, 5.93%; N, 9.70% Cl, 12.28%.

(3) p-Nitrobenzyl (1R,5S,6S)-2-{1-[4-((1S)-2-methyl-1-(p-nitrobenzyloxycarbonyl)-propylcarbamoyl)-1,3-thiazol-2-yl]azetidin-3-yl}thio-6-[(R)-1-t-butyldimethylsilyloxyethyl]-1-methylcarbapen-2-em-3-carboxylate To a solution of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (1.00 g, 1.48 mmol) (obtained as described in Reference Example 41(7)) and L-valine p-nitrobenzyl ester hydrochloride (514 mg, 1.78 mmol) (obtained as described in Reference Example 46(2)) in dimethylformamide (50 ml) were added diethylphosphoryl cyanide (275 μl, 1.78 mmol) and diisopropylethylamine (620 μl, 3.56 mmol) in an ice bath under an atmosphere of nitrogen. The mixture was stirred at room temperature for 2 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1→1:1) as the eluant to afford p-nitrobenzyl(1R,5S,6S)-2-{1-[4-((1S)-2-methyl-1-(p-nitrobenzyloxycarbonyl)-propylcarbamoyl)-1,3-thiazol-2-yl]azetidin-3-yl}thio-6-[(R)-1-t-butyldimethylsilyloxyethyl]-1-methylcarbapen-2-em-3-carboxylate (1.15 g, yield 86%).

$^1$H-NMR (400 MHz, CDCl$_3$): δ (ppm) 8.23 (2H, d, J=8.8 Hz), 8.21 (2H, d, J=8.8 Hz), 7.65 (2H, d, J=8.8 Hz), 7.58–7.55 (1H, br s), 7.54 (2H, d, J=8.8 Hz), 7.45 (1H, s), 5.46 (1H, d, J=13.9 Hz), 5.28 (2H, s), 5.27 (1H, d, J=13.9 Hz), 4.74 (1H, dd, J=9.5, 5.9 Hz), 4.51 (2H, t, J=8.8 Hz), 4.33–4.24 (3H, m), 4.08 (2H, dd, J=8.8, 5.9 Hz), 3.27 (1H, dd, J=5.1, 2.9 Hz), 3.17 (1H, dq, J=9.5, 7.3 Hz), 2.33–2.24 (1H, m), 1.26 (3H, d, J=7.3 Hz), 1.25 (3H, d, J=5.9 Hz), 1.01 (3H, d, J=6.6 Hz), 0.97 (3H, d, J=7.3 Hz), 0.87 (9H, s), 0.09 (6H, d, J=5.1 Hz).

REFERENCE EXAMPLE 47 p-Nitrobenzyl (1R,5S,6S)-2-{1-[4-((1S)-1-carbamoyl-2-methylpropylcarbamoyl)-1,3-thiazol-2-yl]azetidin-3-yl}thio-6-[(R)-1-t-butyldimethylsilyloxyethyl]-1-methylcarbapen-2-em-3-carboxylate

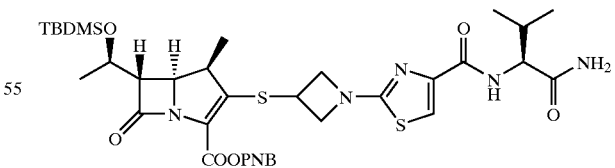

(1) (1S)-1-Carbamoyl-2-methylcarbamic acid t-butyl ester

To a solution of N-(t-butoxycarbonyl)-L-valine (3.00 g, 13.8 mmol) in anhydrous methylene chloride (150 ml) were added 1-hydroxybenzotriazole (3.73 g, 27.6 mmol), WSC (5.29 g, 27.6 mmol) and 4-dimethylaminopyridine (169 mg, 1.38 mmol) in an ice bath, and the mixture was stirred at room temperature under an atmosphere of nitrogen for 3 hours. After checking the completion of the reaction, 28% aqueous ammonia solution was added thereto and the reaction mixture was stirred for 30 minutes. After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using methylene chloride:methanol (9:1) as the eluant to afford (1S)-1-carbamoyl-2-methylcarbamic acid t-butyl ester (2.81 g, yield 94%) as white crystals.

$^1$H-NMR (400 MHz, CDCl$_3$): δ (ppm) 5.93–5.84 (1H, br s), 5.45–5.36 (1H, br s), 5.06–5.00 (1H, br s), 3.98–3.91 (1H, m), 2.21–2.12 (1H, m), 1.45 (9H, s), 0.99 (3H, d, J=6.6 Hz), 0.94 (3H, d, J=6.6 Hz).

(2) (2S)-2-Amino-3-methylbutylamine hydrochloride

To a solution of (1S)-1-carbamoyl-2-methylcarbamic acid t-butyl ester (2.81 g, 13.0 mmol) (obtained as described in Reference Example 47(1)) in 1,4-dioxane (28 ml) was added a solution of 4N hydrogen chloride in 1,4-dioxane (28 ml) in an ice bath, and then the mixture was stirred at room temperature overnight. After checking the completion of the reaction, ethyl acetate was added thereto, the reaction mixture was filtered and the obtained residue washed with ethyl acetate and dried to give (2S)-2-amino-3-methylbutylamine hydrochloride (1.94 g, yield 98%).

Elemental analysis:
Observed value: C, 39.21%; H, 8.34%; N, 18.31% Cl,23.38%. Calculated value: C, 39.35%; H, 8.59%; N, 18.35% Cl,23.23%.

(3) p-Nitrobenzyl (1R,5S,6S)-2-{1-[4-((1S)-1-carbamoyl-2-methyl-propylcarbamoyl)-1,3-thiazol-2-yl]azetidin-3-yl}thio-6-[(R)-1-t-butyldimethylsilyloxyethyl]-1-methylcarbapen-2-em-3-carboxylate To a solution of p-nitrobenzyl (1R,5S,6S)-2-[1-(4-carboxy-1,3-thiazol-2-yl)azetidin-3-yl]thio-6-[(R)-1-t-butyldimethylsilyloxyethyl]-1-methylcarbapen-2-em-3-carboxylate (1.00 g, 1.48 mmol) (obtained as described in Reference Example 41(7)) and L-valinamide hydrochloride (272 mg, 1.78 mmol) obtained as described in Reference Example 47(2) in dimethylformamide (50 ml) were added diethylphosphoryl cyanide (275 μl, 1.78 mmol) and diisopropylethylamine (620 μl, 3.56 mmol) in an ice bath under an atmosphere of nitrogen. The mixture was stirred at room temperature for 2.5 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:3)→methylene chloride:ethyl acetate (3:1) as the eluant to afford p-nitrobenzyl (1R,5S,6S)-2-{1-[4-((1S)-1-carbamoyl-2-methylpropylcarbamoyl)-1,3-thiazol-2-yl]azetidin-3-yl}thio-6-[(R)-1-t-butyldimethylsilyloxyethyl]-1-methylcarbapen-2-em-3-carboxylate (934 mg, yield 82%).

$^1$H-NMR (400 MHz, CDCl$_3$): δ (ppm) 8.22 (2H, d, J=8.8 Hz), 7.65 (2H, d, J=8.8 Hz), 7.61–7.56 (1H, br d, J=9.5 Hz), 7.43 (1H, s), 6.06–6.00 (1H, br s), 5.46 (1H, d, J=13.9 Hz), 5.42–5.37 (1H, br s), 5.27 (1H, d, J=13.9 Hz), 4.50 (1H, dt, J=8.1, 4.4 Hz), 4.36 (1H, dd, J=8.8, 6.6 Hz), 4.32–4.25 (3H, m), 4.08 (2H, dd, J=8.1, 5.1 Hz), 3.27 (1H, dd, J=5.1, 2.2 Hz), 3.16 (1H, dq, J=9.5, 7.3 Hz), 2.34–2.24 (1H, m), 1.26 (3H, d, J=7.3 Hz), 1.25 (3H, d, J=6.6 Hz), 1.03 (3H, d, J=6.6 Hz), 1.01 (3H, d, J=6.6 Hz), 0.87 (9H, s), 0.08 (6H, d, J=4.4 Hz).

REFERENCE EXAMPLE 48

3-Acetylthio-1-{4-[N-isopropyl-N-(p-nitrobenzyloxycarbonylmethyl)-carbamoyl]-1,3-thiazol-2-yl}azetidine (1) N-(t-Butoxycarbonyl-N-isopropyl-amino)acetic acid methyl ester To a solution of glycine methyl ester hydrochloride (3.03 g, 24.1 mmol) in methanol (150 ml) were added triethylamine (3.4 ml, 24.4 mmol) and acetone (17.7 ml, 241.1 mmol), and the mixture was stirred in a water bath (50° C.) for 1.5 hours. Subsequently, sodium cyanoborohydride (3.03 g, 48.2 mmol) was added thereto in an ice bath, and a solution of 10% hydrogen chloride in methanol was added to the reaction mixture to adjust the pH of the reaction mixture to 3 to 4, and the resulting reaction mixture was stirred for 30 minutes. After checking the completion of the reaction, the reaction mixture was concentrated under reduced pressure, and the residue was dried under reduced pressure. To a suspension of the obtained crude product in a mixture of methanol (45 ml) and methylene chloride (90 ml) were added di-t-butoxycarbonic anhydride (10.5 g, 48.1 mmol) and triethylamine (13.5 ml, 96.9 mmol) in an ice bath, and the reaction mixture was stirred at room temperature overnight. After checking the completion of the reaction, the reaction mixture was partitioned between ethyl acetate and saturated aqueous sodium chloride solution. The obtained organic layer was dried over anhydrous sodium sulfate, filtered and concentrated under reduced pressure. The residue was purified by chromatography on a silica gel column using toluene:ethyl acetate (5:1) as the eluant to afford (N-t-butoxycarbonyl-N-isopropyl-amino)-acetic acid methyl ester (3.93 g, yield 70%) as a colorless transparent syrup.

$^1$H-NMR (400 MHz, CDCl$_3$): δ (ppm) 4.54–4.40 (0.6H, m), 4.24–4.10 (0.4H, m), 3.86 (0.8H, s), 3.74 (1.2H, s), 3.72 (3H, s), 1.48 (3.6H, s), 1.42 (5.4H, s), 1.11 (2.4H, d, J=7.7 Hz), 1.09 (3.6H, d, J=7.7 Hz).

(2) (N-t-Butoxycarbonyl-N-isopropyl-amino)-acetic acid p-nitrobenzyl ester

To a solution of (N-t-butoxycarbonyl-N-isopropyl-amino)-acetic acid methyl ester (5.59 g, 24.2 mmol) in a mixture of methanol (112 ml) and distilled water (56 ml) was added 1M aqueous sodium hydroxide solution (37 ml) in an ice bath, and the mixture was stirred at room temperature for 7 hours. After checking the completion of the reaction, Dowex-50W was added thereto in the ice bath to adjust the pH of the reaction mixture to 5 to 4. The reaction mixture was filtered and the filtrate concentrated under reduced pressure to give (N-t-butoxycarbonyl-N-isopropyl-amino)acetic acid (5.25 g) as a crude product.

Subsequently, to a solution of (N-t-butoxycarbonyl-N-isopropyl-amino)-acetic acid (2.05 g, 9.44 mmol) and p-nitrobenzyl alcohol (2.89 g, 18.9 mmol) in methylene chloride (100 ml) were added WSC (3.62 g, 18.9 mmol) and 4-dimethylaminopyridine (120 mg, 0.98 mmol) in an ice bath under an atmosphere of nitrogen, and then the mixture was stirred at room temperature overnight. After checking the completion of the reaction, the reaction mixture was partitioned between ethyl acetate and saturated aqueous sodium chloride solution. The organic layer was dried over anhydrous magnesium sulfate, filtered and concentrated under reduced pressure. The residue was purified by chromatography on a silica gel column using hexane:ethyl acetate (5:2) as the eluant to afford (N-t-butoxycarbonyl-N-isopropyl-amino)acetic acid p-nitrobenzyl ester (1.93 g, yield 58%) as a pale yellow transparent syrup.

$^1$H-NMR (400 MHz, CDCl$_3$): δ (ppm) 8.24 (1H, d, J=8.0 Hz), 8.22 (1H, d, J=8.0 Hz), 7.53 (2H, d, J=8.0 Hz), 5.26

(2H, s), 4.54–4.42 (0.5H, m), 4.28–4.16 (0.5H, m), 3.94 (1H, s), 3.84 (1H, s), 1.48 (4.5H, s), 1.36 (4.5H, s), 1.12 (3H, d, J=7.7 Hz), 1.10 (3H, d, J=7.7 Hz).

(3) (Isopropylamino)acetic acid p-nitrobenzyl ester hydrochloride

To a solution of (N-t-butoxycarbonyl-N-isopropylamino)-acetic acid p-nitrobenzyl ester (1.93 g, 5.48 mmol) in 1,4-dioxane (20 ml) was added a solution of 4N hydrogen chloride in 1,4-dioxane (20 ml) in an ice bath, and the mixture was stirred at room temperature overnight. After checking the completion of the reaction, diethyl ether was added thereto the reaction mixture was stirred for 30 minutes and filtered, and the obtained residue was washed with diethyl ether and dried to give (isopropylamino)acetic acid p-nitrobenzyl ester hydrochloride (1.50 g, yield 95%) as white crystals.

$^1$H-NMR (400 MHz, CDCl$_3$): δ (ppm) 8.26 (2H, d, J=8.8 Hz), 7.67 (2H, d, J=8.8 Hz), 5.43 (2H, s), 4.11 (2H, s), 3.50–3.40 (1H, m), 1.34 (6H, d, J=5.9 Hz).

(4) 3-t-Butyldiphenylsilyloxy-1-{4-[N-isopropyl-N-(p-nitrobenzyloxycarbonylmethyl)carbamoyl]-1,3-thiazol-2-yl}azetidine To a solution of (isopropylamino)acetic acid p-nitrobenzyl ester hydrochloride (500 mg, 1.73 mmol) (obtained as described in Reference Example 48(3)) and 3-t-butyldiphenylsilyloxy-1-(4-carboxyl-1,3-thiazol-2-yl)azetidine (506 mg,1.15 mmol) (obtained as described in Reference Example 2(4)) in dimethylformamide (15 ml) were added diethylphosphoryl cyanide (0.28 ml, 1.73 mmol) and triethylamine (0.60 ml, 4.32 mmol) in an ice bath under an atmosphere of nitrogen. The mixture was stirred at room temperature for 2 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using hexane:ethyl acetate (1:1) as the eluant to afford 3-t-butyldiphenylsilyloxy-1-{4-[N-isopropyl-N-(p-nitrobenzyloxycarbonylmethyl)carbamoyl]-1,3-thiazol-2-yl}azetidine (578 mg, yield 75%) as a pale yellow syrup.

$^1$H-NMR (400 MHz, CDCl$_3$): δ (ppm) 8.28–8.18 (2H, m), 7.70–7.30 (12H, m), 7.38 (0.4H, br s), 7.10 (0.6H, br s), 5.29 (0.8H, br s), 5.16 (1.2H, br s), 5.04–4.44 (3H, m), 4.20–3.85 (5H, m), 1.17 (6H, br s), 1.06 (9H, br s).

(5) 3-Hydroxy-1-{4-[N-isopropyl-N-(p-nitrobenzyloxycarbonylmethyl)carbamoyl]-1,3-thiazol-2-yl}azetidine To a solution of 3-t-butyldiphenylsilyloxy-1-{4-[N-isopropyl-N-(p-nitrobenzyloxycarbonylmethyl)carbamoyl]-1,3-thiazol-2-yl}azetidine (1.81 g, 2.69 mmol) (obtained as described in Reference Example 48(4)) in anhydrous tetrahydrofuran (90 ml) were added acetic acid (0.18 ml, 3.23 mmol) and a solution of 1.0M tetra-n-butylammonium fluoride in tetrahydrofuran (3.23 ml, 3.23 mmol) in an ice bath. The mixture was stirred in the ice bath for 2 hours. After checking the completion of the reaction, the reaction mixture was concentrated under reduced pressure. The residue was purified by chromatography on a silica gel column using methylene chloride:ethyl acetate (1:1) as the eluant to afford 3-hydroxy-1-{4-[N-isopropyl-N-(p-nitrobenzyloxycarbonylmethyl)carbamoyl]-1,3-thiazol-2-yl}azetidine (968 mg, yield 83%) as a white solid.

$^1$H-NMR (400 MHz, CDCl$_3$): δ (ppm) 7.22 (2H, d, J=8.0 Hz), 7.55 (1H, d, J=8.0 Hz), 7.42 (1H, d, J=8.0 Hz), 7.39 (0.4H, s), 7.12 (0.6H, s), 5.29 (1.2H, br s), 5.22 (0.8H, br s), 5.03–4.89 (0.5H, m), 4.89–4.76 (1H, m), 4.59 (1H, br s), 4.32 (1H, t, J=7.3 Hz), 4.22–4.02 (2H, m), 4.02–3.85 (1H, m), 3.85 (1H, m), 1.10–1.03 (6H, m).

(6) 1-{4-[N-Isopropyl-N-(p-nitrobenzyloxycarbonylmethyl)carbamoyl]-1,3-thiazol-2-yl}-3-methanesulfonyloxyazetidine To a solution of 3-hydroxy-1-{4-[N-isopropyl-(p-N-nitrobenzyloxycarbonylmethyl)carbamoyl]-1,3-thiazol-2-yl}azetidine (968 mg, 2.23 mmol) (obtained as described in Reference Example 48(5)) in methylene chloride (50 ml) were added methanesulfonyl chloride (0.42 ml, 5.34 mmol) and triethylamine (0.37 ml, 2.67 mmol) in an ice bath. The reaction mixture was stirred in the ice bath for 2 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using methylene chloride:ethyl acetate (1:1) as the eluant to afford 1-{4-[N-isopropyl-N-(p-nitrobenzyloxycarbonylmethyl)carbamoyl]-1,3-thiazol-2-yl}-3-methanesulfonyloxyazetidine (835 mg, yield 73%) as a pale yellow solid.

$^1$H-NMR (400 MHz, CDCl$_3$): δ (ppm) 8.22 (2H, d, J=7.9 Hz), 7.55 (1H, d, J=7.9 Hz), 7.48 (0.4H, br s), 7.43 (1H, d, J=7.9 Hz), 7.26 (0.6H, br s), 5.51–5.16 (3H, m including 5.29 (1.2H, s), 5.22 (0.8H, s)), 5.04–4.89 (0.4H, m), 4.89–4.72 (1H, m), 4.59–4.48 (1H, m), 4.48–4.37 (1H, m), 4.37–4.18 (2H, m), 4.18–3.96 (2H, m), 3.11 (3H, s), 1.30–1.17 (6H, m).

(7) 3-Acetylthio-1-{4-[N-isopropyl-N-(p-nitrobenzyloxycarbonylmethyl)carbamoyl]-1,3-thiazol-2-yl}azetidine To a solution of 1-{4-[N-isopropyl-N-(p-nitrobenzyloxycarbonylmethyl)carbamoyl]-1,3-thiazol-2-yl}-3-methanesulfonyloxyazetidine (835 mg, 1.63 mmol) (obtained as described in Reference Example 48(6)) in dimethylformamide (42 ml) was added potassium thioacetate (1.12 g, 9.77 mmol) at room temperature. The mixture was stirred in an oil bath (90° C.) for 7 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford methylene chloride (50 ml) were added 3-acetylthio-1-{4-[N-isopropyl-N-(p-nitorobenzyloxycarbonylmethyl)carbamoyl]-1,3-thiazol-2-yl}azetidine (312 mg, yield 39%) as a pale brown solid.

$^1$H-NMR (400 MHz, CDCl$_3$): δ (ppm) 8.21 (2H, d, J=6.9 Hz), 7.55 (1H, d, J=8.3 Hz), 7.44 (0.6H, br s), 7.43 (1H, d, J=8.3 Hz), 7.17 (0.6H, br s), 5.19 (1.2H, s), 5.22 (0.8H, br s), 5.02–4.90 (0.6H, m), 4.90–4.78 (0.4H, m), 4.65–3.65 (7H, m), 2.36 (3H, br s), 1.40–1.18 (6H, m).

REFERENCE EXAMPLE 49

3-Acetylthio-1-[4-(N-carbamoylmethyl-N-isopropyl-carbamoyl)-1,3-thiazol-2-yl]azetidine

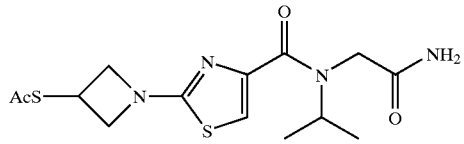

(1) N-Carbamoylmethyl-N-isopropyl-carbamic acid t-butyl ester

To a solution of (t-buthoxycarbonyl-N-isopropyl-amino)-acetic acid (3.20 mg, 14.7 mmol) (obtained as described in Reference Example 48(2)) and 1-hydroxybenzotriazole (4.0 g, 29.6 mmol) in methylene chloride (150 ml) were added WSC (5.6 g, 29.2 mmol) and 4-dimethylaminopyridine (200 mg, 1.64 mmol) in an ice bath under an atmosphere of nitrogen. The mixture was stirred at room temperature overnight. After checking the completion of the reaction, 28% aqueous ammonia solution (40 ml) was added thereto and the resulting mixture was stirred for 30 minutes. After checking the completion of the reaction, the reaction mixture was partitioned between methylene chloride and saturated aqueous sodium chloride solution. The organic layer was dried over anhydrous magnesium sulfate, filtered and concentrated under reduced pressure. The residue was purified by chromatography on a silica gel column using methylene chloride:methanol (10:1) as the eluant to afford N-carbamoylmethyl-N-isopropyl-carbamic acid t-butyl ester (2.67 g, yield 84%) as a white solid.

$^1$H-NMR (400 MHz, CDCl$_3$): δ (ppm) 5.434 (1H, br s), 4.25 (1H, br s), 3.735 (2H, s), 1.478 (9H, s), 1.14 (6H, d, J=6.6 Hz).

(2) 2-Isopropylaminoacetamide hydrochloride

To a solution of N-carbamoylmethyl-N-isopropyl-carbamic acid t-butyl ester (2.67 g, 12.3 mmol) (obtained as described in Reference Example 49(1)) in 1,4-dioxane (30 ml) was added a solution of 4N hydrogen chloride in 1,4-dioxane (30 ml) in an ice bath, and then the mixture was stirred at room temperature overnight. After checking the completion of the reaction, diethyl ether was added thereto and the reaction mixture was stirred for 30 minutes. The resulting mixture was filtered, and the residue was washed with diethyl ether and then dried under reduced pressure to give 2-isopropylaminoacetamide hydrochloride (1.82 g, yield 97%) as white crystals.

$^1$H-NMR (500 MHz, CD$_3$OD): δ (ppm) 3.80 (2H, s), 3.46–3.38 (1H, m), 1.34 (6H, d, J=6.8 Hz)

(3) 3-t-Butyldiphenylsilyloxy-1-[4-(N-carbamoylmethyl-N-isopropyl-carbamoyl)-1,3-thiazol-2-yl]azetidine To a solution of 2-isopropylamino-acetamide hydrochloride (500 mg, 3.28 mmol) (obtained as described in Reference Example 49(2)) and 3-t-butyldiphenylsilyloxy-1-(4-carboxyl-1,3-thiazol-2-yl)azetidine (961 mg, 2.19 mmol) in dimethylformamide (29 ml) were added diethylphosphoryl cyanide (0.54 ml, 3.29 mmol) and triethylamine (1.15 ml, 8.19 mmol) in an ice bath under an atmosphere of nitrogen. The mixture was stirred at room temperature for 2 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate as the eluant to afford 3-t-butyldiphenylsilyloxy-1-[4-(N-carbamoylmethyl-N-isopropyl-carbamoyl)-1,3-thiazol-2-yl]azetidine (1.18 g, yield 100%) as a pale yellow oil.

$^1$H-NMR (400 MHz, CDCl$_3$): δ (ppm) 7.62 (4H, d, J=6.6 Hz), 7.52–7.36 (6H, m), 7.21–6.85 (1H, m), 4.80–4.72 (1H, m), 4.28 (1H, t, J=7.3 Hz), 4.24 (1H, t, J=7.3 Hz), 4.16–4.01 (2H, m), 4.01–3.88 (2H, m), 1.25 (6H, d, J=6.7 Hz), 1.07 (9H, br s).

(4) 1-[4-(N-Carbamoylmethyl-N-isopropyl-carbamoyl)-1,3-thiazol-2-yl]-3-hydroxyazetidine To a solution of 3-t-butyldiphenylsilyloxy-1-[4-(N-carbamoylmethyl-N-isopropyl-carbamoyl)-1,3-thiazol-2-yl]azetidine (6.52 g, 11.8 mmol) (obtained as described in Reference Example 49(3)) in anhydrous tetrahydrofuran (326 ml) was added a 1.0M solution of tetra-n-butylammonium fluoride in tetrahydrofuran (14.2 ml, 14.2 mmol) in an ice bath, and the mixture was stirred in the ice bath for 2 hours. After checking the completion of the reaction, the reaction mixture was concentrated under reduced pressure. The residue was purified by chromatography on a silica gel column using ethyl acetate:methanol (10:1) as the eluant to afford 1-[4-(N-carbamoylmethyl-N-isopropyl-carbamoyl)-1,3-thiazol-2-yl]-3-hydroxyazetidine (2.35 g, yield 67%) as a white solid.

$^1$H-NMR (400 MHz, CDCl$_3$): δ (ppm) 7.20–7.02 (0.6H, m), 7.02–6.80 (0.6H, m), 5.86–5.62 (0.4H, m), 5.62–5.32 (0.6H, m), 5.25–5.14 (0.3H, m), 4.90–4.75 (0.7H, m), 4.67 (0.7H, quint., J=6.6 Hz), 4.43–4.34 (0.4H, m), 4.34–4.22 (0.6H, m), 4.03 (2H, s), 4.00–3.91 (2H, m), 3.89 (0.3H, quint., J=6.0 Hz), 1.26 (6H, dd, J=6.7, 2.4 Hz).

(5) 1-[4-(N-Carbamoylmethyl-N-isopropyl-carbamoyl)-1,3-thiazol-2-yl]-3-methanesulfonyloxyazetidine and 1-[4-(N-cyanomethyl-N-isopropyl-carbamoyl)-1,3-thiazol-2-yl]-3-methanesulfonyloxyazetidine To a solution of 1-[4-(N-carbamoylmethyl-N-isopropyl-carbamoyl)-1,3-thiazol-2-yl]-3-hydroxyazetidine (2.35 g, 7.88 mmol) (obtained as described in Reference Example 49(4)) in methylene chloride (120 ml) were added methanesulfonyl chloride (0.91 ml, 11.8 mmol) and triethylamine (1.66 ml, 11.8 mmol) in an ice bath. The reaction mixture was stirred in the ice bath for 2 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using ethyl acetate:methanol (10:1) as the eluant to afford 1-[4-(N-carbamoylmethyl-N-isopropyl-carbamoyl)-1,3-thiazol-2-yl]-3-methanesulfonyloxyazetidine (516 mg, yield 17%) as a pale yellow solid and 1-[4-(cyanomethyl-isopropyl-carbamoyl)-1,3-thiazol-2-yl]-3-methanesulfonyloxyazetidine (634 mg, yield 22%) as a pale yellow solid.

1-[4-(N-Carbamoylmethyl-N-isopropyl-carbamoyl)-1,3-thiazol-2-yl]-3-methanesulfonyloxyazetidine $^1$H-NMR (400 MHz, CDCl$_3$): δ (ppm) 7.15–6.72 (1H, m), 5.65–5.15 (1H, m), 4.79–4.62 (1H, m), 4.44 (2H, t, J=6.7 Hz), 4.26 (2H, d, J=6.7 Hz), 4.05 (2H, m), 3.11 (3H, s), 1.26 (6H, m).

1-[4-(N-Cyanomethyl-N-isopropyl-carbamoyl)-1,3-thiazol-2-yl]-3-methanesulfonyloxyazetidine $^1$H-NMR (400 MHz, CDCl$_3$): δ (ppm) 7.55–7.10 (1H, m), 5.50–5.38 (1H, m), 4.93–4.78 (1H, m), 4.60–4.00 (6H, m including 4.51 (2H, t, J=9.6 Hz), 4.32 (2H, dd, J=9.6, 3.7 Hz)), 3.11 (3H, s), 1.31 (6H, d, J=6.8 Hz).

(6) 3-Acetylthio-1-[4-(N-carbamoylmethyl-N-isopropyl-carbamoyl)-1,3-thiazol-2-yl]azetidine To a solution of 1-[4-(N-carbamoylmethyl-N-isopropyl-carbamoyl)-1,3-thiazol-2-yl]-3-methanesulfonyloxyazetidine (516 mg, 1.37 mmol) (obtained as described in Reference Example 49(5)) in dimethylformamide (15 ml) was added potassium thioacetate (939 mg, 8.22 mmol) at room temperature. The mixture was stirred in an oil bath (90° C.) for 3 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate→ethyl acetate:methanol (20:1) as the eluant to afford 3-acetylthio-1-[4-(N-carbamoylmethyl-N-isopropyl-carbamoyl)-1,3-thiazol-2-yl]azetidine (347 mg, yield 71%) as a pale brown solid.

¹H-NMR (400 MHz, CDCl₃): δ (ppm) 7.45–6.72 (1H, m), 4.76–4.61 (1H, m), 4.51 (2H, t, J=7.4 Hz), 4.47–4.40 (1H, m), 4.40 (2H, s), 3.98 (2H, t, J=7.4 Hz), 2.37 (3H, s), 1.26 (6H, d, J=6.8 Hz).

REFERENCE EXAMPLE 50

3-Acetylthio-1-[4-(N-cyanomethyl-N-isopropyl-carbamoyl)-1,3-thiazol-2-yl]azetidine

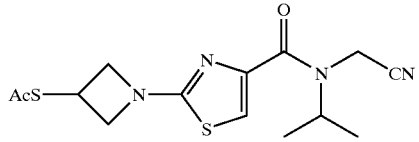

(1) 3-Acetylthio-1-[4-(N-cyanomethyl-N-isopropyl-carbamoyl)-1,3-thiazol-2-yl]azetidine To a solution of 1-[4-(N-cyanomethyl-N-isopropyl-carbamoyl)-1,3-thiazol-2-yl]-3-methanesulfonyloxyazetidine (635 mg, 1.77 mmol) (obtained as described in Reference Example 49(5)) in dimethylformamide (19 ml) was added potassium thioacetate (1.21 g, 10.6 mmol) at room temperature, and the reaction mixture was stirred in an oil bath (90° C.) for 3 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The obtained residue was purified by chromatography on a silica gel column using hexane:ethyl acetate (1:1)→ethyl acetate as the eluant to afford 3-acetylthio-1-[4-(N-cyanomethyl-N-isopropyl-carbamoyl)-1,3-thiazol-2-yl]azetidine (344 mg, yield 57%) as a pale brown solid.

¹H-NMR (400 MHz, CDCl₃): δ (ppm) 7.58–7.18 (1H, m), 4.96–4.82 (1H, m), 4.82–4.10 (5H, m including 4.54 (2H, t, J=8.4 Hz), 4.50–4.40 (1H, m)), 4.01 (2H, t, J=8.4 Hz), 2.36 (3H, s), 1.30 (6H, d, J=6.8 Hz).

REFERENCE EXAMPLE 51

3-Acetylthio-1-{4-[1-(p-nitrobenzyloxycarbonyl)-piperidin-4-ylcarbamoyl]-1,3-thiazol-2-yl}azetidine

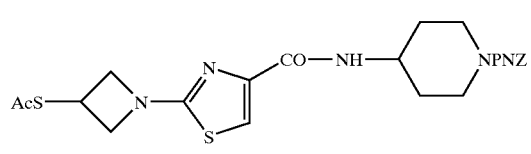

(1) 4-Hydroxy-1-(p-nitrobenzyloxycarbonyl)piperidine

To a solution of 4-hydroxypiperidine hydrochloride (3.0 g, 21.8 mmol) in a mixture of methylene chloride (90 ml) and pyridine (15 ml) were added chloroformic acid p-nitrobenzyl ester (15.4 g, 72.0 mmol) and triethylamine (13.1 ml, 93.8 mmol) in an ice bath. The mixture was stirred at room temperature for 3 days. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1)→ethyl acetate as the eluant to afford 4-hydroxy-1-(p-nitrobenzyloxycarbonyl)piperidine (2.96 g, yield 48%) as pale yellow crystals.

¹H-NMR (400 MHz, CDCl₃): δ (ppm) 8.23 (2H, d, J=8.1 Hz), 8.51 (2H, d, J=8.1 Hz), 5.23 (2H, s), 3.98–3.87 (3H, m), 3.30–3.15 (2H, m), 1.96–1.85 (2H, m), 1.59–1.48 (2H, m).

(2) 4-Methanesulfonyloxy-1-(p-nitrobenzyloxycarbonyl)piperidine

To a solution of 4-hydroxy-1-(p-nitrobenzyloxycarbonyl)piperidine (2.96 g, 14.8 mmol) (obtained as described in Reference Example 51(1)) in methylene chloride (90 ml) were added methanesulfonyl chloride (1.15 ml, 14.8 mmol) and triethylamine (2.07 ml, 14.8 mmol) in an ice bath. The reaction mixture was brought to room temperature in 10 minutes, and then stirred for 6 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The obtained residue was recrystallized from a solution of n-hexane:ethyl acetate (1:1) to afford 4-methanesulfonyloxy-1-(p-nitrobenzyloxycarbonyl)piperidine (3.31 g, yield 87%) as pale yellow crystals.

¹H-NMR (400 MHz, CDCl₃): δ (ppm) 8.23 (2H, d, J=8.8 Hz), 7.51 (2H, d, J=8.8 Hz), 5.23,(2H, s), 4.96–4.90 (1H, m), 3.79–3.72 (2H, m), 3.51–3.44 (2H, m), 3.05 (3H, s), 2.10–1.96 (2H, m), 1.92–1.84 (2H, m).

(3) 4-Azido-1-(p-nitrobenzyloxycarbonyl)piperidine

To a solution of 4-methanesulfonyloxy-1-(p-nitrobenzyloxycarbonyl)piperidine (3.31 g, 9.24 mmol) (obtained as described in Reference Example 51(2)) in dimethylformamide (100 ml) was added sodium azide (660 mg, 10.2 mmol), and the mixture was stirred in an oil bath (100° C.) for 3 hours. After checking the completion of the reaction, the reaction mixture was partitioned between ethyl acetate and 10% aqueous sodium chloride solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (3:1→1:1) as the eluant to afford 4-azido-1-(p-nitrobenzyloxycarbonyl)piperidine (2.81 g, yield 100%) as pale yellow crystals.

$^1$H-NMR (400 MHz, CDCl$_3$): δ (ppm) 8.23 (2H, d, J=8.8 Hz), 7.51 (2H, d, J=8.8 Hz), 5.22 (2H, s), 3.86 (2H, dt, J=13.9, 5.1 Hz), 3.68–3.62 (1H, m), 3.32–3.20 (2H, m), 1.98–1.85 (2H, m), 1.68–1.61 (2H, m).

(4) 4-Amino-1-(p-nitrobenzyloxycarbonyl)piperidine

To a solution of 4-azido-1-(p-nitrobenzyloxycarbonyl)-piperidine (2.81 g, 9.17 mmol) (obtained as described in Reference Example 51(3)) in acetonitrile (84 ml) was added triphenylphosphine (2.53 g, 9.63 mmol), and the mixture was stirred in an oil bath (70° C.) for 3 hours. After checking the completion of the reaction, sodium sulfate decahydrate (3.10 g, 9.63 mmol) was added thereto and the reaction mixture was stirred for 3 hours. After checking the completion of the reaction, the reaction mixture was filtered and partitioned between methylene chloride and 0.1M aqueous hydrogen chloride solution. To the obtained aqueous layer were added methylene chloride and sodium hydrogencarbonate, and the aqueous layer was extracted with methylene chloride. The obtained organic layer was dried over anhydrous sodium sulfate, filtered and concentrated under reduced pressure. The residue was dried under reduced pressure to give 4-amino-1-(p-nitrobenzyloxycarbonyl)-piperidine (2.33 g, yield 91%) as pale yellow crystals.

$^1$H-NMR (400 MHz, CDCl$_3$): δ (ppm) 8.22 (2H, d, 8.8 Hz), 7.51 (2H, d, 8.8 Hz), 5.22 (2H, s), 4.18–4.06 (2H, m), 3.01–2.83 (2H, m), 1.88–1.80 (2H, m), 1.34–1.22 (2H, m).

(5) 3-t-Butyldiphenylsilyloxy-1-{4-(1-(p-nitrobenzyloxycarbonyl)-piperidin-4-ylcarbamoyl]-1,3-thiazol-2-yl}azetidine To a solution of 4-amino-1-(p-nitrobenzyloxycarbonyl) piperidine (382 mg, 1.37 mmol) (obtained as described in Reference Example 51(4)) and 3-t-butyldiphenylsilyloxy-1-(4-carboxyl-1,3-thiazol-2-yl)azetidine (500 mg, 1.14 mmol) (obtained as described in Reference Example 2(4)) in dimethylformamide (25 ml) were added diethylphosphoryl cyanide (208 μl, 1.37 mmol) and triethylamine (192 μl, 1.37 mmol) in an ice bath under an atmosphere of nitrogen. The mixture was stirred at room temperature for 1.5 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1→1:3) as the eluant to afford 3-t-butyldiphenylsilyloxy-1-{4-[1-(p-nitrobenzyloxycarbonyl)-piperidin-4-ylcarbamoyl]-1,3-thiazol-2-yl}azetidine (574 mg, yield 72%) as a pale yellow solid.

$^1$H-NMR (400 MHz, CDCl$_3$): δ (ppm) 8.24 (2H, d, J=8.8 Hz), 7.62 (4H, d, J=8.8 Hz), 7.54–7.38 (6H, m), 7.36 (1H, s), 7.09–7.04 (1H, br d, J=8.8 Hz), 5.23 (2H, s), 4.79–4.72 (1H, m), 4.22–4.04 (5H, m), 4.01 (2H, dd, J=8.8, 5.1 Hz), 3.08–2.97 (2H, m), 2.08–2.00 (2H, m), 1.55–1.42 (2H, m), 1.07 (9H, s).

(6) 3-Hydroxy-1-{4-[1-(p-nitrobenzyloxycarbonyl)-piperidin-4-ylcarbamoyl]-1,3-thiazol-2-yl}azetidine To a solution of 3-t-butyldiphenylsilyloxy-1-{4-[1-(p-nitrobenzyloxycarbonyl)-piperidin-4-ylcarbamoyl]-1,3-thiazol-2-yl}azetidine (570 mg, 0.820 mmol) (obtained as described in Reference Example 51(5)) in anhydrous tetrahydrofuran (17 ml) were added successively acetic acid (56 μl, 0.984 mmol) and a 1.0M solution of tetra-n-butylammonium fluoride in tetrahydrofuran (984 μl, 0.984 mmol) in an ice bath, and the mixture was stirred in the ice bath for 1 hour. After checking the completion of the reaction, the reaction mixture was partitioned between ethyl acetate and saturated aqueous sodium hydrogencarbonate solution. The organic layer was washed successively with a saturated aqueous sodium hydrogencarbonate solution and a saturated aqueous sodium chloride solution, dried over anhydrous sodium sulfate, filtered and concentrated under reduced pressure. The residue was purified by chromatography on a silica gel column using n-hexane:ethyl acetate (1:3)→ethyl acetate:methanol (95:5) as the eluant to afford 3-hydroxy-1-{4-[1-(p-nitrobenzyloxycarbonyl)-piperidin-4-ylcarbamoyl]-1,3-thiazol-2-yl}azetidine (360 mg, yield 95%) as a white solid.

$^1$H-NMR (400 MHz, CDCl$_3$): δ (ppm) 8.23 (2H, d, J=8.8 Hz), 7.51 (2H, d, J=8.8 Hz), 7.39 (1H, s), 7.11–7.06 (1H, br d, J=8.1 Hz), 5.23 (2H, s), 4.88–4.80 (1H, m), 4.32 (2H, dd, J=8.8, 6.6 Hz), 4.24–4.04 (3H, m), 3.96 (2H, dd, J=9.5, 4.4 Hz), 3.12–2.95 (2H, m), 2.37–2.32 (1H, d, J=5.9 Hz), 2.04–1.99 (2H, m), 1.55–1.43 (2H, m).

(7) 3-Methanesulfonyloxy-1-{4-[1-(p-nitrobenzyloxycarbonyl)-piperidin-4-ylcarbamoyl]-1,3-thiazol-2-yl}azetidine To a solution of 3-hydroxy-1-{4-[1-(p-nitrobenzyloxycarbonyl)-piperidin-4-ylcarbamoyl]-1,3-thiazol-2-yl}azetidine (360 mg, 0.780 mmol) (obtained as described in Reference Example 51(6)) in methylene chloride (18 ml) were added methanesulfonyl chloride (181 μl, 2.34 mmol) and triethylamine (328 μl, 2.34 mmol) in an ice bath. After stirring the mixture in the ice bath for 10 minutes, the mixture was stirred at room temperature for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate→ethyl acetate:methanol (98:2) as the eluant to afford 3-methanesulfonyloxy-1-{4-[1-(p-nitrobenzyloxycarbonyl)-piperidin-4-ylcarbamoyl]-1,3-thiazol-2-yl}azetidine (390 mg, yield 93%) as a pale yellow solid.

$^1$H-NMR (400 MHz, CDCl$_3$): δ (ppm) 8.23 (2H, d, J=8.8 Hz), 7.52 (2H, d, J=8.8 Hz), 7.52 (1H, s), 7.06–7.02 (1H, br d, J=7.7 Hz), 5.45–5.40 (1H, m), 5.23 (2H, s), 4.45 (2H, dd, J=10.3, 6.8 Hz), 4.27 (2H, dd, J=10.3, 4.3 Hz), 4.24–4.06 (3H, m), 3.11 (3H, s), 3.10–2.95 (2H, m), 2.07–2.00 (2H, m), 1.56–1.44 (2H, m).

(8) 3-Acetylthio-1-{4-[1-(p-nitrobenzyloxycarbonyl)-piperidin-4-ylcarbamoyl]-1,3-thiazol-2-yl}azetidine To a solution of 3-methanesulfonyloxy-1-{4-[1-(p-nitrobenzyloxycarbonyl)-piperidin-4-ylcarbamoyl]-1,3-thiazol-2-yl}azetidine (390 mg, 0.723 mmol) (obtained as described in Reference Example 51(7)) in dimethylformamide (20 ml) was added potassium thioacetate (496 mg, 4.34 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate as the eluant to afford 3-acetylthio-1-{4-[1-(p-nitrobenzyloxycarbonyl)-piperidin-4-ylcarbamoyl]-1,3-thiazol-2-yl}azetidine (262 mg, yield 70%) as a pale brown solid.

¹H-NMR (400 MHz, CDCl₃): δ (ppm) 8.23 (2H, d, J=8.1 Hz), 7.51 (2H, d, J=8.1 Hz), 7.41 (1H, s), 7.08–7.04 (1H, br d, J=7.8 Hz), 5.23 (2H, s), 4.53 (2H, t, J=8.8 Hz), 4.46–4.40 (1H, m), 4.22–4.04 (3H, m), 3.98 (2H, dd, J=8.8, 5.9 Hz), 3.12–2.96 (2H, m), 2.37 (3H, s), 2.06–2.00 (2H, m), 1.55–1.43 (2H, m).

REFERENCE EXAMPLE 52

3-Acetylthio-1-{4-[(3S)-1-(p-nitrobenzyloxycarbonyl)-pyrrolidin-3-ylcarbamoyl]-1,3-thiazol-2-yl}azetidine

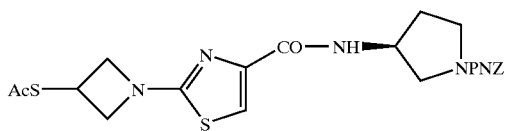

(1) (3R)-3-Hydroxy-1-(p-nitrobenzyloxycarbonyl)pyrrolidine

To a suspension of (3R)-3-hydroxypyrrolidine hydrochloride (7.00 g, 56.6 mmol) in methylene chloride (210 ml) were added chloroformic acid p-nitrobenzyl ester (13.4 g, 62.3 mmol) and triethylamine (17.4 ml, 125 mmol) in an ice bath. The mixture was stirred at room temperature for 5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1)→ethyl acetate as the eluant to afford (3R)-3-hydroxy-1-(p-nitrobenzyloxycarbonyl)-pyrrolidine (13.6 g, yield 90%) as a pale yellow solid.

¹H-NMR (400 MHz, CDCl₃): δ (ppm) 8.22 (2H, d, J=8.1 Hz), 7.53 (2H, d, J=8.1 Hz), 5.24 (2H, s), 4.55–4.50 (1H, m), 3.63–3.53 (3H, m), 3.51–3.44 (1H, m), 2.09–1.93 (2H, m).

(2) (3R)-3-Methanesulfonyloxy-1-(p-nitrobenzyloxycarbonyl)pyrrolidine

To a solution of (3R)-3-hydroxy-1-(p-nitrobenzyloxycarbonyl)pyrrolidine (9.0 g, 33.8 mmol) in methylene chloride (270 ml) were added methanesulfonyl chloride (2.88 ml, 37.2 mmol) and triethylamine (5.21 ml, 37.2 mmol) in an ice bath. After stirring the mixture in the ice bath for 10 minutes, the mixture was stirred at room temperature for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate as the eluant to afford (3R)-3-methanesulfonyloxy-1-(p-nitrobenzyloxycarbonyl)-pyrrolidine (11.5 g, yield 99%) as a pale yellow solid.

¹H-NMR (400 MHz, CDCl₃): δ (ppm) 8.23 (2H, d, J=8.1 Hz), 7.53 (2H, m), 5.33–5.23 (1H, m), 5.24 (2H, s), 3.82 (1H, dd, J=12.5, 5.1 Hz), 3.72–3.53 (3H, m), 3.06 (3H, s), 2.42–2.26 (1H, m), 2.26–2.11 (1H, m).

(3) (3S)-3-Azido-1-(p-nitrobenzyloxycarbonyl)pyrrolidine

To a solution of (3R)-3-methanesulfonyloxy-1-(p-nitrobenzyloxycarbonyl)-pyrrolidine (4.00 g, 11.6 mmol) (obtained as described in Reference Example 52(2)) in dimethylformamide (120 ml) was added sodium azide (831 mg, 12.8 mmol), and the mixture was stirred in an oil bath (100° C.) for 2 hours. After checking the completion of the reaction, the reaction mixture was partitioned between ethyl acetate and 10% aqueous sodium chloride solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (3:1→1:2) as the eluant to afford (3S)-3-azido-1-(p-nitrobenzyloxycarbonyl)pyrrolidine (3.43 g, yield 100%) as a pale yellow solid.

¹H-NMR (400 MHz, CDCl₃): δ (ppm) 8.23 (2H, d, J=8.7 Hz), 7.54 (2H, d, J=8.7 Hz), 5.18 (2H, s), 4.24–4.38 (1H, m), 3.62–3.48 (4H, m), 2.19–2.11 (2H, m).

(4) (3S)-3-Amino-1-(p-nitrobenzyloxycarbonyl)pyrrolidine

To a solution of (3S)-3-azido-1-(p-nitrobenzyloxycarbonyl)pyrrolidine (3.43 g, 11.6 mmol) (obtained as described in Reference Example 52(3)) in acetonitrile (103 ml) was added triphenylphosphine (3.19 g, 12.2 mmol), and the mixture was stirred in an oil bath (70° C.) for 2 hours. After checking the completion of the reaction, sodium sulfate decahydrate (3.93 g, 12.2 mmol) was added thereto and the reaction mixture was stirred for 5 hours. After checking the completion of the reaction, the reaction mixture was filtered and partitioned between methylene chloride and 0.1M aqueous hydrogen chloride solution. To the obtained aqueous layer were added methylene chloride and sodium hydrogencarbonate, and the aqueous layer was extracted with methylene chloride. The obtained organic layer was dried over anhydrous sodium sulfate, filtered and concentrated under reduced pressure. The residue was dried under reduced pressure to give (3S)-3-amino-1-(p-nitrobenzyloxycarbonyl)pyrrolidine (2.83 g, yield 92%) as a pale yellow solid.

¹H-NMR (400 MHz, CDCl₃): δ (ppm) 8.22 (2H, d, J=8.7 Hz), 7.52 (2H, d, J=8.7 Hz), 5.23 (2H, s), 3.68–3.57 (3H, m), 3.52–3.44 (1H, m), 3.19–3.11 (1H, m), 2.14–2.04 (1H, m), 1.77–1.64 (1H, m).

(5) 3-t-Butyldiphenylsilyloxy-1-{4-[(3S)-1-(p-nitrobenzyloxycarbonyl)-pyrrolidin-3-ylcarbamoyl]-1,3-thiazol-2-yl}azetidine To a suspension of (3S)-3-amino-1-(p-nitrobenzyloxycarbonyl)pyrrolidine (363 mg, 1.37 mmol) (obtained as described in Reference Example 52(4)) and 3-t-butyldiphenylsilyloxy-1-(4-carboxyl-1,3-thiazol-2-yl)azetidine (500 mg, 1.14 mmol) (obtained as described in Reference Example 2(4)) in dimethylformamide (25 ml) were added diethylphosphoryl cyanide (208 μl, 1.37 mmol) and triethylamine (192 μl, 1.37 mmol) in an ice bath under an atmosphere of nitrogen. The mixture was stirred at room temperature for 2 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1→1:3) as the eluant to afford 3-t-butyldiphenylsilyloxy-1-{4-[(3S)-1-(p-nitrobenzyloxycarbonyl)-pyrrolidin-3-ylcarbamoyl]-1,3-thiazol-2-yl}azetidine (566 mg, yield 72%) as a pale yellow solid.

¹H-NMR (400 MHz, CDCl₃): δ (ppm) 8.22 (2H, m), 7.61 (4H, d, J=8.8 Hz), 7.53 (2H, m), 7.48–7.38 (6H, m), 7.37 (1H, s), 7.22–7.15 (1H, br t, J=8.3 Hz), 5.24 (2H, d, J=10.7 Hz), 4.80–4.74 (1H, m), 4.67–4.59 (1H, m), 4.11 (2H, t, J=7.3 Hz), 4.07–4.00 (2H, m), 3.81 (1H, dt, J=10.7, 5.9 Hz), 3.67–3.52 (2H, m), 3.40 (1H, dd, J=11.2, 5.4 Hz), 2.33–2.22 (1H, m), 2.08–1.92 (1H, m), 1.07 (9H, s).

(6) 3-Hydroxy-1-{4-[(3S)-1-(p-nitrobenzyloxycarbonyl)-pyrrolidin-3-ylcarbamoyl]-1,3-thiazol-2-yl}azetidine To a solution of 3-t-butyldiphenylsilyloxy-1-{4-[(3S)-1-(p-nitrobenzyloxycarbonyl)-pyrrolidin-3-ylcarbamoyl]-1,3-thiazol-2-yl}azetidine (560 mg, 0.816 mmol) (obtained as described in Reference Example 52(5)) in anhydrous tetrahydrofuran (17 ml) was added successively acetic acid (56 μl, 0.980 mmol) and a solution of 1.0M tetra-n-butylammonium fluoride in tetrahydrofuran (980 μl, 0.980 mmol) in an ice bath. The mixture was stirred in the ice bath for 1.5 hours. After checking the completion of the reaction, ethyl acetate and water were added thereto and the aqueous layer was extracted with ethyl acetate. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate→ethyl acetate:methanol (95:1) as the eluant to afford 3-hydroxy-1-{4-[(3S)-1-(p-nitrobenzyloxycarbonyl)-pyrrolidin-3-ylcarbamoyl]-1,3-thiazol-2-yl}azetidine (359 mg, yield 98%) as a white solid.

¹H-NMR (400 MHz, CDCl₃): δ (ppm) 8.22 (2H, m), 7.53 (2H, m), 7.40 (1H, s), 7.24–7.17 (1H, br s), 5.30–5.18 (2H, m), 4.89–4.82 (1H, m), 4.66–4.58 (1H, m), 4.33 (2H, t, J=7.8 Hz), 3.96 (2H, dd, J=8.8, 3.9 Hz), 3.80 (1H, dt, J=11.2, 5.8 Hz), 3.66–3.52 (2H, m), 3.46–3.39 (1H, m), 2.44–2.37 (1H, br s), 2.33–2.22 (1H, m), 2.10–1.95 (1H, m).

(7) 3-Methanesulfonyloxy-1-{4-[(3S)-1-(p-nitrobenzyloxycarbonyl)-pyrrolidin-3-ylcarbamoyl]-1,3-thiazol-2-yl}azetidine To a solution of 3-hydroxy-1-{4-[(3S)-1-(p-nitrobenzyloxycarbonyl)-pyrrolidin-3-ylcarbamoyl]-1,3-thiazol-2-yl}azetidine (350 mg, 0.782 mmol) (obtained as described in Reference Example 52(6)) in methylene chloride (18 ml) were added methanesulfonyl chloride (182 μl, 2.35 mmol) and triethylamine (329 μl, 2.35 mmol) in an ice bath. After stirring the mixture in the ice bath for 10 minutes, the mixture was stirred at room temperature for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate→ethyl acetate:methanol (98:2) as the eluant to afford 3-methanesulfonyloxy-1-{4-[(3S)-1-(p-nitrobenzyloxycarbonyl)-pyrrolidin-3-ylcarbamoyl]-1,3-thiazol-2-yl}azetidine (410 mg, yield 99%) as a pale yellow solid.

¹H-NMR (400 MHz, CDCl₃): δ (ppm) 8.21 (2H, m), 7.53 (2H, m), 7.46 (1H, s), 7.20–7.14 (1H, br s), 5.45–5.40 (1H, m), 5.24 (2H, d, J=8.8 Hz), 4.66–4.59 (1H, m), 4.46 (2H, t, J=8.1 Hz), 4.27 (2H, dd, J=9.9, 4.0 Hz), 3.81 (1H, dt, J=1.0, 6.3 Hz), 3.67–3.52 (2H, m), 3.42 (1H, dd, J=11.0, 5.1 Hz), 3.12 (3H, s), 2.31–2.24 (1H, m), 2.07–1.95 (1H, m).

(8) 3-Acetylthio-1-{4-[(3S)-1-(p-nitrobenzyloxycarbonyl)-pyrrolidin-3-ylcarbamoyl]-1,3-thiazol-2-yl}azetidine To a solution of 3-methanesulfonyloxy-1-{4-[(3S)-1-(p-nitrobenzyloxycarbonyl)-pyrrolidin-3-ylcarbamoyl]-1,3-thiazol-2-yl}azetidine (410 mg, 0.780 mmol) (obtained as described in Reference Example 52(7)) in dimethylformamide (21 ml) was added potassium thioacetate (534 mg, 4.68 mmol) at room temperature, and the reaction mixture was stirred in an oil bath (80° C.) for 5 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The obtained residue was purified by chromatography on a silica gel column using n-hexane:ethyl acetate (1:2)→ethyl acetate as the eluant to afford 3-acetylthio-1-{4-[(3S)-1-(p-nitrobenzyloxycarbonyl)-pyrrolidin-3-ylcarbamoyl]-1,3-thiazol-2-yl}azetidine (287 mg, yield 73%) as a pale brown solid.

¹H-NMR (400 MHz, CDCl₃): δ (ppm) 8.22 (2H, m), 7.52 (2H, m), 7.42 (1H, s), 7.20–7.15 (1H, br s), 5.24 (2H, d, J=10.7 Hz), 4.66–4.59 (1H, m), 4.53 (2H, t, J=8.3 Hz), 4.47–4.41 (1H, m), 3.99 (2H, t, J=6.4 Hz), 3.84–3.76 (1H, m), 3.65–3.53 (2H, m), 3.41 (1H, dd, J=11.7, 4.9 Hz), 2.37 (3H, s), 2.33–2.20 (1H, m), 2.07–1.93 (1H, m).

REFERENCE EXAMPLE 53

3-Acetylthio-1-{4-[(3R)-1-(p-nitrobenzyloxycarbonyl)-pyrrolidin-3-ylcarbamoyl]-1,3-thiazol-2-yl}azetidine

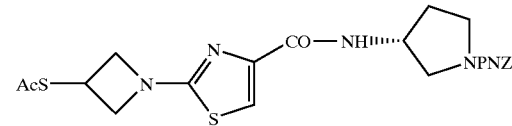

(1) (3S)-3-Acetoxy-1-(p-nitrobenzyloxycarbonyl)pyrrolidine

To a solution of (3R)-3-methanesulfonyloxy-1-(p-nitrobenzyloxycarbonyl)pyrrolidine (7.50 g, 21.8 mmol) (obtained as described in Reference Example 52(2)) in dimethylformamide (225 ml) was added potassium acetate (6.41 g, 65.3 mmol), and the mixture was stirred in an oil bath (80° C.) overnight. After checking the completion of the reaction, the reaction mixture was partitioned between ethyl acetate and saturated aqueous sodium hydrogencarbonate solution. The organic layer was washed successively with 10% aqueous sodium chloride solution and saturated aqueous sodium chloride solution, dried over anhydrous sodium sulfate, filtered and concentrated under reduced pressure. The obtained residue was purified by chromatography on a silica gel column using n-hexane:ethyl acetate (2:1→1:2) as the eluant to afford (3S)-3-acetoxy-1-(p-nitrobenzyloxycarbonyl)pyrrolidine (5.51 g, yield 82%) as white crystals.

¹H-NMR (400 MHz, CDCl₃): δ (ppm) 8.23 (2H, d, J=8.1 Hz), 7.53 (2H, d, J=8.1 Hz), 5.33–5.29 (1H, m), 5.24 (2H, s), 3.68–3.50 (4H, m), 2.19–2.02 (2H, m), 2.04 (3H, s).

(2) (3S)-3-Hydroxy-1-(p-nitrobenzyloxycarbonyl)pyrrolidine

To a solution of (3S)-3-acetoxy-1-(p-nitrobenzyloxycarbonyl)-pyrrolidine (5.51 g, 17.8 mmol) (obtained as described in Reference Example 53(1)) in methanol (200 ml) was added a catalytic amount of sodium methoxide, and the mixture was stirred at room temperature for 4.5 hours. After checking the completion of the reaction, a solution of 4N hydrogen chloride in 1,4-dioxane (4.3 ml) was added thereto to neutralize the reaction mixture. The resulting reaction mixture was partitioned between ethyl acetate and saturated aqueous sodium hydrogencarbonate solution. The organic layer was washed with saturated aqueous sodium chloride solution, dried over-anhydrous sodium sulfate, filtered and concentrated under reduced pressure. The obtained residue was purified by chromatography on a silica gel column using n-hexane:ethyl acetate (1:2)→ethyl acetate as the eluant to afford (3S)-3-hydroxy-1-(p-nitrobenzyloxycarbonyl)pyrrolidine (4.00 g, yield 84%) as white crystals.

$^1$H-NMR (400 MHz, CDCl$_3$): δ (ppm) 8.22 (2H, d, J=8.1 Hz), 7.53 (2H, d, J=8.1 Hz), 5.24 (2H, s), 4.55–4.50 (1H, m), 3.63–3.52 (3H, m), 3.52–3.44 (1H, m), 2.09–1.92 (2H, m).

(3) (3S)-3-Methanesulfonyloxy-1-(p-nitrobenzyloxycarbonyl)pyrrolidine

To a solution of (3S)-3-hydroxy-1-(p-nitrobenzyloxycarbonyl)pyrrolidine (4.00 g, 15.0 mmol) (obtained as described in Reference Example 53(2)) in methylene chloride (120 ml) were added methanesulfonyl chloride (1.28 ml, 16.5 mmol) and triethylamine (2.31 ml, 16.5 mmol) in an ice bath. After stirring the mixture in the ice bath for 10 minutes, the mixture was stirred at room temperature for 2.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate as the eluant to afford (3S)-3-methanesulfonyloxy-1-(p-nitrobenzyloxycarbonyl) pyrrolidine (5.33 g, yield 100%) as a colorless and transparent syrup.

$^1$H-NMR (400 MHz, CDCl$_3$): δ (ppm) 8.23 (2H, d, J=8.8 Hz), 7.53 (2H, dd, J=8.1, 3.7 Hz), 5.33–5.23 (1H, m), 5.24 (2H, s), 3.82 (1H, dd, J=12.5, 5.1 Hz), 3.72–3.53 (3H, m), 3.06 (3H, s), 2.42–2.26 (1H, m), 2.26–2.11 (1H, m).

(4) (3R)-3-Azido-1-(p-nitrobenzyloxycarbonyl)-pyrrolidine

To a solution of (3S)-3-methanesulfonyloxy-1-(p-nitrobenzyloxycarbonyl)pyrrolidine (5.33 g, 15.0 mmol) (obtained as described in Reference Example 53(3)) in dimethylformamide (159 ml) was added sodium azide (1.07 g, 16.5 mmol), and the mixture was stirred in an oil bath (100° C.) for 3.5 hours. After checking the completion of the reaction, the reaction mixture was partitioned between ethyl acetate and saturated aqueous sodium hydrogencarbonate solution. The organic layer was washed successively with 10% aqueous sodium chloride solution and saturated aqueous sodium chloride solution, dried over anhydrous sodium sulfate, filtered and concentrated under reduced pressure. The residue was purified by chromatography on a silica gel column using n-hexane:ethyl acetate (3:1→1:2) as the eluant to afford (3R)-3-azido-1-(p-nitrobenzyloxycarbonyl) pyrrolidine (4.48 g, yield 100%) as a colorless oil.

$^1$H-NMR (400 MHz, CDCl$_3$): δ (ppm) 8.23 (2H, d, J=8.8 Hz), 7.53 (2H, d, J=8.8 Hz), 5.24 (2H, s), 4.24–4.18 (1H, m), 3.62–3.48 (4H, m), 2.19–2.02 (2H, m).

(5) (3R)-3-Amino-1-(p-nitrobenzyloxycarbonyl)pyrrolidine

To a solution of (3R)-3-azido-1-(p-nitrobenzyloxycarbonyl)pyrrolidine (4.48 g, 15.4 mmol) (obtained as described in Reference Example 53(4)) in acetonitrile (134 ml) was added triphenylphosphine (4.22 g, 16.1 mmol), and the mixture was stirred in an oil bath (70° C.) for 1.5 hours. After checking the disappearance of the raw materials, sodium sulfate decahydrate (5.19 g, 16.1 mmol) was added thereto and then the reaction mixture was stirred for 5 hours. After checking the completion of the reaction, the reaction mixture was filtered and partitioned between methylene chloride and 0.1M aqueous hydrogen chloride solution. To the obtained aqueous layer were added methylene chloride and sodium hydrogencarbonate, and the aqueous layer was extracted with methylene chloride. The obtained organic layer was dried over anhydrous sodium sulfate, filtered and concentrated under reduced pressure. The residue was dried under reduced pressure to give (3R)-3-amino-1-(p-nitrobenzyloxycarbonyl)pyrrolidine (3.53 g, yield 86%) as pale yellow crystals.

$^1$H-NMR (400 MHz, CDCl$_3$): δ (ppm) 8.22 (2H, d, J=8.8 Hz), 7.52 (2H, d, J=8.8 Hz), 5.23 (2H, s), 3.66–3.58 (3H, m), 3.52–3.45 (1H, m), 3.19–3.12 (1H, m), 2.13–2.04 (1H, m), 1.76–1.66 (1H, m).

(6) 3-t-Butyldiphenylsilyloxy-1-{4-[(3R)-1-(p-nitrobenzyloxycarbonyl)-pyrrolidin-3-ylcarbamoyl]-1,3-thiazol-2-yl}azetidine To a suspension of (3R)-3-amino-1-(p-nitrobenzyloxycarbonyl)pyrrolidine (363 mg, 1.37 mmol) (obtained as described in Reference Example 53(5)) and 3-t-butyldiphenylsilyloxy-1-(4-carboxyl-1,3-thiazol-2-yl) azetidine (500 mg, 1.14 mmol) (obtained as described in Reference Example 2(4)) in dimethylformamide (25 ml) were added diethylphosphoryl cyanide (208 μl, 1.37 mmol) and triethylamine (192 μl, 1.37 mmol) in an ice bath under an atmosphere of nitrogen. The mixture was stirred at room temperature for 2 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1→1:3) as the eluant to afford 3-t-butyldiphenylsilyloxy-1-{4-[(3R)-1-(p-nitrobenzyloxycarbonyl)-pyrrolidin-3-ylcarbamoyl]-1,3-thiazol-2-yl}azetidine (598 mg, yield 51%) as a pale yellow solid.

$^1$H-NMR (400 MHz, CDCl$_3$): δ (ppm) 8.22 (2H, d, J=8.8 Hz), 7.62 (4H, d, J=8.1 Hz), 7.56–7.38 (8H, m), 7.37 (1H, s), 7.22–7.16 (1H, br s), 5.24 (2H, d, J=8.8 Hz), 4.76 (1H, ddd, J=6.6, 5.1 Hz), 4.67–4.58 (1H, m), 4.15–4.07 (2H, m), 4.06–3.98 (2H, m), 3.86–3.78 (1H, m), 3.67–3.52 (2H, m), 3.40 (1H, dd, J=11.0, 5.1 Hz), 2.34–2.20 (1H, m), 2.02–1.90 (1H, m), 1.07 (9H, s).

(7) 3-Hydroxy-1-{4-[(3R)-1-(p-nitrobenzyloxycarbonyl)-pyrrolidin-3-ylcarbamoyl]-1,3-thiazol-2-yl}azetidine To a suspension of 3-t-butyldiphenylsilyloxy-1-{4-[(3R)-1-(p-nitrobenzyloxycarbonyl)-pyrrolidin-3-ylcarbamoyl]-1,3-thiazol-2-yl}azetidine (590 mg, 0.860 mmol) (obtained as described in Reference Example 53(6)) in anhydrous tetrahydrofuran (18 ml) were added successively acetic acid (59 μl, 1.03 mmol) and a solution of 1.0M tetra-n-butylammonium fluoride in tetrahydrofuran (1.03 ml, 1.03 mmol) in an ice bath, and the mixture was stirred in the ice bath for 1 hour. After checking the completion of the reaction, the reaction mixture was partitioned between ethyl acetate and water. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate→ethyl acetate:methanol (95:5) as the eluant to afford 3-hydroxy-1-{4-[(3R)-1-(p-nitrobenzyloxycarbonyl)-pyrrolidin-3-ylcarbamoyl]-1,3-thiazol-2-yl}azetidine (378 mg, yield 98%) as a white solid.

$^1$H-NMR (400 MHz, CDCl$_3$): δ (ppm) 8.21 (2H, m), 7.53 (2H, m), 7.40 (1H, s), 7.24–7.18 (1H, br s), 5.30–5.18 (2H, m), 4.88–4.81 (1H, m), 4.66–4.58 (1H, m), 4.32 (2H, t, J=7.8 Hz), 3.96 (2H, dd, J=8.8, 4.9 Hz), 3.80 (1H, dt, J=12.2, 6.8 Hz), 3.66–3.52 (2H, m), 3.46–3.40 (1H, m), 2.49–2.41 (1H, br s), 2.33–2.22 (1H, m), 2.09–1.95 (1H, m).

(8) 3-Methanesulfonyloxy-1-{4-[(3R)-1-(p-nitrobenzyloxycarbonyl)-pyrrolidin-3-ylcarbamoyl]-1,3-thiazol-2-yl}azetidine To a solution of 3-hydroxy-1-{4-[(3R)-1-(p-nitrobenzyloxycarbonyl)-pyrrolidin-3-ylcarbamoyl]-1,3-thiazol-2-yl}azetidine (370 mg, 0.827 mmol) (obtained as described in Reference Example 53(7)) in methylene chloride (19 ml) were added methanesulfonyl chloride (192 μl, 2.48 mmol) and triethylamine (348 μl, 2.48 mmol) in an ice bath. The reaction mixture was brought to room temperature in 10 minutes, and then stirred at room temperature for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The obtained residue was purified by chromatography on a silica gel column using ethyl acetate→ethyl acetate:methanol (98:2) as the eluant to afford 3-methanesulfonyloxy-1-{4-[(3R)-1-(p-nitrobenzyloxycarbonyl)-pyrrolidin-3-ylcarbamoyl]-1,3-thiazol-2-yl}azetidine (422 mg, yield 97%) as a pale yellow solid.

$^1$H-NMR (400 MHz, CDCl$_3$): δ (ppm) 8.21 (2H, m), 7.53 (2H, m), 7.46 (1H, s), 7.19–7.13 (1H, br s), 5.45–5.40 (1H, m), 5.24 (2H, d, J=10.7 Hz), 4.66–4.59 (1H, m), 4.46 (2H, t, J=7.8 Hz), 4.27 (2H, dd, J=9.8, 2.9 Hz), 3.81 (1H, dt, J=13.7, 5.9 Hz), 3.66–3.54 (2H, m), 3.43 (1H, dd, J=11.2, 4.4 Hz), 3.12 (3H, s), 2.30–2.22 (1H, m), 2.09–1.95 (1H, m).

(9) 3-Acetylthio-1-{4-[(3R)-1-(p-nitrobenzyloxycarbonyl)-pyrrolidin-3-ylcarbamoyl]-1,3-thiazol-2-yl}azetidine To a solution of 3-methanesulfonyloxy-1-{4-[(3R)-1-(p-nitrobenzyloxycarbonyl)-pyrrolidin-3-ylcarbamoyl]-1,3-thiazol-2-yl}azetidine (420 mg, 0.799 mmol) (obtained as described in Reference Example 53(8)) in dimethylformamide (21 ml) was added potassium thioacetate (548 mg, 4.79 mmol) at room temperature. The mixture was stirred in an oil bath (80° C.) overnight. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate:methanol (99:1) as the eluant to afford 3-acetylthio-1-{4-[(3R)-1-(p-nitrobenzyloxycarbonyl)-pyrrolidin-3-ylcarbamoyl]-1,3-thiazol-2-yl}azetidine (280 mg, yield 69%) as a pale brown solid.

$^1$H-NMR (400 MHz, CDCl$_3$): δ (ppm) 8.22 (2H, m), 7.3 (2H, m), 7.42 (1H, s), 7.21–7.15 (1H, br s), 5.24 (2H, d, J=10.7 Hz), 4.66–4.58 (1H, m), 4.53 (2H, dd, J=8.8, 7.8 Hz), 4.47–4.41 (1H, m), 3.99 (2H, dd, J=6.8, 5.9 Hz), 3.84–3.76 (1H, m), 3.66–3.53 (2H, m), 3.41 (1H, dd, J=11.7, 4.9 Hz), 2.37 (3H, s), 2.33–2.23 (1H, m), 2.03–1.94 (1H, m).

REFERENCE EXAMPLE 54

3-Acetylthio-1-{4-[(1-p-nitrobenzyloxycarbonyl)-azetidin-3-ylcarbamoyl]-1,3-thiazol-2-yl}azetidine

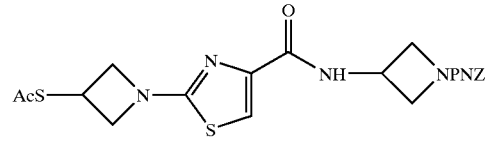

(1) 3-Hydroxy-1-(p-nitrobenzyloxycarbonyl)azetidine

A solution of 1-benzhydryl-3-hydroxyazetidine (9.00 g, 37.6 mmol) in methanol (270 ml) was subjected to catalytic hydrogenation in the presence of 10% palladium on charcoal (9.00 g) in a water bath (50° C.) for 5.5 hours. After checking the completion of the reaction, the reaction mixture was filtered in order to remove the catalyst and the filtrate concentrated under reduced pressure. The residue was partitioned between ethyl acetate and distilled water. The organic layer was concentrated under reduced pressure and dried in vacuo to give a crude product. To a solution of the crude product in a mixture of methylene chloride (82 ml) and methanol (55 ml) were added chloroformic acid p-nitrobenzyl ester (8.90 g, 41.3 mmol) and triethylamine (5.79 ml, 41.3 mmol) in an ice bath. The mixture was stirred at room temperature for 1.5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1)→ethyl acetate as the eluant to afford 3-hydroxy-1-(p-nitrobenzyloxycarbonyl)azetidine (3.52 g, yield 37%) as pale yellow crystals.

$^1$H-NMR (400 MHz, CDCl$_3$): δ (ppm) 8.22 (2H, d, J=8.8 Hz), 7.50 (2H, d, J=8.8 Hz), 5.19 (2H, s), 4.71–4.64 (1H, m), 4.27 (2H, dd, J=9.9, 7.0 Hz), 3.93 (2H, dd, J=9.9, 4.0 Hz), 2.20–2.16 (1H, br d, J=5.9 Hz).

(2) 3-Methanesulfonyloxy-1-(p-nitrobenzyloxycarbonyl)azetidine

To a solution of 3-hydroxy-1-(p-nitrobenzyloxycarbonyl)azetidine (3.52 g, 14.0 mmol) (obtained as described in Reference Example 54(1)) in methylene chloride (106 ml) were added methanesulfonyl chloride (1.19 ml, 15.4 mmol) and triethylamine (2.16 ml, 15.4 mmol) in an ice bath. After stirring the mixture in the ice bath for 10 minutes, the mixture was stirred at room temperature overnight. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1→1:3) as the eluant to afford 3-methanesulfonyloxy-1-(p-nitrobenzyloxycarbonyl)-azetidine (4.63 g, yield 100%) as pale yellow crystals.

$^1$H-NMR (400 MHz, CDCl$_3$): δ (ppm) 8.22 (2H, d, J=8.8 Hz), 7.50 (2H, d, J=8.8 Hz), 5.29–5.22 (1H, m), 5.20 (2H, s), 4.40 (2H, dd, J=10.2, 6.2 Hz), 4.22 (2H, dd, J=10.2, 4.0 Hz), 3.08 (3H, s).

(3) 3-Azido-1-(p-nitrobenzyloxycarbonyl)azetidine

To a solution of 3-methanesulfonyloxy-1-(p-nitrobenzyloxycarbonyl)azetidine (4.63 g, 14.0 mmol)

(obtained as described in Reference Example 54(2)) in dimethylformamide (140 ml) was added sodium azide (1.37 g, 21.0 mmol), and the mixture was stirred in an oil bath (100° C.) for 4 hours. After checking the completion of the reaction, the reaction mixture was partitioned between ethyl acetate and 10% aqueous sodium chloride solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (2:1→1:1) as the eluant to afford 3-azido-1-(p-nitrobenzyloxycarbonyl)azetidine (2.15 g, yield 55%) as pale yellow crystals.

$^1$H-NMR (400 MHz, CDCl$_3$): δ (ppm) 8.22 (2H, d, J=8.8 Hz), 7.50 (2H, d, J=8.8 Hz), 5.19 (2H, s), 4.33–4.28 (3H, m), 4.03–3.96 (2H, m).

(4) 3-Amino-1-(p-nitrobenzyloxycarbonyl)azetidine

To a solution of 3-azido-1-(p-nitrobenzyloxycarbonyl) azetidine (2.15 g, 7.76 mmol) (obtained as described in Reference Example 54(3)) in acetonitrile (65 ml) was added triphenylphosphine (2.14 g, 8.14 mmol), and the mixture was stirred in an oil bath (70° C.) for 2 hours. After checking the disappearance of the raw materials, sodium sulfate decahydrate (2.62 g, 8.14 mmol) was added thereto and then the reaction mixture was stirred for 3 hours. After checking the completion of the reaction, the reaction mixture was filtered and partitioned between methylene chloride and 0.1M aqueous hydrogen chloride solution. To the obtained aqueous layer were added methylene chloride and sodium hydrogencarbonate, and the aqueous layer was extracted with methylene chloride. The obtained organic layer was dried over anhydrous sodium sulfate, filtered and concentrated under reduced pressure. The residue was dried under reduced pressure to give 3-amino-1-(p-nitrobenzyloxycarbonyl)-azetidine (1.87 g, yield 96%) as pale yellow crystals.

$^1$H-NMR (400 MHz, CDCl$_3$): δ (ppm) 8.22 (2H, d, J=8.8 Hz), 7.50 (2H, d, J=8.8 Hz), 5.18 (2H, s), 4.27 (2H, dd, J=8.6, 8.6 Hz), 3.87 (1H, tt, J=5.1, 7.3 Hz), 3.70 (2H, dd, J=8.8, 5.1 Hz).

(5) 3-t-Butyldiphenylsilyloxy-1-{4-[(1-p-nitrobenzyloxycarbonyl)-azetidin-3-ylcarbamoyl]-1,3-thiazol-2-yl}azetidine To a solution of 3-amino-1-(p-nitrobenzyloxycarbonyl)-azetidine (549 mg, 2.18 mmol) (obtained as described in Reference Example 54(4)) and 3-t-butyldiphenylsilyloxy-1-(4-carboxyl-1,3-thiazol-2-yl)azetidine (800 mg, 1.82 mmol) in dimethylformamide (40 ml) were added diethylphosphoryl cyanide (331 µl, 2.18 mmol) and triethylamine (306 µl, 2.18 mmol) in an ice bath under an atmosphere of nitrogen. The mixture was stirred at room temperature for 5 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1→1:3) as the eluant to afford 3-t-butyldiphenylsilyloxy-1-{4-[(1-p-nitrobenzyloxycarbonyl)-azetidin-3-ylcarbamoyl]-1,3-thiazol-2-yl}azetidine (1.06 g, yield 49%) as a pale yellow solid.

$^1$H-NMR (400 MHz, CDCl$_3$): δ (ppm) 8.23 (2H, d, J=8.1 Hz), 7.62 (4H, d, J=8.1 Hz), 7.54–7.39 (8H, m), 7.37 (1H, s), 5.21 (2H, s), 4.89–4.81 (1H, m), 4.81–4.73 (1H, m), 4.41 (2H, dd, J=8.8, 8.8 Hz), 4.12 (2H, dd, J=8.8, 8.8 Hz), 4.05–3.98 (4H, m), 1.07 (9H, s).

(6) 3-Hydroxy-1-{4-[(1-p-nitrobenzyloxycarbonyl)-azetidin-3-ylcarbamoyl]-1,3-thiazol-2-yl}azetidine To a solution of 3-t-butyldiphenylsilyloxy-1-{4-[(1-p-nitrobenzyloxycarbonyl)-azetidin-3-ylcarbamoyl]-1,3-thiazol-2-yl}azetidine (1.06 g, 1.58 mmol) (obtained as described in Reference Example 54(5)) in anhydrous tetrahydrofuran (53 ml) were added successively acetic acid (109 µl, 1.90 mmol) and a 1.0M solution of tetra-n-butylammonium fluoride in tetrahydrofuran (1.90 ml, 1.90 mmol) in an ice bath, and then the mixture was stirred in the ice bath for 2 hours. After checking the completion of the reaction, the reaction mixture was partitioned between ethyl acetate and water. The obtained organic layer was washed successively with saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using ethyl acetate→ethyl acetate:methanol (95:5) as the eluant to afford 3-hydroxy-1-{4-[(1-p-nitrobenzyloxycarbonyl)-azetidin-3-ylcarbamoyl]-1,3-thiazol-2-yl}azetidine (649 mg, yield 95%) as a white solid.

$^1$H-NMR (400 MHz, CDCl$_3$): δ (ppm) 8.22 (2H, d, J=8.8 Hz), 7.58–7.50 (1H, br s), 7.52 (2H, d, J=8.8 Hz), 7.40 (1H, s), 5.20 (2H, s), 4.90–4.80 (1H, m), 4.42 (2H, dd, J=8.8, 8.8 Hz), 4.34 (2H, dd, J=9.5, 6.6 Hz), 4.02 (2H, dd, J=9.5, 5.2 Hz), 4.00–3.96 (2H, m).

(7) 3-Methanesulfonyloxy-1-{4-[(1-p-nitrobenzyloxycarbonyl)-azetidin-3-ylcarbamoyl]-1,3-thiazol-2-yl}azetidine To a solution of 3-hydroxy-1-{4-[(1-p-nitrobenzyloxycarbonyl)-azetidin-3-ylcarbamoyl]-1,3-thiazol-2-yl}azetidine (640 mg, 1.48 mmol) (obtained as described in Reference Example 54(6)) in methylene chloride (20 ml) were added methanesulfonyl chloride (343 µl, 4.43 mmol) and triethylamine (621 µl, 4.43 mmol) in an ice bath. After stirring the mixture in the ice bath for 10 minutes, the mixture was stirred at room temperature overnight. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate→ethyl acetate:methanol (98:2) as the eluant to afford 3-methanesulfonyloxy-1-{4-[(1-p-nitrobenzyloxycarbonyl)-azetidin-3-ylcarbamoyl]-1,3-thiazol-2-yl}azetidine (611 mg, yield 81%) as a pale yellow solid.

$^1$H-NMR (400 MHz, CDCl$_3$): δ (ppm) 8.22 (2H, d, J=8.8 Hz), 7.51 (2H, d, J=8.8 Hz), 7.50–7.46 (1H, br s), 7.46 (1H, s), 5.46–5.41 (1H, m), 5.20 (2H, s), 4.89–4.80 (1H, m), 4.49–4.38 (4H, m), 4.28 (2H, dd, J=11.8, 4.4 Hz), 4.01 (2H, dd, J=9.5, 5.3 Hz), 3.12 (3H, s).

(8) 3-Acetylthio-1-{4-[(1-p-nitrobenzyloxycarbonyl)-azetidin-3-ylcarbamoyl]-1,3-thiazol-2-yl}azetidine To a solution of 3-methanesulfonyloxy-1-{4-[(1-p-nitrobenzyloxycarbonyl)-azetidin-3-ylcarbamoyl]-1,3-thiazol-2-yl}azetidine (610 mg, 1.19 mmol) (obtained as described in Reference Example 54(7)) in dimethylformamide (81 ml) was added potassium thioacetate (817 mg, 7.15 mmol) at room temperature. The reaction mixture was stirred in an oil bath (80° C.) overnight. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate as the eluant to afford 3-acetylthio-1-{4-[(1-p-nitrobenzyloxycarbonyl)-azetidin-3-ylcarbamoyl]-1,3-thiazol-2-yl}azetidine (405 mg, yield 69%) as a pale brown solid.

$^1$H-NMR (400 MHz, CDCl$_3$): δ (ppm) 8.22 (2H, d, J=8.8 Hz), 7.53–7.49 (1H, m), 7.51 (2H, d, J=8.8 Hz), 7.43 (1H, s), 5.20 (2H, s), 4.89–4.79 (1H, m), 4.54 (2H, dd, J=8.1, 8.1 Hz), 4.48–4.18 (3H, m), 4.04–3.97 (2H, m), 2.37 (3H, s).

REFERENCE EXAMPLE 55

3-Acetylthio-1-{4-[(4-p-nitrobenzyloxycarbonyl)-piperazine-1-carbonyl]-1,3-thiazol-2-yl}azetidine

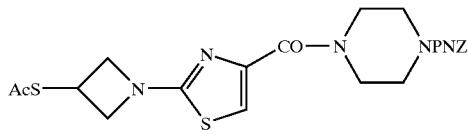

(1) 4-(p-Nitrobenzyloxycarbonyl)piperazine hydrochloride

To a solution of 4-(t-butoxycarbonyl)piperazine (1.50 g, 8.05 mmol) in methylene chloride (68 ml) were added chloroformic acid p-nitrobenzyl ester (1.90 g, 8.86 mmol) and triethylamine (1.24 ml, 8.86 mmol) in an ice bath. The mixture was stirred in the ice bath for 1.5 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using hexane:ethyl acetate=(1:3) as the eluant to afford 1-(t-butoxycarbonyl)-4-(p-nitrobenzyloxycarbonyl)piperazine (2.60 g, yield 89%) as a pale yellow oil.

Subsequently, to a solution of this product (2.60 g, 7.12 mmol) in acetonitrile (100 ml) was added a 4N solution of hydrogen chloride in ethyl acetate (15.0 ml) in an ice bath, and then the reaction mixture was stirred in the ice bath for 2 hours. After checking the completion of the reaction, diethyl ether was added thereto and the reaction mixture was stirred for 30 minutes. The reaction mixture was filtered off and washed with diethyl ether to give 4-(p-nitrobenzyloxycarbonyl)-piperazine hydrochloride (2.4 g, yield 86%) as a white solid.

(2) 3-t-Butyldiphenylsilyloxy-1-{4-[(4-p-nitrobenzyloxycarbonyl)-piperazine-1-carbonyl]-1,3-thiazol-2-yl}azetidine To a solution of 4-(p-nitrobenzyloxycarbonyl)piperazine hydrochloride (874 mg, 2.19 mmol) (obtained as described in Reference Example 55(1)) and 3-t-butyldiphenylsilyloxy-1-(4-carboxyl-1,3-thiazol-2-yl)azetidine (800 mg, 1.82 mmol) (obtained as described in Reference Example 2(4)) in dimethylformamide (40 ml) were added diethylphosphoryl cyanide (0.33 ml, 2.19 mmol) and triethylamine (0.30 ml, 2.19 mmol) in an ice bath under an atmosphere of nitrogen. The mixture was stirred in the ice bath for 1 hour. After checking the completion of the reaction, the reaction mixture was partitioned between ethyl acetate and saturated aqueous sodium hydrogencarbonate solution. The obtained organic layer was washed successively with a 0.5M aqueous hydrochloric acid solution, saturated aqueous sodium hydrogencarbonate solution, and saturated aqueous sodium chloride solution, dried over anhydrous magnesium sulfate, filtered and concentrated under reduced pressure. The residue was purified by chromatography on a silica gel column using hexane:ethyl acetate (1:1) as the eluant to afford 3-t-butyldiphenylsilyloxy-1-{4-[(4-p-nitrobenzyloxycarbonyl)-piperazine-1-carbonyl]-1,3-thiazol-2-yl}azetidine (915 mg, yield 73%) as a pale yellow oil.

$^1$H-NMR (400 MHz, CDCl$_3$): δ (ppm) 8.24 (2H, d, J=8.7 Hz), 7.61 (4H, dd, J=7.9, 1.4 Hz), 7.52 (2H, d, J=8.7 Hz), 7.49–7.37 (6H, m), 7.14 (1H, s), 5.25 (2H, s), 4.80–4.71 (1H, m), 4.11 (2H, dd, J=8.7, 6.6 Hz), 4.01 (2H, dd, J=8.7, 4.9 Hz), 3.95–3.66 (4H, m), 3.65–3.52 (4H, m), 1.06 (9H, s).

(3) 3-Hydroxy-1-{4-[(4-p-nitrobenzyloxycarbonyl)-piperazine-1-carbonyl]-1,3-thiazol-2-yl}azetidine To a solution of 3-t-butyldiphenylsilyloxy-1-{4-[(4-p-nitrobenzyloxycarbonyl)-piperazine-1-carbonyl]-1,3-thiazol-2-yl}azetidine (1.77 g, 1.71 mmol) (obtained as described in Reference Example 55(2)) in anhydrous tetrahydrofuran (35 ml) were added successively acetic acid (0.11 ml, 1.88 mmol) and a solution of 1.0M tetra-n-butylammonium fluoride in tetrahydrofuran (1.88 ml, 1.88 mmol) in an ice bath, and then the mixture was stirred in the ice bath for 1 hour. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using ethyl acetate→ethyl acetate:methanol (9:1) as the eluant to afford 3-hydroxy-1-{4-[(4-p-nitrobenzyloxycarbonyl)-piperazine-1-carbonyl]-1,3-thiazol-2-yl}azetidine (726 mg, yield 95%) as a white solid.

$^1$H-NMR (400 MHz, CDCl$_3$): δ (ppm) 8.24 (2H, d, J=8.6 Hz), 7.52 (2H, d, J=8.6 Hz), 7.17 (1H, s), 5.25 (2H, s), 4.89–4.79 (1H, m), 4.32 (2H, dd, J=9.1, 6.7 Hz), 3.96 (2H, dd, J=9.1, 4.5 Hz), 3.93–3.68 (4H, m), 3.66–3.52 (4H, m).

(4) 3-Methanesulfonyloxy-1-{4-[(4-p-nitrobenzyloxycarbonyl)-piperazine-1-carbonyl]-1,3-thiazol-2-yl}azetidine To a solution of 3-hydroxy-1-{4-[(4-p-nitrobenzyloxycarbonyl)-piperazine-1-carbonyl]-1,3-thiazol-2-yl}azetidine (804 mg, 1.80 mmol) (obtained as described in Reference Example 55(3)) in methylene chloride (40 ml) were added methanesulfonyl chloride (0.30 ml, 2.15 mmol) and triethylamine (0.17 ml, 2.15 mmol) in an ice bath. The mixture was stirred in the ice bath for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate→ethyl acetate:methanol (9:1) as the eluant to afford 3-methanesulfonyloxy-1-{4-[(4-p-nitrobenzyloxycarbonyl)-piperazine-1-carbonyl]-1,3-thiazol-2-yl}azetidine (550 mg, yield 58%) as a pale yellow solid.

$^1$H-NMR (400 MHz, CDCl$_3$): δ (ppm) 8.23 (2H, d, J=8.5 Hz), 7.53 (2H, d, J=8.5 Hz), 7.25 (1H, s), 5.50–5.39 (1H, m), 5.26 (2H, s), 4.49 (2H, t, J=9.6 Hz), 4.26 (2H, dd, J=9.6, 4.2 Hz), 4.00–3.66 (4H, m), 3.66–3.47 (4H, m), 3.11 (3H, s).

(5) 3-Acetylthio-1-{4-[(4-p-nitrobenzyloxycarbonyl)-piperazine-1-carbonyl]-1,3-thiazol-2-yl}azetidine To a solution of 3-methanesulfonyloxy-1-{4-[(4-p-nitrobenzyloxycarbonyl)-piperazine-1-carbonyl]-1,3-thiazol-2-yl}azetidine (550 mg, 1.05 mmol) (obtained as described in Reference Example 55(4)) in dimethylformamide (40 ml) was added potassium thioacetate (717 mg, 6.28 mmol) at room temperature. The reaction mixture was stirred in an oil bath (90° C.) for 3 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-acetylthio-1-{4-[(4-p-nitrobenzyloxycarbonyl)-piperazine-1-carbonyl]-1,3-thiazol-2-yl}azetidine (345 mg, yield 64%) as a pale brown solid.

$^1$H-NMR (400 MHz, CDCl$_3$): δ (ppm) 8.23 (2H, d, J=8.7 Hz), 7.53 (2H, d, J=8.7 Hz), 7.22 (1H, s), 5.25 (2H, s), 4.52 (2H, t, J=8.4 Hz), 4.48–4.39 (1H, m), 3.98 (2H, dd, J=8.4, 5.3 Hz), 3.95–3.68 (4H, m), 3.45–3.68 (4H, m), 2.33 (3H, s).

REFERENCE EXAMPLE 56

3-Acetylthio-1-{4-[2-(p-nitrobenzyloxycarbonylamino)ethylcarbamoyl]-1,3-thiazol-2-yl}azetidine

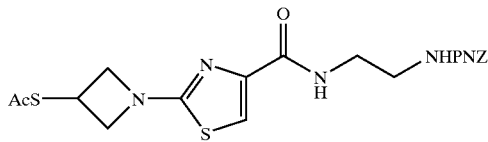

(1) (2-Hydroxyethyl)carbamic acid t-butyl ester

To a solution of aminoethanol (2.51 g, 41.1 mmol) in a mixture of methylene chloride (50 ml) and methanol (50 ml) were added di-t-butoxycarbonic anhydride (13.5 g, 61.9 mmol) and triethylamine (8.6 ml, 61.7 mmol) in an ice bath. The mixture was stirred at room temperature for 3 hours. After checking the completion of the reaction, the reaction mixture was concentrated under reduced pressure. The obtained residue was partitioned between ethyl acetate and saturated aqueous sodium chloride solution. The obtained organic layer was dried over anhydrous sodium sulfate, filtered and concentrated under reduced pressure. The residue was purified by chromatography on a silica gel column using hexane:ethyl acetate (1:1) as the eluant to afford (2-hydroxyethyl)carbamic acid t-butyl ester (6.18 g, yield 93%) as a colorless and transparent syrup.

$^1$H-NMR (400 MHz, CDCl$_3$): δ (ppm) 5.01 (1H, br s), 3.70 (2H, br s), 3.29 (2H, q, J=5.1 Hz), 2.65 (1H, br s), 1.45 (9H, s).

(2) (2-Azidoethyl)carbamic acid t-butyl ester

To a solution of (2-hydroxyethyl)carbamic acid t-butyl ester (1.5 g, 6.2 mmol) in tetrahydrofuran (75 ml) were added diphenylphosphoryl azide (3.0 ml, 13.9 mmol), triphenylphosphine (3.7 g, 14.1 mmol), and a 40% solution of diethylazodicarboxylate in toluene (5.1 g, 13.9 mmol) in an ice bath under an atmosphere of nitrogen, and then the mixture was stirred for 4 hours under the same conditions. After checking the completion of the reaction, the reaction mixture was partitioned between ethyl acetate and saturated aqueous sodium chloride solution. The organic layer was dried over anhydrous sodium sulfate, filtered and concentrated under reduced pressure. The obtained residue was purified by chromatography on a silica gel column using hexane:ethyl acetate (3:1) as the eluant to afford (2-azidoethyl)carbamic acid t-butyl ester (1.24 g, yield 72%) as a colorless and transparent syrup.

$^1$H-NMR (500 MHz, CDCl$_3$): δ (ppm) 4.85 (1H, br s), 3.42 (2H, t, J=4.8 Hz), 3.31 (2H, t, J=4.8 Hz), 1.45 (9H, s).

IR (liquid film): 2103, 1697, 1521, 1368, 1272, 1253 cm$^{-1}$.

Mass spectrum (FAB$^+$): 187 [M+H]$^+$.

High resolution mass spectrum (FAB$^+$): Observed value: 187.1186 [M+H]$^+$, Calculated value: 187.1195 (C$_7$H$_{15}$O$_2$N$_4$).

(3) (2-t-Butoxycarbonylaminoethyl)carbamic acid p-nitrobenzyl ester

A solution of (2-azidoethyl)carbamic acid t-butyl ester (1.22 g, 6.55 mmol) in methanol (60 ml) was subjected to catalytic hydrogenation in the presence of 20% palladium hydroxide on charcoal (1.22 g) at room temperature. After checking the completion of the reaction, the reaction mixture was filtered, and the filtrate concentrated under reduced pressure. To a solution of the obtained crude product in methylene chloride (60 ml) were added chloroformic acid p-nitrobenzyl ester (2.12 g, 9.8 mmol) and triethylamine (1.37 ml, 9.8 mmol) in an ice bath, and the reaction mixture was stirred at room temperature overnight. After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using toluene:acetonitrile (3:1) as the eluant to afford (2-t-butoxycarbonylaminoethyl)carbamic acid p-nitrobenzyl ester (1.46 g, yield 66%) as a white solid.

$^1$H-NMR (500 MHz, CDCl$_3$): δ (ppm) 8.22 (2H, d, J=9.0 Hz), 7.51 (2H, d, J=9.0 Hz), 5.37 (1H, br s), 5.20 (2H, s), 4.82 (1H, br s), 3.35–3.25 (4H, m), 1.45 (9H, s).

IR (KBr): 3355, 1708, 1692, 1534, 1350, 1263, 1170 cm$^{-1}$.

Mass spectrum (FAB$^+$): 340 [M+H]$^+$.

High resolution mass spectrum (FAB$^+$): Observed value: 340.1512 [M+H]$^+$, Calculated value: 340.1508 (C$_{15}$H$_{22}$O$_6$N$_3$).

(4) 3-t-Butyldiphenylsilyloxy-1-{4-[2-(p-nitrobenzyloxycarbonylamino)ethylcarbamoyl]-1,3-thiazol-2-yl}azetidine To a solution of (2-t-butoxycarbonylaminoethyl)carbamic acid p-nitrobenzyl ester (1.46 g, 4.3 mmol) in 1,4-dioxane (15 ml) was added a 4N solution of hydrogen chloride in 1,4-dioxane (15 ml) in an ice bath, and the mixture was stirred at room temperature for 5.5 hours. After checking the completion of the reaction, diethyl ether was added thereto and the reaction mixture was stirred for 30 minutes. The resulting reaction mixture was filtered off and washed with diethyl ether to give 1-(p-nitrobenzyloxycarbonylamino)ethylamine hydrochloride (1.18 g, yield 100%) as a white solid.

Subsequently, to a suspension of 2-(p-nitrobenzyloxycarbonylamino)ethylamine hydrochloride (490 mg, 1.77 mmol) described above and 3-t-butyldiphenylsilyloxy-1-(4-carboxyl-1,3-thiazol-2-yl)azetidine (530 mg, 1.21 mmol) (obtained as described in Reference Example 2(4)) in dimethylformamide (26.5 ml) were added diethylphosphoryl cyanide (0.3 ml, 1.98 mmol) and triethylamine (0.5 ml, 3.59 mmol) in an ice bath under an atmosphere of nitrogen. The mixture was stirred at room temperature for 1.5 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution and saturated aqueous sodium chloride solution, dried over anhydrous magnesium sulfate, filtered and concentrated under reduced pressure. The residue was purified by chromatography on a silica gel column using toluene:acetonitrile (2:1) as the eluant to afford 3-t-butyldiphenylsilyloxy-1-{4-[2-(p-nitrobenzyloxycarbonylamino)ethylcarbamoyl]-1,3-thiazol-2-yl}azetidine (630 mg, yield 79%) as a pale yellow solid.

$^1$H-NMR (500 MHz, CDCl$_3$): δ (ppm) 8.16 (2H, d, J=8.8 Hz), 7.62 (4H, d, J=6.8 Hz), 7.50–7.38 (9H, m), 7.35 (1H, s), 5.62 (1H, br t, J=5.9 Hz), 5.17 (2H, s), 4.79–4.72 (1H, m), 4.09 (2H, dd, J=8.8, 6.6 Hz), 4.00 (2H, dd, J=8.8, 4.9 Hz), 3.55 (2H, q, J=5.9 Hz), 3.43 (2H, q, J=5.9 Hz), 1.07 (9H, s).

IR (KBr): 1724, 1660, 1547, 1523, 1346, 1318, 1255, 1113 cm$^{-1}$.

Mass spectrum (FAB$^+$): 660 [M+H]$^+$.

High resolution mass spectrum (FAB$^+$): Observed value: 660.2324 [M+H]$^+$, Calculated value: 660.2312 (C$_{33}$H$_{38}$O$_6$SSi).

(5) 3-Hydroxy-1-{4-[2-(p-nitrobenzyloxycarbonylamino) ethylcarbamoyl]-1,3-thiazol-2-yl}azetidine To a solution of 3-t-butyldiphenylsilyloxy-1-{4-[2-(p-nitrobenzyloxycarbonylamino)-ethylcarbamoyl]-1,3-thiazol-2-yl}azetidine (1.21 g, 1.84 mmol) (obtained as described in Reference Example 56(4)) in anhydrous tetrahydrofuran (60.6 ml) were added successively acetic acid (0.13 ml, 2.27 mmol) and a solution of 1.0M tetra-n-butylammonium fluoride in tetrahydrofuran (2.2 ml, 2.2 mmol) in an ice bath. The mixture was stirred for 2.5 hours under the same conditions. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. To the residue was added isopropyl ether, and the mixture was stirred, washed and filtered off to give 3-hydroxy-1-{4-[2-(p-nitrobenzyloxycarbonylamino)-ethylcarbamoyl]-1,3-thiazol-2-yl}azetidine (667 mg, yield 86%) as a yellow solid.

$^1$H-NMR (500 MHz, DMSO-d$_6$): δ (ppm) 8.21 (2H, d, J=8.8 Hz), 8.03 (1H, t, J=5.9 Hz), 7.59 (2H, d, J=8.8 Hz), 7.50 (1H, t, J=5.9 Hz), 7.41 (1H, s), 5.83 (1H, d, J=5.9 Hz), 5.17 (2H, s), 4.66–4.58 (1H, m), 4.23 (2H, dd, J=8.8, 7.0 Hz), 3.79 (2H, dd, J=8.8, 4.9 Hz), 3.31 (2H, q, J=5.9 Hz), 3.16 (2H, q, J=5.9 Hz).

IR (KBr): 1698. 1655, 1552, 1520, 1343, 1279 cm$^{-1}$.

Mass spectrum (FAB$^+$): 422 [M+H]$^+$.

High resolution mass spectrum (FAB$^+$): Observed value: 444.0952 [M+Na]$^+$, Calculated value: 444.0953 (C$_{17}$H$_{19}$O$_6$N$_5$SNa).

(6) 3-Methanesulfonyloxy-1-{4-[2-(p-nitrobenzyloxycarbonylamino)ethylcarbamoyl]-1,3-thiazol-2-yl}azetidine To a solution of 3-hydroxy-1-{4-[2-(p-nitrobenzyloxycarbonylamino)ethylcarbamoyl]-1,3-thiazol-2-yl}azetidine (658.4 mg, 1.56 mmol) (obtained as described in Reference Example 56(5)) in a mixture of methylene chloride (33 ml) and pyridine (5 ml) were added methanesulfonyl chloride (0.31 ml, 4.00 mmol) and triethylamine (0.57 ml, 4.09 mmol) in an ice bath. After stirring the mixture in the ice bath for 10 minutes, the resulting mixture was stirred at room temperature for 4 hours. After checking the completion of the reaction, the reaction mixture was partitioned between ethyl acetate and saturated aqueous sodium hydrogencarbonate solution. The organic layer was washed successively with 0.5M aqueous hydrochloric acid solution, saturated aqueous sodium hydrogencarbonate solution, and saturated aqueous sodium chloride solution, dried over anhydrous sodium sulfate, filtered and concentrated under reduced pressure. The residue was purified by chromatography on a silica gel column using toluene:acetonitrile (1:2) as the eluant to afford 3-methanesulfonyloxy-1-{4-[2-(p-nitrobenzyloxycarbonylamino)-ethylcarbamoyl]-1,3-thiazol-2-yl}azetidine (607.3 mg, yield 78%) as a pale yellow solid.

$^1$H-NMR (400 MHz, DMSO-d$_6$): δ (ppm) 8.21 (2H, d, J=8.8 Hz), 8.10 (1H, t, J=5.9 Hz), 7.59 (2H, d, J=8.8 Hz), 7.51 (1H, t, J=5.9 Hz), 7.50 (1H, s), 5.46–5.41 (1H, m), 5.17 (2H, s), 4.45 (2H, dd, J=9.9, 6.6 Hz), 4.17 (2H, dd, J=9.9, 4.0 Hz), 3.29 (3H, s).

IR (KBr): 1720, 1658, 1547, 1523, 1348, 1255, 1184, 1169 cm$^{-1}$.

Mass spectrum (FAB$^+$): 500 [M+H]$^+$.

High resolution mass spectrum (FAB$^+$): Observed value: 500.0910 [M+H]$^+$, Calculated value: 500.0910 (C$_{18}$H$_{22}$O$_8$N$_5$S$_2$).

(7) 3-Acetylthio-1-{4-[2-(p-nitrobenzyloxycarbonylamino)-ethylcarbamoyl]-1,3-thiazol-2-yl}azetidine To a solution of 3-methanesulfonyloxy-1-{4-[2-(p-nitrobenzyloxycarbonylamino)-ethylcarbamoyl]-1,3-thiazol-2-yl}azetidine (607.3 mg, 1.22 mmol) (obtained as described in Reference Example 56(6)) in dimethylformamide (33 ml) was added potassium thioacetate (1.06 g, 7.35 mmol) at room temperature. The reaction mixture was stirred in an oil bath (80° C.) for 7 hours. After checking the completion of the reaction, the reaction mixture was partitioned between ethyl acetate and saturated aqueous sodium hydrogencarbonate solution. The organic layer was washed successively with 0.5M aqueous hydrochloric acid solution, saturated aqueous sodium hydrogencarbonate solution, and saturated aqueous sodium chloride solution, dried over anhydrous sodium sulfate, filtered and concentrated under reduced pressure. The residue was purified by chromatography on a silica gel column using toluene:acetonitrile (1:2) as the eluant to afford 3-acetylthio-1-{4-[2-(p-nitrobenzyloxycarbonylamino)-ethylcarbamoyl]-1,3-thiazol-2-yl}azetidine (335.8 mg, yield 58%) as a pale brown solid.

$^1$H-NMR (500 MHz, DMSO-d$_6$): δ (ppm) 8.21 (2H, d, J=8.3 Hz), 8.05 (1H, t, J=5.9 Hz), 7.58 (2H, d, J=8.3 Hz), 7.50 (1H, t, J=5.9 Hz), 7.47 (1H, s), 5.17 (2H, s), 4.50 (2H, t, J=8.8 Hz), 4.42–4.36 (1H, m), 3.92 (2H, dd, J=8.8, 4.6 Hz), 3.305 (2H, q, J=5.9 Hz), 3.16 (2H, q, J=5.9 Hz), 2.36 (3H, s).

IR (KBr): 3368, 1690, 1677, 1543, 1520, 1494, 1349, 1255, 1239, 1108 cm$^{-1}$.

Mass spectrum (FAB$^+$): 480 [M+H]$^+$.

High resolution mass spectrum (FAB$^+$): Observed value: 480.1002 [M+H]$^+$, Calculated value: 480.1011 (C$_{19}$H$_{22}$O$_6$N$_5$S$_2$).

REFERENCE EXAMPLE 57

3-Acetylthio-1-{4-[3-(p-nitrobenzyloxycarbonylamino)-azetidine-1-carbonyl]-1,3-thiazol-2-yl}azetidine

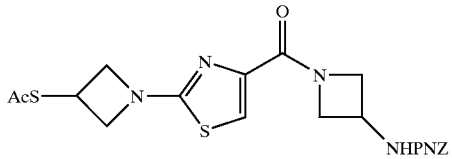

(1) 1-t-Butoxycarbonyl-3-(methanesulfonyloxy)azetidine

To a solution of 1-t-butoxycarbonyl-3-hydroxyazetidine (3.24 g, 18.7 mmol) (obtained as described in Reference Example 31(1)) in methylene chloride (160 ml) were added methanesulfonyl chloride (1.59 ml, 20.6 mmol) and triethylamine (2.89 ml, 20.6 mmol) in an ice bath. After stirring the mixture in the ice bath for 10 minutes, the mixture was stirred at room temperature for 6 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1→1:2) as the eluant to afford 1-t-butoxycarbonyl-3-(methanesulfonyloxy)azetidine (4.71 mg, yield 100%) as a pale yellow oil.

$^1$H-NMR (400 MHz, CDCl$_3$): δ (ppm) 5.23–5.17 (1H, m), 4.28 (2H, dd, J=6.6, 1.5 Hz), 4.10 (2H, m), 3.07 (3H, s), 1.46 (9H, s).

(2) 3-Azido-1-(t-butoxycarbonyl)azetidine

To a solution of 1-t-butoxycarbonyl-3-(methanesulfonyloxy)azetidine (4.71 g, 18.7 mmol) (obtained as described in Reference Example 57(1)) in dimethylformamide (140 ml) was added sodium azide (3.65 g, 56.1 mmol), and the mixture was stirred in an oil bath (90° C.) overnight. After checking the completion of the reaction, the reaction mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane: ethyl acetate (4:1) as the eluant to afford 3-azido-1-(t-butoxycarbonyl)-azetidine (3.44 g, yield 93%) as a colorless oil.

$^1$H-NMR (400 MHz, CDCl$_3$): δ (ppm) 4.25–4.15 (3H, m), 3.92–3.87 (2H, m), 1.45 (9H, s).

(3) 1-t-Butoxycarbonyl-3-(p-nitrobenzyloxycarbonylamino)azetidine

A solution of 3-azido-1-(t-butoxycarbonyl)azetidine (3.44 g, 17.4 mmol) (obtained as described in Reference Example 57(2)) in methanol (170 ml) was subjected to catalytic hydrogenation in the presence of 10% palladium on charcoal (3.44 g) at room temperature for 2 hours. After checking the completion of the reaction, the reaction mixture was filtered in order to remove the catalyst. The filtrate was concentrated under reduced pressure to give 3-amino-1-t-butoxycarbonylazetidine as a crude product. This product was dissolved in methylene chloride (170 ml), and chloroformic acid p-nitrobenzyl ester (5.63 g, 26.1 mmol) and triethylamine (3.66 ml, 26.1 mmol) were added thereto in an ice bath. The mixture was stirred at room temperature overnight. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane: ethyl acetate (1:1→1:2) as the eluant to afford 1-t-butoxycarbonyl-3-(p-nitrobenzyloxycarbonylamino)azetidine (4.84 g, yield 79%) as a colorless oil.

$^1$H-NMR (400 MHz, CDCl$_3$): δ (ppm) 8.23 (2H, d, J=8.1 Hz), 7.50 (2H, d, J=8.1 Hz), 5.26–5.18 (1H, br s), 5.26 (2H, s), 5.84 (1H, d, J=5.1 Hz), 4.50–4.40 (1H, m), 4.24 (2H, t, J=9.5 Hz), 3.76 (2H, dd, J=9.5, 5.1 Hz), 1.43 (9H, s).

(4) 3-t-Butyldiphenylsilyloxy-1-{4-[3-(p-nitrobenzyloxycarbonylamino)-azetidine-1-carbonyl]-1,3-thiazol-2-yl}azetidine To a solution of 1-t-butoxycarbonyl-3-(p-nitrobenzyloxycarbonylamino)azetidine (4.84 g, 13.8 mmol) (obtained as described in Reference Example 57(3)) in 1,4-dioxane (50 ml) was added a 4N solution of hydrogen chloride in 1,4-dioxane (50 ml) in an ice bath, and the mixture was stirred at room temperature for 2.5 hours. After checking the completion of the reaction, the reaction mixture was concentrated under reduced pressure. To the residue was added ethyl acetate, and the resulting mixture was filtered, and the residue was washed with ethyl acetate and then dried under reduced pressure to give 3-(p-nitrobenzyloxycarbonylamino)azetidine hydrochloride (2.31 g, yield 58%) as pale yellow crystals.

Subsequently, to a suspension of 3-(p-nitrobenzyloxycarbonylamino)-azetidine hydrochloride (944 mg, 3.28 mmol) (obtained as described above) and 3-t-butyldiphenylsilyloxy-1-(4-carboxyl-1,3-thiazol-2-yl)azetidine (1.2 g, 2.74 mmol) (obtained as described in Reference Example 2(4)) in dimethylformamide (60 ml) were added diethylphosphoryl cyanide (498 μl, 3.28 mmol) and triethylamine (922 μl, 6.58 mmol) in an ice bath under an atmosphere of nitrogen. The mixture was stirred at room temperature overnight. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3-t-butyldiphenylsilyloxy-1-{4-[3-(p-nitrobenzyloxycarbonylamino)-azetidine-1-carbonyl]-1,3-thiazol-2-yl}azetidine (853 mg, yield 53%) as a pale yellow solid.

$^1$H-NMR (400 MHz, CDCl$_3$): δ (ppm) 8.23 (2H, d, J=8.8 Hz), 7.64–7.59 (4H, m), 7.52 (2H, d, J=8.8 Hz), 7.48–7.37 (6H, m), 7.37 (1H, s), 5.58–5.51 (1H, br d, J=8.1 Hz), 5.22 (2H, s), 4.93–4.84 (1H, m), 4.76–4.70 (1H, m), 4.60–4.50 (1H, m), 4.50–4.41 (1H, m), 4.39–4.30 (1H, m), 4.11–4.03 (2H, m), 3.97 (2H, dd, J=8.1, 5.1 Hz), 4.00–3.92 (1H, m), 1.06 (9H, s).

(5) 3-Hydroxy-1-{4-[3-(p-nitrobenzyloxycarbonylamino)-azetidine-1-carbonyl]-1,3-thiazol-2-yl}azetidine To a solution of 3-t-butyldiphenylsilyloxy-1-{4-[3-(p-nitrobenzyloxycarbonylamino)-azetidine-1-carbonyl]-1,3-thiazol-2-yl}azetidine (850 mg, 1.27 mmol) (obtained as described in Reference Example 57(4)) in anhydrous tetrahydrofuran (43 ml) were added successively acetic acid (87 μl, 1.52 mmol) and a solution of 1.0M tetra-n-butylammonium fluoride in tetrahydrofuran (1.52 ml, 1.52 mmol) in an ice bath. The mixture was stirred in the ice bath for 30 minutes. After checking the completion of the reaction, the reaction mixture was partitioned between ethyl acetate and water. The obtained organic layer was washed successively with saturated aqueous sodium hydrogencarbonate solution and saturated aqueous sodium chloride solution, dried over anhydrous sodium sulfate, filtered and concentrated under reduced pressure. To the residue were added ethyl acetate and diisopropyl ether, and the resulting mixture was filtered off and washed with diisopropyl ether to give 3-hydroxy-1-{4-[3-(p-nitrobenzyloxycarbonylamino)-azetidine-1-carbonyl]-1,3-thiazol-2-yl}azetidine (486 mg, yield 88%) as a white solid.

$^1$H-NMR (400 MHz, CDCl$_3$): δ (ppm) 8.25 (2H, d, J=8.8 Hz), 8.14 (1H, d, J=7.3 Hz), 7.61 (2H, d, J=8.8 Hz), 7.43 (1H, s), 5.83 (1H, d, J=5.9 Hz), 5.19 (2H, s), 4.74–4.67 (1H, m), 4.66–4.58 (1H, m), 4.40–4.34 (1H, m), 4.32–4.26 (1H, m), 4.24–4.17 (3H, m), 3.86–3.80 (1H, m), 3.79–3.71 (2H, m).

(6) 3-Methanesulfonyloxy-1-{4-[3-(p-nitrobenzyloxycarbonylamino)-azetidine-1-carbonyl]-1,3-thiazol-2-yl}azetidine To a solution of 3-hydroxy-1-{4-[3-(p-nitrobenzyloxycarbonylamino)-azetidine-1-carbonyl]-1,3-thiazol-2-yl}azetidine (630 mg, 1.45 mmol) (obtained as described in Reference Example 57(5)) in a mixture of methylene chloride (32 ml) and pyridine (12 ml) were added methanesulfonyl chloride (377 μl, 4.36 mmol) and triethylamine (611 μl, 4.36 mmol) in an ice bath. After stirring the mixture in the ice bath for 10 minutes, the mixture was stirred at room temperature for 4 hours. After checking the completion of the reaction, the reaction mixture was partitioned between ethyl acetate and saturated aqueous sodium chloride solution. The organic layer was washed with saturated aqueous sodium chloride solution, dried over anhydrous sodium sulfate, filtered and concentrated under reduced pressure. To the residue were added ethyl acetate and diisopropyl ether, and the mixture was filtered off and washed with diisopropyl ether to afford 3-methanesulfonyloxy-1-{4-[3-(p-nitrobenzyloxycarbonylamino)-azetidine-1-carbonyl]-1,3-thiazol-2-yl}azetidine (766 mg, yield 100%) as a white solid.

$^1$H-NMR (400 MHz, CDCl$_3$): δ (ppm) 8.25 (2H, d, J=8.8 Hz), 8.15 (2H, d, J=7.3 Hz), 7.61 (2H, d, J=8.8 Hz), 7.52 (1H, s), 5.50–5.43 (1H, m), 5.19 (2H, s), 4.72 (1H, t, J=8.8 Hz), 4.46–4.27 (4H, m), 4.25–4.11 (3H, m), 3.85 (1H, dd, J=9.9, 5.5 Hz), 3.29 (3H, s).

(7) 3-Acetylthio-1-{4-[3-(p-nitrobenzyloxycarbonylamino)-azetidine-1-carbonyl]-1,3-thiazol-yl}azetidine To a solution of 3-methanesulfonyloxy-1-{4-[3-(p-nitrobenzyloxycarbonylamino)-azetidine-1-carbonyl]-1,3-thiazol-2-yl}azetidine (760 mg, 1.45 mmol) (obtained as described in Reference Example 57(6)) in dimethylformamide (38 ml) was added potassium thioacetate (993 mg, 8.70 mmol) at room temperature. The mixture was stirred in an oil bath (80° C.) for 9 hours. After checking the completion of the reaction, the reaction mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3acetylthio-1-{4-[3-(p-nitrobenzyloxycarbonylamino)-azetidine-1-carbonyl]-1,3-thiazol-2-yl}azetidine (397 mg, yield 56%) as a pale brown solid.

$^1$H-NMR (400 MHz, CDCl$_3$): δ (ppm) 8.23 (2H, d, J=8.8 Hz), 7.52 (2H, d, J=8.8 Hz), 7.44 (1H, s), 5.36–5.30 (1H, m), 5.21 (2H, s), 4.74–4.83 (1H, m), 4.60–4.34 (6H, m), 3.95 (3H, m), 2.37 (3H, s).

REFERENCE EXAMPLE 58

3-Acetylthio-1-(4-{N-methyl-N-[2-(p-nitrobenzyloxycarbonylamino)-ethyl]carbamoyl}-1,3-thiazol-2-yl)azetidine

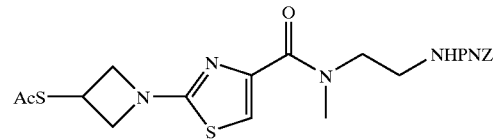

(1) 3-t-Butyldiphenylsilyloxy-1-{4-[N-methyl-N-(2-hydroxyethyl)carbamoyl]-1,3-thiazol-2-yl}azetidine To a suspension of N-methylaminoethanol (1.0 ml, 12.4 mmol) and 3-t-butyldiphenylsilyloxy-1-(4-carboxyl-1,3-thiazol-2-yl)azetidine (3.64 g, 8.3 mmol) (obtained as described in Reference Example 2(4)) in dimethylformamide (180 ml) were added diethylphosphoryl cyanide (1.9 ml, 12.5 mmol) and triethylamine (1.73 ml, 12.4 mmol) in an ice bath under an atmosphere of nitrogen. The mixture was stirred at room temperature for 7 hours. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution, and saturated aqueous sodium chloride solution, dried over anhydrous magnesium sulfate, filtered and concentrated under reduced pressure. The residue was purified by chromatography on a silica gel column using toluene: acetonitrile (1:1) as the eluant to afford 3-t-butyldiphenylsilyloxy-1-{4-[N-methyl-N-(2-hydroxyethyl)carbamoyl]-1,3-thiazol-2-yl}azetidine (3.41 g, yield 83%) as a pale yellow and transparent syrup.

$^1$H-NMR (400 MHz, CDCl$_3$): δ (ppm) 7.61 (4H, d, J=7.0 Hz), 7.48–7.36 (6H, m), 7.17 (1H, s), 4.79–4.71 (1H, m), 4.17 (2H, t, J=6.8 Hz), 4.05 (2H, dd, J=6.8, 2.7 Hz), 3.84 (2H, t, J=5.4 Hz), 3.64 (2H, t, J=5.4 Hz), 3.28 (1H, br s), 3.05 (3H, s), 1.06 (9H, s).

(2) 3-t-Butyldiphenylsilyloxy-1-{4-[N-(2-azidoethyl)-N-methyl-carbamoyl]-1,3-thiazol-2-yl}azetidine To a solution of 3-t-butyldiphenylsilyloxy-1-{4-[N-methyl-N-(2-hydroxyethyl)carbamoyl]-1,3-thiazol-2-yl}azetidine (997.5 mg, 2.0 mmol) (obtained as described in Reference Example 58(1)) in tetrahydrofuran (50 ml) were added diphenylphosphoryl azide (0.65 ml, 3.02 mmol), triphenylphosphine (793 mg, 3.02 mmol), and a 40% solution of diethylazodicarboxylate in toluene (1.12 g, 3.04 mmol) in an ice bath under an atmosphere of nitrogen, and the mixture was stirred overnight under the same conditions. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The obtained residue was purified by chromatography on a silica gel column using toluene:ethyl acetate (1:1) as the eluant to afford 3-t-butyldiphenylsilyloxy-1-{4-[N-(2-azidoethyl)-N-methylcarbamoyl]-1,3-thiazol-2-yl}azetidine (1.05 g, yield 100%) as a colorless and transparent syrup.

$^1$H-NMR (400 MHz, CDCl$_3$): δ (ppm) 7.80–7.00 (11H, m), 4.90–3.00 (11H, m), 1.06 (9H, s).

(3) 3-t-Butyldiphenylsilyloxy-1-(4-{N-methyl-N-[2-(p-nitrobenzyloxycarbonylamino)-ethyl]carbamoyl}-1,3-thiazol-2-yl)azetidine A solution of 3-t-butyldiphenylsilyloxy-1-{4-[N-(2-azidoethyl)-N-methyl-carbamoyl]-1,3-thiazol-2-yl}azetidine (1.05 g, 2.02 mmol) (obtained as described in Reference Example 58(2)) in methanol (60 ml) was subjected to catalytic hydrogenation in the presence of 20% palladium hydroxide on charcoal (1.05 g) at room temperature. After checking the completion of the reaction, the reaction mixture was filtered in order to remove the catalyst, and the filtrate concentrated under reduced pressure. To a solution of the obtained crude product in methylene chloride (52.3 ml) were added chloroformic acid p-nitrobenzyl ester (650.7 mg, 3.02 mmol) and triethylamine (0.42 ml, 3.01 mmol) in an ice bath. The mixture was stirred at room temperature for 1.5 hours. After checking the completion of the reaction, the reaction mixture was partitioned between ethyl acetate and saturated aqueous sodium chloride solution. The obtained organic layer was dried over anhydrous sodium sulfate, filtered and concentrated under reduced pressure. The residue was purified by chromatography on a silica gel column using toluene:acetonitrile (2:1) as the eluant to afford 3-t-butyldiphenylsilyloxy-1-(4-{N-methyl-N-[2-(p-nitrobenzyloxycarbonylamino)-ethyl]carbamoyl}-1,3-thiazol-2-yl)azetidine (699.5 mg, yield 52%) as a pale yellow solid.

$^1$H-NMR (500 MHz, CDCl$_3$): δ (ppm) 8.12 (2H, d, J=7.8 Hz), 7.78 (1H, br s), 7.68–7.30 (13H, m), 5.18 (0.5H, s), 5.13 (1.5H, s), 4.80–4.64 (1H, m), 4.10 (2H, t, J=7.3 Hz), 4.01 (2H, dd, J=7.3, 5.4 Hz), 3.72 (2H, m), 3.50 (2H, m), 3.25 (0.75H, s), 3.02 (2.25H, s), 1.03 (9H, s).

Mass spectrum (FAB$^+$): 674 [M+H]$^+$.

High resolution mass spectrum (FAB$^+$): Observed value: 674.2490 [M+H]$^+$, Calculated value: 674.2468 (C$_{34}$H$_{40}$O$_6$N$_5$SSi).

(4) 3-Hydroxy-1-(4-{N-methyl-N-[2-(p-nitrobenzyloxycarbonylamino)-ethyl]carbamoyl}-1,3-thiazol-2-yl)azetidine To a solution of 3-t-butyldiphenylsilyloxy-1-(4-{N-methyl-N-[2-(p-nitrobenzyloxycarbonylamino)-ethyl]carbamoyl}-1,3-thiazol-2-yl)azetidine (806.9 mg, 1.20 mmol) (obtained as described in Reference Example 58(3)) in anhydrous tetrahydrofuran (40 ml) were added successively acetic acid (0.09 ml, 1.57 mmol) and a solution of 1.0M tetra-n-butylammonium fluoride in tetrahydrofuran (1.44 ml, 1.44 mmol) in an ice bath, and then the mixture was stirred in the ice bath for 4 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using ethyl acetate: methanol (15:1) as the eluant to afford 3-hydroxy-1-(4-{N-methyl-N-[2-(p-nitrobenzyloxycarbonylamino)-ethyl]carbamoyl}-1,3-thiazol-2-yl)azetidine (428.2 mg, yield 84%) as a white solid.

$^1$H-NMR (400 MHz, CDCl$_3$): δ (ppm) 8.21 (2H, d, J=8.8 Hz), 7.71 (1H, t, J=5.5 Hz), 7.49 (2H, d, J=8.8 Hz), 7.17 (1H, s), 5.18 (2H, s), 4.88–4.70 (1H, m), 4.27 (2H, dd, J=9.1, 7.8 Hz), 3.93 (2H, dd, J=9.1, 4.8 Hz), 3.68 (2H, t, J=5.5 Hz), 3.47 (2H, q, J=5.5 Hz), 3.25 (0.8H, s), 3.03 (2.2H, s), 2.40 (1H, d, J=5.9 Hz).

(5) 3-Methanesulfonyloxy-1-(4-{N-methyl-N-[2-(p-nitrobenzyloxycarbonylamino)ethyl]carbamoyl}-1,3-thiazol-2-yl)azetidine To a solution of 3-hydroxy-1-(4-{N-methyl-N-[2-(p-nitrobenzyloxycarbonylamino)-ethyl]carbamoyl}-1,3-thiazol-2-yl)azetidine (428.2 mg, 1.01 mmol) (obtained as described in Reference Example 58(4)) in methylene chloride (21.4 ml) were added methanesulfonyl chloride (0.25 ml, 3.23 mmol) and triethylamine (0.45 ml, 3.23 mmol) in an ice bath. After stirring the mixture in the ice bath for 10 minutes, the mixture was stirred at room temperature for 6 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate:methanol (15:1) as the eluant to afford 3-methanesulfonyloxy-1-(4-{N-methyl-N-[2-(p-nitrobenzyloxycarbonylamino)-ethyl]carbamoyl}-1,3-thiazol-2-yl)azetidine (480.1 mg, yield 93%) as a pale yellow solid.

$^1$H-NMR (400 MHz, CDCl$_3$): δ (ppm) 8.22 (2H, d, J=8.1 Hz), 7.60–7.44 (3H, m including d, at 7.50 ppm, J=8.1 Hz), 7.26 (0.3H, s), 7.24 (0.7H, s), 5.41 (0.3H, m), 5.34 (0.7H, m), 5.18 (2H, s), 4.42 (2H, dd, J=9.0, 7.4 Hz), 4.25 (2H, dd, J=9.0, 3.2 Hz), 3.66 (2H, t, J=5.2 Hz), 3.60–3.42 (2H, m), 3.26 (0.9H, br s), 3.10 (0.9H, br s), 3.08 (2.1H, s), 3.03 (2.1H, s).

(6) 3-Acetylthio-1-(4-{N-methyl-N-[2-(p-nitrobenzyloxycarbonylamino)ethyl]carbamoyl}-1,3-thiazol-2-yl)azetidine To a solution of 3-methanesulfonyloxy-1-(4-{N-methyl-N-[2-(p-nitrobenzyloxycarbonylamino)-ethyl]carbamoyl}-1,3-thiazol-2-yl)azetidine (480.1 mg, 0.93 mmol) (obtained as described in Reference Example 58(5)) in dimethylformamide (24 ml) was added potassium thioacetate (820 mg, 5.69 mmol) at room temperature. The mixture was stirred in an oil bath (80° C.) for 5 hours. After checking the completion of the reaction, the reaction mixture was partitioned between ethyl acetate and saturated aqueous sodium hydrogencarbonate solution. The organic layer was washed successively with 0.5M aqueous hydrochloric acid solution, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate:methanol (15:1) as the eluant to afford 3-acetylthio-1-(4-{N-methyl-N-[2-(p-nitrobenzyloxycarbonylamino)ethyl]carbamoyl}-1,3-thiazol-2-yl)azetidine (348.9 mg, yield 76%) as a pale brown solid.

$^1$H-NMR (500 MHz, CDCl$_3$): δ (ppm) 8.22 (2H, d, J=8.8 Hz), 7.73 (1H, br s), 7.49 (2H, d, J=8.8 Hz), 7.29 (0.4H, s), 7.20 (0.6H, s), 5.18 (2H, s), 4.47 (2H, t, J=8.8 Hz), 4.40–4.28 (1H, m), 3.92 (2H, dd, J=8.8, 5.7 Hz), 3.66 (2H, t, J=5.4 Hz), 3.52–3.44 (2H, m), 3.26 (1.2H, s), 3.03 (1.8H, s), 2.36 (1.2H, s), 2.34 (1.8H, s).

REFERENCE EXAMPLE 59

3-Acetylthio-1-(4-{N-[2-(t-butyldimethylsilyloxy)ethyl]-N-isopropyl-carbamoyl}-1,3-thiazol-2-yl)azetidine

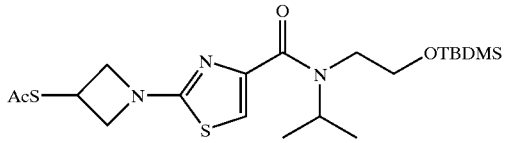

(1) 3-t-Butyldiphenylsilyloxy-1-{4-[N-(2-hydroxyethyl)-N-isopropyl-carbamoyl]-1,3-thiazol-2-yl}azetidine To a suspension of N-isopropylaminoethanol (0.61 ml, 1.38 mmol) and 3-t-butyldiphenylsilyloxy-1-(4-carboxyl-1,3-thiazol-2-yl)azetidine (500 mg, 1.14 mmol) in dimethylformamide (15 ml) were added diethylphosphoryl cyanide (0.23 ml, 1.38 mmol) and triethylamine (0.19 ml, 0.23 mmol) in an ice bath under an atmosphere of nitrogen. The mixture was stirred for 2 hours under the same conditions. After checking the completion of the reaction, the reaction mixture was partitioned between ethyl acetate and saturated aqueous sodium hydrogencarbonate solution. The obtained organic layer was washed successively with 0.5M aqueous hydrochloric acid solution, saturated aqueous sodium hydrogencarbonate solution, and saturated aqueous sodium chloride solution, dried over anhydrous magnesium sulfate, filtered and concentrated under reduced pressure. The residue was purified by chromatography on a silica gel column using ethyl acetate as the eluant to afford 3-t-butyldiphenylsilyloxy-1-{4-[N-(2-hydroxyethyl)-N-isopropyl-carbamoyl]-1,3-thiazol-2-yl}azetidine (318 mg, yield 56%) as a pale yellow oil.

$^1$H-NMR (400 MHz, CDCl$_3$): δ (ppm) 7.57 (4H, d, J=6.5 Hz), 7.50–7.30 (6H, m), 7.07 (0.6H, s), 6.92 (0.4H, s), 4.81–4.63 (1H, m), 4.49 (0.5H, s), 4.33 (0.5H, s), 4.22–3.88 (4H, m, including 4.06 (2H, dd, J=14.3, 7.7 Hz)), 3.88–3.62 (2H, m), 1.39–1.08 (6H, m), 1.02 (9H, s).

(2) 3-Hydroxy-1-{4-[N-(2-hydroxyethyl)-N-isopropyl-carbamoyl]-1,3-thiazol-2-yl}azetidine To a solution of 3-t-butyldiphenylsilyloxy-1-{4-[N-(2-hydroxyethyl)-N-isopropyl-carbamoyl]-1,3-thiazol-2-yl}azetidine (2.49 g, 4.75 mmol) (obtained as described in Reference Example 59(1)) in anhydrous tetrahydrofuran (100 ml) was added a solution of 1.0M tetra-n-butylammonium fluoride in tetrahydrofuran (5.70 ml, 5.70 mmol) in an ice bath. The mixture was stirred in the ice bath for 1 hour. After checking the completion of the reaction, the reaction mixture was concentrated under reduced pressure. The residue was purified by chromatography on a silica gel column using ethyl acetate:methanol (10:1) as the eluant to afford 3-hydroxy-1-{4-[N-(2-hydroxyethyl)-N-isopropyl-carbamoyl]-1,3-thiazol-2-yl}azetidine (1.33 g, yield 98%) as a white solid.

$^1$H-NMR (400 MHz, CDCl$_3$): δ (ppm) 7.13 (0.7H, s), 7.03 (0.3H, s), 4.62–4.48 (1H, m), 4.48–4.36 (1H, m), 4.29 (2H, t, J=8.0 Hz), 3.94 (2H, dd, J=8.0, 4.1 Hz), 3.80 (2H, br s), 1.35 (3H, br s), 1.20 (3H, br s).

(3) 1-(4-{N-[2-(t-Butyldimethylsilyloxy)ethyl]-N-isopropyl-carbamoyl}-1,3-thiazol-2-yl)-3-hydroxyazetidine To a solution of 3-hydroxy-1-{4-[N-(2-hydroxyethyl)-N-isopropyl-carbamoyl]-1,3-thiazol-2-yl}azetidine (1.33 g, 4.66 mmol) (obtained as described in Reference Example 59(2)) in dimethylformamide (40 ml) were added t-butyldimethylsilyl chloride (738 mg, 4.89 mmol) and imidazole (333 mg, 4.89 mmol) in an ice bath, and the mixture was stirred in the ice bath for 2 hours. After checking the completion of the reaction, methanol was added thereto and the mixture was stirred for 30 minutes. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (1:1) ethyl acetate as the eluant to afford 1-(4-{N-[2-(t-butyldimethylsilyloxy)-ethyl]-N-isopropyl-carbamoyl}-1,3-thiazol-2-yl)-3-hydroxyazetidine (1.26 g, yield 69%) as a pale yellow oil.

$^1$H-NMR (400 MHz, CDCl$_3$): δ (ppm) 6.99 (0.2H, s), 6.91 (0.8H, s), 4.84–4.72 (1H, m), 4.72–4.35 (1H, m), 4.27 (2H, dd, J=9.4, 6.8 Hz), 3.91 (2H, dd, J=9.4, 4.8 Hz), 3.71–3.35 (1H, m), 3.71–3.50 (2H, m), 3.50–3.28 (1H, m), 1.17 (6H, br s), 0.87 (9H, br s), 0.06 (6H, d, J=2.8 Hz).

(4) 1-(4-{N-[2-(t-Butyldimethylsilyloxy)ethyl]-N-isopropyl-carbamoyl}-1,3-thiazol-2-yl)-3-methanesulfonyloxyazetidine To a solution of 1-(4-{N-[2-(t-butyldimethylsilyloxy)ethyl]-N-isopropyl-carbamoyl}-1,3-thiazol-2-yl)-3-hydroxyazetidine (1.24 g, 3.23 mmol) (obtained as described in Reference Example 59(3)) in methylene chloride (62 ml) were added methanesulfonyl chloride (0.30 ml, 3.88 mmol) and triethylamine (0.54 ml, 3.88 mmol) in an ice bath, and then the mixture was stirred in the ice bath for 1.5 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (1:1) ethyl acetate as the eluant to afford 1-(4-{N-[2-(t-butyldimethylsilyloxy)-ethyl]-N-isopropyl-carbamoyl}-1,3-thiazol-2-yl)-3-methanesulfonyloxyazetidine (649 mg, yield 42%) as a pale yellow solid.

$^1$H-NMR (400 MHz, CDCl$_3$): δ (ppm) 7.16–6.95 (1H, m), 5.46–5.36 (1H, m), 4.49–3.68 (3H, m including 4.41 (2H, ddd, J=9.6, 6.6, 1.0 Hz)), 4.23 (2H, dd, J=9.6, 4.4 Hz), 3.91–3.72 (1H, m), 3.72–3.51 (2H, m), 3.51–3.30 (1H, m), 3.07 (3H, s), 1.24 (6H, br s), 0.83 (9H, s), 0.06 (6H, d, J=3.4 Hz).

(5) 3-Acetylthio-1-(4-{N-[2-(t-butyldimethylsilyloxy)ethyl]-N-isopropyl-carbamoyl}-1,3-thiazol-2-yl)azetidine To a solution of 1-(4-{N-[2-(t-butyldimethylsilyloxy)ethyl]-N-isopropyl-carbamoyl}-1,3-thiazol-2-yl)-3-methanesulfonyloxyazetidine (649 mg, 1.35 mmol) (obtained as described in Reference Example 59(4)) in dimethylformamide (19 ml) was added potassium thioacetate (930 mg, 8.14 mmol) at room temperature. The mixture was stirred in an oil bath (90° C.) for 3 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (3:1) ethyl acetate as the eluant to afford 3-acetylthio-1-(4-{N-[2-(t-butyldimethylsilyloxy)-ethyl]-N-isopropyl-carbamoyl}-1,3-thiazol-2-yl)azetidine (618 mg, yield 100%) as a pale brown solid.

¹H-NMR (400 MHz, CDCl₃): δ (ppm) 7.20–6.89 (1H, m), 4.68–4.18 (4H, m including 4.48 (2H, t, J=8.5 Hz)), 3.94 (2H, dd, J=8.5, 5.3 Hz), 3.88–3.23 (4H, m), 2.39 (3H, s), 1.16 (6H, br s), 0.86 (9H, s), 0.04 (6H, d, J=1.4 Hz).

REFERENCE EXAMPLE 60

3-Acetylthio-1-(4-{N-isopropyl-N-[2-(p-nitrobenzyloxycarbonylamino)ethyl-carbamoyl]-1,3-thiazol-2-yl}azetidine

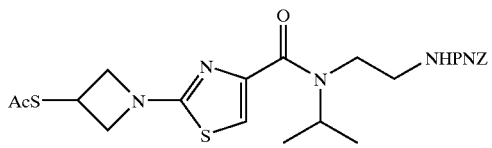

(1) 1-{4-[N-(2-Azidoethyl)-N-isopropyl-carbamoyl]-1,3-thiazol-2-yl}azetidine-3-t-butyldiphenylsilyloxyazetidine To a solution of 3-t-butyldiphenylsilyloxy-1-{4-[N-(2-hydroxyethyl)-N-isopropyl-carbamoyl]-1,3-thiazol-2-yl}azetidine (1.46 g, 2.79 mmol) (obtained as described in Reference Example 59(1)) in tetrahydrofuran (73 ml) were added diphenylphosphoryl azide (0.90 ml, 4.18 mmol), triphenylphosphine (1.10 g, 4.18 mmol), and a 40% solution of diethylazodicarboxylate in toluene (1.54 g, 4.18 mmol) in an ice bath under an atmosphere of nitrogen, and then the mixture was stirred for 3 hours under the same conditions. After checking the completion of the reaction, the reaction mixture was partitioned between ethyl acetate and saturated aqueous sodium chloride solution. The organic layer was dried over anhydrous sodium sulfate, filtered and concentrated under reduced pressure. The obtained residue was purified by chromatography on a silica gel column using hexane:ethyl acetate (2:1) as the eluant to afford 1-{4-[N-(2-azidoethyl)-N-isopropyl-carbamoyl]-1,3-thiazol-2-yl}azetidine-3-t-butyldiphenylsilyloxyazetidine (1.38 g, yield 87%) as a pale yellow oil.

¹H-NMR (400 MHz, CDCl₃): δ (ppm) 7.62 (4H, dd, J=8.0, 1.4 Hz), 7.36–7.26 (6H, m), 7.26–6.90 (1H, m), 4.80–4.76 (1H, m), 4.75–4.61 (1H, m), 4.13 (1H, t, J=7.4 Hz), 4.10 (1H, t, J=7.4 Hz), 4.01 (2H, dd, J=8.7, 4.0 Hz), 3.80–3.33 (4H, m including 3.56 (2H, br s)), 1.20 (6H, br s), 1.06 (9H, s).

(2) 3-t-Butyldiphenylsilyloxy-1-(4-{N-isopropyl-N-[2-(p-nitrobenzyloxycarbonylamino)-ethyl]-carbamoyl}-1,3-thiazol-2-yl)azetidine A solution of 1-{4-[N-(2-azido-ethyl)-N-isopropyl-carbamoyl]-1,3-thiazol-2-yl}azetidine-3-t-butyldiphenylsilyloxyazetidine (1.33 g, 2.42 mmol) (obtained as described in Reference Example 60(1)) in methanol (65 ml) was subjected to catalytic hydrogenation in the presence of 20% palladium hydroxide on charcoal (1.33 g) at room temperature. After checking the completion of the reaction, the reaction mixture was filtered in order to remove the catalyst and the filtrate concentrated under reduced pressure. To a solution of the obtained crude product in methylene chloride (63 ml) were added chloroformic acid p-nitrobenzyl ester (627 mg, 2.90 mmol) and triethylamine (0.41 ml, 2.90 mmol) in an ice bath, and the mixture was stirred for 1 hour under the same conditions. After checking the completion of the reaction, the reaction mixture was partitioned between ethyl acetate and saturated aqueous sodium chloride solution. The obtained organic layer was dried over anhydrous sodium sulfate, filtered and concentrated under reduced pressure. The residue was purified by chromatography on a silica gel column using ethyl acetate ethyl acetate:methanol (10:1) as the eluant to afford 3-t-butyldiphenylsilyloxy-1-(4-{N-isopropyl-N-[2-(p-nitrobenzyloxycarbonylamino)ethyl]-carbamoyl}-1,3-thiazol-2-yl)azetidine (945 mg, yield 56%) as a pale yellow oil.

¹H-NMR (400 MHz, CDCl₃): δ (ppm) 7.60 (4H, d, J=1.0 Hz), 7.55–7.32 (10H, m), 7.12 (0.4H, br s), 6.95 (0.6H, br s), 5.28–5.18 (2H, m), 4.81–4.67 (1H, m), 4.24–4.06 (2H, m), 4.00 (2H, dd, J=8.7, 4.9 Hz), 3.70–3.18 (4H, m), 1.20 (6H, br s), 1.06 (9H, d, J=1.6 Hz).

(3) 3-Hydroxy-1-(4-{N-isopropyl-N-[2-(p-nitrobenzyloxycarbonylamino)ethyl]-carbamoyl}-1,3-thiazol-2-yl)azetidine A solution of 3-t-butyldiphenylsilyloxy-1-(4-{N-isopropyl-N-[2-(p-nitrobenzyloxycarbonylamino)-ethyl]-carbamoyl}-1,3-thiazol-2-yl)azetidine (945 mg, 1.38 mmol) (obtained as described in Reference Example 60(2)) in anhydrous tetrahydrofuran (50 ml) were added successively acetic acid (0.10 ml, 1.66 mmol) and a 1.0M solution of tetra-n-butylammonium fluoride in tetrahydrofuran (1.66 ml, 1.66 mmol) in an ice bath, and the mixture was stirred in the ice bath for 3 hours. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous magnesium sulfate, filtered and concentrated under reduced pressure. The residue was purified by chromatography on a silica gel column using ethyl acetate ethyl acetate:methanol (10:1) as the eluant to afford 3-hydroxy-1-(4-{N-isopropyl-N-[2-(p-nitrobenzyloxycarbonylamino)-ethyl]-carbamoyl}-1,3-thiazol-2-yl)azetidine (433 mg, yield 66%) as a white solid.

¹H-NMR (400 MHz, CDCl₃): δ (ppm) 8.21 (2H, d, J=8.5 Hz), 7.49 (2H, d, J=8.5 Hz), 7.11 (0.4H, s), 6.95 (0.6H, s), 5.18 (2H, s), 4.88–4.62 (1H, m), 4.62–4.18 (3H, m), 3.93 (2H, dd, J=8.8, 4.4 Hz), 3.72–3.36 (4H, m), 1.30 (3H, br s), 1.20 (3H, br s).

(4) 1-(4-{N-isopropyl-N-[2-(p-nitrobenzyloxycarbonylamino)-ethyl]-carbamoyl}-1,3-thiazol-2-yl)-3-methanesulfonyloxyazetidine A solution of 3-hydroxy-1-(4-{N-isopropyl-N-[2-(p-nitrobenzyloxycarbonylamino)-ethyl]-carbamoyl}-1,3-thiazol-2-yl)azetidine (1.43 g, 3.09 mmol) (obtained as described in Reference Example 60(3)) in methylene chloride (72 ml) were added methanesulfonyl chloride (0.29 ml, 3.70 mmol) and triethylamine (0.52 ml, 3.70 mmol) in an ice bath, and the mixture was stirred in the ice bath for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate ethyl acetate:methanol (20:1) as the eluant to afford 1-(4-{N-isopropyl-N-[2-(p-nitrobenzyloxycarbonylamino)ethyl]-carbamoyl}-1,3-thiazol-2-yl)-3-methanesulfonyloxyazetidine (766 mg, yield 46%) as a pale yellow solid.

¹H-NMR (400 MHz, CDCl₃): δ (ppm) 8.20 (2H, d, J=8.4 Hz), 7.50 (2H, d, J=8.4 Hz), 7.20 (0.4H, br s), 7.07 (0.6H, br s), 5.41 (1H, br s), 5.19 (2H, s), 4.66–4.18 (5H, m including 4.44 (2H, t, J=8.8 Hz), 4.25 (2H, t, J=8.8 Hz)), 3.68–3.36 (4H, m), 3.10 (3H, br s), 1.22 (3H, br s).

(5) 3-Acetylthio-1-(4-{N-isopropyl-N-[2-(p-nitrobenzyloxycarbonylamino)ethyl]-carbamoyl}-1,3-thiazol-2-yl)azetidine A solution of 1-(4-{N-isopropyl-N-[2-(p-nitrobenzyloxycarbonylamino)ethyl]-carbamoyl}-1,3-thiazol-2-yl)-3-methanesulfonyloxyazetidine (776 mg, 1.43 mmol) (obtained as described in Reference Example 60(4)) in dimethylformamide (23 ml) was added potassium thioacetate (982 mg, 8.60 mmol) at room temperature. The mixture was stirred in an oil bath (90° C.) for 4 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:2) as the eluant to afford 3-acetylthio-1-(4-{N-isopropyl-N-[2-(p-nitrobenzyloxycarbonylamino)ethyl]-carbamoyl}-1,3-thiazol-2-yl)azetidine (746 mg, yield 46%) as a pale brown solid.

$^1$H-NMR (400 MHz, CDCl$_3$): δ (ppm) 8.21 (2H, d, J=8.4 Hz), 7.50 (2H, d, J=8.4 Hz), 7.15 (0.4H, br s), 7.04 (0.6H, br s), 5.19 (2H, s), 4.66–4.20 (4H, m), 4.08–3.88 (2H, m), 3.66–3.26 (4H, m), 2.96 (3H, s), 2.36 (3H, br s), 1.63 (3H, br s).

REFERENCE EXAMPLE 61

3-Acetylthio-1-(4-{(1S)-2-methyl-[1-(2-(p-nitrobenzyloxycarbonylamino)methyl)propylcarbamoyl]-1,3-thiazol-2-yl}azetidine

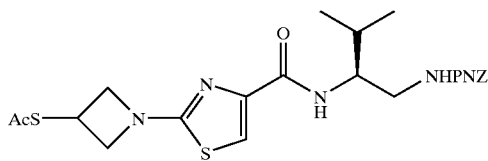

(1) ((1S)-1-Hydroxymethyl-2-methylpropyl)carbamic acid t-butyl ester

To a solution of L-valinol (2.00 g, 19.4 mmol) in a mixture of methylene chloride (50 ml) and methanol (50 ml) was added di-t-butoxycarbonic anhydride (5.08 g, 23.3 mmol) in an ice bath, and the reaction mixture was stirred at room temperature for 3 hours. After checking the completion of the reaction, the reaction mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using n-hexane:ethyl acetate (1:1) as the eluant to afford ((1S)-1-hydroxymethyl-2-methylpropyl)carbamic acid t-butyl ester (4.19 mg, yield 100%) as a colorless oil.

$^1$H-NMR (400 MHz, CDCl$_3$): δ (ppm) 4.70–4.59 (1H, br s), 3.74–3.66 (1H, m), 3.65–3.57 (1H, m), 3.48–3.39 (1H, m), 2.38–2.30 (1H, br s), 1.89–1.78 (1H, m), 1.45 (9H, s), 0.96 (3H, d, J=6.6 Hz), 0.94 (3H, d, J=6.6 Hz).

(2) ((1S)-1-Azidomethyl-2-methylpropyl)carbamic acid t-butyl ester

To a solution of ((1S)-1-hydroxymethyl-2-methylpropyl)carbamic acid t-butyl ester (3.00 g, 14.8 mmol) (obtained as described in Reference Example 61(1)) in tetrahydrofuran (150 ml) were added diphenylphosphoryl azide (4.78 ml, 22.2 mmol), triphenylphosphine (5.82 g, 22.2 mmol) and a 40% solution of diethylazodicarboxylate in toluene (9.67 g, 22.2 mmol) in an ice bath under an atmosphere of nitrogen, and the mixture was stirred for 2 hours under the same conditions. After checking the completion of the reaction, the reaction mixture was partitioned between ethyl acetate and saturated aqueous sodium chloride solution. The organic layer was dried over anhydrous sodium sulfate, filtered and concentrated under reduced pressure. The obtained residue was purified by chromatography on a silica gel column using n-hexane:ethyl acetate (9:1) as the eluant to afford ((1S)-1-azidomethyl-2-methylpropyl)carbamic acid t-butyl ester (3.26 g, yield 90%) as a colorless oil.

$^1$H-NMR (400 MHz, CDCl$_3$): δ (ppm) 4.59–4.45 (1H, m), 3.56–3.47 (1H, m), 3.42 (2H, d, J=4.4 Hz), 1.86–1.74 (1H, m), 1.45 (9H, s), 0.95 (3H, d, J=6.6 Hz), 0.93 (3H, d, J=7.3 Hz).

(3) ((2S)-2-t-Butoxycarbonylamino-3-methylbutyl)carbamic acid p-nitrobenzyl ester A solution of ((1S)-1-azidomethyl-2methylpropyl)-carbamic acid t-butyl ester (3.26 g, 13.3 mmol) (obtained as described in Reference Example 61(2)) in methanol (160 ml) was subjected to catalytic hydrogenation in the presence of 10% palladium on charcoal (3.26 g) at room temperature for 1 hour. After checking the completion of the reaction, the reaction mixture was filtered in order to remove the catalyst and the filtrate concentrated under reduced pressure. To a solution of the obtained crude product in methylene chloride (160 ml) were added chloroformic acid p-nitrobenzyl ester (4.31 g, 20.0 mmol) and triethylamine (2.80 ml, 20.0 mmol) in an ice bath, and then the mixture was stirred at room temperature overnight. After checking the completion of the reaction, the reaction mixture was partitioned between ethyl acetate and saturated aqueous sodium hydrogencarbonate solution. The obtained organic layer was washed with saturated aqueous sodium chloride solution, dried over anhydrous sodium sulfate, filtered and concentrated under reduced pressure. The residue was purified by chromatography on a silica gel column using n-hexane:ethyl acetate (8:1→1:1) as the eluant to afford ((2S)-2-t-butoxycarbonylamino-3-methylbutyl)carbamic acid p-nitrobenzyl ester (3.13 mg, yield 62%) as pale yellow crystals.

$^1$H-NMR (400 MHz, CDCl$_3$): δ (ppm) 8.21 (2H, d, J=8.8 Hz), 7.50 (2H, d, J=8.8 Hz), 5.43–5.31 (1H, br s), 5.19 (2H, s), 4.57–4.49 (1H, br d, J=8.8 Hz), 3.60–3.49 (1H, m), 3.40–3.29 (1H, m), 3.26–3.13 (1H, m), 1.82–1.71 (1H, m), 1.43 (9H, s), 0.96 (3H, d, J=7.3 Hz), 0.93 (3H, d, J=6.6 Hz).

(4) 3-t-Butyldiphenylsilyloxy-1-(4-{(1S)-2-methyl-[1-(p-nitrobenzyloxycarbonylamino)methyl]-propylcarbamoyl}-1,3-thiazol-2-yl)azetidine To a solution of ((2S)-2-t-butoxycarbonylamino-3-methylbutyl)-carbamic acid p-nitrobenzyl ester (3.13 g, 8.21 mmol) (obtained as described in Reference Example 61(3)) in 1,4-dioxane (31 ml) was added a 4N solution of hydrogen chloride in 1,4-dioxane (31 ml) in an ice bath, and the mixture was stirred at room temperature for 4 hours. After checking the completion of the reaction, the reaction mixture was concentrated under reduced pressure. Ethyl acetate was added to the residue, and the resulting mixture was filtered off and washed with ethyl acetate to give ((2S)-2-amino-3-methylbutyl)carbamic acid p-nitrobenzyl ester hydrochloride (1.82 g, yield 70%) as pale yellow crystals.

Subsequently, to a suspension of ((2S)-2-amino-3-methylbutyl)carbamic acid p-nitrobenzyl ester hydrochloride (1.29 g, 4.05 mmol) obtained as described above and 3-t-butyldiphenylsilyloxy-1-(4-carboxyl-1,3-thiazol-2-yl)azetidine (1.48 g, 3.37 mmol) (obtained as described in Reference Example 2(4)) in dimethylformamide (74 ml)

were added diethylphosphoryl cyanide (615 μl, 4.05 mmol) and triethylamine (1.14 ml, 8.10 mmol) in an ice bath under an atmosphere of nitrogen. The mixture was stirred at room temperature for 2 hours. After checking the completion of the reaction, the reaction mixture was partitioned between ethyl acetate and 10% aqueous sodium chloride solution. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1) as the eluant to afford 3-t-butyldiphenylsilyloxy-1-(4-{(1S)-2-methyl-[1-(p-nitrobenzyloxycarbonylamino)methyl]-propylcarbamoyl}-1,3-thiazol-2-yl)azetidine (1.55 g, yield 74%) as a pale yellow solid.

$^1$H-NMR (400 MHz, CDCl$_3$): δ (ppm) 8.11 (2H, d, J=8.8 Hz), 7.64–7.60 (4H, m), 7.49–7.39 (8H, m), 7.35 (1H, s), 7.20–7.18 (1H, br d, J=9.8 Hz), 5.56–5.48 (1H, br s), 5.20 (1H, d, J=13.7 Hz), 5.08 (1H, d, J=13.7 Hz), 4.78–4.72 (1H, m), 4.14–4.06 (2H, m), 4.04–3.94 (3H, m), 3.46 (1H, dt, J=13.7, 3.9 Hz), 3.31 (1H, ddd, J=13.7, 10.7, 5.9 Hz), 1.95–1.86 (1H, m), 1.07 (9H, s), 1.01 (3H, d, J=6.8 Hz), 0.99 (3H, d, J=6.8 Hz).

(5) 3-Hydroxy-1-(4-{(1S)-2-methyl-[1-(p-nitrobenzyloxycarbonylamino)methyl]-propylcarbamoyl}-1,3-thiazol-2-yl)azetidine To a solution of 3-t-butyldiphenylsilyloxy-1-(4-{(1S)-2-methyl-[1-(p-nitrobenzyloxycarbonylamino)methyl] propylcarbamoyl}-1,3-thiazol-2-yl)azetidine (1.54 g, 2.20 mmol) (obtained as described in Reference Example 61(4)) in anhydrous tetrahydrofuran (78 ml) was added successively acetic acid (151 μl) and a 1.0M solution of tetra-n-butylammonium fluoride in tetrahydrofuran (2.64 ml, 2.64 mmol) in an ice bath. The mixture was stirred in the ice bath for 1 hour. After checking the completion of the reaction, the reaction mixture was partitioned between ethyl acetate and water. The obtained organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3-hydroxy-1-(4-{(1S)-2-methyl-[1-(p-nitrobenzyloxycarbonylamino)methyl]-propylcarbamoyl}-1,3-thiazol-2-yl)azetidine (927 mg, yield 91%) as a white solid.

$^1$H-NMR (400 MHz, CDCl$_3$): δ (ppm) 8.09 (2H, d, J=8.8 Hz), 7.41 (2H, d, J=8.8 Hz), 7.39 (1H, s), 7.19–7.14 (1H, br d, J=9.5 Hz), 5.54–5.46 (1H, m), 5.22 (1H, d, J=13.6 Hz), 5.06 (1H, d, J=13.6 Hz), 4.87–4.78 (1H, m), 4.37–4.26 (2H, m), 4.04–3.90 (3H, m), 3.47–3.40 (1H, m), 3.38–3.30 (1H, m), 2.38 (1H, d, J=7.3 Hz), 1.94–1.83 (1H, m), 1.00 (3H, d, J=7.3 Hz), 0.99 (3H, d, J=7.3 Hz).

(6) 3-Methanesulfonyloxy-1-(4-{(1S)-2-methyl-[1-(p-nitrobenzyloxycarbonylamino)methyl]-propylcarbamoyl}-1,3-thiazol-2-yl)azetidine To a solution of 3-hydroxy-1-(4-{(1S)-2-methyl-[1-(nitrobenzyloxycarbonylamino)methyl]-propylcarbamoyl}-1,3-thiazol-2-yl)azetidine (920 mg, 1.98 mmol) (obtained as described in Reference Example 61(5)) in methylene chloride (46 ml) were added methanesulfonyl chloride (461 μl, 5.95 mmol) and triethylamine (834 μl, 5.95 mmol) in an ice bath. After stirring the mixture in the ice bath for 10 minutes, the mixture was stirred at room temperature for 1 hour. After checking the completion of the reaction, the reaction mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using n-hexane:ethyl acetate (1:4) as the eluant to afford 3-methanesulfonyloxy-1-(4-{(1S)-2-methyl-[1-(p-nitrobenzyloxycarbonylamino)methyl]-propylcarbamoyl}-1,3-thiazol-2-yl)azetidine (1.06 g, yield 99%) as a pale yellow solid.

$^1$H-NMR (400 MHz, CDCl$_3$): δ (ppm) 8.10 (2H, d, J=8.8 Hz), 7.45 (1H, s), 7.41 (2H, d, J=8.8 Hz), 7.18–7.12 (1H, br d, J=8.8 Hz), 5.50–5.45 (1H, br s), 5.42 (1H, tt, J=6.6, 4.4 Hz), 5.22 (1H, d, J=13.2 Hz), 5.08 (1H, d, J=13.2 Hz), 4.49–4.40 (2H, m), 4.29–4.20 (2H, m), 4.04–3.95 (1H, m), 3.44 (1H, dt, J=13.9, 4.4 Hz), 3.38–3.24 (1H, m), 3.12 (3H, s), 1.94–1.85 (1H, m), 1.01 (3H, d, J=6.6 Hz), 0.99 (3H, d, J=6.6 Hz).

(7) 3-Acetylthio-1-(4-{(1S)-2-methyl-[1-(p-nitrobenzyloxycarbonylamino)methyl]-propylcarbamoyl}-1,3-thiazol-2-yl)azetidine To a solution of 3-methanesulfonyloxy-1-(4-{(1S)-2-methyl-[1-(p-nitrobenzyloxycarbonylamino)methyl] propylcarbamoyl}-1,3-thiazol-2-yl)azetidine (1.06 g, 1.96 mmol) (obtained as described in Reference Example 61(6)) in dimethylformamide (53 ml) was added potassium thioacetate (1.34 mg, 11.7 mmol) at room temperature. The mixture was stirred in an oil bath (80° C.) for 8.5 hours. After checking the completion of the reaction, the reaction mixture was partitioned between ethyl acetate and 10% aqueous sodium chloride solution. The organic layer was washed successively with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:3) as the eluant to afford 3-acetylthio-1-(4-{(1S)-2-methyl-[1-(p-nitrobenzyloxycarbonylamino)methyl]-propylcarbamoyl}-1,3-thiazol-2-yl)azetidine (785 mg, yield 77%) as a pale brown solid.

$^1$H-NMR (400 MHz, CDCl$_3$): δ (ppm) 8.12 (2H, d, J=8.8 Hz), 7.42 (2H, d, J=8.8 Hz), 7.41 (1H, s), 7.20–7.16 (1H, br d, J=9.5 Hz), 5.54–5.45 (1H, br s), 5.21 (1H, d, J=13.2 Hz), 5.09 (1H, d, J=13.2 Hz), 4.51 (2H, dt, J=11.0, 8.4 Hz), 4.47–4.39 (1H, m), 4.03–3.93 (3H, m), 3.45 (1H, dt, J=13.2, 4.0 Hz), 3.37–3.68 (1H, m), 2.37 (3H, s), 1.95–1.84 (1H, m), 1.00 (3H, d, J=7.3 Hz), 0.99 (3H, d, J=7.3 Hz).

REFERENCE EXAMPLE 62

3-Acetylthio-1-{4-(p-nitrobenzyloxycarbonylamino) methyl-1,3-thiazol-2-yl}azetidine

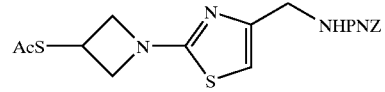

(1) 1-(4-Azidomethyl-1,3-thiazol-2-yl)-3-t-butyldiphenylsilyloxyazetidine

To a solution of 3-t-butyldiphenylsilyloxy-1-(4-hydroxymethyl-1,3-thiazol-2-yl)azetidine (1.02 g, 2.39 mmol) (obtained as described in Reference Example 2(2)) in tetrahydrofuran (50 ml) were added diphenylphosphoryl azide (0.8 ml, 3.71 mmol), triphenylphosphine (950 mg, 3.62 mmol) and 40% diethylazodicarboxylate in toluene solution (1.32 g, 3.59 mmol) in an ice bath under an atmosphere of nitrogen. The mixture was stirred in an ice bath for 2 hours. After checking the completion of the reaction, the mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using hexane:ethyl acetate (8:1) as the eluant to afford 1-(4-azidomethyl-1,3-thiazol-2-yl)-3-t-butyldiphenylsilyloxyazetidine (1.06 g, yield 99%) as colorless syrup.

$^1$H-NMR (400 MHz, CDCl$_3$): δ (ppm) 7.66–7.36 (10H, m), 6.45 (1H, s), 4.78–4.71 (1H, m), 4.24 (2H, s), 4.12 (2H, dd, J=8.6, 6.2 Hz), 4.02 (2H, dd, J=8.6, 5.7 Hz), 1.06 (9H, s).

IR (liquid film): 2858, 2170, 2100, 1527, 1313, 1182, 1143, 1114 cm$^{-1}$.

Mass spectrum (FAB$^+$) 450 [M+H]$^+$.

High-resolution mass spectrum (FAB$^+$): calculated for C$_{23}$H$_{28}$ON$_5$SSi: 450.1784; Found: 450.1793 [M+H]$^+$.

(2) 3-t-Butyldiphenylsilyloxy-1-[4-(p-nitrobenzyloxycarbonylaminomethyl)-1,3-thiazol-2-yl] azetidine 1-(4-Azidomethyl-1,3-thiazol-2-yl)-3-t-butyldiphenylsilyloxyazetidine (1.06 g, 2.37 mmol) (obtained as described in Reference Example 62(1)) in methanol (53 ml) was subjected to catalytic hydrogenation in the presence of 20% palladium hydroxide on charcoal (1.05 g) at room temperature. After checking the completion of the reaction, the reaction mixture was filtered in order to remove the catalyst and the filtrate concentrated under reduced pressure. The residue was dissolved in methylene chloride (53.2 ml). To the mixture were added p-nitrobenzyl chloroformate (0.76 g, 3.52 mmol) and triethylamine (0.5 ml, 3.59 mmol) in an ice bath, and the mixture was stirred at room temperature overnight. After checking the completion of the reaction, the mixture was distilled under reduced pressure. The residue was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using toluene:ethyl acetate (3:2) as the eluant to afford 3-t-butyldiphenylsilyloxy-1-[4-(p-nitrobenzyloxycarbonylaminomethyl)-1,3-thiazol-2-yl] azetidine (867.2 mg, yield 61%) as a yellow solid.

$^1$H-NMR (500 MHz, CDCl$_3$): δ (ppm) 8.21 (2H, d, J=8.3 Hz), 7.62 (4H, d, J=8.3 Hz), 7.50 (2H, d, J=8.3 Hz), 7.50–7.34 (6H, m), 6.37 (1H, s), 5.38 (1H, br t, J=5.4 Hz), 5.20 (2H, s), 4.78–4.71 (1H, m), 4.26 (2H, d, J=5.4 Hz), 4.10 (2H, dd, J=8.3, 6.8 Hz), 4.00 (2H, dd, J=8.3, 4.7 Hz), 1.06 (9H, s).

(3) 3-Hydroxy-1-[4-(p-nitrobenzyloxycarbonylaminomethyl)-1,3-thiazol-2-yl] azetidine To a solution of 3-t-butyldiphenylsilyloxy-1-[4-(p-nitrobenzyloxycarbonylaminomethyl)-1,3-thiazol-2-yl] azetidine (867.2 mg, 1.44 mmol) (obtained as described in Reference Example 62(2)) in anhydrous tetrahydrofuran (45 ml) were added acetic acid (0.1 ml, 1.75 mmol) and 1.0 M tetra-n-butylammonium fluoride in tetrahydrofuran (1.72 ml, 1.72 mmol) in an ice bath and the mixture was stirred in an ice bath for 4.5 hours. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate methanol (15:1) as the eluant to afford 3-hydroxy-1-[4-(p-nitrobenzyloxycarbonylaminomethyl)-1,3-thiazol-2-yl] azetidine (457 mg, yield 87%) as a yellow solid.

$^1$H-NMR (500 MHz, CDCl$_3$): δ (ppm) 8.21 (2H, d, J=8.6 Hz), 7.51 (2H, d, J=8.6 Hz), 6.40 (1H, s), 5.38 (1H, br s), 5.21 (2H, s), 4.88–4.80 (1H, m), 4.32 (2H, dd, J=9.1, 6.8 Hz), 4.27 (2H, d, J=5.7 Hz), 3.95 (2H, dd, J=9.1, 4.5 Hz), 2.23 (1H, d, J=7.9 Hz).

(4) 3-Methanesulfonyloxy-1-[4-(p-nitrobenzyloxycarbonylaminomethyl)-1,3-thiazol-2-yl] azetidine To a solution of 3-hydroxy-1-[4-(p-nitrobenzyloxycarbonylaminomethyl)-1,3-thiazol-2-yl] azetidine (457 mg, 1.25 mmol) (obtained as described in Reference Example 62(3)) in methylene chloride (25 ml) were added methanesulfonyl chloride (0.29 ml, 3.75 mmol) and triethylamine (0.53 ml, 3.80 mmol) in an ice bath. After stirring the mixture for 10 minutes in the ice bath, the resulting mixture was stirred at room temperature for 2 hours. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using toluene:acetonitrile (1:1) as the eluant to afford 3-methanesulfonyloxy-1-[4-(p-nitrobenzyloxycarbonylaminomethyl)-1,3-thiazol-2-yl) azetidine (499.4 mg, yield 90%) as a yellow solid.

$^1$H-NMR (400 MHz, CDCl$_3$): δ (ppm) 8.21 (2H, d, J=7.8 Hz), 7.51 (2H, d, J=7.8 Hz), 6.46 (1H, s), 5.44–5.38 (2H, m), 5.26 (2H, s), 4.43 (2H, dd, J=9.8, 6.8 Hz), 4.28 (2H, d, J=5.9 Hz), 4.24 (2H, dd, J=9.8, 4.4 Hz), 3.10 (3H, s).

(5) 3-Acetylthio-1-[4-(p-nitrobenzyloxycarbonylaminomethyl)-1,3-thiazol-2-yl] azetidine To a solution of 3-methanesulfonyloxy-1-[4-(p-nitrobenzyloxycarbonylaminomethyl)-1,3-thiazol-2-yl] azetidine (499.4 mg, 1.13 mmol) (obtained as described in Reference Example 62(4)) in dimethylformamide (25 ml) was added potassium thioacetate (1.0 g, 6.93 mmol) at room temperature, and the mixture was stirred in an oil bath (80° C.) for 6.5 hours. After checking the completion of the reaction, the mixture was partitioned between ethyl acetate and saturated aqueous sodium hydrogencarbonate solution. The organic layer was washed with 0.5 M hydrochloric acid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using toluene:acetonitrile (2:1) as the eluant to afford 3-acetylthio-1-[4-(p-nitrobenzyloxycarbonylaminomethyl)-1,3-thiazol-2-yl] azetidine (265.2 mg, yield 56%) as a pale brown solid.

$^1$H-NMR (400 MHz, CDCl$_3$): δ (ppm) 8.21 (2H, d, J=8.42 Hz), 7.51 (2H, d, J=8.4 Hz), 6.42 (1H, s), 5.39 (1H, br t, J=7.5 Hz), 5.21 (2H, s), 4.51 (2H, t, J=8.1 Hz), 4.50–4.38 (1H, m), 4.27 (2H, d, J=7.5 Hz), 3.96 (2H, dd, J=8.1, 5.1 Hz), 2.36 (3H, s).

REFERENCE EXAMPLE 63

3-Acetylthio-1-[4-(methoxycarbonylamino)methyl-1,3-thiazol-2-yl]azetidine

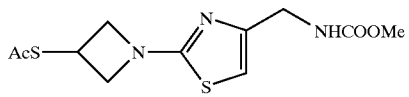

(1) 3-t-Butyldiphenylsilyloxy-1-[4-(methoxycarbonylaminomethyl)-1,3-thiazol-2-yl]azetidine 1-(4-Azidomethyl-1,3-thiazol-2-yl)-3-t-butyldiphenylsilyloxyazetidine (2.12 g, 4.71 mmol) (obtained as described in Reference Example 62(1)) in methanol (106 ml) was subjected to catalytic reduction in the presence of 20% palladium hydroxide (2.12 g) at room temperature. After checking the completion of the reaction, the reaction mixture was filtered in order to remove the catalyst and the filtrate concentrated under reduced pressure. The residue was dissolved in methylene chloride (100 ml). To the mixture were added methyl chloroformate (0.43 ml, 5.65 mmol) and triethylamine (0.79 ml, 5.65 mmol), and the mixture was stirred at room temperature for 2 hours. After checking the completion of the reaction, the mixture was distilled under reduced pressure. The residue was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 3-t-butyldiphenylsilyloxy-1-[4-(methoxycarbonylamino-methyl)-1,3-thiazol-2-yl]azetidine (1.88 g, yield 45%) as pale yellow oil.

$^1$H-NMR (400 MHz, CDCl$_3$): δ (ppm) 7.60 (4H, d, J=1.5 Hz), 7.48–7.31 (6H, m), 7.19 (1H, t, J=8.1 Hz), 7.00 (1H, s), 4.78–4.68 (1H, m), 4.24 (2H, d, J=5.8 Hz), 4.09 (2H, t, J=9.0, 6.6 Hz), 3.99 (2H, t, J=9.0, 5.0 Hz), 3.67 (3H, s), 1.06 (9H, s).

(2) 3-Hydroxy-1-[4-(methoxycarbonylaminomethyl)-1,3-thiazol-2-yl]azetidine

To a solution of 3-t-butyldiphenylsilyloxy-1-[4-(methoxycarbonylaminomethyl)-1,3-thiazol-2-yl]azetidine (1.88 g, 3.90 mmol) (obtained as described in Reference Example 63(1)) in anhydrous tetrahydrofuran (94 ml) were added acetic acid (0.27 ml, 4.68 mmol) and 1.0 M tetra-n-butylammonium fluoride in tetrahydrofuran (4.68 ml, 4.68 mmol) in an ice bath and the mixture was stirred in an ice bath for 30 minutes. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate as the eluant to afford 3-hydroxy-1-[4-(methoxycarbonylaminomethyl)-1,3-thiazol-2-yl] azetidine (426 mg, yield 45%) as a white solid.

$^1$H-NMR (400 MHz, CDCl$_3$): δ (ppm) 6.39 (1H, s), 4.79–4.39 (1H, m), 4.31 (2H, dd, J=9.1, 6.7 Hz), 4.25 (2H, d, J=5.8 Hz), 3.94 (2H, dd, J=9.1, 4.3 Hz), 3.68 (3H, s).

(3) 3-Methanesulfonyloxy-1-[4-(methoxycarbonylamino-methyl)-1,3-thiazol-2-yl]azetidine To a solution of 3-hydroxy-1-[4-(methoxycarbonylamino-methyl)-1,3-thiazol-2-yl]azetidine (426 mg, 1.75 mmol) (obtained as described in Reference Example 63(2)) in methylene chloride (20 ml) were added methanesulfonyl chloride (0.16 ml, 2.10 mmol) and triethylamine (0.29 ml, 2.10 mmol) in an ice bath and the mixture was stirred for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 3-methanesulfonyloxy-1-[4-(methoxycarbonylaminomethyl)-1,3-thiazol-2-yl]azetidine (448 mg, yield 80%) as a pale yellow solid.

$^1$H-NMR (400 MHz, CDCl$_3$): δ (ppm) 6.45 (1H, s), 5.45–5.36 (1H, m), 4.43 (2H, dd, J=9.6, 6.7 Hz), 4.25 (2H, s), 4.25 (1H, t, J=5.8 Hz), 4.23 (1H, t. J=5.8 Hz), 3.69 (3H, s), 3.10 (3H, s).

(4) 3-Acetylthio-1-[4-(methoxycarbonylaminomethyl)-1,3-thiazol-2-yl]azetidine

To a solution of 3-methanesulfonyloxy-1-[4-(methoxycarbonylamino-methyl)-1,3-thiazol-2-yl]azetidine (448 mg, 1.39 mmol) (obtained as described in Reference Example 63(3)) in dimethylformamide (13 ml) was added potassium thioacetate (952 mg, 8.34 mmol) at room temperature, and the mixture was stirred in an oil bath (90° C.) for 6 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:2) as the eluant to afford 3-acetylthio-1-[4-(methoxycarbonylaminomethyl)-1,3-thiazol-2-yl] azetidine (441 mg, yield 100%) as a pale brown solid.

$^1$H-NMR (400 MHz, CDCl$_3$): δ (ppm) 6.41 (1H, s), 4.50 (2H, t, J=8.5 Hz), 4.49–4.45 (1H, m), 4.25 (2H, d, J=5.7 Hz), 3.56 (2H, dd, J=8.5, 5.3 Hz), 3.68 (3H, s), 2.05 (3H, s).

REFERENCE EXAMPLE 64

3-Acetylthio-1-[4-(benzoylaminomethyl)-1,3-thiazol-2-yl]azetidine

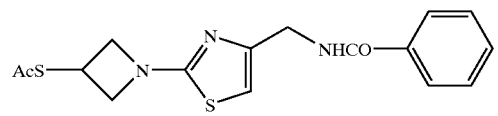

(1) 1-[4-(Benzoylaminomethyl)-1,3-thiazol-2-yl]-3-t-butyldiphenylsilyloxyazetidine 1-(4-Azidomethyl-1,3-thiazol-2-yl)-3-t-butyldiphenylsilyloxyazetidine (2.53 g, 5.60 mmol) (obtained as described in Reference Example 62(1) in methanol (120 ml) was subjected to catalytic reduction in the presence of 20% palladium hydroxide (2.53 g) at room temperature. After checking the completion of the reaction, the reaction mixture was filtered in order to remove the catalyst. To the filtrate was added benzoic anhydride (1.90 ml, 8.40 mmol) in an ice bath and the mixture was stirred for 2.5 hours. After checking the completion of the reaction, the mixture was distilled under reduced pressure. The residue was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane ethyl acetate (3:1) ethyl acetate as the eluant to afford 1-[4-(benzoylaminomethyl)-1,3-thiazol-2-yl]-3-t-butyldiphenylsilyloxyazetidine (1.49 g, yield 50%) as pale yellow oil.

$^1$H-NMR (400 MHz, CDCl$_3$): δ (ppm) 7.79 (2H, d, J=7.3 Hz), 7.63–7.55 (4H, m), 7.55–7.31 (9H, m), 6.79 (1H, br s), 6.44 (1H, s), 4.79–4.68 (1H, m), 4.51 (2H, d, J=5.4 Hz), 4.11 (2H, dd, J=8.4, 7.3 Hz), 4.01 (2H, dd, J=8.4, 5.0 Hz), 1.06 (9H, s).

(2) 1-[4-(Benzoylaminomethyl)-1,3-thiazol-2-yl]-3-hydroxyazetidine

To a solution of 1-[4-(benzoylaminomethyl)-1,3-thiazol-2-yl]-3-t-butyldiphenylsilyloxyazetidine (1.49 g, 2.82 mmol) (obtained as described in Reference Example 64(1)) in anhydrous tetrahydrofuran (75 ml) was added a 1.0 M solution of tetra-n-butylammonium fluoride in tetrahydrofuran (3.39 ml, 3.39 mmol) in an ice bath and the mixture was stirred in an ice bath for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using hexane:ethyl acetate (1:2) ethyl acetate:methanol (9:1) as the eluant to afford 1-[4-(benzoylaminomethyl)-1,3-thiazol-2-yl]-3-hydroxyazetidine (582 mg, yield 71%) as a white solid.

$^1$H-NMR (400 MHz, CDCl$_3$): δ (ppm) 7.79 (2H, dd, J=7.4 Hz), 7.60–7.36 (3H, m), 6.82 (1H, br s), 6.46 (1H, s), 4.85–4.77 (1H, m), 4.51 (2H, d, J=5.6 Hz), 4.31 (2H, dd, J=8.9, 6.6 Hz), 3.95 (2H, dd, J=8.5, 4.4 Hz).

(3) 1-[4-(Benzoylaminomethyl)-1,3-thiazol-2-yl]-3-methanesulfonyloxyazetidine

To a solution of 1-[4-(benzoylaminomethyl)-1,3-thiazol-2-yl]-3-hydroxyazetidine (582 mg, 2.01 mmol) (obtained as described in Reference Example 64(2)) in methylene chloride (30 ml) were added methanesulfonyl chloride (0.19 ml, 2.41 mmol), triethylamine (0.34 ml, 2.41 mmol) and pyridine (5.8 ml) in an ice bath and the mixture was stirred for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 1-[4-(benzoylaminomethyl)-1,3-thiazol-2-yl]-3-methanesulfonyloxyazetidine (739 mg, yield 100%) as a pale yellow solid.

$^1$H-NMR (400 MHz, CDCl$_3$): δ (ppm) 7.80 (2H, d, J=6.9 Hz), 7.57–7.41 (3H, m), 6.71 (1H, bs), 6.53 (1H, s), 5.46–5.38 (1H, m), 4.54 (2H, d, J=5.2 Hz), 4.44 (2H, ddd, J=9.6, 6.6, 0.9 Hz), 4.25 (2H, ddd, J=9.6, 9.3, 0.9 Hz), 3.10 (3H, s).

(4) 3-Acetylthio-1-[4-(benzoylamino-methyl)-1,3-thiazol-2-yl]azetidine

To a solution of 1-[4-(benzoylaminomethyl)-1,3-thiazol-2-yl]-3-methanesulfonyloxyazetidine (739 mg, 2.01 mmol) (obtained as described in Reference Example 64(3)) in dimethylformamide (20 ml) was added potassium thioacetate (1.38 g, 12.1 mmol) at room temperature, and the mixture was stirred in an oil bath (90° C.) for 3.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate= (1:1)→ethyl acetate as the eluant to afford 3-acetylthio-1-[4-(benzoylaminomethyl)-1,3-thiazol-2-yl]azetidine (698 mg, yield 100%) as a pale brown solid.

$^1$H-NMR (400 MHz, CDCl$_3$): δ (ppm) 7.08 (2H, d, J=7.8 Hz), 7.55–7.46 (3H, m), 6.77 (1H, br s), 6.49 (1H, s), 4.47–4.38 (4H, m), 4.47–4.38 (1H, m), 3.97 (2H, dd, J=8.6, 5.2 Hz), 2.37 (3H, s).

REFERENCE EXAMPLE 65

3-Acetylthio-1-[4-(benzenesulfonylamino)methyl-1,3-thiazol-2-yl]azetidine

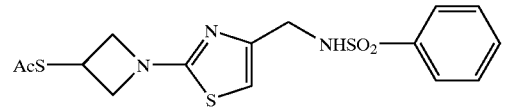

(1) 3-t-Butyldiphenylsilyloxy-1-[4-(benzenesulfonylamino)methyl-1,3-thiazol-2-yl]azetidine 1-(4-Azidomethyl-1,3-thiazol-2-yl)-3-t-butyldiphenylsilyloxyazetidine (2.12 g, 4.71 mmol) (obtained as described in Reference Example 62(1)) in methanol (106 ml) was subjected to catalytic hydrogenation in the presence of 20% palladium hydroxide (2.12 g) at room temperature. After checking the completion of the reaction, the reaction mixture was filtered in order to remove the catalyst and the filtrate concentrated under reduced pressure. The residue was dissolved in methylene chloride (100 ml). To the mixture were added benzenesulfonyl chloride (0.90 g, 7.07 mmol) and triethylamine (0.98 ml, 7.07 mmol) in an ice bath, and the mixture was stirred at room temperature for 2 hours. After checking the completion of the reaction, the mixture was distilled under reduced pressure. The residue was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 3-t-butyldiphenylsilyloxy-1-[4-(benzenesulfonylamino)methyl-1,3-thiazol-2-yl]azetidine (755 mg, yield 28%) as pale yellow oil.

$^1$H-NMR (400 MHz, CDCl$_3$): δ (ppm) 7.80 (2H, d, J=7.5 Hz), 7.61 (4H, d, J=6.3 Hz), 7.54–7.30 (9H, m), 6.21 (1H, s), 5.07 (1H, t, J=6.0 Hz), 4.74–4.66 (1H, m), 4.05 (2H, d, J=6.3 Hz), 3.99 (2H, dd, J=7.6 Hz), 3.89 (2H, dd, J=8.8, 4.8 Hz), 1.07 (9H, s).

(2) 1-[4-(Benzenesulfonylamino)methyl-1,3-thiazol-2-yl]-3-hydroxyazetidine

To a solution of 3-t-butyldiphenylsilyloxy-1-[4-(benzenesulfonylamino)methyl-1,3-thiazol-2-yl]azetidine (2.79 g, 4.95 mmol) (obtained as described in Reference Example 65(1)) in anhydrous tetrahydrofuran (140 ml) was added a solution of 1.0 M tetra-n-butylammonium fluoride in tetrahydrofuran (5.94 ml, 5.94 mmol) in an ice bath and the mixture was stirred in an ice bath for 2 hours. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate as the eluant to afford 1-[4-(benzenesulfonylamino) methyl-1,3-thiazol-2-yl]-3-hydroxyazetidine (1.06 g, yield 66%) as a white solid.

$^1$H-NMR (400 MHz, CDCl$_3$): δ (ppm) 7.79 (2H, d, J=7.5 Hz), 7.50–7.41 (3H, m), 6.25 (1H, s), 5.51 (1H, br s), 4.80–4.70 (1H, m), 4.19 (2H, t, J=9.1 Hz), 4.03 (2H, t, J=3.5 Hz), 3.83 (2H, dd, J=9.1, 4.3 Hz).

(3) 1-[4-(Benzenesulfonylamino)methyl-1,3-thiazol-2-yl]-3-methanesulfonyloxyazetidine To a solution of 1-[4-(benzenesulfonylamino)methyl-1,3-thiazol-2-yl]-3-hydroxyazetidine (1.06 g, 3.26 mmol) (obtained as described in Reference Example 65(2)) in methylene chloride (50 ml) were added methanesulfonyl chloride (0.38 ml, 4.89 mmol) and triethylamine (0.68 ml, 4.89 mmol) in an ice bath and the mixture was stirred for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 1-[4-(benzenesulfonylamino) methyl-1,3-thiazol-2-yl]-3-methanesulfonyloxyazetidine (1.16 mg, yield 91%) as a pale yellow solid.

$^1$H-NMR (400 MHz, CDCl$_3$): δ (ppm) 7.82 (2H, d, J=7.3 Hz), 7.61–7.46 (3H, m), 6.33 (1H, s), 5.42–5.33 (1H, m), 5.15 (1H, t, J=5.9 Hz), 4.34 (2H, dd, J=9.8, 6.7 Hz), 4.14 (2H, dd, J=9.8, 4.1 Hz), 4.08 (2H, d, J=6.3 Hz), 3.10 (3H, s).

(4) 3-Acetylthio-1-[4-(benzenesulfonylamino)methyl-1,3-thiazol-2-yl]azetidine

To a solution of 1-[4-(benzenesulfonylamino)methyl-1,3-thiazol-2-yl]-3-methanesulfonyloxyazetidine (1.16 g, 2.98 mmol) (obtained as described in Reference Example 65(3)) in dimethylformamide (35 ml) was added potassium thioacetate (2.04 g, 17.9 mmol) at room temperature, and the mixture was stirred in an oil bath (90° C.) for 4 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using methylene chloride:ethyl acetate (5:1) as the eluant to afford 3-acetylthio-1-[4-(benzenesulfonylamino)methyl-1,3-thiazol-2-yl]azetidine (1.00 g, yield 91%) as a pale brown solid.

$^1$H-NMR (400 MHz, CDCl$_3$): δ (ppm) 7.82 (2H, d, J=7.4 Hz), 7.58–7.42 (3H, m), 6.23 (1H, s), 5.40–5.50 (1H, m), 4.48–4.30 (3H, m), 4.09 (2H, d, J=5.8 Hz), 3.90 (2H, dd, J=8.3, 4.5 Hz), 2.37 (3H, s).

REFERENCE EXAMPLE 66

3-Acetylthio-1-[4-(thiophene-2-carbonylamino) methyl-1,3-thiazol-2-yl]azetidine

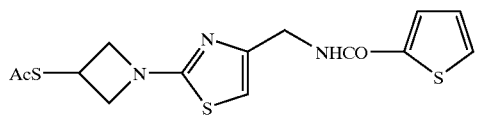

(1) 3-t-Butyldiphenylsilyloxy-1-[4-(thiophene-2-carbonylamino)methyl-1,3-thiazol-2-yl]azetidine 1-(4-Azidomethyl-1,3-thiazol-2-yl)-3-t-butyldiphenylsilyloxyazetidine (2.47 g, 5.50 mmol) (obtained as described in Reference Example 62(1)) in methanol (120 ml) was subjected to catalytic hydrogenation in the presence of 20% palladium hydroxide (2.47 g) at room temperature. After checking the completion of the reaction, the reaction mixture was filtered in order to remove the catalyst and the filtrate concentrated under reduced pressure. The residue was dissolved in methylene chloride (115 ml). To the mixture were added thenoyl chloride (0.71 ml, 6.60 mmol) and triethylamine (0.92 ml, 6.60 mmol), and the mixture was stirred at room temperature for 1 hour. After checking the completion of the reaction, the mixture was distilled under reduced pressure. The residue was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-t-butyldiphenylsilyloxy-1-[4-(thiophene-2-carbonylamino)methyl-1,3-thiazol-2-yl] azetidine (1.88 g, yield 64%) as a pale yellow oil.

$^1$H-NMR (400 MHz, CDCl$_3$): δ (ppm) 7.75–7.32 (13H, m), 7.11–7.03 (1H, m), 6.65 (1H, br s), 4.80–4.70 (1H, m), 4.47 (2H, d, J=5.0 Hz), 4.11 (2H, t, J=8.5 Hz), 4.01 (2H, dd, J=8.5, 5.0 Hz), 1.06 (9H, s).

(2) 3-Hydroxy-1-[4-(thiophene-2-carbonylamino)methyl-1, 3-thiazol-2-yl]azetidine To a solution of 3-t-butyldiphenylsilyloxy-1-[4-(thiophene-2-carbonylamino)methyl-1,3-thiazol-2-yl] azetidine (2.18 g, 4.08 mmol) (obtained as described in Reference Example 66(1)) in anhydrous tetrahydrofuran (110 ml) was added a solution of 1.0 M tetra-n-butylammonium fluoride in tetrahydrofuran (4.90 ml, 4.90 mmol) in an ice bath and the mixture was stirred in an ice bath for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford 3-hydroxy-1-[4-(thiophene-2-carbonylamino)methyl-1,3-thiazol-2-yl]azetidine (571 mg, yield 47%) as a white solid.

$^1$H-NMR (400 MHz, CDCl$_3$): δ (ppm) 7.53 (1H, d, J=3.5 Hz), 7.46 (1H, d, J=5.4 Hz), 7.60 (1H, dd, J=4.9, 3.8 Hz), 6.87 (1H, br s), 6.46 (1H, s), 4.87–4.78 (1H, m), 4.48 (2H, d, J=5.6 Hz), 4.33 (2H, dd, J=8.7, 4.6 Hz), 3.98 (2H, dd, J=8.7, 4.6 Hz).

(3) 3-Methanesulfonyloxy-1-[4-(thiophene-2-carbonylamino)methyl-1,3-thiazol-2-yl]azetidine To a solution of 3-hydroxy-1-[4-(thiophene-2-carbonylamino)methyl-1,3-thiazol-2-yl]azetidine (571 mg, 1.93 mmol) (obtained as described in Reference Example 66(2)) in methylene chloride (28 ml) were added methanesulfonyl chloride (0.18 ml, 2.32 mmol) and triethylamine (0.33 ml, 2.32 mmol) in an ice bath and the mixture was stirred for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate:methanol (1:1) as the eluant to afford 3-methanesulfonyloxy-1-[4-(thiophene-2-carbonyl-amino)methyl-1,3-thiazol-2-yl]azetidine (490 mg, yield 91%) as a pale yellow solid.

$^1$H-NMR (400 MHz, CDCl$_3$): δ (ppm) 7.56 (1H, d, J=5.4 Hz), 7.47 (1H, d, J=5.4 Hz), 7.07 (1H, dd, J=5.1, 3.7 Hz), 6.87 (1H, br s), 6.50 (1H, s), 4.57 (2H, t, J=8.6 Hz), 4.50 (2H, t, J=5.4 Hz), 4.50 (2H, d, J=5.4 Hz), 4.48–4.37 (1H, m), 4.36 (2H, dd, J=8.6, 5.5 Hz), 2.36 (3H, s).

(4) 3-Acetylthio-1-[4-(thiophene-2-carbonylamino)methyl-1,3-thiazol-2-yl]azetidine To a solution of 3-methanesulfonyloxy-1-[4-(thiophene-2-carbonylamino)methyl-1,3-thiazol-2-yl]azetidine (623 mg, 1.67 mmol) (obtained as described in Reference Example 66(3)) in dimethylformamide (18 ml) was added potassium thioacetate (1.14 g, 10.0 mmol) at room temperature, and the mixture was stirred in an oil bath (90° C.) for 4 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) ethyl acetate as the eluant to afford 3-acetylthio-1-[4-(thiophene-2-carbonyl-amino)methyl-1,3-thiazol-2-yl]azetidine (490 mg, yield 91%) as a pale brown solid.

$^1$H-NMR (400 MHz, CDCl$_3$): δ (ppm) 7.56 (1H, d, J=5.4 Hz), 7.47 (1H, d, J=5.4 Hz), 7.07 (1H, dd, J=5.1, 3.7 Hz), 6.87 (1H, br s), 6.50 (1H, s), 4.57 (2H, t, J=8.6 Hz), 4.50 (2H, t, J=5.4 Hz), 4.50 (2H, d, J=5.4 Hz), 4.48–4.37 (1H, m), 4.36 (2H, dd, J=8.6, 5.5 Hz), 2.36 (3H, s).

REFERENCE EXAMPLE 67

3-Acetylthio-1-[4-(furan-2-carbonylamino)methyl-1,3-thiazol-2-yl]azetidine

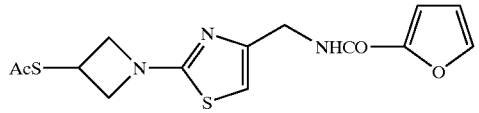

(1) 3-t-Butyldiphenylsilyloxy-1-[4-(furan-2-carbonylamino)methyl-1,3-thiazol-2-yl]azetidine 1-(4-Azidomethyl-1,3-thiazol-2-yl)-3-t-butyldiphenylsilyloxyazetidine (2.47 g, 5.50 mmol) (obtained as described in Reference Example 62(1)) in methanol (120 ml) was subjected to catalytic reduction in the presence of 20% palladium hydroxide (2.47 g) at room temperature. After checking the completion of the reaction, the reaction mixture was filtered in order to remove the catalyst and the filtrate concentrated under reduced pressure. The residue was dissolved in methylene chloride (115 ml). To the mixture were added 2-furoyl chloride (0.65 ml, 6.60 mmol) and triethylamine (0.92 ml, 6.60 mmol), and the mixture was stirred at room temperature for 1 hour. After checking the completion of the reaction, the mixture was distilled under reduced pressure. The residue was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-t-butyldiphenylsilyloxy-1-[4-(furan-2-carbonylamino)methyl-1,3-thiazol-2-yl]azetidine (1.60 g, yield 60%) as a pale yellow oil.

$^1$H-NMR (400 MHz, CDCl$_3$): δ (ppm) 7.75–7.58 (4H, m), 7.50–7.09 (9H, m), 6.68 (1H, br s), 4.82–4.70 (1H, m), 4.47 (2H, d, J=5.5 Hz), 4.11 (2H, t, J=8.3 Hz), 4.02 (2H, dd, J=8.3, 5.0 Hz), 1.06 (9H, s).

(2) 1-[4-(Furan-2-carbonylamino)methyl-1,3-thiazol-2-yl]-3-hydroxyazetidine

To a solution of 3-t-butyldiphenylsilyloxy-1-[4-(furan-2-carbonyl-amino)methyl-1,3-thiazol-2-yl]azetidine (1.90 g, 3.68 mmol) (obtained as described in Reference Example 67(1)) in anhydrous tetrahydrofuran (95 ml) was added a solution of 1.0 M tetra-n-butylammonium fluoride in tetrahydrofuran (4.41 ml, 4.41 mmol) in an ice bath and the mixture was stirred in an ice bath for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate:methanol (10:1) as the eluant to afford 1-[4-(furan-2-carbonylamino)methyl-1,3-thiazol-2-yl]-3-hydroxyazetidine (426 mg, yield 47%) as a white solid.

$^1$H-NMR (400 MHz, CDCl$_3$): δ (ppm) 7.44 (1H, s), 7.12 (1H, d, J=3.5 Hz), 7.04 (1H, br s), 6.49 (1H, dd, J=3.4, 1.7 Hz), 6.45 (1H, s), 4.86–4.78 (1H, m), 4.48 (2H, d, J=5.7 Hz), 4.33 (2H, t, J=8.8 Hz), 3.98 (2H, dd, J=8.8, 4.4 Hz).

(3) 1-[4-(Furan-2-carbonylamino)methyl-1,3-thiazol-2-yl]-3-methanesulfonyloxyazetidine To a solution of 1-[4-(furan-2-carbonylamino)methyl-1,3-thiazol-2-yl]-3-hydroxyazetidine (426 mg, 1.72 mmol) (obtained as described in Reference Example 67(2)) in methylene chloride (20 ml) were added methanesulfonyl chloride (0.16 ml, 2.07 mmol) and triethylamine (0.29 ml, 2.07 mmol) in an ice bath and the mixture was stirred for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate:methanol (20:1) as the eluant to afford 1-[4-(furan-2-carbonylamino)methyl-1,3-thiazol-2-yl]-3-methanesulfonyloxyazetidine (481 mg, yield 78%) as a pale yellow solid.

$^1$H-NMR (400 MHz, CDCl$_3$): δ (ppm) 7.45 (1H, d, J=0.9 Hz), 7.13 (1H, d, J=3.5 H), 7.00 (1H, s), 6.53 (1H, s), 6.50 (1H, dd, J=3.5, 1.8 Hz), 5.49–5.38 (1H, m), 4.51 (2H, d, J=5.8 Hz), 4.48 (2H, dd, J=3.1, 1.0 Hz), 4.29 (2H, dd, J=5.8, 4.9 Hz), 3.10 (3H, s).

(4) 3-Acetylthio-1-[4-(furan-2-carbonylamino)methyl-1,3-thiazol-2-yl]azetidine

To a solution of 1-[4-(furan-2-carbonylamino)methyl-1,3-thiazol-2-yl]-3-methanesulfonyloxyazetidine (481 mg, 1.34 mmol) (obtained as described in Reference Example 67(3)) in dimethylformamide (14 ml) was added potassium thioacetate (921 mg, 8.07 mmol) at room temperature and the mixture was stirred in an oil bath (90° C.) for 6 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-acetylthio-1-[4-(furan-2-carbonylamino)methyl-1,3-thiazol-2-yl]azetidine (341 mg, yield 83%) as a pale brown solid.

¹H-NMR (400 MHz, CDCl₃): δ (ppm) 7.45 (1H, s), 7.12 (1H, d, J=3.5 Hz), 7.09–6.94 (2H, m), 6.49 (2H, t, J=2.5 Hz), 4.56 (2H, t, J=8.5 Hz), 4.50 (2H, d, J=5.7 Hz), 4.48–4.38 (1H, m), 4.02 (2H, dd, J=8.5, 6.1 Hz), 2.36 (3H, s).

REFERENCE EXAMPLE 68

3-Acetylthio-1-(4-phthalimidomethyl-1,3-thiazol-2-yl)azetidine

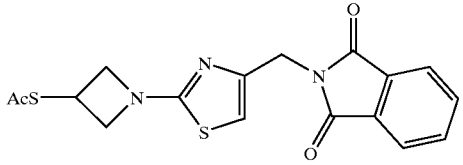

(1) 3-t-Butyldiphenylsilyloxy-1-(4-phthalimidomethyl-1,3-thiazol-2-yl)azetidine

To a solution of 3-t-butyldiphenylsilyloxy-1-(4-hydroxymethyl-1,3-thiazol-2-yl)azetidine (1.50 g, 3.53 mmol) (obtained as described in Reference Example 2(2)) in tetrahydrofuran (75 ml) were added phthalimide (519 mg, 5.30 mmol), triphenylphosphine (1.39 g, 5.30 mmol) and 40% diethyl azodicarboxylate in toluene solution (2.03 ml, 5.30 mmol) in an ice bath under an atmosphere of nitrogen. The mixture was stirred in an ice bath for 2 hours. After checking the completion of the reaction, the mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using hexane:ethyl acetate (1:5) as the eluant to afford 3-t-butyldiphenylsilyloxy-1-(4-phthalimidomethyl-1,3-thiazol-2-yl)azetidine (1.52 mg, yield 78%) as pale yellow oil.

¹H-NMR (400 MHz, CDCl₃): δ (ppm) 7.88 (2H, dd, J=5.5, 3.1 Hz), 7.33 (2H, dd, J=5.5, 3.1 Hz), 7.60 (4H, dd, J=7.9, 1.4 Hz), 7.47–7.34 (6H, m), 6.26 (1H, s), 4.83 (2H, s), 4.76–4.68 (1H, m), 4.26–4.08 (2H, m), 4.08–3.92 (2H, m), 1.05 (9H, s).

(2) 1-(4-Phthalimidomethyl-1,3-thiazol-2-yl)-3-hydroxyazetidine

To a solution of 3-t-butyldiphenylsilyloxy-1-(4-phthalimidomethyl-1,3-thiazol-2-yl)azetidine (1.52 g, 2.57 mmol) (obtained as described in Reference Example 68(1)) in anhydrous tetrahydrofuran (76 ml) was added a 1.0 M solution of tetra-n-butylammonium fluoride in tetrahydrofuran (3.29 ml, 3.29 mmol) in an ice bath and the mixture was stirred in an ice bath for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate as the eluant to afford 1-(4-phthalimidomethyl-1,3-thiazol-2-yl)-3-hydroxyazetidine (864 mg, yield 100%) as a white solid.

¹H-NMR (400 MHz, CDCl₃): δ (ppm) 7.87 (2H, dd, J=5.4, 3.1 Hz), 7.73 (2H, dd, J=5.4, 3.1 Hz), 6.32 (1H, s), 4.79 (2H, s), 4.78–4.70 (1H, m), 4.27 (2H, dd, J=9.2, 6.9 Hz), 3.91 (2H, dd, J=9.2, 4.6 Hz).

(3) 1-(4-Phthalimidomethyl-1,3-thiazol-2-yl)-3-methanesulfonyloxyazetidine

To a solution of 1-(4-phthalimidomethyl-1,3-thiazol-2-yl)-3-hydroxyazetidine (864 mg, 2.74 mmol) (obtained as described in Reference Example 68(2)) in methylene chloride (35 ml) were added methanesulfonyl chloride (0.25 ml, 3.29 mmol) and triethylamine (0.46 ml, 3.29 mmol) in an ice bath and the mixture was stirred for 1 hour. After checking the completion of the reaction, the mixture was added to diethyl ether and stirred for 30 minutes. The mixture was then filtered and the solid was collected by filtration and washed with diethyl ether to afford 1-(4-phthalimidomethyl-1,3-thiazol-2-yl)-3-methanesulfonyloxyazetidine (726 mg, yield 67%) as a white solid.

¹H-NMR (400 MHz, CDCl₃): δ (ppm) 7.91 (2H, dd, J=5.5, 2.8 Hz), 7.86 (2H, dd, J=5.5, 3.5 Hz), 6.70 (1H, s), 5.46–5.39 (1H, m), 4.63 (2H, s), 4.36 (2H, dd, J=10.0, 6.6 Hz), 4.09 (2H, dd, J=10.0, 3.4 Hz), 3.27 (3H, s).

(4) 3-Acetylthio-1-(4-phthalimidomethyl-1,3-thiazol-2-yl)azetidine

To a solution of 1-(4-phthalimidomethyl-1,3-thiazol-2-yl)-3-methanesulfonyloxyazetidine (726 mg, 1.85 mmol) (obtained as described in Reference Example 68(3)) in dimethylformamide (22 ml) was added potassium thioacetate (1.26 g, 11.1 mmol) at room temperature, and the mixture was stirred in an oil bath (90° C.) for 6.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using hexane:ethyl acetate (1:1) as the eluant to afford 3-acetylthio-1-(4-phthalimidomethyl-1,3-thiazol-2-yl)azetidine (599 mg, yield 87%) as a pale brown solid.

¹H-NMR (400 MHz, CDCl₃): δ (ppm) 7.88 (2H, dd, J=5.4, 2.9 Hz), 7.73 (2H, dd, J=5.4, 3.1 Hz), 6.35 (1H, s), 4.82 (2H, s), 4.52 (2H, t, J=8.4 Hz), 4.45–4.35 (1H, m), 3.98 (2H, dd, J=8.4, 5.7 Hz), 2.34 (3H, s).

REFERENCE EXAMPLE 69

3-Acetylthio-1-(4-succinimidomethyl-1,3-thiazol-2-yl)azetidine

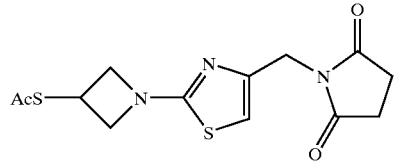

(1) 3-t-Butyldiphenylsilyloxy-1-(4-succinimidomethyl-1,3-thiazol-2-yl)azetidine

To a solution of 3-t-butyldiphenylsilyloxy-1-(4-hydroxymethyl-1,3-thiazol-2-yl)azetidine (1.50 g, 3.53 mmol) (obtained as described in Reference Example 2(2)) in tetrahydrofuran (75 ml) were added succinimide (525 mg, 5.30 mmol), triphenylphosphine (1.39 g, 5.30 mmol) and 40% diethyl azodicarboxylate in toluene solution (2.03 ml, 5.30 mmol) in an ice bath under an atmosphere of nitrogen. The mixture was stirred in an ice bath for 4 hours. After checking the completion of the reaction, the mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using hexane:ethyl acetate (1:1) as the eluant to afford 3-t-butyldiphenylsilyloxy-1-(4-succinimidomethyl-1,3-thiazol-2-yl)azetidine (1.79 g, yield 100%) as pale yellow oil.

$^1$H-NMR (400 MHz, CDCl$_3$): δ (ppm) 7.65–7.57 (4H, m), 7.49–7.36 (6H, m), 6.30 (1H, s), 4.75–4.66 (1H, m), 4.60 (2H, s), 4.21 (4H, dd, J=14.2, 7.1 Hz), 4.12 (4H, dd, J=14.2, 7.1 Hz), 4.09 (2H, t, J=8.5 Hz), 3.99 (2H, dd, J=8.5, 4.9 Hz), 1.05 (9H, s).

(2) 3-Hydroxy-1-(4-succinimidomethyl-1,3-thiazol-2-yl)azetidine

To a solution of 3-t-butyldiphenylsilyloxy-1-(4-succinimidomethyl-1,3-thiazol-2-yl)azetidine (1.79 g, 3.53 mmol) (obtained as described in Reference Example 69(1)) in anhydrous tetrahydrofuran (141 ml) was added a solution of 1.0 M tetra-n-butylammonium fluoride in tetrahydrofuran (4.24 ml, 4.24 mmol) in an ice bath and the mixture was stirred in an ice bath for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous magnesium sulfate, filtered and concentrated under reduced pressure. The residue was purified by chromatography on a silica gel column using ethyl acetate→ethyl acetate:methanol (20:1) as the eluant to afford 3-hydroxy-1-(4-succinimidomethyl-1,3-thiazol-2-yl)azetidine (456 mg, yield 49%) as a white solid.

$^1$H-NMR (400 MHz, CDCl$_3$): δ (ppm) 6.34 (1H, s), 4.84–4.74 (1H, m), 4.62 (2H, s), 4.31 (2H, dd, J=9.9, 6.6 Hz), 3.94 (2H, dd, J=9.9, 4.4 Hz), 2.76 (4H, m).

(3) 3-Methanesulfonyloxy-1-(4-succinimidomethyl-1,3-thiazol-2-yl)azetidine

To a solution of 3-hydroxy-1-(4-succinimidomethyl-1,3-thiazol-2-yl)azetidine (459 mg, 1.72 mmol) (obtained as described in Reference Example 69(2)) in methylene chloride (50 ml) were added methanesulfonyl chloride (0.16 ml, 2.06 mmol) and triethylamine (0.29 ml, 2.06 mmol) in an ice bath and the mixture was stirred for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium sulfate, filtered and concentrated under reduced pressure. The residue was purified by chromatography on a silica gel column using ethyl acetate as the eluant to afford 3-methanesulfonyloxy-1-(4-succinimidomethyl-1,3-thiazol-2-yl)azetidine (515 mg, yield 87%) as a pale yellow solid.

$^1$H-NMR (400 MHz, CDCl$_3$): δ (ppm) 6.43 (1H, s), 5.44–5.34 (1H, m), 4.62 (2H, s), 4.44 (2H, dd, J=10.3, 6.6 Hz), 4.24 (2H, dd, J=10.3, 4.2 Hz), 3.09 (3H, s), 2.76 (4H, s).

(4) 3-Acetylthio-1-(4-succinimidomethyl-1,3-thiazol-2-yl)azetidine

To a solution of 3-methanesulfonyloxy-1-(4-succinimidomethyl-1,3-thiazol-2-yl)azetidine (515 mg, 1.49 mmol) (obtained as described in Reference Example 69(3)) in dimethylformamide (15 ml) was added potassium thioacetate (1.02 g, 8.95 mmol) at room temperature, and then stirred in an oil bath (90° C.) for 8 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3-acetylthio-1-(4-succinimidomethyl-1,3-thiazol-2-yl)azetidine (238 mg, yield 49%) as a pale brown solid.

$^1$H-NMR (400 MHz, CDCl$_3$): δ (ppm) 6.37 (1H, s), 4.62 (2H, s), 4.51 (2H, t, J=8.5 Hz), 4.45–4.35 (1H, m), 3.97 (2H, dd, J=8.4, 5.4 Hz), 2.76 (4H, s), 2.35 (3H, m).

REFERENCE EXAMPLE 70

3-t-Butyldiphenylsilyloxy-1-(4-carboxyl-1,3-oxazol-2-yl)azetidine

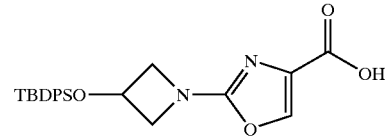

(1) (2S)-3-(t-Butyldiphenylsilyloxy)-2-isothiocyanatopropionic acid methyl ester t-Butyldiphenylsilyloxy-N-benzyloxycarbonyl-L-serine methyl ester (32.0 g, 65.1 mmol) (obtained as described in Reference Example 39(1)) in methanol (960 ml) was subjected to catalytic hydrogenation in the presence of 10% palladium on charcoal at room temperature for 2 hours. At the end of this time, the reaction mixture was filtered and the filtrate was concentrated under reduced pressure. The residue was purified by chromatography on a silica gel column using methylene chloride:methanol (95:5) as the eluant to afford t-butyldiphenylsilyloxy-L-serine methyl ester (19.7 g, yield 85%) as a colorless oil. To a solution of the product (t-butyldiphenylsilyloxy-L-serine methyl ester) (19.7 g, 55.0 mmol) in methylene chloride (590 ml) were added carbon disulfide (6.62 ml, 110 mmol) and triethylamine (19.3 ml, 138 mmol) at room temperature and the mixture was stirred overnight. To the resulting mixture were added ethyl chloroformate (13.2 ml, 138 mmol) and triethylamine (19.3 ml, 138 mmol) and the mixture was stirred for 1 hour. After checking the completion of the reaction, methanol was added to the reaction mixture and the resulting mixture was stirred for 30 minutes. The reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using toluene as the eluant to afford (2S)-3-(t-butyldiphenylsilyloxy)-2-isothiocyanatopropionic acid methyl ester (14.8 g, yield 67%) as yellow crystals.

$^1$H-NMR (400 MHz, CDCl$_3$): δ (ppm) 7.70–7.62 (4H, m), 7.48–7.38 (6H, m), 4.28 (1H, dd, J=3.7, 5.1 Hz), 4.05 (1H, dd, J=5.1, 10.3 Hz), 3.95 (1H, dd, J=3.7, 10.3 Hz), 3.80 (3H, s), 1.06 (9H, s).

(2) (2S)-3-(t-Butyldiphenylsilyloxy)-2-[(3-hydroxyazetidine-1-carbothioyl)amino]propionic acid methyl ester To a solution of 3-(t-butyldiphenylsilyloxy)-2-isothiocyanatopropionic acid methyl ester (13.4 g, 33.5 mmol) (obtained as described in Reference Example 70(1)) in tetrahydrofuran (245 ml) was added a solution of 3-hydroxyazetidine (4.90 g, 67.1 mmol) (obtained as described in Reference Example 31(1)) in water (50 ml) at room temperature and the mixture was stirred overnight.

After checking the completion of the reaction, the reaction mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using toluene and toluene:acetonitrile (3:1) as the eluant to afford (2S)-3-(t-butyldiphenylsilyloxy)-2-[(3-hydroxyazetidine-1-carbothioyl)amino]propionic acid methyl ester (9.60 g, yield 61%) as an yellow solid.

$^1$H-NMR (400 MHz, CDCl$_3$): δ (ppm) 7.61–7.55 (4H, m), 7.47–7.36 (6H, m), 5.94 (1H, br d, J=8.1 Hz), 5.19 (1H, dt, J=2.9, 8.1 Hz), 4.71–4.64 (1H, m), 4.40–4.33 (1H, m), 4.31–4.23 (1H, m), 4.18 (1H, dd, J=2.2, 10.3 Hz), 4.04 (1H, dd, J=2.9, 10.3 Hz), 4.02–3.96 (1H, m), 3.94–3.88 (1H, m), 3.76 (3H, s), 2.24 (1H, br d, J=5.9 Hz), 1.04 (9H, s).

(3) (2S)-2-{[3-(Benzoyloxy)-azetidine-1-carbothioyl]amino}-3-(t-butyldiphenylsilyloxy)propionic acid methyl ester To a solution of (2S)-3-(t-butyldiphenylsilyloxy)-2-[(3-hydroxyazetidine-1-carbothioyl)-amino]propionic acid methyl ester (21.1 g, 44.6 mmol) (obtained as described in Reference Example 70(2)) in pyridine (630 ml) were added a solution of benzoic anhydride (30.0 g, 133 mmol) and 4-dimethylaminopyridine (545 mg, 4.46 mmol) in an ice bath and the mixture was stirred at room temperature for 2 hours. After checking the completion of the reaction, the mixture was partitioned between ethyl acetate and saturated aqueous sodium hydrogencarbonate solution; The organic layer was washed with 0.5 N hydrochloric aid, saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:1) as the eluant to afford (2S)-2-{[3-(benzoyloxy)-azetidine-1-carbothioyl]amino}-3-(t-butyldiphenylsilyloxy)propionic acid methyl ester (23.3 g, yield 91%) as a pale yellow solid.

$^1$H-NMR (400 MHz, CDCl$_3$): δ (ppm) 8.10–8.05 (2H, m), 7.65–7.54 (4H, m), 7.52–7.45 (3H, m), 7.44–7.35 (6H, m), 5.96 (1H, br d, J=8.1 Hz), 5.47–5.40 (1H, m), 5.20 (1H, dt, J=8.1, 2.9 Hz), 4.57–4.51 (1H, m), 4.49–4.40 (1H, m), 4.27–4.20 (1H, m), 4.20 (1H, dd, J=2.2, 10.3 Hz), 4.06 (1H, dd, J=2.9, 10.3 Hz), 3.77 (3H, s), 1.04 (9H, s).

(4) (2S)-2-{(3-(Benzoyloxy)-azetidine-1-carbothioyl]amino}-3-hydroxypropionic acid methyl ester To a solution of (2S)-2-{[3-(benzoyloxy)-azetidine-1-carbothioyl]amino}-3-(t-butyldiphenylsilyloxy)propionic acid methyl ester (23.3 g, 40.0 mmol) (obtained as described in Reference Example 70(3)) in tetrahydrofuran (700 ml) was added a 1.0 M solution of tetra-n-butylammonium fluoride in tetrahydrofuran (48.4 g, 48.4 mmol) in an ice bath and the mixture was stirred overnight. After checking the completion of the reaction, the mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using toluene:acetonitrile (3:1) as the eluant to afford (2S)-2-{[3-(benzoyloxy)-azetidine-1-carbothioyl]amino}-3-hydroxy-propionic acid methyl ester (12.6 g, yield 92%) as a white solid.

$^1$H-NMR (400 MHz, CDCl$_3$): δ (ppm) 8.08–8.04 (2H, m), 7.64–7.59 (1H, m), 7.51–7.45 (2H, m), 6.00 (1H, d, J=7.3 Hz), 5.49–5.43 (1H, m), 5.25 (1H, dt, J=7.3, 3.7 Hz), 4.63–4.56 (2H, m), 4.32–4.24 (2H, m), 4.12–4.02 (2H, m), 3.82 (3H, s).

(5) 3-Benzoyloxy-1-[(4S)-4-methoxycarbonyl-1,3-oxazolin-2-yl]azetidine

To a solution of 2-chloro-3-ethylbenzoxazolium tetrafluoroborate (15.1 g, 55.9 mmol) in acetonitrile (380 ml) was added dropwise a solution of (2S)-2-{[3-(benzoyloxy)-azetidine-1-carbothioyl]amino}-3-hydroxypropionic acid methyl ester (obtained as described in Reference Example 70(4)) (12.6 g, 37.2 mmol) in acetonitrile (500 ml) in an ice bath under an atmosphere of nitrogen and the mixture was stirred for 1 hour. To the resulting mixture was added triethylamine (10.4 ml, 74.4 mmol) and the mixture was stirred for 1.5 hours. After checking the completion of the reaction, the mixture was partitioned between ethyl acetate and saturated aqueous sodium hydrogencarbonate solution and the organic layer was washed with saturated aqueous sodium chloride solution, dried over anhydrous sodium sulfate, filtered and concentrated under reduced pressure. The residue was purified by chromatography on a silica gel column using ethyl acetate and ethyl acetate:methanol (95:5) as the eluant to afford 3-benzoyloxy-1-[(4S)-(4-methoxycarbonyl-1,3-oxazolin-2-yl)azetidine (9.12 g, yield 81%) as a pale brown solid.

$^1$H-NMR (400 MHz, CDCl$_3$): δ (ppm) 8.08–8.04 (2H, m), 7.63–7.58 (1H, m), 7.49–7.44 (2H, m), 5.50–5.44 (1H, m), 4.69 (1H, dd, J=6.6, 9.5 Hz), 4.55 (1H, dd, J=6.6, 8.1 Hz), 4.51–4.44 (3H, m), 4.20–4.14 (2H, m), 3.78 (3H, s).

(6) 3-Benzoyloxy-1-[4-methoxycarbonyl-1,3-oxazol-2-yl]azetidine

To a solution of 3-benzoyloxy-1-(4-methoxycarbonyl-1,3-oxazolin-2-yl)azetidine (9.12 g, 30.0 mmol) (obtained as described in Reference Example 70(5)) in a mixture of toluene (450 ml) and methylene chloride (180 ml) was added manganese dioxide (63.8 g) and the mixture was heated under reflux for 5 hours. After checking the completion of the reaction, the mixture was filtered and the filtrate concentrated under reduced pressure. The residue was purified by chromatography on a silica gel column using toluene:acetonitrile=1:1 as the eluant to afford 3-benzoyloxy-1-(4-methoxycarbonyl-1,3-oxazol-2-yl)azetidine (5.24 g, yield 58%) as pale yellow crystals.

$^1$H-NMR (400 MHz, CDCl$_3$): δ (ppm) 8.08–8.04 (2H, m), 7.84 (1H, s), 7.63–7.58 (1H, m), 7.50–7.44 (2H, m), 5.60–5.53 (1H, m), 4.61 (1H, dd, J=5.9, 9.5 Hz), 4.31 (1H, dd, J=6.6, 9.5 Hz), 3.89 (3H, s).

(7) 3-Hydroxy-1-[4-methoxycarbonyl-1,3-oxazol-2-yl]azetidine

To a solution of 3-benzoyloxy-1-(4-methoxycarbonyl-1,3-oxazol-2-yl)azetidine (5.24 g, 17.3 mmol) (obtained as described in Reference Example 70(6)) in a mixture of methanol (260 ml) and methylene chloride (80 ml) was added a catalytic amount of sodium methoxide at room temperature and the mixture was stirred for 1 hour. After checking the completion of the reaction, the mixture was neutralized with 4 N hydrogen chloride gas in dioxane and concentrated under reduced pressure. The residue was purified by chromatography on a silica gel column using methylene chloride:methanol (95:5) as the eluant to afford 3-hydroxy-1-(4-methoxycarbonyl-1,3-oxazol-2-yl)azetidine (2.65 g, yield 77%) as pale brown crystals.

$^1$H-NMR (400 MHz, CDCl$_3$): δ (ppm) 7.81 (1H, s), 4.83–4.76 (1H, br s), 4.41 (2H, dd, J=6.6, 9.5 Hz), 4.06 (2H, dd, J=4.4, 9.5 Hz), 3.88 (3H, s), 2.39–2.30 (1H, br s).

(8) 3-t-Butyldiphenylsilyloxy-1-(4-methoxycarbonyl-1,3-oxazol-2-yl)azetidine

To a solution of 3-hydroxy-1-(4-methoxycarbonyl-1,3-oxazol-2-yl)azetidine (2.64 g, 13.4 mmol) (obtained as described in Reference Example 70(7)) in dimethylformamide (80 ml) were added t-butyldiphenylsilane (6.97 ml, 26.8 mmol) and imidazole (1.82 g, 26.8 mmol) in an ice bath and the mixture was stirred in an ice bath overnight. After checking the completion of the reaction, methanol was added to the reaction mixture and the mixture was stirred for 30 minutes. The resulting mixture was partitioned between ethyl acetate and 1 0% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (4:3→3:1) as the eluant to afford 3-t-butyldiphenylsilyloxy-1-(4-methoxycarbonyl-1,3-oxazol-2-yl)azetidine (4.95 g, yield 85%) as a pale yellow solid.

$^1$H-NMR (400 MHz, CDCl$_3$): δ (ppm) 7.78 (1H, s), 7.62–7.58 (4H, m), 7.48–7.36 (6H, m), 4.74–4.67 (1H, m), 4.15 (1H, dd, J=6.6, 9.5 Hz), 4.08 (1H, dd, J=5.1, 9.5 Hz), 3.87 (3H, s), 1.06 (9H, s).

(9) 3-t-Butyldiphenylsilyloxy-1-(4-hydroxymethyl-1,3-oxazol-2-yl]azetidine

To a solution of 3-t-butyldiphenylsilyloxy-1-(4-methoxycarbonyl-1,3-oxazol-2-yl)azetidine (4.95 g, 11.3 mmol) (obtained as described in Reference Example 70(8)) in anhydrous tetrahydrofuran (100 ml) was added dropwise a suspension of lithium aluminium hydride (1.29 g, 33.9 mmol) in anhydrous tetrahydrofuran (250 ml) in an ice bath under an atmosphere of nitrogen and the mixture was stirred in an ice bath for 5 minutes. After checking the completion of the reaction, magnesium sulfate decahydrate was gradually added to the reaction mixture in an ice bath. After termination of foaming, the resulting mixture was stirred at room temperature for 1 hour. Ethyl acetate was gradually added to the reaction mixture. The resulting mixture was partitioned between ethyl acetate and saturated aqueous sodium chloride solution. The organic layer was dried over anhydrous sodium sulfate, filtered and concentrated under reduced pressure. The residue was purified by chromatography on a silica gel column using toluene:acetonitrile (3:1) as the eluant to afford 3-t-butyldiphenylsilyloxy-1-(4-hydroxymethyl-1,3-oxazol-2-yl)azetidine (3.88 g, yield 84%) as a white solid.

$^1$H-NMR (400 MHz, CDCl$_3$): δ (ppm) 7.63–7.59 (4H, m), 7.47–7.36 (6H, m), 7.13 (1H, s), 4.73–4.66 (1H, m), 4.45 (2H, s), 4.11 (2H, dd, J=6.6, 8.8 Hz), 4.04 (2H, dd, J=5.1, 8.8 Hz), 2.21–2.15 (1H, br s), 1.06 (9H, s).

(10) 3-t-Butyldiphenylsilyloxy-1-(4-formyl-1,3-oxazol-2-yl)azetidine

To a solution of 3-t-butyldiphenylsilyloxy-1-(4-hydroxymethyl-1,3-oxazol-2-yl)azetidine (3.88 g, 9.50 mmol) (obtained as described in Reference Example 70(9)) in methylene chloride (190 ml) was added activated manganese dioxide (19.4 g) and the mixture was stirred at room temperature for 2 hours. After checking the completion of the reaction, the mixture was filtered and the filtrate was concentrated under reduced pressure. The residue was purified by chromatography on a silica gel column using n-hexane:ethyl acetate (3:1) as the eluant to afford 3-t-butyldiphenylsilyloxy-1-(4-formyl-1,3-oxazol-2-yl)azetidine (3.09 g, yield 80%) as pale yellow crystals.

$^1$H-NMR (400 MHz, CDCl$_3$): δ (ppm) 9.75 (1H, s), 7.80 (1H, s), 7.63–7.58 (4H, m), 7.48–7.37 (6H, m), 4.75–4.68 (1H, s), 4.16 (2H, dd, J=6.6, 9.5 Hz), 4.10 (2H, dd, J=5.1, 9.5 Hz), 1.06 (9H, s).

(11) 3-t-Butyldiphenylsilyloxy-1-(4-carboxyl-2-yl)azetidine

To a solution of 3-t-butyldiphenylsilyloxy-1-(4-formyl-1,3-oxazol-2-yl)azetidine (3.09 g, 7.60 mmol) (obtained as described in Reference Example 70(10)) in anhydrous methylene chloride (18 ml) were added t-butanol (93 ml) and a solution of 2 M 2-methyl-2-butene in tetrahydrofuran (5.70 ml, 11.4 mmol), followed by dropwise addition of a solution of sodium chlorite (1.72 g, 15.2 mmol) and sodium dihydrogenphosphate (1.82 g, 15.2 mmol) in water (18 ml) in an ice bath, and the mixture was stirred for 1 hour. After checking the completion of the reaction to the reaction mixture was added 1 M hydrochloric acid to a pH of from 2 to 3. The resulting mixture was extracted with ethyl acetate. The organic layer was separated, washed with saturated aqueous sodium chloride solution, dried over anhydrous sodium sulfate, filtered and concentrated under reduced pressure. The residue was purified by chromatography on a silica gel column using methylene chloride and methylene chloride (9:1) as the eluant to afford 3-t-butyldiphenylsilyloxy-1-(4-carboxyl-1,3-thiazol-2-yl) azetidine (1.90 g, yield 59%) as a brown solid.

Mass spectrum (FAB$^+$): m/z: 423 [M+H]$^+$.

REFERENCE EXAMPLE 71

3-Acetylthio-1-(4-azetidinocarbonyl-1,3-oxazol-2-yl)azetidine

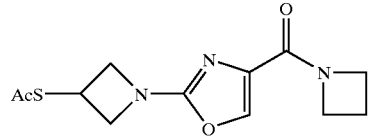

(1) 1-(4-Azetidinocarbonyl-1,3-oxazol-2-yl)-3-t-butyldiphenylsilyloxyazetidine

To a solution of 3-t-butyldiphenylsilyloxy-1-(4-methoxycarbonyl-1,3-oxazol-2-yl)azetidine (2.00 g, 4.58 mmol) in toluene (100 ml) was added a solution of 0.67 M azetidine-trimethylaluminium in benzene (13.7 ml) at room temperature under an atmosphere of nitrogen and the mixture was stirred in an oil bath (100° C.) for 5.5 hours. After checking the completion of the reaction, to the reaction mixture were added 10% aqueous acetic acid (100 ml) and ethyl acetate (200 ml) in an ice bath and the mixture was stirred at room temperature for 1 hour. The reaction mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:1) and ethyl acetate as the eluant to afford 1-(4-azetidinocarbonyl-1,3-oxazol-2-yl)-3-t-butyldiphenylsilyloxyazetidine (875 mg, yield 41%) as a pale brown solid.

$^1$H-NMR (400 MHz, CDCl$_3$): δ (ppm) 7.67 (1H, s), 7.65–7.57 (4H, m), 7.48–7.37 (6H, m), 4.72–4.66 (1H, m), 4.54–4.47 (2H, m), 4.18–4.11 (2H, m), 4.10 (2H, dd, J=6.6, 8.8 Hz), 4.04 (2H, dd, J=5.1, 8.8 Hz), 2.30 (2H, quintet, J=7.7 Hz), 1.06 (9H, s).

(2) 1-(4-Azetidinocarbonyl-1,3-oxazol-2-yl)-3-hydroxyazetidine

To a solution of 1-(4-azetidinocarbonyl-1,3-oxazol-2-yl)-3-t-butyldiphenylsilyloxyazetidine (870 mg, 1.88 mmol) (obtained as described in Reference Example 71(1)) in anhydrous tetrahydrofuran (44 ml) was added a solution of 1.0 M tetra-n-butylammonium fluoride in tetrahydrofuran (2.26 ml, 2.26 mmol) in an ice bath and the mixture was stirred in an ice bath for 1 hour. After checking the completion of the reaction, the mixture was concentrated under reduced pressure. The residue was purified by chromatography on a silica gel column using ethyl acetate:methanol (9:1) as the eluant to afford 1-(4-azetidinocarbonyl-1,3-oxazol-2-yl)-3-hydroxyazetidine (396 mg, yield 94%) as white crystals.

$^1$H-NMR (400 MHz, CDCl$_3$): δ (ppm) 7.70 (1H, s), 4.81–4.74 (1H, m), 4.53 (2H, dd, J=6.8, 7.8 Hz), 4.34 (2H, dd, J=6.8, 9.8 Hz), 4.16 (2H, dd, J=6.8, 7.8 Hz), 3.99 (2H, dd, J=4.9, 8.8 Hz), 2.34 (1H, d, J=7.8 Hz), 2.31 (2H, quintet, J=7.8 Hz).

(3) 1-(4-Azetidinocarbonyl-1,3-oxazol-2-yl)-3-methanesulfonyloxyazetidine

To a solution of 1-(4-azetidinocarbonyl-1,3-oxazol-2-yl)-3-hydroxyazetidine (390 mg, 1.75 mmol) (obtained as described in Reference Example 71(2)) in methylene chloride (20 ml) were added methanesulfonyl chloride (406 μl, 5.24 mmol) and triethylamine (734 μl, 5.24 mmol) in an ice bath and the mixture was stirred for 10 minutes and then at room temperature for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium chloride, filtered and concentrated under reduced pressure. To the residue were added ethyl acetate and diisopropyl ether to give a solid and the solid was collected by filtration, washed with diisopropyl ether and dried in vacuo to afford 1-(4-azetidinocarbonyl-1,3-oxazol-2-yl)-3-methanesulfonyloxyazetidine (449 mg, yield 85%) as a pale yellow solid.

$^1$H-NMR (400 MHz, CDCl$_3$): δ (ppm) 7.74 (1H, m), 5.40–5.34 (1H, m), 4.55–4.49 (2H, br t, J=7.3 Hz), 4.47 (2H, ddd, J=11.0, 6.6, 0.7 Hz), 4.29 (2H, dd, J=11.0, 4.4 Hz), 4.19–4.12 (2H, br t, J=7.3 Hz), 3.09 (3H, s), 2.32 (2H, quintet, J=7.3 Hz).

(4) 3-Acetylthio-1-(4-azetidinocarbonyl-1,3-oxazol-2-yl)azetidine

To a solution of 1-(4-azetidinocarbonyl-1,3-oxazol-2-yl)-3-methanesulfonyloxyazetidine (470 mg, 1.56 mmol) (obtained as described in Reference Example 71(3)) in dimethylformamide (25 ml) was added potassium thioacetate (1.07 g, 9.36 mmol) at room temperature and the mixture was stirred in an oil bath (80° C.) for 8.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate and ethyl acetate:methanol (95:5) as the eluant to afford 3-acetylthio-1-(4-azetidinocarbonyl-1,3-oxazol-2-yl)azetidine (330 mg, yield 75%) as a pale brown solid.

$^1$H-NMR (400 MHz, CDCl$_3$): δ (ppm) 7.71 (1H, s), 4.54 (2H, t, J=8.8 Hz), 4.55–4.49 (2H, br t, J=8.1 Hz), 4.43–4.35 (1H, m), 4.18–4.12 (2H, br t, J=8.1 Hz), 4.00 (2H, dd, J=8.8, 5.9 Hz), 2.35 (3H, s), 2.36–2.26 (2H, m).

REFERENCE EXAMPLE 72

3-Acetylthio-1-(4-morpholinocarbonyl-1,3-oxazol-2-yl)azetidine

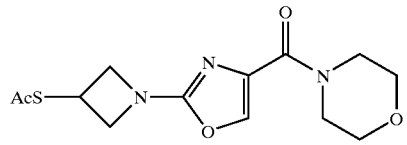

(1) 3-t-Butyldiphenylsilyloxy-1-(4-morpholinocarbonyl-1,3-oxazol-2-yl)azetidine

To a solution of 3-t-butyldiphenylsilyloxy-1-(4-methoxycarbonyl-1,3-oxazol-2-yl)azetidine (1.00 g, 2.29 mmol) (obtained as described in Reference Example 70(8)) in toluene (50 ml) was added a solution of 0.67 M morpholine-trimethylaluminium in toluene (6.87 ml) at room temperature under an atmosphere of nitrogen and the mixture was stirred in an oil bath (80° C.) for 4 hours. After checking the completion of the reaction, to the reaction mixture were added 10% aqueous acetic acid (50 ml) and ethyl acetate (100 ml) in an ice bath and the mixture was stirred at room temperature for 1 hour. To the reaction mixture was added ethyl acetate. The mixture was partitioned between ethyl acetate and water. The organic layer was washed with saturated aqueous sodium hydrogencarbonate and saturated aqueous sodium chloride solution, dried over anhydrous sodium sulfate, filtered and concentrated under reduced pressure. The residue was purified by chromatography on a silica gel column using n-hexane:ethyl acetate (1:2) as the eluant to afford 3-t-butyldiphenylsilyloxy-1-(4-morpholinocarbonyl-1,3-oxazol-2-yl)azetidine (400 mg, yield 36%) as a pale brown solid.

$^1$H-NMR (400 MHz, CDCl$_3$): δ (ppm) 7.68 (1H, s), 7.62–7.59 (4H, m), 7.48–7.37 (6H, m), 4.73–4.67 (1H, m), 4.15–4.09 (2H, m), 4.05 (2H, dd, J=8.8, 5.1 Hz), 3.75–3.65 (8H, br s), 1.06 (9H, s).

(2) 3-Hydroxy-1-(4-morpholinocarbonyl-1,3-oxazol-2-yl)azetidine

To a solution of 3-t-butyldiphenylsilyloxy-1-(4-morpholinocarbonyl-1,3-oxazol-2-yl)azetidine (730 mg, 1.48 mmol) (obtained as described in Reference Example 72(1)) in anhydrous tetrahydrofuran (37 ml) was added a solution of 1.0 M tetra-n-butylammonium fluoride in tetrahydrofuran (1.78 ml, 1.78 mmol) in an ice bath and the mixture was stirred in an ice bath for 1.5 hours. After checking the completion of the reaction, the reaction mixture was concentrated under reduced pressure. The residue was purified by chromatography on a silica gel column using ethyl acetate:methanol (95:5→9:1) as the eluant to afford 3-hydroxy-1-(4-morpholinocarbonyl-1,3-oxazol-2-yl)azetidine (377 mg, yield 100%) as white crystals.

$^1$H-NMR (400 MHz, CDCl$_3$): δ (ppm) 7.71 (1H, s), 4.82–4.74 (1H, m), 4.35 (2H, dd, J=9.5, 6.6 Hz), 4.00 (2H, dd, J=9.5, 4.4 Hz), 3.76–3.65 (8H, m), 2.42–2.30 (1H, br s).

(3) 3-Methanesulfonyloxy-1-(4-morpholinocarbonyl-1,3-oxazol-2-yl)azetidine

To a solution of 3-hydroxy-1-(4-morpholinocarbonyl-1,3-oxazol-2-yl)azetidine (370 mg, 1.48 mmol) (obtained as described in Reference Example 72(2)) in methylene chloride (19 ml) were added methanesulfonyl chloride (344 μl, 4.44 mmol) and triethylamine (622 μl, 4.44 mmol) in an ice bath and the mixture was stirred for 10 minutes and then at room temperature for 1 hour. After checking the completion of the reaction, the mixture was partitioned between ethyl acetate and saturated aqueous sodium hydrogencarbonate solution. The organic layer was washed with saturated aqueous sodium chloride solution, dried over anhydrous sodium chloride, filtered and concentrated under reduced pressure. The residue was purified by chromatography on a silica gel column using ethyl acetate:methanol (93:7) as the eluant to afford 3-methanesulfonyloxy-1-(4-morpholinocarbonyl-1,3-oxazol-2-yl)azetidine (404 mg, yield 100%) as pale yellow crystals.

$^1$H-NMR (400 MHz, CDCl$_3$): δ (ppm) 7.75 (1H, s), 5.41–5.34 (1H, m), 4.48 (2H, ddd, J=9.5, 6.6, 1.5 Hz), 4.30 (2H, ddd, J=9.5, 4.0, 1.5 Hz), 3.78–3.65 (8H, m), 3.10 (3H, s).

(4) 3-Acetylthio-1-(4-morpholinocarbonyl-1,3-oxazol-2-yl)azetidine

To a solution of 3-methanesulfonyloxy-1-(4-morpholinocarbonyl-1,3-oxazol-2-yl)azetidine (400 mg, 1.21 mmol) (obtained as described in Reference Example 72(3)) in dimethylformamide (20 ml) was added potassium thioacetate (827 mg, 7.24 mmol) at room temperature and was stirred in an oil bath (80° C.) for 6 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate→ethyl acetate:methanol (95:5) as the eluant to afford 3-acetylthio-1-(4-morpholinocarbonyl-1,3-oxazol-2-yl)azetidine (266 mg, yield 71%) as a pale brown solid.

$^1$H-NMR (400 MHz, CDCl$_3$): δ (ppm) 7.72 (1H, s), 4.55 (2H, t, J=8.4 Hz), 4.43–4.36 (1H, m), 4.02 (2H, dd, J=9.5, 5.9 Hz), 3.76–3.66 (8H, br s), 2.36 (3H, s).

REFERENCE EXAMPLE 73

3-Acetylthio-1-[4-(3-methoxyazetidine-1-carbonyl)-1,3-oxazol-2-yl]azetidine

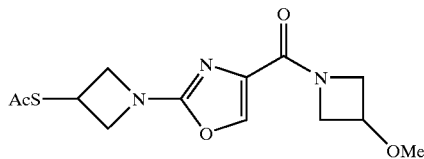

(1) 3-t-Butyldiphenylsilyloxy-1-[4-(3-methoxyazetidine-1-carbonyl)-1,3-oxazol-2-yl]azetidine To a solution of 3-t-butyldiphenylsilyloxy-1-(4-methoxycarbonyl-1,3-oxazol-2-yl)azetidine (1.57 g, 3.60 mmol) (obtained as described in Reference Example 70(8)) in toluene (80 ml) was added a solution of 0.67 M 3-methoxyazetidine (obtained as described in Reference Example 31(2))-trimethylaluminium in toluene (10.8 ml) at room temperature under an atmosphere of nitrogen and the mixture was stirred in an oil bath (60° C.) for 30 minutes. After checking the completion of the reaction, to the reaction mixture were added 10% aqueous acetic acid (100 ml) and ethyl acetate (200 ml) in an ice bath and the mixture was stirred at room temperature for 1 hour. To the reaction mixture was added ethyl acetate. The mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate as the eluant to afford 3-t-butyldiphenylsilyloxy-1-[4-(3-methoxyazetidine-1-carbonyl)-1,3-oxazol-2-yl]azetidine (1.50 g, yield 90%) as a pale brown solid.

$^1$H-NMR (400 MHz, CDCl$_3$): δ (ppm) 7.69 (1H, s), 7.63–7.59 (4H, m), 7.48–7.37 (6H, m), 4.73–4.76 (2H, m), 4.37–4.19 (3H, m), 4.10 (2H, dd, J=8.8, 6.6 Hz), 4.03 (2H, dd, J=8.8, 5.1 Hz), 4.02–3.98 (1H, m), 3.32 (3H, s), 1.06 (9H, s).

(2) 3-Hydroxy-1-[4-(3-methoxyazetidine-1-carbonyl)-1,3-oxazol-2-yl]azetidine

To a solution of 3-t-butyldiphenylsilyloxy-1-[4-(3-methoxyazetidine-1-carbonyl)-1,3-oxazol-2-yl]azetidine (1.49 g, 3.23 mmol) (obtained as described in Reference Example 72(1)) in anhydrous tetrahydrofuran (75 ml) was added a solution of 1.0 M tetra-n-butylammonium fluoride in tetrahydrofuran (3.88 ml, 3.88 mmol) in an ice bath and the mixture was stirred in an ice bath for 1 hour. After checking the completion of the reaction, the mixture was concentrated under reduced pressure. The residue was purified by chromatography on a silica gel column using ethyl acetate:methanol (95:5→9:1) as the eluant to afford 3-hydroxy-1-[4-(3-methoxyazetidine-1-carbonyl)-1,3-oxazol-2-yl]azetidine (486 mg, yield 60%) as a white solid.

$^1$H-NMR (400 MHz, CDCl$_3$): δ (ppm) 7.71 (1H, s), 4.81–4.66 (2H, m), 4.34 (2H, dd, J=9.5, 6.6 Hz), 4.39–4.20 (3H, m), 4.04–3.98 (1H, m), 3.99 (2H, dd, J=9.6, 4.4 Hz), 3.32 (3H, s), 2.45 (1H, d, J=6.6 Hz).

(3) 3-Methanesulfonyloxy-1-[4-(3-methoxyazetidine-1-carbonyl)-1,3-oxazol-2-yl]azetidine To a solution of 3-hydroxy-1-[4-(3-methoxyazetidine-1-carbonyl)-1,3-oxazol-2-yl]azetidine (480 mg, 1.89 mmol) (obtained as described in Reference Example 73(2)) in methylene chloride (24 ml) were added methanesulfonyl chloride (439 μl, 5.67 mmol) and triethylamine (795 ml, 5.67 mmol) in an ice bath and the mixture was stirred for 10 minutes and then at room temperature for 30 minutes. After checking the completion of the reaction, the mixture was partitioned between ethyl acetate and saturated aqueous sodium hydrogencarbonate solution. The organic layer was washed with saturated aqueous sodium chloride solution, dried over anhydrous sodium chloride, filtered and concentrated under reduced pressure. To the residue were added ethyl acetate and diisopropyl ether to give a solid and the solid was collected by filtration, washed with diisopropyl ether to afford 3-methanesulfonyloxy-1-[4-(3-methoxyazetidine-1-carbonyl)-1,3-oxazol-2-yl]azetidine (586 mg, yield 94%) as a pale yellow solid.

$^1$H-NMR (400 MHz, CDCl$_3$): δ (ppm) 7.76 (1H, s), 5.41–5.34 (1H, m), 4.72–4.63 (1H, m), 4.29 (2H, dd, J=11.0, 4.4 Hz), 4.38–4.20 (5H, m), 4.03–3.97 (1H, m), 3.32 (3H, s), 3.10 (3H, s).

(4) 3-Acetylthio-1-[4-(3-methoxy-azetidine-1-carbonyl)-1,3-oxazol-2-yl]azetidine To a solution of 3-methanesulfonyloxy-1-[4-(3-methoxyazetidine-1-carbonyl)-1,3-oxazol-2-yl]azetidine (580 mg, 1.75 mmol) (obtained as described in Reference Example 73(3)) in dimethylformamide (30 ml) was added potassium thioacetate (1.20 g, 10.5 mmol) at room temperature and the mixture was stirred in an oil bath (80° C.) for 6 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using ethyl acetate→ethyl acetate:methanol (97:3) as the eluant to afford 3-acetylthio-1-[4-(3-methoxyazetidine-1-carbonyl)-1,3-oxazol-2-yl]azetidine (336 mg, yield 62%) as a pale brown solid.

¹H-NMR (400 MHz, CDCl₃): δ (ppm) 7.73 (1H, s), 4.72–4.65 (1H, m), 4.54 (2H, t, J=8.8 Hz), 4.43–4.19 (4H, m), 4.03–3.97 (1H, m), 4.01 (2H, dd, J=8.8, 5.1 Hz), 3.31 (3H, s), 2.35 (3H, s).

REFERENCE EXAMPLE 74

3-Acetylthio-1-[4-(3-t-butyldiphenylsilyloxyazetidine-1-carbonyl)-1,3-oxazol-2-yl]azetidine

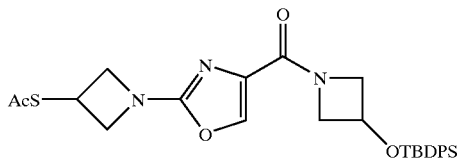

(1) 1-[4-(3-t-butyldiphenylsilyloxyazetidine-1-carbonyl)-1,3-oxazol-2-yl]-3-hydroxyazetidine To a solution of 3-hydroxy-1-(4-methoxycarbonyl-1,3-oxazol-2-yl)azetidine (500 mg, 2.52 mmol) (obtained as described in Reference Example 70(7)) in toluene (25 ml) was added a solution of 0.67 M 3-t-butyldiphenylsilyloxyazetidine (obtained as described in Reference Example 42(2))-trimethylaluminium in toluene (11.3 ml) at room temperature under an atmosphere of nitrogen and the mixture was stirred in an oil bath (80° C.) for 15 minutes. After checking the completion of the reaction, to the reaction mixture were added 10% aqueous acetic acid (20 ml) and ethyl acetate (50 ml) in an ice bath and the mixture was stirred at room temperature for 0.5 hours. To the reaction mixture was added ethyl acetate. The mixture was partitioned between ethyl acetate and water. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using methylene chloride:methanol (95:5→9:1) as the eluant to afford 1-[4-(3-t-butyldiphenylsilyloxyazetidine-1-carbonyl)-1,3-oxazol-2-yl]-3-hydroxyazetidine (1.24 g, yield 100%) as a pale brown solid.

¹H-NMR (400 MHz, CDCl₃): δ (ppm) 7.68 (1H, s), 7.61 (4H, dd, J=8.1, 1.5 Hz), 7.47–7.36 (6H, m), 4.81–4.74 (1H, m), 4.65–4.52 (2H, m), 4.40–4.36 (1H, m), 4.33 (2H, dd, J=9.5, 6.6 Hz), 4.18–4.11 (1H, m), 4.06–3.97 (1H, m), 3.98 (2H, dd, J=9.5, 5.1 Hz), 1.06 (9H, s).

(2) 1-[4-(3-t-Butyldiphenylsilyloxyazetidine-1-carbonyl)-1,3-oxazol-2-yl]-3-methanesulfonyloxyazetidine To a solution of 1-[4-(3-t-butyldiphenylsilyloxyazetidine-1-carbonyl)-1,3-oxazol-2-yl]-3-hydroxyazetidine (1.68 g, 3.53 mmol) (obtained as described in Reference Example 74(1)) in methylene chloride (84 ml) were added methanesulfonyl chloride (820 μl, 10.6 mmol) and triethylamine (1.49 ml, 10.6 mmol) in an ice bath and the mixture was stirred for 10 minutes and then at room temperature for 0.5 hour. After checking the completion of the reaction, the mixture was partitioned between ethyl acetate and saturated aqueous sodium hydrogencarbonate. The organic layer was washed with saturated aqueous sodium chloride solution, dried over anhydrous sodium sulfate, filtered and concentrated under reduced pressure. The residue was purified by chromatography on a silica gel column using methylene chloride:ethyl acetate (1:1) as the eluant to afford 1-[4-(3-t-butyldiphenylsilyloxyazetidine-1-carbonyl)-1,3-oxazol-2-yl]-3-methanesulfonyloxyazetidine (1.56 g, yield 80%) as a pale yellow solid.

¹H-NMR (400 MHz, CDCl₃): δ (ppm) 7.72 (1H, s), 7.61 (4H, d, J=6.8 Hz), 7.45 (2H, t, J=6.8 Hz), 7.39 (4H, t, J=6.8 Hz), 5.40–5.34 (1H, m), 4.64–4.59 (1H, m), 4.59–4.52 (1H, m), 4.45 (2H, dd, J=10.7, 5.9 Hz), 4.39–4.32 (1H, m), 4.28 (2H, dd, J=10.7, 4.9 Hz), 4.18–4.12 (1H, m), 4.05–4.00 (1H, m), 3.10 (3H, s), 1.07 (9H, s).

(3) 3-Acetylthio-1-[4-(3-t-butyldiphenylsilyloxyazetidine-1-carbonyl)-1,3-oxazol-2-yl]azetidine To a solution of 1-[4-(3-t-butyldiphenylsilyloxyazetidine-1-carbonyl)-1,3-oxazol-2-yl]-3-methanesulfonyloxyazetidine (1.56 g, 2.81 mmol) (obtained as described in Reference Example 74(2)) in dimethylformamide (80 ml) was added potassium thioacetate (1.92 g, 16.8 mmol) at room temperature and the mixture was stirred in an oil bath (80° C.) for 7.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (2:1→1:1) as the eluant to afford 3-acetylthio-1-[4-(3-t-butyldiphenylsilyloxyazetidine-1-carbonyl)-1,3-oxazol-2-yl]azetidine (863 mg, yield 57%) as a pale brown solid.

¹H-NMR (400 MHz, CDCl₃): δ (ppm) 7.69 (1H, s), 7.63–7.60 (4H, m), 7.47–7.36 (6H, m), 4.64–4.54 (2H, m), 4.53 (2H, t, J=8.8 Hz), 4.43–4.32 (2H, m), 4.18–4.13 (1H, m), 4.06–4.00 (1H, m), 4.00 (2H, dd, J=8.8, 5.9 Hz), 2.36 (3H, s), 1.06 (9H, s).

REFERENCE EXAMPLE 75

3-Acetylthio-1-{4-[3-(p-nitrobenzyloxycarbonylamino)azetidine-1-carbonyl]-1,3-oxazol-2-yl}azetidine

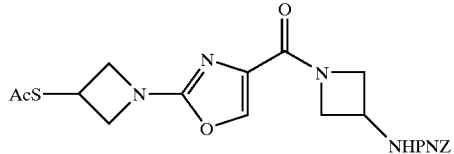

(1) 3-t-Butyldiphenylsilyloxy-1-{4-[3-(p-nitrobenzyloxycarbonylamino)azetidine-1-carbonyl]-1,3-thiazol-2-yl}azetidine To a solution of 3-(p-nitrobenzyloxycarbonylamino) azetidine hydrochloride (1.39 g, 4.83 mmol) (obtained as described in Reference Example 57(4)) and 3-t-butyldiphenylsilyloxy-1-(4-carboxyl-1,3-oxazol-2-yl) azetidine (1.70 g, 4.02 mmol) (obtained as described in Reference Example 70(11)) in dimethylformamide (85 ml) were added diethylphosphoryl cyanide (801 μl, 4.83 mmol) and triethylamine (1.70 ml, 12.1 mmol) in an ice bath and the mixture was stirred at room temperature overnight. After checking the completion of the reaction, the mixture was partitioned between ethyl acetate and saturated aqueous sodium hydrogencarbonate. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:2)→ethyl acetate as the eluant to afford 3-t-butyldiphenylsilyloxy-1-{4-[3-(p-nitrobenzyloxycarbonylamino)azetidine-1-carbonyl]-1,3-thiazol-2-yl}azetidine (596 mg, yield 23%) as a pale yellow solid.

$^1$H-NMR (400 MHz, CDCl$_3$): δ (ppm) 8.23 (2H, d, J=8.8 Hz), 7.71 (1H, s), 7.61 (4H, d, J=8.8 Hz), 7.53–7.49 (2H, m), 7.47–7.38 (6H, m), 5.30–5.26 (1H, m), 5.21 (2H, s), 4.89–4.80 (1H, m), 4.72–4.66 (1H, m), 4.59–4.51 (1H, m), 4.51–4.42 (1H, m), 4.37–4.30 (1H, m), 4.12–4.06 (2H, m), 4.02 (2H, dd, J=8.8, 4.9 Hz), 3.97–3.90 (1H, m), 1.06 (9H, s).

(2) 3-Hydroxy-1-{4-[3-(p-nitrobenzyloxycarbonylamino)azetidine-1-carbonyl]-1,3-thiazol-2-yl}azetidine To a solution of 3-t-butyldiphenylsilyloxy-1-{4-[3-(p-nitrobenzyloxycarbonylamino)-azetidine-1-carbonyl]-1,3-thiazol-2-yl}azetidine (640 mg, 0.976 mmol) (obtained as described in Reference Example 75(1)) in anhydrous tetrahydrofuran (32 ml) was added a solution of acetic acid (67 μl, 1.17 mmol) and 1.0 M tetra-n-butylammonium fluoride in tetrahydrofuran (1.17 ml, 1.17 mmol) in an ice bath and the mixture was stirred in an ice bath for 1.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using methylene chloride:methanol (95:5→9:1) as the eluant to afford 3-hydroxy-1-{4-[3-(p-nitrobenzyloxycarbonylamino)azetidine-1-carbonyl]-1,3-thiazol-2-yl}azetidine (360 mg, yield 88%) as a white solid.

$^1$H-NMR (400 MHz, CDCl$_3$): δ (ppm) 8.23 (2H, d, J=8.8 Hz), 7.73 (1H, s), 7.51 (2H, d, J=8.8 Hz), 5.46–5.40 (1H, m), 5.21 (2H, s), 4.89–4.74 (2H, m), 4.60–4.40 (2H, m), 4.39–4.31 (1H, m), 4.33 (2H, dd, J=9.5, 6.6 Hz), 3.98 (2H, dd, J=9.5, 5.1 Hz), 3.96–3.90 (1H, m).

(3) 3-Methanesulfonyloxy-1-{4-[3-(p-nitrobenzyloxycarbonylamino)azetidine-1-carbonyl]-1,3-thiazol-2-yl}azetidine To a solution of 3-hydroxy-1-{4-[3-(p-nitrobenzyloxycarbonylamino)azetidine-1-carbonyl]-1,3-thiazol-2-yl}azetidine (360 mg, 0.863 mmol) (obtained as described in Reference Example 75(2)) in methylene chloride (18 ml) were added methanesulfonyl chloride (200 μl, 2.59 mmol) and triethylamine (363 μl, 2.59 mmol) in an ice bath and the mixture was stirred for 10 minutes and then at room temperature for 2 hours. After checking the completion of the reaction, the mixture was partitioned between ethyl acetate and saturated aqueous sodium hydrogencarbonate. The organic layer was washed with saturated aqueous sodium chloride solution, dried over anhydrous sodium sulfate, filtered and concentrated under reduced pressure. The residue was purified by chromatography on a silica gel column using methylene chloride→methylene chloride:methanol (95:5) as the eluant to afford 3-methanesulfonyloxy-1-{4-[3-(p-nitrobenzyloxycarbonylamino)-azetidine-1-carbonyl]-1,3-thiazol-2-yl}azetidine (390 mg, yield 91%) as a pale yellow solid.

$^1$H-NMR (400 MHz, CDCl$_3$): δ (ppm) 8.23 (2H, d, J=8.8 Hz), 7.77 (1H, s), 7.51 (2H, d, J=8.8 Hz), 5.40–5.34 (1H, m), 5.11–5.27 (1H, m), 5.21 (2H, s), 4.90–4.81 (1H, m), 4.60–4.53 (1H, m), 4.45 (2H, dd, J=10.3, 6.6 Hz), 4.39–4.30 (1H, m), 4.27 (2H, dd, J=10.3, 4.4 Hz), 3.99–3.92 (1H, m), 3.10 (3H, s).

(4) 3-Acetylthio-1-{4-[3-(p-nitrobenzyloxycarbonylamino)azetidine-1-carbonyl]-1,3-thiazol-2-yl}azetidine To a solution of 3-methanesulfonyloxy-1-{4-[3-(p-nitrobenzyloxycarbonylamino)azetidine-1-carbonyl]-1,3-thiazol-2-yl}azetidine (390 mg, 0.787 mmol) (obtained as described in Reference Example 75(3)) in dimethylformamide (20 ml) was added potassium thioacetate (539 mg, 4.72 mmol) at room temperature and the mixture was stirred in an oil bath (80° C.) for 10.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:3)→ethyl acetate as the eluant to afford 3-acetylthio-1-{4-[3-(p-nitrobenzyloxycarbonylamino)azetidine-1-carbonyl]-1,3-thiazol-2-yl}azetidine (195 mg, yield 52%) as a pale brown solid.

$^1$H-NMR (400 MHz, CDCl$_3$): δ (ppm) 8.24 (2H, d, J=8.8 Hz), 7.75 (1H, s), 7.51 (2H, d, J=8.8 Hz), 5.16–5.10 (1H, br d, J=5.9 Hz), 5.21 (2H, s), 4.89–4.80 (1H, m), 4.60–4.10 (4H, m), 4.53 (2H, t, J=8.8 Hz), 3.99 (2H, dd, J=9.5, 5.9 Hz), 3.98–3.91 (1H, m), 2.36 (3H, s).

REFERENCE EXAMPLE 76

3-Acetylthio-1-{4-[(3S)-1-(p-nitrobenzyloxycarbonyl)-pyrrolidin-3-ylcarbamoyl]-1,3-oxazol-2-yl}azetidine

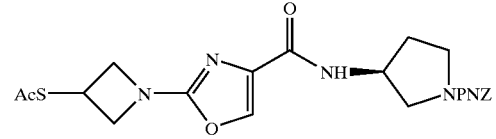

(1) 3-t-Butyldiphenylsilyloxy-1-{4-[(3S)-1-(p-nitrobenzyloxycarbonyl)-pyrrolidin-3-ylcarbamoyl]-1,3-oxazol-2-yl}azetidine To a solution of (3S)-3-amino-1-p-nitrobenzyloxycarbonylpyrrolidine (905 mg, 3.41 mmol) (obtained as described in Reference Example 52(4)) and 3-t-butyldiphenylsilyloxy-1-(4-carboxyl-1,3-oxazol-2-yl)azetidine (1.20 g, 2.84 mmol) (obtained as described in Reference Example 70(11)) in dimethylformamide (36 ml) were added diethylphosphoryl cyanide (556 μl, 3.41 mmol) and triethylamine (478 μl, 3.41 mmol) in an ice bath under an atmosphere of nitrogen and the mixture was stirred at room temperature overnight. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:2→1:3) as the eluant to afford 3-t-butyldiphenylsilyloxy-1-{4-[(3S)-1-(p- nitrobenzyloxycarbonyl)-pyrrolidin-3-ylcarbamoyl]-1,3-oxazol-2-yl}azetidine (936 mg, yield 49%) as a pale yellow solid.

¹H-NMR (400 MHz, CDCl₃): δ (ppm) 8.22 (2H, m), 7.72 (1H, s), 7.63–7.58 (4H, m), 7.53 (2H, m), 7.48–7.37 (6H, m), 6.85–6.80 (1H, br t, J=8.1 Hz), 5.24 (2H, d, J=8.1 Hz), 4.75–4.67 (1H, m), 4.65–4.58 (1H, m), 4.16–4.09 (2H, m), 4.06,(2H, dd, J=8.8, 5.1 Hz), 3.83–3.75 (1H, m), 3.64–3.46 (2H, m), 3.38 (1H, dd, J=11.0, 4.4 Hz), 2.30–2.20 (1H, m), 2.04–1.90 (1H, m), 1.06 (9H, s).

(2) 3-Hydroxy-1-{4-[(3S)-1-(p-nitrobenzyloxycarbonyl)pyrrolidin-3-ylcarbamoyl]-1,3-oxazol-2-yl}azetidine To a solution of 3-t-butyldiphenylsilyloxy-1-{4-[(3S)-1-(p-nitrobenzyloxycarbonyl)pyrrolidin-3-ylcarbamoyl]-1,3-oxazol-2-yl)azetidine (1.10 g, 1.64 mmol) (obtained as described in Reference Example 76(1)) in anhydrous tetrahydrofuran (55 ml) was added a solution of acetic acid (113 μl, 1.97 mmol) and 1.0 M tetra-n-butylammonium fluoride in tetrahydrofuran (1.97 ml, 1.97 mmol) in an ice bath and the mixture was stirred in an ice bath overnight. After checking the completion of the reaction, the reaction mixture was concentrated under reduced pressure. The residue was purified by chromatography on a silica gel column using ethyl acetate→ethyl acetate:methanol (95:5) as the eluant to afford 3-hydroxy-1-{4-t(3S)-1-(p-nitrobenzyloxycarbonyl)pyrrolidin-3-ylcarbamoyl]-1,3-oxazol-2-yl}azetidine (687 mg, yield 97%) as a white solid.

¹H-NMR (400 MHz, CDCl₃): δ (ppm) 8.22 (2H, m), 7.75 (1H, s), 7.52 (2H, m), 6.89–6.82 (1H, m), 5.27–5.20 (2H, m), 4.84–4.77 (1H, m), 4.66–4.59 (1H, m), 4.36 (2H, dd, J=8.8, 7.3 Hz), 4.01 (2H, dd, J=8.8, 5.2 Hz), 3.82–3.74 (1H, m), 3.67–3.52 (3H, m), 3.45–3.39 (1H, m), 2.30–2.20 (1H, m), 2.03–1.93 (1H, m).

(3) 3-Methanesulfonyloxy-1-{4-[(3S)-1-(p-nitrobenzyloxycarbonyl)pyrrolidin-3-ylcarbamoyl]-1,3-oxazol-2-yl}azetidine To a solution of 3-hydroxy-1-{4-[(3S)-1-(p-nitrobenzyloxycarbonyl)pyrrolidin-3-ylcarbamoyl]-1,3-oxazol-2-yl}azetidine (680 mg, 1.58 mmol) (obtained as described in Reference Example 76(2)) in methylene chloride (34 ml) were added methanesulfonyl chloride (366 μl, 4.73 mmol) and triethylamine (663 μl, 4.73 mmol) in an ice bath and the mixture was stirred for 10 minutes and at room temperature for 2 hours. After checking the completion of the reaction, the mixture was partitioned between ethyl acetate and saturated aqueous sodium hydrogencarbonate. The organic layer was washed with saturated aqueous sodium chloride solution, dried over anhydrous sodium sulfate, filtered and concentrated under reduced pressure. The residue was purified by chromatography on a silica gel column using ethyl acetate→ethyl acetate:methanol (96:4) as the eluant to afford 3-methanesulfonyloxy-1-{4-[(3S)-1-(p-nitrobenzyloxycarbonyl)pyrrolidin-3-ylcarbamoyl]-1,3-oxazol-2-yl}azetidine (760 mg, yield 95%) as a pale yellow solid.

¹H-NMR (400 MHz, CDCl₃): δ (ppm) 8.22 (2H, m), 7.78 (1H, s), 7.52 (2H, m), 6.85–6.80 (1H, m), 5.42–5.37 (1H, m), 5.24 (2H, d, J=8.1 Hz), 4.66–4.58 (1H, m), 4.49 (2H, dd, J=10.3, 6.6 Hz), 4.31 (2H, dd, J=10.3, 4.4 Hz), 3.82–3.74 (1H, m), 3.64–3.75 (2H, m), 3.44–3.38 (1H, m), 3.11 (3H, s), 2.30–2.20 (1H, m), 2.04–1.96 (1H, m).

(4) 3-Acetylthio-1-{4-[(3S)-1-(p-nitrobenzyloxycarbonyl)pyrrolidin-3-ylcarbamoyl]-1,3-oxazol-2-yl}azetidine To a solution of 3-methanesulfonyloxy-1-{4-[(3S)-1-(p-nitrobenzyloxycarbonyl)pyrrolidin-3-ylcarbamoyl]-1,3-oxazol-2-yl}azetidine (760 mg, 1.49 mmol) (obtained as described in Reference Example 76(3)) in dimethylformamide (38 ml) was added potassium thioacetate (1.02 g, 8.95 mmol) at room temperature and was stirred in an oil bath (80° C.) for 10.5 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane: ethyl acetate (1:6)→ethyl acetate as the eluant to afford 3-acetylthio-1-{4-[(3S)-1-(p-nitrobenzyloxycarbonyl)pyrrolidin-3-ylcarbamoyl]-1,3-oxazol-2-yl}azetidine (533 mg, yield 73%) as a pale brown solid.

¹H-NMR (400 MHz, CDCl₃): δ (ppm) 8.22 (2H, m), 7.76 (1H, s), 7.52 (2H, m), 6.87–6.80 (1H, br s), 5.24 (2H, d, J=7.3 Hz), 4.66–4.58 (1H, m), 4.56 (2H, t, J=8.8 Hz), 4.44–4.36 (1H, m), 4.03 (2H, dd, J=8.8, 5.9 Hz), 3.79 (1H, dt, J=11.0, 6.6 Hz), 3.65–3.51 (2H, m), 3.40 (1H, dd, J=11.0, 4.4 Hz), 2.36 (3H, s), 2.32–2.20 (1H, m), 2.23–1.91 (1H, m).

REFERENCE EXAMPLE 77

3-Acetylthio-1-{4-[(3R)-1-(p-nitrobenzyloxycarbonyl)pyrrolidin-3-ylcarbamoyl]-1,3-oxazol-2-yl}azetidine

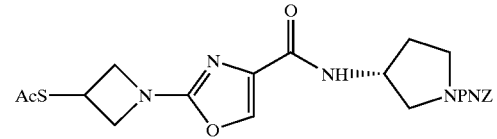

(1) 3-t-Butyldiphenylsilyloxy-1-{4-[(3R)-1-(p-nitrobenzyloxycarbonyl)pyrrolidin-3-ylcarbamoyl]-1,3-oxazol-2-yl}azetidine To a solution of (3R)-3-amino-1-p-nitrobenzyloxycarbonylpyrrolidine (798 mg, 3.01 mmol) (obtained as described in Reference Example 53(5)) and 3-t-butyldiphenylsilyloxy-1-(4-carboxyl-1,3-oxazol-2-yl)azetidine (1.06 g, 2.51 mmol) (obtained as described in Reference Example 70(11)) in dimethylformamide (50 ml) were added diethylphosphoryl cyanide (464 μl, 3.01 mmol) and triethylamine (422 μl, 3.01 mmol) in an ice bath under an atmosphere of nitrogen and the mixture was stirred at room temperature overnight. After checking the completion of the reaction, the mixture was partitioned between ethyl acetate and 10% aqueous sodium chloride solution. The organic layer was washed with saturated aqueous sodium hydrogencarbonate and saturated aqueous sodium chloride solution, dried over anhydrous sodium sulfate, filtered and concentrated under reduced pressure. The residue was purified by chromatography on a silica gel column using n-hexane:ethyl acetate (1:2→1:3) as the eluant to afford 3-t-butyldiphenylsilyloxy-1-{4-[(3R)-1-(p-nitrobenzyloxycarbonyl)pyrrolidin-3-ylcarbamoyl]-1,3-oxazol-2-yl}azetidine (813 mg, yield 48%) as a pale brown solid.

¹H-NMR (400 MHz, CDCl₃): δ (ppm) 8.22 (2H, m), 7.72 (1H, s), 7.63–7.59 (4H, m), 7.53(2H, m), 7.48–7.38 (6H, m), 6.86–6.60 (1H, m), 5.24 (2H, d, J=8.1 Hz), 4.77–4.68 (1H, m), 4.64–4.58 (1H, m), 4.15–4.09 (2H, m), 4.05 (2H, dd, J=8.8, 5.1 Hz), 3.82–3.75 (1H, m), 3.64–3.49 (2H, m), 3.38 (1H, dd, J=11.0, 5.1 Hz), 2.30–2.20 (1H, m), 2.06–1.90 (1H, m), 1.06 (9H, s).

(2) 3-Hydroxy-1-{4-[(3R)-1-(p-nitrobenzyloxycarbonyl)pyrrolidin-3-ylcarbamoyl]-1,3-oxazol-2-yl}azetidine To a solution of 3-t-butyldiphenylsilyloxy-1-(4-[(3R)-1-(p-nitrobenzyloxycarbonyl)-pyrrolidin-3-ylcarbamoyl]-1,3-oxazol-2-yl}azetidine (810 mg, 1.21 mmol) (obtained as described in Reference Example 77(1)) in anhydrous tetrahydrofuran (40 ml) was added a solution of acetic acid (83 µl, 1.45 mmol) and 1.0 M tetra-n-butylammonium fluoride in tetrahydrofuran (1.45 ml, 1.45 mmol) in an ice bath and the mixture was stirred in an ice bath overnight. After checking the completion of the reaction, the reaction mixture was concentrated under reduced pressure. The residue was purified by chromatography on a silica gel column using ethyl acetate→ethyl acetate:methanol (95:5) as the eluant to afford 3-hydroxy-1-{4-[(3R)-1-(p-nitrobenzyloxycarbonyl)pyrrolidin-3-ylcarbamoyl]-1,3-oxazol-2-yl}azetidine (507 mg, yield 97%) as a pale yellow oil.

$^1$H-NMR (400 MHz, CDCl$_3$): δ (ppm) 8.22 (2H, m), 7.75 (1H, s), 7.52 (2H, m), 6.89–6.83 (1H, br s), 5.28–5.20 (2H, m), 4.84–4.76 (1H, m), 4.66–4.58 (1H, m), 4.36 (2H, dd, J=8.8, 6.6 Hz), 4.01 (2H, dd, J=8.8, 4.4 Hz), 3.82–3.74 (1H, m), 3.64–3.51 (2H, m), 3.44–3.37 (1H, m), 2.32–2.20 (1H, m), 2.08–1.92 (1H, m).

(3) 3-Methanesulfonyloxy-1-{4-[(3R)-1-(p-nitrobenzyloxycarbonyl)pyrrolidin-3-ylcarbamoyl]-1,3-oxazol-2-yl}azetidine To a solution of 3-hydroxy-1-{4-[(3R)-1-(p-nitrobenzyloxycarbonyl)-pyrrolidin-3-ylcarbamoyl]-1,3-oxazol-2-yl}azetidine (500 mg, 1.16 mmol) (obtained as described in Reference Example 77(2)) in methylene chloride (25 ml) were added methanesulfonyl chloride (269 µl, 3.48 mmol) and triethylamine (488 µl, 3.48 mmol) in an ice bath and the mixture was stirred for 10 minutes and then at room temperature for 3 hours. After checking the completion of the reaction, the mixture was partitioned between ethyl acetate and saturated aqueous sodium hydrogencarbonate. The organic layer was washed with saturated aqueous sodium chloride solution, dried over anhydrous sodium sulfate, filtered and concentrated under reduced pressure. The residue was purified by chromatography on a silica gel column using ethyl acetate→ethyl acetate:methanol (96:4) as the eluant to afford 3-methanesulfonyloxy-1-{4-[(3R)-1-(p-nitrobenzyloxycarbonyl)pyrrolidin-3-ylcarbamoyl]-1,3-oxazol-2-yl}azetidine (546 mg, yield 92%) as a pale yellow solid.

Mass spectrum (FAB$^+$): m/z: 510 [M+H]$^+$.

(4) 3-Acetylthio-1-{4-[(3R)-1-(p-nitrobenzyloxycarbonyl)pyrrolidin-3-ylcarbamoyl]-1,3-oxazol-2-yl}azetidine To a solution of 3-methanesulfonyloxy-1-{4-[(3R)-1-(p-nitrobenzyloxycarbonyl)-pyrrolidin-3-ylcarbamoyl]-1,3-oxazol-2-yl}azetidine (540 mg, 1.06 mmol) (obtained as described in Reference Example 77(3)) in dimethylformamide (27 ml) was added potassium thioacetate (726 mg, 6.36 mmol) at room temperature, and the mixture was stirred in an oil bath (80° C.) for 9 hours. After checking the completion of the reaction, the mixture was partitioned between ethyl acetate and 10% aqueous sodium chloride solution. The organic layer was washed with saturated aqueous sodium hydrogencarbonate solution and saturated aqueous sodium chloride solution, dried over anhydrous sodium sulfate, filtered and concentrated under reduced pressure. The residue was purified by chromatography on a silica gel column using n-hexane:ethyl acetate (1:6)→ethyl acetate as the eluant to afford 3-acetylthio-1-{4-[(3R)-1-(p-nitrobenzyloxycarbonyl)-pyrrolidin-3-ylcarbamoyl]-1,3-oxazol-2-yl}azetidine (281 mg, yield 54%) as a pale brown solid.

$^1$H-NMR (400 MHz, CDCl$_3$): δ (ppm) 8.22 (2H, m), 7.76 (1H, s), 7.52 (2H, m), 6.86–6.80 (1H, m), 5.23 (2H, d, J=7.3 Hz), 4.64–4.58 (1H, m), 4.56 (2H, t, J=8.8 Hz), 4.44–3.86 (1H, m), 4.03 (2H, dd, J=8.8, 5.9 Hz), 3.79 (1H, dd, J=11.0, 6.6 Hz), 3.65–3.52 (2H, m), 3.40 (1H, dd, J=1.0, 4.4 Hz), 2.12 (3H, s), 2.32–2.20 (1H, m), 2.23–1.92 (1H, m).

TEST EXAMPLE 1

In Vitro Antibacterial Activities

To assess the antibacterial activities of the compounds, the minimum concentrations (µg/ml) of the compounds to inhibit growth of various pathogenic bacteria were determined by agar plate dilution method. The results are shown in Table 6. In this Table, the employed bacteria A, B, and C were as follow:

A: *Staphylococcus aureus*
B: *Streptococcus pneumoniae*
C: *Haemophilis influenzae* strain 9787 (a strain producing β-lactamase)

TABLE 6

| Compounds | | Minimum Concentration to Inhibit Growth (µg/ml) of the Employed Bacteria | | |
|---|---|---|---|---|
| | | A | B | C |
| Example | 3 | 0.05 | 0.20 | 0.10 |
| Example | 4 | 0.05 | 0.20 | 0.20 |
| Example | 5 | 0.05 | 0.20 | 0.20 |
| Example | 6 | 0.05 | 0.20 | 0.20 |
| Example | 19 | 0.05 | 0.20 | 0.10 |
| Example | 22 | 0.05 | 0.20 | 0.10 |
| Example | 24 | ≦0.012 | 0.025 | 0.05 |
| Example | 25 | 0.025 | 0.10 | 0.39 |
| Example | 56 | 0.05 | 0.20 | 0.20 |
| Example | 57 | 0.025 | 0.20 | 0.20 |
| Example | 58 | ≦0.012 | 0.20 | 0.20 |
| Example | 59 | ≦0.012 | 0.20 | 0.20 |
| Example | 60 | 0.025 | 0.39 | 0.39 |
| Example | 61 | 0.025 | 0.20 | 0.39 |
| Example | 67 | ≦0.012 | 0.39 | 0.20 |
| Example | 69 | ≦0.012 | ≦0.012 | 0.78 |
| Example | 70 | ≦0.012 | ≦0.012 | 0.78 |
| Example | 71 | ≦0.012 | ≦0.012 | 0.39 |
| Example | 72 | ≦0.012 | 0.025 | 0.20 |
| Example | 76 | 0.05 | 0.20 | 0.39 |
| Example | 80 | 0.025 | 0.20 | 0.39 |
| Example | 81 | ≦0.012 | 0.20 | 0.39 |

These results indicate that the compounds of the present invention exert potent antibacterial activities.

TEST EXAMPLE 2

Pharmacokinetics

The compounds of the present invention compound (20 mg/kg) was subcutaneously injected to mice (n=3, ddY, male, purchased from SLC Japan). The plasma concentration of the compound was determined by a bioassay method at 5, 15, and 30 min, and 1, 1.5, and 2 hr after administration. The pharmacokinetic parameters determined are summarized in Table 7. In the Table, $C_{max}$, $T_{1/2}$, and $AUC_{all}$ indicate the maximal plasma concentration, half-life in plasma concentration, and area under the concentration-time curve in plasma of the compound, respectively.

TABLE 7

| Compound | | $C_{max}$ (µg/ml) | $T_{1/2}$ (hr) | $AUC_{all}$ (µg·hr/ml) |
| --- | --- | --- | --- | --- |
| Example | 3 | 127.17 | 0.25 | 83.90 |
| Example | 4 | 157.38 | 1.02 | 165.19 |
| Example | 11 | 56.56 | 0.33 | 40.38 |
| Example | 57 | 48.15 | 0.38 | 45.31 |
| Example | 58 | 63.88 | 0.41 | 47.38 |
| Example | 60 | 46.14 | 0.30 | 27.88 |
| Example | 67 | 40.20 | 0.45 | 34.13 |
| Example | 76 | 52.80 | 0.19 | 27.88 |

TEST EXAMPLE 3

In Vivo Antibacterial Activities

Male ddY mice of 4 weeks old (purchased from SLC Japan) were intraperitoneally inoculated with *S. pneumoniae* 9605 (PRSP) at a volume of 0.2 ml (containing 5% mucin, $1-5\times10^3$ colony forming unit (cfu)/mouse). Immediately after the mice were infected, they were subcutaneously treated with the test compound singly at a volume of 0.1 ml. Seven mice were used per group. A solution of the test compound prepared by 2-step dilution was used for the experiment. $ED_{50}$ values of the compounds were calculated by the Probit method from survival rates 7 days after infection. The results are summarized in Table 8.

TABLE 8

| Compounds | | $ED_{50}$ (mg/kg) |
| --- | --- | --- |
| Example | 57 | 0.855 |
| Example | 58 | 0.899 |
| Example | 59 | 1.08 |
| Example | 60 | 1.41 |
| Example | 61 | 1.79 |
| Example | 67 | 1.60 |
| Example | 76 | 0.534 |

PREPARATION EXAMPLE 1

Injecting Agent 500 mg of the compound of Example 3 dissolved in 5 ml of distilled water for injection and the solution was freeze-dried after passing it through a sterilization filter to prepare a freeze-dried preparation for injection.

| Preparation Example 2 (capsules) | |
| --- | --- |
| Compound of Example 24 | 50 mg |
| Lactose | 128 mg |
| Corn starch | 70 mg |
| Magnesium stearate | 2 mg |
| | 250 mg |

Powders of the above formulation were mixed and after the mixture was passed through a sieve of 60 mesh, the powders were charged in a No. 3 gelatin capsule of 250 mg to prepare a capsule.

| Preparation Example 3 (tablets) | |
| --- | --- |
| Compound of Example 24 | 50 mg |
| Lactose | 126 mg |
| Corn starch | 23 mg |
| Magnesium stearate | 1 mg |
| | 200 mg |

Powders of the above formulation were mixed and after the mixture was wet-granulated using corn starch and dried, a 200 mg tablet was prepared. This tablet can be sugar-coated if necessary.

The 1-methylcarbapenem compounds of formula (I) of the present invention and pharmacologically acceptable salts thereof have excellent antibacterial activity, are stable against dehydropeptidase I and β-lactamase, and have a high recovery ratio in urine. In addition, since they exhibit low toxicity to the kidney, the compounds are useful as pharmaceuticals, particularly antibacterial agents.

What is claimed is:

1. A 1-methylcarbapenem compound represented by the formula (I):

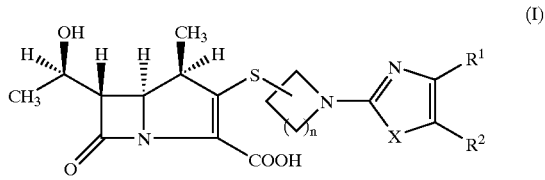

wherein:

$R^1$ is selected from the group consisting of (1) a group represented by the formula $COOR^3$ wherein $R^3$ is selected from the group consisting of a hydrogen atom, a $C_1-C_6$ alkyl group and a $C_3-C_6$ cycloalkyl group, (2) a group represented by the formula $CONR^4R^5$ wherein $R^4$ and $R^5$ may be the same or different and each is selected from the group consisting of a hydrogen atom, a $C_1-C_6$ alkyl group which is optionally substituted by one or two groups, which are the same or different and are selected from substituent group A below, a $C_3-C_6$ cycloalkyl group, a 3- to 6-membered heterocyclic group which is a saturated heterocyclic group including one or two hetero atoms selected from the group consisting of oxygen, nitrogen and sulfur atoms and a $C_6-C_{10}$ aryl group which is optionally substituted by one or two groups which are the same or different arid are selected from substituent group B below, or $R^4$ and $R^5$, together with the nitrogen atom to which they are bonded, represent a 3- to 6-membered nitrogen-containing heterocycle which is a saturated heterocyclic group containing one or two nitrogen atoms and optionally, oxygen or sulfur and is optionally substituted by one or two groups which are the same or different and are selected from substituent group B below, (3) a cyano group, (4) a group represented by the formula $CH_2OR^6$ wherein $R^6$ is selected from the group consisting of a hydrogen atom, a $C_1-C_6$ alkyl group and a $C_3-C_6$ cycloalkyl group or (5) a group represented by the formula $CH_2NR^7R^8$
wherein $R^7$ is selected from the group consisting of a hydrogen atom, a $C_1$–$C_6$ alkyl group and a $C_3$–$C_6$ cycloalkyl group, and $R^8$ is selected from the group consisting of a hydrogen atom, a $C_1$–$C_6$ alkyl group, a $C_3$–$C_6$ cycloalkyl group, a $C_1$–$C_6$ alkanoyl group, a ($C_6$–$C_{10}$ aryl)carbonyl group which is optionally substituted by one or two groups which are the same or different and are selected from substituent group B below, a ($C_1$–$C_6$ alkoxy)carbonyl group, a 5- or 6-membered aromatic heterocyclylcarbonyl group wherein the heterocyclic moiety is a heterocycle containing 1 to 3 hetero atoms selected from the group consisting of oxygen, nitrogen and sulfur, a $C_1$–$C_6$ alkylsulfonyl group and a $C_6$–$C_{10}$ arylsulfonyl group, or $R^7$ and $R^8$, together with the nitrogen atom to which they are bonded, represent a succinimide group which is optionally condensed with a phenyl group;

$R^2$ is selected from the group consisting of a hydrogen atom and a $C_1$–$C_6$ alkyl group;

n is 1, 2 or 3;

X is selected from the group consisting of a sulfur atom and an oxygen atom;

substituent group A consists of a hydroxyl group; an amino group which is optionally substituted by one or two $C_1$–$C_6$ alkyl groups; a carbamoyl group the amino moiety of which is optionally substituted by one or two $C_1$–$C_6$ alkyl groups; a carboxyl group; a cyano group and a $C_1$–$C_6$ alkoxy group; and substituent group B consists of a hydroxy-$C_1$–$C_4$-alkyl group; an amino-$C_1$–$C_4$-alkyl group the amino moiety of which is optionally substituted by one or two $C_1$–$C_6$ alkyl groups; a carbamoyl group the amino moiety of which is optionally substituted by one or two $C_1$–$C_6$ alkyl groups; a carboxyl group; a hydroxyl group; an amino group which is optionally substituted by one or two $C_1$–$C_6$ alkyl groups; a $C_1$–$C_6$ alkoxy group and a $C_1$–$C_6$ alkyl group;

or a pharmacologically acceptable salt or ester thereof.

2. A 1-methylcarbapenem compound or a pharmacologically acceptable salt or ester thereof in accordance with claim 1, wherein $R^1$ is a cyano group.

3. A 1-methylcarbapenem compound or a pharmacologically acceptable salt or ester thereof in accordance with claim 1, wherein $R^2$ is selected from the group consisting of a hydrogen atom and a $C_1$–$C_3$ alkyl group.

4. A 1-methylcarbapenem compound or a pharmacologically acceptable salt or ester thereof in accordance with claim 1, wherein $R^2$ is a hydrogen atom.

5. A 1-methylcarbapenem compound or a pharmacologically acceptable salt or ester thereof in accordance with claim 1, wherein $R^1$ is a group represented by the formula $COOR^3$.

6. A 1-methylcarbapenem compound or a pharmacologically acceptable salt or ester thereof in accordance with claim 5, wherein $R^3$ is selected from the group consisting of a hydrogen atom and a $C_1$–$C_3$ alkyl group.

7. A 1-methylcarbapenem compound or a pharmacologically acceptable salt or ester thereof in accordance with claim 5, wherein $R^3$ is selected from the group consisting of a hydrogen atom, a methyl group and an ethyl group.

8. A 1-methylcarbapenem compound or a pharmacologically acceptable salt or ester thereof in accordance with claim 1, wherein $R^1$ is a group represented by the formula $CONR^4R^5$.

9. A 1-methylcarbapenem compound or a pharmacologically acceptable salt or ester thereof in accordance with claim 8, wherein $R^4$ is selected from the group consisting of a hydrogen atom and a $C_1$–$C_3$ alkyl group.

10. A 1-methylcarbapenem compound or a pharmacologically acceptable salt or ester thereof in accordance with claim 8, wherein $R^4$ is selected from the group consisting of a hydrogen atom, a methyl group and an isopropyl group.

11. A 1-methylcarbapenem compound or a pharmacologically acceptable salt or ester thereof in accordance with claim 8, wherein $R^5$ is selected from the group consisting of a hydrogen atom, a $C_1$–$C_6$ alkyl group which is optionally substituted by one or two groups which are the same or different and are selected from substituent group A and a 4- to 6-membered nitrogen-containing heterocyclic group.

12. A 1-methylcarbapenem compound or a pharmacologically acceptable salt or ester thereof in accordance with claim 8, wherein $R^5$ is selected from the group consisting of a hydrogen atom, a $C_1$–$C_6$ alkyl group which is optionally substituted by one or two groups which are the same or different and are selected from substituent group A, an azetidinyl group, a pyrrolidinyl group and a piperidinyl group.

13. A 1-methylcarbapenem compound or a pharmacologically acceptable salt or ester thereof in accordance with claim 8, wherein $R^4$ and $R^5$, together with the nitrogen atom to which they are bonded, represent a 4- to 6-membered nitrogen-containing heterocycle which is optionally substituted by one or two groups which are the same or different and are selected from substituent group B.

14. A 1-methylcarbapenem compound or a pharmacologically acceptable salt or ester thereof in accordance with claim 8, wherein $R^4$ and $R^5$, together with the nitrogen atom to which they are bonded, represent a group selected from the group consisting of an azetidino group, a piperazino group, a morpholino group and a thiomorpholino group said group being optionally substituted by one or two groups which are the same or different and are selected from substituent group B.

15. A 1-methylcarbapenem compound or a pharmacologically acceptable salt or ester thereof in accordance with claim 1, wherein $R^1$ is $CH_2OR^6$ where $R^6$ is a $C_1$–$C_3$ alkyl group.

16. A 1-methylcarbapenem compound or a pharmacologically acceptable salt or ester thereof in accordance with claim 1, wherein $R^6$ is a hydrogen atom.

17. A 1-methylcarbapenem compound or a pharmacologically acceptable salt or ester thereof in accordance with claim 1, wherein $R^1$ is a group represented by the formula $CH_2NR^7R^8$.

18. A 1-methylcarbapenem compound or a pharmacologically acceptable salt or ester thereof in accordance with claim 17, wherein $R^7$ is selected from the group consisting of a hydrogen atom and a $C_1$–$C_3$ alkyl group.

19. A 1-methylcarbapenem compound or a pharmacologically acceptable salt or ester thereof in accordance with claim 17, wherein $R^7$ is selected from the group consisting of a methyl group.

20. A 1-methylcarbapenem compound or a pharmacologically acceptable salt or ester thereof in accordance with claim 17, wherein $R^7$ is a hydrogen atom.

21. A 1-methylcarbapenem compound or a pharmacologically acceptable salt or ester thereof in accordance with claim 17, wherein $R^8$ is selected from the group consisting of a $C_1$–$C_3$ alkyl group, a $C_1$–$C_3$ alkanoyl group, a ($C_1$–$C_3$ alkoxy)carbonyl group, a thienylcarbonyl group, a furylcarbonyl group and a pyridylcarbonyl group.

22. A 1-methylcarbapenem compound or a pharmacologically acceptable salt or ester thereof in accordance with claim 17, wherein $R^8$ is selected from the group consisting of a hydrogen atom, a benzoyl group which is optionally substituted by one or two groups which are the same or different and are selected from substituent group B, a (2-thienyl)carbonyl group, a (2-furyl)carbonyl group and a (3-pyridyl)carbonyl group.

23. A 1-methylcarbapenem compound or a pharmacologically acceptable salt or ester thereof in accordance with claim 1, wherein n is 1.

24. A 1-methylcarbapenem compound or a pharmacologically acceptable salt or ester thereof in accordance with claim 1, wherein X is an oxygen atom.

25. An 1-methylcarbapenem compound or a pharmacologically acceptable salt or ester thereof in accordance with claim 1, wherein:
- $R^1$ represents a group represented by the formula CONR$^4$R$^5$ wherein $R^4$ is selected from the group consisting of a hydrogen atom and a $C_1$–$C_3$ alkyl group; and $R^5$ is selected from the group consisting of a hydrogen atom, a $C_1$–$C_6$ alkyl group which is optionally substituted by one or two groups which are the same or different and are selected from substituent group A and a 4- to 6-membered nitrogen-containing heterocyclic group;
- $R^2$ is a hydrogen atom;
- n is 1; and
- X is selected from the group consisting of an oxygen atom and a sulfur atom.

26. A 1-methylcarbapenem compound or a pharmacologically acceptable salt or ester thereof in accordance with claim 1, wherein:
- $R^1$ represents a group represented by the formula CONR$^4$R$^5$ wherein $R^4$ is selected from the group consisting of a hydrogen atom, a methyl group and an isopropyl group; and $R^5$ is selected from the group consisting of a hydrogen atom, a $C_1$–$C_6$ alkyl group which is optionally substituted by one or two groups which are the same or different and are selected from substituent group A, an azetidinyl group, a pyrrolidinyl group and a piperidinyl group;
- n is 1; and
- X is selected from the group consisting of an oxygen atom and a sulfur atom.

27. A 1-methylcarbapenem compound or a pharmacologically acceptable salt or ester thereof in accordance with claim 1, wherein:
- $R^1$ represents a group represented by the formula CONR$^4$R$^5$ wherein $R^4$ and $R^5$, together with the nitrogen atom to which they are bonded, represent a 4- to 6-membered nitrogen-containing heterocycle which may be substituted by one or two groups which are the same or different and are selected from substituent group B;
- $R^2$ is a hydrogen atom;
- n is 1; and
- X is selected from the group consisting of an oxygen atom and a sulfur atom.

28. A 1-methylcarbapenem compound or a pharmacologically acceptable salt or ester thereof in accordance with claim 1, wherein:
- $R^1$ represents a group represented by the formula CONR$^4$R$^5$, wherein $R^4$ and $R^5$, together with the nitrogen atom to which they are bonded, represent a group selected from the group consisting of an azetidino group, a piperazino group, a morpholino group and a thiomorpholino group (said group may be substituted by one or two groups which are the same or different and are selected from substituent group B);
- $R^2$ is a hydrogen atom;
- n is 1; and
- X is selected from the group consisting of an oxygen atom and a sulfur atom.

29. A 1-methylcarbapenem compound or a pharmacologically acceptable salt or ester thereof in accordance with claim 1, wherein:
- $R^1$ is a cyano group;
- $R^2$ is a hydrogen atom;
- n is 1; and
- X is selected from the group consisting of an oxygen atom and a sulfur atom.

30. A 1-methylcarbapenem compound or a pharmacologically acceptable salt or ester thereof in accordance with claim 1, wherein:
- $R^1$ represents a group represented by the formula CH$_2$NR$^7$R$^8$ wherein $R^7$ is selected from the group consisting of a hydrogen atom and $C_1$–$C_3$ alkyl group; and $R^8$ is selected from the group consisting of a hydrogen atom, a $C_1$–$C_3$ alkyl group, a $C_1$–$C_3$ alkanoyl group, a benzoyl group which is optionally substituted by one or two groups which are the same or different and are selected from substituent group B, a ($C_1$–$C_3$ alkoxy)carbonyl group, a thienylcarbonyl group, a furylcarbonyl group and a pyridylcarbonyl group;
- $R^2$ is a hydrogen atom;
- n is 1; and
- X is selected from the group consisting of an oxygen atom and a sulfur atom.

31. A 1-methylcarbapenem compound or a pharmacologically acceptable salt or ester thereof in accordance with claim 1, wherein:
- $R^1$ represents a group represented by the formula CH$_2$NR$^7$R$^8$ wherein $R^7$ is selected from the group consisting of a hydrogen atom and a methyl group; and $R^8$ is selected from the group consisting of a hydrogen atom, a benzoyl group which is optionally substituted by one or two groups which are the same or different and are selected from substituent group B, a (2-thienyl)carbonyl group, a (2-furyl)carbonyl group and a (3-pyridyl)carbonyl group;
- $R^2$ is a hydrogen atom;
- n is 1; and
- X is selected from the group consisting of an oxygen atom and a sulfur atom.

32. A 1-methylcarbapenem compound selected from the following group of compounds:
- (1R,5S,6S)-2-[1-(4-carbamoyl-1,3-thiazol-2-yl)azetidin-3-yl]thio-6-[(1R)-1-hydroxyethyl]-1-methylcarbapen-2-em-3-carboxylic acid,
- (1R,5S,6S)-2-[1-(4-carbamoyl-1,3-oxazol-2-yl)azetidin-3-yl]thio-6-[(1R)-1-hydroxyethyl]-1-methylcarbapen-2-em-3-carboxylic acid,
- (1R,5S,6S)-2-[1-(4-hydroxymethyl-1,3-thiazol-2-yl)azetidin-3-yl]thio-6-[(1R)-1-hydroxyethyl]-1-methylcarbapen-2-em-3-carboxylic acid,
- (1R,5S,6S)-2-[1-(4-hydroxymethyl-1,3-oxazol-2-yl)azetidin-3-yl]thio-6-[(1R)-1-hydroxyethyl]-1-methylcarbapen-2-em-3-carboxylic acid,
- (1R,5S,6S)-2-[1-(4-cyano-1,3-thiazol-2-yl)azetidin-3-yl]thio-6-[(1R)-1-hydroxyethyl]-1-methylcarbapen-2-em-3-carboxylic acid, (1R,5S,6S)-2-[1-(4-cyano-1,3-oxazol-2-yl)azetidin-3-yl]thio-6-[(1R)-1-hydroxyethyl]-1-methylcarbapen-2-em-3-carboxylic acid, (1R,5S,6S)-2-[1-(4-morpholinocarbonyl-1,3-thiazol-2-yl)azetidin-3-yl]thio-6-[(1R)-1-hydroxyethyl]-1-methylcarbapen-2-em-3-carboxylic acid, (1R,5S,6S)-2-[1-(4-morpholinocarbonyl-1,3-oxazol-2-yl)azetidin-3-yl]thio-6-[(1R)-1-hydroxyethyl]-1-methylcarbapen-2-em-3-carboxylic acid, (1R,5S,6S)-2-[1-(4-azetidinocarbonyl-1,3-thiazol-2-yl)azetidin-3-yl]thio-6-[(1R)-1-hydroxyethyl]-1-methylcarbapen-2-em-3-carboxylic acid, (1R,5S,6S)-2-[1-(4-azetidinocarbonyl-1,3-oxazol-2-yl)azetidin-3-yl]thio-6-[(1R)-1-hydroxyethyl]-1-methylcarbapen-2-em-3-carboxylic acid, (1R,5S,6S)-2-{1-[4-(3-aminoazetidino)carbonyl-1,3-thiazol-2-yl]azetidin-3-yl}thio-6-[(1R)-1-hydroxyethyl]-1-methylcarbapen-2-em-3-carboxylic acid, (1R,5S,6S)-2-{1-[4-(3-aminoazetidino)carbonyl-1,3-oxazol-2-yl]azetidin-3-yl}thio-6-[(1R)-1-hydroxyethyl]-1-methylcarbapen-2-em-3-carboxylic acid, (1R,5S,6S)-2-{1-[4-(3-hydroxyazetidino)carbonyl-1,3-thiazol-2-yl]azetidin-3-yl}thio-6-[(1R)-1-hydroxyethyl]-1-methylcarbapen-2-em-3-carboxylic acid, (1R,5S,6S)-2-{1-[4-(3-hydroxyazetidino)carbonyl-1,3-oxazol-2-yl]azetidin-3-yl}thio-6-[(1R)-1-hydroxyethyl]-1-methylcarbapen-2-em-3-carboxylic acid, (1R,5S,6S)-2-[1-(4-thiomorpholinocarbonyl-1,3-thiazol-2-yl)azetidin-3-yl]thio-6-[(1R)-1-hydroxyethyl]-1-methylcarbapen-2-em-3-carboxylic acid, (1R,5S,6S)-2-[1-(4-thiomorpholinocarbonyl-1,3-oxazol-2-yl)azetidin-3-yl]thio-6-[(1R)-1-hydroxyethyl]-1-methylcarbapen-2-em-3-carboxylic acid, (1R,5S,6S)-2-{1-[4-(piperidin-4-ylcarbamoyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-(piperidin4-ylcarbamoyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-(azetidin-3-ylcarbamoyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-(azetidin-3-ylcarbamoyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-((3S)-pyrrolidin-3-ylcarbamoyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-((3S)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-((3R)-pyrrolidin-3-ylcarbamoyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-((3R)-pyrrolidin-3-ylcarbamoyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-(piperazine-1-carbonyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-(piperazine-1-carbonyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-(2-aminoethylcarbamoyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-(2-aminoethylcarbamoyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-((1S)-1-aminomethyl-2-methyl-propylcarbamoyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-((1S)-1-aminomethyl-2-methyl-propylcarbamoyl)-1,3-oxazol-2-yl]azetidin-3-yl}thio-6-[(R)-1-hydroxyethyl]-1-methylcarbapen-2-em-3-carboxylic acid, (1R,5S,6S)-2-(1-{4-[N-(2-aminoethyl)-N-isopropylcarbamoyl]-1,3-thiazol-2-yl}azetidin-3-yl)thio-6-[(R)-1-hydroxyethyl]-1-methylcarbapen-2-em-3-carboxylic acid, (1R,5S,6S)-2-(1-{4-[N-(2-aminoethyl)-N-isopropylcarbamoyl]-1,3-oxazol-2-yl}azetidin-3-yl)thio-6-[(R)-1-hydroxyethyl]-1-methylcarbapen-2-em-3-carboxylic acid, (1R,5S,6S)-2-(1-{4-[N-(2-hydroxyethyl)-N-isopropylcarbamoyl]-1,3-thiazol-2-yl}azetidin-3-yl)thio-6-[(R)-1-hydroxyethyl]-1-methylcarbapen-2-em-3-carboxylic acid, (1R,5S,6S)-2-(1-{4-[N-(2-hydroxyethyl)-N-isopropylcarbamoyl]-1,3-oxazol-2-yl}azetidin-3-yl)thio-6-[(R)-1-hydroxyethyl]-1-methylcarbapen-2-em-3-carboxylic acid, (1R,5S,6S)-2-[1-(4-aminomethyl-1,3-thiazol-2-yl)azetidin-3-yl]thio-6-[(R)-1-hydroxyethyl]-1-methylcarbapen-2-em-3-carboxylic acid, (1R,5S,6S)-2-[1-(4-aminomethyl-1,3-oxazol-2-yl)azetidin-3-yl]thio-6-[(R)-1-hydroxyethyl]-1-methylcarbapen-2-em-3-carboxylic acid, (1R,5S,6S)-2-{1-[4-(benzoylaminomethyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-(benzoylaminomethyl)-1,3-oxazol-2-yl]azetidin-3-yl}thio-6-[(R)-1-hydroxyethyl]-1-methylcarbapen-2-em-3-carboxylic acid, (1R,5S,6S)-2-{1-[4-(benzenesulfonylaminomethyl)-1,3-thiazol-2-yl]azetidin-3-yl}thio-6-[(R)-1-hydroxyethyl]-1-methylcarbapen-2-em-3-carboxylic acid, (1R,5S,6S)-2-{1-[4-(benzenesulfonylaminomethyl)-1,3-oxazol-2-yl]azetidin-3-yl}thio-6-[(R)-1-hydroxyethyl]-1-methylcarbapen-2-em-3-carboxylic acid, (1R,5S,6S)-2-(1-{4-[(thiophene-2-carbonylamino)methyl]-1,3-thiazol-2-yl}azetidin-3-yl)thio-6-[(R)-1-hydroxyethyl]-1-methylcarbapen-2-em-3-carboxylic acid, (1R,5S,6S)-2-(1-{4-[(thiophene-2-carbonylamino)methyl]-1,3-oxazol-2-yl}azetidin-3-yl)thio-6-[(R)-1-hydroxyethyl]-1-methylcarbapen-2-em-3-carboxylic acid, (1R,5S,6S)-2-(1-{4-[(furan-2-carbonylamino)methyl]-1,3-thiazol-2-yl}azetidin-3-yl)thio-6-[(R)-1-hydroxyethyl]-1-methylcarbapen-2-em-3-carboxylic acid, and (1R,5S,6S)-2-(1-{4-[(furan-2-carbonylamino)methyl]-1,3-oxazol-2-yl}azetidin-3-yl)thio-6-[(R)-1-hydroxyethyl]-1-methylcarbapen-2-em-3-carboxylic acid;

or a pharmacologically acceptable salt or ester thereof.

33. A 1-methylcarbapenem compound or a pharmacologically acceptable salt or ester thereof in accordance with claim 1, wherein $R^4$ and $R^5$ are the same or different and each is selected from the group consisting of a hydrogen atom, a $C_1$–$C_6$ alkyl group which is optionally substituted by one or two groups, which are the same or different and are selected from substituent group A' below, a $C_3$–$C_6$ cycloalkyl group, a 3- to 6-membered heterocyclic group and a $C_6$–$C_{10}$ aryl group which is optionally substituted by one or two groups which are the same or different and are selected from substituent group B' below, or $R^4$ and $R^5$, together with the nitrogen atom to which they are bonded, represent a 3- to 6-membered nitrogen-containing heterocycle which is optionally substituted by one or two groups which are the same or different and are selected from substituent group C below, and $R^7$ is selected from the group consisting of a hydrogen atom, a $C_1$–$C_6$ alkyl group and a $C_3$–$C_6$ cycloalkyl group, and $R^8$ is selected from the group consisting of a hydrogen atom, a $C_1$–$C_6$ alkyl group, a $C_3$–$C_6$ cycloalkyl group, a $C_1$–$C_6$ alkanoyl group, a ($C_6$–$C_{10}$ aryl)carbonyl group or a ($C_1$–$C_6$ alkoxy)carbonyl group;

substituent group A' is a hydroxyl group, an amino group, a carbamoyl group or a carboxyl group;

substituent group B' is a carbamoyl group or a carboxyl group;

substituent group C is a hydroxy-$C_1$–$C_4$-alkyl group, an amino-$C_1$–$C_4$-alkyl group, a carbamoyl group or a carboxyl group.

34. A pharmaceutical composition for the prevention or treatment of bacterial infections containing a pharmacologically active amount of a compound or a pharmacologically acceptable salt or ester thereof as defined in claim 1 as an active ingredient, together with a pharmaceutically acceptable carrier or diluent.

35. A method for the prevention or treatment of a bacterial infections, which comprises administering to a warm-blooded animal in need thereof a pharmacologically effective amount of a compound or a pharmacologically acceptable salt or ester thereof as defined in claim 1.

36. A method in accordance with claim 35, wherein the warm-blooded animal is a human being.

37. A 1-methylcarbapenem compound as claimed in claim 32 which is (1R,5S,6S)-2-[1-(4-carbamoyl-1,3-thiazol-2-yl)azetidin-3-yl]thio-6-[(1R)-1-hydroxyethyl]-1-methyl-carbapen-2-em-3-carboxylic acid or a pharmacologically acceptable salt or ester thereof.

38. A 1-methylcarbapenem compound as claimed in claim 32 which is (1R,5S,6S)-2-[1-(4-morpholinocarbonyl-1,3-oxazol-2-yl)azetidin-3-yl]thio-6-[(1R)-1-hydroxyethyl]-1-methyl-carbapen-2-em-3-carboxylic acid or a pharmacologically acceptable salt or ester thereof.

39. A 1-methylcarbapenem compound as claimed in claim 32 which is (1R,5S,6S)-2-{1-[4-(azetidin-3-ylcarbamoyl)-1,3-thiazol-2-yl]azetidin-3-yl}thio-6-[(R)-1-hydroxyethyl]-1-methyl-carbapen-2-em-3-carboxylic acid or a pharmacologically acceptable salt or ester thereof.

40. A 1-methylcarbapenem compound as claimed in claim 32 which is (1R,5S,6S)-2-{1-[4-((3S)-pyrrolidin-3-ylcarbamoyl)-1,3-thiazol-2-yl]azetidin-3-yl}thio-6-[(R)-1-hydroxyethyl]-1-methyl-carbapen-2-em-3-carboxylic acid or a pharmacologically acceptable salt or ester thereof.

41. A 1-methylcarbapenem compound as claimed in claim 32 which is (1R,5S,6S)-2-{1-[4-((3R)-pyrrolidin-3-ylcarbamoyl)-1,3-thiazol-2-yl]azetidin-3-yl}thio-6-[(R)-1-hydroxyethyl]-1-methyl-carbapen-2-em-3-carboxylic acid or a pharmacologically acceptable salt or ester thereof.

* * * * *